(12) United States Patent
Schnall-Levin et al.

(10) Patent No.: US 12,270,077 B2
(45) Date of Patent: *Apr. 8, 2025

(54) METHOD FOR TRANSPOSASE-MEDIATED SPATIAL TAGGING AND ANALYZING GENOMIC DNA IN A BIOLOGICAL SAMPLE

(71) Applicant: 10x Genomics, Inc., Pleasanton, CA (US)

(72) Inventors: Michael Schnall-Levin, San Francisco, CA (US); Michael Ybarra Lucero, South San Francisco, CA (US); Tarjei Sigurd Mikkelsen, Hayward, CA (US); Patrik Stahl, Stockholm (SE); Jonas Frisen, Stockholm (SE); Maja Marklund, Stockholm (SE); Enric Llorens Bobadilla, Stockholm (SE)

(73) Assignee: 10x Genomics, Inc., Pleasanton, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/348,072

(22) Filed: Jul. 6, 2023

(65) Prior Publication Data

US 2024/0018589 A1 Jan. 18, 2024

Related U.S. Application Data

(63) Continuation of application No. 17/933,347, filed on Sep. 19, 2022, which is a continuation of application No. 17/688,241, filed on Mar. 7, 2022, now Pat. No. 11,519,033, which is a continuation of application No. 16/876,682, filed on May 18, 2020, now abandoned, which is a continuation of application No. PCT/US2019/048425, filed on Aug. 27, 2019.

(60) Provisional application No. 62/858,331, filed on Jun. 7, 2019, provisional application No. 62/839,223, filed on Apr. 26, 2019, provisional application No. 62/822,592, filed on Mar. 22, 2019, provisional application No. 62/822,627, filed on Mar. 22, 2019, provisional application No. 62/822,605, filed on Mar. 22, 2019, provisional application No. 62/822,565, filed on Mar. 22, 2019, provisional application No. 62/812,219, filed on Feb. 28, 2019, provisional application No. 62/788,905, filed on Jan. 6, 2019, provisional application No. 62/788,897, filed on Jan. 6, 2019, provisional application No. 62/788,885, filed on Jan. 6, 2019, provisional application No. 62/788,871, filed on Jan. 6, 2019, provisional application No. 62/779,342, filed on Dec. 13, 2018, provisional application No. 62/724,483, filed on Aug. 29, 2018, provisional application No. 62/724,487, filed on Aug. 29, 2018, provisional application No. 62/724,489, filed on Aug. 29, 2018, provisional application No. 62/723,970, filed on Aug. 28, 2018, provisional application No. 62/723,972, filed on Aug. 28, 2018.

(51) Int. Cl.
| | |
|---|---|
| C12Q 1/6881 | (2018.01) |
| C12Q 1/48 | (2006.01) |
| C12Q 1/6806 | (2018.01) |
| C12Q 1/6841 | (2018.01) |
| C12Q 1/6874 | (2018.01) |

(52) U.S. Cl.
CPC ............. *C12Q 1/6881* (2013.01); *C12Q 1/48* (2013.01); *C12Q 1/6806* (2013.01); *C12Q 1/6841* (2013.01); *C12Q 1/6874* (2013.01); *C12Y 207/07* (2013.01)

(58) Field of Classification Search
CPC ...... C12Q 1/6881; C12Q 1/48; C12Q 1/6806; C12Q 1/6841; C12Q 1/6874; C12Q 2565/513; C12Q 2563/179; C12Q 2521/507; C12Q 2525/191; C12Y 207/07; G01N 2458/10

See application file for complete search history.

(56) References Cited

U.S. PATENT DOCUMENTS

| | | | |
|---|---|---|---|
| 4,683,195 A | 7/1987 | Mullis | |
| 4,683,202 A | 7/1987 | Mullis | |
| 4,800,159 A | 1/1989 | Mullis | |
| 4,883,867 A | 11/1989 | Lee | |
| 4,965,188 A | 10/1990 | Mullis | |
| 4,968,601 A | 11/1990 | Jacobson et al. | |
| 4,988,617 A | 1/1991 | Landegren et al. | |
| 5,002,882 A | 3/1991 | Lunnen | |
| 5,130,238 A | 7/1992 | Malek | |
| 5,308,751 A | 5/1994 | Ohkawa | |
| 5,321,130 A | 6/1994 | Yue | |

(Continued)

FOREIGN PATENT DOCUMENTS

| | | |
|---|---|---|
| AU | 2003200718 | 10/2006 |
| CN | 1273609 | 11/2000 |

(Continued)

OTHER PUBLICATIONS

Belaghzal et al., "Hi-C 2.0: An Optimized Hi-C Procedure for High-Resolution Genome-Wide Mapping of Chromosome Conformation," Methods, Jul. 1, 2017, 123:56-65, 20 pages.

(Continued)

*Primary Examiner* — Narayan K Bhat
(74) *Attorney, Agent, or Firm* — Fish & Richardson P.C.

(57) ABSTRACT

The present disclosure relates to materials and methods for spatially analyzing nucleic acids that have been fragmented with a transposase enzyme, alone or in combination with other types of analytes.

22 Claims, 53 Drawing Sheets

Specification includes a Sequence Listing.

(56) References Cited

U.S. PATENT DOCUMENTS

| | | |
|---|---|---|
| 5,410,030 A | 4/1995 | Yue |
| 5,436,134 A | 7/1995 | Haugland |
| 5,455,166 A | 10/1995 | Walker |
| 5,472,881 A | 12/1995 | Beebe et al. |
| 5,494,810 A | 2/1996 | Barany et al. |
| 5,503,980 A | 4/1996 | Cantor |
| 5,512,439 A | 4/1996 | Hornes |
| 5,512,462 A | 4/1996 | Cheng |
| 5,582,977 A | 12/1996 | Yue |
| 5,599,675 A | 2/1997 | Brenner |
| 5,610,287 A | 3/1997 | Nikiforov et al. |
| 5,641,658 A | 6/1997 | Adams |
| 5,648,245 A | 7/1997 | Fire et al. |
| 5,658,751 A | 8/1997 | Yue |
| 5,695,940 A | 12/1997 | Drmanac et al. |
| 5,750,341 A | 5/1998 | Macevicz |
| 5,763,175 A | 6/1998 | Brenner |
| 5,807,522 A | 9/1998 | Brown et al. |
| 5,817,783 A | 10/1998 | Calabretta et al. |
| 5,830,711 A | 11/1998 | Barany et al. |
| 5,837,832 A | 11/1998 | Chee et al. |
| 5,837,860 A | 11/1998 | Anderson et al. |
| 5,854,033 A | 12/1998 | Lizardi |
| 5,863,753 A | 1/1999 | Haugland |
| 5,871,921 A | 2/1999 | Landegren et al. |
| 5,912,148 A | 6/1999 | Eggerding |
| 5,919,626 A | 7/1999 | Shi et al. |
| 5,925,545 A | 7/1999 | Reznikoff et al. |
| 5,928,906 A | 7/1999 | Koester et al. |
| 5,958,775 A | 9/1999 | Wickstrrom |
| 5,962,271 A | 10/1999 | Chenchik et al. |
| 5,962,272 A | 10/1999 | Chenchik et al. |
| 5,965,443 A | 10/1999 | Reznikoff et al. |
| 6,013,440 A | 1/2000 | Lipshutz |
| 6,027,889 A | 2/2000 | Barany et al. |
| 6,054,274 A | 4/2000 | Sampson et al. |
| 6,060,240 A | 5/2000 | Kamb et al. |
| 6,130,073 A | 10/2000 | Eggerding |
| 6,143,496 A | 11/2000 | Brown |
| 6,153,389 A | 11/2000 | Haarer |
| 6,159,736 A | 12/2000 | Reznikoff et al. |
| 6,165,714 A | 12/2000 | Lane et al. |
| 6,172,218 B1 | 1/2001 | Brenner |
| 6,210,891 B1 | 4/2001 | Nyren |
| 6,210,894 B1 | 4/2001 | Brennan |
| 6,214,587 B1 | 4/2001 | Dattagupta |
| 6,251,639 B1 | 6/2001 | Kurn |
| 6,258,568 B1 | 7/2001 | Nyren |
| 6,265,552 B1 | 7/2001 | Schatz |
| 6,266,459 B1 | 7/2001 | Walt |
| 6,268,148 B1 | 7/2001 | Barany et al. |
| 6,274,320 B1 | 8/2001 | Rothberg |
| 6,291,180 B1 | 9/2001 | Chu |
| 6,291,187 B1 | 9/2001 | Kingsmore et al. |
| 6,300,063 B1 | 10/2001 | Lipshutz et al. |
| 6,306,597 B1 | 10/2001 | Macevicz |
| 6,309,824 B1 | 10/2001 | Drmanac |
| 6,323,009 B1 | 11/2001 | Lasken et al. |
| 6,344,316 B1 | 2/2002 | Lockhart |
| 6,344,329 B1 | 2/2002 | Lizardi et al. |
| 6,355,431 B1 | 3/2002 | Chee |
| 6,368,801 B1 | 4/2002 | Faruqi |
| 6,391,937 B1 | 5/2002 | Beuhler et al. |
| 6,401,267 B1 | 6/2002 | Drmanac |
| 6,404,907 B1 | 6/2002 | Gilchrist |
| 6,432,360 B1 | 8/2002 | Church et al. |
| 6,444,661 B1 | 9/2002 | Barton et al. |
| 6,503,713 B1 | 1/2003 | Rana |
| 6,506,561 B1 | 1/2003 | Cheval et al. |
| 6,534,266 B1 | 3/2003 | Singer |
| 6,544,732 B1 | 4/2003 | Chee |
| 6,573,043 B1 | 6/2003 | Cohen et al. |
| 6,579,695 B1 | 6/2003 | Lambalot |
| 6,620,584 B1 | 9/2003 | Chee |
| 6,632,641 B1 | 10/2003 | Brennan |
| 6,737,236 B1 | 5/2004 | Pieken et al. |
| 6,770,441 B2 | 8/2004 | Dickinson |
| 6,773,886 B2 | 8/2004 | Kaufman |
| 6,787,308 B2 | 9/2004 | Balasubramanian |
| 6,797,470 B2 | 9/2004 | Barany et al. |
| 6,800,453 B2 | 10/2004 | Labaer |
| 6,812,005 B2 | 11/2004 | Fan et al. |
| 6,828,100 B1 | 12/2004 | Ronaghi |
| 6,833,246 B2 | 12/2004 | Balasubramanian |
| 6,852,487 B1 | 2/2005 | Barany et al. |
| 6,859,570 B2 | 2/2005 | Walt |
| 6,864,052 B1 | 3/2005 | Drmanac |
| 6,867,028 B2 | 3/2005 | Janulaitis |
| 6,872,816 B1 | 3/2005 | Hall et al. |
| 6,875,572 B2 | 4/2005 | Prudent et al. |
| 6,890,741 B2 | 5/2005 | Fan et al. |
| 6,897,023 B2 | 5/2005 | Fu |
| 6,913,881 B1 | 7/2005 | Aizenstein et al. |
| 6,942,968 B1 | 9/2005 | Dickinson et al. |
| 6,969,488 B2 | 11/2005 | Bridgham |
| 7,001,792 B2 | 2/2006 | Sauer et al. |
| 7,011,944 B2 | 3/2006 | Prudent et al. |
| 7,057,026 B2 | 6/2006 | Barnes |
| 7,083,980 B2 | 8/2006 | Reznikoff et al. |
| 7,115,400 B1 | 10/2006 | Adessi |
| 7,118,883 B2 | 10/2006 | Inoue |
| 7,166,431 B2 | 1/2007 | Chee et al. |
| 7,192,735 B2 | 3/2007 | Lambalot |
| 7,211,414 B2 | 5/2007 | Hardin |
| 7,255,994 B2 | 8/2007 | Lao |
| 7,258,976 B2 | 8/2007 | Mitsuhashi |
| 7,259,258 B2 | 8/2007 | Kozlov et al. |
| 7,264,929 B2 | 9/2007 | Rothberg |
| 7,282,328 B2 | 10/2007 | Kong et al. |
| 7,297,518 B2 | 11/2007 | Quake |
| 7,329,492 B2 | 2/2008 | Hardin |
| 7,358,047 B2 | 4/2008 | Hafner et al. |
| 7,361,488 B2 | 4/2008 | Fan et al. |
| 7,375,234 B2 | 5/2008 | Sharpless et al. |
| 7,378,242 B2 | 5/2008 | Hurt |
| 7,393,665 B2 | 7/2008 | Brenner |
| 7,405,281 B2 | 7/2008 | Xu |
| 7,407,757 B2 | 8/2008 | Brenner |
| 7,427,678 B2 | 9/2008 | Pieken et al. |
| 7,473,767 B2 | 1/2009 | Dimitrov |
| 7,499,806 B2 | 3/2009 | Kermani et al. |
| 7,537,897 B2 | 5/2009 | Brenner |
| 7,563,576 B2 | 7/2009 | Chee |
| 7,579,153 B2 | 8/2009 | Brenner |
| 7,582,420 B2 | 9/2009 | Oliphant et al. |
| 7,601,498 B2 | 10/2009 | Mao |
| 7,608,434 B2 | 10/2009 | Reznikoff et al. |
| 7,611,869 B2 | 11/2009 | Fan |
| 7,635,566 B2 | 12/2009 | Brenner |
| 7,666,612 B2 | 2/2010 | Johnsson |
| 7,674,752 B2 | 3/2010 | He |
| 7,700,286 B2 | 4/2010 | Stroun et al. |
| 7,709,198 B2 | 5/2010 | Luo et al. |
| 7,776,547 B2 | 8/2010 | Roth |
| 7,776,567 B2 | 8/2010 | Mao |
| 7,803,943 B2 | 9/2010 | Mao |
| 7,888,009 B2 | 2/2011 | Barany et al. |
| 7,892,747 B2 | 2/2011 | Barany et al. |
| 7,910,304 B2 | 3/2011 | Drmanac |
| 7,914,981 B2 | 3/2011 | Barany et al. |
| 7,955,794 B2 | 6/2011 | Shen et al. |
| 7,960,119 B2 | 6/2011 | Chee |
| 7,985,565 B2 | 7/2011 | Mayer et al. |
| 8,003,354 B2 | 8/2011 | Shen et al. |
| 8,076,063 B2 | 12/2011 | Fan |
| 8,092,784 B2 | 1/2012 | Mao |
| 8,148,068 B2 | 4/2012 | Brenner |
| 8,206,917 B2 | 6/2012 | Chee |
| 8,268,554 B2 | 9/2012 | Schallmeiner |
| 8,288,103 B2 | 10/2012 | Oliphant |
| 8,288,122 B2 | 10/2012 | O'Leary et al. |
| 8,383,338 B2 | 2/2013 | Kitzman |
| 8,431,691 B2 | 4/2013 | McKernan et al. |
| 8,460,865 B2 | 6/2013 | Chee |

(56) References Cited

U.S. PATENT DOCUMENTS

| | | |
|---|---|---|
| 8,481,257 B2 | 7/2013 | Van Eijk |
| 8,481,258 B2 | 7/2013 | Church et al. |
| 8,481,292 B2 | 7/2013 | Casbon |
| 8,481,698 B2 | 7/2013 | Lieberman et al. |
| 8,507,204 B2 | 8/2013 | Pierce et al. |
| 8,519,115 B2 | 8/2013 | Webster et al. |
| 8,551,710 B2 | 10/2013 | Bernitz et al. |
| 8,568,979 B2 | 10/2013 | Stuelpnagel et al. |
| 8,586,310 B2 | 11/2013 | Mitra |
| 8,597,891 B2 | 12/2013 | Barany et al. |
| 8,603,743 B2 | 12/2013 | Liu et al. |
| 8,604,182 B2 | 12/2013 | Luo et al. |
| 8,614,073 B2 | 12/2013 | Van Eijk |
| 8,624,016 B2 | 1/2014 | Barany et al. |
| 8,685,889 B2 | 4/2014 | Van Eijk |
| 8,741,564 B2 | 6/2014 | Seligmann |
| 8,741,606 B2 | 6/2014 | Casbon |
| 8,748,103 B2 | 6/2014 | Faham et al. |
| 8,771,950 B2 | 7/2014 | Church et al. |
| 8,785,353 B2 | 7/2014 | Van Eijk |
| 8,790,873 B2 | 7/2014 | Namsaraev et al. |
| 8,809,238 B2 | 8/2014 | Livak et al. |
| 8,815,512 B2 | 8/2014 | Van Eijk |
| 8,835,358 B2 | 9/2014 | Fodor |
| 8,865,410 B2 | 10/2014 | Shendure |
| 8,906,626 B2 | 12/2014 | Oliphant et al. |
| 8,911,945 B2 | 12/2014 | Van Eijk |
| 8,936,912 B2 | 1/2015 | Mitra |
| 8,951,726 B2 | 2/2015 | Luo et al. |
| 8,951,728 B2 | 2/2015 | Rasmussen |
| 8,986,926 B2 | 3/2015 | Ferree et al. |
| 9,005,891 B2 | 4/2015 | Sinicropi et al. |
| 9,005,935 B2 | 4/2015 | Belyaev |
| 9,023,768 B2 | 5/2015 | Van Eijk |
| 9,062,348 B1 | 6/2015 | Van Eijk |
| 9,080,210 B2 | 7/2015 | Van Eijk |
| 9,194,001 B2 | 11/2015 | Brenner |
| 9,201,063 B2 | 12/2015 | Sood et al. |
| 9,273,349 B2 | 3/2016 | Nguyen et al. |
| 9,290,808 B2 | 3/2016 | Fodor |
| 9,290,809 B2 | 3/2016 | Fodor |
| 9,328,383 B2 | 5/2016 | Van Eijk |
| 9,334,536 B2 | 5/2016 | Van Eijk |
| 9,371,563 B2 | 6/2016 | Geiss et al. |
| 9,371,598 B2 | 6/2016 | Chee |
| 9,376,716 B2 | 6/2016 | Van Eijk |
| 9,376,717 B2 | 6/2016 | Gao et al. |
| 9,376,719 B2 | 6/2016 | Van Eijk |
| 9,416,409 B2 | 8/2016 | Hayden |
| 9,447,459 B2 | 9/2016 | Van Eijk |
| 9,453,256 B2 | 9/2016 | Van Eijk |
| 9,493,820 B2 | 11/2016 | Van Eijk |
| 9,506,061 B2 | 11/2016 | Brown et al. |
| 9,512,422 B2 | 12/2016 | Barnard et al. |
| 9,574,230 B2 | 2/2017 | Van Eijk |
| 9,593,365 B2 | 3/2017 | Frisen et al. |
| 9,598,728 B2 | 3/2017 | Barany et al. |
| 9,624,538 B2 | 4/2017 | Church et al. |
| 9,644,204 B2 | 5/2017 | Hindson et al. |
| 9,657,335 B2 | 5/2017 | Van Eijk |
| 9,670,542 B2 | 6/2017 | Van Eijk |
| 9,694,361 B2 | 7/2017 | Bharadwaj |
| 9,702,004 B2 | 7/2017 | Van Eijk |
| 9,714,446 B2 | 7/2017 | Webster et al. |
| 9,714,937 B2 | 7/2017 | Dunaway |
| 9,727,810 B2 | 8/2017 | Fodor et al. |
| 9,745,627 B2 | 8/2017 | Van Eijk |
| 9,777,324 B2 | 10/2017 | Van Eijk |
| 9,783,841 B2 | 10/2017 | Nolan et al. |
| 9,790,476 B2 | 10/2017 | Gloeckner et al. |
| 9,816,134 B2 | 11/2017 | Namsaraev |
| 9,834,814 B2 | 12/2017 | Peter et al. |
| 9,850,536 B2 | 12/2017 | Oliphant et al. |
| 9,856,521 B2 | 1/2018 | Stevens et al. |
| 9,868,979 B2 | 1/2018 | Chee et al. |
| 9,879,313 B2 | 1/2018 | Chee et al. |
| 9,889,422 B2 | 2/2018 | Smith et al. |
| 9,896,721 B2 | 2/2018 | Van Eijk |
| 9,898,576 B2 | 2/2018 | Van Eijk |
| 9,898,577 B2 | 2/2018 | Van Eijk |
| 9,902,991 B2 | 2/2018 | Sinicropi et al. |
| 9,909,167 B2 | 3/2018 | Samusik et al. |
| 9,938,566 B2 | 4/2018 | Shepard et al. |
| 9,957,550 B2 | 5/2018 | Yeakley et al. |
| 10,002,316 B2 | 6/2018 | Fodor et al. |
| 10,023,907 B2 | 7/2018 | Van Eijk |
| 10,030,261 B2 | 7/2018 | Frisen et al. |
| 10,035,992 B2 | 7/2018 | Gloeckner et al. |
| 10,041,949 B2 | 8/2018 | Bendall et al. |
| 10,059,989 B2 | 8/2018 | Giresi et al. |
| 10,059,990 B2 | 8/2018 | Boyden et al. |
| 10,095,832 B2 | 10/2018 | Van Eijk |
| 10,138,509 B2 | 11/2018 | Church et al. |
| 10,144,966 B2 | 12/2018 | Cantor |
| 10,179,932 B2 | 1/2019 | Church et al. |
| 10,208,982 B2 | 2/2019 | Bannish et al. |
| 10,227,639 B2 | 3/2019 | Levner et al. |
| 10,273,541 B2 | 4/2019 | Hindson et al. |
| 10,308,982 B2 | 6/2019 | Chee |
| 10,357,771 B2 | 7/2019 | Bharadwaj |
| 10,370,698 B2 | 8/2019 | Nolan et al. |
| 10,415,080 B2 | 9/2019 | Dunaway et al. |
| 10,465,235 B2 | 11/2019 | Gullberg et al. |
| 10,472,669 B2 | 11/2019 | Chee |
| 10,480,022 B2 | 11/2019 | Chee |
| 10,480,029 B2 | 11/2019 | Bent et al. |
| 10,494,667 B2 | 12/2019 | Chee |
| 10,495,554 B2 | 12/2019 | Deisseroth et al. |
| 10,501,777 B2 | 12/2019 | Beechem et al. |
| 10,501,791 B2 | 12/2019 | Church et al. |
| 10,510,435 B2 | 12/2019 | Cai et al. |
| 10,544,403 B2 | 1/2020 | Gloeckner et al. |
| 10,550,429 B2 | 2/2020 | Harada et al. |
| 10,590,244 B2 | 3/2020 | Delaney et al. |
| 10,633,648 B2 | 4/2020 | Seelig et al. |
| 10,640,816 B2 | 5/2020 | Beechem et al. |
| 10,640,826 B2 | 5/2020 | Church et al. |
| 10,662,468 B2 | 5/2020 | Chee |
| 10,669,569 B2 | 6/2020 | Gullberg et al. |
| 10,724,078 B2 | 7/2020 | Van Driel et al. |
| 10,725,027 B2 | 7/2020 | Bell |
| 10,774,372 B2 | 9/2020 | Chee et al. |
| 10,774,374 B2 | 9/2020 | Frisen et al. |
| 10,787,701 B2 | 9/2020 | Chee |
| 10,815,519 B2 | 10/2020 | Husain et al. |
| 10,829,803 B2 | 11/2020 | Terbrueggen et al. |
| 10,844,426 B2 | 11/2020 | Daugharthy et al. |
| 10,858,698 B2 | 12/2020 | Church et al. |
| 10,858,702 B2 | 12/2020 | Lucero et al. |
| 10,913,975 B2 | 2/2021 | So et al. |
| 10,914,730 B2 | 2/2021 | Chee et al. |
| 10,927,403 B2 | 2/2021 | Chee et al. |
| 10,961,566 B2 | 3/2021 | Chee |
| 11,001,879 B1 | 5/2021 | Chee |
| 11,008,607 B2 | 5/2021 | Chee |
| 11,046,996 B1 | 6/2021 | Chee et al. |
| 11,067,567 B2 | 7/2021 | Chee |
| 11,104,936 B2 | 8/2021 | Zhang et al. |
| 11,118,216 B2 | 9/2021 | Koshinsky et al. |
| 11,156,603 B2 | 10/2021 | Chee |
| 11,162,132 B2 | 11/2021 | Frisen et al. |
| 11,208,684 B2 | 12/2021 | Chee |
| 11,214,796 B2 | 1/2022 | Shirai et al. |
| 11,286,515 B2 | 3/2022 | Chee et al. |
| 11,293,917 B2 | 4/2022 | Chee |
| 11,299,774 B2 | 4/2022 | Frisen et al. |
| 11,313,856 B2 | 4/2022 | Chee |
| 11,332,790 B2 | 5/2022 | Chell et al. |
| 11,352,659 B2 | 6/2022 | Frisen et al. |
| 11,352,667 B2 | 6/2022 | Hauling et al. |
| 11,359,228 B2 | 6/2022 | Chee et al. |
| 11,365,442 B2 | 6/2022 | Chee |
| 11,371,086 B2 | 6/2022 | Chee |
| 11,384,386 B2 | 7/2022 | Chee |

(56) References Cited

U.S. PATENT DOCUMENTS

| | | |
|---|---|---|
| 11,390,912 B2 | 7/2022 | Frisen et al. |
| 11,401,545 B2 | 8/2022 | Chee |
| 11,407,992 B2 | 8/2022 | Dadhwal |
| 11,408,029 B2 | 8/2022 | Katiraee et al. |
| 11,434,524 B2 | 9/2022 | Ramachandran Iyer et al. |
| 11,459,607 B1 | 10/2022 | Terry et al. |
| 11,479,809 B2 | 10/2022 | Frisen et al. |
| 11,479,810 B1 | 10/2022 | Chee |
| 11,492,612 B1 | 11/2022 | Dadhwal |
| 11,501,440 B2 | 11/2022 | Weisenfeld et al. |
| 11,505,828 B2 | 11/2022 | Chell et al. |
| 11,512,308 B2 | 11/2022 | Gallant et al. |
| 11,519,022 B2 | 12/2022 | Chee |
| 11,519,033 B2 * | 12/2022 | Schnall-Levin ......... C12Q 1/48 |
| 11,530,438 B2 | 12/2022 | Persson et al. |
| 11,535,887 B2 | 12/2022 | Gallant et al. |
| 11,542,543 B2 | 1/2023 | Chee |
| 11,549,138 B2 | 1/2023 | Chee |
| 11,560,587 B2 | 1/2023 | Chee |
| 11,560,592 B2 | 1/2023 | Chew et al. |
| 11,560,593 B2 | 1/2023 | Chell et al. |
| 11,592,447 B2 | 2/2023 | Uytingco et al. |
| 11,608,498 B2 | 3/2023 | Gallant et al. |
| 11,608,520 B2 | 3/2023 | Galonska et al. |
| 11,613,773 B2 | 3/2023 | Frisen et al. |
| 11,618,897 B2 | 4/2023 | Kim et al. |
| 11,618,918 B2 | 4/2023 | Chee et al. |
| 11,624,063 B2 | 4/2023 | Dadhwal |
| 11,624,086 B2 | 4/2023 | Uytingco et al. |
| 11,634,756 B2 | 4/2023 | Chee |
| 11,649,485 B2 | 5/2023 | Yin et al. |
| 11,661,626 B2 | 5/2023 | Katiraee et al. |
| 11,680,260 B2 | 6/2023 | Kim et al. |
| 11,692,218 B2 | 7/2023 | Engblom et al. |
| 11,702,693 B2 | 7/2023 | Bharadwaj |
| 11,702,698 B2 | 7/2023 | Stoeckius |
| 11,732,292 B2 | 8/2023 | Chee |
| 11,732,299 B2 | 8/2023 | Ramachandran Iyer |
| 11,732,300 B2 | 8/2023 | Bava |
| 11,733,238 B2 | 8/2023 | Chee |
| 11,739,372 B2 | 8/2023 | Frisen et al. |
| 11,739,381 B2 | 8/2023 | Chew et al. |
| 11,753,673 B2 | 9/2023 | Chew et al. |
| 11,753,674 B2 | 9/2023 | Chee et al. |
| 11,753,675 B2 | 9/2023 | Ramachandran Iyer |
| 11,761,030 B2 | 9/2023 | Chee |
| 11,761,038 B1 | 9/2023 | Stoeckius |
| 11,767,550 B2 | 9/2023 | Chee |
| 11,768,175 B1 | 9/2023 | Kim et al. |
| 11,773,433 B2 | 10/2023 | Gallant et al. |
| 11,781,130 B2 | 10/2023 | Dadhwal |
| 11,788,122 B2 | 10/2023 | Frisen et al. |
| 11,795,498 B2 | 10/2023 | Frisen et al. |
| 11,795,507 B2 | 10/2023 | Chell et al. |
| 11,808,769 B2 | 11/2023 | Uytingco et al. |
| 11,821,024 B2 | 11/2023 | Chee et al. |
| 11,821,035 B1 | 11/2023 | Bent et al. |
| 11,827,935 B1 | 11/2023 | Ramachandran Iyer et al. |
| 11,835,462 B2 | 12/2023 | Bava |
| 11,840,687 B2 | 12/2023 | Gallant et al. |
| 11,840,724 B2 | 12/2023 | Chew et al. |
| 11,845,979 B2 | 12/2023 | Engblom et al. |
| 11,859,178 B2 | 1/2024 | Gallant et al. |
| 11,866,767 B2 | 1/2024 | Uytingco et al. |
| 11,866,770 B2 | 1/2024 | Chee |
| 11,873,482 B2 | 1/2024 | Kim et al. |
| 11,891,654 B2 | 2/2024 | Alvarado Martinez et al. |
| 11,898,205 B2 | 2/2024 | Bava |
| 11,926,822 B1 | 3/2024 | Gohil et al. |
| 11,926,863 B1 | 3/2024 | Boutet |
| 11,926,867 B2 | 3/2024 | Yin et al. |
| 11,933,957 B1 | 3/2024 | Tentori et al. |
| 11,952,627 B2 | 4/2024 | Stoeckius |
| 11,959,076 B2 | 4/2024 | Kim et al. |
| 11,959,130 B2 | 4/2024 | Galonska et al. |
| 11,965,213 B2 | 4/2024 | Williams |
| 11,970,739 B2 | 4/2024 | Chew et al. |
| 11,981,958 B1 | 5/2024 | Galonska |
| 11,981,960 B1 | 5/2024 | Lin et al. |
| 11,981,965 B2 | 5/2024 | Chell et al. |
| RE50,065 E | 7/2024 | Frisen et al. |
| 12,024,741 B2 | 7/2024 | Tentori et al. |
| 12,031,177 B1 | 7/2024 | Tentori et al. |
| 12,060,604 B2 | 8/2024 | Katiraee et al. |
| 12,071,655 B2 | 8/2024 | Sukovich et al. |
| 12,076,701 B2 | 9/2024 | Bava |
| 12,098,417 B2 | 9/2024 | Engblom et al. |
| 12,098,985 B2 | 9/2024 | Cox et al. |
| 12,110,541 B2 | 10/2024 | Bava |
| 12,117,439 B2 | 10/2024 | Delaney et al. |
| 12,128,403 B2 | 10/2024 | Kim et al. |
| 12,129,516 B2 | 10/2024 | Tentori et al. |
| 2001/0055764 A1 | 12/2001 | Empendocles et al. |
| 2002/0040275 A1 | 4/2002 | Cravatt |
| 2002/0051986 A1 | 5/2002 | Baez et al. |
| 2002/0055100 A1 | 5/2002 | Kawashima |
| 2002/0058250 A1 | 5/2002 | Firth |
| 2002/0086441 A1 | 7/2002 | Baranov et al. |
| 2002/0164611 A1 | 11/2002 | Bamdad |
| 2003/0017451 A1 | 1/2003 | Wang et al. |
| 2003/0022207 A1 | 1/2003 | Balasubramanian |
| 2003/0064398 A1 | 4/2003 | Barnes |
| 2003/0092624 A1 | 5/2003 | Wang et al. |
| 2003/0138879 A1 | 7/2003 | Lambalot |
| 2003/0148335 A1 | 8/2003 | Shen et al. |
| 2003/0162216 A1 | 8/2003 | Gold |
| 2003/0165948 A1 | 9/2003 | Alsmadi et al. |
| 2003/0211489 A1 | 11/2003 | Shen et al. |
| 2003/0224419 A1 | 12/2003 | Corcoran |
| 2003/0232348 A1 | 12/2003 | Jones et al. |
| 2003/0232382 A1 | 12/2003 | Brennan |
| 2003/0235854 A1 | 12/2003 | Chan et al. |
| 2004/0019005 A1 | 1/2004 | Van Ness |
| 2004/0033499 A1 | 2/2004 | Ilsley et al. |
| 2004/0067492 A1 | 4/2004 | Peng et al. |
| 2004/0067493 A1 | 4/2004 | Matsuzaki |
| 2004/0082059 A1 | 4/2004 | Webb et al. |
| 2004/0096853 A1 | 5/2004 | Mayer |
| 2004/0106110 A1 | 6/2004 | Balasubramanian |
| 2004/0235103 A1 * | 11/2004 | Reznikoff ............... C12N 9/22 435/320.1 |
| 2004/0248325 A1 | 12/2004 | Bukusoglu et al. |
| 2004/0259105 A1 | 12/2004 | Fan et al. |
| 2005/0003431 A1 | 1/2005 | Wucherpfennig |
| 2005/0014203 A1 | 1/2005 | Darfler et al. |
| 2005/0037393 A1 | 2/2005 | Gunderson et al. |
| 2005/0048580 A1 | 3/2005 | Labaer |
| 2005/0064460 A1 | 3/2005 | Holliger et al. |
| 2005/0095627 A1 | 5/2005 | Kolman et al. |
| 2005/0100900 A1 | 5/2005 | Kawashima et al. |
| 2005/0130173 A1 | 6/2005 | Leamon et al. |
| 2005/0136414 A1 | 6/2005 | Gunderson et al. |
| 2005/0164292 A1 | 7/2005 | Farooqui |
| 2005/0170373 A1 | 8/2005 | Monforte |
| 2005/0191656 A1 | 9/2005 | Drmanac et al. |
| 2005/0191698 A1 | 9/2005 | Chee et al. |
| 2005/0202433 A1 | 9/2005 | Van Beuningen |
| 2005/0227271 A1 | 10/2005 | Kwon |
| 2005/0239119 A1 | 10/2005 | Tsukada et al. |
| 2005/0260653 A1 | 11/2005 | LaBaer |
| 2005/0266417 A1 | 12/2005 | Barany et al. |
| 2006/0041385 A1 | 2/2006 | Bauer et al. |
| 2006/0046313 A1 | 3/2006 | Roth |
| 2006/0084078 A1 | 4/2006 | Zhao |
| 2006/0105352 A1 | 5/2006 | Qiao et al. |
| 2006/0154286 A1 | 7/2006 | Kong et al. |
| 2006/0188901 A1 | 8/2006 | Barnes et al. |
| 2006/0199183 A1 | 9/2006 | Valat et al. |
| 2006/0211001 A1 | 9/2006 | Yu et al. |
| 2006/0216775 A1 | 9/2006 | Burkart et al. |
| 2006/0240439 A1 | 10/2006 | Smith et al. |
| 2006/0263789 A1 | 11/2006 | Kincaid |
| 2006/0275782 A1 | 12/2006 | Gunderson et al. |
| 2006/0281109 A1 | 12/2006 | Barr Ost et al. |

(56) References Cited

U.S. PATENT DOCUMENTS

| | | |
|---|---|---|
| 2007/0020640 A1 | 1/2007 | McCloskey et al. |
| 2007/0020669 A1 | 1/2007 | Ericsson |
| 2007/0026430 A1 | 2/2007 | Andersen et al. |
| 2007/0048812 A1 | 3/2007 | Moravec et al. |
| 2007/0054288 A1 | 3/2007 | Su et al. |
| 2007/0087360 A1 | 4/2007 | Boyd |
| 2007/0099208 A1 | 5/2007 | Drmanac et al. |
| 2007/0128624 A1 | 6/2007 | Gormley et al. |
| 2007/0128656 A1 | 6/2007 | Agrawal |
| 2007/0134723 A1 | 6/2007 | Kozlov et al. |
| 2007/0161020 A1 | 7/2007 | Luo et al. |
| 2007/0166705 A1 | 7/2007 | Milton et al. |
| 2007/0172873 A1 | 7/2007 | Brenner et al. |
| 2007/0207482 A1 | 9/2007 | Church et al. |
| 2007/0254305 A1 | 11/2007 | Paik et al. |
| 2007/0264656 A1 | 11/2007 | Kawamura |
| 2007/0269805 A1 | 11/2007 | Hogers |
| 2008/0003586 A1 | 1/2008 | Hyde et al. |
| 2008/0009420 A1 | 1/2008 | Schroth et al. |
| 2008/0047835 A1 | 2/2008 | MacConnell |
| 2008/0108082 A1 | 5/2008 | Rank et al. |
| 2008/0108804 A1 | 5/2008 | Hayashizaki et al. |
| 2008/0132429 A1 | 6/2008 | Perov et al. |
| 2008/0160580 A1 | 7/2008 | Adessi et al. |
| 2008/0220434 A1 | 9/2008 | Thomas |
| 2008/0261204 A1 | 10/2008 | Lexow |
| 2008/0280773 A1 | 11/2008 | Fedurco et al. |
| 2008/0286795 A1 | 11/2008 | Kawashima et al. |
| 2008/0293046 A1 | 11/2008 | Allawi et al. |
| 2009/0005252 A1 | 1/2009 | Drmanac et al. |
| 2009/0006002 A1 | 1/2009 | Honisch et al. |
| 2009/0011943 A1 | 1/2009 | Drmanac et al. |
| 2009/0018024 A1 | 1/2009 | Church et al. |
| 2009/0026082 A1 | 1/2009 | Rothberg et al. |
| 2009/0036323 A1 | 2/2009 | van Eijk et al. |
| 2009/0082212 A1 | 3/2009 | Williams |
| 2009/0099041 A1 | 4/2009 | Church et al. |
| 2009/0105959 A1 | 4/2009 | Braverman et al. |
| 2009/0117573 A1 | 5/2009 | Fu et al. |
| 2009/0127589 A1 | 5/2009 | Rothberg et al. |
| 2009/0155781 A1 | 6/2009 | Drmanac et al. |
| 2009/0170713 A1 | 7/2009 | van Eijk et al. |
| 2009/0202998 A1 | 8/2009 | Schlumpberger et al. |
| 2009/0233802 A1 | 9/2009 | Bignell et al. |
| 2009/0239232 A1 | 9/2009 | Kurn |
| 2009/0253581 A1 | 10/2009 | van Eijk et al. |
| 2009/0270273 A1 | 10/2009 | Burns et al. |
| 2009/0283407 A1 | 11/2009 | Van Eijk |
| 2009/0286249 A1 | 11/2009 | Bekcer et al. |
| 2009/0291854 A1 | 11/2009 | Weisinger-Mayr et al. |
| 2009/0312193 A1 | 12/2009 | Kim et al. |
| 2010/0035249 A1 | 2/2010 | Hayashizaki et al. |
| 2010/0055733 A1 | 3/2010 | Lutolf et al. |
| 2010/0069263 A1 | 3/2010 | Shendure et al. |
| 2010/0105052 A1 | 4/2010 | Drmanac et al. |
| 2010/0105112 A1 | 4/2010 | Heltze et al. |
| 2010/0120097 A1 | 5/2010 | Matz et al. |
| 2010/0120098 A1 | 5/2010 | Grunenwald et al. |
| 2010/0129874 A1 | 5/2010 | Mitra et al. |
| 2010/0137143 A1 | 6/2010 | Rothberg et al. |
| 2010/0145037 A1 | 6/2010 | Brive et al. |
| 2010/0173384 A1 | 7/2010 | Johnsson et al. |
| 2010/0184618 A1 | 7/2010 | Namsaraev et al. |
| 2010/0210475 A1 | 8/2010 | Lee et al. |
| 2010/0227329 A1 | 9/2010 | Cuppens |
| 2010/0273219 A1 | 10/2010 | May et al. |
| 2010/0282617 A1 | 11/2010 | Rothberg et al. |
| 2011/0028685 A1 | 2/2011 | Purkayastha et al. |
| 2011/0033854 A1 | 2/2011 | Drmanac et al. |
| 2011/0045462 A1 | 2/2011 | Fu et al. |
| 2011/0059436 A1 | 3/2011 | Hardin et al. |
| 2011/0059865 A1 | 3/2011 | Smith et al. |
| 2011/0111409 A1 | 5/2011 | Sinicropi et al. |
| 2011/0152111 A1 | 6/2011 | Fan et al. |
| 2011/0245101 A1 | 10/2011 | Chee et al. |
| 2011/0245111 A1 | 10/2011 | Chee |
| 2011/0287435 A1 | 11/2011 | Grunenwald et al. |
| 2012/0021930 A1 | 1/2012 | Schoen et al. |
| 2012/0046175 A1 | 2/2012 | Rodesch et al. |
| 2012/0046178 A1 | 2/2012 | Van Den Boom et al. |
| 2012/0065081 A1 | 3/2012 | Chee |
| 2012/0135871 A1 | 5/2012 | van Eijk et al. |
| 2012/0202698 A1 | 8/2012 | van Eijk et al. |
| 2012/0202704 A1 | 8/2012 | Fan et al. |
| 2012/0220479 A1 | 8/2012 | Ericsson et al. |
| 2012/0245053 A1 | 9/2012 | Shirai et al. |
| 2012/0252702 A1 | 10/2012 | Muratani et al. |
| 2012/0258871 A1 | 10/2012 | Kozlov et al. |
| 2012/0270305 A1 | 10/2012 | Reed et al. |
| 2012/0289414 A1 | 11/2012 | Mitra et al. |
| 2012/0301925 A1 | 11/2012 | Belyaev |
| 2013/0005594 A1 | 1/2013 | Terbrueggen et al. |
| 2013/0005600 A1 | 1/2013 | Olek |
| 2013/0023433 A1 | 1/2013 | Luo et al. |
| 2013/0035239 A1 | 2/2013 | Kong et al. |
| 2013/0040842 A1 | 2/2013 | Lim et al. |
| 2013/0065768 A1 | 3/2013 | Zheng et al. |
| 2013/0079232 A1 | 3/2013 | Kain et al. |
| 2013/0244884 A1 | 9/2013 | Jacobson et al. |
| 2013/0260372 A1 | 10/2013 | Buermann et al. |
| 2013/0261019 A1 | 10/2013 | Lin et al. |
| 2013/0302801 A1 | 11/2013 | Asbury et al. |
| 2013/0338042 A1 | 12/2013 | Shen et al. |
| 2014/0066318 A1 | 3/2014 | Frisen et al. |
| 2014/0079923 A1 | 3/2014 | George et al. |
| 2014/0080715 A1 | 3/2014 | Lo et al. |
| 2014/0121118 A1 | 5/2014 | Warner |
| 2014/0155295 A1 | 6/2014 | Hindson et al. |
| 2014/0270435 A1 | 9/2014 | Dunn |
| 2014/0274731 A1 | 9/2014 | Raymond et al. |
| 2014/0323330 A1 | 10/2014 | Glezer et al. |
| 2014/0342921 A1 | 11/2014 | Weiner |
| 2014/0378345 A1 | 12/2014 | Hindson et al. |
| 2014/0378350 A1 | 12/2014 | Hindson et al. |
| 2015/0292988 A1 | 10/2015 | Bharadwaj et al. |
| 2015/0344942 A1 | 12/2015 | Frisen et al. |
| 2015/0376609 A1 | 12/2015 | Hindson et al. |
| 2016/0019337 A1 | 1/2016 | Roberts et al. |
| 2016/0024576 A1 | 1/2016 | Chee |
| 2016/0041159 A1 | 2/2016 | Labaer et al. |
| 2016/0060687 A1 | 3/2016 | Zhu et al. |
| 2016/0108458 A1 | 4/2016 | Frei et al. |
| 2016/0122817 A1 | 5/2016 | Jarosz et al. |
| 2016/0138091 A1 | 5/2016 | Chee et al. |
| 2016/0145677 A1 | 5/2016 | Chee et al. |
| 2016/0194692 A1 | 7/2016 | Gore et al. |
| 2016/0201125 A1 | 7/2016 | Samuels et al. |
| 2016/0253584 A1 | 9/2016 | Fodor et al. |
| 2016/0289740 A1 | 10/2016 | Fu et al. |
| 2016/0298180 A1 | 10/2016 | Chee |
| 2016/0303534 A1 | 10/2016 | Zhou et al. |
| 2016/0305856 A1 | 10/2016 | Boyden et al. |
| 2016/0333403 A1 | 11/2016 | Chee |
| 2016/0376642 A1 | 12/2016 | Landegren et al. |
| 2017/0009278 A1 | 1/2017 | Söderberg et al. |
| 2017/0016053 A1 | 1/2017 | Beechem et al. |
| 2017/0058339 A1 | 3/2017 | Chee |
| 2017/0058340 A1 | 3/2017 | Chee |
| 2017/0058345 A1 | 3/2017 | Chee |
| 2017/0088881 A1 | 3/2017 | Chee |
| 2017/0159109 A1 | 6/2017 | Zheng et al. |
| 2017/0166962 A1 | 6/2017 | van Eijk et al. |
| 2017/0220733 A1 | 8/2017 | Zhuang et al. |
| 2017/0233722 A1 | 8/2017 | Seelig et al. |
| 2017/0253918 A1 | 9/2017 | Kohman |
| 2017/0283860 A1 | 10/2017 | Kool et al. |
| 2017/0335297 A1 | 11/2017 | Ha et al. |
| 2017/0335410 A1 | 11/2017 | Driscoll et al. |
| 2017/0342405 A1 | 11/2017 | Fu et al. |
| 2017/0343545 A1 | 11/2017 | Hadrup et al. |
| 2017/0349940 A1 | 12/2017 | Morin et al. |
| 2018/0052081 A1 | 2/2018 | Kohman |
| 2018/0057873 A1 | 3/2018 | Zhou et al. |
| 2018/0080019 A1 | 3/2018 | Blainey et al. |

(56) References Cited

U.S. PATENT DOCUMENTS

| | | |
|---|---|---|
| 2018/0088112 A1 | 3/2018 | Fan et al. |
| 2018/0094316 A1 | 4/2018 | Oliphant et al. |
| 2018/0105808 A1 | 4/2018 | Mikkelsen et al. |
| 2018/0112209 A1 | 4/2018 | Eshoo |
| 2018/0112261 A1 | 4/2018 | Van Driel et al. |
| 2018/0127817 A1 | 5/2018 | Borchert et al. |
| 2018/0156784 A1 | 6/2018 | Usmani et al. |
| 2018/0163265 A1 | 6/2018 | Zhang et al. |
| 2018/0179591 A1 | 6/2018 | van Eijk |
| 2018/0180601 A1 | 6/2018 | Pedersen et al. |
| 2018/0201925 A1 | 7/2018 | Steemers et al. |
| 2018/0201980 A1 | 7/2018 | Chee et al. |
| 2018/0208967 A1 | 7/2018 | Larman et al. |
| 2018/0216161 A1 | 8/2018 | Chen et al. |
| 2018/0216162 A1 | 8/2018 | Belhocine et al. |
| 2018/0237864 A1 | 8/2018 | Imler et al. |
| 2018/0245142 A1 | 8/2018 | So et al. |
| 2018/0247017 A1 | 8/2018 | van Eijk et al. |
| 2018/0291427 A1* | 10/2018 | Edelman ............... C12Q 1/6827 |
| 2018/0291439 A1 | 10/2018 | van Eijk et al. |
| 2018/0305681 A1 | 10/2018 | Jovanovich et al. |
| 2018/0312822 A1 | 11/2018 | Lee et al. |
| 2018/0320226 A1 | 11/2018 | Church et al. |
| 2018/0334670 A1 | 11/2018 | Bharadwaj et al. |
| 2019/0002971 A1 | 1/2019 | Koslover et al. |
| 2019/0032121 A1 | 1/2019 | Daugharthy et al. |
| 2019/0055594 A1 | 2/2019 | Samusik et al. |
| 2019/0064173 A1 | 2/2019 | Bharadwaj et al. |
| 2019/0071656 A1* | 3/2019 | Chang ..................... C12N 9/22 |
| 2019/0119735 A1 | 4/2019 | Deisseroth et al. |
| 2019/0135774 A1 | 5/2019 | Orbai |
| 2019/0145982 A1 | 5/2019 | Chee et al. |
| 2019/0161796 A1 | 5/2019 | Hauling et al. |
| 2019/0177777 A1 | 6/2019 | Chee |
| 2019/0177778 A1 | 6/2019 | Chee |
| 2019/0177789 A1 | 6/2019 | Hindson et al. |
| 2019/0177800 A1 | 6/2019 | Boutet et al. |
| 2019/0203275 A1 | 7/2019 | Frisen et al. |
| 2019/0218276 A1 | 7/2019 | Regev et al. |
| 2019/0218608 A1 | 7/2019 | Daugharthy et al. |
| 2019/0233878 A1 | 8/2019 | Delaney et al. |
| 2019/0233880 A1 | 8/2019 | Mir |
| 2019/0249226 A1 | 8/2019 | Bent et al. |
| 2019/0262831 A1 | 8/2019 | West et al. |
| 2019/0264268 A1 | 8/2019 | Frisen et al. |
| 2019/0271028 A1 | 9/2019 | Khafizov et al. |
| 2019/0271030 A1 | 9/2019 | Chee |
| 2019/0271031 A1 | 9/2019 | Chee |
| 2019/0300943 A1 | 10/2019 | Chee et al. |
| 2019/0300944 A1 | 10/2019 | Chee et al. |
| 2019/0300945 A1 | 10/2019 | Chee et al. |
| 2019/0309353 A1 | 10/2019 | Chee |
| 2019/0309354 A1 | 10/2019 | Chee |
| 2019/0309355 A1 | 10/2019 | Chee |
| 2019/0323071 A1 | 10/2019 | Chee |
| 2019/0323088 A1 | 10/2019 | Boutet et al. |
| 2019/0338353 A1 | 11/2019 | Belgrader et al. |
| 2019/0345543 A1* | 11/2019 | Bonyhadi ............ A61K 39/0011 |
| 2019/0360034 A1 | 11/2019 | Zhou et al. |
| 2019/0360043 A1 | 11/2019 | Pham et al. |
| 2019/0367969 A1 | 12/2019 | Belhocine et al. |
| 2019/0367982 A1 | 12/2019 | Belhocine et al. |
| 2019/0367997 A1 | 12/2019 | Bent et al. |
| 2020/0002763 A1 | 1/2020 | Belgrader et al. |
| 2020/0010891 A1 | 1/2020 | Beechem et al. |
| 2020/0024641 A1 | 1/2020 | Nolan et al. |
| 2020/0047010 A1 | 2/2020 | Lee et al. |
| 2020/0048690 A1 | 2/2020 | Chee |
| 2020/0063191 A1 | 2/2020 | Kennedy-Darling et al. |
| 2020/0063195 A1 | 2/2020 | Chee |
| 2020/0063196 A1 | 2/2020 | Chee |
| 2020/0071751 A1 | 3/2020 | Daugharthy et al. |
| 2020/0080136 A1 | 3/2020 | Zhang et al. |
| 2020/0109443 A1 | 4/2020 | Chee |
| 2020/0123597 A1 | 4/2020 | Daniel |
| 2020/0140920 A1 | 5/2020 | Pierce et al. |
| 2020/0173985 A1 | 6/2020 | Dong et al. |
| 2020/0199565 A1* | 6/2020 | Chen ................... C12N 9/1241 |
| 2020/0199572 A1 | 6/2020 | Kuersten et al. |
| 2020/0224244 A1 | 7/2020 | Nilsson et al. |
| 2020/0239874 A1 | 7/2020 | Mikkelsen |
| 2020/0256867 A1 | 8/2020 | Hennek et al. |
| 2020/0277663 A1 | 9/2020 | Iyer |
| 2020/0277664 A1 | 9/2020 | Frenz |
| 2020/0283852 A1 | 9/2020 | Oliphant et al. |
| 2020/0299757 A1 | 9/2020 | Chee et al. |
| 2020/0325531 A1 | 10/2020 | Chee |
| 2020/0362398 A1 | 11/2020 | Kishi et al. |
| 2020/0370095 A1 | 11/2020 | Farmer et al. |
| 2020/0399687 A1 | 12/2020 | Frisen et al. |
| 2020/0407781 A1 | 12/2020 | Schnall-Levin |
| 2021/0010068 A1 | 1/2021 | Chee et al. |
| 2021/0010070 A1 | 1/2021 | Schnall-Levin et al. |
| 2021/0017587 A1 | 1/2021 | Cai et al. |
| 2021/0095331 A1 | 4/2021 | Fan et al. |
| 2021/0115504 A1 | 4/2021 | Cai et al. |
| 2021/0123040 A1 | 4/2021 | Macosko et al. |
| 2021/0130881 A1 | 5/2021 | Cox |
| 2021/0140982 A1 | 5/2021 | Uytingco et al. |
| 2021/0155982 A1 | 5/2021 | Yin et al. |
| 2021/0158522 A1 | 5/2021 | Weisenfeld et al. |
| 2021/0172007 A1 | 6/2021 | Chee et al. |
| 2021/0189475 A1 | 6/2021 | Tentori et al. |
| 2021/0190770 A1 | 6/2021 | Delaney et al. |
| 2021/0198741 A1 | 7/2021 | Williams |
| 2021/0199660 A1 | 7/2021 | Williams et al. |
| 2021/0207202 A1 | 7/2021 | Chee |
| 2021/0214785 A1 | 7/2021 | Stoeckius |
| 2021/0222235 A1 | 7/2021 | Chee |
| 2021/0222241 A1 | 7/2021 | Bharadwaj |
| 2021/0222242 A1 | 7/2021 | Ramachandran Iyer |
| 2021/0222253 A1 | 7/2021 | Uytingco |
| 2021/0223227 A1 | 7/2021 | Stoeckius |
| 2021/0230584 A1 | 7/2021 | Mikkelsen et al. |
| 2021/0230681 A1 | 7/2021 | Patterson et al. |
| 2021/0230692 A1 | 7/2021 | Daugharthy et al. |
| 2021/0237022 A1 | 8/2021 | Bava |
| 2021/0238581 A1 | 8/2021 | Mikkelsen et al. |
| 2021/0238664 A1 | 8/2021 | Bava et al. |
| 2021/0238675 A1 | 8/2021 | Bava |
| 2021/0238680 A1 | 8/2021 | Bava |
| 2021/0247316 A1 | 8/2021 | Bava |
| 2021/0255175 A1 | 8/2021 | Chee et al. |
| 2021/0262018 A1 | 8/2021 | Bava et al. |
| 2021/0262019 A1 | 8/2021 | Alvarado Martinez et al. |
| 2021/0269864 A1 | 9/2021 | Chee |
| 2021/0270822 A1 | 9/2021 | Chee |
| 2021/0285036 A1 | 9/2021 | Yin et al. |
| 2021/0285046 A1 | 9/2021 | Chell et al. |
| 2021/0292748 A1 | 9/2021 | Frisen et al. |
| 2021/0292822 A1 | 9/2021 | Frisen et al. |
| 2021/0317510 A1 | 10/2021 | Chee et al. |
| 2021/0317524 A1 | 10/2021 | Lucero et al. |
| 2021/0324457 A1 | 10/2021 | Ramachandran Iyer et al. |
| 2021/0332424 A1 | 10/2021 | Schnall-Levin |
| 2021/0332425 A1 | 10/2021 | Pfeiffer et al. |
| 2021/0348221 A1 | 11/2021 | Chell et al. |
| 2022/0002791 A1 | 1/2022 | Frisen et al. |
| 2022/0003755 A1 | 1/2022 | Chee |
| 2022/0010367 A1 | 1/2022 | Ramachandran Iyer et al. |
| 2022/0017951 A1 | 1/2022 | Ramachandran Iyer et al. |
| 2022/0025446 A1 | 1/2022 | Shah |
| 2022/0025447 A1 | 1/2022 | Tentori et al. |
| 2022/0033888 A1 | 2/2022 | Schnall-Levin et al. |
| 2022/0049293 A1 | 2/2022 | Frenz et al. |
| 2022/0064630 A1 | 3/2022 | Bent et al. |
| 2022/0081728 A1 | 3/2022 | Williams |
| 2022/0090058 A1 | 3/2022 | Frisen et al. |
| 2022/0090175 A1 | 3/2022 | Uytingco et al. |
| 2022/0090181 A1 | 3/2022 | Gallant et al. |
| 2022/0098576 A1 | 3/2022 | Dadhwal |
| 2022/0098661 A1 | 3/2022 | Chew et al. |
| 2022/0106632 A1 | 4/2022 | Galonska et al. |
| 2022/0106633 A1 | 4/2022 | Engblom et al. |

(56) References Cited

U.S. PATENT DOCUMENTS

| | | |
|---|---|---|
| 2022/0112486 A1 | 4/2022 | Ramachandran Iyer et al. |
| 2022/0112545 A1 | 4/2022 | Chee |
| 2022/0119869 A1 | 4/2022 | Ramachandran Iyer et al. |
| 2022/0127659 A1 | 4/2022 | Frisen et al. |
| 2022/0127666 A1 | 4/2022 | Katiraee et al. |
| 2022/0127672 A1 | 4/2022 | Stoeckius |
| 2022/0145361 A1 | 5/2022 | Frenz et al. |
| 2022/0154255 A1 | 5/2022 | Chee et al. |
| 2022/0170083 A1 | 6/2022 | Khaled et al. |
| 2022/0195422 A1 | 6/2022 | Gallant et al. |
| 2022/0195505 A1 | 6/2022 | Frisen et al. |
| 2022/0196644 A1 | 6/2022 | Chee |
| 2022/0213526 A1 | 7/2022 | Frisen et al. |
| 2022/0220544 A1 | 7/2022 | Ach et al. |
| 2022/0241780 A1 | 8/2022 | Tentori et al. |
| 2022/0267844 A1 | 8/2022 | Ramachandran Iyer et al. |
| 2022/0282329 A1 | 9/2022 | Chell et al. |
| 2022/0290217 A1 | 9/2022 | Frenz et al. |
| 2022/0290219 A1 | 9/2022 | Chee |
| 2022/0298560 A1 | 9/2022 | Frisen et al. |
| 2022/0325325 A1 | 10/2022 | Chee et al. |
| 2022/0326251 A1 | 10/2022 | Uytingco et al. |
| 2022/0333171 A1 | 10/2022 | Chee |
| 2022/0333191 A1 | 10/2022 | Mikkelsen et al. |
| 2022/0333192 A1 | 10/2022 | Uytingco |
| 2022/0333195 A1 | 10/2022 | Schnall-Levin et al. |
| 2022/0334031 A1 | 10/2022 | Delaney et al. |
| 2022/0348905 A1 | 11/2022 | Dadhwal |
| 2022/0348992 A1 | 11/2022 | Stoeckius et al. |
| 2022/0356464 A1 | 11/2022 | Kim et al. |
| 2022/0364163 A1 | 11/2022 | Stahl et al. |
| 2022/0389491 A1 | 12/2022 | Chee |
| 2022/0389503 A1 | 12/2022 | Mikkelsen et al. |
| 2022/0389504 A1 | 12/2022 | Chew et al. |
| 2022/0403455 A1 | 12/2022 | Ramachandran Iyer et al. |
| 2022/0404245 A1 | 12/2022 | Chell et al. |
| 2023/0002812 A1 | 1/2023 | Stoeckius et al. |
| 2023/0014008 A1 | 1/2023 | Shastry |
| 2023/0017773 A1 | 1/2023 | Kim et al. |
| 2023/0416807 A1 | 1/2023 | Chee |
| 2023/0416808 A1 | 1/2023 | Sukovich et al. |
| 2023/0033960 A1 | 2/2023 | Gallant et al. |
| 2023/0034039 A1 | 2/2023 | Shahjamali |
| 2023/0034216 A1 | 2/2023 | Bava |
| 2023/0040363 A1 | 2/2023 | Chee |
| 2023/0042088 A1 | 2/2023 | Chee |
| 2023/0042817 A1 | 2/2023 | Mignardi |
| 2023/0047782 A1 | 2/2023 | Tentori et al. |
| 2023/0056549 A1 | 2/2023 | Dadhwal |
| 2023/0064372 A1 | 3/2023 | Chell et al. |
| 2023/0069046 A1 | 3/2023 | Chew et al. |
| 2023/0077364 A1 | 3/2023 | Patterson et al. |
| 2023/0080543 A1 | 3/2023 | Katiraee et al. |
| 2023/0081381 A1 | 3/2023 | Chew et al. |
| 2023/0100497 A1 | 3/2023 | Frisen et al. |
| 2023/0107023 A1 | 4/2023 | Chee |
| 2023/0111225 A1 | 4/2023 | Chew et al. |
| 2023/0113230 A1 | 4/2023 | Kim et al. |
| 2023/0126825 A1 | 4/2023 | Nagendran et al. |
| 2023/0129552 A1 | 4/2023 | Ramachandran Iyer |
| 2023/0135010 A1 | 5/2023 | Tentori et al. |
| 2023/0143569 A1 | 5/2023 | Iyer et al. |
| 2023/0145575 A1 | 5/2023 | Gallant et al. |
| 2023/0147726 A1 | 5/2023 | Hadrup et al. |
| 2023/0151412 A1 | 5/2023 | Chee |
| 2023/0159994 A1 | 5/2023 | Chee |
| 2023/0159995 A1 | 5/2023 | Iyer et al. |
| 2023/0160008 A1 | 5/2023 | Chell et al. |
| 2023/0175045 A1 | 6/2023 | Katsori et al. |
| 2023/0183785 A1 | 6/2023 | Frisen et al. |
| 2023/0194469 A1 | 6/2023 | Tentori et al. |
| 2023/0194470 A1 | 6/2023 | Kim et al. |
| 2023/0203478 A1 | 6/2023 | Kim et al. |
| 2023/0183684 A1 | 7/2023 | Gallant et al. |
| 2023/0212650 A1 | 7/2023 | Chew et al. |
| 2023/0212655 A1 | 7/2023 | Chee |
| 2023/0220368 A1 | 7/2023 | Kim |
| 2023/0220454 A1 | 7/2023 | Bent et al. |
| 2023/0220455 A1 | 7/2023 | Galonska et al. |
| 2023/0227811 A1 | 7/2023 | Dadhwal |
| 2023/0228762 A1 | 7/2023 | Uytingco et al. |
| 2023/0242973 A1 | 8/2023 | Frisen et al. |
| 2023/0242976 A1 | 8/2023 | Tentori et al. |
| 2023/0265488 A1 | 8/2023 | Gohil et al. |
| 2023/0265489 A1 | 8/2023 | Uytingco et al. |
| 2023/0265491 A1 | 8/2023 | Tentori et al. |
| 2023/0267625 A1 | 8/2023 | Tentori et al. |
| 2023/0279474 A1 | 9/2023 | Katiraee |
| 2023/0279477 A1 | 9/2023 | Kvastad et al. |
| 2023/0279481 A1 | 9/2023 | Marrache et al. |
| 2023/0287399 A1 | 9/2023 | Gallant et al. |
| 2023/0287475 A1 | 9/2023 | Chell et al. |
| 2023/0287481 A1 | 9/2023 | Katsori et al. |
| 2023/0295699 A1 | 9/2023 | Sukovich et al. |
| 2023/0295722 A1 | 9/2023 | Bharadwaj |
| 2023/0304072 A1 | 9/2023 | Gohil et al. |
| 2023/0304074 A1 | 9/2023 | Chee et al. |
| 2023/0304078 A1 | 9/2023 | Frisen et al. |
| 2023/0313279 A1 | 10/2023 | Giacomello et al. |
| 2023/0323340 A1 | 10/2023 | Dadhwal |
| 2023/0323434 A1 | 10/2023 | Yin et al. |
| 2023/0323436 A1 | 10/2023 | Chee |
| 2023/0323447 A1 | 10/2023 | Schnall-Levin et al. |
| 2023/0323453 A1 | 10/2023 | Stoeckius |
| 2023/0332138 A1 | 10/2023 | Kim et al. |
| 2023/0332211 A1 | 10/2023 | Chee |
| 2023/0332212 A1 | 10/2023 | Chew et al. |
| 2023/0332227 A1 | 10/2023 | Ramachandran Iyer |
| 2023/0332247 A1 | 10/2023 | Singh et al. |
| 2023/0351619 A1 | 11/2023 | Tentori et al. |
| 2023/0358733 A1 | 11/2023 | Chee |
| 2023/0366008 A1 | 11/2023 | Chew et al. |
| 2023/0383285 A1 | 11/2023 | Kim et al. |
| 2023/0383344 A1 | 11/2023 | Stoeckius |
| 2023/0392204 A1 | 12/2023 | Chell et al. |
| 2023/0393071 A1 | 12/2023 | Bava |
| 2023/0407404 A1 | 12/2023 | Baumgartner et al. |
| 2023/0416850 A1 | 12/2023 | Singh et al. |
| 2024/0002931 A1 | 1/2024 | Bava |
| 2024/0011081 A1 | 1/2024 | Chee |
| 2024/0011090 A1 | 1/2024 | Chew et al. |
| 2024/0018572 A1 | 1/2024 | Mignardi |
| 2024/0018575 A1 | 1/2024 | Gallant et al. |
| 2024/0026445 A1 | 1/2024 | Ramachandran Iyer et al. |
| 2024/0033743 A1 | 2/2024 | Tentori et al. |
| 2024/0035937 A1 | 2/2024 | Cox et al. |
| 2024/0043908 A1 | 2/2024 | Chew et al. |
| 2024/0043925 A1 | 2/2024 | Bent et al. |
| 2024/0052343 A1 | 2/2024 | Gallant et al. |
| 2024/0053351 A1 | 2/2024 | Uytingco et al. |
| 2024/0060115 A1 | 2/2024 | Chee et al. |
| 2024/0067953 A1 | 2/2024 | Mikkelsen et al. |
| 2024/0068016 A1 | 2/2024 | Frisen et al. |
| 2024/0068017 A1 | 2/2024 | Lundeberg et al. |
| 2024/0076723 A1 | 3/2024 | Mignardi |
| 2024/0080346 A1 | 3/2024 | Engblom et al. |
| 2024/0084365 A1 | 3/2024 | Frisen et al. |
| 2024/0084366 A1 | 3/2024 | Chee |
| 2024/0084383 A1 | 3/2024 | Ramachandran Iyer et al. |
| 2024/0093274 A1 | 3/2024 | Frisen et al. |
| 2024/0093290 A1 | 3/2024 | Stahl et al. |
| 2024/0110228 A1 | 4/2024 | Uytingco et al. |
| 2024/0124933 A1 | 4/2024 | Chell et al. |
| 2024/0125772 A1 | 4/2024 | Delaney et al. |
| 2024/0141327 A1 | 5/2024 | Kim et al. |
| 2024/0158838 A1 | 5/2024 | Alvarado Martinez et al. |
| 2024/0175080 A1 | 5/2024 | Galonska et al. |
| 2024/0182968 A1 | 6/2024 | Bava |
| 2024/0191286 A1 | 6/2024 | Boutet et al. |
| 2024/0200121 A1 | 6/2024 | Boutet |
| 2024/0209425 A1 | 6/2024 | Yin et al. |
| 2024/0218427 A1 | 7/2024 | Sukovich et al. |
| 2024/0218432 A1 | 7/2024 | Mielinis |
| 2024/0219701 A1 | 7/2024 | Tentori et al. |

(56) References Cited

U.S. PATENT DOCUMENTS

| | | |
|---|---|---|
| 2024/0253036 A1 | 8/2024 | Kim et al. |
| 2024/0263218 A1 | 8/2024 | Katiraee et al. |
| 2024/0271190 A1 | 8/2024 | Stoeckius et al. |
| 2024/0271195 A1 | 8/2024 | Mikhaiel et al. |
| 2024/0279747 A1 | 8/2024 | Williams |
| 2024/0287600 A1 | 8/2024 | Iyer et al. |
| 2024/0294971 A1 | 9/2024 | Galonska |
| 2024/0294974 A1 | 9/2024 | Galonska et al. |
| 2024/0294975 A1 | 9/2024 | Lin et al. |
| 2024/0301488 A1 | 9/2024 | Stoeckius |
| 2024/0301489 A1 | 9/2024 | Chew et al. |
| 2024/0360494 A1 | 10/2024 | Costa et al. |

FOREIGN PATENT DOCUMENTS

| | | |
|---|---|---|
| CN | 1537953 | 10/2004 |
| CN | 1680604 | 10/2005 |
| CN | 1749752 | 3/2006 |
| CN | 1898398 | 1/2007 |
| CN | 101142325 | 3/2008 |
| CN | 101221182 | 7/2008 |
| CN | 101522915 | 9/2009 |
| CN | 107849606 | 3/2018 |
| CN | 108949924 | 12/2018 |
| DE | 102008025656 | 12/2009 |
| EP | 1782737 | 5/2007 |
| EP | 1910562 | 4/2008 |
| EP | 1923471 | 5/2008 |
| EP | 2002017 | 12/2008 |
| EP | 2130913 | 12/2009 |
| EP | 2292788 | 3/2011 |
| EP | 2302070 | 3/2011 |
| EP | 2881465 | 6/2015 |
| EP | 3013984 | 5/2016 |
| EP | 3511423 | 7/2019 |
| EP | 3541956 | 9/2019 |
| GB | 2520765 | 6/2015 |
| JP | 2007-014297 | 1/2007 |
| JP | 2007-074967 | 3/2007 |
| JP | 2009-036694 | 2/2009 |
| WO | WO 1989/010977 | 11/1989 |
| WO | WO 1991/006678 | 5/1991 |
| WO | WO 1993/004199 | 3/1993 |
| WO | WO 1995/023875 | 9/1995 |
| WO | WO 1995/025116 | 9/1995 |
| WO | WO 1995/035505 | 12/1995 |
| WO | WO 1997/031256 | 8/1997 |
| WO | WO 2000/017390 | 3/2000 |
| WO | WO 2000/063437 | 10/2000 |
| WO | WO 2001/006012 | 1/2001 |
| WO | WO 2001/009363 | 2/2001 |
| WO | WO 2001/012862 | 2/2001 |
| WO | WO 2001/042796 | 6/2001 |
| WO | WO 2001/046402 | 6/2001 |
| WO | WO 2001/059161 | 8/2001 |
| WO | WO 2001/090415 | 11/2001 |
| WO | WO 2001/096608 | 12/2001 |
| WO | WO 2002/040874 | 5/2002 |
| WO | WO 2002/059355 | 8/2002 |
| WO | WO 2002/059364 | 8/2002 |
| WO | WO 2002/077283 | 10/2002 |
| WO | WO 2003/002979 | 1/2003 |
| WO | WO 2003/008538 | 1/2003 |
| WO | WO 2003/010176 | 2/2003 |
| WO | WO 2003/102233 | 12/2003 |
| WO | WO 2004/015080 | 2/2004 |
| WO | WO 2004/067759 | 8/2004 |
| WO | WO 2004/081225 | 9/2004 |
| WO | WO 2005/007814 | 1/2005 |
| WO | WO 2005/010145 | 2/2005 |
| WO | WO 2005/026387 | 3/2005 |
| WO | WO 2005/042759 | 5/2005 |
| WO | WO 2005/065814 | 7/2005 |
| WO | WO 2005/113804 | 12/2005 |
| WO | WO 2006/020515 | 2/2006 |
| WO | WO 2006/064199 | 6/2006 |
| WO | WO 2006/124771 | 11/2006 |
| WO | WO 2007/010251 | 1/2007 |
| WO | WO 2007/041689 | 4/2007 |
| WO | WO 2007/060599 | 5/2007 |
| WO | WO 2007/073171 | 6/2007 |
| WO | WO 2007/076726 | 7/2007 |
| WO | WO 2007/139766 | 12/2007 |
| WO | WO 2007/145612 | 12/2007 |
| WO | WO 2008/069906 | 6/2008 |
| WO | WO 2008/075086 | 6/2008 |
| WO | WO 2009/032167 | 3/2009 |
| WO | WO 2009/137521 | 11/2009 |
| WO | WO 2009/152928 | 12/2009 |
| WO | WO 2010/019826 | 2/2010 |
| WO | WO 2010/027870 | 3/2010 |
| WO | WO 2010/088517 | 8/2010 |
| WO | WO 2010/126614 | 11/2010 |
| WO | WO 2010/127186 | 11/2010 |
| WO | WO 2011/008502 | 1/2011 |
| WO | WO 2011/062933 | 5/2011 |
| WO | WO 2011/068088 | 6/2011 |
| WO | WO 2011/094669 | 8/2011 |
| WO | WO 2011/127099 | 10/2011 |
| WO | WO 2012/049316 | 4/2012 |
| WO | WO 2012/061832 | 5/2012 |
| WO | WO 2012/071428 | 5/2012 |
| WO | WO 2012/129242 | 9/2012 |
| WO | WO 2012/140224 | 10/2012 |
| WO | WO 2012/159089 | 11/2012 |
| WO | WO 2013/123442 | 8/2013 |
| WO | WO 2013/131962 | 9/2013 |
| WO | WO 2013/138510 | 9/2013 |
| WO | WO 2013/142389 | 9/2013 |
| WO | WO 2013/150082 | 10/2013 |
| WO | WO 2013/150083 | 10/2013 |
| WO | WO 2014/044724 | 3/2014 |
| WO | WO 2014/060483 | 4/2014 |
| WO | WO 2014/071361 | 5/2014 |
| WO | WO 2014/085725 | 6/2014 |
| WO | WO 2014/130576 | 8/2014 |
| WO | WO 2014/144713 | 9/2014 |
| WO | WO 2014/152397 | 9/2014 |
| WO | WO 2014/163886 | 10/2014 |
| WO | WO 2014/210223 | 12/2014 |
| WO | WO 2014/210225 | 12/2014 |
| WO | WO 2014/210233 | 12/2014 |
| WO | WO 2014/210353 | 12/2014 |
| WO | WO 2015/031691 | 3/2015 |
| WO | WO 2015/069374 | 5/2015 |
| WO | WO 2015/161173 | 10/2015 |
| WO | WO 2016/007839 | 1/2016 |
| WO | WO 2016/057552 | 4/2016 |
| WO | WO 2016/077763 | 5/2016 |
| WO | WO 2016/100196 | 6/2016 |
| WO | WO 2016/138496 | 9/2016 |
| WO | WO 2016/138500 | 9/2016 |
| WO | WO 2016/162309 | 10/2016 |
| WO | WO 2016/166128 | 10/2016 |
| WO | WO 2016/168825 | 10/2016 |
| WO | WO 2016/172362 | 10/2016 |
| WO | WO 2017/019456 | 2/2017 |
| WO | WO 2017/019481 | 2/2017 |
| WO | WO 2017/027367 | 2/2017 |
| WO | WO 2017/027368 | 2/2017 |
| WO | WO 2017/044993 | 3/2017 |
| WO | WO 2017/075293 | 5/2017 |
| WO | WO 2017/096158 | 7/2017 |
| WO | WO 2017/143155 | 8/2017 |
| WO | WO 2017/144338 | 8/2017 |
| WO | WO 2017/147483 | 8/2017 |
| WO | WO 2017/156336 | 9/2017 |
| WO | WO 2017/184984 | 10/2017 |
| WO | WO 2017/192633 | 11/2017 |
| WO | WO 2017/222453 | 12/2017 |
| WO | WO 2018/022809 | 2/2018 |
| WO | WO 2018/023068 | 2/2018 |
| WO | WO 2018/026873 | 2/2018 |
| WO | WO 2018/045181 | 3/2018 |

(56) References Cited

FOREIGN PATENT DOCUMENTS

| | | |
|---|---|---|
| WO | WO 2018/045186 | 3/2018 |
| WO | WO 2018/057999 | 3/2018 |
| WO | WO 2018/064640 | 4/2018 |
| WO | WO 2018/075693 | 4/2018 |
| WO | WO-2018064640 A1 * | 4/2018 |
| WO | WO 2018/085599 | 5/2018 |
| WO | WO 2018/089550 | 5/2018 |
| WO | WO 2018/091676 | 5/2018 |
| WO | WO 2018/107054 | 6/2018 |
| WO | WO 2018115855 * | 6/2018 |
| WO | WO 2018/136397 | 7/2018 |
| WO | WO 2018/136856 | 7/2018 |
| WO | WO 2018/144582 | 8/2018 |
| WO | WO 2018/175779 | 9/2018 |
| WO | WO 2018/209398 | 11/2018 |
| WO | WO 2019/023214 | 1/2019 |
| WO | WO 2019/032760 | 2/2019 |
| WO | WO 2019/068880 | 4/2019 |
| WO | WO 2019/075091 | 4/2019 |
| WO | WO 2019/113457 | 6/2019 |
| WO | WO 2019/113533 | 6/2019 |
| WO | WO 2019/126313 | 6/2019 |
| WO | WO 2019/140201 | 7/2019 |
| WO | WO 2019/165318 | 8/2019 |
| WO | WO 2019/213254 | 11/2019 |
| WO | WO 2019/213294 | 11/2019 |
| WO | WO 2019/241290 | 12/2019 |
| WO | WO 2020/028194 | 2/2020 |
| WO | WO 2020/047002 | 3/2020 |
| WO | WO 2020/047005 | 3/2020 |
| WO | WO 2020/047010 | 3/2020 |
| WO | WO 2020/056381 | 3/2020 |
| WO | WO 2020/076979 | 4/2020 |
| WO | WO 2020/099640 | 5/2020 |
| WO | WO 2020/112604 | 6/2020 |
| WO | WO 2020/117914 | 6/2020 |
| WO | WO 2020/123301 | 6/2020 |
| WO | WO 2020/123305 | 6/2020 |
| WO | WO 2020/123309 | 6/2020 |
| WO | WO 2020/123311 | 6/2020 |
| WO | WO 2020/123316 | 6/2020 |
| WO | WO 2020/123317 | 6/2020 |
| WO | WO 2020/123318 | 6/2020 |
| WO | WO 2020/123319 | 6/2020 |
| WO | WO 2020/123320 | 7/2020 |
| WO | WO 2020/160044 | 8/2020 |
| WO | WO 2020/167862 | 8/2020 |
| WO | WO 2020/176788 | 9/2020 |
| WO | WO 2020/176882 | 9/2020 |
| WO | WO 2020/190509 | 9/2020 |
| WO | WO 2020/198071 | 10/2020 |
| WO | WO 2020/206285 | 10/2020 |
| WO | WO 2020/219901 | 10/2020 |
| WO | WO 2020/240025 | 12/2020 |
| WO | WO 2020/243579 | 12/2020 |
| WO | WO 2020/254519 | 12/2020 |
| WO | WO 2021/041974 | 3/2021 |
| WO | WO 2021/067246 | 4/2021 |
| WO | WO 2021/091611 | 5/2021 |
| WO | WO 2021/092433 | 5/2021 |
| WO | WO 2021/097255 | 5/2021 |
| WO | WO 2021/116715 | 6/2021 |
| WO | WO 2021/119320 | 6/2021 |
| WO | WO 2021/133842 | 7/2021 |
| WO | WO 2021/133849 | 7/2021 |
| WO | WO 2021/142233 | 7/2021 |
| WO | WO 2021/168261 | 8/2021 |
| WO | WO 2021/168278 | 8/2021 |
| WO | WO 2021/207610 | 10/2021 |
| WO | WO 2021/216708 | 10/2021 |
| WO | WO 2021/225900 | 11/2021 |
| WO | WO 2021/236625 | 11/2021 |
| WO | WO 2021/236929 | 11/2021 |
| WO | WO 2021/237056 | 11/2021 |
| WO | WO 2021/237087 | 11/2021 |
| WO | WO 2021/242834 | 12/2021 |
| WO | WO 2021/247543 | 12/2021 |
| WO | WO 2021/247568 | 12/2021 |
| WO | WO 2021/252499 | 12/2021 |
| WO | WO 2021/252576 | 12/2021 |
| WO | WO 2021/252591 | 12/2021 |
| WO | WO 2021/263111 | 12/2021 |
| WO | WO 2022/025965 | 2/2022 |
| WO | WO 2022/060798 | 3/2022 |
| WO | WO 2022/060953 | 3/2022 |
| WO | WO 2022/061150 | 3/2022 |
| WO | WO 2022/087273 | 4/2022 |
| WO | WO 2022/099037 | 5/2022 |
| WO | WO 2022/103712 | 5/2022 |
| WO | WO 2022/109181 | 5/2022 |
| WO | WO 2022/132645 | 6/2022 |
| WO | WO 2022/140028 | 6/2022 |
| WO | WO 2022/147005 | 7/2022 |
| WO | WO 2022/147296 | 7/2022 |
| WO | WO 2022/164615 | 8/2022 |
| WO | WO 2022/178267 | 8/2022 |
| WO | WO 2022/198068 | 9/2022 |
| WO | WO 2022/212269 | 10/2022 |
| WO | WO 2022/221425 | 10/2022 |
| WO | WO 2022/226057 | 10/2022 |
| WO | WO 2022/236054 | 11/2022 |
| WO | WO 2022/243303 | 11/2022 |
| WO | WO 2022/226372 | 12/2022 |
| WO | WO 2022/256503 | 12/2022 |
| WO | WO 2022/271820 | 12/2022 |
| WO | WO 2023/287765 | 1/2023 |
| WO | WO 2023/018799 | 2/2023 |
| WO | WO 2023/034489 | 3/2023 |
| WO | WO 2023/044071 | 3/2023 |
| WO | WO 2023/076345 | 5/2023 |
| WO | WO 2023/086880 | 5/2023 |
| WO | WO 2023/102118 | 6/2023 |
| WO | WO 2023/122033 | 6/2023 |
| WO | WO 2023/150098 | 8/2023 |
| WO | WO 2023/150163 | 8/2023 |
| WO | WO 2023/150171 | 8/2023 |
| WO | WO 2023/215552 | 11/2023 |
| WO | WO 2023/225519 | 11/2023 |
| WO | WO 2023/229988 | 11/2023 |
| WO | WO 2023/250077 | 12/2023 |
| WO | WO 2024/015578 | 1/2024 |
| WO | WO 2024/035844 | 2/2024 |
| WO | WO 2024/081212 | 4/2024 |
| WO | WO 2024/086167 | 4/2024 |
| WO | WO 2024/086776 | 4/2024 |
| WO | WO 2024/102809 | 5/2024 |
| WO | WO 2024/137826 | 6/2024 |
| WO | WO 2024/145224 | 7/2024 |
| WO | WO 2024/145441 | 7/2024 |
| WO | WO 2024/145445 | 7/2024 |
| WO | WO 2024/145491 | 7/2024 |
| WO | WO 2024/206603 | 10/2024 |
| WO | WO 2024/220882 | 10/2024 |

OTHER PUBLICATIONS

Belton et al., "Hi-C: A comprehensive technique to capture the conformation of genomes," Methods, Nov. 2012, 58(3):268-276, 16 pages.

Bentzen et al., "Large-scale detection of antigen-specific T cells using peptide-MHC-I multimers labeled with DNA barcodes," Nat Biotechnol., Oct. 2016, 34(10):1037-1045, 12 pages.

Fan et al., "Illumina Universal Bead Arrays," Methods in Enzymology, 2006, 410:57-73.

Hadrup et al., "Parallel detection of antigen-specific T-cell responses by multidimensional encoding of MHC multimers," Nat. Methods., Jul. 2009, 6(7), 520-526.

Hobro et al., "An evaluation of fixation methods: Spatial and compositional cellular changes observed by Raman imaging," Vibrational Spectroscopy, Jul. 2017, 91:31-45.

Landegren et al., "A Ligase-Mediated Gene Detection Technique," Science, 1988, 241(4869):1077-1080.

(56) References Cited

OTHER PUBLICATIONS

Mamedov et al., "Preparing unbiased T-cell receptor and antibody cDNA libraries for the deep next generation sequencing profiling," Frontiers in Immunol., Dec. 23, 2013, 4(456):1-10.
Oksuz et al., "Systematic evaluation of chromosome conformation capture assays," Nature Methods, Sep. 2021, 18:1046-1055.
Rohland et al., "Partial uracil-DNA-glycosylase treatment for screening of ancient DNA," Phil. Trans. R. Soc. B, Jan. 19, 2015, 370(1660): 20130624, 11 pages.
Schmidl et al., "ChIPmentation: fast, robust, low-input ChIP-seq for histones and transcription factors," Nature Methods, Oct. 2015, 12:963-965.
Su et al., "Restriction enzyme selection dictates detection range sensitivity in chromatin conformation capture-based variant-to-gene mapping approaches," bioRxiv, Dec. 15, 2020, 22 pages.
U.S. Appl. No. 16/353,937, filed Mar. 14, 2019, Frisen et al.
U.S. Appl. No. 16/876,709, filed May 18, 2020, Schnall-Levin et al.
U.S. Appl. No. 17/707,189, filed Mar. 29, 2022, Chell et al.
U.S. Appl. No. 60/416,118, filed Oct. 3, 2002, Fan et al.
U.S. Appl. No. 61/267,363, filed Dec. 7, 2009, Fan et al.
[No Author Listed], "Chromium Next GEM Single Cell 3' Reagent Kits v3.1—User Guide," 10x Genomics, Document No. CG000204, Nov. 2019, 58 pages.
[No Author Listed], "Chromium Next GEM Single Cell 3' Reagent Kits v3.1 (Dual Index)—User Guide," 10x Genomics, Mar. 2021, Document No. CG000315, 61 pages.
[No Author Listed], "HuSNP Mapping Assay User's Manual," Affymetrix Part No. 90094 (Affymetrix, Santa Clara, Calif.), GeneChip, 2000, 104 pages.
[No Author Listed], "Microarray technologies have excellent possibilities in genomics-related researches," Science Tools From Amersham Pharmacia Biotech, 1998, 3(4): 8 pages (with English Translation).
[No Author Listed], "Proseek® Multiplex 96×96 User Manual," Olink Proteomics, Olink Bioscience, Uppsala, Sweden, 2017, 20 pages.
10xGenomics.com, [online], "Visium Spatial Gene Expression Reagent Kits—Tissue Optimization—User Guide," Jul. 2020, retrieved on May 25, 2021, retrieved from URL<https://assets.ctfassets.net/an68im79xiti/5UJrN0CH17rEk0UXwd19It/e54d99fb08a8f1500aba503005a04a56/CG000238_VisiumSpatialTissueOptimizationUserGuide_RevD.pdf>, 42 pages.
10xGenomics.com, [online], "Visium Spatial Gene Expression Reagent Kits—Tissue Optimization," Nov. 2019, retrieved on Jan. 25, 2022, retrieved from URL<https://assets.ctfassets.net/an68im79xiti/4q03w6959AJFxffSw51ee9/6a2ac61cf6388a72564eeb96bc294967/CG000238_VisiumSpatialTissueOptimizationUserGuide_Rev_A.pdf>, 46 pages.
10xGenomics.com, [online], "Visium Spatial Gene Expression Reagent Kits—Tissue Optimization," Oct. 2020, retrieved on Dec. 28, 2021, retrieved from URL<https://assets.ctfassets.net/an68im79xiti/5UJrN0CH17rEk0UXwd19It/e54d99fb08a8f1500aba503005a04a56/CG000238_VisiumSpatialTissueOptimizationUserGuide_RevD.pdf>, 43 pages.
10xGenomics.com, [online], "Visium Spatial Gene Expression Reagent Kits—User Guide," Jun. 2020, retrieved on May 25, 2021, retrieved from URL<https://assets.ctfassets.net/an68im79xiti/3GGIfH3RWpd1bFVha1pexR/8baa08d9007157592b65b2cdc7130990/CG000239_VisiumSpatialGeneExpression_UserGuide_RevD.pdf>, 69 pages.
10xGenomics.com, [online], "Visium Spatial Gene Expression Reagent Kits—User Guide," Oct. 2020, retrieved on Dec. 28, 2021, retrieved from URL<https://assets.ctfassets.net/an68im79xiti/3GGIfH3RWpd1bFVha1pexR/8baa08d9007157592b65b2cdc7130990/CG000239_VisiumSpatialGeneExpression_UserGuide_RevD.pdf>, 70 pages.
Abaan et al., "The exomes of the NCI-60 panel: a genomic resource for cancer biology and systems pharmacology," Cancer Res., Jul. 2013, 73(14):4372-82.
Adessi et al., "Solid phase DNA amplification: characterisation of primer attachment and amplification mechanisms," Nucl. Acids Res., 2000, 28(20):E87, 8 pages.
Adiconis et al., "Comparative analysis of RNA sequencing methods for degraded or low-input samples," Nat Methods, Jul. 2013, 10(7):623-9.
Affymetrix, "GeneChip Human Genome U133 Set," retrieved from the Internet: on the World Wide Web at affymetrix.com/support/technical/datasheets/hgu133_datasheet.pdf, retrieved on Feb. 26, 2003, 2 pages.
Affymetrix, "Human Genome U95Av2," Internet Citation, retrieved from the internet: on the World Wide Web affymetrix.com, retrieved on Oct. 2, 2002, 1 page.
Ahern, "Biochemical, Reagents Kits Offer Scientists Good Return on Investment," The Scientist, Jul. 1995, 9(15):20, 7 pages.
Alam, "Proximity Ligation Assay (PLA)," Curr Protoc Immunol., Nov. 2018, 123(1):e58, 8 pages.
Albretsen et al., "Applications of magnetic beads with covalently attached oligonucleotides in hybridization: Isolation and detection of specific measles virus mRNA from a crude cell lysate," Anal. Biochem., 1990, 189(1):40-50.
Allawi et al., "Thermodynamics and NMR of Internal GâT Mismatches in DNA," Biochemistry, 1996, 36(34):10581-10594.
Amidzadeh et al., "Assessment of different permeabilization methods of minimizing damage to the adherent cells for detection of intracellular RNA by flow cytometry," Avicenna J Med Biotechnol., Jan. 2014, 6(1):38-46.
Andresen et al., "Helicase-dependent amplification: use in OnChip amplification and potential for point-of-care diagnostics," Expert Rev Mol Diagn., Oct. 2009, 9(7):645-650.
Appella, "Non-natural nucleic acids for synthetic biology," Current Opinion in Chemical Biology, Dec. 2009, 13(5-6): 687-696.
Aran et al., "xCell: digitally portraying the tissue cellular heterogeneity landscape," Genome Biol., Nov. 2017, 18(1):220, 14 pages.
Archer et al., "Selective and flexible depletion of problematic sequences from RNA-seq libraries at the cDNA stage," BMC Genomics, May 2014, 15(1):401, 9 pages.
Armani et al, "2D-PCR: a method of mapping DNA in tissue sections," Lab Chip, 2009, 9(24):3526-34.
Arslan et al., "Engineering of a superhelicase through conformational control (Supplementary Materials)," Science, Apr. 17, 2015, 348(6232):344-347, 18 pages.
Arslan et al., "Engineering of a superhelicase through conformational control," Science, Apr. 17, 2015, 348(6232):344-347.
Asp et al., "Spatially Resolved Transcriptomes—Next Generation Tools for Tissue Exploration," Bioessays, Oct. 2020, 42(10):e1900221, 16 pages.
Atkinson et al., "An Updated Protocol for High Throughput Plant Tissue Sectioning," Front Plant Sci, 2017, 8:1721, 8 pages.
Atkinson, "Overview of Translation: Lecture Manuscript," U of Texas, 2000, DD, pp. 6.1-6.8.
Bains et al., "A novel method for nucleic acid sequence determination," Journal of Theoretical Biology, 1988, 135(3), 303-7.
Balakrishnan et al., "Flap endonuclease 1," Annu Rev Biochem., Jun. 2013, 82:119-138.
Baner et al., "Signal amplification of padlock probes by rolling circle replication," Nucleic Acids Res., 1998, 26(22):5073-5078.
Barnes, "PCR amplification of up to 35-kb DNA with high fidelity and high yield from lambda bacteriophage templates," Proc. Natl. Acad. Sci USA, 1994, 91(6):2216-2220.
Barnett et al., "ATAC-Me Captures Prolonged DNA Methylation of Dynamic Chromatin Accessibility Loci during Cell Fate Transitions," Mol Cell., Mar. 2020, 77(6):1350-1364.e6.
Bartosovic et al., "Single-cell CUT&Tag profiles histone modifications and transcription factors in complex tissues," Nat Biotechnol., Jul. 2021, 39(7):825-835, Abstract.
Baugh et al., "Quantitative analysis of mRNA amplification by in vitro transcription," Nucleic Acids Res., 2001, 29(5):e29, 9 pages.
Beattie et al., "Advances in genosensor research," Clin Chem., May 1995, 41(5):700-6.
Bechara et al., "Cell-penetrating peptides: 20 years later, where do we stand?," FEBS Lett., Jun. 2013, 587(12):1693-702.

(56) References Cited

OTHER PUBLICATIONS

Beechem et al., "High-Plex Spatially Resolved RNA and Protein Detection Using Digital Spatial Profiling: A Technology Designed for Immuno-oncology Biomarker Discovery and Translational Research," Methods Mol Biol, 2020, Chapter 25, 2055:563-583.
Beier et al., "Versatile derivatisation of solid support media for covalent bonding on DNA-microchips," Nucleic Acids Res., May 1999, 27(9):1970-7.
Bell, "A simple way to treat PCR products prior to sequencing using ExoSAP-IT," Biotechniques, 2008, 44(6):834, 1 page.
Bentley et al., "Accurate whole human genome sequencing using reversible terminator chemistry," Nature, 2008, 456(7218):53-59.
Bergenstråhle et al., "Seamless integration of image and molecular analysis for spatial transcriptomics workflows," BMC Genomics, Jul. 2020, 21(1):482, 7 pages.
Berger et al., "Universal bases for hybridization, replication and chain termination," Nucleic Acid Res., Aug. 2000, 28(15):2911-2914.
Bibikova et al., "Quantitative gene expression profiling in formalin-fixed paraffin-embedded tissues using universal bead arrays," The American Journal of Pathology, Nov. 1, 2004, 165(5):1799-1807.
Birney et al., "Identification and analysis of functional elements in 1% of the human genome by the ENCODE pilot project," Nature, 2007, 447(7146):799-816.
Blair et al., "Microarray temperature optimization using hybridization kinetics," Methods Mol Biol., 2009, 529:171-96.
Blanchard et al., "High-density oligonucleotide arrays," Biosensors & Bioelectronics, 1996, 11(6-7):687-690.
Blanco et al., "A practical approach to FRET-based PNA fluorescence in situ hybridization," Methods, Dec. 2010, 52(4):343-51.
Blokzijl et al., "Profiling protein expression and interactions: proximity ligation as a tool for personalized medicine," J Intern. Med., 2010, 268(3):232-245.
Blow, "Tissue Issues," Nature, 2007, 448(7156):959-962.
Boeke et al., "Transcription and reverse transcription of retrotransposons," Annu Rev Microbiol, 1989, 43:403-34.
Bolognesi et al., "Multiplex Staining by Sequential Immunostaining and Antibody Removal on Routine Tissue Sections," J. Histochem. Cytochem., Aug. 2017, 65(8):431-444.
Bolotin et al., "MiXCR: software for comprehensive adaptive immunity profiling," Nat Methods., May 2015, 12(5):380-1.
Borm et al., "High throughput human embryo spatial transcriptome mapping by surface transfer of tissue RNA," Abstracts Selected Talks, Single Cell Genomics mtg, (SCG2019), 2019, 1 pages (Abstract Only).
Boulé et al., "Terminal deoxynucleotidyl transferase indiscriminately incorporates ribonucleotides and deoxyribonucleotides," J Biol Chem., Aug. 2001, 276(33):31388-93.
Brandon et al., "Mitochondrial mutations in cancer," Oncogene, 2006, 25(34):4647-4662.
Brenner et al., "Gene expression analysis by massively parallel signature sequencing (MPSS) on microbead arrays," Nat. Biotech., 2000, 18(6):630-634.
Brenner et al., "In vitro cloning of complex mixtures of DNA on microbeads: physical separation of differentially expressed cDNAs," Proc. Natl. Acad. Sci. USA, 2000, 97(4):1665-1670.
Brow, "35—The Cleavase I enzyme for mutation and polymorphism scanning," PCR Applications Protocols for Functional Genomics, 1999, pp. 537-550.
Brown et al., "Retroviral integration: structure of the initial covalent product and its precursor, and a role for the viral IN protein," Proc Natl Acad Sci USA, Apr. 1989, 86(8):2525-9.
Buenrostro et al., "Transposition of native chromatin for multimodal regulatory analysis and personal epigenomics," Nat Methods, Dec. 2013, 10(12):1213-1218.
Bullard et al., "Direct comparison of nick-joining activity of the nucleic acid ligases from bacteriophage T4," Biochem. J. 2006, 398(1):135-144.
Bunt et al., "FRET from single to multiplexed signaling events," Biophys Rev. Apr. 2017, 9(2): 119-129.
Burgess, "A space for transcriptomics," Nature Reviews Genetics, 2016, 17(8):436-7.
Burgess, "Finding structure in gene expression," Nature Reviews Genetics, 2018, 19(5):249, 1 page.
Burgess, "Spatial transcriptomics coming of age," Nat Rev Genet., Jun. 2019, 20(6):317, 1 page.
Burton et al., "Coverslip Mounted-Immersion Cycled in Situ RT-PCR for the Localization of mRNA in Tissue Sections," Biotechniques, 1998, 24(1):92-100.
Caliari et al., "A practical guide to hydrogels for cell culture," Nat Methods., Apr. 2016, 13(5):405-14.
Carter et al., "Stabilization of an optical microscope to 0.1 nm in three dimensions," Applied Optics, 2007, 46:421-427.
Cdc.gov [online], "New COVID-19 Variants," Jan. 15, 2021, retrieved on Jan. 21, 2021, retrieved from URL<https://www.cdc.gov/coronavirus/2019-ncov/transmission/variant.html>, 3 pages.
Cha et al., "Specificity, efficiency, and fidelity of PCR," Genome Res., 1993, 3(3):S18-29.
Chandra et al., "Cell-free synthesis-based protein microarrays and their applications," Proteomics, 2009, 5(6):717-30.
Chatterjee et al., "Mitochondrial DNA mutations in human cancer. Oncogene," 2006, 25(34):4663-4674.
Chen et al. "Arrayed profiling of multiple glycans on whole living cell surfaces." Analytical chemistry, Oct. 15, 2013, 85(22):11153-11158.
Chen et al., "ATAC-see reveals the accessible genome by transposase-mediated imaging and sequencing," Nature Methods, Dec. 2016, 13(12):1013-1020.
Chen et al., "DNA hybridization detection in a microfluidic Channel using two fluorescently labelled nucleic acid probes," Biosensors and Bioelectronics, 2008, 23(12):1878-1882.
Chen et al., "Efficient in situ barcode sequencing using padlock probe-based BaristaSeq," Nucleic Acids Res., 2018, 46(4): e22, 11 pages.
Chen et al., "Expansion microscopy," Science, 2015, 347(6221):543-548.
Chen et al., "Large field of view-spatially resolved transcriptomics at nanoscale resolution," bioRxiv, Jan. 19, 2021, retrieved from URL <https://www.biorxiv.org/node/1751045.abstract>, 37 pages.
Chen et al., "Nanoscale imaging of RNA with expansion microscopy," Nat Methods, Aug. 2016, 13(8):679-84.
Chen et al., "Parallel single nucleotide polymorphism genotyping by surface invasive cleavage with universal detection," Anal Chem., Apr. 2005, 77(8):2400-5.
Chen et al., "RNA imaging. Spatially resolved, highly multiplexed RNA profiling in single cells," Science, Apr. 2015, 348(6233):aaa6090, 21 pages.
Chen et al., "Spatial Transcriptomics and In Situ Sequencing to Study Alzheimer's Disease," Cell, Aug. 2020, 182(4):976-991.
Chen et al., "Spatially resolved, highly multiplexed RNA profiling in single cells," Science, 2015, 348(6233):aaa6090, 21 pages.
Chen et al., "μCB-seq: microfluidic cell barcoding and sequencing for high-resolution imaging and sequencing of single cells," Lab Chip, Nov. 2020, 20(21):3899-3913.
Chester et al., "Dimethyl sulfoxide-mediated primer Tm reduction: a method for analyzing the role of renaturation temperature in the polymerase chain reaction," Anal Biochem, Mar. 1993, 209(2):284-90.
Cheung et al., "Chitosan: An Update on Potential Biomedical and Pharmaceutical Applications," Mar Drugs, Aug. 2015, 13(8):5156-86.
Chial, "DNA Sequencing Technologies Key to the Human Genome Project," Nature Education, 2008, 1(1):219, 7 pages.
Choi et al., "Multiplexed detection of mRNA using porosity-tuned hydrogel microparticles," Analytical chemistry, Sep. 28, 2012, 84(21):9370-9378.
Chrisey et al., "Covalent attachment of synthetic DNA to self-assembled monolayer films," Nucleic Acids Res., Aug. 1996, 24(15):3031-9.
Ciaccio et al., "Systems analysis of EGF receptor signaling dynamics with microwestern arrays," Nat Methods, Feb. 2010, 7(2):148-55.

(56) References Cited

OTHER PUBLICATIONS

Cockroft et al., "A single-molecule nanopore device detects DNA polymerase activity with single-nucleotide resolution," J Am Chem Soc., Jan. 2008, 130(3):818-20.
Codeluppi et al., "Spatial organization of the somatosensory cortex revealed by osmFISH," Nature Methods, Nov. 2018, 15:932-935.
Colegio et al., "In vitro transposition system for efficient generation of random mutants of Campylobacter jejuni," J Bacteriol., Apr. 2001, 183(7):2384-8.
Constantine et al., "Use of genechip high-density oligonucleotide arrays for gene expression monitoring," Life Science News, Amersham Life Science, 1998, pp. 11-14.
Corces et al., "An improved ATAC-seq protocol reduces background and enables interrogation of frozen tissues," Nat. Methods, 2017, 14(10):959-962.
Corces et al., "Lineage-specific and single-cell chromatin accessibility charts human hematopoiesis and leukemia evolution," Nature Genetics, Oct. 2016, 48(10):1193-1203.
Craig, "Transposon Tn7" Curr Top Microbiol Immunol., 1996, 204:27-48.
Craig, "V(D)J recombination and transposition: closer than expected," Science, Mar. 1996, 271(5255):1512, 1 page.
Credle et al., "Multiplexed analysis of fixed tissue RNA using Ligation in situ Hybridization," Nucleic Acids Research, 2017, 45(14):e128, 9 pages.
Crosetto et al., "Spatially resolved transcriptomics and beyond," Nature Review Genetics, 2015, 16(1):57-66.
Cruz et al., "Methylation in cell-free DNA for early cancer detection," Ann Oncol., Jun. 2018, 29(6):1351-1353.
Cujec et al., "Selection of v-Abl tyrosine kinase substrate sequences from randomized peptide and cellular proteomic libraries using mRNA display," Chemistry and Biology, 2002, 9(2):253-264.
Czarnik, "Encoding methods for combinatorial chemistry," Curr Opin Chem Biol., Jun. 1997, 1(1):60- 6.
Dahl et al., "Circle-to-circle amplification for precise and sensitive DNA analysis," Proc. Natl. Acad. Sci., 2004, 101(13):4548-4553.
Dalma-Weiszhausz et al., "The affymetrix GeneChip platform: an overview," Methods Enzymol., 2006, 410:3-28.
Darmanis et al., "ProteinSeq: High-Performance Proteomic Analyses by Proximity, Ligation and Next Generation Sequencing," PLos One, 2011, 6(9):e25583, 10 pages.
Darnell, Jr., "Reflections on the history of pre-mRNA processing and highlights of current knowledge: A unified picture," RNA, Feb. 2013, 19:443-460, 19 pages.
Daubendiek et al., "Rolling-Circle RNA Synthesis: Circular Oligonucleotides as Efficient Substrates for T7 RNA Polymerase," J. Am. Chem. Soc., 1995, 117(29):7818-7819.
Davies et al., "How best to identify chromosomal interactions: a comparison of approaches," Nat. Methods, 2017, 14(2):125-134.
Deamer et al., "Characterization of nucleic acids by Nanopore analysis," Acc Chem Res., Oct. 2002, 35(10):817-25.
Deamer et al., "Nanopores and nucleic acids: prospects for ultrarapid sequencing," Trends Biotechnol., Apr. 2000, 18(4):147-51.
Dean et al., "Comprehensive human genome amplification using multiple displacement amplification," Proc Natl. Acad. Sci. USA, 2002, 99(8):5261-66.
Dean et al., "Rapid Amplification of Plasmid and Phage DNA Using Phi29 DNA Polymerase and Multiply-Primed Rolling Circle Amplification," Genome Research, Jun. 2001, 11:1095-1099.
Devine et al., "Efficient integration of artificial transposons into plasmid targets in vitro: a useful tool for DNA mapping, sequencing and genetic analysis," Nucleic Acids Res., Sep. 1994, 22(18):3765-72.
Dressman et al., "Transforming single DNA molecules into fluorescent magnetic particles for detection and enumeration of genetic variations," Proc. Natl. Acad. Sci. USA, 2003, 100(15):8817-8822.
Drmanac et al., "CoolMPS™: Advanced massively parallel sequencing using antibodies specific to each natural nucleobase," BioRxiv, 2020, 19 pages.
Druley et al., "Quantification of rare allelic variants from pooled genomic DNA," Nat. Methods, 2009, 6(4):263-65.
Dtp.cancer.gov, [online], "A Catalog of in Vitro Cell Lines, Transplantable Animal and Human Tumors and Yeast," The Division of Cancer Treatment and Diagnosis (DCTD), National Cancer Institute, May 5, 2020, retrieved on Jun. 7, 2021, retrieved from URL<https://dtp.cancer.gov/organization/btb/docs/DCTDTumor-RepositoryCatalog.pdf>, 77 pages.
Duncan et al., "Affinity chromatography of a sequence-specific DNA binding protein using Teflon-linked oligonucleotides," Anal. Biochem., 1988, 169(1):104-108.
Eagen, "Principles of Chromosome Architecture Revealed by Hi-C," Trends in Biochemical Sciences, Jun. 2018, 43(6):469-478.
Eberwine, "Amplification of mRNA populations using aRNA generated from immobilized oligo(dT)-T7 primed cDNA," BioTechniques, 1996, 20(4):584-91.
Echeverria et al., "Functional Stimuli-Responsive Gels: Hydrogels and Microgels," Gels., Jun. 2018, 4(2):54, 37 pages.
Eguiluz et al., "Multitissue array review: a chronological description of tissue array techniques, applications and procedures," Pathology Research and Practice, 2006, 202(8):561-568.
Eldridge et al., "An in vitro selection strategy for conferring protease resistance to ligand binding peptides," Protein Eng Des Sel., 2009, 22(11):691-698.
Ellington et al., "Antibody-based protein multiplex platforms: technical and operational challenges," Clin Chem, 2010, 56(2):186-193.
Eng et al., "Profiling the transcriptome with RNA SPOTs," Nat Methods., 2017, 14(12):1153-1155.
Eng et al., "Transcriptome-scale super-resolved imaging in tissues by RNA seqFISH+," Nature, Apr. 2019, 568(7751):235-239, 37 pages.
Ergin et al., "Proteomic Analysis of PAXgene-Fixed Tissues," J Proteome Res., 2010, 9(10):5188-96.
Evers et al., "The effect of formaldehyde fixation on RNA: optimization of formaldehyde adduct removal," J Mol Diagn., May 2011, 13(3):282-8.
Fahy et al., "Design and synthesis of polyacrylamide-based oligonucleotide supports for use in nucleic acid diagnostics," Nucleic Acids Res., Apr. 1993, 21(8):1819-26.
Fan et al., "A versatile assay for high-throughput gene expression profiling on universal array matrices," Genome Research, May 1, 2004, 14(5):878-885.
Fang et al., "Fluoride-cleavable biotinylation phosphoramidite for 5'-end-labeling and affinity purification of synthetic oligonucleotides," Nucleic Acids Res., Jan. 2003, 31(2):708-715.
Faruqi et al., "High-throughput genotyping of single nucleotide polymorphisms with rolling circle amplification," BMC Genomics, Aug. 2001, 2:4, 10 pages.
Fire et al., "Rolling replication of short DNA circles," Proc. Natl. Acad. Sci., 1995, 92(10):4641-4645.
Flanigon et al., "Multiplex protein detection with DNA readout via mass spectrometry," N. Biotechnol., 2013, 30(2):153-158.
FLUIDIGM, "Equivalence of Imaging Mass Cytometry and Immunofluorescence on FFPE Tissue Sections," White Paper, 2017, 12 pages.
Fodor et al., "Light-directed, spatially addressable parallel chemical synthesis," Science, 1995, 251(4995):767-773.
Forcucci et al., "All-plastic miniature fluorescence microscope for point-of-care readout of bead-based bioassays.," J. Biomed Opt., 2015, 20(10):105010, 15 pages.
Forster et al., "A human gut bacterial genome and culture collection for improved metagenomic analyses," Nature Biotechnology, 2019, 37(2):186-192.
Frese et al., "Formylglycine aldehyde Tag—protein engineering through a novel post-translational modification," ChemBioChem., 2009, 10(3):425-27.
Fu et al., "Continuous Polony Gels for Tissue Mapping with High Resolution and RNA Capture Efficiency," bioRxiv, 2021, 20 pages.
Fu et al., "Counting individual DNA molecules by the stochastic attachment of diverse labels," PNAS, 2011, 108(22):9026-9031.
Fu et al., "Repeat subtraction-mediated sequence capture from a complex genome," Plant J., Jun. 2010, 62(5):898-909.

(56) References Cited

OTHER PUBLICATIONS

Fullwood et al., "Next-generation DNA sequencing of paired-end tags (PET) for transcriptome and genome analyses," Genome Res., 2009, 19(4):521-532.
Gabbatiss et al. "New form of DNA discovered inside living human cells", The Independent, 2018, pp. 1-3.
Ganguli et al., "Pixelated spatial gene expression analysis from tissue," Nat Commun., Jan. 2018, 9(1):202, 9 pages.
Gans et al., "Inkjet Printing of Polymers: State of the Art and Future Developments," Advanced Materials, Feb. 2004, 16(3):203-213.
Gansauge et al., "Single-stranded DNA library preparation from highly degraded DNA using T4 DNA ligase," Nucleic Acids Res., Jun. 2017, 45(10):e79, 10 pages.
Gao et al., "Q&A: Expansion microscopy," BMC Biology, 15:50, 9 pages, 2017.
Gene@arrays[online], BeadArray Technology, available on or before Feb. 14, 2015, via Internet Archive: Wayback Machine URL <https://web.archive.org/web/20150214084616/http://genearrays.com/services/microarrays/illumina/beadarray-technology/>, [retrieved on Jan. 30, 2020], 3 pages.
Gerard et al., "Excess dNTPs minimize RNA hydrolysis during reverse transcription," Biotechniques, Nov. 2002, 33(5):984, 986, 988, 990.
Gilar et al., "Study of phosphorothioate-modified oligonucleotide resistance to 3'-exonuclease using capillary electrophoresis," J Chromatogr B Biomed Sci Appl., Aug. 28, 1998, 714(1):13-20.
Gill et al., "Nucleic acid isothermal amplification technologies: a review," Nucleosides Nucleotides Nucleic Acids, Mar. 2008, 27(3):224-43.
Gilles et al., "Single nucleotide polymorphic discrimination by an electronic dot blot assay on semiconductor microchips," Nat Biotechnol, Apr. 1999, 17(4):365-70.
Glass et al., "SIMPLE: a sequential immunoperoxidase labeling and erasing method," J. Histochem. Cytochem., Oct. 2009, 57(10):899-905.
Gloor, "Gene targeting in *Drosophila*," Methods Mol Biol., 2004, 260:97-114.
Gnanapragasam, "Unlocking the molecular archive: the emerging use of formalin-fixed paraffin-embedded tissue for biomarker research in urological cancer," BJU International, 2009, 105(2):274-278.
Goldkorn et al., "A simple and efficient enzymatic method for covalent attachment of DNA to cellulose. Application for hybridization-restriction analysis and for in vitro synthesis of DNA probes," Nucleic Acids Res., 1986, 14(22):9171-9191.
Goldmeyer et al., "Development of a novel one-tube isothermal reverse transcription thermophilic helicase-dependent amplification platform for rapid RNA detection," Journal of Molecular Diagnostics, American Society for Investigative Pathology and the Association for Molecular Pathology, Nov. 1, 2007, 9(5):639-644.
Goransson et al., "A single molecule array for digital targeted molecular analyses," Nucleic Acids Res., Nov. 25, 2009, 37(1):e7, 9 pages.
Goryshin et al., "Tn5 in vitro transposition," J Biol Chem., Mar. 1998, 273(13):7367-74.
Gracia Villacampa et al., "Genome-wide Spatial Expression Profiling in FFPE Tissues," bioRxiv, 2020, pp. 38 pages.
Grokhovsky, "Specificity of DNA cleavage by ultrasound," Molecular Biology, 2006, 40(2):276-283.
Grünweller et al., "Locked Nucleic Acid Oligonucleotides," BioDrugs, Jul. 2007, 21(4): 235-243.
Gu et al., "Multiplex single-molecule interaction profiling of DNA-barcoded proteins," Nature, Sep. 21, 2014, 515:554-557.
Gu et al., "Protein tag-mediated conjugation of oligonucleotides to recombinant affinity binders for proximity ligation," N Biotechnol., 2013, 30(2):144-152.
Gunderson et al., "Decoding randomly ordered DNA arrays," Genome Research, 2004, 14(5):870-877.
Guo et al., "Direct fluorescence analysis of genetic polymorphisms by hybridization with oligonucleotide arrays on glass supports," Nucleic Acids Res., Dec. 1994, 22(24):5456-65.
Gupta et al., "Single-cell isoform RNA sequencing characterizes isoforms in thousands of cerebellar cells," Nature Biotechnol., Oct. 2018, 36:1197-1202.
Hafner et al., "Identification of microRNAs and other small regulatory RNAs using cDNA library sequencing," Methods, Jan. 2008, 44(1):3-12.
Hahnke et al., "Striptease on glass: validation of an improved stripping procedure for in situ microarrays," J Biotechnol., Jan. 2007, 128(1):1-13.
Hamaguchi et al., "Direct reverse transcription-PCR on oligo(dT)-immobilized polypropylene microplates after capturing total mRNA from crude cell lysates," Clin Chem., Nov. 1998, 44(11):2256-63.
Hanauer et al., "Separation of nanoparticles by gel electrophoresis according to size and shape," Nano Lett., Sep. 2007, 7(9):2881-5.
Hardenbol et al., "Highly multiplexed molecular inversion probe genotyping: over 10,000 targeted SNPs genotyped in a single tube assay," Genome Res., Feb. 2005, 15(2):269-75.
Hardenbol et al., "Multiplexed genotyping with sequence-tagged molecular inversion probes," Nature Biotechnol., Jun. 2003, 21(6):673-678.
Hattersley et al., "Development of a microfluidic device for the maintenance and interrogation of viable tissue biopsies," Lab Chip., Nov. 2008, 8(11):1842-6.
Hayes et al., "Electrophoresis of proteins and nucleic acids: I—Theory," BMJ, Sep. 1989, 299(6703):843-6.
He et al., "In situ synthesis of protein arrays," Current Opinion in Biotechnology, 2008, 19(1):4-9.
He et al., "Printing protein arrays from DNA arrays," Nature Methods, 2008, 5(2):175-77.
He, "Cell-free protein synthesis: applications in proteomics and biotechnology," New Biotechnology, 2008, 25(2-3):126-132.
Healy, "Nanopore-based single-molecule DNA analysis," Nanomedicine (Lond), Aug. 2007, 2(4):459-81.
Hein et al., "Click Chemistry, A Powerful Tool for Pharmaceutical Sciences," Pharm Res, 2008, 25(10): 2216-2230.
Hejatko et al., "In situ hybridization technique for mRNA detection in whole mount *Arabidopsis* samples," Nature Protocols, 2006, 1(4):1939-1946.
Hessner et al., "Genotyping of factor V G1691A (Leiden) without the use of PCR by invasive cleavage of oligonucleotide probes," Clin Chem., Aug. 2000, 46(8 Pt 1):1051-6.
Hiatt et al., "Parallel, tag-directed assembly of locally derived short sequence reads," Nature Methods, 2010, 7(2):119-25.
Ho et al., "Bacteriophage T4 RNA ligase 2 (gp24.1) exemplifies a family of RNA ligases found in all phylogenetic domains," PNAS, Oct. 2002, 99(20):12709-14.
Ho et al., "Characterization of an ATP-Dependent DNA Ligase Encoded by Chlorella Virus PBCV-1," Journal of Virology, Mar. 1997, 71(3):1931-1937.
Hoffman et al., "Formaldehyde crosslinking: a tool for the study of chromatin complexes," J Biol Chem., Oct. 2015, 290(44):26404-11.
Holmstrøm et al., "A highly sensitive and fast nonradioactive method for detection of polymerase chain reaction products," Anal Biochem, Mar. 1993, 209(2):278-83.
Hoyer et al., "Electrostatic spraying: a novel technique for preparation of polymer coatings on electrodes," Anal Chem, Nov. 1996, 68(21):3840-4.
Hsuih et al., "Novel, Ligation-Dependent PCR Assay for Detection of Hepatitis C Virus in Serum," Journal of Clinical Microbiology, Mar. 1996, 34(3):501-507.
Hu et al., "High reproducibility using sodium hydroxide-stripped long oligonucleotide DNA microarrays," Biotechniques, Jan. 2005, 38(1):121-4.
Hughes et al., "Microfluidic Western blotting," PNAS, Dec. 2012, 109(52):21450-21455.
Hycultbiotech.com, [online], "Immunohistochemistry, Paraffin" Apr. 2010, retrieved on Apr. 16, 2020, retrieved from URL<https://www.hycultbiotech.com/media/wysiwyg/Protocol_Immunohistochemistry_Paraffin_2.pdf>, 3 pages.
Ichikawa et al., "In vitro transposition of transposon Tn3," J Biol. Chem., Nov. 1990, 265(31):18829-32, Abstract.
Illumina.com [online], "Ribo-Zero® rRNA Removal Kit Reference Guide," Aug. 2016, retrieved on Apr. 26, 2022, retrieved from

(56) References Cited

OTHER PUBLICATIONS

URL<https://jp.support.illumina.com/content/dam/illumina-support/documents/documentation/chemistry_documentation/ribosomal-depletion/ribo-zero/ribo-zero-reference-guide-15066012-02.pdf>, 36 pages.
Im et al., "An Introduction to Performing Immunofluorescence Staining," Biobanking: Methods and Protocols, Method in Molecular Biology, Yong (ed.), 2019, 1897, Chapter 26, 299-311.
Jamur et al., "Permeabilization of cell membranes.," Method Mol. Biol., 2010, 588:63-66.
Jemt et al., "An automated approach to prepare tissue-derived spatially barcoded RNA-sequencing libraries," Scientific Reports, 2016, 6:37137, 10 pages.
Jensen et al., "Zinc fixation preserves flow cytometry scatter and fluorescence parameters and allows simultaneous analysis of DNA content and synthesis, and intracellular and surface epitopes," Cytometry A., Aug. 2010, 77(8):798-804.
Joos et al., "Covalent attachment of hybridizable oligonucleotides to glass supports," Anal Biochem., Apr. 1997, 247(1):96-101.
Jucá et al., "Effect of dimethyl sulfoxide on reverse transcriptase activity," Braz. J. Med. Biol. Res., Mar. 1995, 28(3):285-90.
Juliano, "The delivery of therapeutic oligonucleotides," Nucleic Acids Res., Aug. 2016, 44(14):6518-6548.
Kalantari et al., "Deparaffinization of formalin-fixed paraffin-embedded tissue blocks using hot water instead of xylene," Anal Biochem., Aug. 2016, 507:71-3.
Kap et al., "Histological assessment of PAXgene tissue fixation and stabilization reagents," PLoS One, 2011, 6:e27704, 10 pages.
Kapteyn et al., "Incorporation of non-natural nucleotides into template-switching oligonucleotides reduces background and improves cDNA synthesis from very small RNA samples," BMC Genomics, Jul. 2010, 11:413, 9 pages.
Karmakar et al., "Organocatalytic removal of formaldehyde adducts from RNA and DNA bases," Nature Chemistry, Aug. 3, 2015, 7(9):752-758.
Kaya-Okur et al., "CUT&Tag for efficient epigenomic profiling of small samples and single cells," Apr. 2019, 10(1):1930, 10 pages.
Ke et al., "In situ sequencing for RNA analysis in preserved tissue and cells," Nat Methods., Sep. 2013, Supplementary Materials, 29 pages.
Kennedy-Darling et al., "Measuring the Formaldehyde Protein-DNA Cross-Link Reversal Rate," Analytical Chemistry, 2014, 86(12):5678-5681.
Kent et al., "Polymerase θ is a robust terminal transferase that oscillates between three different mechanisms during end-joining" Elife, Jun. 2016, 5:e13740, 25 pages.
Kirby et al., "Cryptic plasmids of *Mycobacterium avium*: Tn552 to the rescue," Mol Microbiol., Jan. 2002, 43(1):173-86.
Kleckner et al., "Tn10 and IS10 transposition and chromosome rearrangements: mechanism and regulation in vivo and in vitro," Curr Top Microbiol Immunol., 1996, 204:49-82.
Koch et al., "Photochemical immobilization of anthraquinone conjugated oligonucleotides and PCR amplicons on solid surfaces," Bioconjugate Chem., Jul. 2000, 11(4):474-483.
Kolb et al., "Click Chemistry: Diverse Chemical Function from a Few Good Reactions," Angew. Chem. Int. Ed., Jun. 2001, 40(11):2004-2021.
Korbel et al., "Paired-end mapping reveals extensive structural variation in the human genome," Science, 2007, 318(5849):420-426.
Korlach et al., "Selective aluminum passivation for targeted immobilization of single DNA polymerase molecules in zero-mode waveguide nanostructures," Proc. Natl. Acad. Sci. USA, 2008, 105:1176-1181.
Kozlov et al., "A highly scalable peptide-based assay system for proteomics," PLoS ONE, 2012, 7(6):e37441, 10 pages.
Kozlov et al., "A method for rapid protease substrate evaluation and optimization," Comb Chem High Throughput Screen, 2006, 9(6):481-87.
Kristensen et al., "High-Throughput Methods for Detection of Genetic Variation," BioTechniques, Feb. 2001, 30(2):318-332.
Krzywkowski et al., "Chimeric padlock and iLock probes for increased efficiency of targeted RNA detection," RNA, Jan. 2019, 25(1):82-89.
Krzywkowski et al., "Fidelity of RNA templated end-joining by Chlorella virus DNA ligase and a novel iLock assay with improved direct RNA detection accuracy," Nucleic Acids Research, Oct. 2017, 45(18):e161, 9 pages.
Kumar et al., "Template-directed oligonucleotide strand ligation, covalent intramolecular DNA circularization and catenation using click chemistry," J Am Chem Soc., May 2007, 129(21):6859-64.
Kurz et al., "cDNA-protein fusions: covalent protein-gene conjugates for the in vitro selection of peptides and proteins," ChemBioChem., 2001, 2(9):666-72.
Kwok, "High-throughput genotyping assay approaches," Pharmocogenomics, Feb. 2000, 1(1):95-100.
Lage et al., "Whole genome analysis of genetic alterations in small DNA samples using hyperbranched strand displacement amplification and array-CGH," Genome Research, 2003, 13(2):294-307.
Lahiani et al., "Enabling Histopathological Annotations on Immunofluorescent Images through Virtualization of Hematoxylin and Eosin," J Pathol Inform., Feb. 2018, 9:1, 8 pages.
Lampe et al., "A purified mariner transposase is sufficient to mediate transposition in vitro," EMBO J., Oct. 1996, 15(19):5470-9.
Lamture et al., "Direct detection of nucleic acid hybridization on the surface of a charge coupled device," Nucleic Acid Res., Jun. 1994, 22(11):2121-5.
Landegren et al., "Reading bits of genetic information: methods for single-nucleotide polymorphism analysis," Genome Res., Aug. 1998, 8(8):769-76.
Langdale et al., "A rapid method of gene detection using DNA bound to Sephacryl," Gene, 1985, 36(3):201-210.
Larman et al., "Sensitive, multiplex and direct quantification of RNA sequences using a modified RASL assay," Nucleic Acids Research, 2014, 42(14):9146-9157.
Lee et al., "Assembly of metallic nanoparticle arrays on glass via nanoimprinting and thin-film dewetting," Beilstein J Nanotechnol., May 2017, 8:1049-1055.
Lee et al., "Fluorescent in situ sequencing (FISSEQ) of RNA for gene expression profiling in intact cells and tissues," Nature Protocols, 2015, 10(3):442-458.
Lee et al., "Highly multiplexed subcellular RNA sequencing in situ", Science, 2014, 343(6177):1360-1363.
Lee et al., "Improving the efficiency of genomic loci capture using oligonucleotide arrays for high throughput resequencing," BMC Genomics, Dec. 2009, 10:646, 12 pages.
Leriche et al., "Cleavable linkers in chemical biology," Bioorganic & Medicinal Chemistry, 2012, 20:571-582.
Levene et al., "Zero-Mode Waveguides for Single-Molecule Analysis at High Concentrations," Science, 2003, 299:682-686.
Li et al., "A photocleavable fluorescent nucleotide for DNA sequencing and analysis," Proc. Natl. Acad. Sci., 2003, 100(2):414-419.
Li et al., "An activity-dependent proximity ligation platform for spatially resolved quantification of active enzymes in single cells," Nat Commun, Nov. 2017, 8(1):1775, 12 pages.
Li et al., "DNA molecules and configurations in a solid-state nanopore microscope," Nat Mater., Sep. 2003, 2(9):611-5.
Li et al., "RASL-seq for Massively Parallel and Quantitative Analysis of Gene Expression," Curr Protoc Mol Biol., Apr. 2012, 4(13):1-10.
Li et al., "Review: a comprehensive summary of a decade development of the recombinase polymerase amplification," Analyst, Dec. 2018, 144(1):31-67.
Lin et al., "Highly multiplexed imaging of single cells using a high-throughput cyclic immunofluorescence method," Nat Commun., Sep. 2015, 6:8390, 7 pages.
Linnarsson, "Recent advances in DNA sequencing methods—general principles of sample preparation," Experimental Cell Research, 2010, 316(8):1339-1343.
Liu et al., "High-Spatial-Resolution Multi-Omics Atlas Sequencing of Mouse Embryos via Deterministic Barcoding in Tissue," BioRxiv, 2019, 55 pages.

(56) References Cited

OTHER PUBLICATIONS

Liu et al., "Surface and interface control on photochemically initiated immobilization," J Am Chem Soc., Nov. 2006, 128(43):14067-72.
Lizardi et al., "Mutation detection and single-molecule counting using isothermal rolling-circle amplification," Nat. Genet., 1998, 19(3):225-232.
Lou et al., "A review of room temperature storage of biospecimen tissue and nucleic acids for anatomic pathology laboratories and biorepositories," Clin Biochem., Mar. 2014, 47(4-5):267-73.
Lovatt et al., "Transcriptome in vivo analysis (TIVA) of spatially defined single cells in live tissue," Nature Methods, 2013, 11(2):190-196.
Lund et al., "Assessment of methods for covalent binding of nucleic acids to magnetic beads, Dynabeads, and the characteristics of the bound nucleic acids in hybridization reactions," Nucleic Acids Res., 1988, 16(22):10861-80.
Lundberg et al., "High-fidelity amplification using a thermostable DNA polymerase isolated from Pyrococcus furiosus," Gene, 1991, 108(1):1-6.
Lundberg et al., "Homogeneous antibody-based proximity extension assays provide sensitive and specific detection of low-abundant proteins in human blood," Nucleic Acids Res., 2011, 39(15):e102, 8 pages.
Lundberg et al., "Multiplexed homogeneous proximity ligation assays for high-throughput protein biomarker research in serological material," Mol Cell Proteomics, 2011, 10(4):M110.004978, 11 pages.
Lundin et al., "Increased throughput by parallelization of library preparation for massive sequencing," PLoS One, Apr. 2010, 5(4):e10029, 7 pages.
Lundquist et al., "Parallel confocal detection of single molecules in real time," Opt. Lett., 2008, 33:1026-1028.
Lyamichev et al., "Invader assay for SNP genotyping," Methods Mol Biol., 2003, 212:229-40.
Lyamichev et al., "Polymorphism identification and quantitative detection of genomic DNA by invasive cleavage of oligonucleotide probes," Nat Biotechnol., Mar. 1999, 17(3):292-6.
Lyck et al., "Immunohistochemical markers for quantitative studies of neurons and glia in human neocortex," J Histochem Cytochem, 2008, 56(3):201-21.
Lykidis et al., "Novel zinc-based fixative for high quality DNA, RNA and protein analysis," Nucleic Acids Res., Jun. 2007, 35(12):e85, 10 pages.
Ma et al., "Isothermal amplification method for next-generation sequencing," PNAS, Aug. 12, 2013, 110(35):14320-14323.
MacBeath et al., "Printing proteins as microarrays for high-throughput function determination," Science, Sep. 2000, 289(5485):1760-1763.
MacIntyre, "Unmasking antigens for immunohistochemistry.," Br J Biomed Sci., 2001, 58(3):190-6.
Macosko et al., "Highly Parallel Genome-wide Expression Profiling of Individual Cells Using Nanoliter Droplets," Cell, 2015, 161:1202-1214.
Magaki et al., "An introduction to Performance of Immunohistochemistry," Biobanking: Methods and Protocols, Method in Molecular Biology, Yong (ed.), 2019, 1897, Chapter 25, 289-298.
Marx, "Method of the Year: spatially resolved transcriptomics," Nature Methods, 2021, 18(1):9-14.
Mathieson et al., "A Critical Evaluation of the PAXgene Tissue Fixation System: Morphology, Immunohistochemistry, Molecular Biology, and Proteomics," Am J Clin Pathol., Jul. 8, 2016, 146(1):25-40.
McCloskey et al., "Encoding PCR products with batch-stamps and barcodes," Biochem. Genet., 2007, 45(11-12):761-767.
Meers et al., "Improved CUT&RUN chromatin profiling tools," Elife, Jun. 2019, 8:e46314, 16 pages.
Mele et al., "The Human Transcriptome Across Tissues and Individuals," Science, May 2015, 348(6235):660-5.
Merritt et al., "Multiplex digital spatial profiling of proteins and RNA in fixed tissue," Nat Biotechnol, May 2020, 38(5):586-599.
Metzker, "Sequencing technologies—the next generation," Nature Reviews Genetics, 2010, 11(1):31-46.
Miele et al., "Mapping cis- and trans-chromatin interaction networks using chromosome conformation capture (3C)," Methods Mol Biol., 2009, 464:105-21.
Mignardi et al., "Oligonucleotide gap-fill ligation for mutation detection and sequencing in situ," Nucleic Acids Research, Aug. 3, 2015, 43(22):e151, 12 pages.
Miller et al., "Basic concepts of microarrays and potential applications in clinical microbiology," Clinical Microbiology Reviews, 2009, 22(4):611-633.
Miller et al., "Chapter 11—Solid and Suspension Microarrays for Microbial Diagnostics," Methods in Microbiology, 2015, 42:395-431.
Miner et al., "Molecular barcodes detect redundancy and contamination in hairpin-bisulfite PCR," Nucleic Acids Res., Sep. 2004, 32(17):e135, 4 pages.
Mishra et al., "Three-dimensional genome architecture and emerging technologies: looping in disease," Genome Medicine, 2017, 9(1):87, 14 pages.
Mitra et al., "Digital genotyping and haplotyping with polymerase colonies," Proc. Natl. Acad. Sci. USA, May 2003, 100(10):5926-5931.
Mitra et al., "Fluorescent in situ sequencing on polymerase colonies," Anal Biochem, Sep. 2003, 320(1):55-65.
Miura et al., "Highly efficient single-stranded DNA ligation technique improves low-input whole-genome bisulfite sequencing by post-bisulfite adaptor tagging," Nucleic Acids Res., Sep. 2019, 47(15):e85, 10 pages.
Mizusawa et al., "A bacteriophage lambda vector for cloning with BamHI and Sau3A," Gene, 1982, 20(3):317-322.
Moffitt et al., "RNA Imaging with Multiplexed Error-Robust Fluorescence In Situ Hybridization (MERFISH)," Methods Enzymol., 2016, 572:1-49.
Mohsen et al., "The Discovery of Rolling Circle Amplification and Rolling Circle Transcription," Acc Chem Res., Nov. 15, 2016, 49(11):2540-2550, 25 pages.
Morlan et al., "Selective depletion of rRNA enables whole transcriptome profiling of archival fixed tissue," PLoS One, Aug. 2012, 7(8):e42882, 8 pages.
Moshrefzadeh et al., "Nonuniform photobleaching of dyed polymers for optical waveguides," Applied Physics Letters, 1993, 62:16-18.
Motea et al., "Terminal deoxynucleotidyl transferase: the story of a misguided DNA polymerase," Biochim Biophys Acta., May 2010, 1804(5):1151-66.
Mulder et al., "CapTCR-seq: hybrid capture for T-cell receptor repertoire profiling," Blood Advances, Dec. 2018, 2(23):3506-3514.
Nadji et al., "Immunohistochemistry of tissue prepared by a molecular-friendly fixation and processing system," Appl Immunohistochem Mol Morphol., Sep. 2005, 13(3):277-82.
Nallur et al., "Signal amplification by rolling circle amplification on DNA microarrays," Nucleic Acids Res., Dec. 1, 2001, 29(23):e118, 9 pages.
Nandakumar et al., "How an RNA Ligase Discriminates RNA versus DNA Damage," Molecular Cell, 2004, 16:211-221.
Nandakumar et al., "RNA Substrate Specificity and Structure-guided Mutational Analysis of Bacteriophage T4 RNA Ligase 2," Journal of Biological Chemistry, Jul. 2004, 279(30):31337-31347.
Ncbi.nlm.nih.gov, [online], "Molecular Inversion Probe Assay," available on or before Oct. 14, 2014, via Internet Archive: Wayback Machine URL<https://web.archive.org/web/20141014124037/https://www.ncbi.nlm.nih.gov/probe/docs/techmip/>, retrieved on Jun. 16, 2021, retrieved from URL<https://www.ncbi.nlm.nih.gov/probe/docs/techmip/>, 2 pages.
Ng et al., "Gene identification signature (GIS) analysis for transcriptome characterization and genome annotation," Nature Methods, 2005, 2(2):105-111.
Nguyen et al., "Two-photon polymerization for biological applications," Materials Today, Jul. 2017, 20(6):314-322.

(56) References Cited

OTHER PUBLICATIONS

Nichols et al., "RNA Ligases," Curr Protoc Mol Biol., Oct. 2008, 84(1):3.15.1-3.15.4.
Niedringhaus et al., "Landscape of next-generation sequencing technologies," Anal Chem., Jun. 2011, 83(12):4327-41.
Nikiforov et al., "The use of 96-well polystyrene plates for DNA hybridization-based assays: an evaluation of different approaches to oligonucleotide immobilization," Anal Biochem, May 1995, 227(1):201-9.
Niklas et al., "Selective permeabilization for the high-throughput measurement of compartmented enzyme activities in mammalian cells," Anal Biochem, Sep. 2011, 416(2):218-27.
Nilsson et al., "RNA-templated DNA ligation for transcript analysis," Nucleic Acids Res., Jan. 2001, 29(2):578-81.
Nowak et al., "Entering the Postgenome Era," Science, 1995, 270(5235):368-71.
Ohtsubo et al., "Bacterial insertion sequences," Curr Top Microbiol Immunol., 1996, 204:1-26.
Olivier, "The Invader assay for SNP genotyping," Mutat. Res., Jun. 2005, 573(1-2):103-110.
Orenstein et al., "γPNA FRET Pair Miniprobes for Quantitative Fluorescent In Situ Hybridization to Telomeric DNA in Cells and Tissue," Molecules, Dec. 2, 2017, 22(12):2117, 15 pages.
Ozsolak et al., "Digital transcriptome profiling from attomole-level RNA samples," Genome Res., Apr. 2010, 20(4):519-25.
Pandey et al., "Inhibition of terminal deoxynucleotidyl transferase by adenine dinucleotides. Unique inhibitory action of Ap5A," FEBS Lett., Mar. 1987, 213(1):204-8.
Park et al., "Single cell trapping in larger microwells capable of supporting cell spreading and proliferation," Microfluid Nanofluid, 2010, 8:263-268.
Passow et al., "RNAlater and flash freezing storage methods nonrandomly influence observed gene expression in RNAseq experiments," bioRxiv, Jul. 2018, 28 pages.
PCT International Preliminary Report on Patentability in International Appln. No. PCT/US2019/048425, dated Mar. 2, 2021, 9 pages.
PCT International Search Report in International Appln. No. PCT/US2019/048425, dated Dec. 17, 2019, 13 pages.
Pellestor et al., "The peptide nucleic acids (PNAs), powerful tools for molecular genetics and cytogenetics," Eur J Hum Genet., Sep. 2004, 12(9):694-700.
Pemov et al., "DNA analysis with multiplex microarray-enhanced PCR," Nucl. Acids Res., Jan. 2005, 33(2):e11, 9 pages.
Penno et al., "Stimulation of reverse transcriptase generated cDNAs with specific indels by template RNA structure: retrotransposon, dNTP balance, RT-reagent usage," Nucleic Acids Res., Sep. 2017, 45(17):10143-10155.
Perler et al., "Intervening sequences in an Archaea DNA polymerase gen," Proc Natl Acad Sci USA, Jun. 1992, 89(12):5577-5581.
Perocchi et al., "Antisense artifacts in transcriptome microarray experiments are resolved by actinomycin D," Nucleic Acids Res., 2007, 35(19):e128, 7 pages.
Petterson et al., "Generations of sequencing technologies," Genomics, 2009, 93(2):105-111.
Picelli et al., "Full-length RNA-seq from single cells using Smart-seq2," Nat Protoc., Jan. 2014, 9(1):171-81.
Picelli et al., "Tn5 transposase and tagmentation procedures for massively scaled sequencing projects," Genome Res., Dec. 2014, 24(12):2033-40.
Pipenburg et al., "DNA detection using recombination proteins," PLoS Biol., Jul. 2006, 4(7):e204, 7 pages.
Pirici et al., "Antibody elution method for multiple immunohistochemistry on primary antibodies raised in the same species and of the same subtypem," J. Histochem. Cytochem., Jun. 2009, 57(6):567-75.
Plasterk, "The Tc1/mariner transposon family," Curr Top Microbiol Immunol., 1996, 204:125-43.
Plongthongkum et al., "Advances in the profiling of DNA modifications: cytosine methylation and beyond," Nature Reviews Genetics, Aug. 2014, 15(10):647-661.
Polsky-Cynkin et al., "Use of DNA immobilized on plastic and agarose supports to detect DNA by sandwich hybridization," Clin. Chem., 1985, 31(9):1438-1443.
Porreca et al., "Polony DNA sequencing," Curr Protoc Mol Biol., Nov. 2006, Chapter 7, Unit 7.8, pp. 7.8.1-7.8.22.
U.S. Appl. No. 61/267,363, filed Dec. 7, 2009, 33 pages.
Qiu et al., "Combination probes with intercalating anchors and proximal fluorophores for DNA and RNA detection," Nucleic Acids Research, Sep. 2016, 44(17):e138, 12 pages.
Raab et al., "Human tRNA genes function as chromatin insulators," EMBO J., Jan. 2012, 31(2):330-50.
Raj et al., "Imaging individual mRNA molecules using multiple singly labeled probes," Nature Methods, Oct. 2008, 5(10):877-879, 9 pages.
Rajeswari et al., "Multiple pathogen biomarker detection using an encoded bead array in droplet PCR," J. Microbial Methods, Aug. 2017, 139:22-28.
Ranki et al., "Sandwich hybridization as a convenient method for the detection of nucleic acids in crude samples," Gene, 1983, 21(1-2):77-85.
Raouane et al., "Lipid conjugated oligonucleotides: a useful strategy for delivery," Bioconjug Chem., Jun. 2012, 23(6):1091-104.
Reinartz et al., "Massively parallel signature sequencing (MPSS) as a tool for in-depth quantitative gene expression profiling in all organisms," Brief Funct Genomic Proteomic, Feb. 2002, 1(1):95-104.
Reznikoff, "Tn5 as a model for understanding DNA transposition," Mol Microbiol., Mar. 2003, 47(5):1199-206.
Rideau et al., "Liposomes and polymersomes: a comparative review towards cell mimicking," Chem Soc Rev., Nov. 2018, 47(23):8572-8610.
Rie et al., "An integrated expression atlas of miRNAs and their promoters in human and mouse," Nat Biotechnol, Sep. 2017, 35(9):872-878.
Ristic et al., "Detection of Protein-Protein Interactions and Post-translational Modifications Using the Proximity Ligation Assay: Application to the Study of the SUMO Pathway," Methods Mol. Biol., 2016, 1449:279-90.
Rodriques et al., "Slide-seq: A scalable technology for measuring genome-wide expression at high spatial resolution," Science, 2019, 363(6434):1463-1467.
Rogers et al., "Immobilization of oligonucleotides onto a glass support via disulfide bonds: A method for preparation of DNA microarrays," Anal Biochem., Jan. 1999, 266(1):23-30.
Rogers et al., "Use of a novel cross-linking method to modify adenovirus tropism," Gene Ther., Dec. 1997, 4(12):1387-92.
Ronaghi et al., "A sequencing method based on real-time pyrophosphate," Science, Jul. 1998, 281(5375):363-365.
Ronaghi et al., "Real-time DNA sequencing using detection of pyrophosphate release," Analytical Biochemistry, Nov. 1996, 242(1):84-89.
Ronaghi, "Pyrosequencing sheds light on DNA sequencing," Genome Res, Jan. 2001, 11(1):3-11.
Roy et al., "Assessing long-distance RNA sequence connectivity via RNA-templated DNA-DNA ligation," eLife, 2015, 4:e03700, 21 pages.
Running et al., "A procedure for productive coupling of synthetic oligonucleotides to polystyrene microtiter wells for hybridization capture," Biotechniques, Mar. 1990, 8(3):276-279.
Sah et al., "Complete Genome Sequence of a 2019 Novel Coronavirus (SARS-COV-2) Strain Isolated in Nepal", Microbiology Resource Announcements, vol. 9(11):1-3, 2020.
Salmén et al., "Barcoded solid-phase RNA capture for Spatial Transcriptomics profiling in mammalian tissue sections," Nature Protocols, Oct. 2018, 13(11):2501-2534.
Satpathy et al., "Massively parallel single-cell chromatin landscapes of human immune cell development and intratumoral T cell exhaustion," Nat Biotechnol., Aug. 2019, 37(8):925-936.
Saxonov et al., "10x Genomics, Mastering Biology to Advance Human Health," PowerPoint, 10x, 2020, 41 pages.

(56) References Cited

OTHER PUBLICATIONS

Schena et al., "Quantitative monitoring of gene expression patterns with a complementary DNA microarray," Science, Oct. 1995, 270(5235):467-470.
Schouten et al., "Relative quantification of 40 nucleic acid sequences by multiplex ligation-dependent probe amplification," Nucleic Acids Res., Jun. 2002, 30(12):e57, 13 pages.
Schweitzer et al., "Immunoassays with rolling circle DNA amplification: A versatile platform for ultrasensitive antigen detection," Proc. Natl Acad. Sci. USA, May 22, 2000, 97:10113-119.
Schweitzer et al., "Multiplexed protein profiling on microarrays by rolling-circle amplification," Nature Biotechnology, Apr. 2002, 20(4):359-365.
Schwers et al., "A high-sensitivity, medium-density, and target amplification-free planar waveguide microarray system for gene expression analysis of formalin-fixed and paraffin-embedded tissue," Clin. Chem., Nov. 2009, 55(11):1995-2003.
Shalon et al., "A Dna microarray system for analyzing complex DNA samples using two-color fluorescent probe hybridization," Genome Res., Jul. 1996, 6(7):639-45.
Sharma, "Self-Assembly of Colloidal Particles," Resonance, 2018, 23:263-275.
Shelbourne et al., "Fast copper-free click DNA ligation by the ring-strain promoted alkyne-azide cycloaddition reaction," Chem. Commun., 2011, 47(22):6257-6259.
Shendure et al., "Accurate multiplex polony sequencing of an evolved bacterial genome," Science, 2005, 309(5741):1728-1732.
Simonis et al., "Nuclear organization of active and inactive chromatin domains uncovered by chromosome conformation capture-on-chip (4C)," Nat Genet., Nov. 2006, 38(11):1348-54.
Singh et al., "High-throughput targeted long-read single cell sequencing reveals the clonal and transcriptional landscape of lymphocytes," Nat Commun., Jul. 2019, 10(1):3120, 13 pages.
Skene et al., "An efficient targeted nuclease strategy for high-resolution mapping of DNA binding sites," Elife, Jan. 2017, 6:e21856, 35 pages.
Skipper et al., "DNA transposon-based gene vehicles—scenes from an evolutionary drive," J Biomed Sci., Dec. 2013, 20(1):92, 23 pages.
Slomovic et al., "Addition of poly(A) and poly(A)-rich tails during RNA degradation in the cytoplasm of human cells," Proc Natl Acad Sci USA, Apr. 2010, 107(16):7407-12.
Smithsonianmag.com, [online], Daley, "Ambitious Project to Sequence Genomes of 1.5 Million Species Kicks Off," Nov. 5, 2018, retrieved on Jul. 9, 2021, retrieved from URL<https://www.smithsonianmag.com/smart-news/ambitious-project-sequence-genomes-15-million-species-kicks-180970697/>, 2 pages.
Söderberg et al., "Characterizing proteins and their interactions in cells and tissues using the in situ proximity ligation assay," Methods, Jul. 2008, 45(3):227-32.
Soni and Meller, "Progress toward ultrafast DNA sequencing using solid-state nanopores," Clin Chem., 2007, 53:1996-2001.
Sountoulidis et al., "SCRINSHOT, a spatial method for single-cell resolution mapping of cell states in tissue sections," PLOS Biol., Nov. 2020, 18(11):e3000675, 32 pages.
Spiess et al., "A highly efficient method for long-chain cDNA synthesis using trehalose and betaine," Anal. Biochem., Feb. 2002, 301(2):168-74.
Spitale et al., "Structural imprints in vivo decode RNA regulatory mechanisms," Nature, 2015, 519(7544):486-90.
Stahl et al., "Visualization and analysis of gene expression in tissue sections by spatial transcriptomics," Science, Jul. 2016, 353(6294):78-82.
Stahl et al., "Visualization and analysis of gene expression in tissue sections by spatial transcriptomics," Supplementary Materials, Science, Jul. 2016, 353(6294):78-82, 41 pages.
Stimpson et al., "Real-time detection of DNA hybridization and melting on oligonucleotide arrays by using optical wave guides," Proc Natl Acad Sci USA, Jul. 1995, 92(14):6379-83.
Stoddart et al., "Single-nucleotide discrimination in immobilized DNA oligonucleotides with a biological nanopore," PNAS USA., May 2009, 106(19):7702-7707.
Strell et al., "Placing RNA in context and space—methods for spatially resolved transcriptomics," The FEBS Journal, 2019, 286(8):1468-1481.
Stroh et al., "Quantum dots spectrally distinguish multiple species within the tumor milieu in vivo," Nat Med., Jun. 2005, 11(6):678-82.
Sun et al., "Statistical Analysis of Spatial Expression Pattern for Spatially Resolved Transcriptomic Studies," Nature Methods, Jan. 27, 2020, 17(2): 193-200.
Sutherland et al., "Utility of formaldehyde cross-linking and mass spectrometry in the study of protein-protein interactions," J. Mass Spectrom., Jun. 2008, 43(6):699-715.
Svensson et al., "SpatialDE: identification of spatially variable genes," Nature Methods, May 2018, 15:343-346, 15 pages.
Takei et al., "Integrated Spatial Genomics Reveals Global Architecture of Single Nuclei," Nature, Jan. 27, 2021, 590(7845):344-350, 53 pages.
Taylor et al., "Mitochondrial DNA mutations in human disease," Nature Reviews Genetics, May 2005, 6(5):389-402.
Tentori et al., "Detection of Isoforms Differing by a Single Charge Unit in Individual Cells," Chem. Int. Ed., 2016, 55(40):12431-5.
Tian et al., "Antigen peptide-based immunosensors for rapid detection of antibodies and antigens," Anal Chem, 2009, 81(13):5218-5225.
Tijssen et al., "Overview of principles of hybridization and the strategy of nucleic acid assays" in Techniques in Biochemistry and Molecular Biology—Hybridization with Nucleic Acid Probes, 1993, 24(Chapter 2), 65 pages.
Timofeev et al., "Regioselective immobilization of short oligonucleotides to acrylic copolymer gels," Nucleic Acids Res., Aug. 1996, 24(16):3142-8.
Tolbert et al., "New methods for proteomic research: preparation of proteins with N-terminal cysteines for labeling and conjugation," Angewandte Chemie International Edition, Jun. 2002, 41(12):2171-4.
Toubanaki et al., "Dry-reagent disposable biosensor for visual genotyping of single nucleotide polymorphisms by oligonucleotide ligation reaction: application to pharmacogenetic analysis," Hum Mutat., Aug. 2008, 29(8):1071-8.
Trejo et al., "Extraction-free whole transcriptome gene expression analysis of FFPE sections and histology-directed subareas of tissue," PLoS ONE, Feb. 2019, 14(2):e0212031, 22 pages.
Tu et al., "TCR sequencing paired with massively parallel 3' RNA-seq reveals clonotypic T cell signatures," Nature Immunology, Dec. 2019, 20(12):1692-1699.
Twyman et al., "Techniques Patents for SNP Genotyping," Pharmacogenomics, Jan. 2003, 4(1):67-79.
Ulery et al., "Biomedical Applications of Biodegradable Polymers," J Polym Sci B Polym Phys., Jun. 2011, 49(12):832-864.
U.S. Appl. No. 60/416,118 Fan et al., Multiplex Nucleic Acid Analysis Using Archived or Fixed Samples, filed Oct. 3, 2002, 22 pages.
Van Gelder et al., "Amplified RNA synthesized from limited quantities of heterogeneous cDNA," Proc. Natl. Acad. Sci. USA, 1990, 87(5):1663-1667.
Vandenbroucke et al., "Quantification of splice variants using real-time PCR," Nucleic Acids Research, 2001, 29(13):e68, 7 pages.
Vandernoot et al., "cDNA normalization by hydroxyapatite chromatography to enrich transcriptome diversity in RNA-seq applications," Biotechniques, Dec. 2012, 53(6):373-80.
Vasiliskov et al., "Fabrication of microarray of gel-immobilized compounds on a chip by copolymerization," Biotechniques, Sep. 1999, 27(3):592-606.
Vázquez Bernat et al., "High-Quality Library Preparation for NGS-Based Immunoglobulin Germline Gene Inference and Repertoire Expression Analysis," Front Immunol., Apr. 2019, 10:660, 12 pages.
Velculescu et al., "Serial analysis of gene expression," Science, Oct. 1995, 270(5235):484-7.

(56) References Cited

OTHER PUBLICATIONS

Vickovic et al., "High-definition spatial transcriptomics for in situ tissue profiling," Nat Methods, Oct. 2019, 16(10):987-990.
Vickovic et al., "SM-Omics: An automated Platform for High-Throughput Spatial Multi-Omics," bioRxiv, Oct. 2020, 40 pages.
Vincent et al., "Helicase-dependent isothermal DNA amplification," EMBO Rep., Aug. 2004, 5(8):795-800.
Viollet et al., "T4 Rna ligase 2 truncated active site mutants: improved tools for RNA analysis," BMC Biotechnol., Jul. 2011, 11:72, 14 pages.
Vlassakis et al., "Effect of Polymer Hydration State on In-Gel Immunoassays," Anal Chem., Nov. 2015, 87(21):11030-8.
Vogelstein et al., "Digital PCR," Proceedings of the National Academy of Sciences, Aug. 1999, 96(16):9236-9241.
Waichman et al., "Functional immobilization and patterning of proteins by an enzymatic transfer reaction," Analytical chemistry, 2010, 82(4):1478-85.
Walker et al., "Strand displacement amplification—an isothermal, in vitro DNA amplification technique," Nucleic Acids Research, 1992, 20(7):1691-1696.
Wang et al., "Concentration gradient generation methods based on microfluidic systems," RSC Adv., 2017, 7:29966-29984.
Wang et al., "High-fidelity mRNA amplification for gene profiling," Nature Biotechnology, Apr. 2000, 18(4):457-459.
Wang et al., "Imaging plasma membranes without cellular internalization: multisite membrane anchoring reagents based on glycol chitosan derivatives," J Master Chem B., Aug. 2015, 3(30):6165-6173.
Wang et al., "Imaging-based pooled CRISPR screening reveals regulators of lncRNA localization," Proc Natl Acad Sci USA, May 2019, 116(22):10842-10851.
Wang et al., "Optimization of Process Conditions for Infected Animal Tissues by Alkaline Hydrolysis Technology," Procedia Environmental Sciences, 2016, 31:366-374.
Wang et al., "Tagmentation-based whole-genome bisulfite sequencing," Nature Protocols, Oct. 2013, 8(10):2022-2032.
Wang et al., "Three-dimensional intact-tissue sequencing of single-cell transcriptional states," Science, Jul. 2018, 361(6400):eaat5691, 22 pages.
Wang, "RNA amplification for successful gene profiling analysis," J Transl Med., Jul. 2005, 3:28, 11 pages.
Weinreich et al., "Evidence that the cis Preference of the Tn5 Transposase is Caused by Nonproductive Multimerization," Genes and Development, Oct. 1994, 8(19):2363-2374.
Wiedmann et al., "Ligase chain reaction (LCR)—overview and applications," PCR Methods Appl., Feb. 1994, 3(4):S51-64.
Willner, "Stimuli-Controlled Hydrogels and Their Applications," Acc Chem Res., Apr. 2017, 50(4):657-658.
Wilson et al., "New transposon delivery plasmids for insertional mutagenesis in Bacillus anthracis," J Microbiol Methods, Dec. 2007, 71(3):332-5.
Wohnhaas et al., "DMSO cryopreservation is the method of choice to preserve cells for droplet-based single-cell RNA sequencing," Scientific Reports, Jul. 2019, 9(1):10699, 14 pages.
Wolf et al., "Rapid hybridization kinetics of DNA attached to submicron latex particles," Nucleic Acids Res, 1987, 15(7):2911-2926.
Wong et al., "Direct Site-Selective Covalent Protein Immobilization Catalyzed by a Phosphopantetheinyl Transferase," J. Am. Chem Soc., 2008, 130(37):12456-64.
Worthington et al., "Cloning of random oligonucleotides to create single-insert plasmid libraries," Anal Biochem, 2001, 294(2):169-175.
Wu et al., "Detection DNA Point Mutation with Rolling-Circle Amplification Chip," IEEE, 2010 4th International Conference on Bioinformatics and Biomedical Engineering, Jun. 2010, 4 pages.
Wu et al., "RollFISH achieves robust quantification of single-molecule RNA biomarkers in paraffin-embedded tumor tissue samples," Commun Biol., Nov. 2018, 1:209, 8 pages.
Yasukawa et al., "Effects of organic solvents on the reverse transcription reaction catalyzed by reverse transcriptases from avian myeloblastosis virus and Moloney murine leukemia virus," Biosci Biotechnol Biochem., 2010, 74(9):1925-30.
Ye et al., "Triggered self-assembly of magnetic nanoparticles," Sci Rep., Mar. 2016, 6:23145, 9 pages.
Yeakley et al., "A trichostatin A expression signature identified by TempO-Seq targeted whole transcriptome profiling," PLoS One, May 2017, 12(5):e0178302, 22 pages.
Yeakley et al., "Profiling alternative splicing on fiber-optic arrays," Nature biotechnology, 2002, 20:353-358.
Yershov et al., "DNA analysis and diagnostics on oligonucleotide microchips," Proc. Natl. Acad. Sci. USA, May 1996, 93(10):4913-4918.
Yin et al., "Genetically encoded short peptide tag for versatile protein labeling by Sfp phosphopantetheinyl transferase," PNAS, 2005, 102(44):15815-20.
Zahra et al., "Assessment of Different Permeabilization Methods of Minimizing Damage to the Adherent Cells for Detection of Intracellular RNA by Flow Cytometry," Avicenna Journal of Medical Biotechnology, Jan. 1, 2014, 6(1):38-46.
Zeberg et al., The major genetic risk factor for severe COVID-19 is inherited from Neanderthals, Nature, 2020 pp. 1-13.
Zhang et al., "A novel mechanism of transposon-mediated gene activation," PLoS Genet., Oct. 2009, 5(10):e1000689, 10 pages.
Zhang et al., "Archaeal RNA ligase from Thermoccocus kodakarensis for template dependent ligation," RNA Biol., Jan. 2017, 14(1):36-44.
Zhang et al., "Assembling DNA through Affinity Binding to Achieve Ultrasensitive Protein Detection," Angew Chem Int Ed Engl., 2013, 52(41):10698-705.
Zhang et al., "Binding-induced DNA assembly and its application to yoctomole detection of proteins," Anal Chem, 2012, 84(2):877-884.
Zhang et al., "Genome-wide open chromatin regions and their effects on the regulation of silk protein genes in Bombyx mori," Sci Rep., Oct. 2017, 7(1):12919, 9 pages.
Zhang et al., "Multiplex ligation-dependent probe amplification (MLPA) for ultrasensitive multiplexed microRNA detection using ribonucleotide-modified DNA probes†," Chem. Commun., 2013, 49:10013-10015.
Zhang et al., "Single-base mutational analysis of cancer and genetic diseases using membrane bound modified oligonucleotides," Nucleic Acids Res., Jul. 1991, 19(14):3929-33.
Zhao et al., "Isothermal Amplification of Nucleic Acids," Chemical Reviews, Nov. 2015, 115(22):12491-12545.
Zheng et al., "Origins of human mitochondrial point mutations as DNA polymerase gamma-mediated errors," Mutat. Res., 2006, 599(1-2):11-20.
Zhou et al., "Genetically encoded short peptide tags for orthogonal protein labeling by Sfp and AcpS phosphopantetheinyl transferases," ACS Chemical Biol., 2007, 2(5):337-346.
Zhu et al., "Reverse transcriptase template switching: a SMART approach for full-length cDNA library construction," Biotechniques, Apr. 2001, 30(4):892-897.
Howell et al., "iFRET: An Improved Fluorescence System for DNA-Melting Analysis," Genome Research, 2002, 12:1401-1407.
Nam et al., "Nanoparticle-Based Bio-Bar Codes for the Ultrasensitive Detection of Proteins," Science, Sep. 26, 2003, 301(5641):1884-1886.
Redmond et al., "Single-cell TCRseq: paired recovery of entire T-cell alpha and beta chain transcripts in T-cell receptors from single-cell RNAseq," Genome Med, 2016, 8:80, 12 pages.
Kuhn et al., "A novel, high-performance random array platform for quantitative gene expression profiling," Genome Res, 2004, 14:2347-2356.
10xGenomics.com, [online], "Visium Spatial Gene Expression Reagent Kits—User Guide," Jan. 2022, retrieved on Jun. 27, 2024, retrieved from URL<https://web.archive.org/web/20230326192142/https://www.10xgenomics.com/support/spatial-gene-expression-fresh-frozen/documentation/steps/library-construction/visium-spatial-gene-expression-reagent-kits-user-guide>, 71 pages.
Wikipedia, "Algae," Wikipedia.com, retrieved on Mar. 4, 2016, retrieved from URL <https://en.wikipedia.org/wiki/Algae>, 20 pages.

(56) References Cited

OTHER PUBLICATIONS

Wikipedia, "Archaea," Wikipedia.com, retrieved on Sep. 8, 2023, retrieved from URL <https://en.wikipedia.org/wiki/Archaea>, 22 pages.

Wikipedia, "Fish," Wikipedia.com, retrieved on Sep. 8, 2023, retirieved from URL <https://en.wikipedia.org/wiki/Fish>, 19 pages.

Wikipedia, "Fungus," Wikipedia.com, retrieved on Sep. 8, 2023, retrieved from URL <https://en.wikipedia.org/wiki/Fungus>, 26 pages.

Wikipedia, "Insect," Wikipedia.com, retrieved on Jun. 4, 2024, retrieved from URL <https://en.wikipedia.org/wiki/Insect>, 41 pages.

Wikipedia, "Mammal," Wikipedia.com, retrieved on May 11, 2023, retrieved from URL <https://en.wikipedia.org/wiki/Mammal>, pp. 1-49.

Wikipedia, "Murinae," Wikipedia.com, retrieved on Sep. 8, 2023, retrieved from URL <https://en.wikipedia.org/wiki/Murinae>, 12 pages.

Wikipedia, "Oligonucleotide," Wikipedia.com, available on or before Feb. 17, 2019, 7 pages.

Wikipedia, "Plant," Wikipedia.com, retrieved on Sep. 8, 2023, retrieved from URL <https://en.wikipedia.org/wiki/Plant>, 25 pages.

Wikipedia, "Protozoa," Wikipedia.com, retrieved on May 11, 2016, retrieved from URL <https://en.wikipedia.org/wiki/Protozoa>, 10 pages.

Wikipedia, "Viruses," Wikipedia.com, retrieved on Sep. 8, 2023, retrieved from URL <https://en.wikipedia.org/wiki/Viruses>, 43 pages.

Wisegeek, "How many species of bacteria are there," wisegeek.com, retrieved on Jan. 21, 2014, retrieved from URL <http://www.wisegeek.org/how-many-species-of-bacteria-are-there.htm>, 2 pages.

Monaghan et al., "A nuclear role for the respiratory enzyme CLK-1/COQ7 in regulating mitochondrial stress responses and longevity," Nat Cell Bio, May 11, 2015, 17(6):782-792, 20 pages.

Grigoryev, "How DNA microarrays are built," Bitesize Bio, first published Jul. 13, 2011, updated Oct. 2021, retrieved from URL <https://bitesizebio.com/7206/introduction-to-dna-microarrays/#:~:text=Microarrays%20evolved%20from%20a%20technique%20known%20as%20Southern,were%20constructed%20by%20immobilizing%20cDNAs%20onto%20filter%20paper.>, 11 pages.

Voelkerding et al., "Next-Generation Sequencing: From Basic Research to Diagnostics," Clinical Chemistry, 2009, 55(4):641-658.

\* cited by examiner

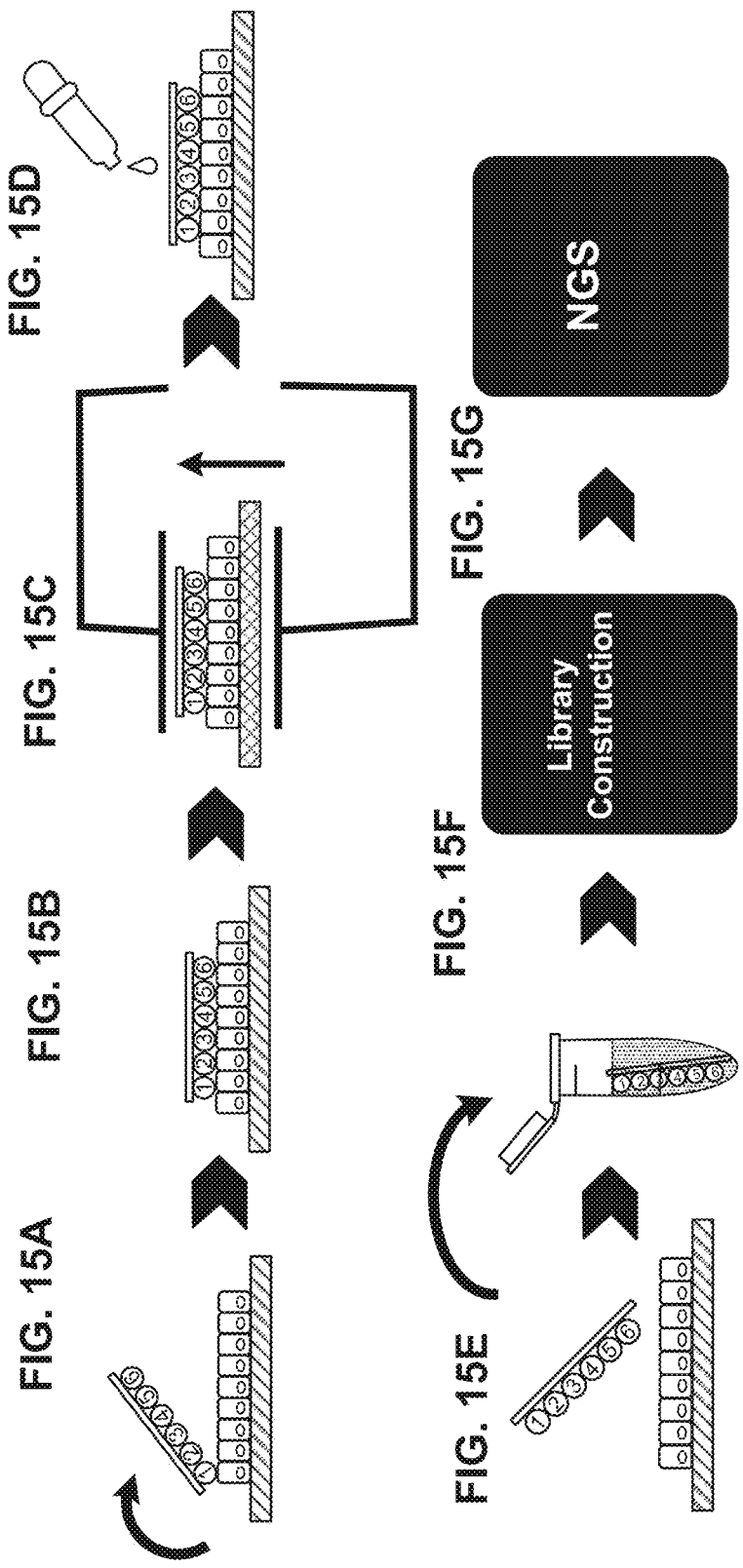

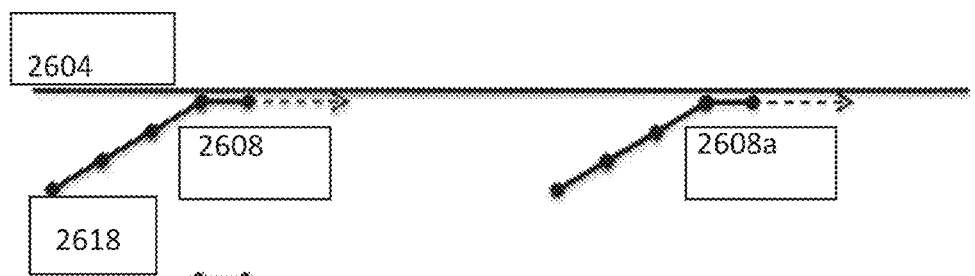
FIG. 22A
FIG. 22B
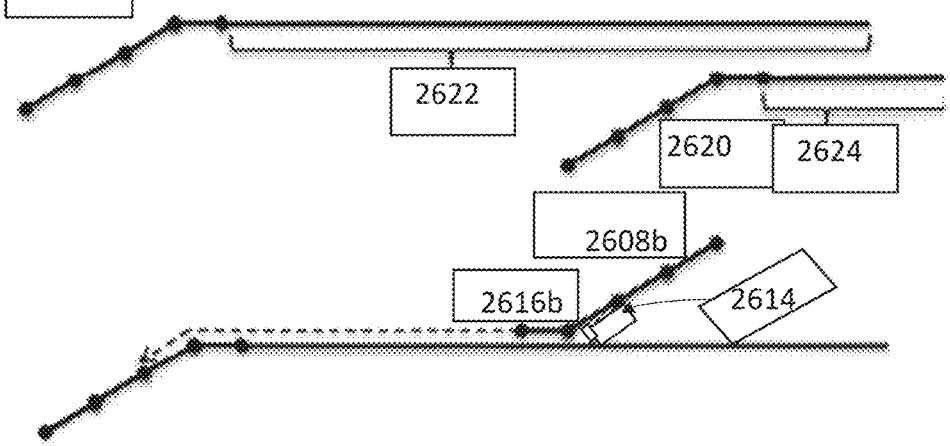
FIG. 22C
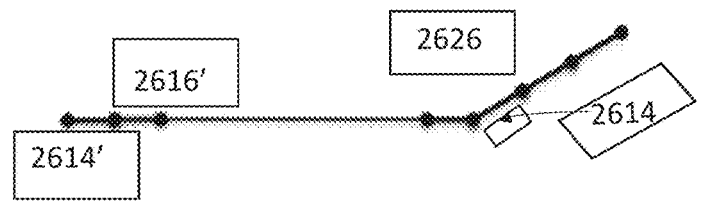
FIG. 22D

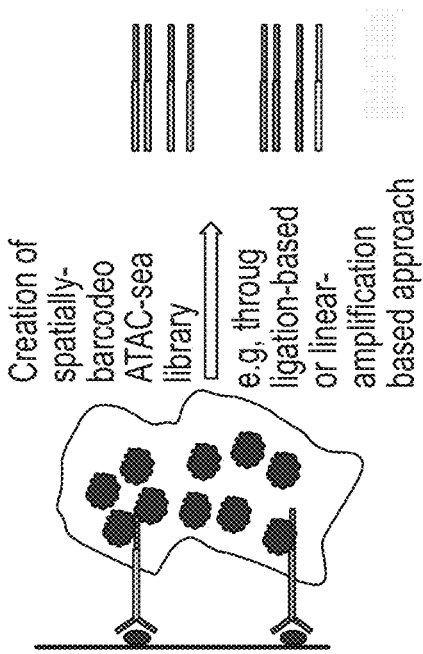
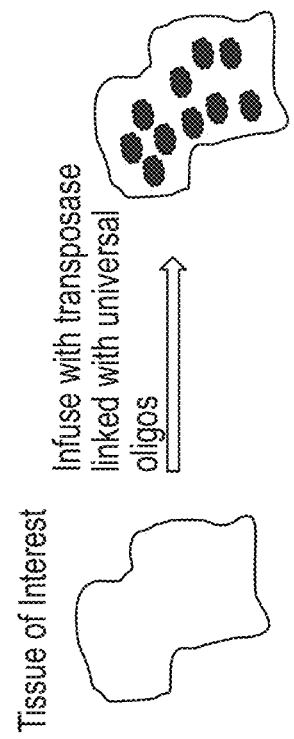
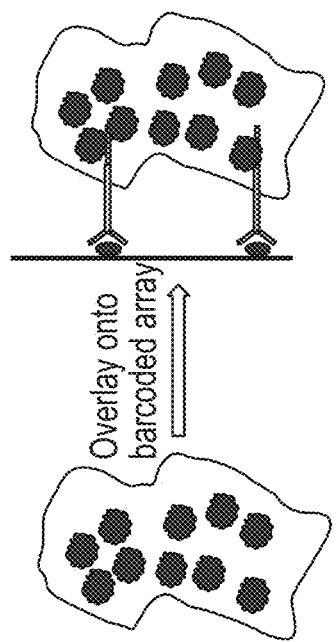
FIG. 23A
FIG. 23B
FIG. 23C

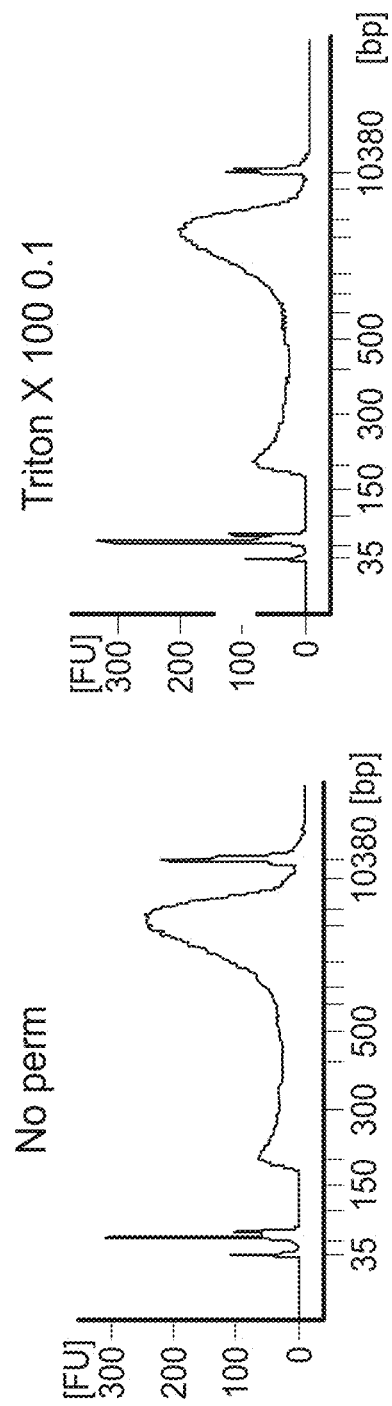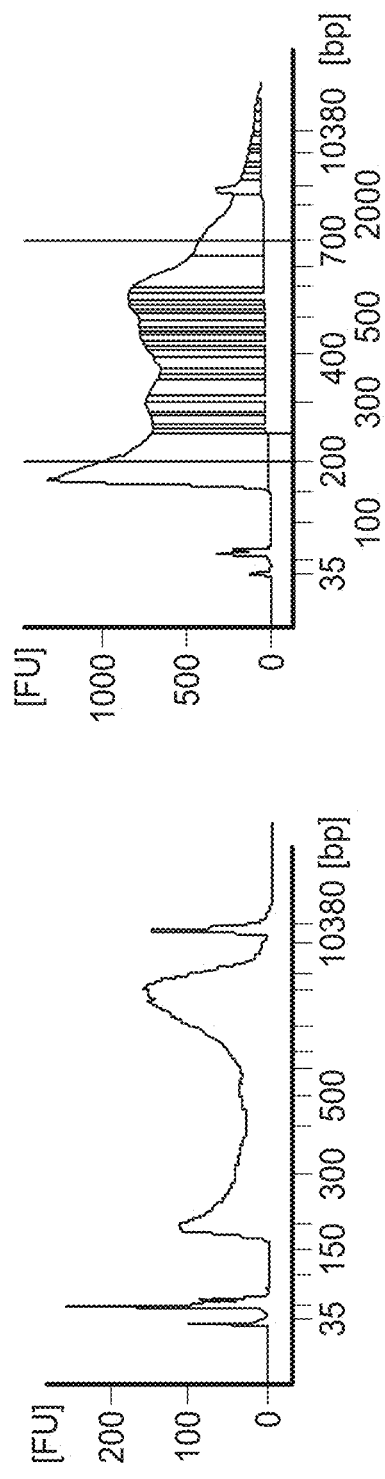
FIG. 30A FIG. 30B FIG. 30C FIG. 30D

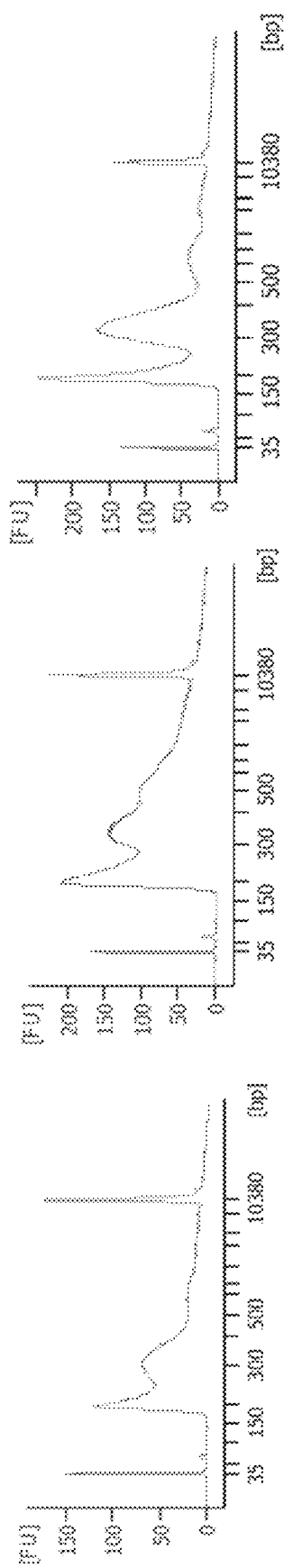

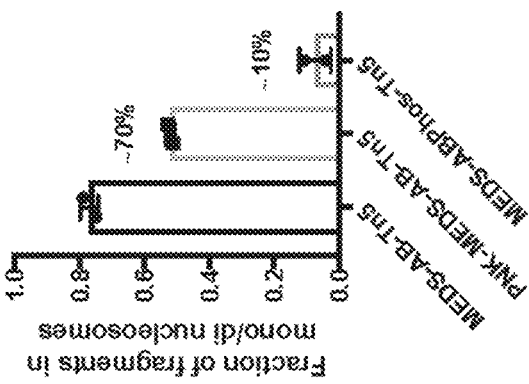
FIG. 35D
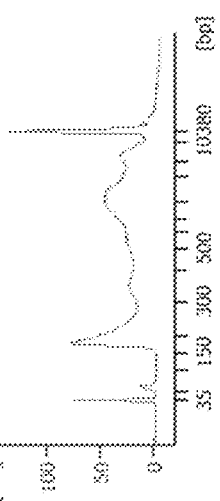
FIG. 35C
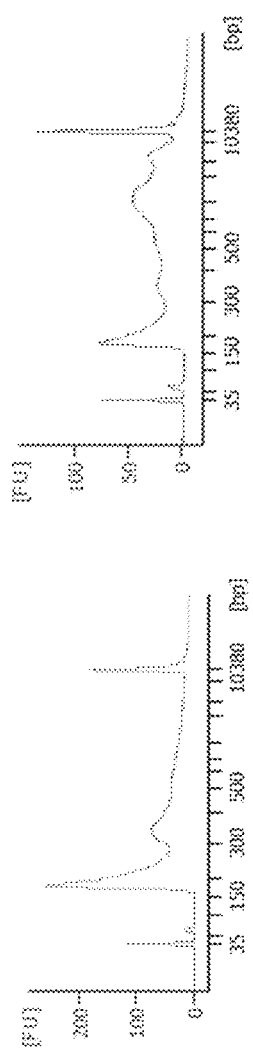
FIG. 35A
FIG. 35B

|   | 1 | 2 |
|---|---|---|
| C | Pre-hyb HP<br>Ligation (TNS PHO+)<br>+<br>strand displacement<br>polymerization | Pre-hyb HP<br>Ligation (TNS PHO+)<br>+<br>strand displacement<br>polymerization |
| D | Pre-hyb HP<br>Ligation (TNS PHO-)<br>+<br>strand displacement<br>polymerization | Pre-hyb HP<br>Ligation (TNS PHO-)<br>+<br>strand displacement<br>polymerization |
| E | Pre-hyb HP<br>Ligation (Water)<br>+<br>strand displacement<br>polymerization | Pre-hyb HP<br>Ligation (water)<br>+<br>strand displacement<br>polymerization |

FIG. 41A

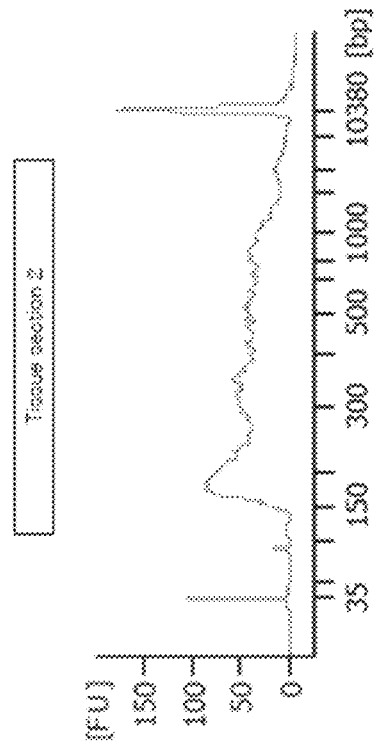
FIG. 45B
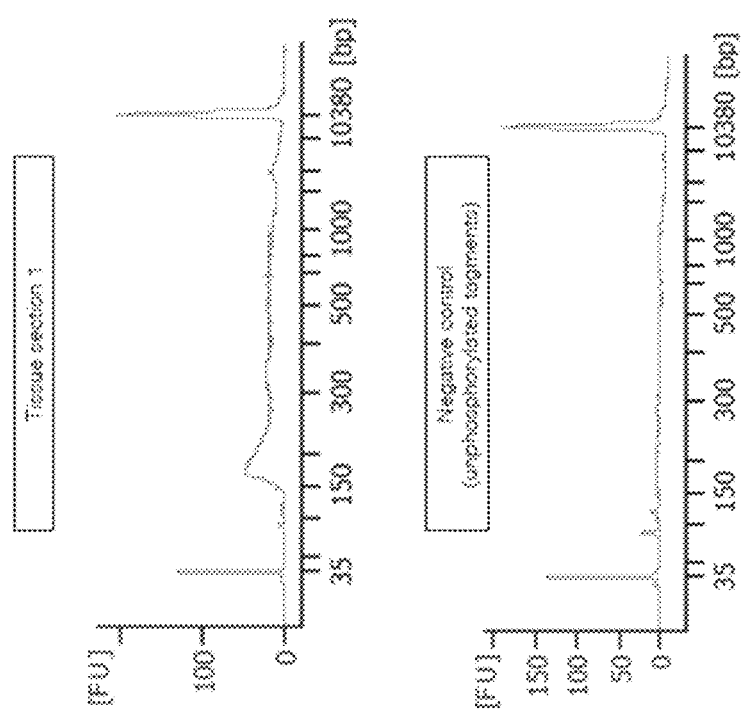
FIG. 45A
FIG. 45C

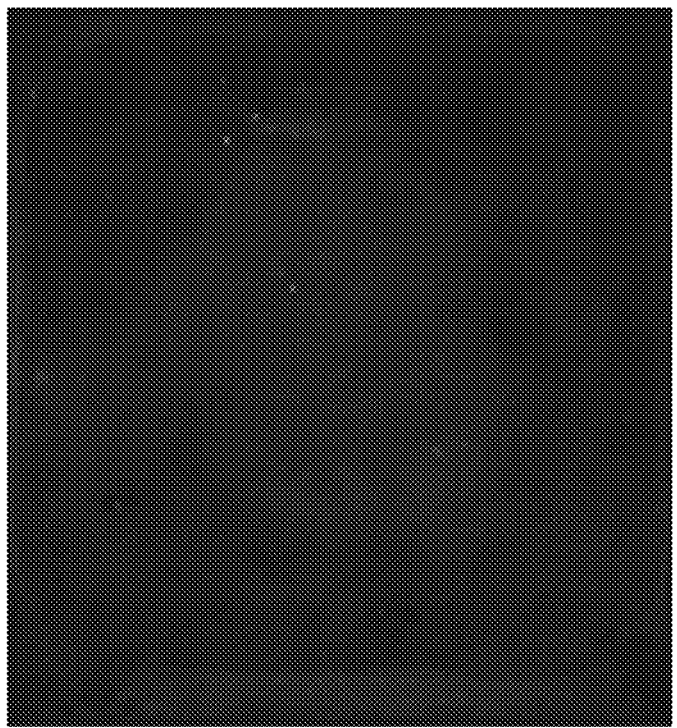
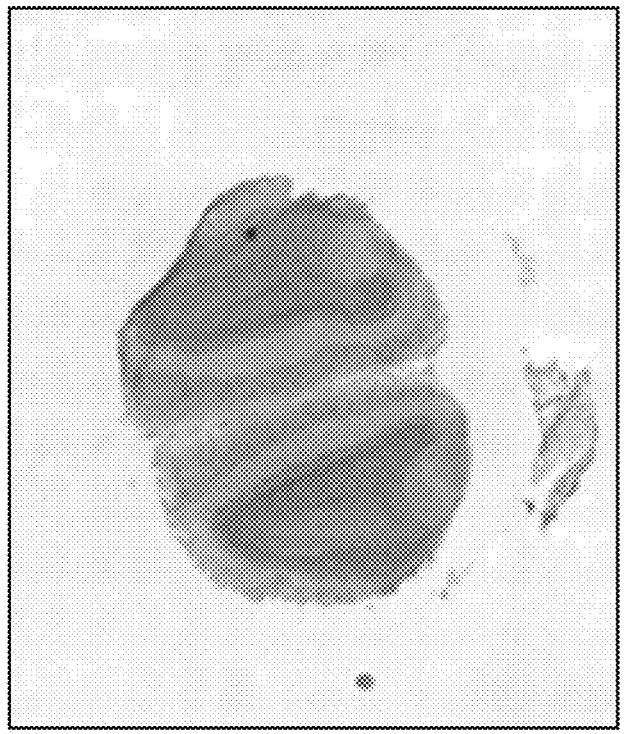
Fluorescent prob hybridisation reveals the ligation of genomic DNA tagments from the immobilized tissue to the surface oligonuclotide
FIG. 45D

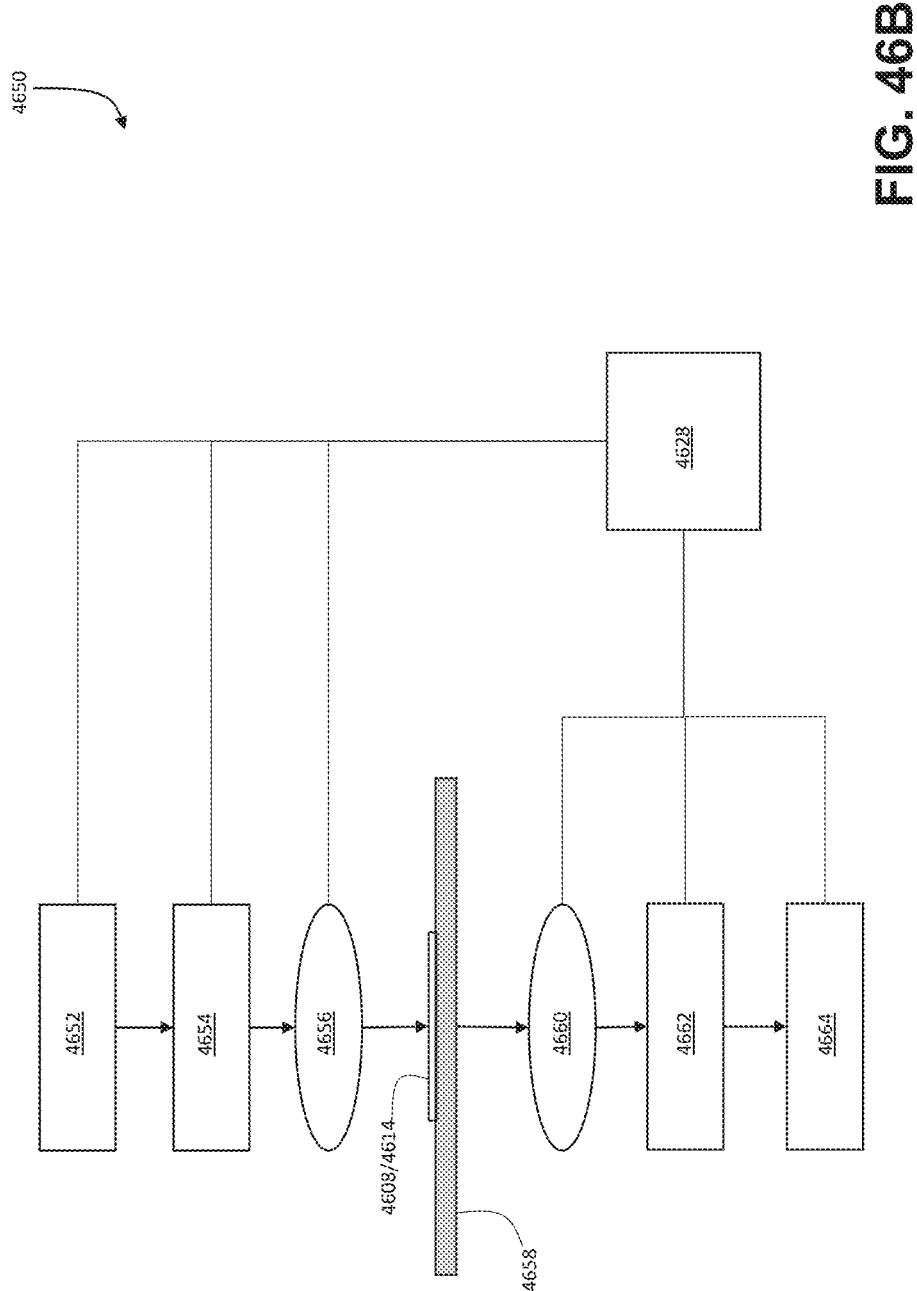

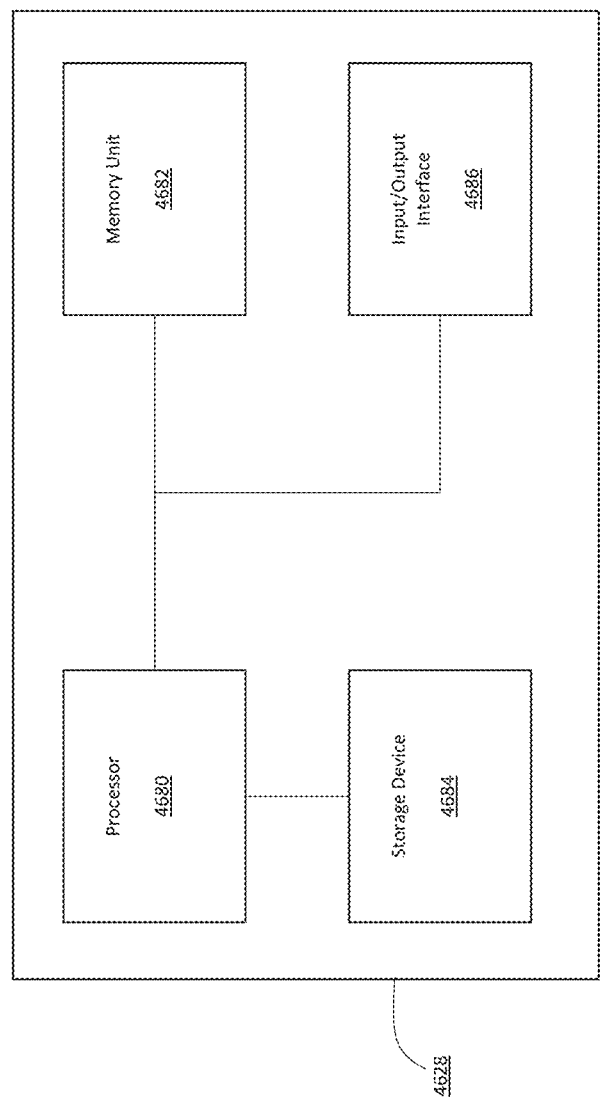

SEQUENCE LISTING

Sequence total quantity: 26
SEQ ID NO: 1                moltype = AA   length = 476
FEATURE                     Location/Qualifiers
source                      1..476
                            mol_type = protein
                            organism = Escherichia coli
SEQUENCE: 1
MITSALHRAA DWAKSVFSSA ALGDPRRTAR LVNVAAQLAK YSGKSITISS EGSEAMQEGA   60
YRFIRNPNVS AEAIRKAGAM QTVKLAQEFP ELLAIEDTTS LSYRHQVAEE LGKLGSIQDK  120
SRGWWVHSVL LLEATTFRTV GLLHQEWWMR PDDPADADEK ESGKWLAAAA TSRLRMGSMM  180
SNVIAVCDRE ADIHAYLQDK LAHNERFVVR SKHPRKDVES GLYLYDHLKN QPELGGYQIS  240
IPQKGVVDKR GKRKNRPARK ASLSLRSGRI TLKQGNITLN AVLAEEINPP KGETPLKWLL  300
LTSEPVESLA QALRVIDIYT HRWRIEEFHK AWKTGAGAER QRMEEPDNLE RMVSILSFVA  360
VRLLQLRESF TLPQALRAQG LLKEAEHVES QSAETVLTPD ECQLLGYLDK GKRKRKEKAG  420
SLQWAYMAIA RLGGFMDSKR TGIASWGALW EGWEALQSKL DGFLAAKDLM AQGIKI       476

SEQ ID NO: 2                moltype = AA   length = 662
FEATURE                     Location/Qualifiers
source                      1..662
                            mol_type = protein
                            organism = Bacteriophage mu
SEQUENCE: 2
MKEWYTAKEL LGLAGLPKQA TNITRKAQRE GWEFRQVAGT KGVSFEFNIK SFPVALRAEI   60
LLQQGRIETS QGYFEIARPT LEAHDYDREA LWSKWDNASD SQRRLAEKWL PAVQAADEML  120
NQGISTKTAF ATVAGHYQVS ASTLRDKYYQ VQKFAKPDWA AALVDGRGAS RRNVHKSEFD  180
EDAWQFLIAD YLRPEKPAFR KCYERELAEA REHGWSIPSR ATAFRRIQQL DEAMVVACRE  240
GEHALMHLIP AQQRTVEHLD AMQWINGDGY LHNVFVRWFN GDVIRPKTWF WQDVKTRKIL  300
GWRCDVSENI DSIRLSFMDV VTRYGIPEDF HITIDNTRGA ANKWLTGGAP NRYRFKVKED  360
DPKGLFLLMG AKMHWTSVVA GKGWGQAKPV ERAFGVGGLE EYVDKHPALA GAYTGPNPQA  420
KPDNYGDRAV DAELFLKTLA EGVAMFNART GRETEMCGGK LSFDDVFERE YARTIVRKPT  480
EEQKRMLLLP AEAVNVSRKG EFALKVGGSL KGAKNVYYNM ALMNAGVKKV VVRFDPQQLH  540
STVYCYTLDG RFICEAECLA PVAFNDAAAG REYRRRQKQL KSATKAAIKA QKQMDALEVA  600
ELLPQIAEPE APESRIVGIF RPSGNTERVK NQERDDEYET ERDEYLNHSL DILEQNRRKK  660
AI                                                                 662

SEQ ID NO: 3                moltype = AA   length = 326
FEATURE                     Location/Qualifiers
source                      1..326
                            mol_type = protein
                            organism = Sus scrofa

```
SEQUENCE: 3
IGDEPLENYL DTEYFGTIGI GTPAQDFTVI FDTGSSNLWV PSVYCSSLAC SDHNQFNPDD    60
SSTFEATSQE LSITYGTGSM TGILGYDTVQ VGGISDTNQI FGLSETEPGS FLYYAPFDGI   120
LGLAYPSISA SGATPVFDNL WDQGLVSQDL FSVYLSSNDD SGSVVLLGGI DSSYYTGSLN   180
WVPVSVEGYW QITLDSITMD GETIACSGGC QAIVDTGTSL LTGPTSAIAN IQSDIGASEN   240
SDGEMVISCS SIDSLPDIVF TINGVQYPLS PSAYILQDDD SCTSGFEGMD VPTSSGELWI   300
LGDVFIRQYY TVFDRANNKV GLAPVA                                       326

SEQ ID NO: 4            moltype = AA  length = 330
FEATURE                 Location/Qualifiers
source                  1..330
                        mol_type = protein
                        organism = Bos taurus
SEQUENCE: 4
AATLVSEQPL QNYLDTEYFG TIGIGTPAQD FTVIFDTGSS NLWVPSIYCS SEACTNHNRF    60
NPQDSSTYEA TSETLSITYG TGSMTGILGY DTVQVGGISD TNQIFGLSET EPGSFLYYAP   120
FDGILGLAYP SISSSGATPV FDNIWDQGLV SQDLFSVYLS SNEESGSVVI FGDIDSSYYS   180
GSLNWVPVSV EGYWQITVDS ITMNGESIAC SDGCQAIVDT GTSLLAGPTT AISNIQSYIG   240
ASEDSSGEVV ISCSSIDSLP DIVFTINGVQ YPVPPSAYIL QSNGICSSGF EGMDISTSSG   300
DLWILGDVFI RQYFTVFDRG NNQIGLAPVA                                   330

SEQ ID NO: 5            moltype = AA  length = 1008
FEATURE                 Location/Qualifiers
source                  1..1008
                        mol_type = protein
                        organism = Clostridium histolyticum
SEQUENCE: 5
IANTNSEKYD FEYLNGLSYT ELTNLIKNIK WNQINGLFNY STGSQKFFGD KNRVQAIINA    60
LQESGRTYTA NDMKGIETFT EVLRAGFYLG YYNDGLSYLN DRNFQDKCIP AMIAIQKNPN   120
FKLGTAVQDE VITSLGKLIG NASANAEVVN NCVPVLKQFR ENLNQYAPDY VKGTAVNELI   180
KGIEFDFSGA AYEKDVKTMP WYGKIDPFIN ELKALGLYGN ITSATEWASD VGIYYLSKFG   240
LYSTNRNDIV QSLEKAVDMY KYGKIAFVAM ERITWDYDGI GSNGKKVDHD KPLDDAEKHY   300
LPKTYTFDNG TFIIRAGDKV SEEKIKRLYW ASREVKSQFH RVVGNDKALE VGNADDVLTM   360
KIFNSPEEYK FNTNINGVST DNGGLYIEPR GTFYTYERTP QQSIFSLEEL FRHEYTHYLQ   420
ARYLVDGLWG QGPFYEKNRL TWFDEGTAEF FAGSTRTSGV LPRKSILGYL AKDKVDHRYS   480
LKKTLNSGYD DSDWMFYNYG FAVAHYLYEK DMPTFIKMNK AILNTDVKSY DEIIKKLSDD   540
ANKNTEYQNH IQELADKYQG AGIPLVSDDY LKDHGYKKAS EVYSEISKAA SLTNTSVTAE   600
KSQYFNTFTL RGTYTGETSK GEFKDWDEMS KKLDGTLESL AKNSWSGYKT LTAYFTNYRV   660
TSDNKVQYDV VFHGVLTDNA DISNNKAPIA KVTGPSTGAV GRNIEFSGKD SKDEDGKIVS   720
YDWDFGDGAT SRGKNSVHAY KKAGTYNVTL KVTDDKGATA TESFTIEIKN EDTTTPITKE   780
MEPNDDIKEA NGPIVEGVTV KGDLNGSDDA DTFYFDVKED GDVTIELPYS GSSNFTWLVY   840
KEGDDQNHIA SGIDKNNSKV GTFKSTKGRH YVFIYKHDSA SNISYSLNIK GLGNEKLKEK   900
ENNDSSDKAT VIPNFNTTMQ GSLLGDDSRD YYSFEVKEEG EVNIELDKKD EFGVTWTLHP   960
ESNINDRITY GQVDGNKVSN KVKLRPGKYY LLVYKYSGSG NYELRVNK              1008

SEQ ID NO: 6            moltype = AA  length = 981
FEATURE                 Location/Qualifiers
source                  1..981
                        mol_type = protein
                        organism = Clostridium histolyticum
SEQUENCE: 6
VQNESKRYTV SYLKTLNYYD LVDLLVKTEI ENLPDLFQYS SDAKEFYGNK TRMSFIMDEI    60
GRRAPQYTEI DHKGIPTLVE VVRAGFYLGF HNKELNEINK RSFKERVIPS ILAIQKNPNF   120
KLGTEVQDKI VSATGLLAGN ETAPPEVVNN FTPILQDCIK NIDRYALDDL KSKALFNVLA   180
APTYDITEYL RATKEKPENT PWYGKIDGFI NELKKLALYG KIDNNSWII DNGIYHIAPL   240
GKLHSNNKIG IETLTEVMKV YPYLSMQHLQ SADQIKRHYD SKDAEGNKIP LDKFKKEGKE   300
KYCPKTYTFD DGKVIIKAGA RVEEEKVKRL YWASKEVNSQ FFRVYGIDKP LEEGNPDDIL   360
TMVIYNSPEE YKLNSVLYGY DTNNGGMYIE PEGTFFTYER EAQESTYTLE ELFRHEYTHY   420
LQGRYAVPGQ WGRTKLYDND RLTWYEEGGA ELFAGSTRTS GILPRKSIVS NIHNTTRNNR   480
YKLSDTVHSK YGASFEFYNY ACMFMDYMYN KDMGILNKLN DLAKNNDVDG YDNYIRDLSS   540
NYALNDKYQD HMQERIDNYE NLTVPFVADD YLVRHAYKNP NEIYSEISEV AKLKDAKSEV   600
KKSQYFSTFT LRGSYTGGAS KGKLEDQKAM NKFIDDSLKK LDTYSWSGYK TLTAYFTNYK   660
VDSSNRVTYD VVFHGYLPNE GDSKNSLPYG KINGTYKGTE KEKIKFSSEG SFPDPDGKIVS  720
YEWDFGDGNK SNEENPEHSY DKVGTYTVKL KVTDDKGESS VSTTTAEIKD LSENKLPVIY   780
MHVPKSGALN QKVVFYGKGT YDPDGSIAGY QWDFGDGSDF SSEQNPSHVY TKKGEYTVTL   840
RVMDSSGQMS EKTMKIKITD PVYPIGTEKE PNNSKETASG PIVPGIPVSG TIENTSDQDY   900
FYFDVITPGE VKIDINKLGY GGATWVVYDE NNNAVSYATD DGQNLSGKFK ADKPGRYYIH   960
LYMFNGSYMP YRINIEGSVG R                                            981

SEQ ID NO: 7            moltype = AA  length = 279
FEATURE                 Location/Qualifiers
source                  1..279
                        mol_type = protein
                        organism = Tritirachium album
SEQUENCE: 7
AAQTNAPWGL ARISSTSPGT STYYYDESAG QGSCVYVIDT GIEASHPEFE GRAQMVKTYY    60
YSSRDGNGHG THCAGTVGSR TYGVAKKTQL FGVKVLDDNG SGQYSTIIAG MDFVASDKNN   120
RNCPKGVVAS LSLGGGYSSS VNSAAARLQS SGVMVAAAG NNNADARNYS PASEPSVCTV   180
GASDRYDRRS SFSNYGSVLD IFGPGTSILS TWIGGSTRSI SGTSMATPHV AGLAAYLMTL   240
```

GKTTAASACR YIADTANKGD LSNIPFGTVN LLAYNNYQA                                         279

```
SEQ ID NO: 8              moltype = DNA   length = 19
FEATURE                   Location/Qualifiers
misc_feature              1..19
                          note = Tn5 Mosaic end sequence
source                    1..19
                          mol_type = other DNA
                          organism = synthetic construct
SEQUENCE: 8
ctgtctctta tacacatct                                                              19

SEQ ID NO: 9              moltype = DNA   length = 27
FEATURE                   Location/Qualifiers
misc_feature              1..27
                          note = Mu transposase recognition sequence
source                    1..27
                          mol_type = other DNA
                          organism = synthetic construct
SEQUENCE: 9
tgaagcggcg cacgaaaaac gcgaaag                                                     27

SEQ ID NO: 10             moltype = DNA   length = 23
FEATURE                   Location/Qualifiers
misc_feature              1..23
                          note = Mu transposase recognition sequence
source                    1..23
                          mol_type = other DNA
                          organism = synthetic construct
SEQUENCE: 10
gcgtttcacg ataaatgcga aaa                                                         23

SEQ ID NO: 11             moltype = DNA   length = 23
FEATURE                   Location/Qualifiers
misc_feature              1..23
                          note = Mu transposase recognition sequence
source                    1..23
                          mol_type = other DNA
                          organism = synthetic construct
SEQUENCE: 11
ctgtttcatt tgaagcgcga aag                                                         23

SEQ ID NO: 12             moltype = DNA   length = 27
FEATURE                   Location/Qualifiers
misc_feature              1..27
                          note = Mu transposase recognition sequence
source                    1..27
                          mol_type = other DNA
                          organism = synthetic construct
SEQUENCE: 12
tgtattgatt cacttgaagt acgaaaa                                                     27

SEQ ID NO: 13             moltype = DNA   length = 23
FEATURE                   Location/Qualifiers
misc_feature              1..23
                          note = Mu transposase recognition sequence
source                    1..23
                          mol_type = other DNA
                          organism = synthetic construct
SEQUENCE: 13
ccttaatcaa tgaaacgcga aag                                                         23

SEQ ID NO: 14             moltype = DNA   length = 23
FEATURE                   Location/Qualifiers
misc_feature              1..23
                          note = Mu transposase recognition sequence
source                    1..23
                          mol_type = other DNA
                          organism = synthetic construct
SEQUENCE: 14
ttgtttcatt gaaaatacga aaa                                                         23

SEQ ID NO: 15             moltype = DNA   length = 79
FEATURE                   Location/Qualifiers
source                    1..79
                          mol_type = other DNA
                          organism = synthetic construct
SEQUENCE: 15
tttttgactc gtaatacgac tcactatagg gacacgacgc tcttccgatc tnnnnnnnnt                 60
```

```
gcacgcggtg tacagacgt                                                  79

SEQ ID NO: 16          moltype = DNA  length = 15
FEATURE                Location/Qualifiers
misc_feature           1..15
                       note = First Adapter
source                 1..15
                       mol_type = other DNA
                       organism = synthetic construct
SEQUENCE: 16
gtctcgtggg ctcgg                                                      15

SEQ ID NO: 17          moltype = DNA  length = 15
FEATURE                Location/Qualifiers
misc_feature           1..15
                       note = Capture Domain
source                 1..15
                       mol_type = other DNA
                       organism = synthetic construct
SEQUENCE: 17
ccgagcccac gagac                                                      15

SEQ ID NO: 18          moltype = DNA  length = 20
FEATURE                Location/Qualifiers
misc_feature           1..20
                       note = Hybridization Domain
source                 1..20
                       mol_type = other DNA
                       organism = synthetic construct
SEQUENCE: 18
tgcacgcggt gtacagacgt                                                 20

SEQ ID NO: 19          moltype = DNA  length = 20
FEATURE                Location/Qualifiers
misc_feature           1..20
                       note = Splint oligonucleotide complementary to
                        hybridization domain
source                 1..20
                       mol_type = other DNA
                       organism = synthetic construct
SEQUENCE: 19
acgtctgtac accgcgtgca                                                 20

SEQ ID NO: 20          moltype = DNA  length = 14
FEATURE                Location/Qualifiers
misc_feature           1..14
                       note = Second adapter
source                 1..14
                       mol_type = other DNA
                       organism = synthetic construct
SEQUENCE: 20
tcgtcggcag cgtc                                                       14

SEQ ID NO: 21          moltype = DNA  length = 20
FEATURE                Location/Qualifiers
misc_feature           1..20
                       note = A-Short forward
source                 1..20
                       mol_type = other DNA
                       organism = synthetic construct
SEQUENCE: 21
acacgacgct cttccgatct                                                 20

SEQ ID NO: 22          moltype = AA  length = 16
FEATURE                Location/Qualifiers
source                 1..16
                       mol_type = protein
                       organism = synthetic construct
SEQUENCE: 22
RADARADARA DARADA                                                     16

SEQ ID NO: 23          moltype = AA  length = 16
FEATURE                Location/Qualifiers
REGION                 1..16
                       note = Synthetic EAK16 polypeptide sequence
source                 1..16
                       mol_type = protein
                       organism = synthetic construct
SEQUENCE: 23
```

```
AEAEAKAKAE AEAKAK                                                              16

SEQ ID NO: 24          moltype = AA  length = 12
FEATURE                Location/Qualifiers
REGION                 1..12
                       note = Synthetic KLD12 polypeptide sequence
source                 1..12
                       mol_type = protein
                       organism = synthetic construct
SEQUENCE: 24
KLDLKLDLKL DL                                                                  12

SEQ ID NO: 25          moltype = DNA  length = 10
FEATURE                Location/Qualifiers
misc_feature           1..10
                       note = Poly(A) tail added to 3' ends of tagmented DNA
source                 1..10
                       mol_type = other DNA
                       organism = synthetic construct
SEQUENCE: 25
aaaaaaaaaa                                                                     10

SEQ ID NO: 26          moltype = AA  length = 20
FEATURE                Location/Qualifiers
REGION                 1..20
                       note = Capture probe
source                 1..20
                       mol_type = protein
                       organism = synthetic construct
SEQUENCE: 26
TTTTTTTTTT TTTTTTTTTT                                                          20
```

METHOD FOR TRANSPOSASE-MEDIATED SPATIAL TAGGING AND ANALYZING GENOMIC DNA IN A BIOLOGICAL SAMPLE

CROSS-REFERENCE TO RELATED APPLICATIONS

Pursuant to 35 U.S.C. § 120, this application is a continuation of U.S. patent application Ser. No. 17/933,347, filed Sep. 19, 2022, which is a continuation of U.S. patent application Ser. No. 17/668,241, filed Mar. 7, 2022 which is a continuation of U.S. patent application Ser. No. 16/876,682, filed May 18, 2020, which is a continuation of International Patent Application PCT/US2019/048425, with an international filing date of Aug. 27, 2019, which claims priority to U.S. Provisional Patent Application No. 62/724,483, filed Aug. 29, 2018, U.S. Provisional Patent Application No. 62/779,342, U.S. Provisional Patent Application No. 62/723,970, filed Aug. 28, 2018, U.S. Provisional Patent Application No. 62/723,972, filed Aug. 28, 2018, U.S. Provisional Patent Application No. 62/724,487, filed Aug. 29, 2018, U.S. Provisional Patent Application No. 62/724,489, filed Aug. 29, 2018, U.S. Provisional Patent Application No. 62/788,905, filed Jan. 6, 2019, U.S. Provisional Patent Application No. 62/788,871, filed Jan. 6, 2019, U.S. Provisional Patent Application No. 62/788,897, filed Jan. 6, 2019, U.S. Provisional Patent Application No. 62/788,885, filed Jan. 6, 2019, U.S. Provisional Patent Application No. 62/822,565, filed Mar. 22, 2019, U.S. Provisional Patent Application No. 62/822,592, filed Mar. 22, 2019, U.S. Provisional Patent Application No. 62/822,627, filed Mar. 22, 2019, U.S. Provisional Patent Application No. 62/822,605, filed Mar. 22, 2019, U.S. Provisional Patent Application No. 62/812,219, filed Feb. 28, 2019, U.S. Provisional Patent Application No. 62/839,223, filed Apr. 26, 2019 and U.S. Provisional Patent Application No. 62/858,331, filed on Jun. 7, 2019. The contents of each of these applications are incorporated herein by reference in their entireties.

SEQUENCE LISTING

This application contains a Sequence Listing that has been submitted electronically as an XML file named "47706-0036006_SL_ST26.XML." The XML file, created on Aug. 17, 2023, is 34,557 bytes in size. The material in the XML file is hereby incorporated by reference in its entirety.

BACKGROUND

Cells within a tissue of a subject have differences in cell morphology and/or function due to varied analyte levels (e.g., gene and/or protein expression) within the different cells. The specific position of a cell within a tissue (e.g., the cell's position relative to neighboring cells or the cell's position relative to the tissue microenvironment) can affect, e.g., the cell's morphology, differentiation, fate, viability, proliferation, behavior, and signaling and cross-talk with other cells in the tissue.

Spatial heterogeneity has been previously studied using techniques that only provide data for a small handful of analytes in the contact of an intact tissue or a portion of a tissue, or provide a lot of analyte data for single cells, but fail to provide information regarding the position of the single cell in a parent biological sample (e.g., tissue sample).

Chromatin structure can be different between cells in a biological sample or between biological samples from the same tissue. Assaying differences in accessible chromatin can be indicative of transcriptionally active sequences, e.g., genes, in a particular cell. Further understanding the transcriptionally active regions within chromatin will enable identification of which genes contribute to a cell's function and/or phenotype.

SUMMARY

The present disclosure generally describes methods for spatially analyzing genomic DNA present in a biological sample. In one aspect, the method comprises providing an array with a plurality of capture probes such that a capture probe of the plurality comprises a spatial barcode and a capture domain; permeabilizing the biological sample under conditions sufficient to make the genomic DNA in the biological sample accessible to a transposon insertion; providing a transposon sequence and a transposase enzyme to the biological sample under conditions wherein the transposon sequence is inserted into the genomic DNA; allowing the transposase enzyme to excise the inserted transposon sequence from the genomic DNA thus generating fragmented genomic DNA; contacting the biological sample comprising the fragmented genomic DNA with an array under conditions such that a capture probe interacts with the fragmented genomic DNA; and correlating the location of the capture probe on the array to a location in the biological sample, thereby spatially analyzing the fragmented genomic DNA.

In some embodiments, the array comprising a plurality of capture probes are provided on a substrate. In some embodiments, the array comprising the plurality of capture probes is provided on a feature. In some embodiments, the capture probe is directly or indirectly attached. In some embodiments, the array comprising the plurality of capture probes is provided on the feature on the substrate. In some embodiments, the substrate comprises a microfluidic channel. In some embodiments, the capture probe further comprises one or more of a cleavage domain, a functional domain, and a unique identifier, or combinations thereof.

In some embodiments, a further migration step comprising a step wherein the fragmented genomic DNA is migrated to the substrate. In some embodiments, the migration step is an active migration step comprising applying an electric field to the fragmented genomic DNA. In some embodiments, the migration step is a passive migration step comprising diffusion. In some embodiments, the migration of the fragmented genomic DNA from the biological sample comprises exposing the biological sample and the feature to heat. In some embodiments, the biological sample is immobilized on the substrate.

In some embodiments, the transposase enzyme is a dimer comprised of a first monomer complexed with a first adapter comprising a transposon end sequence and a sequence complementary to the capture domain and wherein a second monomer is complexed with a second adapter comprising a transposon end sequence and a second adapter sequence, wherein the transposase enzyme ligates the first adapter and the second adapter to the fragmented genomic DNA. In some embodiments, the first adapter and the second adapter have a 5' end and a 3' end, wherein the 5' end is phosphorylated in situ. In some embodiments, prior to fragmenting the DNA, the 5' end of the first adapter complexed with the first monomer and the second adapter complexed with the second monomer are phosphorylated. In some embodiments, the step of phosphorylating the 5' end of the first adapter complexed with the first monomer and the second adapter complexed with the second monomer comprises contacting a first monomer:first adapter complex and a second monomer:second adapter complex with a polynucleotide kinase in the presence of ATP.

In some embodiments, the capture domain of the capture probe comprises a sequence that hybridizes to the sequence complementary to the capture domain of the first adapter. In some embodiments, the capture probe is a partially double stranded molecule comprising a first strand comprising the capture domain hybridized to a second strand, and wherein the first strand templates the ligation of the first adapter to the second strand. In some embodiments, the first adapter sequence complementary to the capture domain, or portion thereof, hybridized to the capture probe templates the ligation and ligating the 5' end of the first adapter to the 3' end of the capture probe. In some embodiments, the capture probe comprises a surface probe and a splint oligonucleotide and the splint oligonucleotide comprises a sequence complementary to a hybridization domain of the surface probe. In some embodiments, the splint oligonucleotide comprises the capture domain with a sequence complementary to the first adapter, or portion thereof. In some embodiments, the splint oligonucleotide hybridizes to the first adapter, or portion thereof, and to the hybridization domain of the surface probe, or portion thereof. In some embodiments, ligation is performed in the presence of the splint oligonucleotide, thereby ligating the surface probe of the capture probe and the first adapter.

In some embodiments, the fragmented genomic DNA hybridized to the capture probe by the first adapter is an extension template used to produce an extended capture probe that comprises the sequences of the spatial barcode and a sequence complementary to the fragmented genomic DNA. In some embodiments, the capture probe hybridized to the fragmented genomic DNA is extended with a DNA polymerase. In some embodiments, the DNA polymerase has strand displacement activity. In some embodiments, a further step of gap repair of single stranded breaks in the fragmented genomic DNA.

In some embodiments, the sequence complementary to the capture domain is a unique sequence. In some embodiments, the capture probe is ligated to the fragmented genomic DNA by a DNA ligase enzyme. In some embodiments, the transposase enzyme is a Tn5 transposase, or a functional derivative thereof. In some embodiments, the Tn5 transposase enzyme comprises a sequence having at least 80% identity to SEQ ID NO: 1. In some embodiments, the transposase enzyme is a Mu transposase, or the functional derivative thereof. In some embodiments, the Mu transposase enzyme comprises a sequence having at least 80% identity to SEQ ID NO: 2. In some embodiments, the transposon end sequence comprises a sequence having at least 80% identity to SEQ ID NO: 8. In some embodiments, the transposon end sequence comprises a sequence having at least 80% identity to any one of SEQ ID NO: 9 to 14.

In some embodiments, permeabilizing the biological sample is performed under a chemical permeabilization condition, an enzymatic permeabilization condition, or both. In some embodiments, the chemical permeabilization condition comprises contacting the biological sample with an alkaline solution. In some embodiments, the enzymatic permeabilization condition comprises contacting the biological sample with an acidic solution comprising a protease enzyme. In some embodiments, the protease enzyme is an aspartyl protease, preferably a pepsin enzyme, a pepsin-like enzyme, or the functional equivalent thereof. In some embodiments, the pepsin enzyme, the pepsin-like enzyme, or the functional equivalent thereof, comprises a sequence having at least 80% identity to SEQ ID NO: 3 or 4.

In some embodiments, the enzymatic permeabilization condition comprises contacting the biological sample with a zinc endopeptidase, a collagenase enzyme, a collagenase-like enzyme, or a functional equivalent thereof, a serine protease, a proteinase K enzyme, a proteinase K-like enzyme, or a functional equivalent thereof, or both. In some embodiments, the collagenase enzyme, the collagenase-like enzyme, or the functional equivalent thereof comprises a sequence having at least 80% identity to SEQ ID NO: 5 or 6. In some embodiments, the proteinase K enzyme, the proteinase K-like enzyme, or the functional equivalent thereof comprises a sequence having at least 80% identity to SEQ ID NO: 7.

In some embodiments, the fragmented genomic DNA hybridized to the capture probe as the extension template generates a DNA molecule. In some embodiments, the fragmented genomic DNA hybridized to the capture probe acts as a ligation template to generate a DNA molecule. In some embodiments, the step comprising a step of analyzing the generated DNA molecule. In some embodiments, the step of analyzing the DNA molecule includes sequencing. In some embodiments, the step of correlating the spatial barcode of the capture probe with the fragmented genomic DNA associated with the capture probe spatially analyzes the fragmented genomic DNA. In some embodiments, the biological sample is imaged before or after contacting the biological sample with the substrate.

In a another aspect, the present disclosure generally describes a kit for use in a method of spatially detecting nucleic acids of a biological sample, wherein the kit comprises any two or more of an array on which plurality of capture probes are present; one or more biological sample permeabilization reagents; one or more transposase enzymes; one or more reverse transcriptases; and one or more cleavage enzymes.

In a different aspect, the present disclosure generally describes a method for spatial analysis of genomic DNA and RNA present in a biological sample wherein an array is provided and the array comprises a plurality of capture probes, wherein a first capture probe of the plurality of capture probes comprises a spatial barcode and a first capture domain, and wherein a second capture probe of the plurality of capture probes comprises the spatial barcode and a second capture domain; permeabilizing the biological sample under conditions sufficient to make the genomic DNA in the biological sample accessible to transposon insertion; providing a transposon sequence and a transposase enzyme to the biological sample under conditions wherein the transposon sequence is inserted into the genomic DNA; allowing the transposase enzyme to excise the inserted transposon sequence from the genomic DNA, thereby generating fragmented genomic DNA; contacting the biological sample comprising the fragmented genomic DNA and RNA with the array under conditions where the first capture domain interacts with the fragmented genomic DNA and the second capture domain interacts with the RNA; and correlating the location of the first capture probe on the array to a location in the biological sample and correlating the location of the second capture probe on the array to a location in the biological sample, thereby spatially analyzing the fragmented genomic DNA and RNA at the location in the biological sample.

In some embodiments, the RNA is a mRNA. In some embodiments, the first capture domain and the second capture domain are identical. In some embodiments, the first capture domain and the second capture domain comprise a homopolymeric poly (T) sequence. In some embodiments, the first capture domain and the second capture domain are different. In some embodiments, the first capture domain comprises a random sequence and the second capture domain comprises a poly (T) sequence. In some embodiments, the array comprising the plurality of capture probes is provided on a substrate. In some embodiments, the array comprising the plurality of capture probes is provided on a feature. In some embodiments, the feature comprises the first capture probe, the second capture probe, or both. In some embodiments, the first capture probe, the second capture probe, or both, are directly or indirectly attached. In some embodiments, the array comprising the plurality of capture probes is provided on the feature on the substrate. In some embodiments, the substrate comprises a microfluidic channel. In some embodiments, the first capture probe, the second capture probe, or both, comprise one or more of a cleavage domain, a functional domain, and a unique identifier, or combinations thereof.

In some embodiments, there is a migration step wherein the fragmented genomic DNA and the RNA are migrated to the substrate. In some embodiments, the migration step is an active migration step. In some embodiments, the migration step is a passive migration step. In some embodiments, the migration of the fragmented genomic DNA and the RNA from the biological sample comprises exposing the biological sample to heat. In some embodiments, the biological sample is immobilized on the substrate.

In some embodiments, the fragmented genomic DNA is repaired by ligating breaks with a ligase enzyme. In some embodiments, single stranded breaks in the fragmented genomic DNA undergo gap repair. In some embodiments, a sequence complementary to the first capture domain of the first capture probe is introduced to the fragmented genomic DNA. In some embodiments, the first capture domain of the first capture probe hybridizes to the sequence complementary to the capture domain introduced to the fragmented genomic DNA. In some embodiments, the random sequence of the first capture domain hybridizes the fragmented genomic DNA. In some embodiments, the second capture domain of the second capture probe hybridizes to a complementary sequence in the mRNA. In some embodiments, the sequence complementary to the first capture domain and the complementary sequence in the mRNA is a homopolymeric sequence. In some embodiments, the homopolymeric sequence is a poly(A) sequence.

In some embodiments, extension of the first capture probe using the fragmented genomic DNA as an extension template, and extension of the second capture probe using the RNA as an extension template is performed. In some embodiments, extending the first capture probe is performed with a DNA polymerase. In some embodiments, extending the second capture probe is performed with reverse transcriptase.

In some embodiments, transposase is a Tn5 transposase, or a functional derivative thereof. In some embodiments, the Tn5 transposase enzyme comprises a sequence having at least 80% identity to SEQ ID NO: 1. In some embodiments, the transposase enzyme is a Mu transposase enzyme, or a functional derivative thereof. In some embodiments, the Mu transposase enzyme comprises a sequence having at least 80% identity to SEQ ID NO: 2. In some embodiments, the transposase enzyme is complexed with an adapter comprising a transposon end sequence. In some embodiments, the transposon end sequence comprises a sequence having at least 80% identity to SEQ ID NO: 8. In some embodiments, the transposon end sequence comprises a sequence having at least 80% identity to any one of SEQ ID NO: 9 to 14.

In some embodiments, a step of permeabilizing the biological sample is performed. In some embodiments wherein permeabilizing the biological sample is performed under a chemical permeabilization condition, an enzymatic permeabilization condition, or both. In some embodiments, the chemical permeabilization condition comprises contacting the biological sample with an alkaline solution. In some embodiments, the enzymatic permeabilization condition comprises contacting the biological sample with an acidic solution comprising a protease enzyme. In some embodiments, the protease enzyme is an aspartyl protease, preferably a pepsin enzyme, a pepsin-like enzyme, or a functional equivalent thereof. In some embodiments, the pepsin enzyme, the pepsin-like enzyme, or functional equivalent thereof, comprises a sequence having at least 80% identity to SEQ ID NO: 3 or 4. In some embodiments, the enzymatic permeabilization condition comprises contacting the biological sample with a zinc endopeptidase, a collagenase enzyme, a collagenase-like enzyme, or a functional equivalent thereof, a serine protease, a proteinase K enzyme, a proteinase K-like enzyme, or a functional equivalent thereof, or both. In some embodiments, the collagenase enzyme, the collagenase-like enzyme, or the functional equivalent thereof comprises a sequence having at least 80% identity to SEQ ID NO: 5 or 6. I some embodiments, the proteinase K enzyme, the proteinase K-like enzyme, or the functional equivalent thereof comprises a sequence having at least 80% identity to SEQ ID NO: 7.

In some embodiments, step of analyzing the DNA molecule includes sequencing. In some embodiments, correlating the spatial barcode of the first capture probe with the fragmented genomic DNA associated with the first capture probe spatially analyzes the fragmented genomic DNA. In some embodiments, correlating the spatial barcode of the second capture probe with the mRNA associated with the second capture probe spatially analyzes the mRNA. In some embodiments, the biological sample is imaged before or after contacting the biological sample with the substrate.

All publications, patents, patent applications, and information available on the internet and mentioned in this specification are herein incorporated by reference to the same extent as if each individual publication, patent, patent application, or item of information was specifically and individually indicated to be incorporated by reference. To the extent publications, patents, patent applications, and items of information incorporated by reference contradict the disclosure contained in the specification, the specification is intended to supersede and/or take precedence over any such contradictory material.

Where values are described in terms of ranges, it should be understood that the description includes the disclosure of all possible sub-ranges within such ranges, as well as specific numerical values that fall within such ranges irrespective of whether a specific numerical value or specific sub-range is expressly stated.

The term "each," when used in reference to a collection of items, is intended to identify an individual item in the collection but does not necessarily refer to every item in the collection, unless expressly stated otherwise, or unless the context of the usage clearly indicates otherwise.

Various embodiments of the features of this disclosure are described herein. However, it should be understood that such embodiments are provided merely by way of example, and numerous variations, changes, and substitutions can occur to those skilled in the art without departing from the scope of this disclosure. It should also be understood that various alternatives to the specific embodiments described herein are also within the scope of this disclosure.

DESCRIPTION OF DRAWINGS

The following drawings illustrate certain embodiments of the features and advantages of this disclosure. These embodiments are not intended to limit the scope of the appended claims in any manner. Like reference symbols in the drawings indicate like elements.

FIGS. 15A-G is a schematic illustrating an exemplary workflow protocol utilizing an electrophoretic transfer system.

FIGS. 22A-D is a schematic diagram showing an example of spatially processing DNA from a biological sample.

FIGS. 23A-C is a schematic diagram showing an example of a spatial ATAC-seq method.

FIGS. 30A-E shows a DNA fragment analysis of tagmentation reactions performed according to the workflow in FIG. 27 comparing different detergents in the permeabilization step performed for 10 minutes at 25° C.: FIG. 30A) no detergent; FIG. 30B) 0.1% Triton-X-100; FIG. 30C) IGEPAL 0.1%; FIG. 30D) Tween 0.1%, Digitonin 0.01% and NP-40 0.1%. In FIG. 30E), insert size distribution analysis on a tissue section permeabilized with IGEBAL 0.1% and processed as in (Chen 2016 Nat Meth) fails to reveal a prominent nucleosome periodicity.

FIG. 31A) Pepsin (0.1 mg/ml) in presence of 100 mM HCL; FIG. 31B) Pepsin (0.5 mg/ml) in the presence of 0.5M acetic acid; FIG. 31C) Pepsin (0.1 mg/ml) in the presence of 0.5M acetic acid; and FIG. 31D) Proteinase K.

FIGS. 32A-C shows a DNA fragment analysis of tagmentation reactions performed according to the workflow in FIG. 27 comparing different permeabilization treatments on an immobilized tissue section: FIG. 32A) Pepsin (0.1 mg/ml) in the presence of 0.5 acetic acid; FIG. 32B) chemical permeabilization using 1× Exonuclease-I buffer (67 mM Glycine-KOH, 6.7 mM $MgCl_2$, 10 mM β-ME); and FIG. 32C) Collagenase.

FIG. 33A) MEDS-Tn5 assembled on column as in (Picelli, S., et. al., Tn5 transposase and tagmentation procedures for massively scaled sequencing projects; *Genome Res.*, vol. 24, 2033-2040 (2014)); FIG. 33B) MEDS-Tn5 assembled in solution as in (Picelli et al., 2014, supra); FIG. 33C) MEDS-Tn5 assembly with 5' phosphorylated oligonucleotides assembled in solution.

FIGS. 35A-D shows a DNA fragment analysis of tagmentation reactions performed according the workflow in FIG. 26 investigating the compatibility of post-assembly 5' phosphorylation with DNA tagmentation FIG. 35A) on-column assembled MEDS-AB-Tn5 as in (Picelli et al., 2014, supra): FIG. 35B) as FIG. 35A) but exposed to T4-PNK reaction conditions for 30 min at 37° C.; FIG. 35C) as FIG. 35B) but including T4-PNK enzyme; and FIG. 35D) a bar chart showing the quantification of the relative proportions of nucleosome-protected fragments recovered in FIGS. 35A-C.

FIG. 41A is a schematic diagram of a substrate outline under various experimental conditions following the workflow shown in FIG. 39 (ligation of phosphorylated DNA fragments from a whole human genome).

FIGS. 45A-D shows graphs and photographs showing the successful capture of DNA tagments from immobilized tissue sections according to the workflow shown in FIG. 44 with collagenase and Proteinase-K pre-permeabilization treatment. Each experiment was performed in duplicate: one experiment for PCR downstream analysis and one experiment for hybridization using a fluorescently labeled (Cy5) oligonucleotide complementary to the ligated tagments. The phosphate positive samples resulted in detectable signal (FIG. 45A and FIG. 45B), whereas the phosphate negative sample did not (FIG. 45C). FIG. 45D shows a hematoxylin-eosin image (left) and the corresponding spatial pattern of ligated DNA tagments (right) showing successful DNA capture from the tissue section.

FIG. 46B is a schematic diagram showing an example imaging apparatus that can be used to obtain images of biological samples, analytes, and arrays of features.

FIG. 46C is a schematic diagram of an example of a control unit of the apparatus of FIGS. 46A and 46B.

DETAILED DESCRIPTION

I. Introduction

Figure 1:
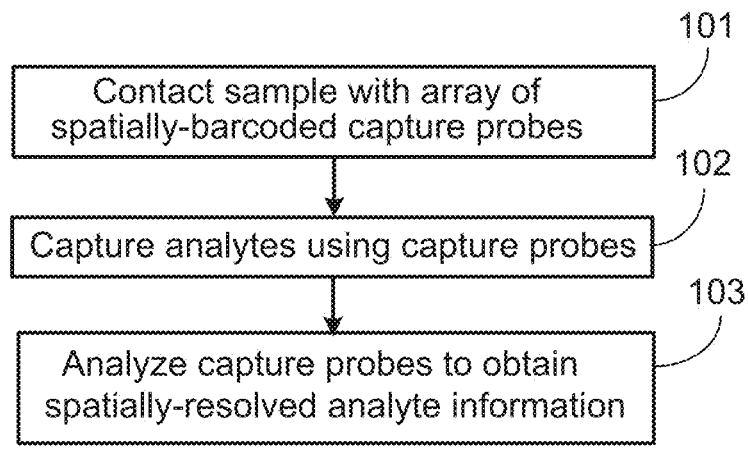
FIG. 1 shows an exemplary spatial analysis workflow.

This disclosure describes apparatus, systems, methods, and compositions for spatial analysis of biological samples. This section in particular describes certain general terminology, analytes, sample types, and preparative steps that are referred to in later sections of the disclosure.

(a) Spatial Analysis

Tissues and cells can be obtained from any source. For example, tissues and cells can be obtained from single-cell or multicellular organisms (e.g., a mammal). Tissues and cells obtained from a mammal, e.g., a human, often have varied analyte levels (e.g., gene and/or protein expression) which can result in differences in cell morphology and/or function. The position of a cell within a tissue can affect, e.g., the cell's fate, behavior, morphology, and signaling and cross-talk with other cells in the tissue. Information regarding the differences in analyte levels (gene and/or protein expression) within different cells in a tissue of a mammal can also help physicians select or administer a treatment that will be effective in the single-cell or multicellular organisms (e.g., a mammal) based on the detected differences in analyte levels within different cells in the tissue. Differences in analyte levels within different cells in a tissue of a mammal can also provide information on how tissues (e.g., healthy and diseased tissues) function and/or develop. Differences in analyte levels within different cells in a tissue of a mammal can also provide information of different mechanisms of disease pathogenesis in a tissue and mechanism of action of a therapeutic treatment within a tissue. Differences in analyte levels within different cells in a tissue of a mammal can also provide information on drug resistance mechanisms and the development of the same in a tissue of a mammal. Differences in the presence or absence of analytes within different cells in a tissue of a multicellular organism (e.g., a mammal) can provide information on drug resistance mechanisms and the development of the same in a tissue of a multicellular organism.

The spatial analysis methodologies provide for the detection of differences in an analyte level (e.g., gene and/or protein expression) within different cells in a tissue of a mammal or within a single cell from a mammal. For example, spatial analysis methodologies can be used to detect the differences in analyte levels (e.g., gene and/or protein expression) within different cells in histological slide samples, the data from which can be reassembled to generate a three-dimensional map of analyte levels (e.g., gene and/or protein expression) of a tissue sample obtained from a mammal, e.g., with a degree of spatial resolution (e.g., single-cell resolution).

Spatial heterogeneity in developing systems has typically been studied via RNA hybridization, immunohistochemistry, fluorescent reporters, or purification or induction of pre-defined subpopulations and subsequent genomic profiling (e.g., RNA-seq). Such approaches, however, rely on a relatively small set of pre-defined markers, therefore introducing selection bias that limits discovery. These prior approaches also rely on a priori knowledge. Spatial RNA assays traditionally relied on staining for a limited number of RNA species. In contrast, single-cell RNA-sequencing allows for deep profiling of cellular gene expression (including non-coding RNA), but the established methods separate cells from their native spatial context.

Current spatial analysis methodologies provide a vast amount of analyte level and/or expression data for a variety of multiple analytes within a sample at high spatial resolution, e.g., while retaining the native spatial context. Spatial analysis methods include, e.g., the use of a capture probe including a spatial barcode (e.g., a nucleic acid sequence that provides information as to the position of the capture probe within a cell or a tissue sample (e.g., mammalian cell or a mammalian tissue sample) and a capture domain that is capable of binding to an analyte (e.g., a protein and/or nucleic acid) produced by and/or present in a cell. As described herein, the spatial barcode can be a nucleic acid that has a unique sequence, a unique fluorophore or a unique combination of fluorophores, a unique amino acid sequence, a unique heavy metal or a unique combination of heavy metals, or any other unique detectable agent. The capture domain can be any agent that is capable of binding to an analyte produced by and/or present in a cell (e.g., a nucleic acid that is capable of hybridizing to a nucleic acid from a cell (e.g., an mRNA, genomic DNA, mitochondrial DNA, or miRNA), a substrate or binding partner of an analyte, or an antibody that binds specifically to an analyte). A capture probe can also include a nucleic acid sequence that is complementary to a sequence of a universal forward and/or universal reverse primer. A capture probe can also include a cleavage site (e.g., a cleavage recognition site of a restriction endonuclease), a photolabile bond, a thermosensitive bond, or a chemical-sensitive bond.

The binding of an analyte to a capture probe can be detected using a number of different methods, e.g., nucleic acid sequencing, fluorophore detection, nucleic acid amplification, detection of nucleic acid ligation, and/or detection of nucleic acid cleavage products. In some examples, the detection is used to associate a specific spatial barcode with a specific analyte produced by and/or present in a cell (e.g., a mammalian cell).

Capture probes can be, e.g., attached to a surface, e.g., a solid array, a bead, or a coverslip. In some examples, capture probes are not attached to a surface. In some examples, capture probes can be encapsulated within, embedded within, or layered on a surface of a permeable composition (e.g., any of the substrates described herein). For example, capture probes can be encapsulated or disposed within a permeable bead (e.g., a gel bead). In some examples, capture probes can be encapsulated within, embedded within, or layered on a surface of a substrate (e.g., any of the exemplary substrates described herein, such as a hydrogel or a porous membrane).

In some examples, a cell or a tissue sample including a cell are contacted with capture probes attached to a substrate (e.g., a surface of a substrate), and the cell or tissue sample is permeabilized to allow analytes to be released from the cell and bind to the capture probes attached to the substrate. In some examples, analytes released from a cell can be actively directed to the capture probes attached to a substrate using a variety of methods, e.g., electrophoresis, chemical gradient, pressure gradient, fluid flow, or magnetic field.

In other examples, a capture probe can be directed to interact with a cell or a tissue sample using a variety of methods, e.g., inclusion of a lipid anchoring agent in the capture probe, inclusion of an agent that binds specifically to, or forms a covalent bond with a membrane protein in the capture probe, fluid flow, pressure gradient, chemical gradient, or magnetic field.

Non-limiting aspects of spatial analysis methodologies are described in WO 2011/127099, WO 2014/210233, WO 2014/210225, WO 2016/162309, WO 2018/091676, WO 2012/140224, WO 2014/060483, U.S. Pat. Nos. 10,002,316, 9,727,810, U.S. Patent Application Publication No. 2017/0016053, Rodriques et al., *Science* 363(6434):1463-1467, 2019; WO 2018/045186, Lee et al., *Nat. Protoc.* 10(3):442-458, 2015; WO 2016/007839, WO 2018/045181, WO 2014/163886, Trejo et al., *PLoS ONE* 14(2):e0212031, 2019, U.S. Patent Application Publication No. 2018/0245142, Chen et al., *Science* 348(6233):aaa6090, 2015, Gao et al., *BMC Biol.* 15:50, 2017, WO 2017/144338, WO 2018/107054, WO 2017/222453, WO 2019/068880, WO 2011/094669, U.S. Pat. Nos. 7,709,198, 8,604,182, 8,951,726, 9,783,841, 10,041,949, WO 2016/057552, WO 2017/147483, WO 2018/022809, WO 2016/166128, WO 2017/027367, WO 2017/027368, WO 2018/136856, WO 2019/075091, U.S. Pat. No. 10,059,990, WO 2018/057999, WO 2015/161173, and Gupta et al., *Nature Biotechnol.* 36:1197-1202, 2018, and can be used herein in any combination. Further non-limiting aspects of spatial analysis methodologies are described herein.

(b) General Terminology

Specific terminology is used throughout this disclosure to explain various aspects of the apparatus, systems, methods, and compositions that are described. This sub-section includes explanations of certain terms that appear in later sections of the disclosure. To the extent that the descriptions in this section are in apparent conflict with usage in other sections of this disclosure, the definitions in this section will control.

(i) Barcode

A "barcode" is a label, or identifier, that conveys or is capable of conveying information (e.g., information about an analyte in a sample, a bead, and/or a capture probe). A barcode can be part of an analyte, or independent of an analyte. A barcode can be attached to an analyte. A particular barcode can be unique relative to other barcodes.

Barcodes can have a variety of different formats. For example, barcodes can include polynucleotide barcodes, random nucleic acid and/or amino acid sequences, and synthetic nucleic acid and/or amino acid sequences. A barcode can be attached to an analyte or to another moiety or structure in a reversible or irreversible manner. A barcode can be added to, for example, a fragment of a deoxyribonucleic acid (DNA) or ribonucleic acid (RNA) sample before or during sequencing of the sample. Barcodes can allow for identification and/or quantification of individual sequencing-reads (e.g., a barcode can be or can include a unique molecular identifier or "UMI").

Barcodes can spatially-resolve molecular components found in biological samples, for example, at single-cell resolution (e.g., a barcode can be or can include a "spatial barcode"). In some embodiments, a barcode includes both a UMI and a spatial barcode. In some embodiments, a barcode includes two or more sub-barcodes that together function as a single barcode. For example, a polynucleotide barcode can include two or more polynucleotide sequences (e.g., sub-barcodes) that are separated by one or more non-barcode sequences.

(ii) Nucleic Acid and Nucleotide

The terms "nucleic acid" and "nucleotide" are intended to be consistent with their use in the art and to include naturally-occurring species or functional analogs thereof. Particularly useful functional analogs of nucleic acids are capable of hybridizing to a nucleic acid in a sequence-specific fashion (e.g., capable of hybridizing to two nucleic acids such that ligation can occur between the two hybridized nucleic acids) or are capable of being used as a template for replication of a particular nucleotide sequence. Naturally-occurring nucleic acids generally have a backbone containing phosphodiester bonds. An analog structure can have an alternate backbone linkage including any of a variety of those known in the art. Naturally-occurring nucleic acids generally have a deoxyribose sugar (e.g., found in deoxyribonucleic acid (DNA)) or a ribose sugar (e.g. found in ribonucleic acid (RNA)).

A nucleic acid can contain nucleotides having any of a variety of analogs of these sugar moieties that are known in the art. A nucleic acid can include native or non-native nucleotides. In this regard, a native deoxyribonucleic acid can have one or more bases selected from the group consisting of adenine (A), thymine (T), cytosine (C), or guanine (G), and a ribonucleic acid can have one or more bases selected from the group consisting of uracil (U), adenine (A), cytosine (C), or guanine (G). Useful non-native bases that can be included in a nucleic acid or nucleotide are known in the art.

(iii) Probe and Target

A "probe" or a "target," when used in reference to a nucleic acid or sequence of a nucleic acids, is intended as a semantic identifier for the nucleic acid or sequence in the context of a method or composition, and does not limit the structure or function of the nucleic acid or sequence beyond what is expressly indicated.

(iv) Oligonucleotide and Polynucleotide

The terms "oligonucleotide" and "polynucleotide" are used interchangeably to refer to a single-stranded multimer of nucleotides from about 2 to about 500 nucleotides in length. Oligonucleotides can be synthetic, made enzymatically (e.g., via polymerization), or using a "split-pool" method. Oligonucleotides can include ribonucleotide monomers (i.e., can be oligoribonucleotides) and/or deoxyribonucleotide monomers (i.e., oligodeoxyribonucleotides). In some examples, oligonucleotides can include a combination of both deoxyribonucleotide monomers and ribonucleotide monomers in the oligonucleotide (e.g., random or ordered combination of deoxyribonucleotide monomers and ribonucleotide monomers). An oligonucleotide can be 4 to 10, 10 to 20, 21 to 30, 31 to 40, 41 to 50, 51 to 60, 61 to 70, 71 to 80, 80 to 100, 100 to 150, 150 to 200, 200 to 250, 250 to 300, 300 to 350, 350 to 400, or 400-500 nucleotides in length, for example. Oligonucleotides can include one or more functional moieties that are attached (e.g., covalently or non-covalently) to the multimer structure. For example, an oligonucleotide can include one or more detectable labels (e.g., a radioisotope or fluorophore).

(v) Subject

A "subject" is an animal, such as a mammal (e.g., human or a non-human simian), or avian (e.g., bird), or other organism, such as a plant. Examples of subjects include, but are not limited to, a mammal such as a rodent, mouse, rat, rabbit, guinea pig, ungulate, horse, sheep, pig, goat, cow, cat, dog, primate (i.e. human or non-human primate); a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, or honey bee; an arachnid such as a spider; a fish such as zebrafish; a reptile; an amphibian such as a frog or *Xenopus laevis*; a Dictyostelium discoideum; a fungi such as *Pneumocystis carinii, Takifugu rubripes*, yeast, *Saccharomyces cerevisiae* or *Schizosaccharomyces pombe*; or a *Plasmodium falciparum*.

(vi) Genome

A "genome" generally refers to genomic information from a subject, which can be, for example, at least a portion of, or the entirety of, the subject's gene-encoded hereditary information. A genome can include coding regions (e.g., that code for proteins) as well as non-coding regions. A genome can include the sequences of some or all of the subject's chromosomes. For example, the human genome ordinarily has a total of 46 chromosomes. The sequences of some or all of these can constitute the genome.

(vii) Adaptor, Adapter, and Tag

An "adaptor," an "adapter," and a "tag" are terms that are used interchangeably in this disclosure, and refer to species that can be coupled to a polynucleotide sequence (in a process referred to as "tagging") using any one of many different techniques including (but not limited to) ligation, hybridization, and tagmentation. Adaptors can also be nucleic acid sequences that add a function, e.g., spacer sequences, primer sequences/sites, barcode sequences, unique molecular identifier sequences.

(viii) Hybridizing, Hybridize, Annealing, and Anneal

The terms "hybridizing," "hybridize," "annealing," and "anneal" are used interchangeably in this disclosure, and refer to the pairing of substantially complementary or complementary nucleic acid sequences within two different molecules. Pairing can be achieved by any process in which a nucleic acid sequence joins with a substantially or fully complementary sequence through base pairing to form a hybridization complex. For purposes of hybridization, two nucleic acid sequences are "substantially complementary" if at least 60% (e.g., at least 70%, at least 80%, or at least 90%) of their individual bases are complementary to one another.

(ix) Primer

A "primer" is a single-stranded nucleic acid sequence having a 3' end that can be used as a substrate for a nucleic acid polymerase in a nucleic acid extension reaction. RNA primers are formed of RNA nucleotides, and are used in RNA synthesis, while DNA primers are formed of DNA nucleotides and used in DNA synthesis. Primers can also include both RNA nucleotides and DNA nucleotides (e.g., in a random or designed pattern). Primers can also include other natural or synthetic nucleotides described herein that can have additional functionality. In some examples, DNA primers can be used to prime RNA synthesis and vice versa (e.g., RNA primers can be used to prime DNA synthesis). Primers can vary in length. For example, primers can be about 6 bases to about 120 bases. For example, primers can include up to about 25 bases.

(x) Primer Extension

A "primer extension" refers to any method where two nucleic acid sequences (e.g., a constant region from each of two distinct capture probes) become linked (e.g., hybridized) by an overlap of their respective terminal complementary nucleic acid sequences (i.e., for example, 3' termini). Such linking can be followed by nucleic acid extension (e.g., an enzymatic extension) of one, or both termini using the other nucleic acid sequence as a template for extension. Enzymatic extension can be performed by an enzyme including, but not limited to, a polymerase and/or a reverse transcriptase.

(xi) Proximity Ligation

A "proximity ligation" is a method of ligating two (or more) nucleic acid sequences that are in proximity with each other through enzymatic means (e.g., a ligase). In some embodiments, proximity ligation can include a "gap-filling" step that involves incorporation of one or more nucleic acids by a polymerase, based on the nucleic acid sequence of a template nucleic acid molecule, spanning a distance between the two nucleic acid molecules of interest (see, e.g., U.S. Pat. No. 7,264,929, the entire contents of which are incorporated herein by reference).

A wide variety of different methods can be used for proximity ligating nucleic acid molecules, including (but not limited to) "sticky-end" and "blunt-end" ligations. Additionally, single-stranded ligation can be used to perform proximity ligation on a single-stranded nucleic acid molecule. Sticky-end proximity ligations involve the hybridization of complementary single-stranded sequences between the two nucleic acid molecules to be joined, prior to the ligation event itself. Blunt-end proximity ligations generally do not include hybridization of complementary regions from each nucleic acid molecule because both nucleic acid molecules lack a single-stranded overhang at the site of ligation.

(xii) Nucleic Acid Extension

A "nucleic acid extension" generally involves incorporation of one or more nucleic acids (e.g., A, G, C, T, U, nucleotide analogs, or derivatives thereof) into a molecule (such as, but not limited to, a nucleic acid sequence) in a template-dependent manner, such that consecutive nucleic acids are incorporated by an enzyme (such as a polymerase or reverse transcriptase), thereby generating a newly synthesized nucleic acid molecule. For example, a primer that hybridizes to a complementary nucleic acid sequence can be used to synthesize a new nucleic acid molecule by using the complementary nucleic acid sequence as a template for nucleic acid synthesis. Similarly, a 3' polyadenylated tail of an mRNA transcript that hybridizes to a poly (dT) sequence (e.g., capture domain) can be used as a template for single-strand synthesis of a corresponding cDNA molecule.

(xiii) PCR Amplification

A "PCR amplification" refers to the use of a polymerase chain reaction (PCR) to generate copies of genetic material, including DNA and RNA sequences. Suitable reagents and conditions for implementing PCR are described, for example, in U.S. Pat. Nos. 4,683,202, 4,683,195, 4,800,159, 4,965,188, and 5,512,462, the entire contents of each of which are incorporated herein by reference. In a typical PCR amplification, the reaction mixture includes the genetic material to be amplified, an enzyme, one or more primers that are employed in a primer extension reaction, and reagents for the reaction. The oligonucleotide primers are of sufficient length to provide for hybridization to complementary genetic material under annealing conditions. The length of the primers generally depends on the length of the amplification domains, but will typically be at least 4 bases, at least 5 bases, at least 6 bases, at least 8 bases, at least 9 bases, at least 10 base pairs (bp), at least 11 bp, at least 12 bp, at least 13 bp, at least 14 bp, at least 15 bp, at least 16 bp, at least 17 bp, at least 18 bp, at least 19 bp, at least 20 bp, at least 25 bp, at least 30 bp, at least 35 bp, and can be as long as 40 bp or longer, where the length of the primers will generally range from 18 to 50 bp. The genetic material can be contacted with a single primer or a set of two primers (forward and reverse primers), depending upon whether primer extension, linear or exponential amplification of the genetic material is desired.

In some embodiments, the PCR amplification process uses a DNA polymerase enzyme. The DNA polymerase activity can be provided by one or more distinct DNA polymerase enzymes. In certain embodiments, the DNA polymerase enzyme is from a bacterium, e.g., the DNA polymerase enzyme is a bacterial DNA polymerase enzyme. For instance, the DNA polymerase can be from a bacterium of the genus *Escherichia*, *Bacillus*, *Thermophilus*, or *Pyrococcus*.

Suitable examples of DNA polymerases that can be used include, but are not limited to: *E. coli* DNA polymerase I, Bsu DNA polymerase, Bst DNA polymerase, Taq DNA polymerase, VENT™ DNA polymerase, DEEPVENT™ DNA polymerase, LongAmp® Taq DNA polymerase, LongAmp® Hot Start Taq DNA polymerase, Crimson LongAmp® Taq DNA polymerase, Crimson Taq DNA polymerase, OneTaq® DNA polymerase, OneTaq® Quick-Load® DNA polymerase, Hemo KlenTaq® DNA polymerase, REDTaq® DNA polymerase, Phusion® DNA polymerase, Phusion® High-Fidelity DNA polymerase, Platinum Pfx DNA polymerase, AccuPrime Pfx DNA polymerase, Phi29 DNA polymerase, Klenow fragment, Pwo DNA polymerase, Pfu DNA polymerase, T4 DNA polymerase and T7 DNA polymerase enzymes.

The term "DNA polymerase" includes not only naturally-occurring enzymes but also all modified derivatives thereof, including also derivatives of naturally-occurring DNA polymerase enzymes. For instance, in some embodiments, the DNA polymerase can have been modified to remove 5'-3' exonuclease activity. Sequence-modified derivatives or mutants of DNA polymerase enzymes that can be used include, but are not limited to, mutants that retain at least some of the functional, e.g. DNA polymerase activity of the wild-type sequence. Mutations can affect the activity profile of the enzymes, e.g. enhance or reduce the rate of polymerization, under different reaction conditions, e.g. temperature, template concentration, primer concentration, etc. Mutations or sequence-modifications can also affect the exonuclease activity and/or thermostability of the enzyme.

In some embodiments, PCR amplification can include reactions such as, but not limited to, a strand-displacement amplification reaction, a rolling circle amplification reaction, a ligase chain reaction, a transcription-mediated amplification reaction, an isothermal amplification reaction, and/or a loop-mediated amplification reaction.

In some embodiments, PCR amplification uses a single primer that is complementary to the 3' tag of target DNA fragments. In some embodiments, PCR amplification uses a first and a second primer, where at least a 3' end portion of the first primer is complementary to at least a portion of the 3' tag of the target nucleic acid fragments, and where at least a 3' end portion of the second primer exhibits the sequence of at least a portion of the 5' tag of the target nucleic acid fragments. In some embodiments, a 5' end portion of the first primer is non-complementary to the 3' tag of the target nucleic acid fragments, and a 5' end portion of the second primer does not exhibit the sequence of at least a portion of the 5' tag of the target nucleic acid fragments. In some embodiments, the first primer includes a first universal sequence and/or the second primer includes a second universal sequence.

In some embodiments (e.g., when the PCR amplification amplifies captured DNA), the PCR amplification products can be ligated to additional sequences using a DNA ligase enzyme. The DNA ligase activity can be provided by one or more distinct DNA ligase enzymes. In some embodiments, the DNA ligase enzyme is from a bacterium, e.g., the DNA ligase enzyme is a bacterial DNA ligase enzyme. In some embodiments, the DNA ligase enzyme is from a virus (e.g., a bacteriophage). For instance, the DNA ligase can be T4 DNA ligase. Other enzymes appropriate for the ligation step include, but are not limited to, Tth DNA ligase, Taq DNA ligase, *Thermococcus* sp. (strain 9oN) DNA ligase (9oN™ DNA ligase, available from New England Biolabs, Ipswich, MA), and Ampligase™ (available from Epicentre Biotechnologies, Madison, WI). Derivatives, e.g. sequence-modified derivatives, and/or mutants thereof, can also be used.

In some embodiments, genetic material is amplified by reverse transcription polymerase chain reaction (RT-PCR). The desired reverse transcriptase activity can be provided by one or more distinct reverse transcriptase enzymes, suitable examples of which include, but are not limited to: M-MLV, MuLV, AMV, HIV, ArrayScript™, MultiScribe™, ThermoScript™, and SuperScript® I, II, III, and IV enzymes. "Reverse transcriptase" includes not only naturally occurring enzymes, but all such modified derivatives thereof, including also derivatives of naturally-occurring reverse transcriptase enzymes.

In addition, reverse transcription can be performed using sequence-modified derivatives or mutants of M-MLV, MuLV, AMV, and HIV reverse transcriptase enzymes, including mutants that retain at least some of the functional, e.g. reverse transcriptase, activity of the wild-type sequence. The reverse transcriptase enzyme can be provided as part of a composition that includes other components, e.g. stabilizing components that enhance or improve the activity of the reverse transcriptase enzyme, such as RNase inhibitor(s), inhibitors of DNA-dependent DNA synthesis, e.g. actinomycin D. Many sequence-modified derivative or mutants of reverse transcriptase enzymes, e.g. M-MLV, and compositions including unmodified and modified enzymes are commercially available, e.g. ArrayScript™, MultiScribe™, ThermoScript™, and SuperScript® I, II, III, and IV enzymes.

Certain reverse transcriptase enzymes (e.g. Avian Myeloblastosis Virus (AMV) Reverse Transcriptase and Moloney Murine Leukemia Virus (M-MuLV, MMLV) Reverse Transcriptase) can synthesize a complementary DNA strand using both RNA (cDNA synthesis) and single-stranded DNA (ssDNA) as a template. Thus, in some embodiments, the reverse transcription reaction can use an enzyme (reverse transcriptase) that is capable of using both RNA and ssDNA as the template for an extension reaction, e.g. an AMV or MMLV reverse transcriptase.

In some embodiments, the quantification of RNA and/or DNA is carried out by real-time PCR (also known as quantitative PCR or qPCR), using techniques well known in the art, such as but not limited to "TAQMAN™" or "SYBR®", or on capillaries ("LightCycler® Capillaries"). In some embodiments, the quantification of genetic material is determined by optical absorbance and with real-time PCR. In some embodiments, the quantification of genetic material is determined by digital PCR. In some embodiments, the genes analyzed can be compared to a reference nucleic acid extract (DNA and RNA) corresponding to the expression (mRNA) and quantity (DNA) in order to compare expression levels of the target nucleic acids.

(xiv) Antibody

An "antibody" is a polypeptide molecule that recognizes and binds to a complementary target antigen. Antibodies typically have a molecular structure shape that resembles a Y shape. Naturally-occurring antibodies, referred to as immunoglobulins, belong to one of the immunoglobulin classes IgG, IgM, IgA, IgD, and IgE. Antibodies can also be produced synthetically. For example, recombinant antibodies, which are monoclonal antibodies, can be synthesized using synthetic genes by recovering the antibody genes from source cells, amplifying into an appropriate vector, and introducing the vector into a host to cause the host to express the recombinant antibody. In general, recombinant antibodies can be cloned from any species of antibody-producing animal using suitable oligonucleotide primers and/or hybridization probes. Recombinant techniques can be used to generate antibodies and antibody fragments, including non-endogenous species.

Synthetic antibodies can be derived from non-immunoglobulin sources. For example, antibodies can be generated from nucleic acids (e.g., aptamers), and from non-immunoglobulin protein scaffolds (such as peptide aptamers) into which hypervariable loops are inserted to form antigen binding sites. Synthetic antibodies based on nucleic acids or peptide structures can be smaller than immunoglobulin-derived antibodies, leading to greater tissue penetration.

Antibodies can also include affimer proteins, which are affinity reagents that typically have a molecular weight of about 12-14 kDa. Affimer proteins generally bind to a target (e.g., a target protein) with both high affinity and specificity. Examples of such targets include, but are not limited to, ubiquitin chains, immunoglobulins, and C-reactive protein. In some embodiments, affimer proteins are derived from cysteine protease inhibitors, and include peptide loops and a variable N-terminal sequence that provides the binding site.

Antibodies can also include single domain antibodies ($V_HH$ domains and VNAR domains), scFvs, and Fab fragments.

(xv) Affinity Group

An "affinity group" is a molecule or molecular moiety which has a high affinity or preference for associating or binding with another specific or particular molecule or moiety. The association or binding with another specific or particular molecule or moiety can be via a non-covalent interaction, such as hydrogen bonding, ionic forces, and van der Waals interactions. An affinity group can, for example, be biotin, which has a high affinity or preference to associate or bind to the protein avidin or streptavidin. An affinity group, for example, can also refer to avidin or streptavidin which has an affinity to biotin. Other examples of an affinity group and specific or particular molecule or moiety to which it binds or associates with include, but are not limited to, antibodies or antibody fragments and their respective antigens, such as digoxigenin and anti-digoxigenin antibodies, lectin, and carbohydrates (e.g., a sugar, a monosaccharide, a disaccharide, or a polysaccharide), and receptors and receptor ligands.

Any pair of affinity group and its specific or particular molecule or moiety to which it binds or associates with can have their roles reversed, for example, such that between a first molecule and a second molecule, in a first instance the first molecule is characterized as an affinity group for the second molecule, and in a second instance the second molecule is characterized as an affinity group for the first molecule.

(xvi) Label, Detectable Label, and Optical Label

The terms "detectable label," "optical label," and "label" are used interchangeably herein to refer to a directly or indirectly detectable moiety that is associated with (e.g., conjugated to) a molecule to be detected, e.g., a capture probe or analyte. The detectable label can be directly detectable by itself (e.g., radioisotope labels or fluorescent labels) or, in the case of an enzymatic label, can be indirectly detectable, e.g., by catalyzing chemical alterations of a substrate compound or composition, which substrate compound or composition is directly detectable. Detectable labels can be suitable for small scale detection and/or suitable for high-throughput screening. As such, suitable detectable labels include, but are not limited to, radioisotopes, fluorophores, chemiluminescent compounds, bioluminescent compounds, and dyes.

The detectable label can be qualitatively detected (e.g., optically or spectrally), or it can be quantified. Qualitative detection generally includes a detection method in which the existence or presence of the detectable label is confirmed, whereas quantifiable detection generally includes a detection method having a quantifiable (e.g., numerically reportable) value such as an intensity, duration, polarization, and/or other properties. In some embodiments, the detectable label is bound to a feature or to a capture probe associated with a feature. For example, detectably labeled features can include a fluorescent, a colorimetric, or a chemiluminescent label attached to a bead (see, for example, Rajeswari et al., *J. Microbiol Methods* 139:22-28, 2017, and Forcucci et al., *J. Biomed Opt.* 10:105010, 2015, the entire contents of each of which are incorporated herein by reference).

In some embodiments, a plurality of detectable labels can be attached to a feature, capture probe, or composition to be detected. For example, detectable labels can be incorporated during nucleic acid polymerization or amplification (e.g., Cy5®-labelled nucleotides, such as Cy5®-dCTP). Any suitable detectable label can be used. In some embodiments, the detectable label is a fluorophore. For example, the fluorophore can be from a group that includes: 7-AAD (7-Aminoactinomycin D), Acridine Orange (+DNA), Acridine Orange (+RNA), Alexa Fluor® 350, Alexa Fluor® 430, Alexa Fluor® 488, Alexa Fluor® 532, Alexa Fluor® 546, Alexa Fluor® 555, Alexa Fluor® 568, Alexa Fluor® 594, Alexa Fluor® 633, Alexa Fluor® 647, Alexa Fluor® 660, Alexa Fluor® 680, Alexa Fluor® 700, Alexa Fluor® 750, Allophycocyanin (APC), AMCA/AMCA-X, 7-Aminoactinomycin D (7-AAD), 7-Amino-4-methylcoumarin, 6-Aminoquinoline, Aniline Blue, ANS, APC-Cy7, ATTO-TAG™ CBQCA, ATTO-TAG™ FQ, Auramine O-Feulgen, BCECF (high pH), BFP (Blue Fluorescent Protein), BFP/GFP FRET, BOBO™-1/BO-PRO™-1, BOBO™-3/BO-PRO™-3, BODIPY® FL, BODIPY® TMR, BODIPY® TR-X, BODIPY® 530/550, BODIPY® 558/568, BODIPY® 564/570, BODIPY® 581/591, BODIPY® 630/650-X, BODIPY® 650-665-X, BTC, Calcein, Calcein Blue, Calcium Crimson™, Calcium Green-1™, Calcium Orange™, Calcofluor® White, 5-Carboxyfluoroscein (5-FAM), 5-Carboxynaphthofluoroscein, 6-Carboxyrhodamine 6G, 5-Carboxytetramethylrhodamine (5-TAMRA), Carboxy-X-rhodamine (5-ROX), Cascade Blue®, Cascade Yellow™, CCF2 (GeneBLAzer™), CFP (Cyan Fluorescent Protein), CFP/YFP FRET, Chromomycin A3, Cl-NERF (low pH), CPM, 6-CR 6G, CTC Formazan, Cy2®, Cy3®, Cy3.5®, Cy5®, Cy5.5®, Cy7®, Cychrome (PE-Cy5), Dansylamine, Dansyl cadaverine, Dansylchloride, DAPI, Dapoxyl, DCFH, DHR, DiA (4-Di-16-ASP), DiD (DilC18 (5)), DIDS, Dil (DilC18(3)), DiO (DiOC18(3)), DiR (DilC18(7)), Di-4 ANEPPS, Di-8 ANEPPS, DM-NERF (4.5-6.5 pH), DsRed (Red Fluorescent Protein), EBFP, ECFP, EGFP, ELF®-97 alcohol, Eosin, Erythrosin, Ethidium bromide, Ethidium homodimer-1 (EthD-1), Europium (III) Chloride, 5-FAM (5-Carboxyfluorescein), Fast Blue, Fluorescein-dT phosphoramidite, FITC, Fluo-3, Fluo-4, FluorX®, Fluoro-Gold™ (high pH), Fluoro-Gold™ (low pH), Fluoro-Jade, FM® 1-43, Fura-2 (high calcium), Fura-2/BCECF, Fura Red™ (high calcium), Fura Red™/Fluo-3, GeneBLAzer™ (CCF2), GFP Red Shifted (rsGFP), GFP Wild Type, GFP/BFP FRET, GFP/DsRed FRET, Hoechst 33342 & 33258, 7-Hydroxy-4-methylcoumarin (pH 9), 1,5 IAEDANS, Indo-1 (high calcium), Indo-1 (low calcium), Indodicarbocyanine, Indotricarbocyanine, JC-1, 6-JOE, JOJO™-1/JO-PRO™-1, LDS 751 (+DNA), LDS 751 (+RNA), LOLO™-1/LO-PRO™-1, Lucifer Yellow, LysoSensor™ Blue (pH 5), LysoSensor™ Green (pH 5), LysoSensor™ Yellow/Blue (pH 4.2), LysoTracker® Green, LysoTracker® Red, LysoTracker® Yellow, Mag-Fura-2, Mag-Indo-1, Magnesium Green™, Marina Blue®, 4-Methylumbelliferone, Mithramycin, MitoTracker® Green, MitoTracker® Orange, MitoTracker® Red, NBD (amine), Nile Red, Oregon Green® 488, Oregon Green® 500, Oregon Green® 514, Pacific Blue, PBF1, PE (R-phycoerythrin), PE-Cy5, PE-Cy7, PE-Texas Red, PerCP (Peridinin chlorophyll protein), PerCP-Cy5.5 (TruRed), PharRed (APC-Cy7), C-phycocyanin, R-phycocyanin, R-phycoerythrin (PE), PI (Propidium Iodide), PKH26, PKH67, POPO™-1/PO-PRO™-1, POPO™-3/PO-PRO™-3, Propidium Iodide (PI), PyMPO, Pyrene, Pyronin Y, Quantam Red (PE-Cy5), Quinacrine Mustard, R670 (PE-Cy5), Red 613 (PE-Texas Red), Red Fluorescent Protein (DsRed), Resorufin, RH 414, Rhod-2, Rhodamine B, Rhodamine Green™, Rhodamine Red™, Rhodamine Phalloidin, Rhodamine 110, Rhodamine 123, 5-ROX (carboxy-X-rhodamine), S65A, S65C, S65L, S65T, SBFI, SITS, SNAFL®-1 (high pH), SNAFL®-2, SNARF®-1 (high pH), SNARF®-1 (low pH), Sodium Green™, SpectrumAqua®, SpectrumGreen® #1, SpectrumGreen® #2, SpectrumOrange®, SpectrumRed®, SYTO® 11, SYTO® 13, SYTO® 17, SYTO® 45, SYTOX® Blue, SYTOX® Green, SYTOX® Orange, 5-TAMRA (5-Carboxytetramethylrhodamine), Tetramethylrhodamine (TRITC), Texas Red®/Texas Red®-X, Texas Red®-X (NHS Ester), Thiadicarbocyanine, Thiazole Orange, TOTO®-1/TO-PRO®-1, TOTO®-3/TO-PRO®-3, TO-PRO®-5, Tri-color (PE-Cy5), TRITC (Tetramethylrhodamine), TruRed (PerCP-Cy5.5), WW 781, X-Rhodamine (XRITC), Y66F, Y66H, Y66 W, YFP (Yellow Fluorescent Protein), YOYO®-1/YO-PRO®-1, YOYO®-3/YO-PRO®-3, 6-FAM (Fluorescein), 6-FAM (NHS Ester), 6-FAM (Azide), HEX, TAMRA (NHS Ester), Yakima Yellow, MAX, TET, TEX615, ATTO 488, ATTO 532, ATTO 550, ATTO 565, ATTO Rho101, ATTO 590, ATTO 633, ATTO 647N, TYE 563, TYE 665, TYE 705, 5' IRDye® 700, 5' IRDye® 800, 5' IRDye® 800CW (NHS Ester), WellRED D4 Dye, WellRED D3 Dye, WellRED D2 Dye, Lightcycler® 640 (NHS Ester), and Dy 750 (NHS Ester).

As mentioned above, in some embodiments, a detectable label is or includes a luminescent or chemiluminescent moiety. Common luminescent/chemiluminescent moieties include, but are not limited to, peroxidases such as horseradish peroxidase (HRP), soybean peroxidase (SP), alkaline phosphatase, and luciferase. These protein moieties can catalyze chemiluminescent reactions given the appropriate substrates (e.g., an oxidizing reagent plus a chemiluminescent compound. A number of compound families are known to provide chemiluminescence under a variety of conditions. Non-limiting examples of chemiluminescent compound families include 2,3-dihydro-1,4-phthalazinedione luminol, 5-amino-6,7,8-trimethoxy- and the dimethylamino[ca]benz analog. These compounds can luminesce in the presence of alkaline hydrogen peroxide or calcium hypochlorite and base. Other examples of chemiluminescent compound families include, e.g., 2,4,5-triphenylimidazoles, para-dimethylamino and -methoxy substituents, oxalates such as oxalyl active esters, p-nitrophenyl, N-alkyl acridinum esters, luciferins, lucigenins, or acridinium esters.

(xvii) Template Switching Oligonucleotide

A "template switching oligonucleotide" is an oligonucleotide that hybridizes to untemplated nucleotides added by a reverse transcriptase (e.g., enzyme with terminal transferase activity) during reverse transcription. In some embodiments, a template switching oligonucleotide hybridizes to untemplated poly(C) nucleotides added by a reverse transcriptase. In some embodiments, the template switching oligonucleotide adds a common 5' sequence to full-length cDNA that is used for cDNA amplification.

In some embodiments, the template switching oligonucleotide adds a common sequence onto the 5' end of the RNA being reverse transcribed. For example, a template switching oligonucleotide can hybridize to untemplated poly(C) nucleotides added onto the end of a cDNA molecule and provide a template for the reverse transcriptase to continue replication to the 5' end of the template switching oligonucleotide, thereby generating full-length cDNA ready for further amplification. In some embodiments, once a full-length cDNA molecule is generated, the template switching oligonucleotide can serve as a primer in a cDNA amplification reaction.

In some embodiments, a template switching oligonucleotide is added before, contemporaneously with, or after a reverse transcription, or other terminal transferase-based reaction. In some embodiments, a template switching oligonucleotide is included in the capture probe. In certain embodiments, methods of sample analysis using template switching oligonucleotides can involve the generation of nucleic acid products from analytes of the tissue sample, followed by further processing of the nucleic acid products with the template switching oligonucleotide.

Template switching oligonucleotides can include a hybridization region and a template region. The hybridization region can include any sequence capable of hybridizing to the target. In some embodiments, the hybridization region can, e.g., include a series of G bases to complement the overhanging C bases at the 3' end of a cDNA molecule. The series of G bases can include 1 G base, 2 G bases, 3 G bases, 4 G bases, 5 G bases, or more than 5 G bases. The template sequence can include any sequence to be incorporated into the cDNA. In other embodiments, the hybridization region can include at least one base in addition to at least one G base. In other embodiments, the hybridization can include bases that are not a G base. In some embodiments, the template region includes at least 1 (e.g., at least 2, 3, 4, 5 or more) tag sequences and/or functional sequences. In some embodiments, the template region and hybridization region are separated by a spacer.

In some embodiments, the template regions include a barcode sequence. The barcode sequence can act as a spatial barcode and/or as a unique molecular identifier. Template switching oligonucleotides can include deoxyribonucleic acids; ribonucleic acids; modified nucleic acids including 2-aminopurine, 2,6-diaminopurine (2-amino-dA), inverted dT, 5-methyl dC, 2'-deoxyInosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' fluoro bases (e.g., Fluoro C, Fluoro U, Fluoro A, and Fluoro G), or any combination of the foregoing.

In some embodiments, the length of a template switching oligonucleotide can be at least about 1, 2, 10, 20, 50, 75, 100, 150, 200, or 250 nucleotides or longer. In some embodiments, the length of a template switching oligonucleotide can be at most about 2, 10, 20, 50, 100, 150, 200, or 250 nucleotides or longer.

(xviii) Splint Oligonucleotide

A "splint oligonucleotide" is an oligonucleotide that, when hybridized to other polynucleotides, acts as a "splint" to position the polynucleotides next to one another so that they can be ligated together. In some embodiments, the splint oligonucleotide is DNA or RNA. The splint oligonucleotide can include a nucleotide sequence that is partially complimentary to nucleotide sequences from two or more different oligonucleotides. In some embodiments, the splint oligonucleotide assists in ligating a "donor" oligonucleotide and an "acceptor" oligonucleotide. In general, an RNA ligase, a DNA ligase, or another other variety of ligase is used to ligate two nucleotide sequences together In some embodiments, the splint oligonucleotide is between 10 and 50 oligonucleotides in length, e.g., between 10 and 45, 10 and 40, 10 and 35, 10 and 30, 10 and 25, or 10 and 20 oligonucleotides in length. In some embodiments, the splint oligonucleotide is between 15 and 50, 15 and 45, 15 and 40, 15 and 35, 15 and 30, 15 and 30, or 15 and 25 nucleotides in length.

(c) Analytes

The apparatus, systems, methods, and compositions described in this disclosure can be used to detect and analyze a wide variety of different analytes. For the purpose of this disclosure, an "analyte" can include any biological substance, structure, moiety, or component to be analyzed. The term "target" can similarly refer to an analyte of interest.

Analytes can be broadly classified into one of two groups: nucleic acid analytes, and non-nucleic acid analytes. Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral coat proteins, extracellular and intracellular proteins, antibodies, and antigen binding fragments. In some embodiments, the analyte can be an organelle (e.g., nuclei or mitochondria).

Cell surface features corresponding to analytes can include, but are not limited to, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, an extracellular matrix protein, a posttranslational modification (e.g., phosphorylation, glycosylation, ubiquitination, nitrosylation, methylation, acetylation or lipidation) state of a cell surface protein, a gap junction, and an adherens junction.

Analytes can be derived from a specific type of cell and/or a specific sub-cellular region. For example, analytes can be derived from cytosol, from cell nuclei, from mitochondria, from microsomes, and more generally, from any other compartment, organelle, or portion of a cell. Permeabilizing agents that specifically target certain cell compartments and organelles can be used to selectively release analytes from cells for analysis.

Examples of nucleic acid analytes include DNA analytes such as genomic DNA, methylated DNA, specific methylated DNA sequences, fragmented DNA, mitochondrial DNA, in situ synthesized PCR products, and RNA/DNA hybrids.

Examples of nucleic acid analytes also include RNA analytes such as various types of coding and non-coding RNA. Examples of the different types of RNA analytes include messenger RNA (mRNA), ribosomal RNA (rRNA), transfer RNA (tRNA), microRNA (miRNA), and viral RNA. The RNA can be a transcript (e.g., present in a tissue section). The RNA can be small (e.g., less than 200 nucleic acid bases in length) or large (e.g., RNA greater than 200 nucleic acid bases in length). Small RNAs mainly include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA), and small rDNA-derived RNA (srRNA). The RNA can be double-stranded RNA or single-stranded RNA. The RNA can be circular RNA. The RNA can be a bacterial rRNA (e.g., 16s rRNA or 23s rRNA).

Additional examples of analytes include mRNA and cell surface features (e.g., using the labelling agents described herein), mRNA and intracellular proteins (e.g., transcription factors), mRNA and cell methylation status, mRNA and accessible chromatin (e.g., ATAC-seq, DNase-seq, and/or MNase-seq), mRNA and metabolites (e.g., using the labelling agents described herein), a barcoded labelling agent (e.g., the oligonucleotide tagged antibodies described herein) and a V(D)J sequence of an immune cell receptor (e.g., T-cell receptor), mRNA and a perturbation agent (e.g., a CRISPR crRNA/sgRNA, TALEN, zinc finger nuclease, and/or antisense oligonucleotide as described herein).

Analytes can include a nucleic acid molecule with a nucleic acid sequence encoding at least a portion of a V(D)J sequence of an immune cell receptor (e.g., a TCR or BCR). In some embodiments, the nucleic acid molecule is cDNA first generated from reverse transcription of the corresponding mRNA, using a poly(T) containing primer. The generated cDNA can then be barcoded using a capture probe, featuring a barcode sequence (and optionally, a UMI sequence) that hybridizes with at least a portion of the generated cDNA. In some embodiments, a template switching oligonucleotide hybridizes to a poly(C) tail added to a 3'end of the cDNA by a reverse transcriptase enzyme. The original mRNA template and template switching oligonucleotide can then be denatured from the cDNA and the barcoded capture probe can then hybridize with the cDNA and a complement of the cDNA generated. Additional methods and compositions suitable for barcoding cDNA generated from mRNA transcripts including those encoding V(D)J regions of an immune cell receptor and/or barcoding methods and composition including a template switch oligonucleotide are described in PCT Patent Application PCT/US2017/057269, filed Oct. 18, 2017, and U.S. patent application Ser. No. 15/825,740, filed Nov. 29, 2017, both of which are incorporated herein by reference in their entireties. V(D)J analysis can also be completed with the use of one or more labelling agents that bind to particular surface features of immune cells and associated with barcode sequences. The one or more labelling agents can include an MHC or MHC multimer.

As described above, the analyte can include a nucleic acid capable of functioning as a component of a gene editing reaction, such as, for example, clustered regularly interspaced short palindromic repeats (CRISPR)-based gene editing. Accordingly, the capture probe can include a nucleic acid sequence that is complementary to the analyte (e.g., a sequence that can hybridize to the CRISPR RNA (crRNA), single guide RNA (sgRNA), or an adapter sequence engineered into a crRNA or sgRNA).

In certain embodiments, an analyte can be extracted from a live cell. Processing conditions can be adjusted to ensure that a biological sample remains live during analysis, and analytes are extracted from (or released from) live cells of the sample. Live cell-derived analytes can be obtained only once from the sample, or can be obtained at intervals from a sample that continues to remain in viable condition.

In general, the systems, apparatus, methods, and compositions can be used to analyze any number of analytes. For example, the number of analytes that are analyzed can be at least about 2, at least about 3, at least about 4, at least about 5, at least about 6, at least about 7, at least about 8, at least about 9, at least about 10, at least about 11, at least about 12, at least about 13, at least about 14, at least about 15, at least about 20, at least about 25, at least about 30, at least about 40, at least about 50, at least about 100, at least about 1,000, at least about 10,000, at least about 100,000 or more different analytes present in a region of the sample or within an individual feature of the substrate. Methods for performing multiplexed assays to analyze two or more different analytes will be discussed in a subsequent section of this disclosure.

(d) Biological Samples
(i) Types of Biological Samples

A "biological sample" is obtained from the subject for analysis using any of a variety of techniques including, but not limited to, biopsy, surgery, and laser capture microscopy (LCM), and generally includes cells and/or other biological material from the subject. In addition to the subjects described above, a biological sample can also be obtained from a prokaryote such as a bacterium, e.g., *Escherichia coli*, Staphylococci or *Mycoplasma pneumoniae*; an archaea; a virus such as Hepatitis C virus or human immunodeficiency virus; or a viroid. A biological sample can be obtained from non-mammalian organisms (e.g., a plants, an insect, an arachnid, a nematode, a fungi, or an amphibian). A biological sample can also be obtained from a eukaryote, such as a patient derived organoid (PDO) or patient derived xenograft (PDX). Subjects from which biological samples can be obtained can be healthy or asymptomatic individuals, individuals that have or are suspected of having a disease (e.g., a patient with a disease such as cancer) or a predisposition to a disease, and/or individuals that are in need of therapy or suspected of needing therapy.

The biological sample can include any number of macromolecules, for example, cellular macromolecules and organelles (e.g., mitochondria and nuclei). The biological sample can be a nucleic acid sample and/or protein sample. The biological sample can be a carbohydrate sample or a lipid sample. The biological sample can be obtained as a tissue sample, such as a tissue section, biopsy, a core biopsy, needle aspirate, or fine needle aspirate. The sample can be a fluid sample, such as a blood sample, urine sample, or saliva sample. The sample can be a skin sample, a colon sample, a cheek swab, a histology sample, a histopathology sample, a plasma or serum sample, a tumor sample, living cells, cultured cells, a clinical sample such as, for example, whole blood or blood-derived products, blood cells, or cultured tissues or cells, including cell suspensions.

Cell-free biological samples can include extracellular polynucleotides. Extracellular polynucleotides can be isolated from a bodily sample, e.g., blood, plasma, serum, urine, saliva, mucosal excretions, sputum, stool, and tears.

Biological samples can be derived from a homogeneous culture or population of the subjects or organisms mentioned herein or alternatively from a collection of several different organisms, for example, in a community or ecosystem.

Biological samples can include one or more diseased cells. A diseased cell can have altered metabolic properties, gene expression, protein expression, and/or morphologic features. Examples of diseases include inflammatory disorders, metabolic disorders, nervous system disorders, and cancer. Cancer cells can be derived from solid tumors, hematological malignancies, cell lines, or obtained as circulating tumor cells.

Biological samples can also include fetal cells. For example, a procedure such as amniocentesis can be performed to obtain a fetal cell sample from maternal circulation. Sequencing of fetal cells can be used to identify any of a number of genetic disorders, including, e.g., aneuploidy such as Down's syndrome, Edwards syndrome, and Patau syndrome. Further, cell surface features of fetal cells can be used to identify any of a number of disorders or diseases.

Biological samples can also include immune cells. Sequence analysis of the immune repertoire of such cells, including genomic, proteomic, and cell surface features, can provide a wealth of information to facilitate an understanding the status and function of the immune system. By way of example, determining the status (e.g., negative or positive) of minimal residue disease (MRD) in a multiple myeloma (MM) patient following autologous stem cell transplantation is considered a predictor of MRD in the MM patient (see, e.g., U.S. Patent Application Publication No. 2018/0156784, the entire contents of which are incorporated herein by reference).

Examples of immune cells in a biological sample include, but are not limited to, B cells, T cells (e.g., cytotoxic T cells, natural killer T cells, regulatory T cells, and T helper cells), natural killer cells, cytokine induced killer (CIK) cells, myeloid cells, such as granulocytes (basophil granulocytes, eosinophil granulocytes, neutrophil granulocytes/hypersegmented neutrophils), monocytes/macrophages, mast cells, thrombocytes/megakaryocytes, and dendritic cells.

As discussed above, a biological sample can include a single analyte of interest, or more than one analyte of interest. Methods for performing multiplexed assays to analyze two or more different analytes in a single biological sample will be discussed in a subsequent section of this disclosure.

(ii) Preparation of Biological Samples

A variety of steps can be performed to prepare a biological sample for analysis. Except where indicated otherwise, the preparative steps described below can generally be combined in any manner to appropriately prepare a particular sample for analysis.

(1) Tissue Sectioning

A biological sample can be harvested from a subject (e.g., via surgical biopsy, whole subject sectioning) or grown in vitro on a growth substrate or culture dish as a population of cells, and prepared for analysis as a tissue slice or tissue section. Grown samples may be sufficiently thin for analysis without further processing steps. Alternatively, grown samples, and samples obtained via biopsy or sectioning, can be prepared as thin tissue sections using a mechanical cutting apparatus such as a vibrating blade microtome. As another alternative, in some embodiments, a thin tissue section can be prepared by applying a touch imprint of a biological sample to a suitable substrate material.

The thickness of the tissue section can be a fraction of (e.g., less than 0.9, 0.8, 0.7, 0.6, 0.5, 0.4, 0.3, 0.2, or 0.1) the maximum cross-sectional dimension of a cell. However, tissue sections having a thickness that is larger than the maximum cross-section cell dimension can also be used. For example, cryostat sections can be used, which can be, e.g., 10-20 micrometers thick.

More generally, the thickness of a tissue section typically depends on the method used to prepare the section and the physical characteristics of the tissue, and therefore sections having a wide variety of different thicknesses can be prepared and used. For example, the thickness of the tissue section can be at least 0.1, 0.2, 0.3, 0.4, 0.5, 0.7, 1.0, 1.5, 2, 3, 4, 5, 6, 7, 8, 9, 10, 12, 13, 14, 15, 20, 30, 40, or 50 micrometers. Thicker sections can also be used if desired or convenient, e.g., at least 70, 80, 90, or 100 micrometers or more. Typically, the thickness of a tissue section is between 1-100 micrometers, 1-50 micrometers, 1-30 micrometers, 1-25 micrometers, 1-20 micrometers, 1-15 micrometers, 1-10 micrometers, 2-8 micrometers, 3-7 micrometers, or 4-6 micrometers, but as mentioned above, sections with thicknesses larger or smaller than these ranges can also be analysed.

Multiple sections can also be obtained from a single biological sample. For example, multiple tissue sections can be obtained from a surgical biopsy sample by performing serial sectioning of the biopsy sample using a sectioning blade. Spatial information among the serial sections can be preserved in this manner, and the sections can be analysed successively to obtain three-dimensional information about the biological sample.

(2) Freezing

In some embodiments, the biological sample (e.g., a tissue section as described above) can be prepared by deep freezing at a temperature suitable to maintain or preserve the integrity (e.g., the physical characteristics) of the tissue structure. Such a temperature can be, e.g., less than −20° C., or less than −25° C., −30° C., −40° C., −50° C., −60° C., −70° C., −80° C. −90° C., −100° C., −110° C., −120° C., −130° C., −140° C., −150° C., −160° C., −170° C., −180° C., −190° C., or −200° C. The frozen tissue sample can be sectioned, e.g., thinly sliced, onto a substrate surface using any number of suitable methods. For example, a tissue sample can be prepared using a chilled microtome (e.g., a cryostat) set at a temperature suitable to maintain both the structural integrity of the tissue sample and the chemical properties of the nucleic acids in the sample. Such a temperature can be, e.g., less than −15° C., less than −20° C., or less than −25° C.

(3) Formalin Fixation and Paraffin Embedding

In some embodiments, the biological sample can be prepared using formalin-fixation and paraffin-embedding (FFPE), which are established methods. In some embodiments, cell suspensions and other non-tissue samples can be prepared using formalin-fixation and paraffin-embedding. Following fixation of the sample and embedding in a paraffin or resin block, the sample can be sectioned as described above. Prior to analysis, the paraffin-embedding material can be removed from the tissue section (e.g., deparaffinization) by incubating the tissue section in an appropriate solvent (e.g., xylene) followed by a rinse (e.g., 99.5% ethanol for 2 minutes, 96% ethanol for 2 minutes, and 70% ethanol for 2 minutes).

(4) Fixation

As an alternative to formalin fixation described above, a biological sample can be fixed in any of a variety of other fixatives to preserve the biological structure of the sample prior to analysis. For example, a sample can be fixed via immersion in ethanol, methanol, acetone, paraformaldehyde-Triton, and combinations thereof.

In some embodiments, acetone fixation is used with fresh frozen samples, which can include, but are not limited to, cortex tissue, mouse olfactory bulb, human brain tumor, human post-mortem brain, and breast cancer samples. When acetone fixation is performed, pre-permeabilization steps (described below) may not be performed. Alternatively, acetone fixation can be performed in conjunction with permeabilization steps.

(5) Embedding

As an alternative to paraffin embedding described above, a biological sample can be embedded in any of a variety of other embedding materials to provide structural substrate to the sample prior to sectioning and other handling steps. In general, the embedding material is removed prior to analysis of tissue sections obtained from the sample. Suitable embedding materials include, but are not limited to, waxes, resins (e.g., methacrylate resins), epoxies, and agar.

(6) Staining

To facilitate visualization, biological samples can be stained using a wide variety of stains and staining techniques. In some embodiments, for example, a sample can be stained using any number of stains, including but not limited to, acridine orange, Bismarck brown, carmine, coomassie blue, cresyl violet, DAPI, eosin, ethidium bromide, acid fuchsine, haematoxylin, Hoechst stains, iodine, methyl green, methylene blue, neutral red, Nile blue, Nile red, osmium tetroxide, propidium iodide, rhodamine, or safranine.

The sample can be stained using hematoxylin and eosin (H&E) staining techniques, using Papanicolaou staining techniques, Masson's trichrome staining techniques, silver staining techniques, Sudan staining techniques, and/or using Periodic Acid Schiff (PAS) staining techniques. PAS staining is typically performed after formalin or acetone fixation. In some embodiments, the sample can be stained using Romanowsky stain, including Wright's stain, Jenner's stain, Can-Grunwald stain, Leishman stain, and Giemsa stain.

In some embodiments, biological samples can be destained. Methods of destaining or discoloring a biological sample are known in the art, and generally depend on the nature of the stain(s) applied to the sample. For example, in some embodiments, one or more immunofluorescent stains are applied to the sample via antibody coupling. Such stains can be removed using techniques such as cleavage of disulfide linkages via treatment with a reducing agent and detergent washing, chaotropic salt treatment, treatment with antigen retrieval solution, and treatment with an acidic glycine buffer. Methods for multiplexed staining and destaining are described, for example, in Bolognesi et al., *J. Histochem. Cytochem.* 2017; 65(8): 431-444, Lin et al., *Nat Commun.* 2015; 6:8390, Pirici et al., *J. Histochem. Cytochem.* 2009; 57:567-75, and Glass et al., *J. Histochem. Cytochem.* 2009; 57:899-905, the entire contents of each of which are incorporated herein by reference.

(7) Hydrogel Embedding

In some embodiments, the biological sample can be embedded in a hydrogel matrix. Embedding the sample in this manner typically involves contacting the biological sample with a hydrogel such that the biological sample becomes surrounded by the hydrogel. For example, the sample can be embedded by contacting the sample with a suitable polymer material, and activating the polymer material to form a hydrogel. In some embodiments, the hydrogel is formed such that the hydrogel is internalized within the biological sample.

In some embodiments, the biological sample is immobilized in the hydrogel via cross-linking of the polymer material that forms the hydrogel. Cross-linking can be performed chemically and/or photochemically, or alternatively by any other hydrogel-formation method known in the art.

The composition and application of the hydrogel-matrix to a biological sample typically depends on the nature and preparation of the biological sample (e.g., sectioned, non-sectioned, type of fixation). As one example, where the biological sample is a tissue section, the hydrogel-matrix can include a monomer solution and an ammonium persulfate (APS) initiator/tetramethylethylenediamine (TEMED) accelerator solution. As another example, where the biological sample consists of cells (e.g., cultured cells or cells disassociated from a tissue sample), the cells can be incubated with the monomer solution and APS/TEMED solutions. For cells, hydrogel-matrix gels are formed in compartments, including but not limited to devices used to culture, maintain, or transport the cells. For example, hydrogel-matrices can be formed with monomer solution plus APS/TEMED added to the compartment to a depth ranging from about 0.1 μm to about 2 mm.

Additional methods and aspects of hydrogel embedding of biological samples are described for example in Chen et al., *Science* 347(6221):543-548, 2015, the entire contents of which are incorporated herein by reference.

(8) Isometric Expansion

In some embodiments, a biological sample embedded in a hydrogel can be isometrically expanded. Isometric expansion methods that can be used include hydration, a preparative step in expansion microscopy, as described in Chen et al., *Science* 347(6221):543-548, 2015.

Isometric expansion can be performed by anchoring one or more components of a biological sample to a gel, followed by gel formation, proteolysis, and swelling. Isometric expansion of the biological sample can occur prior to immobilization of the biological sample on a substrate, or after the biological sample is immobilized to a substrate. In some embodiments, the isometrically expanded biological sample can be removed from the substrate prior to contacting the substrate with capture probes, as will be discussed in greater detail in a subsequent section.

In general, the steps used to perform isometric expansion of the biological sample can depend on the characteristics of the sample (e.g., thickness of tissue section, fixation, cross-linking), and/or the analyte of interest (e.g., different conditions to anchor RNA, DNA, and protein to a gel).

In some embodiments, proteins in the biological sample are anchored to a swellable gel such as a polyelectrolyte gel. An antibody can be directed to the protein before, after, or in conjunction with being anchored to the swellable gel. DNA and/or RNA in a biological sample can also be anchored to the swellable gel via a suitable linker. Examples of such linkers include, but are not limited to, 6-((Acryloyl) amino) hexanoic acid (Acryloyl-X SE) (available from ThermoFisher, Waltham, MA), Label-IT Amine (available from MirusBio, Madison, WI) and Label X (described for example in Chen et al., Nat. Methods 13:679-684, 2016, the entire contents of which are incorporated herein by reference).

Isometric expansion of the sample can increase the spatial resolution of the subsequent analysis of the sample. The increased resolution in spatial profiling can be determined by comparison of an isometrically expanded sample with a sample that has not been isometrically expanded.

In some embodiments, a biological sample is isometrically expanded to a size at least 2×, 2.1×, 2.2×, 2.3×, 2.4×, 2.5×, 2.6×, 2.7×, 2.8×, 2.9×, 3×, 3.1×, 3.2×, 3.3×, 3.4×, 3.5×, 3.6×, 3.7×, 3.8×, 3.9×, 4×, 4.1×, 4.2×, 4.3×, 4.4×, 4.5×, 4.6×, 4.7×, 4.8×, or 4.9× its non-expanded size. In some embodiments, the sample is isometrically expanded to at least 2× and less than 20× of its non-expanded size.

(9) Substrate Attachment

In some embodiments, the biological sample can be attached to a substrate. Examples of substrates suitable for this purpose are described in detail below. Attachment of the biological sample can be irreversible or reversible, depending upon the nature of the sample and subsequent steps in the analytical method.

In certain embodiments, the sample can be attached to the substrate reversibly by applying a suitable polymer coating to the substrate, and contacting the sample to the polymer coating. The sample can then be detached from the substrate using an organic solvent that at least partially dissolves the polymer coating. Hydrogels are examples of polymers that are suitable for this purpose.

More generally, in some embodiments, the substrate can be coated or functionalized with one or more substances to facilitate attachment of the sample to the substrate. Suitable substances that can be used to coat or functionalize the substrate include, but are not limited to, lectins, poly-lysine, antibodies, and polysaccharides.

(10) Disaggregation of Cells

In some embodiments, the biological sample corresponds to cells (e.g., derived from a cell culture or a tissue sample). In a cell sample with a plurality of cells, individual cells can be naturally unaggregated. For example, the cells can be derived from a suspension of cells and/or disassociated or disaggregated cells from a tissue or tissue section.

Alternatively, the cells in the sample may be aggregated, and may be disaggregated into individual cells using, for example, enzymatic or mechanical techniques. Examples of enzymes used in enzymatic disaggregation include, but are not limited to, dispase, collagenase, trypsin, and combinations thereof. Mechanical disaggregation can be performed, for example, using a tissue homogenizer.

(11) Suspended and Adherent Cells

In some embodiments, the biological sample can be derived from a cell culture grown in vitro. Samples derived from a cell culture can include one or more suspension cells which are anchorage-independent within the cell culture. Examples of such cells include, but are not limited to, cell lines derived from hematopoietic cells, and from the following cell lines: Colo205, CCRF-CEM, HL-60, K562, MOLT-4, RPMI-8226, SR, HOP-92, NCI-H322M, and MALME-3M.

Samples derived from a cell culture can include one or more adherent cells which grow on the surface of the vessel that contains the culture medium. Non-limiting examples of adherent cells include DU145 (prostate cancer) cells, H295R (adrenocortical cancer) cells, HeLa (cervical cancer) cells, KBM-7 (chronic myelogenous leukemia) cells, LNCaP (prostate cancer) cells, MCF-7 (breast cancer) cells, MDA-MB-468 (breast cancer) cells, PC3 (prostate cancer) cells, SaOS-2 (bone cancer) cells, SH-SY5Y (neuroblastoma, cloned from a myeloma) cells, T-47D (breast cancer) cells, THP-1 (acute myeloid leukemia) cells, U87 (glioblastoma) cells, National Cancer Institute's 60 cancer cell line panel (NCI60), vero (African green monkey Chlorocebus kidney epithelial cell line) cells, MC3T3 (embryonic calvarium) cells, GH3 (pituitary tumor) cells, PC12 (pheochromocytoma) cells, dog MDCK kidney epithelial cells, Xenopus A6 kidney epithelial cells, zebrafish AB9 cells, and Sf9 insect epithelial cells.

Additional examples of adherent cells are shown in Table 1 and catalogued, for example, in "A Catalog of in Vitro Cell Lines, Transplantable Animal and Human Tumors and Yeast," The Division of Cancer Treatment and Diagnosis (DCTD), National Cancer Institute (2013), and in Abaan et al., "The exomes of the NCI-60 panel: a genomic resource for cancer biology and systems pharmacology," Cancer Research 73(14):4372-82, 2013, the entire contents of each of which are incorporated by reference herein.

TABLE 1

Examples of adherent cells

| Cell Line | Species | Organ of Origin | Disease |
| --- | --- | --- | --- |
| BT549 | Human | Breast | Ductal Carcinoma |
| HS 578T | Human | Breast | Carcinoma |
| MCF7 | Human | Breast | Adenocarcinoma |
| MDA-MB-231 | Human | Breast | Adenocarcinoma |
| MDA-MB-468 | Human | Breast | Adenocarcinoma |
| T-47D | Human | Breast | Ductal Carcinoma |
| SF268 | Human | CNS | Anaplastic Astrocytoma |
| SF295 | Human | CNS | Glioblastoma-Multiforme |
| SF539 | Human | CNS | Glioblastoma |
| SNB-19 | Human | CNS | Glioblastoma |
| SNB-75 | Human | CNS | Astrocytoma |
| U251 | Human | CNS | Glioblastoma |
| Colo205 | Human | Colon | Dukes' type D, Colorectal adenocarcinoma |
| HCC 2998 | Human | Colon | Carcinoma |
| HCT-116 | Human | Colon | Carcinoma |
| HCT-15 | Human | Colon | Dukes' type C, Colorectal adenocarcinoma |
| HT29 | Human | Colon | Colorectal adenocarcinoma |
| KM12 | Human | Colon | Adenocarcinoma, Grade III |
| SW620 | Human | Colon | Adenocarcinoma |
| 786-O | Human | Kidney | renal cell adenocarcinoma |
| A498 | Human | Kidney | Adenocarcinoma |
| ACHN | Human | Kidney | renal cell adenocarcinoma |
| CAKI | Human | Kidney | clear cell carcinoma |

TABLE 1-continued

Examples of adherent cells

| Cell Line | Species | Organ of Origin | Disease |
|---|---|---|---|
| RXF 393 | Human | Kidney | Poorly Differentiated Hypernephroma |
| SN12C | Human | Kidney | Carcinoma |
| TK-10 | Human | Kidney | Spindle Cell carcinoma |
| UO-31 | Human | Kidney | Carcinoma |
| A549 | Human | Lung | Adenocarcinoma |
| EKVX | Human | Lung | Adenocarcinoma |
| HOP-62 | Human | Lung | Adenocarcinoma |
| HOP-92 | Human | Lung | Large Cell, Undifferentiated |
| NCI-H226 | Human | Lung | squamous cell carcinoma; mesothelioma |
| NCI-H23 | Human | Lung | adenocarcinoma; non-small cell lung cancer |
| NCI-H460 | Human | Lung | carcinoma; large cell lung cancer |
| NCI-H522 | Human | Lung | adenocarcinoma; non-small cell lung cancer |
| LOX IMVI | Human | Melanoma | Malignant Amelanotic melanoma |
| M14 | Human | Melanoma | malignant melanoma |
| MALME-3M | Human | Melanoma | malignant melanoma |
| MDA-MB-435 | Human | Melanoma | Adenocarcinoma |
| SK-MEL-2 | Human | Melanoma | malignant melanoma |
| SK-MEL-28 | Human | Melanoma | malignant melanoma |
| SK-MEL-5 | Human | Melanoma | malignant melanoma |
| UACC-257 | Human | Melanoma | malignant melanoma |
| UACC-62 | Human | Melanoma | malignant melanoma |
| IGROV1 | Human | Ovary | Cystoadenocarcinoma |
| OVCAR-3 | Human | Ovary | Adenocarcinoma |
| OVCAR-4 | Human | Ovary | Adenocarcinoma |
| OVCAR-5 | Human | Ovary | Adenocarcinoma |
| OVCAR-8 | Human | Ovary | Adenocarcinoma |
| SK-OV-3 | Human | Ovary | Adenocarcinoma |
| NCI-ADR-RES | Human | Ovary | Adenocarcinoma |
| DU145 | Human | Prostate | Carcinoma |
| PC-3 | Human | Prostate | grade IV, adenocarcinoma |

In some embodiments, the adherent cells are cells that correspond to one or more of the following cell lines: BT549, HS 578T, MCF7, MDA-MB-231, MDA-MB-468, T-47D, SF268, SF295, SF539, SNB-19, SNB-75, U251, Colo205, HCC 2998, HCT-116, HCT-15, HT29, KM12, SW620, 786-0, A498, ACHN, CAKI, RXF 393, SN12C, TK-10, UO-31, A549, EKVX, HOP-62, HOP-92, NCI-H226, NCI-H23, NCI-H460, NCI-H522, LOX IMVI, M14, MALME-3M, MDA-MB-435, SK-, EL-2, SK-MEL-28, SK-MEL-5, UACC-257, UACC-62, IGROV1, OVCAR-3, OVCAR-4, OVCAR-5, OVCAR-8, SK-OV-3, NCI-ADR-RES, DU145, PC-3, DU145, H295R, HeLa, KBM-7, LNCaP, MCF-7, MDA-MB-468, PC3, SaOS-2, SH-SY5Y, T-47D, THP-1, U87, vero, MC3T3, GH3, PC12, dog MDCK kidney epithelial, *Xenopus* A6 kidney epithelial, zebrafish AB9, and Sf9 insect epithelial cell lines.

(12) Tissue Permeabilization

In some embodiments, a biological sample can be permeabilized to facilitate transfer of analytes out of the sample, and/or to facilitate transfer of species (such as capture probes) into the sample. If a sample is not permeabilized sufficiently, the amount of analyte captured from the sample may be too low to enable adequate analysis. Conversely, if the tissue sample is too permeable, the relative spatial relationship of the analytes within the tissue sample can be lost. Hence, a balance between permeabilizing the tissue sample enough to obtain good signal intensity while still maintaining the spatial resolution of the analyte distribution in the sample is desirable.

In general, a biological sample can be permeabilized by exposing the sample to one or more permeabilizing agents. Suitable agents for this purpose include, but are not limited to, organic solvents (e.g., acetone, ethanol, and methanol), cross-linking agents (e.g., paraformaldehyde), detergents (e.g., saponin, Triton X-100™ or Tween-20™), and enzymes (e.g., trypsin, proteases). In some embodiments, the biological sample can be incubated with a cellular permeabilizing agent to facilitate permeabilization of the sample. Additional methods for sample permeabilization are described, for example, in Jamur et al., *Method Mol. Biol.* 588:63-66, 2010, the entire contents of which are incorporated herein by reference. Any suitable method for sample permeabilization can generally be used in connection with the samples described herein.

In some embodiments, where a diffusion-resistant medium is used to limit migration of analytes or other species during the analytical procedure, the diffusion-resistant medium can include at least one permeabilization reagent. For example, the diffusion-resistant medium can include wells (e.g., micro-, nano-, or picowells) containing a permeabilization buffer or reagents. In some embodiments, where the diffusion-resistant medium is a hydrogel, the hydrogel can include a permeabilization buffer. In some embodiments, the hydrogel is soaked in permeabilization buffer prior to contacting the hydrogel with a sample. In some embodiments, the hydrogel or other diffusion-resistant medium can contain dried reagents or monomers to deliver permeabilization reagents when the diffusion-resistant medium is applied to a biological sample. In some embodiments, the diffusion-resistant medium, (i.e. hydrogel) is covalently attached to a solid substrate (i.e. an acrylated glass slide). In some embodiments, the hydrogel can be modified to both contain capture probes and deliver permeabilization reagents. For example, a hydrogel film can be modified to include spatially-barcoded capture probes. The spatially-barcoded hydrogel film is then soaked in permeabilization buffer before contacting the spatially-barcoded hydrogel film to the sample. The spatially-barcoded hydrogel film thus delivers permeabilization reagents to a sample surface in contact with the spatially-barcoded hydrogel, enhancing analyte migration and capture. In some embodiments, the spatially-barcoded hydrogel is applied to a sample and placed in a permeabilization bulk solution. In some embodiments, the hydrogel film soaked in permeabilization reagents is sandwiched between a sample and a spatially-barcoded array. In some embodiments, target analytes are able to diffuse through the permeabilizing reagent soaked hydrogel and hybridize or bind the capture probes on the other side of the hydrogel. In some embodiments, the thickness of the hydrogel is proportional to the resolution loss. In some embodiments, wells (e.g., micro-, nano-, or picowells) can contain spatially-barcoded capture probes and permeabilization reagents and/or buffer. In some embodiments, spatially-barcoded capture probes and permeabilization reagents are held between spacers. In some embodiments, the sample is punch, cut, or transferred into the well, wherein a target analyte diffuses through the permeabilization reagent/buffer and to the spatially-barcoded capture probes. In some embodiments, resolution loss may be proportional to gap thickness (e.g. the amount of permeabilization buffer between the sample and the capture probes). In some embodiments, the diffusion-resistant medium (e.g. hydrogel) is between approximately 50-500 micrometers thick including 500, 450, 400, 350, 300, 250, 200, 150, 100, or 50 micrometers thick, or any thickness within 50 and 500 micrometers.

In some embodiments, permeabilization solution can be delivered to a sample through a porous membrane. In some embodiments, a porous membrane is used to limit diffusive analyte losses, while allowing permeabilization reagents to reach a sample. Membrane chemistry and pore size can be manipulated to minimize analyte loss. In some embodiments, the porous membrane may be made of glass, silicon, paper, hydrogel, polymer monoliths, or other material. In some embodiments, the material may be naturally porous. In some embodiments, the material may have pores or wells etched into solid material. In some embodiments, the permeabilization reagents are flowed through a microfluidic chamber or channel over the porous membrane. In some embodiments, the flow controls the sample's access to the permeabilization reagents. In some embodiments, a porous membrane is sandwiched between a spatially-barcoded array and the sample, wherein permeabilization solution is applied over the porous membrane. The permeabilization reagents diffuse through the pores of the membrane and into the tissue.

In some embodiments, the biological sample can be permeabilized by adding one or more lysis reagents to the sample. Examples of suitable lysis agents include, but are not limited to, bioactive reagents such as lysis enzymes that are used for lysis of different cell types, e.g., gram positive or negative bacteria, plants, yeast, mammalian, such as lysozymes, achromopeptidase, lysostaphin, labiase, kitalase, lyticase, and a variety of other commercially available lysis enzymes.

Other lysis agents can additionally or alternatively be added to the biological sample to facilitate permeabilization. For example, surfactant-based lysis solutions can be used to lyse sample cells. Lysis solutions can include ionic surfactants such as, for example, sarcosyl and sodium dodecyl sulfate (SDS). More generally, chemical lysis agents can include, without limitation, organic solvents, chelating agents, detergents, surfactants, and chaotropic agents.

In some embodiments, the biological sample can be permeabilized by non-chemical permeabilization methods. Non-chemical permeabilization methods are known in the art. For example, non-chemical permeabilization methods that can be used include, but are not limited to, physical lysis techniques such as electroporation, mechanical permeabilization methods (e.g., bead beating using a homogenizer and grinding balls to mechanically disrupt sample tissue structures), acoustic permeabilization (e.g., sonication), and thermal lysis techniques such as heating to induce thermal permeabilization of the sample.

(13) Selective Enrichment of RNA Species

In some embodiments, where RNA is the analyte, one or more RNA analyte species of interest can be selectively enriched. For example, one or more species of RNA of interest can be selected by addition of one or more oligonucleotides to the sample. In some embodiments, the additional oligonucleotide is a sequence used for priming a reaction by a polymerase. For example, one or more primer sequences with sequence complementarity to one or more RNAs of interest can be used to amplify the one or more RNAs of interest, thereby selectively enriching these RNAs. In some embodiments, an oligonucleotide with sequence complementarity to the complementary strand of captured RNA (e.g., cDNA) can bind to the cDNA. For example, biotinylated oligonucleotides with sequence complementary to one or more cDNA of interest binds to the cDNA and can be selected using biotinylation-strepavidin affinity using any of a variety of methods known to the field (e.g., streptavidin beads).

Alternatively, one or more species of RNA can be down-selected (e.g., removed) using any of a variety of methods. For example, probes can be administered to a sample that selectively hybridize to ribosomal RNA (rRNA), thereby reducing the pool and concentration of rRNA in the sample. Subsequent application of the capture probes to the sample can result in improved capture of other types of RNA due to the reduction in non-specific RNA present in the sample. Additionally and alternatively, duplex-specific nuclease (DSN) treatment can remove rRNA (see, e.g., Archer, et al, Selective and flexible depletion of problematic sequences from RNA-seq libraries at the cDNA stage, *BMC Genomics*, 15 401, (2014), the entire contents of which are incorporated herein by reference). Furthermore, hydroxyapatite chromatography can remove abundant species (e.g., rRNA) (see, e.g., Vandernoot, V. A., cDNA normalization by hydroxyapatite chromatography to enrich transcriptome diversity in RNA-seq applications, *Biotechniques*, 53(6) 373-80, (2012), the entire contents of which are incorporated herein by reference).

(14) Other Reagents

Additional reagents can be added to a biological sample to perform various functions prior to analysis of the sample. In some embodiments, DNase and RNase inactivating agents or inhibitors such as proteinase K, and/or chelating agents such as EDTA, can be added to the sample.

In some embodiments, the sample can be treated with one or more enzymes. For example, one or more endonucleases to fragment DNA, DNA polymerase enzymes, and dNTPs used to amplify nucleic acids can be added. Other enzymes that can also be added to the sample include, but are not limited to, polymerase, transposase, ligase, and DNAse, and RNAse.

In some embodiments, reverse transcriptase enzymes can be added to the sample, including enzymes with terminal transferase activity, primers, and switch oligonucleotides. Template switching can be used to increase the length of a cDNA, e.g., by appending a predefined nucleic acid sequence to the cDNA.

(15) Pre-processing for Capture Probe Interaction

In some embodiments, analytes in a biological sample can be pre-processed prior to interaction with a capture probe. For example, prior to interaction with capture probes, polymerization reactions catalyzed by a polymerase (e.g., DNA polymerase or reverse transcriptase) are performed in the biological sample. In some embodiments, a primer for the polymerization reaction includes a functional group that enhances hybridization with the capture probe. The capture probes can include appropriate capture domains to capture biological analytes of interest (e.g., poly(dT) sequence to capture poly(A) mRNA).

In some embodiments, biological analytes are pre-processed for library generation via next generation sequencing. For example, analytes can be pre-processed by addition of a modification (e.g., ligation of sequences that allow interaction with capture probes). In some embodiments, analytes (e.g., DNA or RNA) are fragmented using fragmentation techniques (e.g., using transposases and/or fragmentation buffers).

Fragmentation can be followed by a modification of the analyte. For example, a modification can be the addition through ligation of an adapter sequence that allows hybridization with the capture probe. In some embodiments, where the analyte of interest is RNA, poly(A) tailing is performed. Addition of a poly(A) tail to RNA that does not contain a poly(A) tail can facilitate hybridization with a capture probe that includes a capture domain with a functional amount of poly(dT) sequence.

In some embodiments, prior to interaction with capture probes, ligation reactions catalyzed by a ligase are performed in the biological sample. In some embodiments, ligation can be performed by chemical ligation. In some embodiments, the ligation can be performed using click chemistry as further below. In some embodiments, the capture domain includes a DNA sequence that has complementarity to a RNA molecule, where the RNA molecule has complementarity to a second DNA sequence, and where the RNA-DNA sequence complementarity is used to ligate the second DNA sequence to the DNA sequence in the capture domain. In these embodiments, direct detection of RNA molecules is possible.

In some embodiments, prior to interaction with capture probes, target-specific reactions are performed in the biological sample. Examples of target specific reactions include, but are not limited to, ligation of target specific adaptors, probes and/or other oligonucleotides, target specific amplification using primers specific to one or more analytes, and target-specific detection using in situ hybridization, DNA microscopy, and/or antibody detection. In some embodiments, a capture probe includes capture domains targeted to target-specific products (e.g., amplification or ligation).

II. General Spatial Array-Based Analytical Methodology

This section of the disclosure describes methods, apparatus, systems, and compositions for spatial array-based analysis of biological samples.

(a) Spatial Analysis Methods

Array-based spatial analysis methods involve the transfer of one or more analytes from a biological sample to an array of features on a substrate, each of which is associated with a unique spatial location on the array. Subsequent analysis of the transferred analytes includes determining the identity of the analytes and the spatial location of each analyte within the sample. The spatial location of each analyte within the sample is determined based on the feature to which each analyte is bound in the array, and the feature's relative spatial location within the array.

There are at least two general methods to associate a spatial barcode with one or more neighboring cells, such that the spatial barcode identifies the one or more cells, and/or contents of the one or more cells, as associated with a particular spatial location. One general method is to drive target analytes out of a cell and towards the spatially-barcoded array. FIG. 1 depicts an exemplary embodiment of this general method. In FIG. 1, the spatially-barcoded array populated with capture probes (as described further herein) is contacted with a sample 101, and sample is permeabilized, allowing the target analyte to migrate away from the sample and toward the array. The target analyte interacts with a capture probe on the spatially-barcoded array 102. Once the target analyte hybridizes/is bound to the capture probe, the sample is optionally removed from the array and the capture probes are analyzed in order to obtain spatially-resolved analyte information 103.

Figure 2:
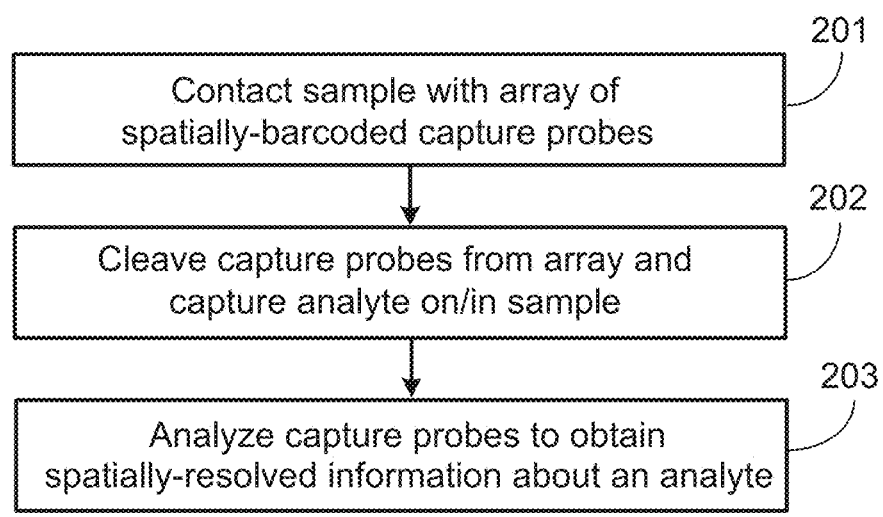
FIG. 2 shows an exemplary spatial analysis workflow.

Another general method is to cleave the spatially-barcoded capture probes from an array, and drive the spatially-barcoded capture probes towards and/or into or onto the sample. FIG. 2 depicts an exemplary embodiment of this general method, the spatially-barcoded array populated with capture probes (as described further herein) can be contacted with a sample 201. The spatially-barcoded capture probes are cleaved and then interact with cells within the provided sample 202. The interaction can be a covalent or non-covalent cell-surface interaction. The interaction can be an intracellular interaction facilitated by a delivery system or a cell penetration peptide. Once the spatially-barcoded capture probe is associated with a particular cell, the sample can be optionally removed for analysis. The sample can be optionally dissociated before analysis. Once the tagged cell is associated with the spatially-barcoded capture probe, the capture probes can be analyzed to obtain spatially-resolved information about the tagged cell 203.

Figure 3:
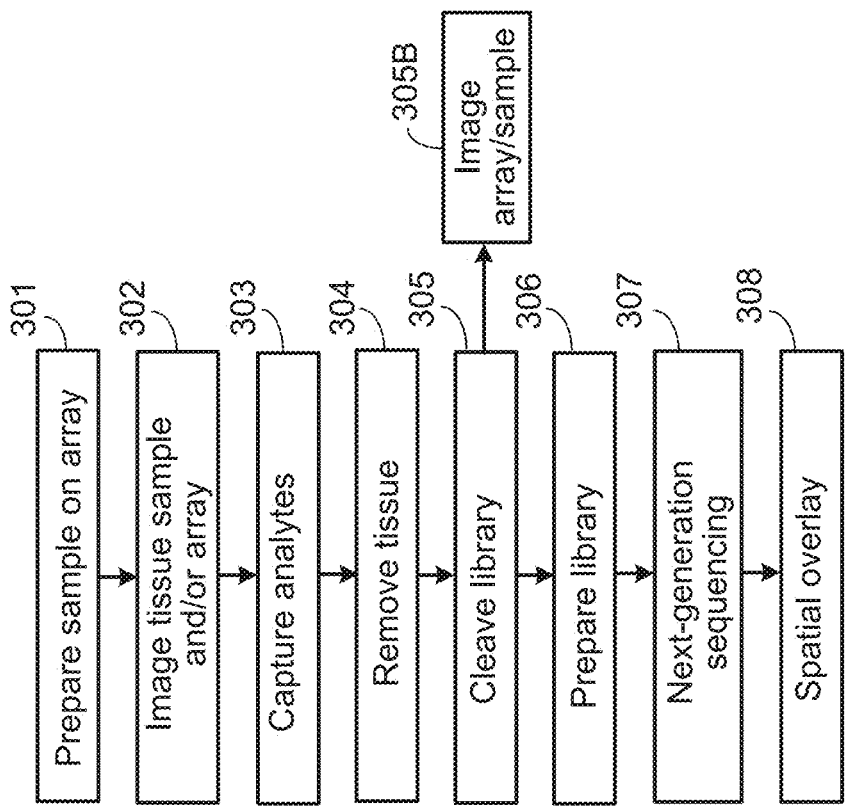
FIG. 3 shows an exemplary spatial analysis workflow.

FIG. 3 shows an exemplary workflow that includes preparing a sample on a spatially-barcoded array 301. Sample preparation may include placing the sample on a slide, fixing the sample, and/or staining the sample for imaging. The stained sample is then imaged on the array 302 using both brightfield (to image the sample hematoxylin and eosin stain) and fluorescence (to image features) modalities. In some embodiments, target analytes are then released from the sample and capture probes forming the spatially-barcoded array hybridize or bind the released target analytes 303. The sample is then removed from the array 304 and the capture probes cleaved from the array 305. The sample and array are then optionally imaged a second time in both modalities 305B while the analytes are reverse transcribed into cDNA, and an amplicon library is prepared 306 and sequenced 307. The two sets of images are then spatially-overlaid in order to correlate spatially-identified sample information 308. When the sample and array are not imaged a second time, 305B, a spot coordinate file is supplied by the manufacturer instead. The spot coordinate file replaces the second imaging step 305B. Further, amplicon library preparation 306 can be performed with a unique PCR adapter and sequenced 307.

Figure 4:
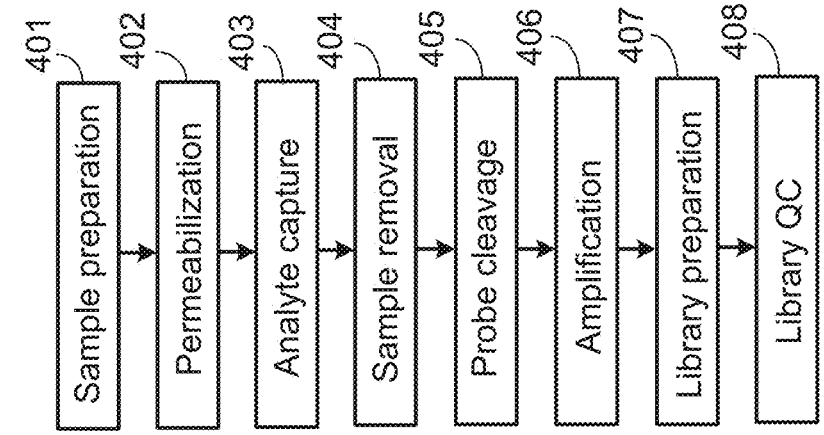
FIG. 4 shows an exemplary spatial analysis workflow.

FIG. 4 shows another exemplary workflow that utilizes a spatially-labelled array on a substrate, where capture probes labelled with spatial barcodes are clustered at areas called features. The spatially-labelled capture probes can include a cleavage domain, one or more functional sequences, a spatial barcode, a unique molecular identifier, and a capture domain. The spatially-labelled capture probes can also include a 5' end modification for reversible attachment to the substrate. The spatially-barcoded array is contacted with a sample 401, and the sample is permeabilized through application of permeabilization reagents 402. Permeabilization reagents may be administered by placing the array/sample assembly within a bulk solution. Alternatively, permeabilization reagents may be administered to the sample via a diffusion-resistant medium and/or a physical barrier such as a lid, wherein the sample is sandwiched between the diffusion-resistant medium and/or barrier and the array-containing substrate. The analytes are migrated toward the spatially-barcoded capture array using any number of techniques disclosed herein. For example, analyte migration can occur using a diffusion-resistant medium lid and passive migration. As another example, analyte migration can be active migration, using an electrophoretic transfer system, for example. Once the analytes are in close proximity to the spatially-barcoded capture probes, the capture probes can hybridize or otherwise bind a target analyte 403. The sample can be optionally removed from the array 404.

The capture probes can be optionally cleaved from the array 405, and the captured analytes can be spatially-tagged by performing a reverse transcriptase first strand cDNA reaction. A first strand cDNA reaction can be optionally performed using template switching oligonucleotides. For example, a template switching oligonucleotide can hybridize to a poly(C) tail added to a 3'end of the cDNA by a reverse transcriptase enzyme. The original mRNA template and template switching oligonucleotide can then be denatured from the cDNA and the barcoded capture probe can then hybridize with the cDNA and a complement of the cDNA can be generated. The first strand cDNA can then be purified and collected for downstream amplification steps. The first strand cDNA can be amplified using PCR 406, wherein the forward and reverse primers flank the spatial barcode and target analyte regions of interest, generating a library associated with a particular spatial barcode. In some embodiments, the cDNA comprises a sequencing by synthesis (SBS) primer sequence. The library amplicons are sequenced and analyzed to decode spatial information 407.

Figure 5:
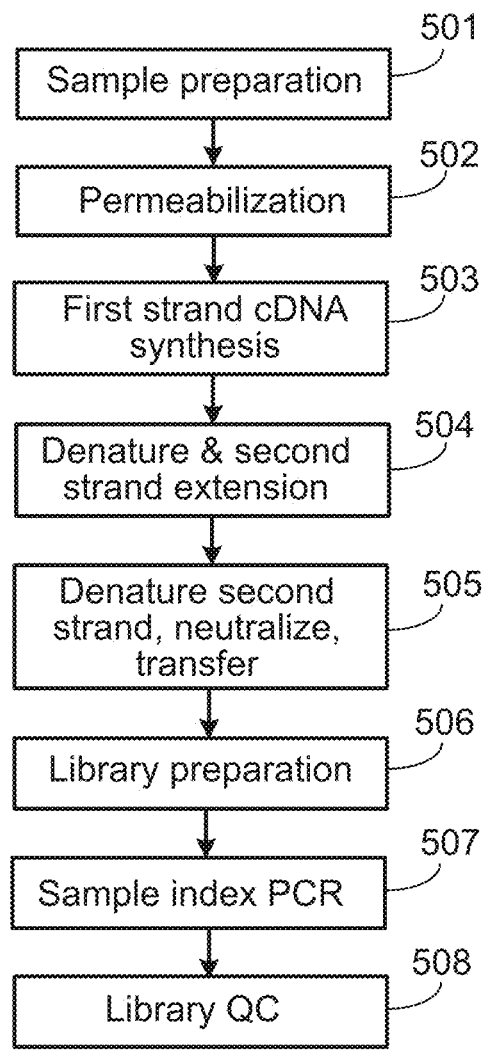
FIG. 5 shows an exemplary spatial analysis workflow.

FIG. 5 depicts an exemplary workflow where the sample is removed from the spatially-barcoded array and the spatially-barcoded capture probes are removed from the array for barcoded analyte amplification and library preparation. Another embodiment includes performing first strand synthesis using template switching oligonucleotides on the spatially-barcoded array without cleaving the capture probes. In this embodiment, sample preparation 501 and permeabilization 502 are performed as described elsewhere herein. Once the capture probes capture the target analyte(s), first strand cDNA created by template switching and reverse transcriptase 503 is then denatured and the second strand is then extended 504. The second strand cDNA is then denatured from the first strand cDNA, neutralized, and transferred to a tube 505. cDNA quantification and amplification can be performed using standard techniques discussed herein. The cDNA can then be subjected to library preparation 506 and indexing 507, including fragmentation, end-repair, and a-tailing, and indexing PCR steps.

In some non-limiting examples of the workflow above, the sample can be immersed in 100% chilled methanol and incubated for 30 minutes at −20° C. After 20 minutes, the sample can be removed and rinsed in ultrapure water. After rinsing the sample, fresh eosin solution is prepared, and the sample can be covered in isopropanol. After incubating the sample in isopropanol for 1 minute, the reagent can be removed by holding the slide at an angle, where the bottom edge of the slide can be in contact with a laboratory wipe and air dried. The sample can be uniformly covered in hematoxylin solution and incubated for 7 minutes at room temperature. After incubating the sample in hematoxylin for 7 minutes, the reagent can be removed by holding the slide at an angle, where the bottom edge of the slide can be in contact with a laboratory wipe. The slide containing the sample can be immersed in water and the excess liquid can be removed. After that, the sample can be covered with blueing buffer and can be incubated for 2 minutes at room temperature. The slide containing the sample can again be immersed in water, and uniformly covered with eosin solution and incubated for 1 minute at room temperature. The slide can be air-dried and incubated for 5 minutes at 37° C. The sample can be imaged using the methods disclosed herein.

The following are non-limiting, exemplary steps for sample permeabilization and cDNA generation. The sample can be exposed to a permeabilization enzyme and incubated for 6 minutes at 37° C. Other permeabilization methods are described herein. The permeabilization enzyme can be removed and the sample prepared for analyte capture by adding SSC buffer. The sample can then subjected to a pre-equilibration thermocycling protocol and the SSC buffer can be removed. A Master Mix, containing nuclease-free water, a reverse transcriptase reagent, a template switch oligo, a reducing agent, and a reverse transcriptase enzyme can be added, and the sample with the Master Mix can be subjected to a thermocycling protocol. The reagents can be removed from the sample and NaOH can be applied and incubated for 5 minutes at room temperature. The NaOH can be removed and elution buffer can be added and removed from the sample. A Second Strand Mix, including a second strand reagent, a second strand primer, and a second strand enzyme, can be added to the sample and the sample can be sealed and incubated. At the end of the incubation, the reagents can be removed and elution buffer can be added and removed from the sample, and NaOH can be added again to the sample and the sample can be incubated for 10 minutes at room temperature. Tris-HCl can be added and the reagents can be mixed.

The following steps are non-limiting, exemplary steps for cDNA amplification and quality control. A qPCR Mix, including nuclease-free water, qPCR Master Mix, and cDNA primers, can be prepared and the NaOH/Tris-HCl mix can be mixed with the qPCR Mix and the sample, and thermocycled according to a predetermined thermocycling protocol. After completing the thermocycling, a cDNA amplification mix can be prepared and combined with the sample and mixed. The sample can then be incubated and thermocycled. The sample can then be resuspended in SPRIselect Reagent and pipetted to ensure proper mixing. The sample can then be incubated at 5 minutes at room temperature, and cleared by placing the sample on a magnet (e.g., the magnet is in the high position). The supernatant can be removed and 80% ethanol can be added to the pellet, and incubated for 30 seconds. The ethanol can be removed and the pellet can be washed again. The sample can then be centrifuged and placed on a magnet (e.g., the magnet is on the low position). Any remaining ethanol can be removed and the sample can be air dried. The magnet can be removed and elution buffer can be added to the sample, mixed, and incubated for 2 minutes at room temperature. The sample can then be placed on the magnet (e.g., on high position) until the solution clears. A portion of the sample can be run on an Agilent Bioanalyzer High Sensitivity chip, where a region can be selected and the cDNA concentration can be measured to calculate the total cDNA yield. Alternatively, the quantification can be determined by Agilent Bioanalyzer or Agilent TapeStation.

The following steps are non-limiting, exemplary steps for spatial gene expression library construction. A Fragmentation Mix, including a fragmentation buffer and fragmentation enzyme, can be prepared on ice. Elution buffer and fragmentation mix can be added to each sample, mixed, and centrifuged. The sample mix can then be placed in a thermocycler and cycled according to a predetermined protocol. The SPRIselect Reagent can be added to the sample and incubated at 5 minutes at room temperature. The sample can be placed on a magnet (e.g., in the high position) until the solution clears, and the supernatant can be transferred to a new tube strip. SPRIselect Reagent can be added to the sample, mixed, and incubated for 5 minutes at room temperature. The sample can be placed on a magnet (e.g., in the high position) until the solution clears. The supernatant can be removed and 80% ethanol can be added to the pellet, the pellet can be incubated for 30 seconds, and the ethanol can be removed. The ethanol wash can be repeated and the sample placed on a magnet (e.g., in the low position) until the solution clears. The remaining ethanol can be removed and elution buffer can be added to the sample, mixed, and incubated for 2 minutes at room temperature. The sample can be placed on a magnet (e.g., in the high position) until the solution clears, and a portion of the sample can be moved to a new tube strip. An Adaptor Ligation Mix, including ligation buffer, DNA ligase, and adaptor oligos, can be prepared and centrifuged. The Adaptor Ligation Mix can be added to the sample, pipette-mixed, and centrifuged briefly. The sample can then be thermocycled according to a predetermined protocol. The SPRIsleect Reagent can be added to the sample, incubated for 5 minutes at room temperature, and placed on a magnet (e.g., in the high position) until the solution clears. The supernatant can be removed and the pellet can be washed with 80% ethanol, incubated for 30 seconds, and the ethanol can be removed. The ethanol wash can be repeated, and the sample can be centrifuged briefly before placing the sample on a magnet (e.g., in the low position). Any remaining ethanol can be removed and the sample can be air dried. Elution buffer can be added to the sample, the sample can be removed from the magnet, and the sample can be pipette-mixed, incubated for 2 minutes at room temperature, and placed on a magnet (e.g., in the low position) until the solution clears. A portion of the sample can be transferred to a new tube strip. A Sample Index PCR Mix, including amplification mix and SI primer, can be prepared and combined with the sample. The sample/Sample Index PCR Mix can be loaded into an individual Chromium i7 Sample Index well and a thermocycling protocol can be used. SPRIselect Reagent can be added to each sample, mixed, and incubated for 5 minutes at room temperature. The sample can be placed on a magnet (e.g., in the high position) until the solution clears, and the supernatant can be transferred to a new tube strip. The SPRIselect Reagent can be added to each sample, pipette-mixed, and incubated for 5 minutes at room temperature. The sample can then be placed on a magnet (e.g., in the high position) until the solution clears. The supernatant can be removed, and the pellet can be washed with 80% ethanol, incubated for 30 seconds, and then the ethanol can be removed. The ethanol wash can be repeated, the sample centrifuged, and placed on a magnet (e.g., in the low position) to remove any remaining ethanol. The sample can be removed from the magnet and Elution Buffer can be added to the sample, pipette-mixed, and incubated at 2 minutes at room temperature. The sample can be placed on a magnet (e.g., in the low position) until the solution clears and a portion of the sample can be transferred to a new tube strip. The average fragment size can be determined using a Bioanalyzer trace or an Agilent TapeStation.

In some embodiments, performing correlative analysis of data produced by this workflow, and other workflows described herein, can yield over 95% correlation of genes expressed across two capture areas (e.g. 95% or greater, 96% or greater, 97% or greater, 98% or greater, or 99% or greater). When performing the described workflows using single cell RNA sequencing of nuclei, in some embodiments, correlative analysis of the data can yield over 90% (e.g. over 90%, 91%, 92%, 93%, 94%, 95%, 96%, 97%, 98%, or 99%) correlation of genes expressed across two capture areas.

(b) Capture Probes

A "capture probe" refers to any molecule capable of capturing (directly or indirectly) and/or labelling an analyte of interest in a biological sample. In some embodiments, the capture probe is a nucleic acid or a polypeptide. In some embodiments, the capture probe is a conjugate (e.g., an oligonucleotide-antibody conjugate). In some embodiments, the capture probe includes a barcode (e.g., a spatial barcode and/or a unique molecular identifier (UMI)) and a capture domain.

Figure 6:
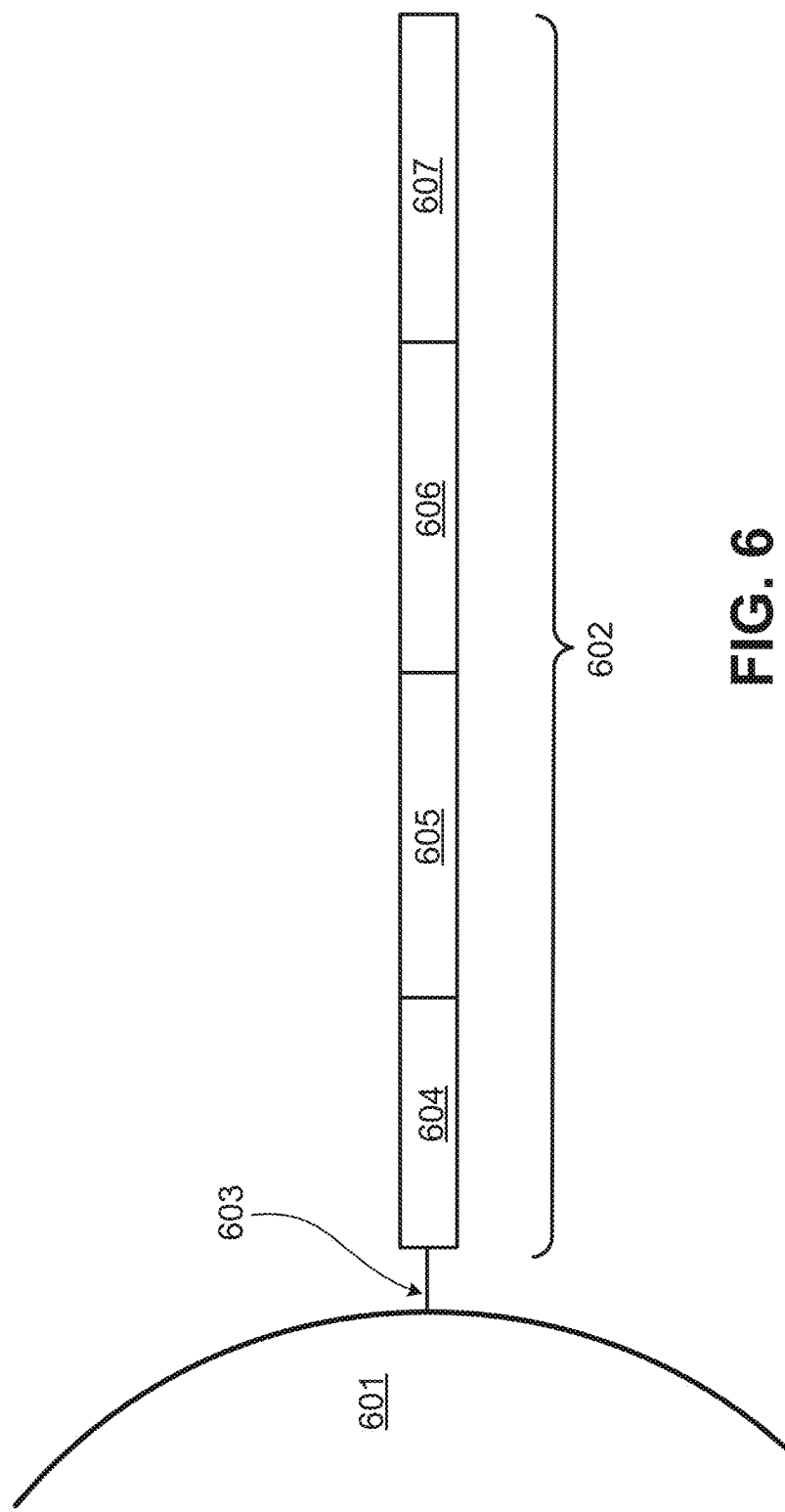
FIG. 6 is a schematic diagram showing an example of a barcoded capture probe, as described herein.

FIG. 6 is a schematic diagram showing an example of a capture probe, as described herein. As shown, the capture probe 602 is optionally coupled to a feature 601 by a cleavage domain 603, such as a disulfide linker. The capture probe can include functional sequences that are useful for subsequent processing, such as functional sequence 604, which can include a sequencer specific flow cell attachment sequence, e.g., a P5 sequence, as well as functional sequence 606, which can include sequencing primer sequences, e.g., a R1 primer binding site. In some embodiments, sequence 604 is a P7 sequence and sequence 606 is a R2 primer binding site. A spatial barcode 605 can be included within the capture probe for use in barcoding the target analyte. The functional sequences can generally be selected for compatibility with any of a variety of different sequencing systems, e.g., 454 Sequencing, Ion Torrent Proton or PGM, Illumina X10, PacBio, Nanopore, etc., and the requirements thereof. In some embodiments, functional sequences can be selected for compatibility with non-commercialized sequencing systems. Examples of such sequencing systems and techniques, for which suitable functional sequences can be used, include (but are not limited to) Roche 454 sequencing, Ion Torrent Proton or PGM sequencing, Illumina X10 sequencing, PacBio SMRT sequencing, and Oxford Nanopore sequencing. Further, in some embodiments, functional sequences can be selected for compatibility with other sequencing systems, including non-commercialized sequencing systems.

In some embodiments, the spatial barcode 605, functional sequences 604 (e.g., flow cell attachment sequence) and 606 (e.g., sequencing primer sequences) can be common to all of the probes attached to a given feature. The spatial barcode can also include a capture domain 607 to facilitate capture of a target analyte.

Capture Domain

As discussed above, each capture probe includes at least one capture domain. The "capture domain" is an oligonucleotide, a polypeptide, a small molecule, or any combination thereof, that binds specifically to a desired analyte. In some embodiments, a capture domain can be used to capture or detect a desired analyte.

In some embodiments, the capture domain is a functional nucleic acid sequence configured to interact with one or more analytes, such as one or more different types of nucleic acids (e.g., RNA molecules and DNA molecules). In some embodiments, the functional nucleic acid sequence can include an N-mer sequence (e.g., a random N-mer sequence), which N-mer sequences are configured to interact with a plurality of DNA molecules. In some embodiments, the functional sequence can include a poly(T) sequence, which poly(T) sequences are configured to interact with messenger RNA (mRNA) molecules via the poly (A) tail of an mRNA transcript. In some embodiments, the functional nucleic acid sequence is the binding target of a protein (e.g., a transcription factor, a DNA binding protein, or a RNA binding protein), where the analyte of interest is a protein.

Capture probes can include ribonucleotides and/or deoxyribonucleotides as well as synthetic nucleotide residues that are capable of participating in Watson-Crick type or analogous base pair interactions. In some embodiments, the capture domain is capable of priming a reverse transcription reaction to generate cDNA that is complementary to the captured RNA molecules. In some embodiments, the capture domain of the capture probe can prime a DNA extension (polymerase) reaction to generate DNA that is complementary to the captured DNA molecules. In some embodiments, the capture domain can template a ligation reaction between the captured DNA molecules and a surface probe that is directly or indirectly immobilized on the substrate. In some embodiments, the capture domain can be ligated to one strand of the captured DNA molecules. For example, SplintR ligase along with RNA or DNA sequences (e.g., degenerate RNA) can be used to ligate a single-stranded DNA or RNA to the capture domain. In some embodiments, ligases with RNA-templated ligase activity, e.g., SplintR ligase, T4 RNA ligase 2 or KOD ligase, can be used to ligate a single-stranded DNA or RNA to the capture domain. In some embodiments, a capture domain includes a splint oligonucleotide. In some embodiments, a capture domain captures a splint oligonucleotide.

In some embodiments, the capture domain is located at the 3' end of the capture probe and includes a free 3' end that can be extended, e.g. by template dependent polymerization, to form an extended capture probe as described herein. In some embodiments, the capture domain includes a nucleotide sequence that is capable of hybridizing to nucleic acid, e.g. RNA or other analyte, present in the cells of the tissue sample contacted with the array. In some embodiments, the capture domain can be selected or designed to bind selectively or specifically to a target nucleic acid. For example, the capture domain can be selected or designed to capture mRNA by way of hybridization to the mRNA poly(A) tail. Thus, in some embodiments, the capture domain includes a poly(T) DNA oligonucleotide, i.e., a series of consecutive deoxythymidine residues linked by phosphodiester bonds, which is capable of hybridizing to the poly(A) tail of mRNA. In some embodiments, the capture domain can include nucleotides that are functionally or structurally analogous to a poly(T) tail. For example, a poly(U) oligonucleotide or an oligonucleotide included of deoxythymidine analogues. In some embodiments, the capture domain includes at least 10, 11, 12, 13, 14, 15, 16, 17, 18, 19, or 20 nucleotides. In some embodiments, the capture domain includes at least 25, 30, or 35 nucleotides.

In some embodiments, random sequences, e.g., random hexamers or similar sequences, can be used to form all or a part of the capture domain. For example, random sequences can be used in conjunction with poly(T) (or poly(T) analogue) sequences. Thus, where a capture domain includes a poly(T) (or a "poly(T)-like") oligonucleotide, it can also include a random oligonucleotide sequence (e.g., "poly(T)-random sequence" probe). This can, for example, be located 5' or 3' of the poly(T) sequence, e.g. at the 3' end of the capture domain. The poly(T)-random sequence probe can facilitate the capture of the mRNA poly(A) tail. In some embodiments, the capture domain can be an entirely random sequence. In some embodiments, degenerate capture domains can be used.

In some embodiments, a pool of two or more capture probes form a mixture, where the capture domain of one or more capture probes includes a poly(T) sequence and the capture domain of one or more capture probes includes random sequences. In some embodiments, a pool of two or more capture probes form a mixture where the capture domain of one or more capture probes includes poly(T)-like sequence and the capture domain of one or more capture probes includes random sequences. In some embodiments, a pool of two or more capture probes form a mixture where the capture domain of one or more capture probes includes a poly(T)-random sequences and the capture domain of one or more capture probes includes random sequences. In some embodiments, probes with degenerate capture domains can be added to any of the preceding combinations listed herein. In some embodiments, probes with degenerate capture domains can be substituted for one of the probes in each of the pairs described herein.

The capture domain can be based on a particular gene sequence or particular motif sequence or common/conserved sequence, that it is designed to capture (i.e., a sequence-specific capture domain). Thus, in some embodiments, the capture domain is capable of binding selectively to a desired sub-type or subset of nucleic acid, for example a particular type of RNA, such as mRNA, rRNA, tRNA, SRP RNA, tmRNA, snRNA, snoRNA, SmY RNA, scaRNA, gRNA, RNase P, RNase MRP, TERC, SL RNA, aRNA, cis-NAT, crRNA, lncRNA, miRNA, piRNA, siRNA, shRNA, tasiRNA, rasiRNA, 7SK, eRNA, ncRNA or other types of RNA. In a non-limiting example, the capture domain can be capable of binding selectively to a desired subset of ribonucleic acids, for example, microbiome RNA, such as 16S rRNA.

In some embodiments, a capture domain includes an "anchor" or "anchoring sequence", which is a sequence of nucleotides that is designed to ensure that the capture domain hybridizes to the intended biological analyte. In some embodiments, an anchor sequence includes a sequence of nucleotides, including a 1-mer, 2-mer, 3-mer or longer sequence. In some embodiments, the short sequence is random. For example, a capture domain including a poly(T) sequence can be designed to capture an mRNA. In such embodiments, an anchoring sequence can include a random 3-mer (e.g., GGG) that helps ensure that the poly(T) capture domain hybridizes to an mRNA. In some embodiments, an anchoring sequence can be VN, N, or NN. Alternatively, the sequence can be designed using a specific sequence of nucleotides. In some embodiments, the anchor sequence is at the 3' end of the capture domain. In some embodiments, the anchor sequence is at the 5' end of the capture domain.

In some embodiments, capture domains of capture probes are blocked prior to contacting the biological sample with the array, and blocking probes are used when the nucleic acid in the biological sample is modified prior to its capture on the array. In some embodiments, the blocking probe is used to block or modify the free 3' end of the capture domain. In some embodiments, blocking probes can be hybridized to the capture probes to mask the free 3' end of the capture domain, e.g., hairpin probes or partially double stranded probes. In some embodiments, the free 3' end of the capture domain can be blocked by chemical modification, e.g., addition of an azidomethyl group as a chemically reversible capping moiety such that the capture probes do not include a free 3' end. Blocking or modifying the capture probes, particularly at the free 3' end of the capture domain, prior to contacting the biological sample with the array, prevents modification of the capture probes, e.g., prevents the addition of a poly(A) tail to the free 3' end of the capture probes.

Non-limiting examples of 3' modifications include dideoxy C-3' (3'-ddC), 3' inverted dT, 3' C3 spacer, 3'Amino, and 3' phosphorylation. In some embodiments, the nucleic acid in the biological sample can be modified such that it can be captured by the capture domain. For example, an adaptor sequence (including a binding domain capable of binding to the capture domain of the capture probe) can be added to the end of the nucleic acid, e.g., fragmented genomic DNA. In some embodiments, this is achieved by ligation of the adaptor sequence or extension of the nucleic acid. In some embodiments, an enzyme is used to incorporate additional nucleotides at the end of the nucleic acid sequence, e.g., a poly(A) tail. In some embodiments, the capture probes can be reversibly masked or modified such that the capture domain of the capture probe does not include a free 3' end. In some embodiments, the 3' end is removed, modified, or made inaccessible so that the capture domain is not susceptible to the process used to modify the nucleic acid of the biological sample, e.g., ligation or extension.

In some embodiments, the capture domain of the capture probe is modified to allow the removal of any modifications of the capture probe that occur during modification of the nucleic acid molecules of the biological sample. In some embodiments, the capture probes can include an additional sequence downstream of the capture domain, i.e., 3' to the capture domain, namely a blocking domain.

In some embodiments, the capture domain of the capture probe can be a non-nucleic acid domain. Examples of suitable capture domains that are not exclusively nucleic-acid based include, but are not limited to, proteins, peptides, aptamers, antigens, antibodies, and molecular analogs that mimic the functionality of any of the capture domains described herein.

Cleavage Domain

Each capture probe can optionally include at least one cleavage domain. The cleavage domain represents the portion of the probe that is used to reversibly attach the probe to an array feature, as will be described further below. Further, one or more segments or regions of the capture probe can optionally be released from the array feature by cleavage of the cleavage domain. As an example spatial barcodes and/or universal molecular identifiers (UMIs) can be released by cleavage of the cleavage domain.

Figure 7:
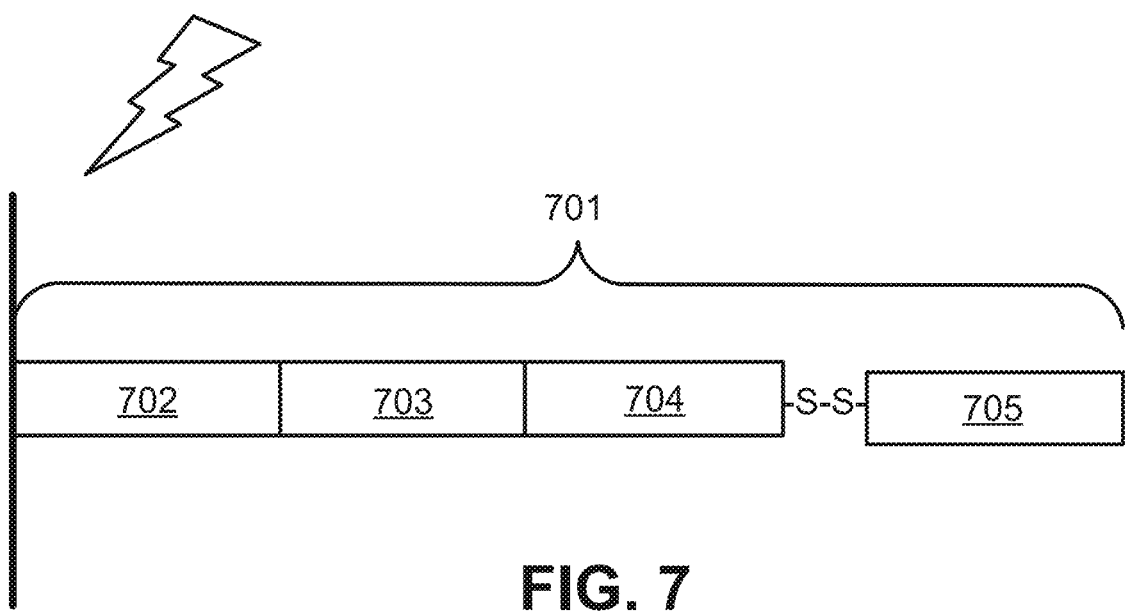
FIG. 7 is a schematic illustrating a cleavable capture probe, wherein the cleaved capture probe can enter into a non-permeabilized cell and bind to target analytes within the sample.

FIG. 7 is a schematic illustrating a cleavable capture probe, wherein the cleaved capture probe can enter into a non-permeabilized cell and bind to target analytes within the sample. The capture probe 701 contains a cleavage domain 702, a cell penetrating peptide 703, a reporter molecule 704, and a disulfide bond (—S—S—). 705 represents all other parts of a capture probe, for example a spatial barcode and a capture domain.

In some embodiments, the cleavage domain linking the capture probe to a feature is a disulfide bond. A reducing agent can be added to break the disulfide bonds, resulting in release of the capture probe from the feature. As another example, heating can also result in degradation of the cleavage domain and release of the attached capture probe from the array feature. In some embodiments, laser radiation is used to heat and degrade cleavage domains of capture probes at specific locations. In some embodiments, the cleavage domain is a photo-sensitive chemical bond (i.e., a chemical bond that dissociates when exposed to light such as ultraviolet light).

Other examples of cleavage domains include labile chemical bonds such as, but not limited to, ester linkages (e.g., cleavable with an acid, a base, or hydroxylamine), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), or a phosphodiester linkage (e.g., cleavable via a nuclease (e.g., DNAase)).

In some embodiments, the cleavage domain includes a sequence that is recognized by one or more enzymes capable of cleaving a nucleic acid molecule, e.g., capable of breaking the phosphodiester linkage between two or more nucleotides. A bond can be cleavable via other nucleic acid molecule targeting enzymes, such as restriction enzymes (e.g., restriction endonucleases). For example, the cleavage domain can include a restriction endonuclease (restriction enzyme) recognition sequence. Restriction enzymes cut double-stranded or single stranded DNA at specific recognition nucleotide sequences known as restriction sites. In some embodiments, a rare-cutting restriction enzyme, i.e., enzymes with a long recognition site (at least 8 base pairs in length), is used to reduce the possibility of cleaving elsewhere in the capture probe.

In some embodiments, the cleavage domain includes a poly(U) sequence which can be cleaved by a mixture of Uracil DNA glycosylase (UDG) and the DNA glycosylase-lyase Endonuclease VIII, commercially known as the USER™ enzyme. Releasable capture probes can be available for reaction once released. Thus, for example, an activatable capture probe can be activated by releasing the capture probes from a feature.

In some embodiments, where the capture probe is attached indirectly to a substrate, e.g., via a surface probe, the cleavage domain includes one or more mismatch nucleotides, so that the complementary parts of the surface probe and the capture probe are not 100% complementary (for example, the number of mismatched base pairs can one, two, or three base pairs). Such a mismatch is recognized, e.g., by the MutY and T7 endonuclease I enzymes, which results in cleavage of the nucleic acid molecule at the position of the mismatch.

In some embodiments, where the capture probe is attached to a feature indirectly, e.g., via a surface probe, the cleavage domain includes a nickase recognition site or sequence. Nickases are endonucleases which cleave only a single strand of a DNA duplex. Thus, the cleavage domain can include a nickase recognition site close to the 5' end of the surface probe (and/or the 5' end of the capture probe) such that cleavage of the surface probe or capture probe destabilizes the duplex between the surface probe and capture probe thereby releasing the capture probe) from the feature.

Nickase enzymes can also be used in some embodiments where the capture probe is attached to the feature directly. For example, the substrate can be contacted with a nucleic acid molecule that hybridizes to the cleavage domain of the capture probe to provide or reconstitute a nickase recognition site, e.g., a cleavage helper probe. Thus, contact with a nickase enzyme will result in cleavage of the cleavage domain thereby releasing the capture probe from the feature. Such cleavage helper probes can also be used to provide or reconstitute cleavage recognition sites for other cleavage enzymes, e.g., restriction enzymes.

Some nickases introduce single-stranded nicks only at particular sites on a DNA molecule, by binding to and recognizing a particular nucleotide recognition sequence. A number of naturally-occurring nickases have been discovered, of which at present the sequence recognition properties have been determined for at least four. Nickases are described in U.S. Pat. No. 6,867,028, which is incorporated herein by reference in its entirety. In general, any suitable nickase can be used to bind to a complementary nickase recognition site of a cleavage domain. Following use, the nickase enzyme can be removed from the assay or inactivated following release of the capture probes to prevent unwanted cleavage of the capture probes.

Examples of suitable capture domains that are not exclusively nucleic-acid based include, but are not limited to, proteins, peptides, aptamers, antigens, antibodies, and molecular analogs that mimic the functionality of any of the capture domains described herein.

In some embodiments, a cleavage domain is absent from the capture probe. Examples of substrates with attached capture probes lacking a cleavage domain are described for example in Macosko et al., (2015) Cell 161, 1202-1214, the entire contents of which are incorporated herein by reference.

In some embodiments, the region of the capture probe corresponding to the cleavage domain can be used for some other function. For example, an additional region for nucleic acid extension or amplification can be included where the cleavage domain would normally be positioned. In such embodiments, the region can supplement the functional domain or even exist as an additional functional domain. In some embodiments, the cleavage domain is present but its use is optional.

Functional Domain

Each capture probe can optionally include at least one functional domain. Each functional domain typically includes a functional nucleotide sequence for a downstream analytical step in the overall analysis procedure.

In some embodiments, the capture probe can include a functional domain for attachment to a sequencing flow cell, such as, for example, a P5 sequence for Illumina® sequencing. In some embodiments, the capture probe or derivative thereof can include another functional domain, such as, for example, a P7 sequence for attachment to a sequencing flow cell for Illumina® sequencing. The functional domains can be selected for compatibility with a variety of different sequencing systems, e.g., 454 Sequencing, Ion Torrent Proton or PGM, Illumina X10, etc., and the requirements thereof.

In some embodiments, the functional domain includes a primer. The primer can include an R1 primer sequence for Illumina® sequencing, and in some embodiments, an R2 primer sequence for Illumina® sequencing. Examples of such capture probes and uses thereof are described in U.S. Patent Publication Nos. 2014/0378345 and 2015/0376609, the entire contents of each of which are incorporated herein by reference.

Spatial Barcode

As discussed above, the capture probe can include one or more spatial barcodes (e.g., two or more, three or more, four or more, five or more) spatial barcodes. A "spatial barcode" is a contiguous nucleic acid segment or two or more non-contiguous nucleic acid segments that function as a label or identifier that conveys or is capable of conveying spatial information. In some embodiments, a capture probe includes a spatial barcode that possesses a spatial aspect, where the barcode is associated with a particular location within an array or a particular location on a substrate.

A spatial barcode can be part of an analyte, or independent from an analyte (i.e., part of the capture probe). A spatial barcode can be a tag attached to an analyte (e.g., a nucleic acid molecule) or a combination of a tag in addition to an endogenous characteristic of the analyte (e.g., size of the analyte or end sequence(s)). A spatial barcode can be unique. In some embodiments where the spatial barcode is unique, the spatial barcode functions both as a spatial barcode and as a unique molecular identifier (UMI), associated with one particular capture probe.

Spatial barcodes can have a variety of different formats. For example, spatial barcodes can include polynucleotide spatial barcodes; random nucleic acid and/or amino acid sequences; and synthetic nucleic acid and/or amino acid sequences. In some embodiments, a spatial barcode is attached to an analyte in a reversible or irreversible manner. In some embodiments, a spatial barcode is added to, for example, a fragment of a DNA or RNA sample before, during, and/or after sequencing of the sample. In some embodiments, a spatial barcode allows for identification and/or quantification of individual sequencing-reads. In some embodiments, a spatial barcode is a used as a fluorescent barcode for which fluorescently labeled oligonucleotide probes hybridize to the spatial barcode.

In some embodiments, the spatial barcode is a nucleic acid sequence that does not substantially hybridize to analyte nucleic acid molecules in a biological sample. In some embodiments, the spatial barcode has less than 80% sequence identity (e.g., less than 70%, 60%, 50%, or less than 40% sequence identity) to the nucleic acid sequences across a substantial part (e.g., 80% or more) of the nucleic acid molecules in the biological sample.

The spatial barcode sequences can include from about 6 to about 20 or more nucleotides within the sequence of the capture probes. In some embodiments, the length of a spatial barcode sequence can be about 6, 7, 8, 9, 10, 11, 12, 13, 14, 15, 16, 17, 18, 19, 20 nucleotides or longer. In some embodiments, the length of a spatial barcode sequence can be at least about 6, 7, 8, 9, 10, 11, 12, 13, 14, 15, 16, 17, 18, 19, 20 nucleotides or longer. In some embodiments, the length of a spatial barcode sequence is at most about 6, 7, 8, 9, 10, 11, 12, 13, 14, 15, 16, 17, 18, 19, 20 nucleotides or shorter.

These nucleotides can be completely contiguous, i.e., in a single stretch of adjacent nucleotides, or they can be separated into two or more separate subsequences that are separated by 1 or more nucleotides. Separated spatial barcode subsequences can be from about 4 to about 16 nucleotides in length. In some embodiments, the spatial barcode subsequence can be about 4, 5, 6, 7, 8, 9, 10, 11, 12, 13, 14, 15, 16 nucleotides or longer. In some embodiments, the spatial barcode subsequence can be at least about 4, 5, 6, 7, 8, 9, 10, 11, 12, 13, 14, 15, 16 nucleotides or longer. In some embodiments, the spatial barcode subsequence can be at most about 4, 5, 6, 7, 8, 9, 10, 11, 12, 13, 14, 15, 16 nucleotides or shorter.

For multiple capture probes that are attached to a common array feature, the one or more spatial barcode sequences of the multiple capture probes can include sequences that are the same for all capture probes coupled to the feature, and/or sequences that are different across all capture probes coupled to the feature.

Figure 8:
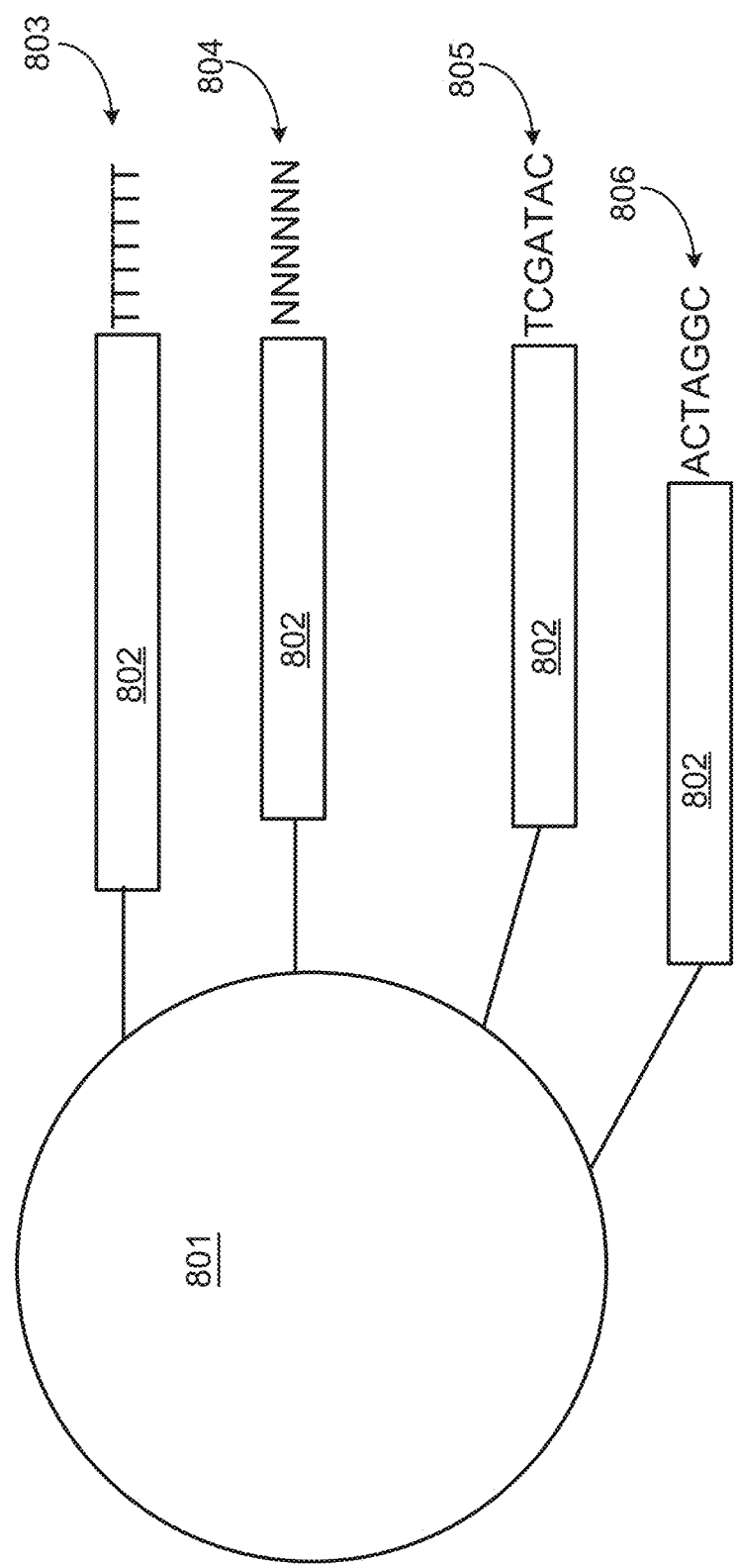
FIG. 8 is a schematic diagram of an exemplary multiplexed spatially-labelled feature.

FIG. 8 is a schematic diagram of an exemplary multiplexed spatially-labelled feature. In FIG. 8, the feature 801 can be coupled to spatially-barcoded capture probes, wherein the spatially-barcoded probes of a particular feature can possess the same spatial barcode, but have different capture domains designed to associate the spatial barcode of the feature with more than one target analyte. For example, a feature may be coupled to four different types of spatially-barcoded capture probes, each type of spatially-barcoded capture probe possessing the spatial barcode 802. One type of capture probe associated with the feature includes the spatial barcode 802 in combination with a poly(T) capture domain 803, designed to capture mRNA target analytes. A second type of capture probe associated with the feature includes the spatial barcode 802 in combination with a random N-mer capture domain 804 for gDNA analysis. A third type of capture probe associated with the feature includes the spatial barcode 802 in combination with a capture domain complementary to the capture domain on an analyte capture agent capture agent barcode domain 805. A fourth type of capture probe associated with the feature includes the spatial barcode 802 in combination with a capture probe that can specifically bind a nucleic acid molecule 806 that can function in a CRISPR assay (e.g., CRISPR/Cas9). While only four different capture probe-barcoded constructs are shown in FIG. 8, capture-probe barcoded constructs can be tailored for analyses of any given analyte associated with a nucleic acid and capable of binding with such a construct. For example, the schemes shown in FIG. 8 can also be used for concurrent analysis of other analytes disclosed herein, including, but not limited to: (a) mRNA, a lineage tracing construct, cell surface or intracellular proteins and metabolites, and gDNA; (b) mRNA, accessible chromatin (e.g., ATAC-seq, DNase-seq, and/or MNase-seq) cell surface or intracellular proteins and metabolites, and a perturbation agent (e.g., a CRISPR crRNA/sgRNA, TALEN, zinc finger nuclease, and/or antisense oligonucleotide as described herein); (c) mRNA, cell surface or intracellular proteins and/or metabolites, a barcoded labelling agent (e.g., the MHC multimers described herein), and a V(D)J sequence of an immune cell receptor (e.g., T-cell receptor).

Capture probes attached to a single array feature can include identical (or common) spatial barcode sequences, different spatial barcode sequences, or a combination of both. Capture probes attached to a feature can include multiple sets of capture probes. Capture probes of a given set can include identical spatial barcode sequences. The identical spatial barcode sequences can be different from spatial barcode sequences of capture probes of another set.

The plurality of capture probes can include spatial barcode sequences (e.g., nucleic acid barcode sequences) that are associated with specific locations on a spatial array. For example, a first plurality of capture probes can be associated with a first region, based on a spatial barcode sequence common to the capture probes within the first region, and a second plurality of capture probes can be associated with a second region, based on a spatial barcode sequence common to the capture probes within the second region. The second region may or may not be associated with the first region. Additional pluralities of capture probes can be associated with spatial barcode sequences common to the capture probes within other regions. In some embodiments, the spatial barcode sequences can be the same across a plurality of capture probe molecules.

In some embodiments, multiple different spatial barcodes are incorporated into a single arrayed capture probe. For example, a mixed but known set of spatial barcode sequences can provide a stronger address or attribution of the spatial barcodes to a given spot or location, by providing duplicate or independent confirmation of the identity of the location. In some embodiments, the multiple spatial barcodes represent increasing specificity of the location of the particular array point.

Unique Molecular Identifier

The capture probe can include one or more (e.g., two or more, three or more, four or more, five or more) Unique Molecular Identifiers (UMIs). A unique molecular identifier is a contiguous nucleic acid segment or two or more non-contiguous nucleic acid segments that function as a label or identifier for a particular analyte, or for a capture probe that binds a particular analyte (e.g., via the capture domain).

A UMI can be unique. A UMI can include one or more specific polynucleotides sequences, one or more random nucleic acid and/or amino acid sequences, and/or one or more synthetic nucleic acid and/or amino acid sequences.

In some embodiments, the UMI is a nucleic acid sequence that does not substantially hybridize to analyte nucleic acid molecules in a biological sample. In some embodiments, the UMI has less than 80% sequence identity (e.g., less than 70%, 60%, 50%, or less than 40% sequence identity) to the nucleic acid sequences across a substantial part (e.g., 80% or more) of the nucleic acid molecules in the biological sample.

The UMI can include from about 6 to about 20 or more nucleotides within the sequence of the capture probes. In some embodiments, the length of a UMI sequence can be about 6, 7, 8, 9, 10, 11, 12, 13, 14, 15, 16, 17, 18, 19, 20 nucleotides or longer. In some embodiments, the length of a UMI sequence can be at least about 6, 7, 8, 9, 10, 11, 12, 13, 14, 15, 16, 17, 18, 19, 20 nucleotides or longer. In some embodiments, the length of a UMI sequence is at most about 6, 7, 8, 9, 10, 11, 12, 13, 14, 15, 16, 17, 18, 19, 20 nucleotides or shorter.

These nucleotides can be completely contiguous, i.e., in a single stretch of adjacent nucleotides, or they can be separated into two or more separate subsequences that are separated by 1 or more nucleotides. Separated UMI subsequences can be from about 4 to about 16 nucleotides in length. In some embodiments, the UMI subsequence can be about 4, 5, 6, 7, 8, 9, 10, 11, 12, 13, 14, 15, 16 nucleotides or longer. In some embodiments, the UMI subsequence can be at least about 4, 5, 6, 7, 8, 9, 10, 11, 12, 13, 14, 15, 16 nucleotides or longer. In some embodiments, the UMI subsequence can be at most about 4, 5, 6, 7, 8, 9, 10, 11, 12, 13, 14, 15, 16 nucleotides or shorter.

In some embodiments, a UMI is attached to an analyte in a reversible or irreversible manner. In some embodiments, a UMI is added to, for example, a fragment of a DNA or RNA sample before, during, and/or after sequencing of the analyte. In some embodiments, a UMI allows for identification and/or quantification of individual sequencing-reads. In some embodiments, a UMI is a used as a fluorescent barcode for which fluorescently labeled oligonucleotide probes hybridize to the UMI.

Other Aspects of Capture Probes

For capture probes that are attached to an array feature, an individual array feature can include one or more capture probes. In some embodiments, an individual array feature includes hundreds or thousands of capture probes. In some embodiments, the capture probes are associated with a particular individual feature, where the individual feature contains a capture probe including a spatial barcode unique to a defined region or location on the array.

In some embodiments, a particular feature can contain capture probes including more than one spatial barcode (e.g., one capture probe at a particular feature can include a spatial barcode that is different than the spatial barcode included in another capture probe at the same particular feature, while both capture probes include a second, common spatial barcode), where each spatial barcode corresponds to a particular defined region or location on the array. For example, multiple spatial barcode sequences associated with one particular feature on an array can provide a stronger address or attribution to a given location by providing duplicate or independent confirmation of the location. In some embodiments, the multiple spatial barcodes represent increasing specificity of the location of the particular array point. In a non-limiting example, a particular array point can be coded with two different spatial barcodes, where each spatial barcode identifies a particular defined region within the array, and an array point possessing both spatial barcodes identifies the sub-region where two defined regions overlap, e.g., such as the overlapping portion of a Venn diagram.

In another non-limiting example, a particular array point can be coded with three different spatial barcodes, where the first spatial barcode identifies a first region within the array, the second spatial barcode identifies a second region, where the second region is a subregion entirely within the first region, and the third spatial barcode identifies a third region, where the third region is a subregion entirely within the first and second subregions.

In some embodiments, capture probes attached to array features are released from the array features for sequencing. Alternatively, in some embodiments, capture probes remain attached to the array features, and the probes are sequenced while remaining attached to the array features (e.g., via in-situ sequencing). Further aspects of the sequencing of capture probes are described in subsequent sections of this disclosure.

In some embodiments, an array feature can include different types of capture probes attached to the feature. For example, the array feature can include a first type of capture probe with a capture domain designed to bind to one type of analyte, and a second type of capture probe with a capture domain designed to bind to a second type of analyte. In general, array features can include one or more (e.g., two or more, three or more, four or more, five or more, six or more, eight or more, ten or more, 12 or more, 15 or more, 20 or more, 30 or more, 50 or more) different types of capture probes attached to a single array feature.

In some embodiments, the capture probe is nucleic acid. In some embodiments, the capture probe is attached to the array feature via its 5' end. In some embodiments, the capture probe includes from the 5' to 3' end: one or more barcodes (e.g., a spatial barcode and/or a UMI) and one or more capture domains. In some embodiments, the capture probe includes from the 5' to 3' end: one barcode (e.g., a spatial barcode or a UMI) and one capture domain. In some embodiments, the capture probe includes from the 5' to 3' end: a cleavage domain, a functional domain, one or more barcodes (e.g., a spatial barcode and/or a UMI), and a capture domain. In some embodiments, the capture probe includes from the 5' to 3' end: a cleavage domain, a functional domain, one or more barcodes (e.g., a spatial barcode and/or a UMI), a second functional domain, and a capture domain. In some embodiments, the capture probe includes from the 5' to 3' end: a cleavage domain, a functional domain, a spatial barcode, a UMI, and a capture domain. In some embodiments, the capture probe does not include a spatial barcode. In some embodiments, the capture probe does not include a UMI. In some embodiments, the capture probe includes a sequence for initiating a sequencing reaction.

In some embodiments, the capture probe is immobilized on a feature via its 3' end. In some embodiments, the capture probe includes from the 3' to 5' end: one or more barcodes (e.g., a spatial barcode and/or a UMI) and one or more capture domains. In some embodiments, the capture probe includes from the 3' to 5' end: one barcode (e.g., a spatial barcode or a UMI) and one capture domain. In some embodiments, the capture probe includes from the 3' to 5' end: a cleavage domain, a functional domain, one or more barcodes (e.g., a spatial barcode and/or a UMI), and a capture domain. In some embodiments, the capture probe includes from the 3' to 5' end: a cleavage domain, a functional domain, a spatial barcode, a UMI, and a capture domain.

In some embodiments, a capture probe includes an in situ synthesized oligonucleotide. In some embodiments, the in situ synthesized oligonucleotide includes one or more constant sequences, one or more of which serves as a priming sequence (e.g., a primer for amplifying target nucleic acids). In some embodiments, a constant sequence is a cleavable sequence. In some embodiments, the in situ synthesized oligonucleotide includes a barcode sequence, e.g., a variable barcode sequence. In some embodiments, the in situ synthesized oligonucleotide is attached to a feature of an array.

In some embodiments, a capture probe is a product of two or more oligonucleotide sequences, e.g., two or more oligonucleotide sequences that are ligated together. In some embodiments, one of the oligonucleotide sequences is an in situ synthesized oligonucleotide.

In some embodiments, the capture probe includes a splint oligonucleotide. Two or more oligonucleotides can be ligated together using a splint oligonucleotide and any variety of ligases known in the art or described herein (e.g., SplintR ligase).

In some embodiments, one of the oligonucleotides includes: a constant sequence (e.g., a sequence complementary to a portion of a splint oligonucleotide), a degenerate sequence, and a capture domain (e.g., as described herein). In some embodiments, the capture probe is generated by having an enzyme add polynucleotides at the end of an oligonucleotide sequence. The capture probe can include a degenerate sequence, which can function as a unique molecular identifier.

A capture probe can include a degenerate sequence, which is a sequence in which some positions of a nucleotide sequence contain a number of possible bases. A degenerate sequence can be a degenerate nucleotide sequence including about or at least 5, 6, 7, 8, 9, 10, 11, 12, 13, 14, 15, 16, 17, 18, 19, 20, 25, 30, 35, 40, 45, or 50 nucleotides. In some embodiments, a nucleotide sequence contains 1, 2, 3, 4, 5, 6, 7, 8, 9, 0, 10, 15, 20, 25, or more degenerate positions within the nucleotide sequence. In some embodiments, the degenerate sequence is used as a UMI.

In some embodiments, a capture probe includes a restriction endonuclease recognition sequence or a sequence of nucleotides cleavable by specific enzyme activities. For example, uracil sequences can be cleaved by specific enzyme activity. As another example, other modified bases (e.g., modified by methylation) can be recognized and cleaved by specific endonucleases. The capture probes can be subjected to an enzymatic cleavage, which removes the blocking domain and any of the additional nucleotides that are added to the 3' end of the capture probe during the modification process. The removal of the blocking domain reveals and/or restores the free 3' end of the capture domain of the capture probe. In some embodiments, additional nucleotides can be removed to reveal and/or restore the 3' end of the capture domain of the capture probe.

In some embodiments, a blocking domain can be incorporated into the capture probe when it is synthesized, or after its synthesis. The terminal nucleotide of the capture domain is a reversible terminator nucleotide (e.g., 3'-O-blocked reversible terminator and 3'-unblocked reversible terminator), and can be included in the capture probe during or after probe synthesis.

Extended Capture Probes

An "extended capture probe" is a capture probe with an enlarged nucleic acid sequence. For example, where the capture probe includes nucleic acid, an "extended 3' end" indicates that further nucleotides were added to the most 3' nucleotide of the capture probe to extend the length of the capture probe, for example, by standard polymerization reactions utilized to extend nucleic acid molecules including templated polymerization catalyzed by a polymerase (e.g., a DNA polymerase or reverse transcriptase).

In some embodiments, extending the capture probe includes generating cDNA from the captured (hybridized) RNA. This process involves synthesis of a complementary strand of the hybridized nucleic acid, e.g., generating cDNA based on the captured RNA template (the RNA hybridized to the capture domain of the capture probe). Thus, in an initial step of extending the capture probe, e.g., the cDNA generation, the captured (hybridized) nucleic acid, e.g., RNA, acts as a template for the extension, e.g., reverse transcription, step.

In some embodiments, the capture probe is extended using reverse transcription. For example, reverse transcription includes synthesizing cDNA (complementary or copy DNA) from RNA, e.g., (messenger RNA), using a reverse transcriptase. In some embodiments, reverse transcription is performed while the tissue is still in place, generating an analyte library, where the analyte library includes the spatial barcodes from the adjacent capture probes. In some embodiments, the capture probe is extended using one or more DNA polymerases.

In some embodiments, the capture domain of the capture probe includes a primer for producing the complementary strand of the nucleic acid hybridized to the capture probe, e.g., a primer for DNA polymerase and/or reverse transcription. The nucleic acid, e.g., DNA and/or cDNA, molecules generated by the extension reaction incorporate the sequence of the capture probe. The extension of the capture probe, e.g., a DNA polymerase and/or reverse transcription reaction, can be performed using a variety of suitable enzymes and protocols.

In some embodiments, a full-length DNA, e.g. cDNA, molecule is generated. In some embodiments, a "full-length" DNA molecule refers to the whole of the captured nucleic acid molecule. However, if the nucleic acid, e.g. RNA, was partially degraded in the tissue sample, then the captured nucleic acid molecules will not be the same length as the initial RNA in the tissue sample. In some embodiments, the 3' end of the extended probes, e.g., first strand cDNA molecules, is modified. For example, a linker or adaptor can be ligated to the 3' end of the extended probes. This can be achieved using single stranded ligation enzymes such as T4 RNA ligase or Circligase™ (available from Epicentre Biotechnologies, Madison, WI). In some embodiments, template switching oligonucleotides are used to extend cDNA in order to generate a full-length cDNA (or as close to a full-length cDNA as possible). In some embodiments, a second strand synthesis helper probe (a partially double stranded DNA molecule capable of hybridizing to the 3' end of the extended capture probe), can be ligated to the 3' end of the extended probe, e.g., first strand cDNA, molecule using a double stranded ligation enzyme such as T4 DNA ligase. Other enzymes appropriate for the ligation step are known in the art and include, e.g., Tth DNA ligase, Taq DNA ligase, *Thermococcus* sp. (strain 9° N) DNA ligase (9° N™ DNA ligase, New England Biolabs), Ampligase™ (available from Epicentre Biotechnologies, Madison, WI), and SplintR (available from New England Biolabs, Ipswich, MA). In some embodiments, a polynucleotide tail, e.g., a poly(A) tail, is incorporated at the 3' end of the extended probe molecules. In some embodiments, the polynucleotide tail is incorporated using a terminal transferase active enzyme.

In some embodiments, double-stranded extended capture probes are treated to remove any unextended capture probes prior to amplification and/or analysis, e.g. sequence analysis. This can be achieved by a variety of methods, e.g., using an enzyme to degrade the unextended probes, such as an exonuclease enzyme, or purification columns.

In some embodiments, extended capture probes are amplified to yield quantities that are sufficient for analysis, e.g., via DNA sequencing. In some embodiments, the first strand of the extended capture probes (e.g., DNA and/or cDNA molecules) acts as a template for the amplification reaction (e.g., a polymerase chain reaction).

In some embodiments, the amplification reaction incorporates an affinity group onto the extended capture probe (e.g., RNA-cDNA hybrid) using a primer including the affinity group. In some embodiments, the primer includes an affinity group and the extended capture probes includes the affinity group. The affinity group can correspond to any of the affinity groups described previously.

In some embodiments, the extended capture probes including the affinity group can be coupled to an array feature specific for the affinity group. In some embodiments, the substrate can include an antibody or antibody fragment. In some embodiments, the array feature includes avidin or streptavidin and the affinity group includes biotin. In some embodiments, the array feature includes maltose and the affinity group includes maltose-binding protein. In some embodiments, the array feature includes maltose-binding protein and the affinity group includes maltose. In some embodiments, amplifying the extended capture probes can function to release the extended probes from the array feature, insofar as copies of the extended probes are not attached to the array feature.

In some embodiments, the extended capture probe or complement or amplicon thereof is released from an array feature. The step of releasing the extended capture probe or complement or amplicon thereof from an array feature can be achieved in a number of ways. In some embodiments, an extended capture probe or a complement thereof is released from the feature by nucleic acid cleavage and/or by denaturation (e.g. by heating to denature a double-stranded molecule).

In some embodiments, the extended capture probe or complement or amplicon thereof is released from the array feature by physical means. For example, methods for inducing physical release include denaturing double stranded nucleic acid molecules. Another method for releasing the extended capture probes is to use a solution that interferes with the hydrogen bonds of the double stranded molecules. In some embodiments, the extended capture probe is released by applying heated water such as water or buffer of at least 85° C., e.g., at least 90, 91, 92, 93, 94, 95, 96, 97, 98, or 99° C. In some embodiments, a solution including salts, surfactants, etc. that can further destabilize the interaction between the nucleic acid molecules is added to release the extended capture probe from the array feature. In some embodiments, a formamide solution can be used to destabilize the interaction between nucleic acid molecules to release the extended capture probe from the array feature.

Analyte Capture Agents

This disclosure also provides methods and materials for using analyte capture agents for spatial profiling of biological analytes (e.g., mRNA, genomic DNA, accessible chromatin, and cell surface or intracellular proteins and/or metabolites). As used herein, an "analyte capture agent" (also referred to previously at times as a "cell labelling" agent") refers to an agent that interacts with an analyte (e.g., an analyte in a sample) and with a capture probe (e.g., a capture probe attached to a substrate) to identify the analyte. In some embodiments, the analyte capture agent includes an analyte binding moiety and a capture agent barcode domain.

Figure 9:
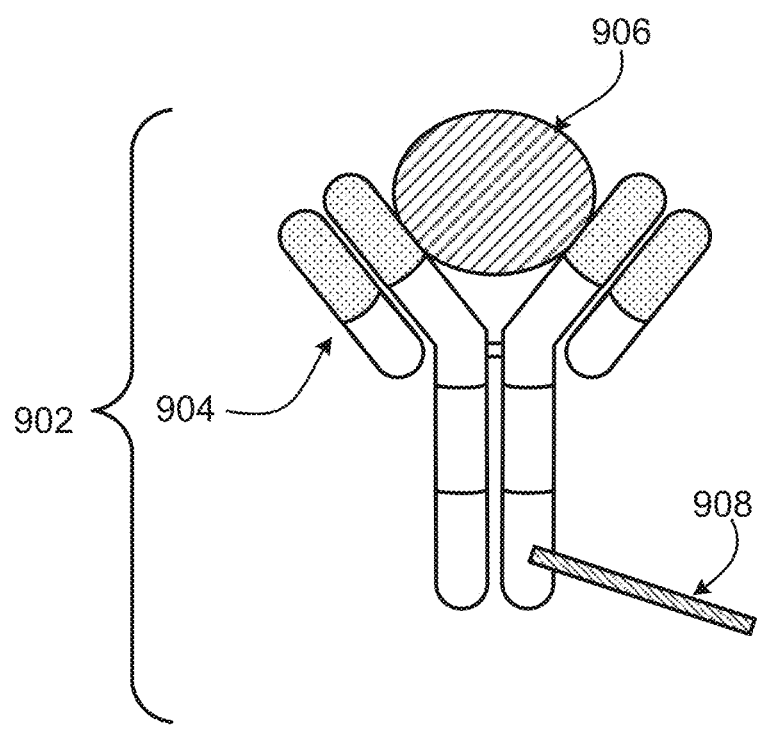
FIG. 9 is a schematic diagram of an exemplary analyte capture agent.

FIG. 9 is a schematic diagram of an exemplary analyte capture agent 902 comprised of an analyte binding moiety 904 and a capture agent barcode domain 908. An analyte binding moiety 904 is a molecule capable of binding to an analyte 906 and interacting with a spatially-barcoded capture probe. The analyte binding moiety can bind to the analyte 906 with high affinity and/or with high specificity. The analyte capture agent can include a capture agent barcode domain 908, a nucleotide sequence (e.g., an oligonucleotide), which can hybridize to at least a portion or an entirety of a capture domain of a capture probe. The analyte binding moiety 904 can include a polypeptide and/or an aptamer (e.g., an oligonucleotide or peptide molecule that binds to a specific target analyte). The analyte binding moiety 904 can include an antibody or antibody fragment (e.g., an antigen-binding fragment).

As used herein, the term "analyte binding moiety" refers to a molecule or moiety capable of binding to a macromolecular constituent (e.g., an analyte, e.g., a biological analyte). In some embodiments of any of the spatial profiling methods described herein, the analyte binding moiety of the analyte capture agent that binds to a biological analyte can include, but is not limited to, an antibody, or an epitope binding fragment thereof, a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, or any combination thereof. The analyte binding moiety can bind to the macromolecular constituent (e.g., analyte) with high affinity and/or with high specificity. The analyte binding moiety can include a nucleotide sequence (e.g., an oligonucleotide), which can correspond to at least a portion or an entirety of the analyte binding moiety. The analyte binding moiety can include a polypeptide and/or an aptamer (e.g., a polypeptide and/or an aptamer that binds to a specific target molecule, e.g., an analyte). The analyte binding moiety can include an antibody or antibody fragment (e.g., an antigen-binding fragment) that binds to a specific analyte (e.g., a polypeptide).

In some embodiments, analyte capture agents are capable of binding to analytes present inside a cell. In some embodiments, analyte capture agents are capable of binding to cell surface analytes that can include, without limitation, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, an extracellular matrix protein, a posttranslational modification (e.g., phosphorylation, glycosylation, ubiquitination, nitrosylation, methylation, acetylation or lipidation) state of a cell surface protein, a gap junction, and an adherens junction. In some embodiments, the analyte capture agents are capable of binding to cell surface analytes that are post-translationally modified. In such embodiments, analyte capture agents can be specific for cell surface analytes based on a given state of posttranslational modification (e.g., phosphorylation, glycosylation, ubiquitination, nitrosylation, methylation, acetylation or lipidation), such that a cell surface analyte profile can include posttranslational modification information of one or more analytes.

In some embodiments, the analyte capture agent includes a capture agent barcode domain that is conjugated or otherwise attached to the analyte binding moiety. In some embodiments, the capture agent barcode domain is covalently-linked to the analyte binding moiety. In some embodiments, a capture agent barcode domain is a nucleic acid sequence. In some embodiments, a capture agent barcode domain includes an analyte binding moiety barcode and an analyte capture sequence.

As used herein, the term "analyte binding moiety barcode" refers to a barcode that is associated with or otherwise identifies the analyte binding moiety. In some embodiments, by identifying an analyte binding moiety by identifying its associated analyte binding moiety barcode, the analyte to which the analyte binding moiety binds can also be identified. An analyte binding moiety barcode can be a nucleic acid sequence of a given length and/or sequence that is associated with the analyte binding moiety. An analyte binding moiety barcode can generally include any of the variety of aspects of barcodes described herein. For example, an analyte capture agent that is specific to one type of analyte can have coupled thereto a first capture agent barcode domain (e.g., that includes a first analyte binding moiety barcode), while an analyte capture agent that is specific to a different analyte can have a different capture agent barcode domain (e.g., that includes a second barcode analyte binding moiety barcode) coupled thereto. In some aspects, such a capture agent barcode domain can include an analyte binding moiety barcode that permits identification of the analyte binding moiety to which the capture agent barcode domain is coupled. The selection of the capture agent barcode domain can allow significant diversity in terms of sequence, while also being readily attachable to most analyte binding moieties (e.g., antibodies) as well as being readily detected, (e.g., using sequencing or array technologies). In some embodiments, the analyte capture agents can include analyte binding moieties with capture agent barcode domains attached to them. For example, an analyte capture agent can include a first analyte binding moiety (e.g., an antibody that binds to an analyte, e.g., a first cell surface feature) having associated with it a capture agent barcode domain that includes a first analyte binding moiety barcode.

In some embodiments, the capture agent barcode domain of an analyte capture agent includes an analyte capture sequence. As used herein, the term "analyte capture sequence" refers to region or moiety of configured to hybridize to, bind to, couple to, or otherwise interact with a capture domain of a capture probe. In some embodiments, an analyte capture sequence includes a nucleic acid sequence that is complementary to or substantially complementary to the capture domain of a capture probe such that the analyte capture sequence hybridizes to the capture domain of the capture probe. In some embodiments, an analyte capture sequence comprises a poly(A) nucleic acid sequence that hybridizes to a capture domain that comprises a poly(T) nucleic acid sequence. In some embodiments, an analyte capture sequence comprises a poly(T) nucleic acid sequence that hybridizes to a capture domain that comprises a poly(A) nucleic acid sequence. In some embodiments, an analyte capture sequence comprises a non-homopolymeric nucleic acid sequence that hybridizes to a capture domain that comprises a non-homopolymeric nucleic acid sequence that is complementary (or substantially complementary) to the non-homopolymeric nucleic acid sequence of the analyte capture region.

In some embodiments of any of the spatial analysis methods described herein that employ an analyte capture agent, the capture agent barcode domain can be directly coupled to the analyte binding moiety, or they can be attached to a bead, molecular lattice, e.g., a linear, globular, cross-slinked, or other polymer, or other framework that is attached or otherwise associated with the analyte binding moiety, which allows attachment of multiple capture agent barcode domains to a single analyte binding moiety. Attachment (coupling) of the capture agent barcode domains to the analyte binding moieties can be achieved through any of a variety of direct or indirect, covalent or non-covalent associations or attachments. For example, in the case of a capture agent barcode domain coupled to an analyte binding moiety that includes an antibody or antigen-binding fragment, such capture agent barcode domains can be covalently attached to a portion of the antibody or antigen-binding fragment using chemical conjugation techniques (e.g., Lightning-Link® antibody labelling kits available from Innova Biosciences). In some embodiments, a capture agent barcode domain can be coupled to an antibody or antigen-binding fragment using non-covalent attachment mechanisms (e.g., using biotinylated antibodies and oligonucleotides or beads that include one or more biotinylated linker, coupled to oligonucleotides with an avidin or streptavidin linker.) Antibody and oligonucleotide biotinylation techniques can be used, and are described for example in Fang et al., Nucleic Acids Res. (2003), 31(2): 708-715, the entire contents of which are incorporated by reference herein. Likewise, protein and peptide biotinylation techniques have been developed and can be used, and are described for example in U.S. Pat. No. 6,265,552, the entire contents of which are incorporated by reference herein. Furthermore, click reaction chemistry such as a methyltetrazine-PEG5-NHS ester reaction, a TCO-PEG4-NHS ester reaction, or the like, can be used to couple capture agent barcode domains to analyte binding moieties. The reactive moiety on the analyte binding moiety can also include amine for targeting aldehydes, amine for targeting maleimide (e.g., free thiols), azide for targeting click chemistry compounds (e.g., alkynes), biotin for targeting streptavidin, phosphates for targeting EDC, which in turn targets active ester (e.g., NH2). The reactive moiety on the analyte binding moiety can be a chemical compound or group that binds to the reactive moiety on the analyte binding moiety. Exemplary strategies to conjugate the analyte binding moiety to the capture agent barcode domain include the use of commercial kits (e.g., Solulink, Thunder link), conjugation of mild reduction of hinge region and maleimide labelling, stain-promoted click chemistry reaction to labeled amides (e.g., copper-free), and conjugation of periodate oxidation of sugar chain and amine conjugation. In the cases where the analyte binding moiety is an antibody, the antibody can be modified prior to or contemporaneously with conjugation of the oligonucleotide. For example, the antibody can be glycosylated with a substrate-permissive mutant of β-1,4-galactosyltransferase, GalT (Y289L) and azide-bearing uridine diphosphate-N-acetylgalactosamine analog uridine diphosphate-GalNAz. The modified antibody can be conjugated to an oligonucleotide with a dibenzocyclooctyne-PEG4-NHS group. In some embodiments, certain steps (e.g., COOH activation (e.g., EDC) and homobifunctional cross linkers) can be avoided to prevent the analyte binding moieties from conjugating to themselves. In some embodiments of any of the spatial profiling methods described herein, the analyte capture agent (e.g., analyte binding moiety coupled to an oligonucleotide) can be delivered into the cell, e.g., by transfection (e.g., using transfectamine, cationic polymers, calcium phosphate or electroporation), by transduction (e.g., using a bacteriophage or recombinant viral vector), by mechanical delivery (e.g., magnetic beads), by lipid (e.g., 1,2-Dioleoyl-sn-glycero-3-phosphocholine (DOPC)), or by transporter proteins. An analyte capture agent can be delivered into a cell using exosomes. For example, a first cell can be generated that releases exosomes comprising an analyte capture agent. An analyte capture agent can be attached to an exosome membrane. An analyte capture agent can be contained within the cytosol of an exosome. Released exosomes can be harvested and provided to a second cell, thereby delivering the analyte capture agent into the second cell. An analyte capture agent can be releasable from an exosome membrane before, during, or after delivery into a cell. In some embodiments, the cell is permeabilized to allow the analyte capture agent to couple with intracellular cellular constituents (such as, without limitation, intracellular proteins, metabolites and nuclear membrane proteins). Following intracellular delivery, analyte capture agents can be used to analyze intracellular constituents as described herein.

In some embodiments of any of the spatial profiling methods described herein, the capture agent barcode domain coupled to an analyte capture agent can include modifications that render it non-extendable by a polymerase. In some embodiments, when binding to a capture domain of a capture probe or nucleic acid in a sample for a primer extension reaction, the capture agent barcode domain can serve as a template, not a primer. When the capture agent barcode domain also includes a barcode (e.g., an analyte binding moiety barcode), such a design can increase the efficiency of molecular barcoding by increasing the affinity between the capture agent barcode domain and unbarcoded sample nucleic acids, and eliminate the potential formation of adaptor artifacts. In some embodiments, the capture agent barcode domain can include a random N-mer sequence that is capped with modifications that render it non-extendable by a polymerase. In some cases, the composition of the random N-mer sequence can be designed to maximize the binding efficiency to free, unbarcoded ssDNA molecules. The design can include a random sequence composition with a higher GC content, a partial random sequence with fixed G or C at specific positions, the use of guanosines, the use of locked nucleic acids, or any combination thereof.

A modification for blocking primer extension by a polymerase can be a carbon spacer group of different lengths or a dideoxynucleotide. In some embodiments, the modification can be an abasic site that has an apurine or apyrimidine structure, a base analog, or an analogue of a phosphate backbone, such as a backbone of N-(2-aminoethyl)-glycine linked by amide bonds, tetrahydrofuran, or 1', 2'-Dideoxyribose. The modification can also be a uracil base, 2'OMe modified RNA, C3-18 spacers (e.g., structures with 3-18 consecutive carbon atoms, such as C3 spacer), ethylene glycol multimer spacers (e.g., spacer 18 (hexa-ethyleneglycol spacer), biotin, di-deoxynucleotide triphosphate, ethylene glycol, amine, or phosphate.

In some embodiments of any of the spatial profiling methods described herein, the capture agent barcode domain coupled to the analyte binding moiety includes a cleavable domain. For example, after the analyte capture agent binds to an analyte (e.g., a cell surface analyte), the capture agent barcode domain can be cleaved and collected for downstream analysis according to the methods as described herein. In some embodiments, the cleavable domain of the capture agent barcode domain includes a U-excising element that allows the species to release from the bead. In some embodiments, the U-excising element can include a single-stranded DNA (ssDNA) sequence that contains at least one uracil. The species can be attached to a bead via the ssDNA sequence. The species can be released by a combination of uracil-DNA glycosylase (e.g., to remove the uracil) and an endonuclease (e.g., to induce an ssDNA break). If the endonuclease generates a 5' phosphate group from the cleavage, then additional enzyme treatment can be included in downstream processing to eliminate the phosphate group, e.g., prior to ligation of additional sequencing handle elements, e.g., Illumina full P5 sequence, partial P5 sequence, full R1 sequence, and/or partial R1 sequence.

In some embodiments, an analyte binding moiety of an analyte capture agent includes one or more antibodies or antigen binding fragments thereof. The antibodies or antigen binding fragments including the analyte binding moiety can specifically bind to a target analyte. In some embodiments, the analyte is a protein (e.g., a protein on a surface of the biological sample (e.g., a cell) or an intracellular protein). In some embodiments, a plurality of analyte capture agents comprising a plurality of analyte binding moieties bind a plurality of analytes present in a biological sample. In some embodiments, the plurality of analytes includes a single species of analyte (e.g., a single species of polypeptide). In some embodiments in which the plurality of analytes includes a single species of analyte, the analyte binding moieties of the plurality of analyte capture agents are the same. In some embodiments in which the plurality of analytes includes a single species of analyte, the analyte binding moieties of the plurality of analyte capture agents are the different (e.g., members of the plurality of analyte capture agents can have two or more species of analyte binding moieties, wherein each of the two or more species of analyte binding moieties binds a single species of analyte, e.g., at different binding sites). In some embodiments, the plurality of analytes includes multiple different species of analyte (e.g., multiple different species of polypeptides).

In some embodiments, multiple different species of analytes (e.g., polypeptides) from the biological sample can be subsequently associated with the one or more physical properties of the biological sample. For example, the multiple different species of analytes can be associated with locations of the analytes in the biological sample. Such information (e.g., proteomic information when the analyte binding moiety(ies) recognizes a polypeptide(s)) can be used in association with other spatial information (e.g., genetic information from the biological sample, such as DNA sequence information, transcriptome information (i.e., sequences of transcripts), or both). For example, a cell surface protein of a cell can be associated with one or more physical properties of the cell (e.g., a shape, size, activity, or a type of the cell). The one or more physical properties can be characterized by imaging the cell. The cell can be bound by an analyte capture agent comprising an analyte binding moiety that binds to the cell surface protein and an analyte binding moiety barcode that identifies that analyte binding moiety, and the cell can be subjected to spatial analysis (e.g., any of the variety of spatial analysis methods described herein). For example, the analyte capture agent bound to the cell surface protein can be bound to a capture probe (e.g., a capture probe on an array), which capture probe includes a capture domain that interacts with an analyte capture sequence present on the capture agent barcode domain of the analyte capture agent. All or part of the capture agent barcode domain (including the analyte binding moiety barcode) can be copied with a polymerase using a 3' end of the capture domain as a priming site, generating an extended capture probe that includes the all or part of the capture probe (including a spatial barcode present on the capture probe) and a copy of the analyte binding moiety barcode. In some embodiments, the spatial array with the extended capture probe(s) can be contacted with a sample, where the analyte capture agent(s) associated with the spatial array capture the target analyte(s). The analyte capture agent(s) containing the extended capture probe(s), which includes the spatial barcode(s) of the capture probe(s) and the analyte binding moiety barcode(s), can then be denatured from the capture probe(s) of the spatial array. This allows the spatial array to be reused. The sample can be dissociated into non-aggregated cells (e.g. single cells) and analyzed by the single cell/droplet methods described herein. The extended capture probe can be sequenced to obtain a nucleic acid sequence, in which the spatial barcode of the capture probe is associated with the analyte binding moiety barcode of the analyte capture agent. The nucleic acid sequence of the extended capture probe can thus be associated with the analyte (e.g., cell surface protein), and in turn, with the one or more physical properties of the cell (e.g., a shape or cell type). In some embodiments, the nucleic acid sequence of the extended capture probe can be associated with an intracellular analyte of a nearby cell, where the intracellular analyte was released using any of the cell permeabilization or analyte migration techniques described herein.

In some embodiments of any of the spatial profiling methods described herein, the capture agent barcode domains released from the analyte capture agents can then be subjected to sequence analysis to identify which analyte capture agents were bound to analytes. Based upon the capture agent barcode domains that are associated with a feature (e.g., a feature at a particular location) on a spatial array and the presence of the analyte binding moiety barcode sequence, an analyte profile can be created for a biological sample. Profiles of individual cells or populations of cells can be compared to profiles from other cells, e.g., 'normal' cells, to identify variations in analytes, which can provide diagnostically relevant information. In some embodiments, these profiles can be useful in the diagnosis of a variety of disorders that are characterized by variations in cell surface receptors, such as cancer and other disorders.

Figure 10:
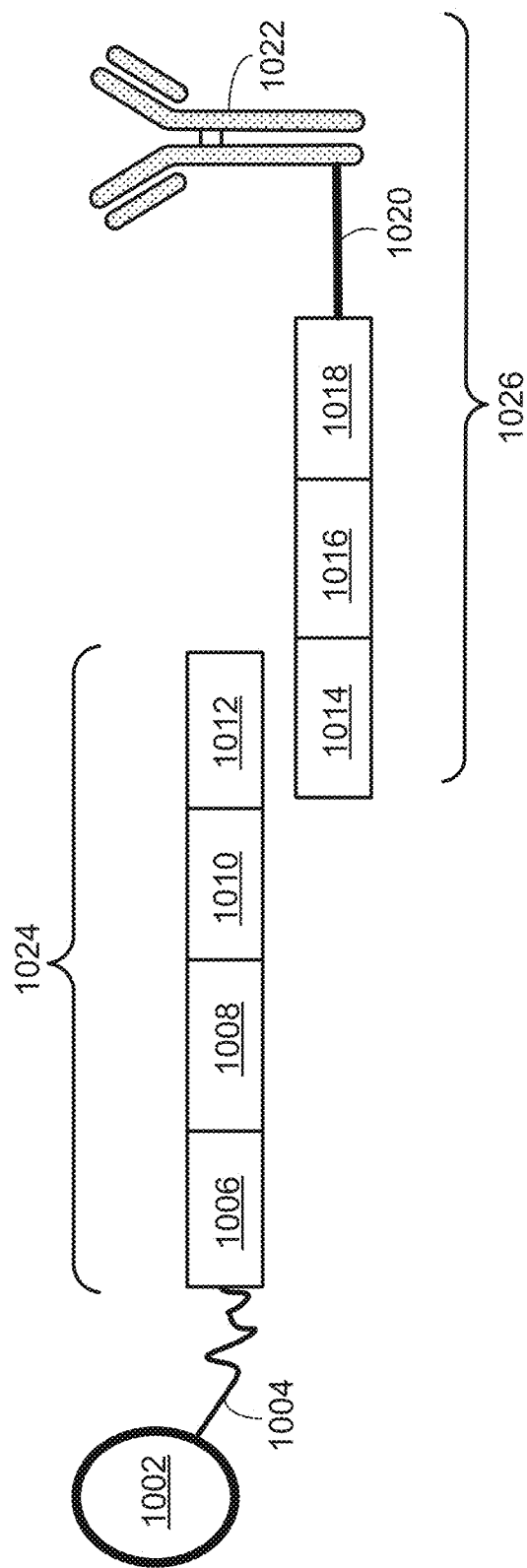
FIG. 10 is a schematic diagram depicting an exemplary interaction between a feature-immobilized capture probe 1024 and an analyte capture agent 1026.

FIG. 10 is a schematic diagram depicting an exemplary interaction between a feature-immobilized capture probe 1024 and an analyte capture agent 1026. The feature-immobilized capture probe 1024 can include a spatial barcode 1008 as well as one or more functional sequences 1006 and 1010, as described elsewhere herein. The capture probe can also include a capture domain 1012 that is capable of binding to an analyte capture agent 1026. The analyte capture agent 1026 can include a functional sequence 1018, capture agent barcode domain 1016, and an analyte capture sequence 1014 that is capable of binding to the capture domain 1012 of the capture probe 1024. The analyte capture agent can also include a linker 1020 that allows the capture agent barcode domain 1016 to couple to the analyte binding moiety 1022.

In some embodiments of any of the spatial profiling methods described herein, the methods are used to identify immune cell profiles. Immune cells express various adaptive immunological receptors relating to immune function, such as T cell receptors (TCRs) and B cell receptors (BCRs). T cell receptors and B cell receptors play a part in the immune response by specifically recognizing and binding to antigens and aiding in their destruction.

The T cell receptor, or TCR, is a molecule found on the surface of T cells that is generally responsible for recognizing fragments of antigen as peptides bound to major histocompatibility complex (MHC) molecules. The TCR is generally a heterodimer of two chains, each of which is a member of the immunoglobulin superfamily, possessing an N-terminal variable (V) domain, and a C terminal constant domain. In humans, in 95% of T cells, the TCR consists of an alpha ($\alpha$) and beta ($\beta$) chain, whereas in 5% of T cells, the TCR consists of gamma and delta ($\gamma/\delta$) chains. This ratio can change during ontogeny and in diseased states as well as in different species. When the TCR engages with antigenic peptide and MHC (peptide/MHC or pMHC), the T lymphocyte is activated through signal transduction.

Each of the two chains of a TCR contains multiple copies of gene segments—a variable 'V' gene segment, a diversity 'D' gene segment, and a joining 'J' gene segment. The TCR alpha chain (TCRa) is generated by recombination of V and J segments, while the beta chain (TCRb) is generated by recombination of V, D, and J segments. Similarly, generation of the TCR gamma chain involves recombination of V and J gene segments, while generation of the TCR delta chain occurs by recombination of V, D, and J gene segments. The intersection of these specific regions (V and J for the alpha or gamma chain, or V, D and J for the beta or delta chain) corresponds to the CDR3 region that is important for antigen-MHC recognition. Complementarity determining regions (e.g., CDR1, CDR2, and CDR3), or hypervariable regions, are sequences in the variable domains of antigen receptors (e.g., T cell receptor and immunoglobulin) that can complement an antigen. Most of the diversity of CDRs is found in CDR3, with the diversity being generated by somatic recombination events during the development of T lymphocytes. A unique nucleotide sequence that arises during the gene arrangement process can be referred to as a clonotype.

The B cell receptor, or BCR, is a molecule found on the surface of B cells. The antigen binding portion of a BCR is composed of a membrane-bound antibody that, like most antibodies (e.g., immunoglobulins), has a unique and randomly determined antigen-binding site. The antigen binding portion of a BCR includes membrane-bound immunoglobulin molecule of one isotype (e.g., IgD, IgM, IgA, IgG, or IgE). When a B cell is activated by its first encounter with a cognate antigen, the cell proliferates and differentiates to generate a population of antibody-secreting plasma B cells and memory B cells. The various immunoglobulin isotypes differ in their biological features, structure, target specificity and distribution. A variety of molecular mechanisms exist to generate initial diversity, including genetic recombination at multiple sites.

The BCR is composed of two genes IgH and IgK (or IgL) coding for antibody heavy and light chains. Immunoglobulins are formed by recombination among gene segments, sequence diversification at the junctions of these segments, and point mutations throughout the gene. Each heavy chain gene contains multiple copies of three different gene segments—a variable 'V' gene segment, a diversity 'D' gene segment, and a joining 'J' gene segment. Each light chain gene contains multiple copies of two different gene segments for the variable region of the protein—a variable 'V' gene segment and a joining 'J' gene segment.

The recombination can generate a molecule with one of each of the V, D, and J segments. Furthermore, several bases can be deleted and others added (called N and P nucleotides) at each of the two junctions, thereby generating further diversity. After B cell activation, a process of affinity maturation through somatic hypermutation occurs. In this process, progeny cells of the activated B cells accumulate distinct somatic mutations throughout the gene with higher mutation concentration in the CDR regions leading to the generation of antibodies with higher affinity to the antigens.

In addition to somatic hypermutation, activated B cells undergo the process of isotype switching. Antibodies with the same variable segments can have different forms (isotypes) depending on the constant segment. Whereas all naïve B cells express IgM (or IgD), activated B cells mostly express IgG but also IgM, IgA and IgE. This expression switching from IgM (and/or IgD) to IgG, IgA, or IgE occurs through a recombination event causing one cell to specialize in producing a specific isotype. A unique nucleotide sequence that arises during the gene arrangement process can similarly be referred to as a clonotype.

Certain methods described herein are utilized to analyze the various sequences of TCRs and BCRs from immune cells, for example, various clonotypes. In some embodiments, the methods are used to analyze the sequence of a TCR alpha chain, a TCR beta chain, a TCR delta chain, a TCR gamma chain, or any fragment thereof (e.g., variable regions including V(D)J or VJ regions, constant regions, transmembrane regions, fragments thereof, combinations thereof, and combinations of fragments thereof). In some embodiments, the methods described herein can be used to analyze the sequence of a B cell receptor heavy chain, B cell receptor light chain, or any fragment thereof (e.g., variable regions including V(D)J or VJ regions, constant regions, transmembrane regions, fragments thereof, combinations thereof, and combinations of fragments thereof).

Where immune cells are to be analyzed, primer sequences useful in any of the various operations for attaching barcode sequences and/or amplification reactions can include gene specific sequences which target genes or regions of genes of immune cell proteins, for example immune receptors. Such gene sequences include, but are not limited to, sequences of various T cell receptor alpha variable genes (TRAV genes), T cell receptor alpha joining genes (TRAJ genes), T cell receptor alpha constant genes (TRAC genes), T cell receptor beta variable genes (TRBV genes), T cell receptor beta diversity genes (TRBD genes), T cell receptor beta joining genes (TRBJ genes), T cell receptor beta constant genes (TRBC genes), T cell receptor gamma variable genes (TRGV genes), T cell receptor gamma joining genes (TRGJ genes), T cell receptor gamma constant genes (TRGC genes), T cell receptor delta variable genes (TRDV genes), T cell receptor delta diversity genes (TRDD genes), T cell receptor delta joining genes (TRDJ genes), and T cell receptor delta constant genes (TRDC genes).

In some embodiments, the analyte binding moiety is based on the Major Histocompatibility Complex (MHC) class I or class II. In some embodiments, the analyte binding moiety is an MHC multimer including, without limitation, MHC dextramers, MHC tetramers, and MHC pentamers (see, for example, U.S. Patent Application Publication Nos. US 2018/0180601 and US 2017/0343545, the entire contents of each of which are incorporated herein by reference. MHCs (e.g., a soluble MHC monomer molecule), including full or partial MHC-peptides, can be used as analyte binding moieties of analyte capture agents that are coupled to capture agent barcode domains that include an analyte binding moiety barcode that identifies its associated MHC (and, thus, for example, the MHC's TCR binding partner). In some embodiments, MHCs are used to analyze one or more cell-surface features of a T-cell, such as a TCR. In some cases, multiple MHCs are associated together in a larger complex (MHC multimer) to improve binding affinity of MHCs to TCRs via multiple ligand binding synergies.

Figure 11A:
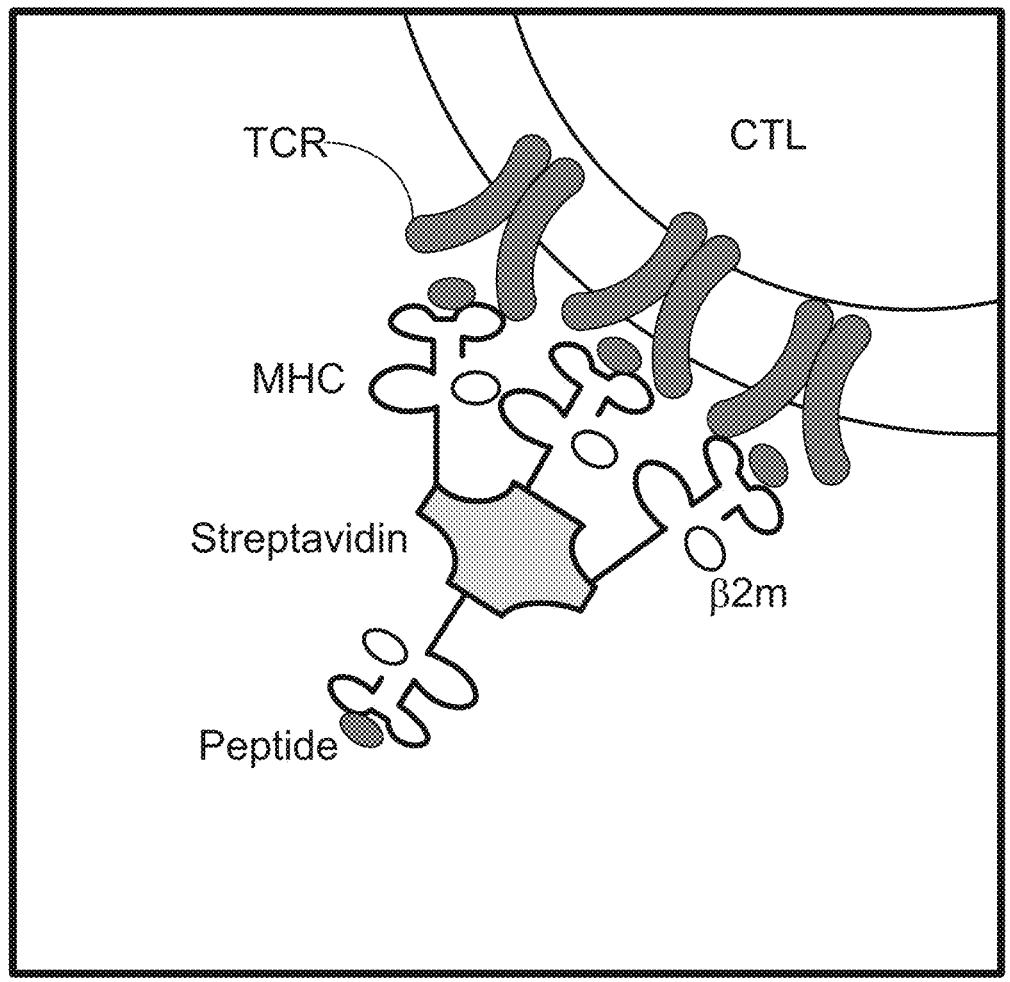
FIGS. 11A, 11B, and 11C are schematics illustrating how streptavidin cell tags can be utilized in an array-based system to produce a spatially-barcoded cells or cellular contents.
Figure 11B:
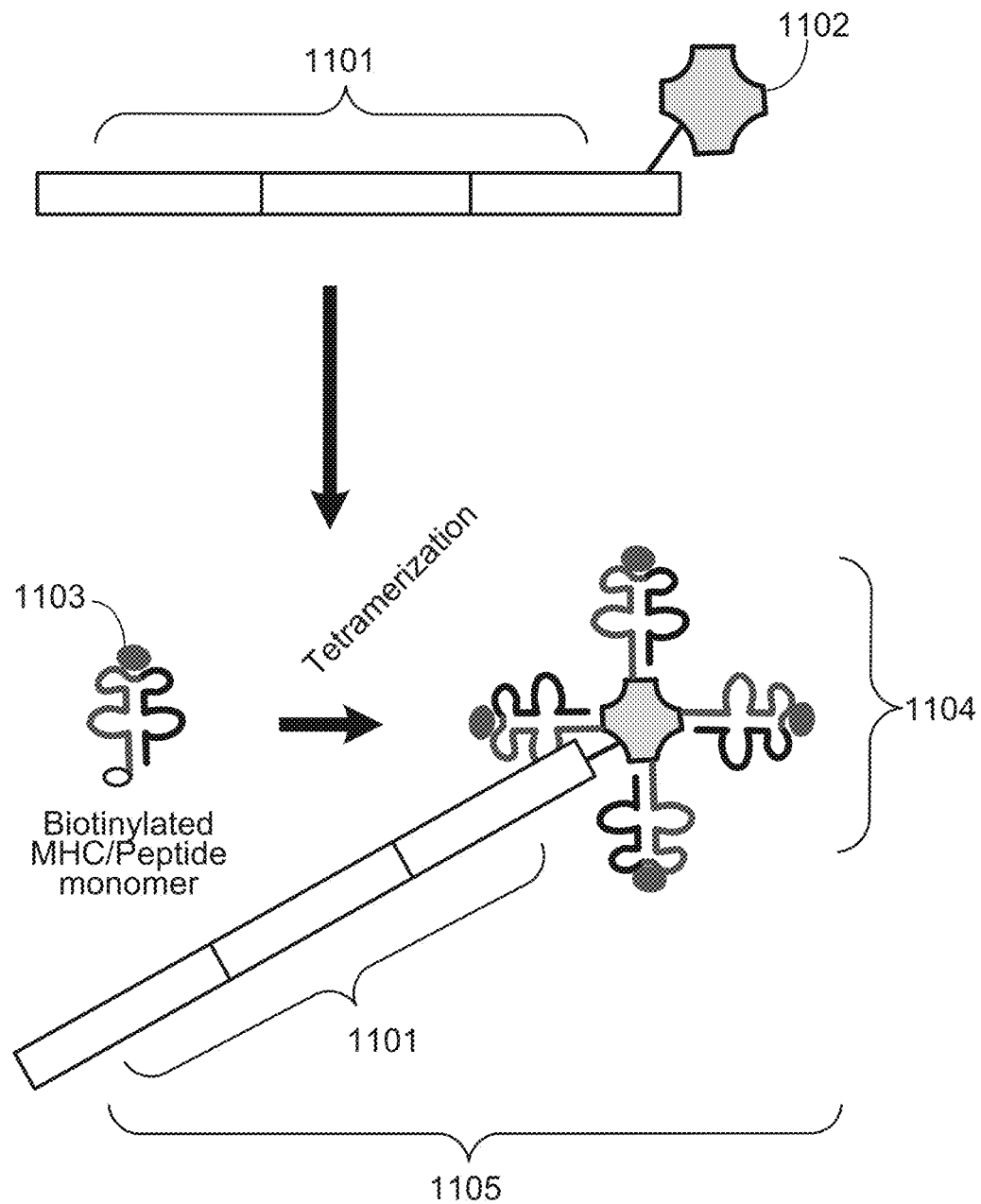
Figure 11C:
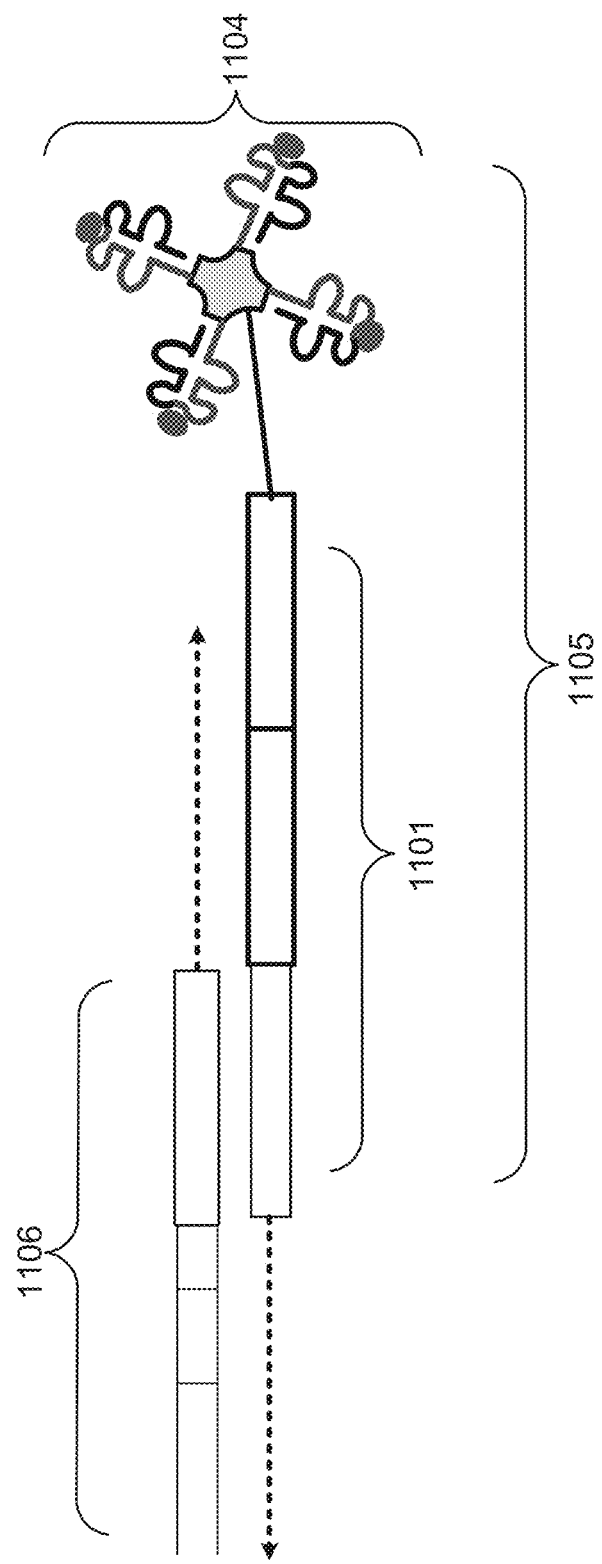

FIGS. 11A, 11B, and 11C are schematics illustrating how streptavidin cell tags can be utilized in an array-based system to produce a spatially-barcoded cell or cellular contents. For example, as shown in FIG. 11, peptide-bound major histocompatibility complex (pMHCs) can be individually associated with biotin and bound to a streptavidin moiety such that the streptavidin moiety comprises multiple pMHC moieties. Each of these moieties can bind to a TCR such that the streptavidin binds to a target T-cell via multiple MCH/TCR binding interactions. Multiple interactions synergize and can substantially improve binding affinity. Such improved affinity can improve labelling of T-cells and also reduce the likelihood that labels will dissociate from T-cell surfaces. As shown in FIG. 11B, a capture agent barcode domain 1101 can be modified with streptavidin 1102 and contacted with multiple molecules of biotinylated MHC 1103 (such as a pMHC) such that the biotinylated MHC 1103 molecules are coupled with the streptavidin conjugated capture agent barcode domain 1101. The result is a barcoded MHC multimer complex 1105. As shown in FIG. 11B, the capture agent barcode domain sequence 1101 can identify the MHC as its associated label and also includes optional functional sequences such as sequences for hybridization with other oligonucleotides. As shown in FIG. 11C, one example oligonucleotide is capture probe 1106 that comprises a complementary sequence (e.g., rGrGrG corresponding to C C C), a barcode sequence and other functional sequences, such as, for example, a UMI, an adapter sequence (e.g., comprising a sequencing primer sequence (e.g., R1 or a partial R1 ("pR1")), a flow cell attachment sequence (e.g., P5 or P7 or partial sequences thereof)), etc. In some cases, capture probe 1106 may at first be associated with a feature (e.g., a gel bead) and released from the feature. In other embodiments, capture probe 1106 can hybridize with a capture agent barcode domain 1101 of the MHC-oligonucleotide complex 1105. The hybridized oligonucleotides (Spacer C C C and Spacer rGrGrG) can then be extended in primer extension reactions such that constructs comprising sequences that correspond to each of the two spatial barcode sequences (the spatial barcode associated with the capture probe, and the barcode associated with the MHC-oligonucleotide complex) are generated. In some cases, one or both of these corresponding sequences may be a complement of the original sequence in capture probe 1106 or capture agent barcode domain 1101. In other embodiments, the capture probe and the capture agent barcode domain are ligated together. The resulting constructs can be optionally further processed (e.g., to add any additional sequences and/or for clean-up) and subjected to sequencing. As described elsewhere herein, a sequence derived from the capture probe 1106 spatial barcode sequence may be used to identify a feature and the sequence derived from spatial barcode sequence on the capture agent barcode domain 1101 may be used to identify the particular peptide MHC complex 1104 bound on the surface of the cell (e.g., when using MHC-peptide libraries for screening immune cells or immune cell populations).

(c) Substrate

For the spatial array-based analytical methods described in this section, the substrate functions as a support for direct or indirect attachment of capture probes to features of the array. In addition, in some embodiments, a substrate (e.g., the same substrate or a different substrate) can be used to provide support to a biological sample, particularly, for example, a thin tissue section. Accordingly, a "substrate" is a support that is insoluble in aqueous liquid and which allows for positioning of biological samples, analytes, features, and/or capture probes on the substrate.

A wide variety of different substrates can be used for the foregoing purposes. In general, a substrate can be any suitable support material. Exemplary substrates include, but are not limited to, glass, modified and/or functionalized glass, hydrogels, films, membranes, plastics (including e.g., acrylics, polystyrene, copolymers of styrene and other materials, polypropylene, polyethylene, polybutylene, polyurethanes, Teflon™, cyclic olefins, polyimides etc.), nylon, ceramics, resins, Zeonor, silica or silica-based materials including silicon and modified silicon, carbon, metals, inorganic glasses, optical fiber bundles, and polymers, such as polystyrene, cyclic olefin copolymers (COCs), cyclic olefin polymers (COPs), polypropylene, polyethylene and polycarbonate.

The substrate can also correspond to a flow cell. Flow cells can be formed of any of the foregoing materials, and can include channels that permit reagents, solvents, features, and molecules to pass through the cell.

Among the examples of substrate materials discussed above, polystyrene is a hydrophobic material suitable for binding negatively charged macromolecules because it normally contains few hydrophilic groups. For nucleic acids immobilized on glass slides, by increasing the hydrophobicity of the glass surface the nucleic acid immobilization can be increased. Such an enhancement can permit a relatively more densely packed formation (e.g., provide improved specificity and resolution).

In some embodiments, a substrate is coated with a surface treatment such as poly(L)-lysine. Additionally or alternatively, the substrate can be treated by silanation, e.g. with epoxy-silane, amino-silane, and/or by a treatment with polyacrylamide.

The substrate can generally have any suitable form or format. For example, the substrate can be flat, curved, e.g. convexly or concavely curved towards the area where the interaction between a biological sample, e.g. tissue sample, and the substrate takes place. In some embodiments, the substrate is a flat, e.g., planar, chip or slide. The substrate can contain one or more patterned surfaces within the substrate (e.g., channels, wells, projections, ridges, divots, etc.).

A substrate can be of any desired shape. For example, a substrate can be typically a thin, flat shape (e.g., a square or a rectangle). In some embodiments, a substrate structure has rounded corners (e.g., for increased safety or robustness). In some embodiments, a substrate structure has one or more cut-off corners (e.g., for use with a slide clamp or crosstable). In some embodiments, where a substrate structure is flat, the substrate structure can be any appropriate type of support having a flat surface (e.g., a chip or a slide such as a microscope slide).

Substrates can optionally include various structures such as, but not limited to, projections, ridges, and channels. A substrate can be micropatterned to limit lateral diffusion (e.g., to prevent overlap of spatial barcodes). A substrate modified with such structures can be modified to allow association of analytes, features (e.g., beads), or probes at individual sites. For example, the sites where a substrate is modified with various structures can be contiguous or non-contiguous with other sites.

In some embodiments, the surface of a substrate can be modified so that discrete sites are formed that can only have or accommodate a single feature. In some embodiments, the surface of a substrate can be modified so that features adhere to random sites.

In some embodiments, the surface of a substrate is modified to contain one or more wells, using techniques such as (but not limited to) stamping techniques, microetching techniques, and molding techniques. In some embodiments in which a substrate includes one or more wells, the substrate can be a concavity slide or cavity slide. For example, wells can be formed by one or more shallow depressions on the surface of the substrate. In some embodiments, where a substrate includes one or more wells, the wells can be formed by attaching a cassette (e.g., a cassette containing one or more chambers) to a surface of the substrate structure.

In some embodiments, the structures of a substrate (e.g., wells) can each bear a different capture probe. Different capture probes attached to each structure can be identified according to the locations of the structures in or on the surface of the substrate. Exemplary substrates include arrays in which separate structures are located on the substrate including, for example, those having wells that accommodate features.

In some embodiments, a substrate includes one or more markings on a surface of the substrate, e.g., to provide guidance for correlating spatial information with the characterization of the analyte of interest. For example, a substrate can be marked with a grid of lines (e.g., to allow the size of objects seen under magnification to be easily estimated and/or to provide reference areas for counting objects). In some embodiments, fiducial markers can be included on the substrate. Such markings can be made using techniques including, but not limited to, printing, sandblasting, and depositing on the surface.

In some embodiments where the substrate is modified to contain one or more structures, including but not limited to wells, projections, ridges, or markings, the structures can include physically altered sites. For example, a substrate modified with various structures can include physical properties, including, but not limited to, physical configurations, magnetic or compressive forces, chemically functionalized sites, chemically altered sites, and/or electrostatically altered sites.

In some embodiments where the substrate is modified to contain various structures, including but not limited to wells, projections, ridges, or markings, the structures are applied in a pattern. Alternatively, the structures can be randomly distributed.

In some embodiments, a substrate is treated in order to minimize or reduce non-specific analyte hybridization within or between features. For example, treatment can include coating the substrate with a hydrogel, film, and/or membrane that creates a physical barrier to non-specific hybridization. Any suitable hydrogel can be used. For example, hydrogel matrices prepared according to the methods set forth in U.S. Pat. Nos. 6,391,937, 9,512,422, and 9,889,422, and U.S. Patent Application Publication Nos. U.S. 2017/0253918 and U.S. 2018/0052081, can be used. The entire contents of each of the foregoing documents are incorporated herein by reference.

Treatment can include adding a functional group that is reactive or capable of being activated such that it becomes reactive after receiving a stimulus (e.g., photoreactive). Treatment can include treating with polymers having one or more physical properties (e.g., mechanical, electrical, magnetic, and/or thermal) that minimize non-specific binding (e.g., that activate a substrate at certain locations to allow analyte hybridization at those locations).

The substrate (e.g., a bead or a feature on an array) can include tens to hundreds of thousands or millions of individual oligonucleotide molecules (e.g., at least about 10,000, 50,000, 100,000, 500,000, 1,000,000, 10,000,000, 100,000,000, 1,000,000,000, or 10,000,000,000 oligonucleotide molecules).

In some embodiments, the surface of the substrate is coated with a cell-permissive coating to allow adherence of live cells. A "cell-permissive coating" is a coating that allows or helps cells to maintain cell viability (e.g., remain viable) on the substrate. For example, a cell-permissive coating can enhance cell attachment, cell growth, and/or cell differentiation, e.g., a cell-permissive coating can provide nutrients to the live cells. A cell-permissive coating can include a biological material and/or a synthetic material. Non-limiting examples of a cell-permissive coating include coatings that feature one or more extracellular matrix (ECM) components (e.g., proteoglycans and fibrous proteins such as collagen, elastin, fibronectin and laminin), poly-lysine, poly (L)-ornithine, and/or a biocompatible silicone (e.g., CYTOSOFT®). For example, a cell-permissive coating that includes one or more extracellular matrix components can include collagen Type I, collagen Type II, collagen Type IV, elastin, fibronectin, laminin, and/or vitronectin. In some embodiments, the cell-permissive coating includes a solubilized basement membrane preparation extracted from the Engelbreth-Holm-Swarm (EHS) mouse sarcoma (e.g., MATRIGEL®). In some embodiments, the cell-permissive coating includes collagen. A cell-permissive coating can be used to culture adherent cells on a spatially-barcoded array, or to maintain cell viability of a tissue sample or section while in contact with a spatially-barcoded array.

Where the substrate includes a gel (e.g., a hydrogel or gel matrix), oligonucleotides within the gel can attach to the substrate. The terms "hydrogel" and "hydrogel matrix" are used interchangeably herein to refer to a macromolecular polymer gel including a network. Within the network, some polymer chains can optionally be cross-linked, although cross-linking does not always occur.

In some embodiments, a hydrogel can include hydrogel subunits. A "hydrogel subunit" is a hydrophilic monomer, a molecular precursor, or a polymer that can be polymerized (e.g., cross-linked) to form a three-dimensional (3D) hydrogel network. The hydrogel subunits can include any convenient hydrogel subunits, such as, but not limited to, acrylamide, bis-acrylamide, polyacrylamide and derivatives thereof, poly(ethylene glycol) and derivatives thereof (e.g. PEG-acrylate (PEG-DA), PEG-RGD), gelatin-methacryloyl (GelMA), methacrylated hyaluronic acid (MeHA), polyaliphatic polyurethanes, polyether polyurethanes, polyester polyurethanes, polyethylene copolymers, polyamides, polyvinyl alcohols, polypropylene glycol, polytetramethylene oxide, polyvinyl pyrrolidone, polyacrylamide, poly(hydroxyethyl acrylate), and poly(hydroxyethyl methacrylate), collagen, hyaluronic acid, chitosan, dextran, agarose, gelatin, alginate, protein polymers, methylcellulose, and the like, and combinations thereof.

In some embodiments, a hydrogel includes a hybrid material, e.g., the hydrogel material includes elements of both synthetic and natural polymers. Examples of suitable hydrogels are described, for example, in U.S. Pat. Nos. 6,391,937, 9,512,422, and 9,889,422, and in U.S. Patent Application Publication Nos. 2017/0253918, 2018/0052081 and 2010/0055733, the entire contents of each of which are incorporated herein by reference.

In some embodiments, cross-linkers and/or initiators are added to hydrogel subunits. Examples of cross-linkers include, without limitation, bis-acrylamide and diazirine. Examples of initiators include, without limitation, azobisisobutyronitrile (AIBN), riboflavin, and L-arginine. Inclusion of cross-linkers and/or initiators can lead to increased covalent bonding between interacting biological macromolecules in later polymerization steps.

In some embodiments, hydrogels can have a colloidal structure, such as agarose, or a polymer mesh structure, such as gelatin.

In some embodiments, some hydrogel subunits are polymerized (e.g., undergo "formation") covalently or physically cross-linked, to form a hydrogel network. For example, hydrogel subunits can be polymerized by any method including, but not limited to, thermal crosslinking, chemical crosslinking, physical crosslinking, ionic crosslinking, photo-crosslinking, irradiative crosslinking (e.g., x-ray, electron beam), and combinations thereof. Techniques such as lithographic photopolymerization can also be used to form hydrogels.

Polymerization methods for hydrogel subunits can be selected to form hydrogels with different properties (e.g., pore size, swelling properties, biodegradability, conduction, transparency, and/or permeability of the hydrogel). For example, a hydrogel can include pores of sufficient size to allow the passage of macromolecules, (e.g., nucleic acids, proteins, chromatin, metabolites, gRNA, antibodies, carbohydrates, peptides, metabolites, and/or small molecules) into the sample (e.g., tissue section). It is known that pore size generally decreases with increasing concentration of hydrogel subunits and generally increases with an increasing ratio of hydrogel subunits to crosslinker. Therefore, a fixative/hydrogel composition can be prepared that includes a concentration of hydrogel subunits that allows the passage of such biological macromolecules.

In some embodiments, the hydrogel can form the substrate. In some embodiments, the substrate includes a hydrogel and one or more second materials. In some embodiments, the hydrogel is placed on top of one or more second materials. For example, the hydrogel can be pre-formed and then placed on top of, underneath, or in any other configuration with one or more second materials. In some embodiments, hydrogel formation occurs after contacting one or more second materials during formation of the substrate. Hydrogel formation can also occur within a structure (e.g., wells, ridges, projections, and/or markings) located on a substrate.

In some embodiments, hydrogel formation on a substrate occurs before, contemporaneously with, or after features (e.g., beads) are attached to the substrate. For example, when a capture probe is attached (e.g., directly or indirectly) to a substrate, hydrogel formation can be performed on the substrate already containing the capture probes.

In some embodiments, hydrogel formation occurs within a biological sample. In some embodiments, a biological sample (e.g., tissue section) is embedded in a hydrogel. In some embodiments, hydrogel subunits are infused into the biological sample, and polymerization of the hydrogel is initiated by an external or internal stimulus.

In embodiments in which a hydrogel is formed within a biological sample, functionalization chemistry can be used. In some embodiments, functionalization chemistry includes hydrogel-tissue chemistry (HTC). Any hydrogel-tissue backbone (e.g., synthetic or native) suitable for HTC can be used for anchoring biological macromolecules and modulating functionalization. Non-limiting examples of methods using HTC backbone variants include CLARITY, PACT, ExM, SWITCH and ePACT. In some embodiments, hydrogel formation within a biological sample is permanent. For example, biological macromolecules can permanently adhere to the hydrogel allowing multiple rounds of interrogation. In some embodiments, hydrogel formation within a biological sample is reversible.

In some embodiments, additional reagents are added to the hydrogel subunits before, contemporaneously with, and/or after polymerization. For example, additional reagents can include but are not limited to oligonucleotides (e.g., capture probes), endonucleases to fragment DNA, fragmentation buffer for DNA, DNA polymerase enzymes, dNTPs used to amplify the nucleic acid and to attach the barcode to the amplified fragments. Other enzymes can be used, including without limitation, RNA polymerase, transposase, ligase, proteinase K, and DNAse. Additional reagents can also include reverse transcriptase enzymes, including enzymes with terminal transferase activity, primers, and switch oligonucleotides. In some embodiments, optical labels are added to the hydrogel subunits before, contemporaneously with, and/or after polymerization.

In some embodiments, HTC reagents are added to the hydrogel before, contemporaneously with, and/or after polymerization. In some embodiments, a cell labelling agent is added to the hydrogel before, contemporaneously with, and/or after polymerization. In some embodiments, a cell-penetrating agent is added to the hydrogel before, contemporaneously with, and/or after polymerization.

Hydrogels embedded within biological samples can be cleared using any suitable method. For example, electrophoretic tissue clearing methods can be used to remove biological macromolecules from the hydrogel-embedded sample. In some embodiments, a hydrogel-embedded sample is stored before or after clearing of hydrogel, in a medium (e.g., a mounting medium, methylcellulose, or other semi-solid mediums).

A "conditionally removable coating" is a coating that can be removed from the surface of a substrate upon application of a releasing agent. In some embodiments, a conditionally removable coating includes a hydrogel as described herein, e.g., a hydrogel including a polypeptide-based material. Non-limiting examples of a hydrogel featuring a polypeptide-based material include a synthetic peptide-based material featuring a combination of spider silk and a transmembrane segment of human muscle L-type calcium channel (e.g., PEPGEL®), an amphiphilic 16 residue peptide containing a repeating arginine-alanine-aspartate-alanine sequence (RADARADARADARADA) (e.g., PURAMATRIX®), EAK16 (AEAEAKAKAEAEAKAK), KLD12 (KLDLKLDLKLDL), and PGMATRIX™.

In some embodiments, the hydrogel in the conditionally removable coating is a stimulus-responsive hydrogel. A stimulus-responsive hydrogel can undergo a gel-to-solution and/or gel-to-solid transition upon application of one or more external triggers (e.g., a releasing agent). See, e.g., Willner, *Acc. Chem. Res.* 50:657-658, 2017, which is incorporated herein by reference in its entirety. Non-limiting examples of a stimulus-responsive hydrogel include a thermoresponsive hydrogel, a pH-responsive hydrogel, a light-responsive hydrogel, a redox-responsive hydrogel, an analyte-responsive hydrogel, or a combination thereof. In some embodiments, a stimulus-responsive hydrogel can be a multi-stimuli-responsive hydrogel.

A "releasing agent" or "external trigger" is an agent that allows for the removal of a conditionally removable coating from a substrate when the releasing agent is applied to the conditionally removable coating. An external trigger or releasing agent can include physical triggers such as thermal, magnetic, ultrasonic, electrochemical, and/or light stimuli as well as chemical triggers such as pH, redox reactions, supramolecular complexes, and/or biocatalytically driven reactions. See e.g., Echeverria, et al., Gels (2018), 4, 54; doi:10.3390/gels4020054, which is incorporated herein by reference in its entirety. The type of "releasing agent" or "external trigger" can depend on the type of conditionally removable coating. For example, a conditionally removable coating featuring a redox-responsive hydrogel can be removed upon application of a releasing agent that includes a reducing agent such as dithiothreitol (DTT). As another example, a pH-responsive hydrogel can be removed upon the application of a releasing agent that changes the pH.

(d) Arrays

In many of the methods described herein, features (as described further below) are collectively positioned on a substrate. An "array" is a specific arrangement of a plurality of features that is either irregular or forms a regular pattern. Individual features in the array differ from one another based on their relative spatial locations. In general, at least two of the plurality of features in the array include a distinct capture probe (e.g., any of the examples of capture probes described herein).

Arrays can be used to measure large numbers of analytes simultaneously. In some embodiments, oligonucleotides are used, at least in part, to create an array. For example, one or more copies of a single species of oligonucleotide (e.g., capture probe) can correspond to or be directly or indirectly attached to a given feature in the array. In some embodiments, a given feature in the array includes two or more species of oligonucleotides (e.g., capture probes). In some embodiments, the two or more species of oligonucleotides (e.g., capture probes) attached directly or indirectly to a given feature on the array include a common (e.g., identical) spatial barcode.

A "feature" is an entity that acts as a support or repository for various molecular entities used in sample analysis. Examples of features include, but are not limited to, a bead, a spot of any two- or three-dimensional geometry (e.g., an ink jet spot, a masked spot, a square on a grid), a well, and a hydrogel pad. In some embodiments, features are directly or indirectly attached or fixed to a substrate. In some embodiments, the features are not directly or indirectly attached or fixed to a substrate, but instead, for example, are disposed within an enclosed or partially enclosed three dimensional space (e.g., wells or divots).

In addition to those above, a wide variety of other features can be used to form the arrays described herein. For example, in some embodiments, features that are formed from polymers and/or biopolymers that are jet printed, screen printed, or electrostatically deposited on a substrate can be used to form arrays. Jet printing of biopolymers is described, for example, in PCT Patent Application Publication No. WO 2014/085725. Jet printing of polymers is described, for example, in de Gans et al., *Adv Mater.* 16(3): 203-213 (2004). Methods for electrostatic deposition of polymers and biopolymers are described, for example, in Hoyer et al., *Anal. Chem.* 68(21): 3840-3844 (1996). The entire contents of each of the foregoing references are incorporated herein by reference.

As another example, in some embodiments, features are formed by metallic micro- or nanoparticles. Suitable methods for depositing such particles to form arrays are described, for example, in Lee et al., *Beilstein J. Nanotechnol.* 8: 1049-1055 (2017), the entire contents of which are incorporated herein by reference.

As a further example, in some embodiments, features are formed by magnetic particles that are assembled on a substrate. Examples of such particles and methods for assembling arrays are described in Ye et al., *Scientific Reports* 6: 23145 (2016), the entire contents of which are incorporated herein by reference.

As another example, in some embodiments, features correspond to regions of a substrate in which one or more optical labels have been incorporated, and/or which have been altered by a process such as permanent photobleaching. Suitable substrates to implement features in this manner include a wide variety of polymers, for example. Methods for forming such features are described, for example, in Moshrefzadeh et al., *Appl. Phys. Lett.* 62: 16 (1993), the entire contents of which are incorporated herein by reference.

As yet another example, in some embodiments, features can correspond to colloidal particles assembled (e.g., via self-assembly) to form an array. Suitable colloidal particles are described for example in Sharma, *Resonance* 23(3): 263-275 (2018), the entire contents of which are incorporated herein by reference.

As a further example, in some embodiments, features can be formed via spot-array photopolymerization of a monomer solution on a substrate. In particular, two-photon and three-photon polymerization can be used to fabricate features of relatively small (e.g., sub-micron) dimensions. Suitable methods for preparing features on a substrate in this manner are described for example in Nguyen et al., *Materials Today* 20(6): 314-322 (2017), the entire contents of which are incorporated herein by reference.

In some embodiments, features are directly or indirectly attached or fixed to a substrate that is liquid permeable. In some embodiments, features are directly or indirectly attached or fixed to a substrate that is biocompatible. In some embodiments, features are directly or indirectly attached or fixed to a substrate that is a hydrogel.

Figure 12:
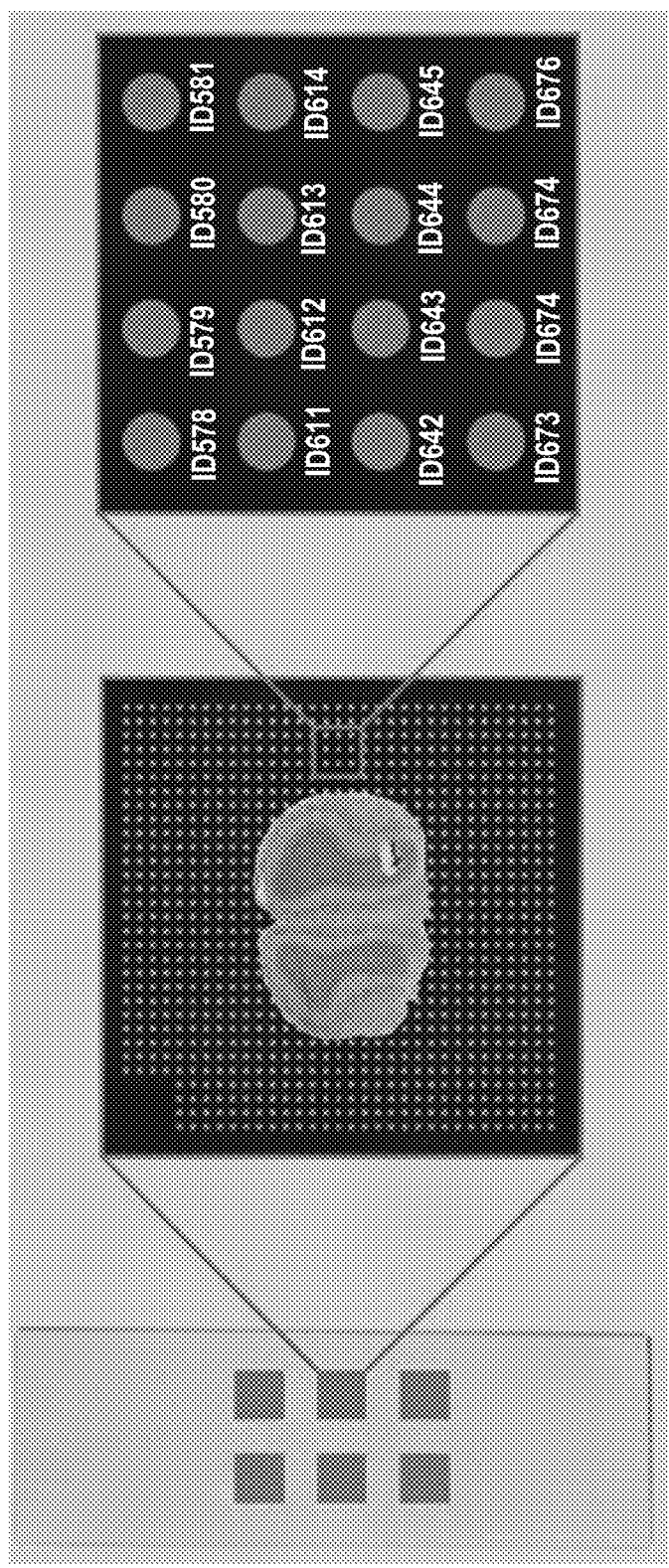
FIG. 12 is a schematic showing the arrangement of barcoded features within an array.

FIG. 12 depicts an exemplary arrangement of barcoded features within an array. From left to right, FIG. 12 shows (L) a slide including six spatially-barcoded arrays, (C) an enlarged schematic of one of the six spatially-barcoded arrays, showing a grid of barcoded features in relation to a biological sample, and (R) an enlarged schematic of one section of an array, showing the specific identification of multiple features within the array (labelled as ID578, ID579, ID560, etc.).

As used herein, the term "bead array" refers to an array that includes a plurality of beads as the features in the array. In some embodiments, the beads are attached to a substrate. For example, the beads can optionally attach to a substrate such as a microscope slide and in proximity to a biological sample (e.g., a tissue section that includes cells). The beads can also be suspended in a solution and deposited on a surface (e.g., a membrane, a tissue section, or a substrate (e.g., a microscope slide)).

Examples of arrays of beads on or within a substrate include beads located in wells such as the BeadChip array (available from Illumina Inc., San Diego, CA), arrays used in sequencing platforms from 454 LifeSciences (a subsidiary of Roche, Basel, Switzerland), and array used in sequencing platforms from Ion Torrent (a subsidiary of Life Technologies, Carlsbad, CA). Examples of bead arrays are described in, e.g., U.S. Pat. Nos. 6,266,459; 6,355,431; 6,770,441; 6,859,570; 6,210,891; 6,258,568; and 6,274,320; U.S. Pat. Application Publication Nos. 2009/0026082; 2009/0127589; 2010/0137143; and 2010/0282617; and PCT Patent Application Publication Nos. WO 00/063437 and WO 2016/162309, the entire contents of each of which is incorporated herein by reference.

In some embodiments, the bead array includes a plurality of beads. For example, the bead array can include at least 10,000 beads (e.g., at least 100,000 beads, at least 1,000,000 beads, at least 5,000,000 beads, at least 10,000,000 beads). In some embodiments, the plurality of beads includes a single type of beads (e.g., substantially uniform in size, shape, and other physical properties, such as translucence). In some embodiments, the plurality of beads includes two or more types of different beads.

In some embodiments, a bead array is formed when beads are embedded in a hydrogel layer where the hydrogel polymerizes and secures the relative bead positions. The bead-arrays can be pre-equilibrated and combined with reaction buffers and enzymes (e.g., reverse-transcription mix). In some embodiments, the bead arrays are frozen.

A "flexible array" includes a plurality of spatially-barcoded features attached to, or embedded in, a flexible substrate (e.g., a membrane or tape) placed onto a biological sample. In some embodiments, a flexible array includes a plurality of spatially-barcoded features embedded within a hydrogel matrix. To form such an array, features of a microarray are copied into a hydrogel, and the size of the hydrogel is reduced by removing water. These steps can be performed multiple times. For example, in some embodiments, a method for preparing a high-density spatially barcoded array can include copying a plurality of features from a microarray into a first hydrogel, where the first hydrogel is in contact with the microarray; reducing the size of the first hydrogel including the copied features by removing water, forming a first shrunken hydrogel including the copied features; copying the features in the first shrunken hydrogel into a second hydrogel, where the second hydrogel is in contact with the first hydrogel; and reducing the size of the second hydrogel including the copied features by removing water, forming a second shrunken hydrogel including the copied features, thus generating a high-density spatially barcoded array. The result is a high-density flexible array including spatially-barcoded features.

In some embodiments, spatially-barcoded beads can be loaded onto a substrate (e.g., a hydrogel) to produce a high-density self-assembled bead array.

Flexible arrays can be pre-equilibrated, combined with reaction buffers and enzymes at functional concentrations (e.g., a reverse-transcription mix). In some embodiments, the flexible bead-arrays can be stored for extended periods (e.g., days) or frozen until ready for use. In some embodiments, permeabilization of biological samples (e.g., a tissue section) can be performed with the addition of enzymes/detergents prior to contact with the flexible array. The flexible array can be placed directly on the sample, or placed in indirect contact with the biological sample (e.g., with an intervening layer or substance between the biological sample and the flexible bead-array). In some embodiments, once a flexible array is applied to the sample, reverse transcription and targeted capture of analytes can be performed on solid microspheres, or circular beads of a first size and circular beads of a second size.

A "microcapillary array" is an arrayed series of features that are partitioned by microcapillaries. A "microcapillary channel" is an individual partition created by the microcapillaries. For example, microcapillary channels can be fluidically isolated from other microcapillary channels, such that fluid or other contents in one microcapillary channel in the array are separated from fluid or other contents in a neighboring microcapillary channel in the array. The density and order of the microcapillaries can be any suitable density or order of discrete sites.

In some embodiments, microcapillary arrays are treated to generate conditions that facilitate loading. An example is the use of a corona wand (BD-20AC, Electro Technic Products) to generate a hydrophilic surface. In some embodiments, a feature (e.g., a bead with capture probe attached) is loaded onto a microcapillary array such that the exact position of the feature within the array is known. For example, a capture probe containing a spatial barcode can be placed into a microcapillary channel so that the spatial barcode can enable identification of the location from which the barcoded nucleic acid molecule was derived.

In some embodiments, when random distribution is used to distribute features, empirical testing can be performed to generate loading/distribution conditions that facilitate a single feature per microcapillary. In some embodiments, it can be desirable to achieve distribution conditions that facilitate only a single feature (e.g., bead) per microcapillary channel. In some embodiments, it can be desirable to achieve distribution conditions that facilitate more than one feature (e.g., bead) per microcapillary channel, by flowing the features through the microcapillary channel.

In some embodiments, the microcapillary array is placed in contact with a sample (e.g., on top or below) so that microcapillaries containing a feature (e.g., a bead, which can include a capture probe) are in contact with the biological sample. In some embodiments, a biological sample is placed onto an exposed side of a microcapillary array and mechanical compression is applied, moving the biological sample into the microcapillary channel to create a fluidically isolated reaction chamber containing the biological sample.

In some embodiments, a biological sample is partitioned by contacting a microcapillary array to the biological sample, thereby creating microcapillary channels including a bead and a portion of the biological sample. In some embodiments, a portion of a biological sample contained in a microcapillary channel is one or more cells. In some embodiments, a feature is introduced into a microcapillary array by flow after one or more cells are added to a microcapillary channel.

In some embodiments, reagents are added to the microcapillary array. The added reagents can include enzymatic reagents, and reagent mixtures for performing amplification of a nucleic acid. In some embodiments, the reagents include a reverse transcriptase, a ligase, one or more nucleotides, and any combinations thereof. One or more microcapillary channels can be sealed after reagents are added to the microcapillary channels, e.g. using silicone oil, mineral oil, a non-porous material, or lid.

In some embodiments, a reagent solution is removed from each microcapillary channel following an incubation for an amount of time and at a certain temperature or range of temperatures, e.g., following a hybridization or an amplification reaction. Reagent solutions can be processed individually for sequencing, or pooled for sequencing analysis.

In some embodiments, some or all features in an array include a capture probe. In some embodiments, an array can include a capture probe attached directly or indirectly to the substrate.

The capture probe includes a capture domain (e.g., a nucleotide sequence) that can specifically bind (e.g., hybridize) to a target analyte (e.g., mRNA, DNA, or protein) within a sample. In some embodiments, the binding of the capture probe to the target (e.g., hybridization) can be detected and quantified by detection of a visual signal, e.g. a fluorophore, a heavy metal (e.g., silver ion), or chemiluminescent label, which has been incorporated into the target. In some embodiments, the intensity of the visual signal correlates with the relative abundance of each analyte in the biological sample. Since an array can contain thousands or millions of capture probes (or more), an array of features with capture probes can interrogate many analytes in parallel.

In some embodiments, a substrate includes one or more capture probes that are designed to capture analytes from one or more organisms. In a non-limiting example, a substrate can contain one or more capture probes designed to capture mRNA from one organism (e.g., a human) and one or more capture probes designed to capture DNA from a second organism (e.g., a bacterium).

The capture probes can be attached to a substrate or feature using a variety of techniques. In some embodiments, the capture probe is directly attached to a feature that is fixed on an array. In some embodiments, the capture probes are immobilized to a substrate by chemical immobilization. For example, a chemical immobilization can take place between functional groups on the substrate and corresponding functional elements on the capture probes. Exemplary corresponding functional elements in the capture probes can either be an inherent chemical group of the capture probe, e.g. a hydroxyl group, or a functional element can be introduced on to the capture probe. An example of a functional group on the substrate is an amine group. In some embodiments, the capture probe to be immobilized includes a functional amine group or is chemically modified in order to include a functional amine group. Means and methods for such a chemical modification are well known in the art.

In some embodiments, the capture probe is a nucleic acid. In some embodiments, the capture probe is immobilized on the feature or the substrate via its 5' end. In some embodiments, the capture probe is immobilized on a feature or a substrate via its 5' end and includes from the 5' to 3' end: one or more barcodes (e.g., a spatial barcode and/or a UMI) and one or more capture domains. In some embodiments, the capture probe is immobilized on a feature via its 5' end and includes from the 5' to 3' end: one barcode (e.g., a spatial barcode or a UMI) and one capture domain. In some embodiments, the capture probe is immobilized on a feature or a substrate via its 5' end and includes from the 5' to 3' end: a cleavage domain, a functional domain, one or more barcodes (e.g., a spatial barcode and/or a UMI), and a capture domain.

In some embodiments, the capture probe is immobilized on a feature or a substrate via its 5' end and includes from the 5' to 3' end: a cleavage domain, a functional domain, one or more barcodes (e.g., a spatial barcode and/or a UMI), a second functional domain, and a capture domain. In some embodiments, the capture probe is immobilized on a feature or a substrate via its 5' end and includes from the 5' to 3' end: a cleavage domain, a functional domain, a spatial barcode, a UMI, and a capture domain. In some embodiments, the capture probe is immobilized on a feature or a substrate via its 5' end and does not include a spatial barcode. In some embodiments, the capture probe is immobilized on a feature or a substrate via its 5' end and does not include a UMI. In some embodiments, the capture probe includes a sequence for initiating a sequencing reaction.

In some embodiments, the capture probe is immobilized on a feature or a substrate via its 3' end. In some embodiments, the capture probe is immobilized on a feature or a substrate via its 3' end and includes from the 3' to 5' end: one or more barcodes (e.g., a spatial barcode and/or a UMI) and one or more capture domains. In some embodiments, the capture probe is immobilized on a feature or a substrate via its 3' end and includes from the 3' to 5' end: one barcode (e.g., a spatial barcode or a UMI) and one capture domain. In some embodiments, the capture probe is immobilized on a feature or a substrate via its 3' end and includes from the 3' to 5' end: a cleavage domain, a functional domain, one or more barcodes (e.g., a spatial barcode and/or a UMI), and a capture domain. In some embodiments, the capture probe is immobilized on a feature or a substrate via its 3' end and includes from the 3' to 5' end: a cleavage domain, a functional domain, a spatial barcode, a UMI, and a capture domain.

The localization of the functional group within the capture probe to be immobilized can be used to control and shape the binding behavior and/or orientation of the capture probe, e.g. the functional group can be placed at the 5' or 3' end of the capture probe or within the sequence of the capture probe. In some embodiments, a capture probe can further include a substrate (e.g., a support attached to the capture probe, a support attached to the feature, or a support attached to the substrate). A typical substrate for a capture probe to be immobilized includes moieties which are capable of binding to such capture probes, e.g., to amine-functionalized nucleic acids. Examples of such substrates are carboxy, aldehyde, or epoxy supports.

In some embodiments, the substrates on which capture probes can be immobilized can be chemically activated, e.g. by the activation of functional groups, available on the substrate. The term "activated substrate" relates to a material in which interacting or reactive chemical functional groups are established or enabled by chemical modification procedures. For example, a substrate including carboxyl groups can be activated before use. Furthermore, certain substrates contain functional groups that can react with specific moieties already present in the capture probes.

In some embodiments, a covalent linkage is used to directly couple a capture probe to a substrate. In some embodiments a capture probe is indirectly coupled to a substrate through a linker separating the "first" nucleotide of the capture probe from the substrate, i.e., a chemical linker. In some embodiments, a capture probe does not bind directly to the array, but interacts indirectly, for example by binding to a molecule which itself binds directly or indirectly to the array. In some embodiments, the capture probe is indirectly attached to a substrate (e.g., via a solution including a polymer).

In some embodiments where the capture probe is immobilized on the feature of the array indirectly, e.g. via hybridization to a surface probe capable of binding the capture probe, the capture probe can further include an upstream sequence (5' to the sequence that hybridizes to the nucleic acid, e.g. RNA of the tissue sample) that is capable of hybridizing to 5' end of the surface probe. Alone, the capture domain of the capture probe can be seen as a capture domain oligonucleotide, which can be used in the synthesis of the capture probe in embodiments where the capture probe is immobilized on the array indirectly.

In some embodiments, a substrate is comprised of an inert material or matrix (e.g., glass slides) that has been functionalization by, for example, treatment with a material comprising reactive groups which enable immobilization of capture probes. See, for example, WO 2017/019456, the entire contents of which are herein incorporated by reference. Non-limiting examples include polyacrylamide hydrogels supported on an inert substrate (e.g., glass slide; see WO 2005/065814 and U.S. Patent Application No. 2008/0280773, the entire contents of which are incorporated herein by reference).

In some embodiments, functionalized biomolecules (e.g., capture probes) are immobilized on a functionalized substrate using covalent methods. Methods for covalent attachment include, for example, condensation of amines and activated carboxylic esters (e.g., N-hydroxysuccinimide esters); condensation of amine and aldehydes under reductive amination conditions; and cycloaddition reactions such as the Diels-Alder [4+2] reaction, 1,3-dipolar cycloaddition reactions, and [2+2] cycloaddition reactions. Methods for covalent attachment also include, for example, click chemistry reactions, including [3+2] cycloaddition reactions (e.g., Huisgen 1,3-dipolar cycloaddition reaction and copper(I)-catalyzed azide-alkyne cycloaddition (CuAAC)); thiol-ene reactions; the Diels-Alder reaction and inverse electron demand Diels-Alder reaction; [4+1] cycloaddition of isonitriles and tetrazines; and nucleophilic ring-opening of small carbocycles (e.g., epoxide opening with amino oligonucleotides). Methods for covalent attachment also include, for example, maleimides and thiols; and para-nitrophenyl ester-functionalized oligonucleotides and polylysine-functionalized substrate. Methods for covalent attachment also include, for example, disulfide reactions; radical reactions (see, e.g., U.S. Pat. No. 5,919,626, the entire contents of which are herein incorporated by reference); and hydrazide-functionalized substrate (e.g., wherein the hydrazide functional group is directly or indirectly attached to the substrate) and aldehyde-functionalized oligonucleotides (see, e.g., Yershov et al. (1996) Proc. Natl. Acad. Sci. USA 93, 4913-4918, the entire contents of which are herein incorporated by reference).

In some embodiments, functionalized biomolecules (e.g., capture probes) are immobilized on a functionalized substrate using photochemical covalent methods. Methods for photochemical covalent attachment include, for example, immobilization of antraquinone-conjugated oligonucleotides (see, e.g., Koch et al. (2000) Bioconjugate Chem. 11, 474-483, the entire contents of which are herein incorporated by reference).

In some embodiments, functionalized biomolecules (e.g., capture probes are immobilized on a functionalized substrate using non-covalent methods. Methods for non-covalent attachment include, for example, biotin-functionalized oligonucleotides and streptavidin-treated substrates (see, e.g., Holmstrsøm et al. (1993) Analytical Biochemistry 209, 278-283 and Gilles et al. (1999) Nature Biotechnology 17, 365-370, the entire contents of which are herein incorporated by reference).

In some embodiments, an oligonucleotide (e.g., a capture probe) can be attached to a substrate or feature according to the methods set forth in U.S. Pat. Nos. 6,737,236, 7,259,258, 7,375,234, 7,427,678, 5,610,287, 5,807,522, 5,837,860, and 5,472,881; U.S. Patent Application Publication Nos. 2008/0280773 and 2011/0059865; Shalon et al. (1996) Genome Research, 639-645; Rogers et al. (1999) Analytical Biochemistry 266, 23-30; Stimpson et al. (1995) Proc. Natl. Acad. Sci. USA 92, 6379-6383; Beattie et al. (1995) Clin. Chem. 45, 700-706; Lamture et al. (1994) Nucleic Acids Research 22, 2121-2125; Beier et al. (1999) Nucleic Acids Research 27, 1970-1977; Joos et al. (1997) Analytical Biochemistry 247, 96-101; Nikiforov et al. (1995) Analytical Biochemistry 227, 201-209; Timofeev et al. (1996) Nucleic Acids Research 24, 3142-3148; Chrisey et al. (1996) Nucleic Acids Research 24, 3031-3039; Guo et al. (1994) Nucleic Acids Research 22, 5456-5465; Running and Urdea (1990) BioTechniques 8, 276-279; Fahy et al. (1993) Nucleic Acids Research 21, 1819-1826; Zhang et al. (1991) 19, 3929-3933; and Rogers et al. (1997) Gene Therapy 4, 1387-1392. The entire contents of each of the foregoing documents are incorporated herein by reference.

Arrays can be prepared by a variety of methods. In some embodiments, arrays are prepared through the synthesis (e.g., in-situ synthesis) of oligonucleotides on the array, or by jet printing or lithography. For example, light-directed synthesis of high-density DNA oligonucleotides can be achieved by photolithography or solid-phase DNA synthesis. To implement photolithographic synthesis, synthetic linkers modified with photochemical protecting groups can be attached to a substrate and the photochemical protecting groups can be modified using a photolithographic mask (applied to specific areas of the substrate) and light, thereby producing an array having localized photo-deprotection. Many of these methods are known in the art, and are described e.g., in Miller et al., "Basic concepts of microarrays and potential applications in clinical microbiology." Clinical microbiology reviews 22.4 (2009): 611-633; US201314111482A; U.S. Pat. No. 9,593,365B2; US2019203275; and WO2018091676, which are incorporated herein by reference in the entirety.

In some embodiments, the arrays are "spotted" or "printed" with oligonucleotides and these oligonucleotides (e.g., capture probes) are then attached to the substrate. The oligonucleotides can be applied by either noncontact or contact printing. A noncontact printer can use the same method as computer printers (e.g., bubble jet or inkjet) to expel small droplets of probe solution onto the substrate. The specialized inkjet-like printer can expel nanoliter to picoliter volume droplets of oligonucleotide solution, instead of ink, onto the substrate. In contact printing, each print pin directly applies the oligonucleotide solution onto a specific location on the surface. The oligonucleotides can be attached to the substrate surface by the electrostatic interaction of the negative charge of the phosphate backbone of the DNA with a positively charged coating of the substrate surface or by UV-cross-linked covalent bonds between the thymidine bases in the DNA and amine groups on the treated substrate surface. In some embodiments, the substrate is a glass slide. In some embodiments, the oligonucleotides (e.g., capture probes) are attached to the substrate by a covalent bond to a chemical matrix, e.g. epoxy-silane, amino-silane, lysine, polyacrylamide, etc.

The arrays can also be prepared by in situ-synthesis. In some embodiments, these arrays can be prepared using photolithography. The method typically relies on UV masking and light-directed combinatorial chemical synthesis on a substrate to selectively synthesize probes directly on the surface of the array, one nucleotide at a time per spot, for many spots simultaneously. In some embodiments, a substrate contains covalent linker molecules that have a protecting group on the free end that can be removed by light. UV light is directed through a photolithographic mask to deprotect and activate selected sites with hydroxyl groups that initiate coupling with incoming protected nucleotides that attach to the activated sites. The mask is designed in such a way that the exposure sites can be selected, and thus specify the coordinates on the array where each nucleotide can be attached. The process can be repeated, a new mask is applied activating different sets of sites and coupling different bases, allowing arbitrary oligonucleotides to be constructed at each site. This process can be used to synthesize hundreds of thousands of different oligonucleotides. In some embodiments, maskless array synthesizer technology can be used. It uses an array of programmable micromirrors to create digital masks that reflect the desired pattern of UV light to deprotect the features.

In some embodiments, the inkjet spotting process can also be used for in-situ oligonucleotide synthesis. The different nucleotide precursors plus catalyst can be printed on the substrate, and are then combined with coupling and deprotection steps. This method relies on printing picoliter volumes of nucleotides on the array surface in repeated rounds of base-by-base printing that extends the length of the oligonucleotide probes on the array.

Arrays can also be prepared by active hybridization via electric fields to control nucleic acid transport. Negatively charged nucleic acids can be transported to specific sites, or features, when a positive current is applied to one or more test sites on the array. The surface of the array can contain a binding molecule, e.g., streptavidin, which allows for the formation of bonds (e.g., streptavidin-biotin bonds) once electronically addressed biotinylated probes reach their targeted location. The positive current is then removed from the active features, and new test sites can be activated by the targeted application of a positive current. The process are repeated until all sites on the array are covered.

An array for spatial analysis can be generated by various methods as described herein. In some embodiments, the array has a plurality of capture probes comprising spatial barcodes. These spatial barcodes and their relationship to the locations on the array can be determined. In some cases, such information is readily available, because the oligonucleotides are spotted, printed, or synthesized on the array with a pre-determined pattern. In some cases, the spatial barcode can be decoded by methods described herein, e.g., by in-situ sequencing, by various labels associated with the spatial barcodes etc. In some embodiments, an array can be used as a template to generate a daughter array. Thus, the spatial barcode can be transferred to the daughter array with a known pattern.

In some embodiments, an array comprising barcoded probes can be generated through ligation of a plurality of oligonucleotides. In some instances, an oligonucleotide of the plurality contains a portion of a barcode, and the complete barcode is generated upon ligation of the plurality of oligonucleotides. For example, a first oligonucleotide containing a first portion of a barcode can be attached to a substrate (e.g., using any of the methods of attaching an oligonucleotide to a substrate described herein), and a second oligonucleotide containing a second portion of the barcode can then be ligated onto the first oligonucleotide to generate a complete barcode. Different combinations of the first, second and any additional portions of a barcode can be used to increase the diversity of the barcodes. In instances where the second oligonucleotide is also attached to the substrate prior to ligation, the first and/or the second oligonucleotide can be attached to the substrate via a surface linker which contains a cleavage site. Upon ligation, the ligated oligonucleotide is linearized by cleaving at the cleavage site.

To increase the diversity of the barcodes, a plurality of second oligonucleotides comprising two or more different barcode sequences can be ligated onto a plurality of first oligonucleotides that comprise the same barcode sequence, thereby generating two or more different species of barcodes. To achieve selective ligation, a first oligonucleotide attached to a substrate containing a first portion of a barcode can initially be protected with a protective group (e.g., a photocleavable protective group), and the protective group can be removed prior to ligation between the first and second oligonucleotide. In instances where the barcoded probes on an array are generated through ligation of two or more oligonucleotides, a concentration gradient of the oligonucleotides can be applied to a substrate such that different combinations of the oligonucleotides are incorporated into a barcoded probe depending on its location on the substrate.

Barcoded probes on an array can also be generated by adding single nucleotides to existing oligonucleotides on an array, for example, using polymerases that function in a template-independent manner. Single nucleotides can be added to existing oligonucleotides in a concentration gradient, thereby generating probes with varying length, depending on the location of the probes on the array.

Arrays can also be prepared by modifying existing arrays, for example, by modifying the oligonucleotides attached to the arrays. For instance, probes can be generated on an array that comprises oligonucleotides that are attached to the array at the 3' end and have a free 5' end. The oligonucleotides can be in situ synthesized oligonucleotides, and can include a barcode. The length of the oligonucleotides can be less than 50 nucleotides (nts) (e.g., less than 45, 40, 35, 30, 25, 20, 15, or 10 nts). To generate probes using these oligonucleotides, a primer complementary to a portion of an oligonucleotide (e.g., a constant sequence shared by the oligonucleotides) can be used to hybridize with the oligonucleotide and extend (using the oligonucleotide as a template) to form a duplex and to create a 3' overhang. The 3' overhang thus allows additional nucleotides or oligonucleotides to be added on to the duplex. A capture probe can be generated by, for instance, adding one or more oligonucleotides to the end of the 3' overhang (e.g., via splint oligonucleotide mediated ligation), where the added oligonucleotides can include the sequence or a portion of the sequence of a capture domain.

In instances where the oligonucleotides on an existing array include a recognition sequence that can hybridize with a splint oligonucleotide, probes can also be generated by directly ligating additional oligonucleotides onto the existing oligonucleotides via the splint oligonucleotide. The recognition sequence can at the free 5' end or the free 3' end of an oligonucleotide on the existing array. Recognition sequences useful for the methods of the present disclosure may not contain restriction enzyme recognition sites or secondary structures (e.g., hairpins), and may include high contents of Guanine and Cytosine nucleotides and thus have high stability.

Bead arrays can be generated by attaching beads (e.g., barcoded beads) to a substrate in a regular pattern, or an irregular arrangement. Beads can be attached to selective regions on a substrate by, e.g., selectively activating regions on the substrate to allow for attachment of the beads. Activating selective regions on the substrate can include activating a coating (e.g., a photocleavable coating) or a polymer that is applied on the substrate. Beads can be attached iteratively, e.g., a subset of the beads can be attached at one time, and the same process can be repeated to attach the remaining beads. Alternatively, beads can be attached to the substrate all in one step.

Barcoded beads, or beads comprising a plurality of barcoded probes, can be generated by first preparing a plurality of barcoded probes on a substrate, depositing a plurality of beads on the substrate, and generating probes attached to the beads using the probes on the substrate as a template.

Large scale commercial manufacturing methods allow for millions of oligonucleotides to be attached to an array. Commercially available arrays include those from Roche NimbleGen, Inc., (Wisconsin) and Affymetrix (ThermoFisher Scientific).

In some embodiments, arrays can be prepared according to the methods set forth in WO 2012/140224, WO 2014/060483, WO 2016/162309, WO 2017/019456, WO 2018/091676, and WO 2012/140224, and U.S. Patent Application No. 2018/0245142. The entire contents of the foregoing documents are herein incorporated by reference.

In some embodiments, a feature on the array includes a bead. In some embodiments, two or more beads are dispersed onto a substrate to create an array, where each bead is a feature on the array. Beads can optionally be dispersed into wells on a substrate, e.g., such that only a single bead is accommodated per well.

A "bead" is a particle. A bead can be porous, non-porous, solid, semi-solid, and/or a combination thereof. In some embodiments, a bead can be dissolvable, disruptable, and/or degradable, whereas in certain embodiments, a bead is not degradable.

A bead can generally be of any suitable shape. Examples of bead shapes include, but are not limited to, spherical, non-spherical, oval, oblong, amorphous, circular, cylindrical, and variations thereof. A cross section (e.g., a first cross-section) can correspond to a diameter or maximum cross-sectional dimension of the bead. In some embodiments, the bead can be approximately spherical. In such embodiments, the first cross-section can correspond to the diameter of the bead. In some embodiments, the bead can be approximately cylindrical. In such embodiments, the first cross-section can correspond to a diameter, length, or width along the approximately cylindrical bead.

Beads can be of uniform size or heterogeneous size. "Polydispersity" generally refers to heterogeneity of sizes of molecules or particles. The polydispersity index (PDI) of a bead can be calculated using the equation PDI=Mw/Mn, where Mw is the weight-average molar mass and Mn is the number-average molar mass. In certain embodiments, beads can be provided as a population or plurality of beads having a relatively monodisperse size distribution. Where it can be desirable to provide relatively consistent amounts of reagents, maintaining relatively consistent bead characteristics, such as size, can contribute to the overall consistency.

In some embodiments, the beads provided herein can have size distributions that have a coefficient of variation in their cross-sectional dimensions of less than 50%, less than 40%, less than 30%, less than 20%, less than 15%, less than 10%, less than 5%, or lower. In some embodiments, a plurality of beads provided herein has a polydispersity index of less than 50%, less than 45%, less than 40%, less than 35%, less than 30%, less than 25%, less than 20%, less than 15%, less than 10%, less than 5%, or lower.

In some embodiments, the bead can have a diameter or maximum dimension no larger than 100 μm (e.g., no larger than 95 μm, 90 μm, 85 μm, 80 μm, 75 μm, 70 μm, 65 μm, 60 μm, 55 μm, 50 μm, 45 μm, 40 μm, 35 μm, 30 μm, 25 μm, 20 μm, 15 μm, 14 μm, 13 μm, 12 μm, 11 μm, 10 μm, 9 μm, 8 μm, 7 μm, 6 μm, 5 μm, 4 μm, 3 μm, 2 μm, or 1 μm.)

In some embodiments, a plurality of beads has an average diameter no larger than 100 μm. In some embodiments, a plurality of beads has an average diameter or maximum dimension no larger than 95 μm, 90 μm, 85 μm, 80 μm, 75 μm, 70 μm, 65 μm, 60 μm, 55 μm, 50 μm, 45 μm, 40 μm, 35 μm, 30 μm, 25 μm, 20 μm, 15 μm, 14 μm, 13 μm, 12 μm, 11 μm, 10 μm, 9 μm, 8 μm, 7 μm, 6 μm, 5 μm, 4 μm, 3 μm, 2 μm, or 1 μm.

In some embodiments, the volume of the bead can be at least about 1 $\mu m^3$, e.g., at least 1 $\mu m^3$, 2 $\mu m^3$, 3 $\mu m^3$, 4 $\mu m^3$, 5 $\mu m^3$, 6 $\mu m^3$, 7 $\mu m^3$, 8 $\mu m^3$, 9 $\mu m^3$, 10 $\mu m^3$, 12 $\mu m^3$, 14 $\mu m^3$, 16 $\mu m^3$, 18 $\mu m^3$, 20 $\mu m^3$, 25 $\mu m^3$, 30 $\mu m^3$, 35 $\mu m^3$, 40 $\mu m^3$, 45 $\mu m^3$, 50 $\mu m^3$, 55 $\mu m^3$, 60 $\mu m^3$, 65 $\mu m^3$, 70 $\mu m^3$, 75 $\mu m^3$, 80 $\mu m^3$, 85 $\mu m^3$, 90 $\mu m^3$, 95 $\mu m^3$, 100 $\mu m^3$, 125 $\mu m^3$, 150 $\mu m^3$, 175 $\mu m^3$, 200 $\mu m^3$, 250 $\mu m^3$, 300 $\mu m^3$, 350 $\mu m^3$, 400 $\mu m^3$, 450 $\mu m^3$, $\mu m^3$, 500 $\mu m^3$, 550 $\mu m^3$, 600 $\mu m^3$, 650 $\mu m^3$, 700 $\mu m^3$, 750 $\mu m^3$, 800 $\mu m^3$, 850 $\mu m^3$, 900 $\mu m^3$, 950 $\mu m^3$, 1000 $\mu m^3$, 1200 $\mu m^3$, 1400 $\mu m^3$, 1600 $\mu m^3$, 1800 $\mu m^3$, 2000 $\mu m^3$, 2200 $\mu m^3$, 2400 $\mu m^3$, 2600 $\mu m^3$, 2800 $\mu m^3$, 3000 $\mu m^3$, or greater.

In some embodiments, the bead can have a volume of between about 1 $\mu m^3$ and 100 $\mu m^3$, such as between about 1 $\mu m^3$ and 10 $\mu m^3$, between about 10 $\mu m^3$ and 50 $\mu m^3$, or between about 50 $\mu m^3$ and 100 $\mu m^3$. In some embodiments, the bead can include a volume of between about 100 $\mu m^3$ and 1000 $\mu m^3$, such as between about 100 $\mu m^3$ and 500 $\mu m^3$ or between about 500 $\mu m^3$ and 1000 $\mu m^3$. In some embodiments, the bead can include a volume between about 1000 $\mu m^3$ and 3000 $\mu m^3$, such as between about 1000 $\mu m^3$ and 2000 $\mu m^3$ or between about 2000 $\mu m^3$ and 3000 $\mu m^3$. In some embodiments, the bead can include a volume between about 1 $\mu m^3$ and 3000 $\mu m^3$, such as between about 1 $\mu m^3$ and 2000 $\mu m^3$, between about 1 $\mu m^3$ and 1000 $\mu m^3$, between about 1 $\mu m^3$ and 500 $\mu m^3$, or between about 1 $\mu m^3$ and 250 $\mu m^3$.

The bead can include one or more cross-sections that can be the same or different. In some embodiments, the bead can have a first cross-section that is different from a second cross-section. The bead can have a first cross-section that is at least about 0.0001 micrometer, 0.001 micrometer, 0.01 micrometer, 0.1 micrometer, or 1 micrometer. In some embodiments, the bead can include a cross-section (e.g., a first cross-section) of at least about 1 μmicrometer (μm), 2 μm, 3 μm, 4 μm, 5 μm, 6 μm, 7 μm, 8 μm, 9 μm, 10 μm, 11 μm, 12 μm, 13 μm, 14 μm, 15 μm, 16 μm, 17 μm, 18 μm, 19 μm, 20 μm, 25 μm, 30 μm, 35 μm, 40 μm, 45 μm, 50 μm, 55 μm, 60 μm, 65 μm, 70 μm, 75 μm, 80 μm, 85 μm, 90 μm, 100 μm, 120 μm, 140 μm, 160 μm, 180 μm, 200 μm, 250 μm, 300 μm, 350 μm, 400 μm, 450 μm, 500 μm, 550 μm, 600 μm, 650 μm, 700 μm, 750 μm, 800 μm, 850 μm, 900 μm, 950 μm, 1 millimeter (mm), or greater. In some embodiments, the bead can include a cross-section (e.g., a first cross-section) of between about 1 μm and 500 μm, such as between about 1 μm and 100 μm, between about 100 μm and 200 μm, between about 200 μm and 300 μm, between about 300 μm and 400 μm, or between about 400 μm and 500 μm. For example, the bead can include a cross-section (e.g., a first cross-section) of between about 1 m and 100 μm. In some embodiments, the bead can have a second cross-section that is at least about 1 μm. For example, the bead can include a second cross-section of at least about 1 micrometer (μm), 2 μm, 3 μm, 4 μm, 5 μm, 6 μm, 7 μm, 8 μm, 9 μm, 10 μm, 11 μm, 12 μm, 13 μm, 14 μm, 15 μm, 16 μm, 17 μm, 18 μm, 19 μm, 20 μm, 25 μm, 30 μm, 35 μm, 40 μm, 45 μm, 50 μm, 55 μm, 60 μm, 65 μm, 70 μm, 75 μm, 80 μm, 85 μm, 90 μm, 100 μm, 120 μm, 140 μm, 160 μm, 180 μm, 200 μm, 250 μm, 300 μm, 350 μm, 400 μm, 450 μm, 500 μm, 550 μm, 600 μm, 650 μm, 700 μm, 750 μm, 800 μm, 850 μm, 900 μm, 950 μm, 1 millimeter (mm), or greater. In some embodiments, the bead can include a second cross-section of between about 1 μm and 500 μm, such as between about 1 μm and 100 μm, between about 100 μm and 200 μm, between about 200 μm and 300 μm, between about 300 μm and 400 μm, or between about 400 μm and 500 μm. For example, the bead can include a second cross-section of between about 1 μm and 100 μm.

In some embodiments, beads can be of a nanometer scale (e.g., beads can have a diameter or maximum cross-sectional dimension of about 100 nanometers (nm) to about 900 nanometers (nm) (e.g., 850 nm or less, 800 nm or less, 750 nm or less, 700 nm or less, 650 nm or less, 600 nm or less, 550 nm or less, 500 nm or less, 450 nm or less, 400 nm or less, 350 nm or less, 300 nm or less, 250 nm or less, 200 nm or less, 150 nm or less). A plurality of beads can have an average diameter or average maximum cross-sectional dimension of about 100 nanometers (nm) to about 900 nanometers (nm) (e.g., 850 nm or less, 800 nm or less, 750 nm or less, 700 nm or less, 650 nm or less, 600 nm or less, 550 nm or less, 500 nm or less, 450 nm or less, 400 nm or less, 350 nm or less, 300 nm or less, 250 nm or less, 200 nm or less, 150 nm or less). In some embodiments, a bead has a diameter or size that is about the size of a single cell (e.g., a single cell under evaluation).

In some embodiments, the bead can be a gel bead. A "gel" is a semi-rigid material permeable to liquids and gases. Exemplary gels include, but are not limited to, those having a colloidal structure, such as agarose; polymer mesh structures, such as gelatin; hydrogels; and cross-linked polymer structures, such as polyacrylamide, SFA (see, for example, U.S. Patent Application Publication No. 2011/0059865, which is incorporated herein by reference in its entirety) and PAZAM (see, for example, U.S. Patent Application Publication No. 2014/0079923, which is incorporated herein by reference in its entirety).

A gel can be formulated into various shapes and dimensions depending on the context of intended use. In some embodiments, a gel is prepared and formulated as a gel bead (e.g., a gel bead including capture probes attached or associated with the gel bead). A gel bead can be a hydrogel bead. A hydrogel bead can be formed from molecular precursors, such as a polymeric or monomeric species.

In some embodiments, a hydrogel bead can include a polymer matrix (e.g., a matrix formed by polymerization or cross-linking). A polymer matrix can include one or more polymers (e.g., polymers having different functional groups or repeat units). Cross-linking can be via covalent, ionic, and/or inductive interactions, and/or physical entanglement.

A semi-solid bead can be a liposomal bead.

Solid beads can include metals including, without limitation, iron oxide, gold, and silver. In some embodiments, the bead can be a silica bead. In some embodiments, the bead can be rigid. In some embodiments, the bead can be flexible and/or compressible.

The bead can be a macromolecule. The bead can be formed of nucleic acid molecules bound together. The bead can be formed via covalent or non-covalent assembly of molecules (e.g., macromolecules), such as monomers or polymers. Polymers or monomers can be natural or synthetic. Polymers or monomers can be or include, for example, nucleic acid molecules (e.g., DNA or RNA).

A bead can be rigid, or flexible and/or compressible. A bead can include a coating including one or more polymers. Such a coating can be disruptable or dissolvable. In some embodiments, a bead includes a spectral or optical label (e.g., dye) attached directly or indirectly (e.g., through a linker) to the bead. For example, a bead can be prepared as a colored preparation (e.g., a bead exhibiting a distinct color within the visible spectrum) that can change color (e.g., colorimetric beads) upon application of a desired stimulus (e.g., heat and/or chemical reaction) to form differently colored beads (e.g., opaque and/or clear beads).

A bead can include natural and/or synthetic materials. For example, a bead can include a natural polymer, a synthetic polymer or both natural and synthetic polymers. Examples of natural polymers include, without limitation, proteins, sugars such as deoxyribonucleic acid, rubber, cellulose, starch (e.g., amylose, amylopectin), enzymes, polysaccharides, silks, polyhydroxyalkanoates, chitosan, dextran, collagen, carrageenan, ispaghula, acacia, agar, gelatin, shellac, sterculia gum, xanthan gum, corn sugar gum, guar gum, gum karaya, agarose, alginic acid, alginate, or natural polymers thereof. Examples of synthetic polymers include, without limitation, acrylics, nylons, silicones, spandex, viscose rayon, polycarboxylic acids, polyvinyl acetate, polyacrylamide, polyacrylate, polyethylene glycol, polyurethanes, polylactic acid, silica, polystyrene, polyacrylonitrile, polybutadiene, polycarbonate, polyethylene, polyethylene terephthalate, poly(chlorotrifluoroethylene), poly(ethylene oxide), poly(ethylene terephthalate), polyethylene, polyisobutylene, poly(methyl methacrylate), poly(oxymethylene), polyformaldehyde, polypropylene, polystyrene, poly(tetrafluoroethylene), poly(vinyl acetate), poly(vinyl alcohol), poly(vinyl chloride), poly(vinylidene dichloride), poly(vinylidene difluoride), poly(vinyl fluoride) and/or combinations (e.g., copolymers) thereof. Beads can also be formed from materials other than polymers, including for example, lipids, micelles, ceramics, glass-ceramics, material composites, metals, and/or other inorganic materials.

In some embodiments, a bead is a degradable bead. A degradable bead can include one or more species (e.g., disulfide linkers, primers, other oligonucleotides, etc.) with a labile bond such that, when the bead/species is exposed to the appropriate stimuli, the labile bond is broken and the bead degrades. The labile bond can be a chemical bond (e.g., covalent bond, ionic bond) or can be another type of physical interaction (e.g., van der Waals interactions, dipole-dipole interactions, etc.). In some embodiments, a cross-linker used to generate a bead can include a labile bond. Upon exposure to the appropriate conditions, the labile bond can be broken and the bead degraded. For example, upon exposure of a polyacrylamide gel bead including cystamine crosslinkers to a reducing agent, the disulfide bonds of the cystamine can be broken and the bead degraded.

Degradation can refer to the disassociation of a bound or entrained species (e.g., disulfide linkers, primers, other oligonucleotides, etc.) from a bead, both with and without structurally degrading the physical bead itself. For example, entrained species can be released from beads through osmotic pressure differences due to, for example, changing chemical environments. By way of example, alteration of bead pore sizes due to osmotic pressure differences can generally occur without structural degradation of the bead itself. In some embodiments, an increase in pore size due to osmotic swelling of a bead can permit the release of entrained species within the bead. In some embodiments, osmotic shrinking of a bead can cause a bead to better retain an entrained species due to pore size contraction.

Any suitable agent that can degrade beads can be used. In some embodiments, changes in temperature or pH can be used to degrade thermo-sensitive or pH-sensitive bonds within beads. In some embodiments, chemical degrading agents can be used to degrade chemical bonds within beads by oxidation, reduction or other chemical changes. For example, a chemical degrading agent can be a reducing agent, such as DTT, where DTT can degrade the disulfide bonds formed between a crosslinker and gel precursors, thus degrading the bead. In some embodiments, a reducing agent can be added to degrade the bead, which can cause the bead to release its contents. Examples of reducing agents can include, without limitation, dithiothreitol (DTT), β-mercaptoethanol, (2S)-2-amino-1,4-dimercaptobutane (dithiobutylamine or DTBA), tris(2-carboxyethyl) phosphine (TCEP), or combinations thereof.

Any of a variety of chemical agents can be used to trigger the degradation of beads. Examples of chemical agents include, but are not limited to, pH-mediated changes to the integrity of a component within the bead, degradation of a component of a bead via cleavage of cross-linked bonds, and depolymerization of a component of a bead.

In some embodiments, a bead can be formed from materials that include degradable chemical crosslinkers, such as N,N'-bis-(acryloyl)cystamine (BAC) or cystamine. Degradation of such degradable crosslinkers can be accomplished through any variety of mechanisms. In some examples, a bead can be contacted with a chemical degrading agent that can induce oxidation, reduction or other chemical changes. For example, a chemical degrading agent can be a reducing agent, such as dithiothreitol (DTT). Additional examples of reducing agents can include β-mercaptoethanol, (2S)-2-amino-1,4-dimercaptobutane (dithiobutylamine or DTBA), tris(2-carboxyethyl) phosphine (TCEP), or combinations thereof.

In some embodiments, exposure to an aqueous solution, such as water, can trigger hydrolytic degradation, and thus degradation of the bead. Beads can also be induced to release their contents upon the application of a thermal stimulus. A change in temperature can cause a variety of changes to a bead. For example, heat can cause a solid bead to liquefy. A change in heat can cause melting of a bead such that a portion of the bead degrades. In some embodiments, heat can increase the internal pressure of the bead components such that the bead ruptures or explodes. Heat can also act upon heat-sensitive polymers used as materials to construct beads.

Where degradable beads are used, it can be beneficial to avoid exposing such beads to the stimulus or stimuli that cause such degradation prior to a given time, in order to, for example, avoid premature bead degradation and issues that arise from such degradation, including for example poor flow characteristics and aggregation. By way of example, where beads include reducible cross-linking groups, such as disulfide groups, it will be desirable to avoid contacting such beads with reducing agents, e.g., DTT or other disulfide cleaving reagents. In such embodiments, treatment of the beads described herein will, in some embodiments be provided free of reducing agents, such as DTT. Because reducing agents are often provided in commercial enzyme preparations, it can be desirable to provide reducing agent free (or DTT free) enzyme preparations in treating the beads described herein. Examples of such enzymes include, e.g., polymerase enzyme preparations, reverse transcriptase enzyme preparations, ligase enzyme preparations, as well as many other enzyme preparations that can be used to treat the beads described herein. The terms "reducing agent free" or "DTT free" preparations refer to a preparation having less than about 1/10th, less than about 1/50th, or less than about 1/100th of the lower ranges for such materials used in degrading the beads. For example, for DTT, the reducing agent free preparation can have less than about 0.01 millimolar (mM), 0.005 mM, 0.001 mM DTT, 0.0005 mM DTT, or less than about 0.0001 mM DTT. In some embodiments, the amount of DTT can be undetectable.

A degradable bead can be useful to more quickly release an attached capture probe (e.g., a nucleic acid molecule, a spatial barcode sequence, and/or a primer) from the bead when the appropriate stimulus is applied to the bead as compared to a bead that does not degrade. For example, for a species bound to an inner surface of a porous bead or in the case of an encapsulated species, the species can have greater mobility and accessibility to other species in solution upon degradation of the bead. In some embodiments, a species can also be attached to a degradable bead via a degradable linker (e.g., disulfide linker). The degradable linker can respond to the same stimuli as the degradable bead or the two degradable species can respond to different stimuli. For example, a capture probe having one or more spatial barcodes can be attached, via a disulfide bond, to a polyacrylamide bead including cystamine. Upon exposure of the spatially barcoded bead to a reducing agent, the bead degrades and the capture probe having the one or more spatial barcode sequences is released upon breakage of both the disulfide linkage between the capture probe and the bead and the disulfide linkages of the cystamine in the bead.

The addition of multiple types of labile bonds to a bead can result in the generation of a bead capable of responding to varied stimuli. Each type of labile bond can be sensitive to an associated stimulus (e.g., chemical stimulus, light, temperature, pH, enzymes, etc.) such that release of reagents attached to a bead via each labile bond can be controlled by the application of the appropriate stimulus. Some non-limiting examples of labile bonds that can be coupled to a precursor or bead include an ester linkage (e.g., cleavable with an acid, a base, or hydroxylamine), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), or a phosphodiester linkage (e.g., cleavable via a nuclease (e.g., DNAase)). A bond can be cleavable via other nucleic acid molecule targeting enzymes, such as restriction enzymes (e.g., restriction endonucleases). Such functionality can be useful in controlled release of reagents from a bead. In some embodiments, another reagent including a labile bond can be linked to a bead after gel bead formation via, for example, an activated functional group of the bead as described above. In some embodiments, a gel bead including a labile bond is reversible. In some embodiments, a gel bead with a reversible labile bond is used to capture one or more regions of interest of a biological sample. For example, without limitation, a bead including a thermolabile bond can be heated by a light source (e.g., a laser) that causes a change in the gel bead that facilitates capture of a biological sample in contact with the gel bead. Capture probes having one or more spatial barcodes that are releasably, cleavably, or reversibly attached to the beads described herein include capture probes that are released or releasable through cleavage of a linkage between the capture probe and the bead, or that are released through degradation of the underlying bead itself, allowing the capture probes having the one or more spatial barcodes to be accessed or become accessible by other reagents, or both.

Beads can have different physical properties. Physical properties of beads can be used to characterize the beads. Non-limiting examples of physical properties of beads that can differ include size, shape, circularity, density, symmetry, and hardness. For example, beads can be of different sizes. Different sizes of beads can be obtained by using microfluidic channel networks configured to provide specific sized beads (e.g., based on channel sizes, flow rates, etc.). In some embodiments, beads have different hardness values that can be obtained by varying the concentration of polymer used to generate the beads. In some embodiments, a spatial barcode attached to a bead can be made optically detectable using a physical property of the capture probe. For example, a nucleic acid origami, such as a deoxyribonucleic acid (DNA) origami, can be used to generate an optically detectable spatial barcode. To do so, a nucleic acid molecule, or a plurality of nucleic acid molecules, can be folded to create two- and/or three-dimensional geometric shapes. The different geometric shapes can be optically detected.

In some embodiments, special types of nanoparticles with more than one distinct physical property can be used to make the beads physically distinguishable. For example, Janus particles with both hydrophilic and hydrophobic surfaces can be used to provide unique physical properties.

In some embodiments, a bead is able to identify multiple analytes (e.g., nucleic acids, proteins, chromatin, metabolites, drugs, gRNA, and lipids) from a single cell. In some embodiments, a bead is able to identify a single analyte from a single cell (e.g., mRNA).

A bead can have a tunable pore size. The pore size can be chosen to, for instance, retain denatured nucleic acids. The pore size can be chosen to maintain diffusive permeability to exogenous chemicals such as sodium hydroxide (NaOH) and/or endogenous chemicals such as inhibitors. A bead can be formed of a biocompatible and/or biochemically compatible material, and/or a material that maintains or enhances cell viability. A bead can be formed from a material that can be depolymerized thermally, chemically, enzymatically, and/or optically.

In some embodiments, beads can be non-covalently loaded with one or more reagents. The beads can be non-covalently loaded by, for instance, subjecting the beads to conditions sufficient to swell the beads, allowing sufficient time for the reagents to diffuse into the interiors of the beads, and subjecting the beads to conditions sufficient to de-swell the beads. Swelling of the beads can be accomplished, for instance, by placing the beads in a thermodynamically favorable solvent, subjecting the beads to a higher or lower temperature, subjecting the beads to a higher or lower ion concentration, and/or subjecting the beads to an electric field.

The swelling of the beads can be accomplished by various swelling methods. In some embodiments, swelling is reversible (e.g., by subjecting beads to conditions that promote de-swelling). In some embodiments, the de-swelling of the beads is accomplished, for instance, by transferring the beads in a thermodynamically unfavorable solvent, subjecting the beads to lower or higher temperatures, subjecting the beads to a lower or higher ion concentration, and/or adding or removing an electric field. The de-swelling of the beads can be accomplished by various de-swelling methods. In some embodiments, de-swelling is reversible (e.g., subject beads to conditions that promote swelling). In some embodiments, the de-swelling of beads can include transferring the beads to cause pores in the bead to shrink. The shrinking can then hinder reagents within the beads from diffusing out of the interiors of the beads. The hindrance created can be due to steric interactions between the reagents and the interiors of the beads. The transfer can be accomplished microfluidically. For instance, the transfer can be achieved by moving the beads from one co-flowing solvent stream to a different co-flowing solvent stream. The swellability and/or pore size of the beads can be adjusted by changing the polymer composition of the bead.

A bead can include a polymer that is responsive to temperature so that when the bead is heated or cooled, the characteristics or dimensions of the bead can change. For example, a polymer can include poly(N-isopropylacrylamide). A gel bead can include poly(N-isopropylacrylamide) and when heated the gel bead can decrease in one or more dimensions (e.g., a cross-sectional diameter, multiple cross-sectional diameters). A temperature sufficient for changing one or more characteristics of the gel bead can be, for example, at least about 0 degrees Celsius (° C.), 1° C., 2° C., 3° C., 4° C., 5° C., 10° C., or higher. For example, the temperature can be about 4° C. In some embodiments, a temperature sufficient for changing one or more characteristics of the gel bead can be, for example, at least about 25° C., 30° C., 35° C., 37° C., 40° C., 45° C., 50° C., or higher. For example, the temperature can be about 37° C.

Functionalization of beads for attachment of capture probes can be achieved through a wide range of different approaches, including, without limitation, activation of chemical groups within a polymer, incorporation of active or activatable functional groups in the polymer structure, or attachment at the pre-polymer or monomer stage in bead production. The bead can be functionalized to bind to targeted analytes, such as nucleic acids, proteins, carbohydrates, lipids, metabolites, peptides, or other analytes.

In some embodiments, a bead can contain molecular precursors (e.g., monomers or polymers), which can form a polymer network via polymerization of the molecular precursors. In some embodiments, a precursor can be an already polymerized species capable of undergoing further polymerization via, for example, a chemical cross-linkage. In some embodiments, a precursor can include one or more of an acrylamide or a methacrylamide monomer, oligomer, or polymer. In some embodiments, the bead can include pre-polymers, which are oligomers capable of further polymerization. For example, polyurethane beads can be prepared using prepolymers. In some embodiments, a bead can contain individual polymers that can be further polymerized together (e.g., to form a co-polymer). In some embodiments, a bead can be generated via polymerization of different precursors, such that they include mixed polymers, co-polymers, and/or block co-polymers. In some embodiments, a bead can include covalent or ionic bonds between polymeric precursors (e.g., monomers, oligomers, and linear polymers), nucleic acid molecules (e.g., oligonucleotides), primers, and other entities. In some embodiments, covalent bonds can be carbon-carbon bonds or thioether bonds.

Cross-linking of polymers can be permanent or reversible, depending upon the particular cross-linker used. Reversible cross-linking can allow the polymer to linearize or dissociate under appropriate conditions. In some embodiments, reversible cross-linking can also allow for reversible attachment of a material bound to the surface of a bead. In some embodiments, a cross-linker can form a disulfide linkage. In some embodiments, a chemical cross-linker forming a disulfide linkage can be cystamine or a modified cystamine.

For example, where the polymer precursor material includes a linear polymer material, such as a linear polyacrylamide, PEG, or other linear polymeric material, the activation agent can include a cross-linking agent, or a chemical that activates a cross-linking agent within formed droplets. Likewise, for polymer precursors that include polymerizable monomers, the activation agent can include a polymerization initiator. For example, in certain embodiments, where the polymer precursor includes a mixture of acrylamide monomer with a N,N'-bis-(acryloyl)cystamine (BAC) comonomer, an agent such as tetraethylmethylenediamine (TEMED) can be provided, which can initiate the copolymerization of the acrylamide and BAC into a cross-linked polymer network, or other conditions sufficient to polymerize or gel the precursors. The conditions sufficient to polymerize or gel the precursors can include exposure to heating, cooling, electromagnetic radiation, and/or light.

Following polymerization or gelling, a polymer or gel can be formed. The polymer or gel can be diffusively permeable to chemical or biochemical reagents. The polymer or gel can be diffusively impermeable to macromolecular constituents. The polymer or gel can include one or more of disulfide cross-linked polyacrylamide, agarose, alginate, polyvinyl alcohol, polyethylene glycol (PEG)-diacrylate, PEG-acrylate, PEG-thiol, PEG-azide, PEG-alkyne, other acrylates, chitosan, hyaluronic acid, collagen, fibrin, gelatin, or elastin. The polymer or gel can include any other polymer or gel.

In some embodiments, disulfide linkages can be formed between molecular precursor units (e.g., monomers, oligomers, or linear polymers) or precursors incorporated into a bead and nucleic acid molecules (e.g., oligonucleotides, capture probes). Cystamine (including modified cystamines), for example, is an organic agent including a disulfide bond that can be used as a crosslinker agent between individual monomeric or polymeric precursors of a bead. Polyacrylamide can be polymerized in the presence of cystamine or a species including cystamine (e.g., a modified cystamine) to generate polyacrylamide gel beads including disulfide linkages (e.g., chemically degradable beads including chemically-reducible cross-linkers). The disulfide linkages can permit the bead to be degraded (or dissolved) upon exposure of the bead to a reducing agent.

In some embodiments, chitosan, a linear polysaccharide polymer, can be cross-linked with glutaraldehyde via hydrophilic chains to form a bead. Crosslinking of chitosan polymers can be achieved by chemical reactions that are initiated by heat, pressure, change in pH, and/or radiation.

In some embodiments, a bead can include an acrydite moiety, which in certain aspects can be used to attach one or more capture probes to the bead. In some embodiments, an acrydite moiety can refer to an acrydite analogue generated from the reaction of acrydite with one or more species (e.g., disulfide linkers, primers, other oligonucleotides, etc.), such as, without limitation, the reaction of acrydite with other monomers and cross-linkers during a polymerization reaction. Acrydite moieties can be modified to form chemical bonds with a species to be attached, such as a capture probe. Acrydite moieties can be modified with thiol groups capable of forming a disulfide bond or can be modified with groups already including a disulfide bond. The thiol or disulfide (via disulfide exchange) can be used as an anchor point for a species to be attached or another part of the acrydite moiety can be used for attachment. In some embodiments, attachment can be reversible, such that when the disulfide bond is broken (e.g., in the presence of a reducing agent), the attached species is released from the bead. In some embodiments, an acrydite moiety can include a reactive hydroxyl group that can be used for attachment of species.

In some embodiments, precursors (e.g., monomers or cross-linkers) that are polymerized to form a bead can include acrydite moieties, such that when a bead is generated, the bead also includes acrydite moieties. The acrydite moieties can be attached to a nucleic acid molecule (e.g., an oligonucleotide), which can include a priming sequence (e.g., a primer for amplifying target nucleic acids, random primer, primer sequence for messenger RNA) and/or one or more capture probes. The one or more capture probes can include sequences that are the same for all capture probes coupled to a given bead and/or sequences that are different across all capture probes coupled to the given bead. The capture probe can be incorporated into the bead. In some embodiments, the capture probe can be incorporated or attached to the bead such that the capture probe retains a free 3' end. In some embodiments, the capture probe can be incorporated or attached to the bead such that the capture probe retains a free 5' end. In some embodiments, beads can be functionalized such that each bead contains a plurality of different capture probes. For example, a bead can include a plurality of capture probes e.g., Capture Probe 1, Capture Probe 2, and Capture Probe 3, and each of Capture Probes 1, Capture Probes 2, and Capture Probes 3 contain a distinct capture domain (e.g., capture domain of Capture Probe 1 includes a poly(dT) capture domain, capture domain of Capture Probe 2 includes a gene-specific capture domain, and capture domain of Capture Probe 3 includes a CRISPR-specific capture domain). By functionalizing beads to contain a plurality of different capture domains per bead, the level of multiplex capability for analyte detection can be improved.

In some embodiments, precursors (e.g., monomers or cross-linkers) that are polymerized to form a bead can include a functional group that is reactive or capable of being activated such that when it becomes reactive it can be polymerized with other precursors to generate beads including the activated or activatable functional group. The functional group can then be used to attach additional species (e.g., disulfide linkers, primers, other oligonucleotides, etc.) to the beads. For example, some precursors including a carboxylic acid (COOH) group can co-polymerize with other precursors to form a bead that also includes a COOH functional group. In some embodiments, acrylic acid (a species including free COOH groups), acrylamide, and bis(acryloyl)cystamine can be co-polymerized together to generate a bead including free COOH groups. The COOH groups of the bead can be activated (e.g., via 1-Ethyl-3-(3-dimethylaminopropyl)carbodiimide (EDC) and N-Hydroxysuccinimide (NHS) or 4-(4,6-Dimethoxy-1,3,5-triazin-2-yl)-4-methylmorpholinium chloride (DMTMM)) such that they are reactive (e.g., reactive to amine functional groups where EDC/NHS or DMTMM are used for activation). The activated COOH groups can then react with an appropriate species (e.g., a species including an amine functional group where the carboxylic acid groups are activated to be reactive with an amine functional group) as a functional group on a moiety to be linked to the bead.

Beads including disulfide linkages in their polymeric network can be functionalized with additional species (e.g., disulfide linkers, primers, other oligonucleotides, etc.) via reduction of some of the disulfide linkages to free thiols. The disulfide linkages can be reduced via, for example, the action of a reducing agent (e.g., DTT, TCEP, etc.) to generate free thiol groups, without dissolution of the bead. Free thiols of the beads can then react with free thiols of a species or a species including another disulfide bond (e.g., via thiol-disulfide exchange) such that the species can be linked to the beads (e.g., via a generated disulfide bond). In some embodiments, free thiols of the beads can react with any other suitable group. For example, free thiols of the beads can react with species including an acrydite moiety. The free thiol groups of the beads can react with the acrydite via Michael addition chemistry, such that the species including the acrydite is linked to the bead. In some embodiments, uncontrolled reactions can be prevented by inclusion of a thiol capping agent such as N-ethylmalieamide or iodoacetate.

Activation of disulfide linkages within a bead can be controlled such that only a small number of disulfide linkages are activated. Control can be exerted, for example, by controlling the concentration of a reducing agent used to generate free thiol groups and/or concentration of reagents used to form disulfide bonds in bead polymerization. In some embodiments, a low concentration of reducing agent (e.g., molecules of reducing agent:gel bead ratios) of less than or equal to about 1:100,000,000,000, less than or equal to about 1:10,000,000,000, less than or equal to about 1:1,000,000,000, less than or equal to about 1:100,000,000, less than or equal to about 1:10,000,000, less than or equal to about 1:1,000,000, less than or equal to about 1:100,000, or less than or equal to about 1:10,000) can be used for reduction. Controlling the number of disulfide linkages that are reduced to free thiols can be useful in ensuring bead structural integrity during functionalization. In some embodiments, optically-active agents, such as fluorescent dyes can be coupled to beads via free thiol groups of the beads and used to quantify the number of free thiols present in a bead and/or track a bead.

In some embodiments, addition of moieties to a bead after bead formation can be advantageous. For example, addition of a capture probe after bead formation can avoid loss of the species (e.g., disulfide linkers, primers, other oligonucleotides, etc.) during chain transfer termination that can occur during polymerization. In some embodiments, smaller precursors (e.g., monomers or cross linkers that do not include side chain groups and linked moieties) can be used for polymerization and can be minimally hindered from growing chain ends due to viscous effects. In some embodiments, functionalization after bead synthesis can minimize exposure of species (e.g., oligonucleotides) to be loaded with potentially damaging agents (e.g., free radicals) and/or chemical environments. In some embodiments, the generated hydrogel can possess an upper critical solution temperature (UCST) that can permit temperature driven swelling and collapse of a bead. Such functionality can aid in oligonucleotide (e.g., a primer) infiltration into the bead during subsequent functionalization of the bead with the oligonucleotide. Post-production functionalization can also be useful in controlling loading ratios of species in beads, such that, for example, the variability in loading ratio is minimized. Species loading can also be performed in a batch process such that a plurality of beads can be functionalized with the species in a single batch.

Reagents can be encapsulated in beads during bead generation (e.g., during polymerization of precursors). Such reagents can or cannot participate in polymerization. Such reagents can be entered into polymerization reaction mixtures such that generated beads include the reagents upon bead formation. In some embodiments, such reagents can be added to the beads after formation. Such reagents can include, for example, capture probes (e.g., oligonucleotides), reagents for a nucleic acid amplification reaction (e.g., primers, polymerases, dNTPs, co-factors (e.g., ionic co-factors), buffers) including those described herein, reagents for enzymatic reactions (e.g., enzymes, co-factors, substrates, buffers), reagents for nucleic acid modification reactions such as polymerization, ligation, or digestion, and/or reagents for template preparation (e.g., tagmentation) for one or more sequencing platforms (e.g., Nextera® for Illumina®). Such reagents can include one or more enzymes described herein, including without limitation, polymerase, reverse transcriptase, restriction enzymes (e.g., endonuclease), transposase, ligase, proteinase K, DNAse, etc. Such reagents can also or alternatively include one or more reagents such as lysis agents, inhibitors, inactivating agents, chelating agents, stimulus agents. Trapping of such reagents can be controlled by the polymer network density generated during polymerization of precursors, control of ionic charge within the bead (e.g., via ionic species linked to polymerized species), or by the release of other species. Encapsulated reagents can be released from a bead upon bead degradation and/or by application of a stimulus capable of releasing the reagents from the bead.

In some embodiments, the beads can also include (e.g., encapsulate or have attached thereto) a plurality of capture probes that include spatial barcodes, and the optical properties of the spatial barcodes can be used for optical detection of the beads. For example, the absorbance of light by the spatial barcodes can be used to distinguish the beads from one another. In some embodiments, a detectable label can directly or indirectly attach to a spatial barcode and provide optical detection of the bead. In some embodiments, each bead in a group of one or more beads has a unique detectable label, and detection of the unique detectable label determines the location of the spatial barcode sequence associated with the bead.

Optical properties giving rise to optical detection of beads can be due to optical properties of the bead surface (e.g., a detectable label attached to the bead or the size of the bead), or optical properties from the bulk region of the bead (e.g., a detectable label incorporated during bead formation or an optical property of the bead itself). In some embodiments, a detectable label can be associated with a bead or one or more moieties coupled to the bead.

In some embodiments, the beads include a plurality of detectable labels. For example, a fluorescent dye can be attached to the surface of the beads and/or can be incorporated into the beads. Different intensities of the different fluorescent dyes can be used to increase the number of optical combinations that can be used to differentiate between beads. For example, if N is the number of fluorescent dyes (e.g., between 2 and 10 fluorescent dyes, such as 4 fluorescent dyes) and M is the possible intensities for the dyes (e.g., between 2 and 50 intensities, such as 20 intensities), then $M^N$ are the possible distinct optical combinations. In one example, 4 fluorescent dyes with 20 possible intensities can be used to generate 160,000 distinct optical combinations.

One or more optical properties of the beads or biological contents, such as cells or nuclei, can be used to distinguish the individual beads or biological contents from other beads or biological contents. In some embodiments, the beads are made optically detectable by including a detectable label having optical properties to distinguish the beads from one another.

In some embodiments, optical properties of the beads can be used for optical detection of the beads. For example, without limitation, optical properties can include absorbance, birefringence, color, fluorescence, luminosity, photosensitivity, reflectivity, refractive index, scattering, or transmittance. For example, beads can have different birefringence values based on degree of polymerization, chain length, or monomer chemistry.

In some embodiments, nanobeads, such as quantum dots or Janus beads, can be used as optical labels or components thereof. For example, a quantum dot can be attached to a spatial barcode of a bead.

Optical labels of beads can provide enhanced spectral resolution to distinguish between beads with unique spatial barcodes (e.g., beads including unique spatial barcode sequences). In some embodiments, a first bead includes a first optical label and spatial barcodes each having a first spatial barcode sequence. A second bead includes a second optical label and spatial barcodes each having a second spatial barcode sequence. The first optical label and second optical label can be different (e.g., provided by two different fluorescent dyes or the same fluorescent dye at two different intensities). The first and second spatial barcode sequences can be different nucleic acid sequences. In some embodiments, the beads can be imaged to identify the first and second optical labels, and the first and second optical barcodes can then be used to associate the first and second optical labels with the first and second spatial barcode sequences, respectively.

Optical labels can be included while generating the beads. For example, optical labels can be included in the polymer structure of a gel bead, or attached at the pre-polymer or monomer stage in bead production. In some embodiments, the beads include moieties that attach to one or more optical labels (e.g., at a surface of a bead and/or within a bead). In some embodiments, optical labels can be loaded into the beads with one or more reagents. For example, reagents and optical labels can be loaded into the beads by diffusion of the reagents (e.g., a solution of reagents including the optical barcodes). In some embodiments, optical labels can be included while preparing spatial barcodes. For example, spatial barcodes can be prepared by synthesizing molecules including barcode sequences (e.g., using a split pool or combinatorial approach). Optical labels can be attached to spatial barcodes prior to attaching the spatial barcodes to a bead. In some embodiments, optical labels can be included after attaching spatial barcodes to a bead. For example, optical labels can be attached to spatial barcodes coupled to the bead. In some embodiments, spatial barcodes or sequences thereof can be releasably or cleavably attached to the bead. Optical labels can be releasably or non-releasably attached to the bead. In some embodiments, a first bead (e.g., a bead including a plurality of spatial barcodes) can be coupled to a second bead including one or more optical labels. For example, the first bead can be covalently coupled to the second bead via a chemical bond. In some embodiments, the first bead can be non-covalently associated with the second bead.

The first and/or second bead can include a plurality of spatial barcodes. The plurality of spatial barcodes coupled to a given bead can include the same barcode sequences. Where both the first and second beads include spatial barcodes, the first and second beads can include spatial barcodes including the same barcode sequences or different barcode sequences.

Bead arrays containing captured analytes can be processed in bulk or partitioned into droplet emulsions for preparing sequencing libraries. In some embodiments, next generation sequencing reads are clustered and correlated to the spatial position of the spatial barcode on the bead array. For example, the information can be computationally superimposed over a high-resolution image of the tissue section to identify the location(s), where the analytes were detected.

In some embodiments, de-cross linking can be performed to account for de-crosslinking chemistries that may be incompatible with certain barcoding/library prep biochemistry (e.g., presence of proteases). For example, a two-step process is possible. In the first step, beads can be provided in droplets such that DNA binds to the beads after the conventional de-crosslinking chemistry is performed. In the second step, the emulsion is broken and beads collected and then re-encapsulated after washing for further processing.

In some embodiments, beads can be affixed or attached to a substrate using photochemical methods. For example, a bead can be functionalized with perfluorophenylazide silane (PFPA silane), contacted with a substrate, and then exposed to irradiation (see, e.g., Liu et al. (2006) Journal of the American Chemical Society 128, 14067-14072). For example, immobilization of antraquinone-functionalized substrates (see, e.g., Koch et al. (2000) Bioconjugate Chem. 11, 474-483, the entire contents of which are herein incorporated by reference).

The arrays can also be prepared by bead self-assembly. Each bead can be covered with hundreds of thousands of copies of a specific oligonucleotide. In some embodiments, each bead can be covered with about 1,000 to about 1,000,000 oligonucleotides. In some embodiments, each bead can be covered with about 1,000,000 to about 10,000,000 oligonucleotides. In some embodiments, each bead can covered with about 2,000,000 to about 3,000,000, about 3,000,000 to about 4,000,000, about 4,000,000 to about 5,000,000, about 5,000,000 to about 6,000,000, about 6,000,000 to about 7,000,000, about 7,000,000 to about 8,000,000, about 8,000,000 to about 9,000,000, or about 9,000,000 to about 10,000,000 oligonucleotides. In some embodiments, each bead can be covered with about 10,000,000 to about 100,000,000 oligonucleotides. In some embodiments, each bead can be covered with about 100,000,000 to about 1,000,000,000 oligonucleotides. In some embodiments, each bead can be covered with about 1,000,000,000 to about 10,000,000,000 oligonucleotides. The beads can be irregularly distributed across etched substrates during the array production process. During this process, the beads can be self-assembled into arrays (e.g., on a fiber-optic bundle substrate or a silica slide substrate). In some embodiments, the beads irregularly arrive at their final location on the array. Thus, the bead location may need to be mapped or the oligonucleotides may need to be synthesized based on a predetermined pattern.

Beads can be affixed or attached to a substrate covalently, non-covalently, with adhesive, or a combination thereof. The attached beads can be, for example, layered in a monolayer, a bilayer, a trilayer, or as a cluster. As defined herein, a "monolayer" generally refers to an arrayed series of probes, beads, spots, dots, features, micro-locations, or islands that are affixed or attached to a substrate, such that the beads are arranged as one layer of single beads. In some embodiments, the beads are closely packed.

As defined herein, the phrase "substantial monolayer" or "substantially form(s) a monolayer" generally refers to (the formation of) an arrayed series of probes, beads, microspheres, spots, dots, features, micro-locations, or islands that are affixed or attached to a substrate, such that about 50% to about 99% (e.g., about 50% to about 98%) of the beads are arranged as one layer of single beads. This arrangement can be determined using a variety of methods, including microscopic imaging.

In some embodiments, the monolayer of beads is a located in a predefined area on the substrate. For example, the predefined area can be partitioned with physical barriers, a photomask, divots in the substrate, or wells in the substrate.

As used herein, the term "reactive element" generally refers to a molecule or molecular moiety that can react with another molecule or molecular moiety to form a covalent bond. Reactive elements include, for example, amines, aldehydes, alkynes, azides, thiols, haloacetyls, pyridyl disulfides, hydrazides, carboxylic acids, alkoxyamines, sulfhydryls, maleimides, Michael acceptors, hydroxyls, and active esters. Some reactive elements, for example, carboxylic acids, can be treated with one or more activating agents (e.g., acylating agents, isourea-forming agents) to increase susceptibility of the reactive element to nucleophilic attack. Non-limiting examples of activating agents include N-hydroxysuccinimide, N-hydroxysulfosuccinimide, 1-ethyl-3-(3-dimethylaminopropyl)carbodiimide, dicyclohexylcarbodiimide, diisopropylcarbodiimide, 1-hydroxybenzotriazole, (benzotriazol-1-yloxy)tripyrrolidinophosphonium hexfluorophosphate, (benzotriazol-1-yl)-N,N,N',N'-tetramethyluronium hexafluorophosphate, 4-(N,N-dimethylamino)pyridine, and carbonyldiimidazole.

In some embodiments, the reactive element is bound directly to a bead. For example, hydrogel beads can be treated with an acrylic acid monomer to form acrylic acid-functionalized hydrogel beads. In some cases, the reactive element is bound indirectly to the bead via one or more linkers. As used herein, a "linker" generally refers to a multifunctional (e.g., bifunctional, trifunctional) reagent used for conjugating two or more chemical moieties. A linker can be a cleavable linker that can undergo induced dissociation. For example, the dissociation can be induced by a solvent (e.g., hydrolysis and solvolysis); by irradiation (e.g., photolysis); by an enzyme (e.g., enzymolysis); or by treatment with a solution of specific pH (e.g., pH 4, 5, 6, 7, or 8).

In some embodiments, the reactive element is bound directly to a substrate. For example, a glass slide can be coated with (3-aminopropyl)triethoxysilane. In some embodiments, the reactive element is bound indirectly to a substrate via one or more linkers.

Methods for Covalently Bonding Beads to a Substrate

Provided herein are methods for the covalent bonding of beads (e.g., optically labeled beads, hydrogel beads, microsphere beads) to a substrate.

In some embodiments, the beads are coupled to a substrate via a covalent bond between a first reactive element and a second reactive element. In some embodiments, the covalently-bound beads substantially form a monolayer of beads (e.g., hydrogel beads, microsphere beads) on the substrate.

In some embodiments, the beads are functionalized with a first reactive element, which is directly bound to the beads. In some embodiments, the beads are functionalized with a first reactive element, which is indirectly bound to the beads via a linker. In some embodiments, the linker is a benzophenone. In some embodiments, the linker is an amino methacrylamide. For example, the linker can be 3-aminopropyl methacrylamide. In some embodiments, the linker is a PEG linker. In some embodiments, the linker is a cleavable linker.

In some embodiments, the substrate is functionalized with a second reactive element, which is directly bound to the substrate. In some embodiments, the substrate is functionalized with a second reactive element, which is indirectly bound to the beads via a linker. In some embodiments, the linker is a benzophenone. For example, the linker can be benzophenone. In some embodiments, the linker is an amino methacrylamide. For example, the linker can be 3-aminopropyl methacrylamide. In some embodiments, the linker is a PEG linker. In some embodiments, the linker is a cleavable linker.

In some embodiments, the substrate is a glass slide. In some embodiments, the substrate is a pre-functionalized glass slide.

In some embodiments, about 99% of the covalently-bound beads form a monolayer of beads on the substrate. In some embodiments, about 50% to about 98% form a monolayer of beads on the substrate. For example, about 50% to about 95%, about 50% to about 90%, about 50% to about 85%, about 50% to about 80%, about 50% to about 75%, about 50% to about 70%, about 50% to about 65%, about 50% to about 60%, or about 50% to about 55% of the covalently-bound beads form a monolayer of beads on the substrate. In some embodiments, about 55% to about 98%, about 60% to about 98%, about 65% to about 98%, about 70% to about 98%, about 75% to about 98%, about 80% to about 98%, about 85% to about 98%, about 90% to about 95%, or about 95% to about 98% of the covalently-bound beads form a monolayer of beads on the substrate. In some embodiments, about 55% to about 95%, about 60% to about 90%, about 65% to about 95%, about 70% to about 95%, about 75% to about 90%, about 75% to about 95%, about 80% to about 90%, about 80% to about 95%, about 85% to about 90%, or about 85% to about 95% of the covalently-bound beads for a monolayer of beads on the substrate.

In some embodiments, at least one of the first reactive element and the second reactive element is selected from the group consisting of:

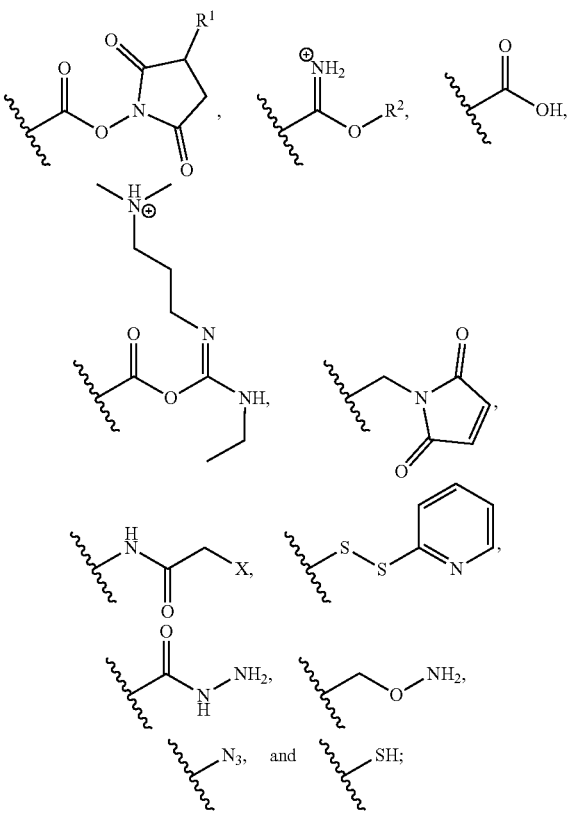

wherein
$R^1$ is selected from H, $C_1$-$C_6$ alkyl, or —$SO_3$;
$R^2$ is $C_1$-$C_6$ alkyl; and
X is a halo moiety.

In some embodiments, at least one of the first reactive element or the second reactive element comprises

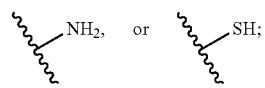

wherein the ⁓ indicates the point of attachment of the first reactive element or the second reactive element to the bead (e.g., hydrogel bead or microsphere bead) or to the substrate.

In some embodiments, at least one of the first reactive element or the second reactive element is selected from the group consisting of:

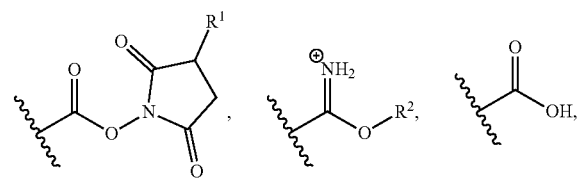

-continued

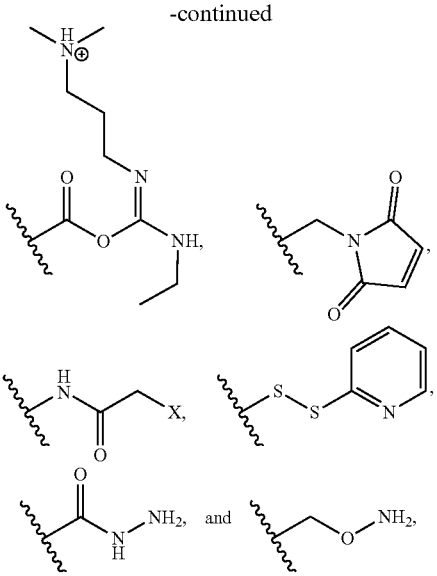

wherein $R^1$ is selected from H, $C_1$-$C_6$ alkyl, or —$SO_3$;

$R^2$ is $C_1$-$C_6$ alkyl; and

X is a halo moiety.

In some embodiments, at least one of the first reactive element or the second reactive element comprises

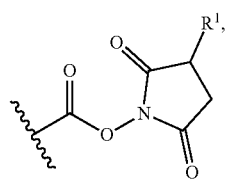

wherein $R^1$ is selected from H, $C_1$-$C_6$ alkyl, or —$SO_3$. In some embodiments, $R^1$ is H. In some embodiments, $R^1$ is $C_1$-$C_6$ alkyl. In some embodiments, $R^1$ is —$SO_3$.

In some embodiments, at least one of the first reactive element or the second reactive element comprises

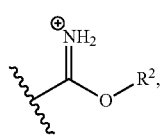

wherein $R^2$ is $C_1$-$C_6$ alkyl. In some embodiments, $R^2$ is methyl.

In some embodiments, at least one of the first reactive element or the second reactive element comprises

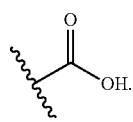

Is some embodiments,

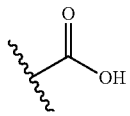 [SMILES: *C(=O)O]

can be reacted with an activating agent to form an active ester. In some embodiments, the active ester is

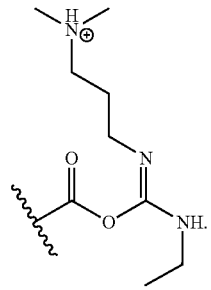

In some embodiments, the activating agent is an acylating agent (e.g., N-hydroxysuccinimide and N-hydroxysulfosuccinimide). In some embodiments, the activating agent is an O-acylisourea-forming agent (e.g., 1-ethyl-3-(3-dimethylaminopropyl)carbodiimide (EDC), dicyclohexylcarbodiimide, and diisopropylcarbodiimide). In some embodiments, the activating agent is a combination of at least one acylating agent and at least one O-isourea-forming agents (e.g., N-hydroxysuccinimide (NHS), 1-ethyl-3-(3-dimethylaminopropyl)carbodiimide (EDC), N-hydroxysulfosuccinimide (sulfo-NHS), and a combination thereof).

In some embodiments, at least one of the first reactive element or the second reactive element comprise

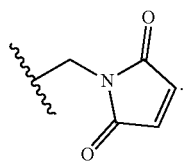 [SMILES: *CN1C(=O)C=CC1=O]

In some embodiments, at least one of the first reactive element or the second reactive element comprises

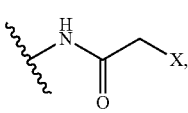

wherein X is a halo moiety. For example, X is chloro, bromo, or iodo.

In some embodiments, at least one of the first reactive element or the second reactive element comprises

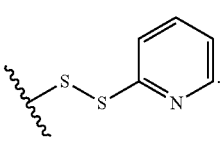

In some embodiments, at least one of the first reactive element or the second reactive element comprises

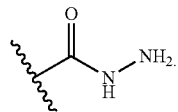

In some embodiments, at least one of the first reactive element or the second reactive element comprises

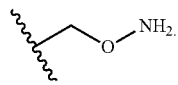

In some embodiments, at least one of the first reactive element or the second reactive element is selected from the group consisting of:

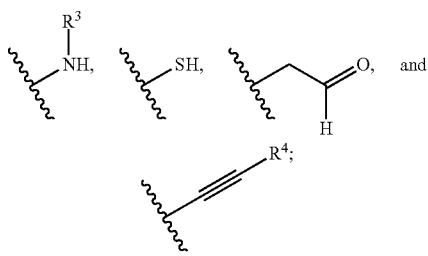

wherein
$R^3$ is H or $C_1$-$C_6$ alkyl; and
$R^4$ is H or trimethylsilyl.

In some embodiments, at least one of the first reactive element or the second reactive element comprises

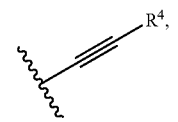

wherein $R^4$ is H or trimethylsilyl. In some embodiments, $R^4$ is H.

In some embodiments, at least one of the first reactive element or the second reactive element is selected from the group consisting of:

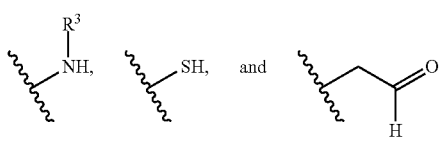

wherein $R^3$ is H or $C_1$-$C_6$ alkyl. In some embodiments, $R^3$ is H. In some embodiments, $R^3$ is $C_1$-$C_6$ alkyl.

In some embodiments, at least one of the first reactive element or the second reactive element comprises

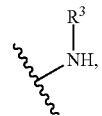

wherein $R^3$ is H or $C_1$-$C_6$ alkyl. In some embodiments, $R^3$ is H. In some embodiments, $R^3$ is $C_1$-$C_6$ alkyl.

In some embodiments, at least one of the first reactive elements or the second reactive elements comprises

In some embodiments, at least one of the first reactive elements or the second reactive elements comprises

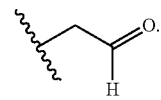 [SMILES: *CC=O]

In some embodiments, one of the first reactive elements or the second reactive elements is selected from the group consisting of:

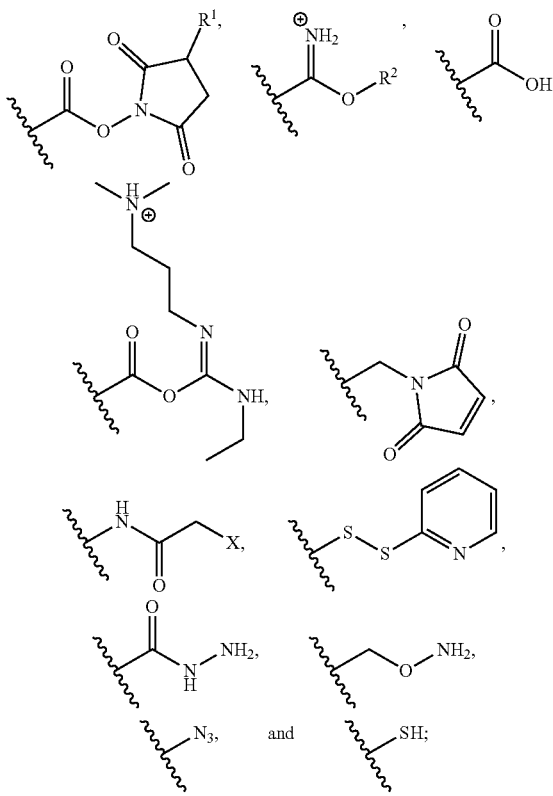

wherein
$R^1$ is selected from H, $C_1$-$C_6$ alkyl, or —$SO_3$;
$R^2$ is $C_1$-$C_6$ alkyl;
X is a halo moiety;

and the other of the first reactive element or the second reactive element is selected from the group consisting of:

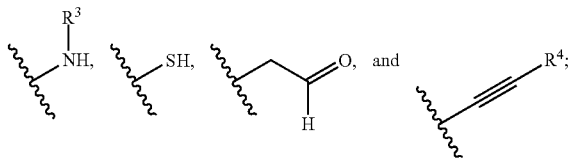

wherein
$R^3$ is H or $C_1$-$C_6$ alkyl; and
$R^4$ is H or trimethylsilyl.

In some embodiments, one of the first reactive elements or the second reactive elements is selected from the group consisting of

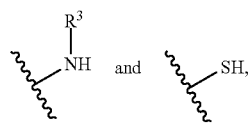

wherein $R^3$ is H or $C_1$-$C_6$ alkyl; and the other of the first reactive element or the second reactive element is

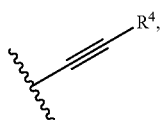

wherein $R^4$ is H or trimethylsilyl. In some embodiments, $R^3$ is H. In some embodiments, $R^3$ is $C_1$-$C_6$ alkyl. In some embodiments, $R^4$ is H. In some embodiments, $R^4$ is trimethylsilyl.

In some embodiments, one of the first reactive element or the second reactive element is selected from the group consisting of:

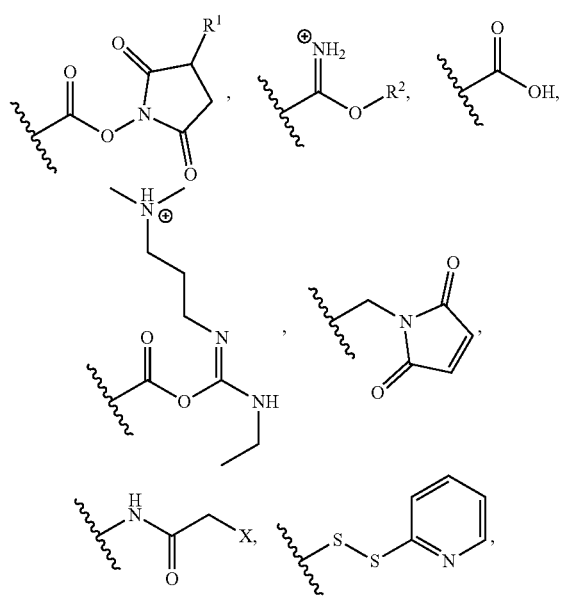

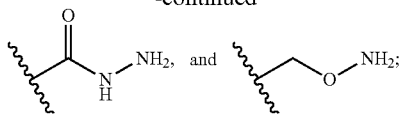

wherein
$R^1$ is selected from H, $C_1$-$C_6$ alkyl, or —$SO_3$;
$R^2$ is $C_1$-$C_6$ alkyl;
X is a halo moiety;
and the other of the first reactive element or the second reactive element is selected from the group consisting of:

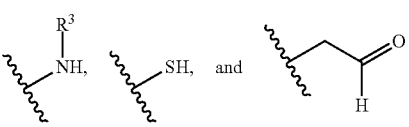

wherein $R^3$ is H or $C_1$-$C_6$ alkyl. In some embodiments, $R^1$ is H. In some embodiments, $R^1$ is $C_1$-$C_6$alkyl. In some embodiments, $R^1$ is —$SO_3$. In some embodiments, $R^2$ is methyl. In some embodiments, X is iodo. In some embodiments, $R^3$ is H. In some embodiments, $R^3$ is $C_1$-$C_6$ alkyl.

In some embodiments, one of the first reactive elements or the second reactive elements is selected from the group consisting of:

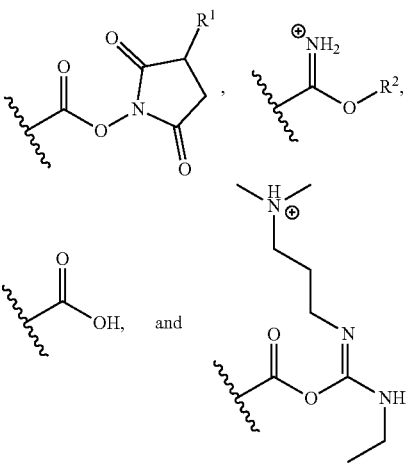

wherein
$R^1$ is selected from H, $C_1$-$C_6$ alkyl, or —$SO_3$;
$R^2$ is $C_1$-$C_6$ alkyl;
and the other of the first reactive elements or the second reactive elements comprises

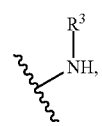

wherein $R^3$ is H or $C_1$-$C_6$ alkyl. In some embodiments, $R^1$ is H. In some embodiments, $R^1$ is $C_1$-$C_6$alkyl. In some embodiments, $R^1$ is —$SO_3$. In some embodiments, $R^2$ is methyl. In some embodiments, $R^3$ is H. In some embodiments, $R^3$ is $C_1$-$C_6$ alkyl.

In some embodiments, one of the first reactive element or the second reactive element is selected from the group consisting of:

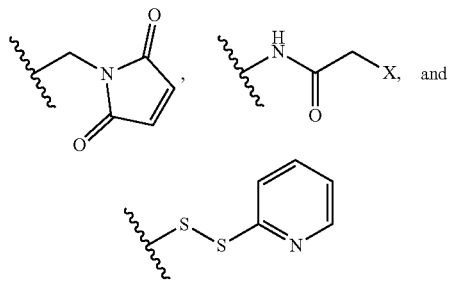

wherein X is a halo moiety;
and the other of the first reactive element or the second reactive element comprises

In some embodiments, X is bromo. In some embodiments, X is iodo.

In some embodiments, one of the first reactive element or the second reactive element is selected from the group consisting of

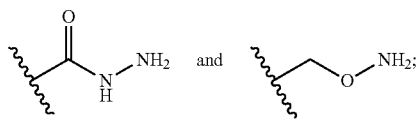

and the other of the first reactive element or the second reactive element comprises

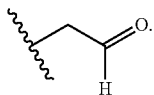 [SMILES: *CC=O]

The term "halo" refers to fluoro (F), chloro (Cl), bromo (Br), or iodo (I).

The term "alkyl" refers to a hydrocarbon chain that may be a straight chain or branched chain, containing the indicated number of carbon atoms. For example, $C_{1-10}$ indicates that the group may have from 1 to 10 (inclusive) carbon atoms in it. Non-limiting examples include methyl, ethyl, iso-propyl, tert-butyl, n-hexyl.

The term "haloalkyl" refers to an alkyl, in which one or more hydrogen atoms is/are replaced with an independently selected halo.

The term "alkoxy" refers to an —O-alkyl radical (e.g., —OCH$_3$).

The term "alkylene" refers to a divalent alkyl (e.g., —CH$_2$—).

The term "alkenyl" refers to a hydrocarbon chain that may be a straight chain or branched chain having one or more carbon-carbon double bonds. The alkenyl moiety contains the indicated number of carbon atoms. For example, $C_{2-6}$ indicates that the group may have from 2 to 6 (inclusive) carbon atoms in it.

The term "alkynyl" refers to a hydrocarbon chain that may be a straight chain or branched chain having one or more carbon-carbon triple bonds. The alkynyl moiety contains the indicated number of carbon atoms. For example, $C_{2-6}$ indicates that the group may have from 2 to 6 (inclusive) carbon atoms in it.

The term "aryl" refers to a 6-20 carbon mono-, bi-, tri- or polycyclic group wherein at least one ring in the system is aromatic (e.g., 6-carbon monocyclic, 10-carbon bicyclic, or 14-carbon tricyclic aromatic ring system); and wherein 0, 1, 2, 3, or 4 atoms of each ring may be substituted by a substituent. Examples of aryl groups include phenyl, naphthyl, tetrahydronaphthyl, and the like.

Methods for Non-Covalently Bonding Beads to a Substrate

Provided herein are methods for the non-covalent bonding of beads (e.g., optically-labeled beads, hydrogel beads, or microsphere beads) to a substrate.

In some embodiments, beads are coupled to a substrate via a non-covalent bond between a first affinity group and a second affinity group. In some embodiments, the non-covalently-bound beads substantially form a monolayer of beads (e.g., hydrogel beads, microsphere beads) on the substrate.

In some embodiments, the beads are functionalized with a first affinity group, which is directly bound to the beads. In some embodiments, the beads are functionalized with a first affinity group, which is indirectly bound to the beads via a linker. In some embodiments, the linker is a benzophenone. In some embodiments, the linker is an amino methacrylamide. For example, the linker can be 3-aminopropyl methacrylamide. In some embodiments, the linker is a PEG linker. In some embodiments, the linker is a cleavable linker.

In some embodiments, the substrate is functionalized with a second affinity group, which is directly bound to the substrate. In some embodiments, the substrate is functionalized with a second affinity group, which is indirectly bound to the beads via a linker. In some embodiments, the linker is a benzophenone. In some embodiments, the linker is an amino methacrylamide. For example, the linker can be 3-aminopropyl methacrylamide. In some embodiments, the linker is a PEG linker. In some embodiments, the linker is a cleavable linker.

In some embodiments the first affinity group or the second affinity group is biotin, and the other of the first affinity group or the second affinity group is streptavidin.

In some embodiments, about 99% of the non-covalently-bound beads form a monolayer of beads on the substrate. In some embodiments, about 50% to about 98% form a monolayer of beads on the substrate. For example, about 50% to about 95%, about 50% to about 90%, about 50% to about 85%, about 50% to about 80%, about 50% to about 75%, about 50% to about 70%, about 50% to about 65%, about 50% to about 60%, or about 50% to about 55% of the non-covalently-bound beads form a monolayer of beads on the substrate. In some embodiments, about 55% to about 98%, about 60% to about 98%, about 65% to about 98%, about 70% to about 98%, about 75% to about 98%, about 80% to about 98%, about 85% to about 98%, about 90% to about 95%, or about 95% to about 98% of the non-covalently-bound beads form a monolayer of beads on the substrate. In some embodiments, about 55% to about 95%, about 60% to about 90%, about 65% to about 95%, about 70% to about 95%, about 75% to about 90%, about 75% to about 95%, about 80% to about 90%, about 80% to about 95%, about 85% to about 90%, or about 85% to about 95% of the non-covalently-bound beads for a monolayer of beads on the substrate.

In some embodiments, the monolayer of beads is a formed in a predefined area on the substrate. In some embodiments, the predefined area is partitioned with physical barriers. For example, divots or wells in the substrate. In some embodiments, the predefined area is partitioned using a photomask. For example, the substrate is coated with a photo-activated solution, dried, then irradiated under a photomask. In some embodiments, the photo-activated solution is UV-activated.

As used herein, an "adhesive" generally refers to a substance used for sticking objects or materials together. Adhesives include, for example, glues, pastes, liquid tapes, epoxy, bioadhesives, gels, and mucilage. In some embodiments, an adhesive is liquid tape. In some embodiments, the adhesive is glue.

In some embodiments, beads are adhered to a substrate using an adhesive (e.g., liquid tape, glue, paste). In some embodiments, the adhered beads substantially form a monolayer of beads on the substrate (e.g., a glass slide). In some embodiments, the beads are hydrogel beads. In some embodiments, the beads are microsphere beads. In some embodiments, the beads are coated with the adhesive, and then the beads are contacted with the substrate. In some embodiments, the substrate is coated with the adhesive, and then the substrate is contacted with the beads. In some embodiments, both the substrate is coated with the adhesive and the beads are coated with the adhesive, and then the beads and substrate are contacted with one another.

In some embodiments, about 99% of the adhered beads form a monolayer of beads on the substrate. In some embodiments, about 50% to about 98% form a monolayer of beads on the substrate. For example, about 50% to about 95%, about 50% to about 90%, about 50% to about 85%, about 50% to about 80%, about 50% to about 75%, about 50% to about 70%, about 50% to about 65%, about 50% to about 60%, or about 50% to about 55% of the adhered beads form a monolayer of beads on the substrate. In some embodiments, about 55% to about 98%, about 60% to about 98%, about 65% to about 98%, about 70% to about 98%, about 75% to about 98%, about 80% to about 98%, about 85% to about 98%, about 90% to about 95%, or about 95% to about 98% of the adhered beads form a monolayer of beads on the substrate. In some embodiments, about 55% to about 95%, about 60% to about 90%, about 65% to about 95%, about 70% to about 95%, about 75% to about 90%, about 75% to about 95%, about 80% to about 90%, about 80% to about 95%, about 85% to about 90%, or about 85% to about 95% of the adhered beads for a monolayer of beads on the substrate.

In some embodiments, beads can be deposited onto a biological sample such that the deposited beads form a monolayer of beads on the biological sample (e.g., over or under the biological sample). In some embodiments, beads deposited on the substrate can self-assemble into a monolayer of beads that saturate the intended surface area of the biological sample under investigation. In this approach, bead arrays can be designed, formulated, and prepared to evaluate a plurality of analytes from a biological sample of any size or dimension. In some embodiments, the concentration or density of beads (e.g., gel beads) applied to the biological sample is such that the area as a whole, or one or more regions of interest in the biological sample, is saturated with a monolayer of beads. In some embodiments, the beads are contacted with the biological sample by pouring, pipetting, spraying, and the like, onto the biological sample. Any suitable form of bead deposition can be used.

In some embodiments, the biological sample can be confined to a specific region or area of the array. For example, a biological sample can be affixed to a glass slide and a chamber, gasket, or cage positioned over the biological sample to act as a containment region or frame within which the beads are deposited. As will be apparent, the density or concentration of beads needed to saturate an area or biological sample can be readily determined by one of ordinary skill in the art (e.g., through microscopic visualization of the beads on the biological sample). In some embodiments, the bead array contains microfluidic channels to direct reagents to the spots or beads of the array.

Feature Geometric Attributes

Features on an array can have a variety of sizes. In some embodiments, a feature of an array can have a diameter or maximum dimension between 1 μm to 100 μm. For example, between 1 μm to 10 μm, 1 μm to 20 μm, 1 μm to 30 μm, 1 μm to 40 μm, 1 μm to 50 μm, 1 μm to 60 μm, 1 μm to 70 μm, 1 μm to 80 μm, 1 μm to 90 μm, 90 μm to 100 μm, 80 μm to 100 μm, 70 μm to 100 μm, 60 μm to 100 μm, 50 μm to 100 μm, 40 μm to 100 μm, 30 μm to 100 μm, 20 m to 100 μm, or 10 μm to 100 μm. In some embodiments, the feature has a diameter or maximum dimension between 30 μm to 100 μm, 40 μm to 90 μm, 50 μm to 80 μm, 60 μm to 70 μm, or any range within the disclosed sub-ranges. In some embodiments, the feature has a diameter or maximum dimension no larger than 95 μm, 90 μm, 85 μm, 80 μm, 75 μm, 70 μm, 65 μm, 60 μm, 55 μm, 50 μm, 45 μm, 40 μm, 35 μm, 30 μm, 25 μm, 20 μm, 15 μm, 14 μm, 13 μm, 12 μm, 11 μm, 10 μm, 9 μm, 8 μm, 7 μm, 6 μm, 5 μm, 4 μm, 3 μm, 2 μm, or 1 μm. In some embodiments, the feature has a diameter or maximum dimension of approximately 65 μm.

In some embodiments, the size and/or shape of a plurality of features of an array are approximately uniform. In some embodiments, the size and/or shape of a plurality of features of an array is not uniform. For example, in some embodiments, features in an array can have an average cross-sectional dimension, and a distribution of cross-sectional dimensions among the features can have a full-width and half-maximum value of 0% or more (e.g., 5% or more, 10% or more, 20% or more, 30% or more, 40% or more, 50% or more, 70% or more, or 100% or more) of the average cross-sectional dimension for the distribution.

In certain embodiments, features in an array can have an average cross-sectional dimension of between about 1 μm and about 10 μm. This range in average feature cross-sectional dimension corresponds to the approximate diameter of a single mammalian cell. Thus, an array of such features can be used to detect analytes at, or below, mammalian single-cell resolution.

In some embodiments, a plurality of features has a mean diameter or mean maximum dimension of about 0.1 μm to about 100 μm (e.g., about 0.1 μm to about 5 μm, about 1 μm to about 10 μm, about 1 μm to about 20 μm, about 1 μm to about 30 μm, about 1 μm to about 40 μm, about 1 μm to about 50 μm, about 1 μm to about 60 μm, about 1 μm to about 70 μm, about 1 μm to about 80 μm, about 1 μm to about 90 μm, about 90 μm to about 100 μm, about 80 μm to about 100 μm, about 70 μm to about 100 μm, about 60 μm to about 100 μm, about 50 μm to about 100 μm, about 40 μm to about 100 μm, about 30 μm to about 100 μm, about 20 μm to about 100 μm, or about 10 μm to about 100 μm). In some embodiments, the plurality of features has a mean diameter or mean maximum dimension between 30 μm to 100 μm, 40 μm to 90 μm, 50 μm to 80 μm, 60 μm to 70 μm, or any range within the disclosed sub-ranges. In some embodiments, the plurality of features has a mean diameter or a mean maximum dimension no larger than 95 µm, 90 µm, 85 µm, 80 µm, 75 µm, 70 µm, 65 µm, 60 µm, 55 µm, 50 µm, 45 µm, m, 35 µm, 30 µm, 25 µm, 20 µm, 15 µm, 14 µm, 13 µm, 12 µm, 11 µm, 10 µm, 9 µm, 8 µm, 7 µm, 6 µm, 5 µm, 4 µm, 3 µm, 2 µm, or 1 µm. In some embodiments, the plurality of features has a mean average diameter or a mean maximum dimension of approximately 65 µm.

In some embodiments, where the feature is a bead, the bead can have a diameter or maximum dimension no larger than 100 µm (e.g., no larger than 95 µm, 90 µm, 85 µm, 80 µm, 75 µm, 70 µm, 65 µm, 60 µm, 55 µm, 50 µm, 45 µm, 40 µm, 35 µm, 30 µm, 25 µm, 20 µm, 15 µm, 14 µm, 13 µm, 12 µm, 11 µm, 10 µm, 9 µm, 8 µm, 7 µm, 6 µm, 5 µm, 4 µm, 3 µm, 2 µm, or 1 µm).

In some embodiments, a plurality of beads has an average diameter no larger than 100 µm. In some embodiments, a plurality of beads has an average diameter or maximum dimension no larger than 95 µm, 90 µm, 85 µm, 80 µm, 75 µm, 70 µm, 65 µm, 60 µm, 55 µm, 50 µm, 45 µm, 40 µm, 35 µm, 30 µm, 25 µm, 20 µm, 15 µm, 14 µm, 13 µm, 12 µm, 11 µm, 10 µm, 9 µm, 8 µm, 7 µm, 6 µm, 5 µm, 4 µm, 3 µm, 2 µm, or 1 µm.

In some embodiments, the volume of the bead can be at least about 1 $\mu m^3$, e.g., at least 1 $\mu m^3$, 2 $\mu m^3$, 3 $\mu m^3$, 4 $\mu m^3$, 5 $\mu m^3$, 6 $\mu m^3$, 7 $\mu m^3$, 8 $\mu m^3$, 9 $\mu m^3$, 10 $\mu m^3$, 12 $\mu m^3$, 14 $\mu m^3$, 16 $\mu m^3$, 18 $\mu m^3$, 20 $\mu m^3$, 25 $\mu m^3$, 30 $\mu m^3$, 35 $\mu m^3$, 40 $\mu m^3$, 45 $\mu m^3$, 50 $\mu m^3$, 55 $\mu m^3$, 60 $\mu m^3$, 65 $\mu m^3$, 70 $\mu m^3$, 75 $\mu m^3$, 80 $\mu m^3$, 85 $\mu m^3$, 90 $\mu m^3$, 95 $\mu m^3$, 100 $\mu m^3$, 125 $\mu m^3$, 150 $\mu m^3$, 175 $\mu m^3$, 200 $\mu m^3$, 250 $\mu m^3$, 300 $\mu m^3$, 350 $\mu m^3$, 400 $\mu m^3$, 450 $\mu m^3$, $\mu m^3$, 500 $\mu m^3$, 550 $\mu m^3$, 600 $\mu m^3$, 650 $\mu m^3$, 700 $\mu m^3$, 750 $\mu m^3$, 800 $\mu m^3$, 850 $\mu m^3$, 900 $\mu m^3$, 950 $\mu m^3$, 1000 $\mu m^3$, 1200 $\mu m^3$, 1400 $\mu m^3$, 1600 $\mu m^3$, 1800 $\mu m^3$, 2000 $\mu m^3$, 2200 $\mu m^3$, 2400 $\mu m^3$, 2600 $\mu m^3$, 2800 $\mu m^3$, 3000 $\mu m^3$, or greater.

In some embodiments, the bead can have a volume of between about 1 $\mu m^3$ and 100 $\mu m^3$, such as between about 1 $\mu m^3$ and 10 $\mu m^3$, between about 10 $\mu m^3$ and 50 $\mu m^3$, or between about 50 $\mu m^3$ and 100 $\mu m^3$. In some embodiments, the bead can include a volume of between about 100 $\mu m^3$ and 1000 $\mu m^3$, such as between about 100 $\mu m^3$ and 500 $\mu m^3$ or between about 500 $\mu m^3$ and 1000 $\mu m^3$. In some embodiments, the bead can include a volume between about 1000 $\mu m^3$ and 3000 $\mu m^3$, such as between about 1000 $\mu m^3$ and 2000 $\mu m^3$ or between about 2000 $\mu m^3$ and 3000 $\mu m^3$. In some embodiments, the bead can include a volume between about 1 $\mu m^3$ and 3000 $\mu m^3$, such as between about 1 $\mu m^3$ and 2000 $\mu m^3$, between about 1 $\mu m^3$ and 1000 $\mu m^3$, between about 1 $\mu m^3$ and 500 $\mu m^3$, or between about 1 $\mu m^3$ and 250 $\mu m^3$.

The bead can include one or more cross-sections that can be the same or different. In some embodiments, the bead can have a first cross-section that is different from a second cross-section. The bead can have a first cross-section that is at least about 0.0001 micrometer, 0.001 micrometer, 0.01 micrometer, 0.1 micrometer, or 1 micrometer. In some embodiments, the bead can include a cross-section (e.g., a first cross-section) of at least about 1 µmicrometer (µm), 2 µm, 3 µm, 4 µm, 5 µm, 6 µm, 7 µm, 8 µm, 9 µm, 10 µm, 11 µm, 12 µm, 13 µm, 14 µm, 15 µm, 16 µm, 17 µm, 18 µm, 19 µm, 20 µm, 25 µm, 30 µm, 35 µm, 40 µm, 45 µm, 50 µm, 55 µm, 60 µm, 65 µm, 70 µm, 75 µm, 80 µm, 85 µm, 90 µm, 100 µm, 120 µm, 140 µm, 160 µm, 180 µm, 200 µm, 250 µm, 300 µm, 350 µm, 400 µm, 450 µm, 500 µm, 550 µm, 600 µm, 650 µm, 700 µm, 750 µm, 800 µm, 850 µm, 900 µm, 950 µm, 1 µmillimeter (mm), or greater. In some embodiments, the bead can include a cross-section (e.g., a first cross-section) of between about 1 µm and 500 µm, such as between about 1 µm and 100 µm, between about 100 µm and 200 µm, between about 200 µm and 300 µm, between about 300 µm and 400 µm, or between about 400 µm and 500 µm. For example, the bead can include a cross-section (e.g., a first cross-section) of between about 1 µm and 100 µm. In some embodiments, the bead can have a second cross-section that is at least about 1 µm. For example, the bead can include a second cross-section of at least about 1 micrometer (µm), 2 µm, 3 µm, 4 µm, 5 µm, 6 µm, 7 µm, 8 µm, 9 µm, 10 µm, 11 µm, 12 µm, 13 µm, 14 µm, 15 µm, 16 µm, 17 µm, 18 µm, 19 µm, 20 µm, 25 µm, 30 µm, 35 µm, 40 µm, 45 µm, 50 µm, 55 µm, 60 µm, 65 µm, 70 µm, 75 µm, 80 µm, 85 µm, 90 µm, 100 µm, 120 µm, 140 µm, 160 µm, 180 µm, 200 µm, 250 µm, 300 µm, 350 µm, 400 µm, 450 µm, 500 µm, 550 µm, 600 µm, 650 µm, 700 µm, 750 µm, 800 µm, 850 µm, 900 µm, 950 µm, 1 millimeter (mm), or greater. In some embodiments, the bead can include a second cross-section of between about 1 µm and 500 µm, such as between about 1 µm and 100 µm, between about 100 µm and 200 µm, between about 200 µm and 300 µm, between about 300 µm and 400 µm, or between about 400 µm and 500 µm. For example, the bead can include a second cross-section of between about 1 µm and 100 µm.

In some embodiments, beads can be of a nanometer scale (e.g., beads can have a diameter or maximum cross-sectional dimension of about 100 nanometers (nm) to about 900 nanometers (nm) (e.g., 850 nm or less, 800 nm or less, 750 nm or less, 700 nm or less, 650 nm or less, 600 nm or less, 550 nm or less, 500 nm or less, 450 nm or less, 400 nm or less, 350 nm or less, 300 nm or less, 250 nm or less, 200 nm or less, 150 nm or less). A plurality of beads can have an average diameter or average maximum cross-sectional dimension of about 100 nanometers (nm) to about 900 nanometers (nm) (e.g., 850 nm or less, 800 nm or less, 750 nm or less, 700 nm or less, 650 nm or less, 600 nm or less, 550 nm or less, 500 nm or less, 450 nm or less, 400 nm or less, 350 nm or less, 300 nm or less, 250 nm or less, 200 nm or less, 150 nm or less). In some embodiments, a bead has a diameter or size that is about the size of a single cell (e.g., a single cell under evaluation).

Beads can be of uniform size or heterogeneous size. "Polydispersity" generally refers to heterogeneity of sizes of molecules or particles. The polydispersity (PDI) can be calculated using the equation PDI=Mw/Mn, where Mw is the weight-average molar mass and Mn is the number-average molar mass. In certain embodiments, beads can be provided as a population or plurality of beads having a relatively monodisperse size distribution. Where it can be desirable to provide relatively consistent amounts of reagents, maintaining relatively consistent bead characteristics, such as size, can contribute to the overall consistency.

In some embodiments, the beads provided herein can have size distributions that have a coefficient of variation in their cross-sectional dimensions of less than 50%, less than 40%, less than 30%, less than 20%, less than 15%, less than 10%, less than 5%, or lower. In some embodiments, a plurality of beads provided herein has a polydispersity index of less than 50%, less than 45%, less than 40%, less than 35%, less than 30%, less than 25%, less than 20%, less than 15%, less than 10%, less than 5%, or lower.

Array Geometric Attributes

In some embodiments, an array includes a plurality of features. For example, an array includes between 4,000 and 10,000 features, or any range within 4,000 to 6000 features. For example, an array includes between 4,000 to 4,400 features, 4,000 to 4,800 features, 4,000 to 5,200 features, 4,000 to 5,600 features, 5,600 to 6,000 features, 5,200 to 6,000 features, 4,800 to 6,000 features, or 4,400 to 6,000 features. In some embodiments, the array includes between 4,100 and 5,900 features, between 4,200 and 5,800 features, between 4,300 and 5,700 features, between 4,400 and 5,600 features, between 4,500 and 5,500 features, between 4,600 and 5,400 features, between 4,700 and 5,300 features, between 4,800 and 5,200 features, between 4,900 and 5,100 features, or any range within the disclosed sub-ranges. For example, the array can include about 4,000 features, about 4,200 features, about 4,400 features, about 4,800 features, about 5,000 features, about 5,200 features, about 5,400 features, about 5,600 features, or about 6,000 features. In some embodiments, the array comprises at least 4,000 features. In some embodiments, the array includes approximately 5,000 features.

In some embodiments, features within an array have an irregular arrangement or relationship to one another, such that no discernable pattern or regularity is evident in the geometrical spacing relationships among the features. For example, features within an array may be positioned randomly with respect to one another. Alternatively, features within an array may be positioned irregularly, but the spacings may be selected deterministically to ensure that the resulting arrangement of features is irregular.

In some embodiments, features within an array are positioned regularly with respect to one another to form a pattern. A wide variety of different patterns of features can be implemented in arrays. Examples of such patterns include, but are not limited to, square arrays of features, rectangular arrays of features, hexagonal arrays of features (including hexagonal close-packed arrays), radial arrays of features, spiral arrays of features, triangular arrays of features, and more generally, any array in which adjacent features in the array are reached from one another by regular increments in linear and/or angular coordinate dimensions.

In some embodiments, features within an array are positioned with a degree of regularity with respect to one another such that the array of features is neither perfectly regular nor perfectly irregular (i.e., the array is "partially regular"). For example, in some embodiments, adjacent features in an array can be separated by a displacement in one or more linear and/or angular coordinate dimensions that is 10% or more (e.g., 20% or more, 30% or more, 40% or more, 50% or more, 60% or more, 70% or more, 80% or more, 90% or more, 100% or more, 110% or more, 120% or more, 130% or more, 140% or more, 150% or more, 160% or more, 170% or more, 180% or more, 190% or more, 200% or more) of an average displacement or a nominal displacement between adjacent features in the array. In certain embodiments, the distribution of displacements (linear and/or angular) between adjacent features in an array has a full-width at half-maximum of between 0% and 200% (e.g., between 0% and 100%, between 0% and 75%, between 0% and 50%, between 0% and 25%, between 0% and 15%, between 0% and 10%) of an average displacement or nominal displacement between adjacent features in the array.

In some embodiments, arrays of features can have a variable geometry. For example, a first subset of features in an array can be arranged according to a first geometrical pattern, and a second subset of features in the array can be arranged according to a second geometrical pattern that is different from the first pattern. Any of the patterns described above can correspond to the first and/or second geometrical patterns, for example.

In general, arrays of different feature densities can be prepared by adjusting the spacing between adjacent features in the array. In some embodiments, the geometric center-to-center spacing between adjacent features in an array is between 100 nm and 100 μm. For example, the center-to-center spacing can be between 20 μm to 40 μm, 20 μm to 60 μm, 20 μm to 80 μm, 80 μm to 100 μm, 60 μm to 100 μm, or 40 μm to 100 μm. In some embodiments, the center-to-center spacing between adjacent array features is between 30 μm and 100 μm, 40 μm and 90 μm, 50 μm and 80 μm, 60 μm and 70 μm, 80 μm and 120 μm, or any range within the disclosed sub-ranges. In some embodiments, the center-to-center spacing between adjacent array features of a feature of an array is approximately 65 μm.

In some embodiments, an array of features can have a spatially varying resolution. In general, an array with a spatially varying resolution is an array in which the center-to-center spacing (along linear, angular, or both linear and angular coordinate dimensions) between adjacent features in the array varies. Such arrays can be useful in a variety of applications. For example, in some embodiments, depending upon the spatial resolution at which the sample is to be investigated, the sample can be selectively associated with the portion of the array that corresponds approximately to the desired spatial resolution of the measurement.

Arrays of spatially varying resolution can be implemented in a variety of ways. In some embodiments, for example, the center-to-center spacing between adjacent features in the array varies continuously along one or more linear and/or angular coordinate directions. Thus, for a rectangular array, the spacing between successive rows of features, between successive columns of features, or between both successive rows and successive columns of features, can vary continuously.

In certain embodiments, arrays of spatially varying resolution can include discrete domains with populations of features. Within each domain, adjacent features can have regular center-to-center spacings. Thus, for example, an array can include a first domain within which adjacent features are spaced from one another along linear and/or angular coordinate dimensions by a first set of uniform coordinate displacements, and a second domain within which adjacent features are spaced from one another along linear and/or angular coordinate dimensions by a second set of uniform coordinate displacements. The first and second sets of displacements differ in at least one coordinate displacement, such that adjacent features in the two domains are spaced differently, and the resolution of the array in the first domain is therefore different from the resolution of the array in the second domain.

In some embodiments, the center-to-center spacing of array features can be sufficiently small such that array features are effectively positioned continuously or nearly continuously along one or more array dimensions, with little or no displacement between array features along those dimensions. For example, in a feature array where the features correspond to regions of a substrate (i.e., oligonucleotides are directly bound to the substrate), the displacement between adjacent oligonucleotides can be very small—effectively, the molecular width of a single oligonucleotide. In such embodiments, each oligonucleotide can include a distinct spatial barcode such that the spatial location of each oligonucleotide in the array can be determined during sample analysis. Arrays of this type can have very high spatial resolution, but may only include a single oligonucleotide corresponding to each distinct spatial location in a sample.

In general, the size of the array (which corresponds to the maximum dimension of the smallest boundary that encloses all features in the array along one coordinate direction) can be selected as desired, based on criteria such as the size of the sample, the feature sizes, and the density of capture probes within each feature. For example, in some embodiments, the array can be a rectangular or square array for which the maximum array dimension along each coordinate direction is 10 mm or less (e.g., 9 mm or less, 8 mm or less, 7 mm or less, 6 mm or less, 5 mm or less, 4 mm or less, 3 mm or less). Thus, for example, a square array of features can have dimensions of 8 mm by 8 mm, 7 mm by 7 mm, 5 mm by 5 mm, or be smaller than 5 mm by 5 mm.

(e) Analyte Capture

In this section, general aspects of methods and systems for capturing analytes are described. Individual method steps and system features can be present in combination in many different embodiments; the specific combinations described herein do not in any way limit other combinations of steps and features.

Generally, analytes can be captured when contacting a biological sample with, e.g., a substrate comprising capture probes (e.g., substrate with capture probes embedded, spotted, printed on the substrate or a substrate with features (e.g., beads, wells) comprising capture probes).

As used herein, "contact," "contacted," and/or "contacting," a biological sample with a substrate comprising features refers to any contact (e.g., direct or indirect) such that capture probes can interact (e.g., capture) with analytes from the biological sample. For example, the substrate may be near or adjacent to the biological sample without direct physical contact, yet capable of capturing analytes from the biological sample. In some embodiments the biological sample is in direct physical contact with the substrate. In some embodiments, the biological sample is in indirect physical contact with the substrate. For example, a liquid layer may be between the biological sample and the substrate. In some embodiments, the analytes diffuse through the liquid layer. In some embodiments the capture probes diffuse through the liquid layer. In some embodiments reagents may be delivered via the liquid layer between the biological sample and the substrate. In some embodiments, indirect physical contact may be the presence of a second substrate (e.g., a hydrogel, a film, a porous membrane) between the biological sample and the first substrate comprising features with capture probes. In some embodiments, reagents may be delivered by the second substrate to the biological sample.

Diffusion-Resistant Media/Lids

To increase efficiency by encouraging analyte diffusion toward the spatially-labelled capture probes, a diffusion-resistant medium can be used. In general, molecular diffusion of biological analytes occurs in all directions, including toward the capture probes (i.e. toward the spatially-barcoded array), and away from the capture probes (i.e. into the bulk solution). Increasing diffusion toward the spatially-barcoded array reduces analyte diffusion away from the spatially-barcoded array and increases the capturing efficiency of the capture probes.

In some embodiments, a biological sample is placed on the top of a spatially-barcoded substrate and a diffusion-resistant medium is placed on top of the biological sample. For example, the diffusion-resistant medium can be placed onto an array that has been placed in contact with a biological sample. In some embodiments, the diffusion-resistant medium and spatially-labelled array are the same component. For example, the diffusion-resistant medium can contain spatially-labelled capture probes within or on the diffusion-resistant medium (e.g., coverslip, slide, hydrogel, or membrane). In some embodiments, a sample is placed on a substrate and a diffusion-resistant medium is placed on top of the biological sample. Additionally, a spatially-barcoded capture probe array can be placed in close proximity over the diffusion-resistant medium. For example, a diffusion-resistant medium may be sandwiched between a spatially-labelled array and a sample on a substrate. In some embodiments, the diffusion-resistant medium is disposed or spotted onto the sample. In other embodiments, the diffusion-resistant medium is placed in close proximity to the sample.

In general, the diffusion-resistant medium can be any material known to limit diffusivity of biological analytes. For example, the diffusion-resistant medium can be a solid lid (e.g., coverslip or glass slide). In some embodiments, the diffusion-resistant medium may be made of glass, silicon, paper, hydrogel polymer monoliths, or other material. In some embodiments, the glass side can be an acrylated glass slide. In some embodiments, the diffusion-resistant medium is a porous membrane. In some embodiments, the material may be naturally porous. In some embodiments, the material may have pores or wells etched into solid material. In some embodiments, the pore size can be manipulated to minimize loss of target analytes. In some embodiments, the membrane chemistry can be manipulated to minimize loss of target analytes. In some embodiments, the diffusion-resistant medium (i.e. hydrogel) is covalently attached to a substrate (i.e. glass slide). In some embodiments, the diffusion-resistant medium can be any material known to limit diffusivity of poly(A) transcripts. In some embodiments, the diffusion-resistant medium can be any material known to limit the diffusivity of proteins. In some embodiments, the diffusion-resistant medium can be any material know to limit the diffusivity of macromolecular constituents.

In some embodiments, a diffusion-resistant medium includes one or more diffusion-resistant media. For example, one or more diffusion-resistant media can be combined in a variety of ways prior to placing the media in contact with a biological sample including, without limitation, coating, layering, or spotting. As another example, a hydrogel can be placed onto a biological sample followed by placement of a lid (e.g., glass slide) on top of the hydrogel. In some embodiments, a force (e.g., hydrodynamic pressure, ultrasonic vibration, solute contrasts, microwave radiation, vascular circulation, or other electrical, mechanical, magnetic, centrifugal, and/or thermal forces) is applied to control diffusion and enhance analyte capture. In some embodiments, one or more forces and one or more diffusion-resistant media are used to control diffusion and enhance capture. For example, a centrifugal force and a glass slide can used contemporaneously. Any of a variety of combinations of a force and a diffusion-resistant medium can be used to control or mitigate diffusion and enhance analyte capture.

In some embodiments, the diffusion-resistant medium, along with the spatially-barcoded array and sample, is submerged in a bulk solution. In some embodiments, the bulk solution includes permeabilization reagents. In some embodiments, the diffusion-resistant medium includes at least one permeabilization reagent. In some embodiments, the diffusion-resistant medium (i.e. hydrogel) is soaked in permeabilization reagents before contacting the diffusion-resistant medium to the sample. In some embodiments, the diffusion-resistant medium can include wells (e.g., micro-, nano-, or picowells) containing a permeabilization buffer or reagents. In some embodiments, the diffusion-resistant medium can include permeabilization reagents. In some embodiments, the diffusion-resistant medium can contain dried reagents or monomers to deliver permeabilization reagents when the diffusion-resistant medium is applied to a biological sample. In some embodiments, the diffusion-resistant medium is added to the spatially-barcoded array and sample assembly before the assembly is submerged in a bulk solution. In some embodiments, the diffusion-resistant medium is added to the spatially-barcoded array and sample assembly after the sample has been exposed to permeabilization reagents. In some embodiments, the permeabilization reagents are flowed through a microfluidic chamber or channel over the diffusion-resistant medium. In some embodiments, the flow controls the sample's access to the permeabilization reagents. In some embodiments, the target analytes diffuse out of the sample and toward a bulk solution and get embedded in a spatially-labelled capture probe-embedded diffusion-resistant medium. In some embodiments, a free solution is sandwiched between the biological sample and a diffusion-resistant medium.

Figure 13:
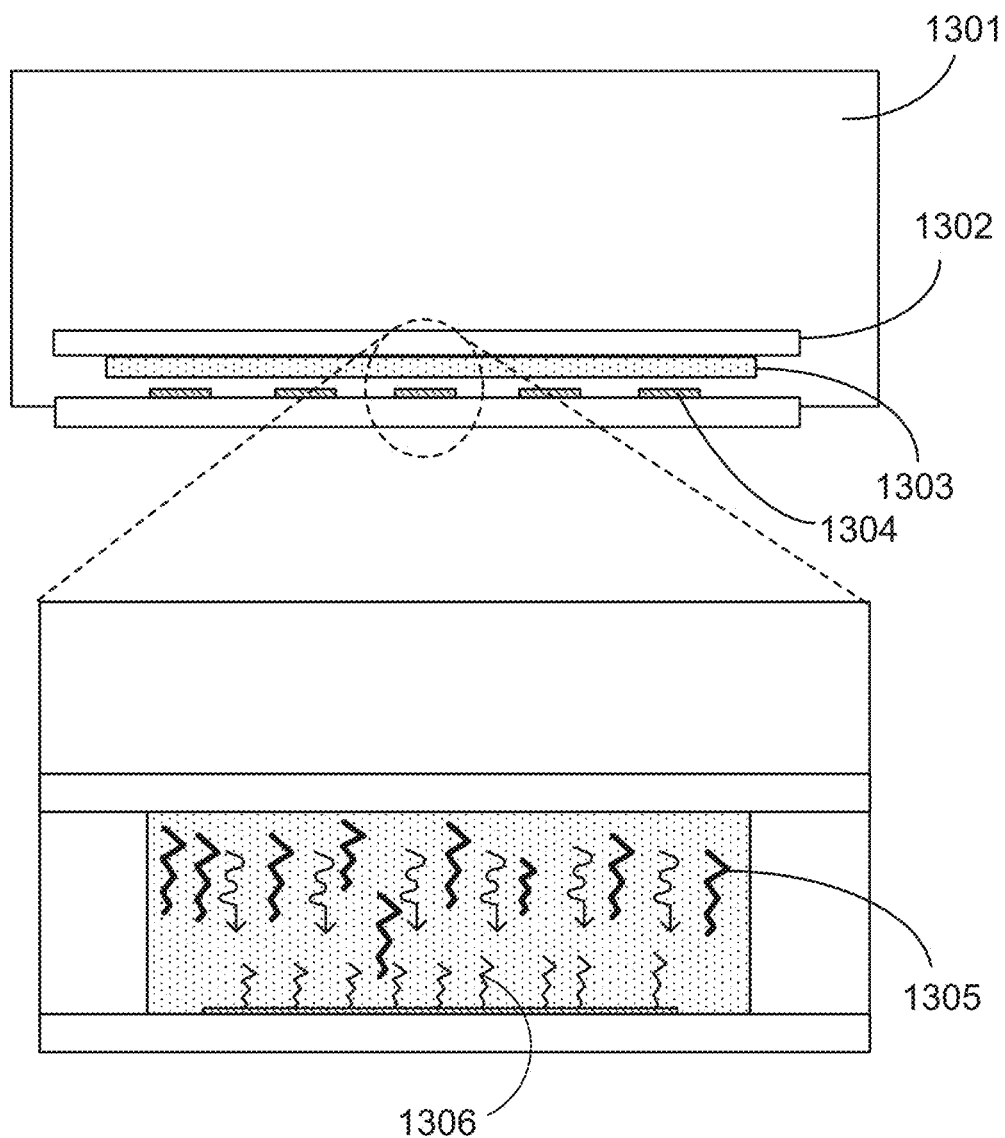
FIG. 13 is a schematic illustrating a side view of a diffusion-resistant medium, e.g., a lid.

FIG. 13 is an illustration of an exemplary use of a diffusion-resistant medium. A diffusion-resistant medium 1302 can be contacted with a sample 1303. In FIG. 13, a glass slide 1304 is populated with spatially-barcoded capture probes 1306, and the sample 1303, 1305 is contacted with the array 1304, 1306. A diffusion-resistant medium 1302 can be applied to the sample 1303, wherein the sample 1303 is sandwiched between a diffusion-resistant medium 1302 and a capture probe coated slide 1304. When a permeabilization solution 1301 is applied to the sample, using the diffusion-resistant medium/lid 1302 directs migration of the analytes 1305 toward the capture probes 1306 by reducing diffusion of the analytes out into the medium. Alternatively, the lid may contain permeabilization reagents.

Conditions for Capture

Capture probes on the substrate (or on a feature on the substrate) interact with released analytes through a capture domain, described elsewhere, to capture analytes. In some embodiments, certain steps are performed to enhance the transfer or capture of analytes by the capture probes of the array. Examples of such modifications include, but are not limited to, adjusting conditions for contacting the substrate with a biological sample (e.g., time, temperature, orientation, pH levels, pre-treating of biological samples, etc.), using force to transport analytes (e.g., electrophoretic, centrifugal, mechanical, etc.), performing amplification reactions to increase the amount of biological analytes (e.g., PCR amplification, in situ amplification, clonal amplification), and/or using labeled probes for detecting of amplicons and barcodes.

In some embodiments, capture of analytes is facilitated by treating the biological sample with permeabilization reagents. If a biological sample is not permeabilized sufficiently, the amount of analyte captured on the substrate can be too low to enable adequate analysis. Conversely, if the biological sample is too permeable, the analyte can diffuse away from its origin in the biological sample, such that the relative spatial relationship of the analytes within the biological sample is lost. Hence, a balance between permeabilizing the biological sample enough to obtain good signal intensity while still maintaining the spatial resolution of the analyte distribution in the biological sample is desired. Methods of preparing biological samples to facilitation are known in the art and can be modified depending on the biological sample and how the biological sample is prepared (e.g., fresh frozen, FFPE, etc.).

Passive Capture Methods

In some embodiments, analytes can be migrated from a sample to a substrate. Methods for facilitating migration can be passive (e.g., diffusion) and/or active (e.g., electrophoretic migration of nucleic acids). Non-limiting examples of passive migration can include simple diffusion and osmotic pressure created by the rehydration of dehydrated objects.

Passive migration by diffusion uses concentration gradients. Diffusion is movement of untethered objects toward equilibrium. Therefore, when there is a region of high object concentration and a region of low object concentration, the object (capture probe, the analyte, etc.) moves to an area of lower concentration. In some embodiments, untethered analytes move down a concentration gradient.

In some embodiments, different reagents may be added to the biological sample, such that the biological sample is rehydrated while improving capture of analytes. In some embodiments, the biological sample can be rehydrated with permeabilization reagents. In some embodiments, the biological sample can be rehydrated with a staining solution (e.g., hematoxylin and eosin stain).

Active Capture Methods

In some examples of any of the methods described herein, an analyte in a cell or a biological sample can be transported (e.g., passively or actively) to a capture probe (e.g., a capture probe affixed to a solid surface).

For example, analytes in a cell or a biological sample can be transported to a capture probe (e.g., an immobilized capture probe) using an electric field (e.g., using electrophoresis), a pressure gradient, fluid flow, a chemical concentration gradient, a temperature gradient, and/or a magnetic field. For example, analytes can be transported through, e.g., a gel (e.g., hydrogel matrix), a fluid, or a permeabilized cell, to a capture probe (e.g., an immobilized capture probe).

In some examples, an electrophoretic field can be applied to analytes to facilitate migration of the analytes towards a capture probe. In some examples, a sample contacts a substrate and capture probes fixed on a substrate (e.g., a slide, cover slip, or bead), and an electric current is applied to promote the directional migration of charged analytes towards the capture probes fixed on the substrate. An electrophoresis assembly, where a cell or a biological sample is in contact with a cathode and capture probes (e.g., capture probes fixed on a substrate), and where the capture probes (e.g., capture probes fixed on a substrate) is in contact with the cell or biological sample and an anode, can be used to apply the current.

Electrophoretic transfer of analytes can be performed while retaining the relative spatial alignment of the analytes in the sample. As such, an analyte captured by the capture probes (e.g., capture probes fixed on a substrate) retains the spatial information of the cell or the biological sample. Applying an electrophoretic field to analytes can also result in an increase in temperature (e.g., heat). In some embodiments, the increased temperature (e.g., heat) can facilitate the migration of the analytes towards a capture probe.

In some examples, a spatially-addressable microelectrode array is used for spatially-constrained capture of at least one charged analyte of interest by a capture probe. The microelectrode array can be configured to include a high density of discrete sites having a small area for applying an electric field to promote the migration of charged analyte(s) of interest. For example, electrophoretic capture can be performed on a region of interest using a spatially-addressable microelectrode array.

A high density of discrete sites on a microelectrode array can be used for small device. The surface can include any suitable density of discrete sites (e.g., a density suitable for processing the sample on the conductive substrate in a given amount of time). In an embodiment, the surface has a density of discrete sites greater than or equal to about 500 sites per 1 mm$^2$. In some embodiments, the surface has a density of discrete sites of about 100, about 200, about 300, about 400, about 500, about 600, about 700, about 800, about 900, about 1,000, about 2,000, about 3,000, about 4,000, about 5,000, about 6,000, about 7,000, about 8,000, about 9,000, about 10,000, about 20,000, about 40,000, about 60,000, about 80,000, about 100,000, or about 500,000 sites per 1 mm$^2$. In some embodiments, the surface has a density of discrete sites of at least about 200, at least about 300, at least about 400, at least about 500, at least about 600, at least about 700, at least about 800, at least about 900, at least about 1,000, at least about 2,000, at least about 3,000, at least about 4,000, at least about 5,000, at least about 6,000, at least about 7,000, at least about 8,000, at least about 9,000, at least about 10,000, at least about 20,000, at least about 40,000, at least about 60,000, at least about 80,000, at least about 100,000, or at least about 500,000 sites per 1 mm$^2$.

Figure 14A:
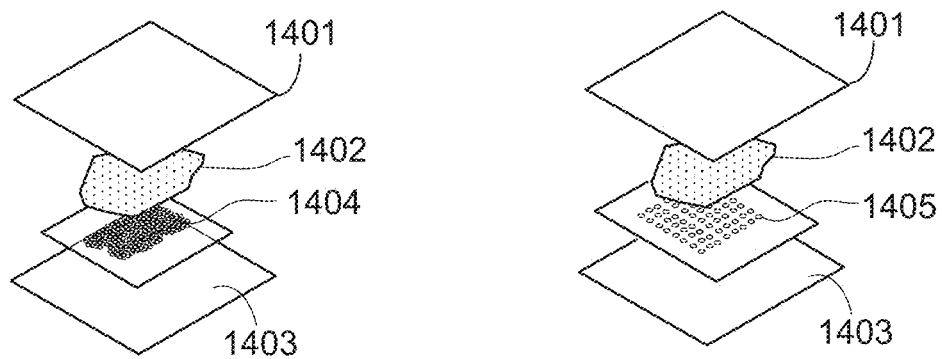
FIGS. 14A and 14B are schematics illustrating expanded FIG. 14A and side views FIG. 14B of an electrophoretic transfer system configured to direct transcript analytes toward a spatially-barcoded capture probe array.
Figure 14B:
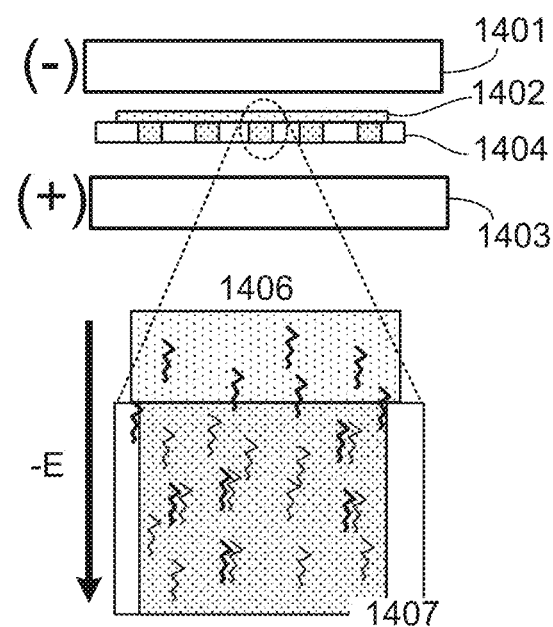

Schematics illustrating an electrophoretic transfer system configured to direct transcript analytes toward a spatially-barcoded capture probe array are shown in FIG. 14A and FIG. 14B. In this exemplary configuration of an electrophoretic system, a sample 1402 is sandwiched between the cathode 1401 and the spatially-barcoded capture probe array 1404, 1405, and the spatially-barcoded capture probe array 1404, 1405 is sandwiched between the sample 1402 and the anode 1403, such that the sample 1402, 1406 is in contact with the spatially-barcoded capture probes 1407. When an electric field is applied to the electrophoretic transfer system, negatively charged mRNA analytes 1406 will be pulled toward the positively charged anode 1403 and into the spatially-barcoded array 1404, 1405 containing the spatially-barcoded capture probes 1407. The spatially-barcoded capture probes 1407 then interact with/hybridize with/immobilize the mRNA target analytes 1406, making the analyte capture more efficient. The electrophoretic system setup may change depending on the target analyte. For example, proteins may be positive, negative, neutral, or polar depending on the protein as well as other factors (e.g. isoelectric point, solubility, etc.). The skilled practitioner has the knowledge and experience to arrange the electrophoretic transfer system to facilitate capture of a particular target analyte.

FIG. 15 is an illustration showing an exemplary workflow protocol utilizing an electrophoretic transfer system. In the example, Panel A depicts a flexible spatially-barcoded feature array being contacted with a sample. The sample can be a flexible array, wherein the array is immobilized on a hydrogel, membrane, or other flexible substrate. Panel B depicts contact of the array with the sample and imaging of the array-sample assembly. The image of the sample/array assembly can be used to verify sample placement, choose a region of interest, or any other reason for imaging a sample on an array as described herein. Panel C depicts application of an electric field using an electrophoretic transfer system to aid in efficient capture of a target analyte. Here, negatively charged mRNA target analytes migrate toward the positively charged anode. Panel D depicts application of reverse transcription reagents and first strand cDNA synthesis of the captured target analytes. Panel E depicts array removal and preparation for library construction (Panel F) and next-generation sequencing (Panel G).

Region of Interest

A biological sample can have regions that show morphological feature(s) that may indicate the presence of disease or the development of a disease phenotype. For example, morphological features at a specific site within a tumor biopsy sample can indicate the aggressiveness, therapeutic resistance, metastatic potential, migration, stage, diagnosis, and/or prognosis of cancer in a subject. A change in the morphological features at a specific site within a tumor biopsy sample often correlate with a change in the level or expression of an analyte in a cell within the specific site, which can, in turn, be used to provide information regarding the aggressiveness, therapeutic resistance, metastatic potential, migration, stage, diagnosis, and/or prognosis of cancer in a subject. A region or area within a biological sample that is selected for specific analysis (e.g., a region in a biological sample that has morphological features of interest) is often described as "a region of interest."

A region of interest in a biological sample can be used to analyze a specific area of interest within a biological sample, and thereby, focus experimentation and data gathering to a specific region of a biological sample (rather than an entire biological sample). This results in increased time efficiency of the analysis of a biological sample.

A region of interest can be identified in a biological sample using a variety of different techniques, e.g., expansion microscopy, bright field microscopy, dark field microscopy, phase contrast microscopy, electron microscopy, fluorescence microscopy, reflection microscopy, interference microscopy, confocal microscopy, and visual identification (e.g., by eye), and combinations thereof. For example, the staining and imaging of a biological sample can be performed to identify a region of interest. In some examples, the region of interest can correspond to a specific structure of cytoarchitecture. In some embodiments, a biological sample can be stained prior to visualization to provide contrast between the different regions of the biological sample. The type of stain can be chosen depending on the type of biological sample and the region of the cells to be stained. In some embodiments, more than one stain can be used to visualize different aspects of the biological sample, e.g., different regions of the sample, specific cell structures (e.g. organelles), or different cell types. In other embodiments, the biological sample can be visualized or imaged without staining the biological sample.

In some embodiments, imaging can be performed using one or more fiducial markers, i.e., objects placed in the field of view of an imaging system which appear in the image produced. Fiducial markers are typically used as a point of reference or measurement scale. Fiducial markers can include, but are not limited to, detectable labels such as fluorescent, radioactive, chemiluminescent, and colorimetric labels. The use of fiducial markers to stabilize and orient biological samples is described, for example, in Carter et al., *Applied Optics* 46:421-427, 2007), the entire contents of which are incorporated herein by reference. In some embodiments, a fiducial marker can be a physical particle (e.g., a nanoparticle, a microsphere, a nanosphere, a bead, or any of the other exemplary physical particles described herein or known in the art).

In some embodiments, a fiducial marker can be present on a substrate to provide orientation of the biological sample. In some embodiments, a microsphere can be coupled to a substrate to aid in orientation of the biological sample. In some examples, a microsphere coupled to a substrate can produce an optical signal (e.g., fluorescence). In another example, a microsphere can be attached to a portion (e.g., corner) of an array in a specific pattern or design (e.g., hexagonal design) to aid in orientation of a biological sample on an array of features on the substrate. In some embodiments, a quantum dot can be coupled to the substrate to aid in the orientation of the biological sample. In some examples, a quantum dot coupled to a substrate can produce an optical signal.

In some embodiments, a fiducial marker can be an immobilized molecule with which a detectable signal molecule can interact to generate a signal. For example, a marker nucleic acid can be linked or coupled to a chemical moiety capable of fluorescing when subjected to light of a specific wavelength (or range of wavelengths). Such a marker nucleic acid molecule can be contacted with an array before, contemporaneously with, or after the tissue sample is stained to visualize or image the tissue section. Although not required, it can be advantageous to use a marker that can be detected using the same conditions (e.g., imaging conditions) used to detect a labelled cDNA.

In some embodiments, fiducial markers are included to facilitate the orientation of a tissue sample or an image thereof in relation to an immobilized capture probes on a substrate. Any number of methods for marking an array can be used such that a marker is detectable only when a tissue section is imaged. For instance, a molecule, e.g. a fluorescent molecule that generates a signal, can be immobilized directly or indirectly on the surface of a substrate. Markers can be provided on a substrate in a pattern (e.g., an edge, one or more rows, one or more lines, etc.).

In some embodiments, a fiducial marker can be randomly placed in the field of view. For example, an oligonucleotide containing a fluorophore can be randomly printed, stamped, synthesized, or attached to a substrate (e.g., a glass slide) at a random position on the substrate. A tissue section can be contacted with the substrate such that the oligonucleotide containing the fluorophore contacts, or is in proximity to, a cell from the tissue section or a component of the cell (e.g., an mRNA or DNA molecule). An image of the substrate and the tissue section can be obtained, and the position of the fluorophore within the tissue section image can be determined (e.g., by reviewing an optical image of the tissue section overlaid with the fluorophore detection). In some embodiments, fiducial markers can be precisely placed in the field of view (e.g., at known locations on a substrate). In this instance, a fiducial marker can be stamped, attached, or synthesized on the substrate and contacted with a biological sample. Typically, an image of the sample and the fiducial marker is taken, and the position of the fiducial marker on the substrate can be confirmed by viewing the image.

In some embodiments, a fiducial marker can be an immobilized molecule (e.g., a physical particle) attached to the substrate. For example, a fiducial marker can be a nanoparticle, e.g., a nanorod, a nanowire, a nanocube, a nanopyramid, or a spherical nanoparticle. In some examples, the nanoparticle can be made of a heavy metal (e.g., gold). In some embodiments, the nanoparticle can be made from diamond. In some embodiments, the fiducial marker can be visible by eye.

As noted herein, any of the fiducial markers described herein (e.g., microspheres, beads, or any of the other physical particles described herein) can be located at a portion (e.g., corner) of an array in a specific pattern or design (e.g., hexagonal design) to aid in orientation of a biological sample on an array of features on the substrate. In some embodiments, the fiducial markers located at a portion (e.g., corner) of an array (e.g., an array on a substrate) can be pattern or designed in at least 1, at least 2, at least 3, or at least 4 unique patterns. In some examples, the fiducial markers located at the corners of the array (e.g., an array on a substrate) can have four unique patterns of fiducial markers.

In some examples, fiducial markers can surround the array. In some embodiments the fiducial markers allow for detection of, e.g., mirroring. In some embodiments, the fiducial markers may completely surround the array. In some embodiments, the fiducial markers may not completely surround the array. In some embodiments, the fiducial markers identify the corners of the array. In some embodiments, one or more fiducial markers identify the center of the array. In some embodiments, the fiducial markers comprise patterned spots, wherein the diameter of one or more patterned spot fiducial markers is approximately 100 micrometers. The diameter of the fiducial markers can be any useful diameter including, but not limited to, 50 micrometers to 500 micrometers in diameter. The fiducial markers may be arranged in such a way that the center of one fiducial marker is between 100 micrometers and 200 micrometers from the center of one or more other fiducial markers surrounding the array. In some embodiments, the array with the surrounding fiducial markers is approximately 8 mm by 8 mm. In some embodiments, the array without the surrounding fiducial markers is smaller than 8 mm by 50 mm.

In some embodiments, an array can be enclosed within a frame. Put another way, the perimeter of an array can have fiducial markers such that the array is enclosed, or substantially enclosed. In some embodiments, the perimeter of an array can be fiducial markers (e.g., any fiducial marker described herein). In some embodiments, the perimeter of an array can be uniform. For example, the fiducial markings can connect, or substantially connect, consecutive corners of an array in such a fashion that the non-corner portion of the array perimeter is the same on all sides (e.g., four sides) of the array. In some embodiments, the fiducial markers attached to the non-corner portions of the perimeter can be pattered or designed to aid in the orientation of the biological sample on the array. In some embodiments, the particles attached to the non-corner portions of the perimeter can be patterned or designed in at least 1, at least 2, at least 3, or at least 4 patterns. In some embodiments, the patterns can have at least 2, at least 3, or at least 4 unique patterns of fiducial markings on the non-corner portion of the array perimeter.

In some embodiments, an array can include at least two fiducial markers (e.g., at least 3, at least 4, at least 5, at least 6, at least 7, at least 8, at least 9, at least 10, at least 12, at least 15, at least 20, at least 30, at least 40, at least 50, at least 60, at least 70, at least 80, at least 90, at least 100 fiducial markers or more (e.g., several hundred, several thousand, or tens of thousands of fiducial markers)) in distinct positions on the surface of a substrate. Fiducial markers can be provided on a substrate in a pattern (e.g., an edge, one or more rows, one or more lines, etc.).

In some embodiments, staining and imaging a biological sample prior to contacting the biological sample with a spatial array is performed to select samples for spatial analysis. In some embodiments, the staining includes applying a fiducial marker as described above, including fluorescent, radioactive, chemiluminescent, or colorimetric detectable markers. In some embodiments, the staining and imaging of biological samples allows the user to identify the specific sample (or region of interest) the user wishes to assess.

In some embodiments, a lookup table (LUT) can be used to associate one property with another property of a feature. These properties include, e.g., locations, barcodes (e.g., nucleic acid barcode molecules), spatial barcodes, optical labels, molecular tags, and other properties.

In some embodiments, a lookup table can associate a nucleic acid barcode molecule with a feature. In some embodiments, an optical label of a feature can permit associating the feature with a biological particle (e.g., cell or nuclei). The association of a feature with a biological particle can further permit associating a nucleic acid sequence of a nucleic acid molecule of the biological particle to one or more physical properties of the biological particle (e.g., a type of a cell or a location of the cell). For example, based on the relationship between the barcode and the optical label, the optical label can be used to determine the location of a feature, thus associating the location of the feature with the barcode sequence of the feature. Subsequent analysis (e.g., sequencing) can associate the barcode sequence and the analyte from the sample. Accordingly, based on the relationship between the location and the barcode sequence, the location of the biological analyte can be determined (e.g., in a specific type of cell or in a cell at a specific location of the biological sample).

In some embodiments, a feature can have a plurality of nucleic acid barcode molecules attached thereto. The plurality of nucleic acid barcode molecules can include barcode sequences. The plurality of nucleic acid molecules attached to a given feature can have the same barcode sequences, or two or more different barcode sequences. Different barcode sequences can be used to provide improved spatial location accuracy.

In some embodiments, a substrate is treated in order to minimize or reduce non-specific analyte hybridization within or between features. For example, treatment can include coating the substrate with a hydrogel, film, and/or membrane that creates a physical barrier to non-specific hybridization. Any suitable hydrogel can be used. For example, hydrogel matrices prepared according to the methods set forth in U.S. Pat. Nos. 6,391,937, 9,512,422, and 9,889,422, and U.S. Patent Application Publication Nos. U.S. 2017/0253918 and U.S. 2018/0052081, can be used. The entire contents of each of the foregoing documents are incorporated herein by reference.

Treatment can include adding a functional group that is reactive or capable of being activated such that it becomes reactive after receiving a stimulus (e.g., photoreactive). Treatment can include treating with polymers having one or more physical properties (e.g., mechanical, electrical, magnetic, and/or thermal) that minimize non-specific binding (e.g., that activate a substrate at certain locations to allow analyte hybridization at those locations).

In some examples, an array (e.g., any of the exemplary arrays described herein) can be contacted with only a portion of a biological sample (e.g., a cell, a feature, or a region of interest). In some examples, a biological sample is contacted with only a portion of an array (e.g., any of the exemplary arrays described herein). In some examples, a portion of the array can be deactivated such that it does not interact with the analytes in the biological sample (e.g., optical deactivation, chemical deactivation, heat deactivation, or blocking of the capture probes in the array (e.g., using blocking probes)). In some examples, a region of interest can be removed from a biological sample and then the region of interest can be contacted to the array (e.g., any of the arrays described herein). A region of interest can be removed from a biological sample using microsurgery, laser capture microdissection, chunking, a microtome, dicing, trypsinization, labelling, and/or fluorescence-assisted cell sorting.

(f) Partitioning

As discussed above, in some embodiments, the sample can optionally be separated into single cells, cell groups, or other fragments/pieces that are smaller than the original, unfragmented sample. Each of these smaller portions of the sample can be analyzed to obtain spatially-resolved analyte information for the sample.

For samples that have been separated into smaller fragments—and particularly, for samples that have been disaggregated, dissociated, or otherwise separated into individual cells—one method for analyzing the fragments involves partitioning the fragments into individual partitions (e.g., fluid droplets), and then analyzing the contents of the partitions. In general, each partition maintains separation of its own contents from the contents of other partitions. The partition can be a droplet in an emulsion, for example.

In addition to analytes, a partition can include additional components, and in particular, one or more beads. A partition can include a single gel bead, a single cell bead, or both a single cell bead and single gel bead.

A partition can also include one or more reagents. Unique identifiers, such as barcodes, can be injected into the droplets previous to, subsequent to, or concurrently with droplet generation, such as via a microcapsule (e.g., bead). Microfluidic channel networks (e.g., on a chip) can be utilized to generate partitions. Alternative mechanisms can also be employed in the partitioning of individual biological particles, including porous membranes through which aqueous mixtures of cells are extruded into non-aqueous fluids.

The partitions can be flowable within fluid streams. The partitions can include, for example, micro-vesicles that have an outer barrier surrounding an inner fluid center or core. In some cases, the partitions can include a porous matrix that is capable of entraining and/or retaining materials within its matrix. The partitions can be droplets of a first phase within a second phase, wherein the first and second phases are immiscible. For example, the partitions can be droplets of aqueous fluid within a non-aqueous continuous phase (e.g., oil phase). In another example, the partitions can be droplets of a non-aqueous fluid within an aqueous phase. In some examples, the partitions can be provided in a water-in-oil emulsion or oil-in-water emulsion. A variety of different vessels are described in, for example, U.S. Patent Application Publication No. 2014/0155295, the entire contents of which are incorporated herein by reference. Emulsion systems for creating stable droplets in non-aqueous or oil continuous phases are described, for example, in U.S. Patent Application Publication No. 2010/0105112, the entire contents of which are incorporated herein by reference.

For droplets in an emulsion, allocating individual particles to discrete partitions can be accomplished, for example, by introducing a flowing stream of particles in an aqueous fluid into a flowing stream of a non-aqueous fluid, such that droplets are generated at the junction of the two streams. Fluid properties (e.g., fluid flow rates, fluid viscosities, etc.), particle properties (e.g., volume fraction, particle size, particle concentration, etc.), microfluidic architectures (e.g., channel geometry, etc.), and other parameters can be adjusted to control the occupancy of the resulting partitions (e.g., number of analytes per partition, number of beads per partition, etc.). For example, partition occupancy can be controlled by providing the aqueous stream at a certain concentration and/or flow rate of analytes.

To generate single analyte partitions, the relative flow rates of the immiscible fluids can be selected such that, on average, the partitions can contain less than one analyte per partition to ensure that those partitions that are occupied are primarily singly occupied. In some cases, partitions among a plurality of partitions can contain at most one analyte. In some embodiments, the various parameters (e.g., fluid properties, particle properties, microfluidic architectures, etc.) can be selected or adjusted such that a majority of partitions are occupied, for example, allowing for only a small percentage of unoccupied partitions. The flows and channel architectures can be controlled as to ensure a given number of singly occupied partitions, less than a certain level of unoccupied partitions and/or less than a certain level of multiply occupied partitions.

The channel segments described herein can be coupled to any of a variety of different fluid sources or receiving components, including reservoirs, tubing, manifolds, or fluidic components of other systems. As will be appreciated, the microfluidic channel structure can have a variety of geometries. For example, a microfluidic channel structure can have one or more than one channel junction. As another example, a microfluidic channel structure can have 2, 3, 4, or 5 channel segments each carrying particles that meet at a channel junction. Fluid can be directed to flow along one or more channels or reservoirs via one or more fluid flow units. A fluid flow unit can include compressors (e.g., providing positive pressure), pumps (e.g., providing negative pressure), actuators, and the like to control flow of the fluid. Fluid can also or otherwise be controlled via applied pressure differentials, centrifugal force, electrokinetic pumping, vacuum, capillary, and/or gravity flow.

A partition can include one or more unique identifiers, such as barcodes. Barcodes can be previously, subsequently, or concurrently delivered to the partitions that hold the compartmentalized or partitioned biological particle. For example, barcodes can be injected into droplets previous to, subsequent to, or concurrently with droplet generation. The delivery of the barcodes to a particular partition allows for the later attribution of the characteristics of the individual biological particle to the particular partition. Barcodes can be delivered, for example on a nucleic acid molecule (e.g., an oligonucleotide), to a partition via any suitable mechanism. Barcoded nucleic acid molecules can be delivered to a partition via a microcapsule. A microcapsule, in some instances, can include a bead.

In some embodiments, barcoded nucleic acid molecules can be initially associated with the microcapsule and then released from the microcapsule. Release of the barcoded nucleic acid molecules can be passive (e.g., by diffusion out of the microcapsule). In addition or alternatively, release from the microcapsule can be upon application of a stimulus which allows the barcoded nucleic acid nucleic acid molecules to dissociate or to be released from the microcapsule. Such stimulus can disrupt the microcapsule, an interaction that couples the barcoded nucleic acid molecules to or within the microcapsule, or both. Such stimulus can include, for example, a thermal stimulus, photo-stimulus, chemical stimulus (e.g., change in pH or use of a reducing agent(s)), a mechanical stimulus, a radiation stimulus; a biological stimulus (e.g., enzyme), or any combination thereof.

In some embodiments, one more barcodes (e.g., spatial barcodes, UMIs, or a combination thereof) can be introduced into a partition as part of the analyte. As described previously, barcodes can be bound to the analyte directly, or can form part of a capture probe or analyte capture agent that is hybridized to, conjugated to, or otherwise associated with an analyte, such that when the analyte is introduced into the partition, the barcode(s) are introduced as well. As described above, FIG. 16 shows an example of a microfluidical channel structure for partitioning individual analytes (e.g., cells) into discrete partitions.

Figure 16:
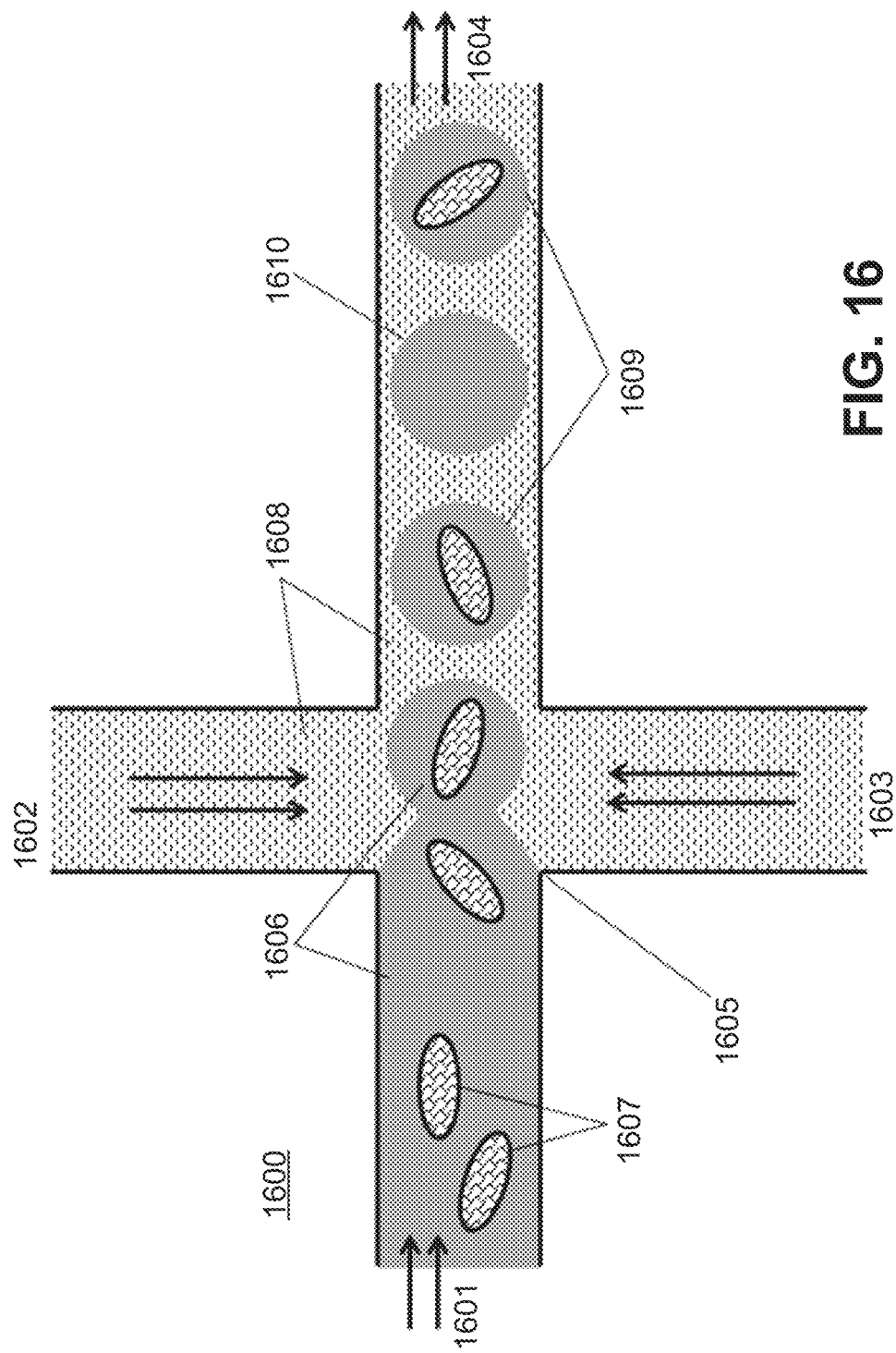
FIG. 16 shows an example of a microfluidic channel structure 1600 for partitioning dissociated sample (e.g. biological particles or individual cells from a sample).

FIG. 16 shows an example of a microfluidic channel structure for partitioning individual analytes (e.g., cells) into discrete partitions. The channel structure can include channel segments 1601, 1602, 1603, and 1604 communicating at a channel junction 1605. In operation, a first aqueous fluid 1606 that includes suspended biological particles (or cells) 1607 may be transported along channel segment 1601 into junction 1605, while a second fluid 1608 that is immiscible with the aqueous fluid 1606 is delivered to the junction 1605 from each of channel segments 1602 and 1603 to create discrete droplets 1609, 1610 of the first aqueous fluid 1606 flowing into channel segment 1604, and flowing away from junction 1605. The channel segment 1604 may be fluidically coupled to an outlet reservoir where the discrete droplets can be stored and/or harvested. A discrete droplet generated may include an individual biological particle 1607 (such as droplets 1609). A discrete droplet generated may include more than one individual biological particle 1607. A discrete droplet may contain no biological particle 1607 (such as droplet 1610). Each discrete partition may maintain separation of its own contents (e.g., individual biological particle 1607) from the contents of other partitions.

Figure 17A:
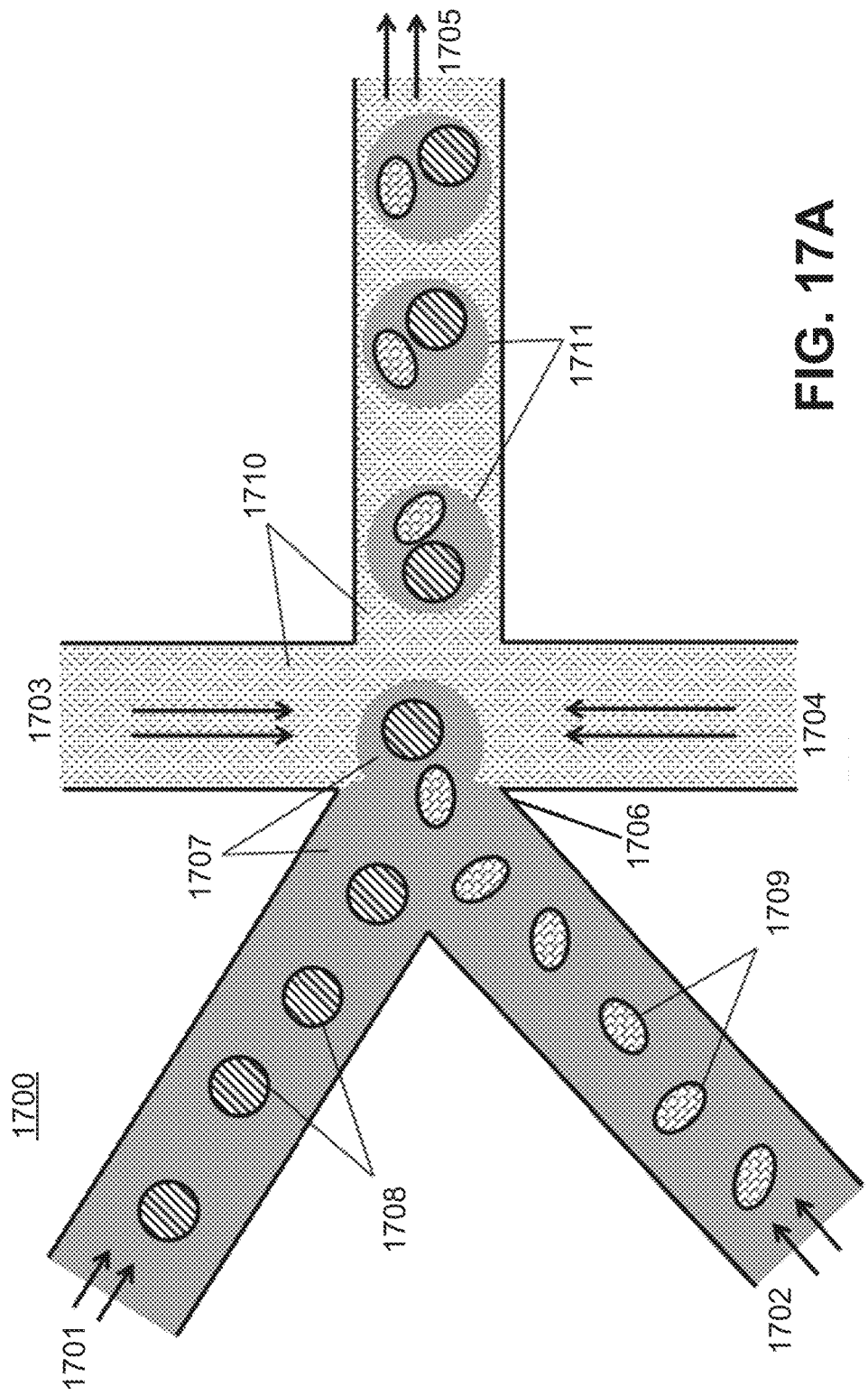
FIG. 17A shows an example of a microfluidic channel structure 1700 for delivering spatial barcode carrying beads to droplets.

FIG. 17A shows another example of a microfluidic channel structure 1700 for delivering beads to droplets. The channel structure includes channel segments 1701, 1702, 1703, 1704 and 1705 communicating at a channel junction 1706. During operation, the channel segment 1701 can transport an aqueous fluid 1707 that includes a plurality of beads 1708 along the channel segment 1701 into junction 1706. The plurality of beads 1708 can be sourced from a suspension of beads. For example, the channel segment 1701 can be connected to a reservoir that includes an aqueous suspension of beads 1708. The channel segment 1702 can transport the aqueous fluid 1707 that includes a plurality of particles 1709 (e.g., cells) along the channel segment 1702 into junction 1706. In some embodiments, the aqueous fluid 1707 in either the first channel segment 1701 or the second channel segment 1702, or in both segments, can include one or more reagents, as further described below.

A second fluid 1710 that is immiscible with the aqueous fluid 1707 (e.g., oil) can be delivered to the junction 1706 from each of channel segments 1703 and 1704. Upon meeting of the aqueous fluid 1707 from each of channel segments 1701 and 1702 and the second fluid 1710 from each of channel segments 1703 and 1704 at the channel junction 1706, the aqueous fluid 1707 can be partitioned as discrete droplets 1711 in the second fluid 1710 and flow away from the junction 1706 along channel segment 1705. The channel segment 1705 can deliver the discrete droplets to an outlet reservoir fluidly coupled to the channel segment 1705, where they can be harvested.

As an alternative, the channel segments 1701 and 1702 can meet at another junction upstream of the junction 1706. At such junction, beads and biological particles can form a mixture that is directed along another channel to the junction 1706 to yield droplets 1711. The mixture can provide the beads and biological particles in an alternating fashion, such that, for example, a droplet includes a single bead and a single biological particle.

The second fluid 1710 can include an oil, such as a fluorinated oil, that includes a fluorosurfactant for stabilizing the resulting droplets, for example, inhibiting subsequent coalescence of the resulting droplets 1711.

The partitions described herein can include small volumes, for example, less than about 10 microliters (TL), 5 TL, 1 TL, 900 picoliters (pL), 800 pL, 700 pL, 600 pL, 500 pL, 400 pL, 300 pL, 200 pL, 100 pL, 50 pL, 20 pL, 10 pL, 1 pL, 500 nanoliters (nL), 100 nL, 50 nL, or less. In the foregoing discussion, droplets with beads were formed at the junction of different fluid streams. In some embodiments, droplets can be formed by gravity-based partitioning methods.

Figure 17B:
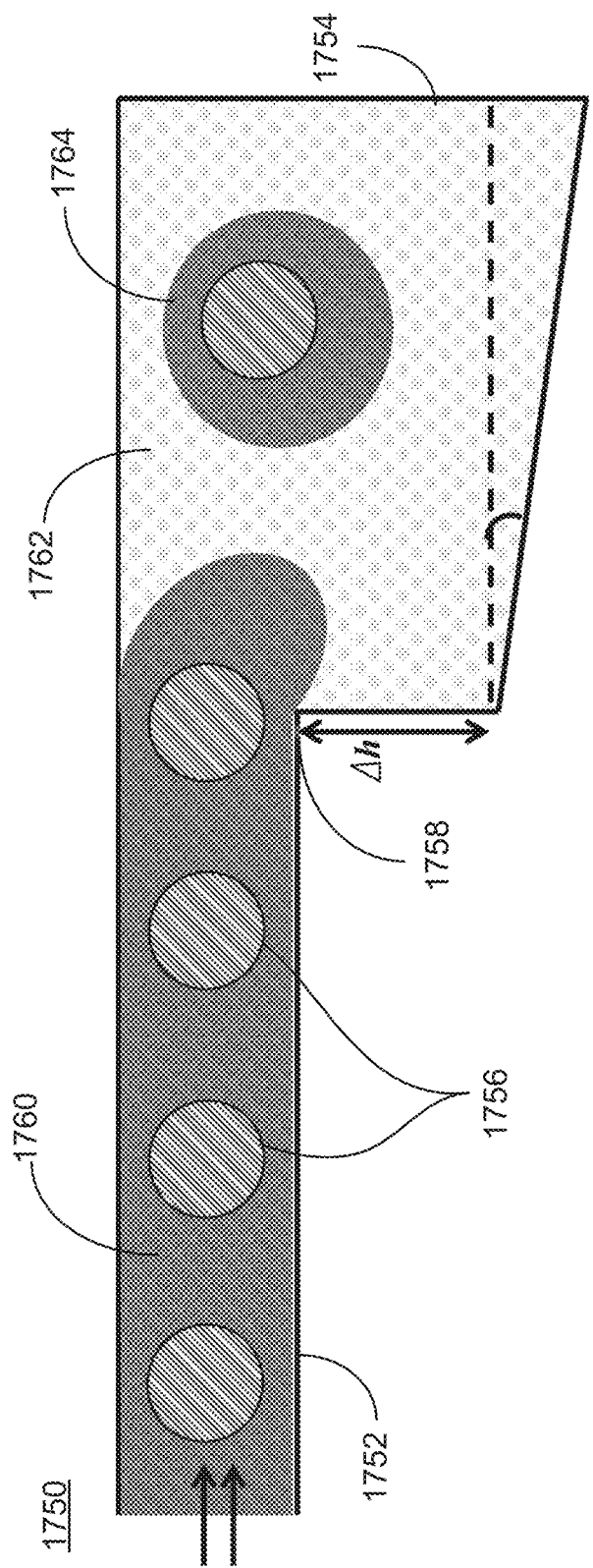
FIG. 17B shows a cross-section view of another example of a microfluidic channel structure 1750 with a geometric feature for controlled partitioning.

FIG. 17B shows a cross-section view of another example of a microfluidic channel structure 1750 with a geometric feature for controlled partitioning. A channel structure 1750 can include a channel segment 1752 communicating at a channel junction 1758 (or intersection) with a reservoir 1754. In some instances, the channel structure 1750 and one or more of its components can correspond to the channel structure 1700 and one or more of its components.

An aqueous fluid 1760 comprising a plurality of particles 1756 may be transported along the channel segment 1752 into the junction 1758 to meet a second fluid 1762 (e.g., oil, etc.) that is immiscible with the aqueous fluid 1760 in the reservoir 1754 to create droplets 1764 of the aqueous fluid 1760 flowing into the reservoir 1754. At the junction 1758 where the aqueous fluid 1760 and the second fluid 1762 meet, droplets can form based on factors such as the hydrodynamic forces at the junction 1758, relative flow rates of the two fluids 1760, 1762, fluid properties, and certain geometric parameters (e.g., Δh, etc.) of the channel structure 1750. A plurality of droplets can be collected in the reservoir 1754 by continuously injecting the aqueous fluid 1760 from the channel segment 1752 at the junction 1758.

A discrete droplet generated may comprise one or more particles of the plurality of particles 1756. As described elsewhere herein, a particle may be any particle, such as a bead, cell bead, gel bead, biological particle, macromolecular constituents of biological particle, or other particles. Alternatively, a discrete droplet generated may not include any particles.

In some instances, the aqueous fluid 1760 can have a substantially uniform concentration or frequency of particles 1756. As described elsewhere herein, the particles 1756 (e.g., beads) can be introduced into the channel segment 1752 from a separate channel (not shown in FIG. 17). The frequency of particles 1756 in the channel segment 1752 may be controlled by controlling the frequency in which the particles 1756 are introduced into the channel segment 1752 and/or the relative flow rates of the fluids in the channel segment 1752 and the separate channel. In some instances, the particles 1756 can be introduced into the channel segment 1752 from a plurality of different channels, and the frequency controlled accordingly. In some instances, different particles may be introduced via separate channels. For example, a first separate channel can introduce beads and a second separate channel can introduce biological particles into the channel segment 1752. The first separate channel introducing the beads may be upstream or downstream of the second separate channel introducing the biological particles.

In some instances, the second fluid 1762 may not be subjected to and/or directed to any flow in or out of the reservoir 1754. For example, the second fluid 1762 may be substantially stationary in the reservoir 1754. In some instances, the second fluid 1762 may be subjected to flow within the reservoir 1754, but not in or out of the reservoir 1754, such as via application of pressure to the reservoir 1754 and/or as affected by the incoming flow of the aqueous fluid 1760 at the junction 1758. Alternatively, the second fluid 1762 may be subjected and/or directed to flow in or out of the reservoir 1754. For example, the reservoir 1754 can be a channel directing the second fluid 1762 from upstream to downstream, transporting the generated droplets.

The channel structure 1750 at or near the junction 1758 may have certain geometric features that at least partly determine the sizes and/or shapes of the droplets formed by the channel structure 1750. The channel segment 1752 can have a first cross-section height, h1, and the reservoir 1754 can have a second cross-section height, h2. The first cross-section height, h1, and the second cross-section height, h2, may be different, such that at the junction 1758, there is a height difference of Δh. The second cross-section height, h2, may be greater than the first cross-section height, h1. In some instances, the reservoir may thereafter gradually increase in cross-section height, for example, the more distant it is from the junction 1758. In some instances, the cross-section height of the reservoir may increase in accordance with expansion angle, β, at or near the junction 1758. The height difference, Δh, and/or expansion angle, β, can allow the tongue (portion of the aqueous fluid 1760 leaving channel segment 1752 at junction 1758 and entering the reservoir 1754 before droplet formation) to increase in depth and facilitate decrease in curvature of the intermediately formed droplet. For example, droplet size may decrease with increasing height difference and/or increasing expansion angle.

The height difference, Δh, can be at least about 1 µm. Alternatively, the height difference can be at least about 1, 2, 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500 µm or more. Alternatively, the height difference can be at most about 500, 400, 300, 200, 100, 90, 80, 70, 60, 50, 45, 40, 35, 30, 25, 20, 19, 18, 17, 16, 15, 14, 13, 12, 11, 10, 9, 8, 7, 6, 5, 4, 3, 2, 1 µm or less. In some instances, the expansion angle, β, may be between a range of from about 0.50 to about 4°, from about 0.1° to about 10°, or from about 0° to about 90°. For example, the expansion angle can be at least about 0.01°, 0.1°, 0.2°, 0.3°, 0.4°, 0.5°, 0.6°, 0.7°, 0.8°, 0.9°, 10, 2°, 3°, 4°, 5°, 6°, 7°, 8°, 9°, 10°, 15°, 20°, 25°, 30°, 35°, 40°, 45°, 50°, 55°, 60°, 65°, 70°, 75°, 80°, 85°, or higher. In some instances, the expansion angle can be at most about 89°, 88°, 87°, 86°, 85°, 84°, 83°, 82°, 81°, 80°, 75°, 70°, 65°, 60°, 55°, 50°, 45°, 40°, 35°, 30°, 25°, 20°, 15°, 10°, 9°, 8°, 7°, 6°, 5°, 4°, 3°, 2°, 1°, 0.1°, 0.01°, or less.

In some instances, the flow rate of the aqueous fluid 1760 entering the junction 1758 can be between about 0.04 microliters (µL)/minute (min) and about 40 µL/min. In some instances, the flow rate of the aqueous fluid 1760 entering the junction 1758 can be between about 0.01 microliters (µL)/minute (min) and about 100 µL/min. Alternatively, the flow rate of the aqueous fluid 1760 entering the junction 1758 can be less than about 0.01 µL/min. alternatively, the flow rate of the aqueous fluid 1760 entering the junction 1758 can be greater than about 40 µL/min, such as 45 µL/min, 50 µL/min, 55 µL/min, 60 µL/min, 65 µL/min, 70 µL/min, 75 µL/min, 80 µL/min, 85 µL/min, 90 µL/min, 95 µL/min, 100 µL/min, 110 µL/min, 120 µL/min, 130 µL/min, 140 µL/min, 150 µL/min, or greater. At lower flow rates, such as flow rates of about less than or equal to 10 microliters/minute, the droplet radius may not be dependent on the flow rate of the aqueous fluid 1760 entering the junction 1758. The second fluid 1762 may be stationary, or substantially stationary, in the reservoir 1754. Alternatively, the second fluid 1762 may be flowing, such as at the above flow rates described for the aqueous fluid 1760.

While FIG. 17B illustrates the height difference, Δh, being abrupt at the junction 1758 (e.g., a step increase), the height difference may increase gradually (e.g., from about 0 µm to a maximum height difference). Alternatively, the height difference may decrease gradually (e.g., taper) from a maximum height difference. A gradual increase or decrease in height difference, as used herein, may refer to a continuous incremental increase or decrease in height difference, wherein an angle between any one differential segment of a height profile and an immediately adjacent differential segment of the height profile is greater than 90°. For example, at the junction 1758, a bottom wall of the channel and a bottom wall of the reservoir can meet at an angle greater than 90°. Alternatively or in addition, a top wall (e.g., ceiling) of the channel and a top wall (e.g., ceiling) of the reservoir can meet an angle greater than 90°. A gradual increase or decrease may be linear or non-linear (e.g., exponential, sinusoidal, etc.). Alternatively or in addition, the height difference may variably increase and/or decrease linearly or non-linearly. While FIG. 17B illustrates the expanding reservoir cross-section height as linear (e.g., constant expansion angle, β), the cross-section height may expand non-linearly. For example, the reservoir may be defined at least partially by a dome-like (e.g., hemispherical) shape having variable expansion angles. The cross-section height may expand in any shape.

A variety of different beads can be incorporated into partitions as described above. In some embodiments, for example, non-barcoded beads can be incorporated into the partitions. For example, where the biological particle (e.g., a cell) that is incorporated into the partitions carries one or more barcodes (e.g., spatial barcode(s), UMI(s), and combinations thereof), the bead can be a non-barcoded bead.

In some embodiments, a barcode carrying bead can be incorporated into partitions. For example, a nucleic acid molecule, such as an oligonucleotide, can be coupled to a bead by a releasable linkage, such as, for example, a disulfide linker. The same bead can be coupled (e.g., via releasable linkage) to one or more other nucleic acid molecules. The nucleic acid molecule can be or include a barcode. As noted elsewhere herein, the structure of the barcode can include a number of sequence elements.

The nucleic acid molecule can include a functional domain that can be used in subsequent processing. For example, the functional domain can include one or more of a sequencer specific flow cell attachment sequence (e.g., a P5 sequence for Illumina® sequencing systems) and a sequencing primer sequence (e.g., a R1 primer for Illumina® sequencing systems). The nucleic acid molecule can include a barcode sequence for use in barcoding the sample (e.g., DNA, RNA, protein, etc.). In some cases, the barcode sequence can be bead-specific such that the barcode sequence is common to all nucleic acid molecules coupled to the same bead. Alternatively or in addition, the barcode sequence can be partition-specific such that the barcode sequence is common to all nucleic acid molecules coupled to one or more beads that are partitioned into the same partition. The nucleic acid molecule can include a specific priming sequence, such as an mRNA specific priming sequence (e.g., poly(T) sequence), a targeted priming sequence, and/or a random priming sequence. The nucleic acid molecule can include an anchoring sequence to ensure that the specific priming sequence hybridizes at the sequence end (e.g., of the mRNA). For example, the anchoring sequence can include a random short sequence of nucleotides, such as a 1-mer, 2-mer, 3-mer or longer sequence, which can ensure that a poly(T) segment is more likely to hybridize at the sequence end of the poly(A) tail of the mRNA.

The nucleic acid molecule can include a unique molecular identifying sequence (e.g., unique molecular identifier (UMI)). In some embodiments, the unique molecular identifying sequence can include from about 5 to about 8 nucleotides. Alternatively, the unique molecular identifying sequence can include less than about 5 or more than about 8 nucleotides. The unique molecular identifying sequence can be a unique sequence that varies across individual nucleic acid molecules coupled to a single bead.

In some embodiments, the unique molecular identifying sequence can be a random sequence (e.g., such as a random N-mer sequence). For example, the UMI can provide a unique identifier of the starting mRNA molecule that was captured, in order to allow quantitation of the number of original expressed RNA.

In general, an individual bead can be coupled to any number of individual nucleic acid molecules, for example, from one to tens to hundreds of thousands or even millions of individual nucleic acid molecules. The respective barcodes for the individual nucleic acid molecules can include both common sequence segments or relatively common sequence segments and variable or unique sequence segments between different individual nucleic acid molecules coupled to the same bead.

Figure 17C:
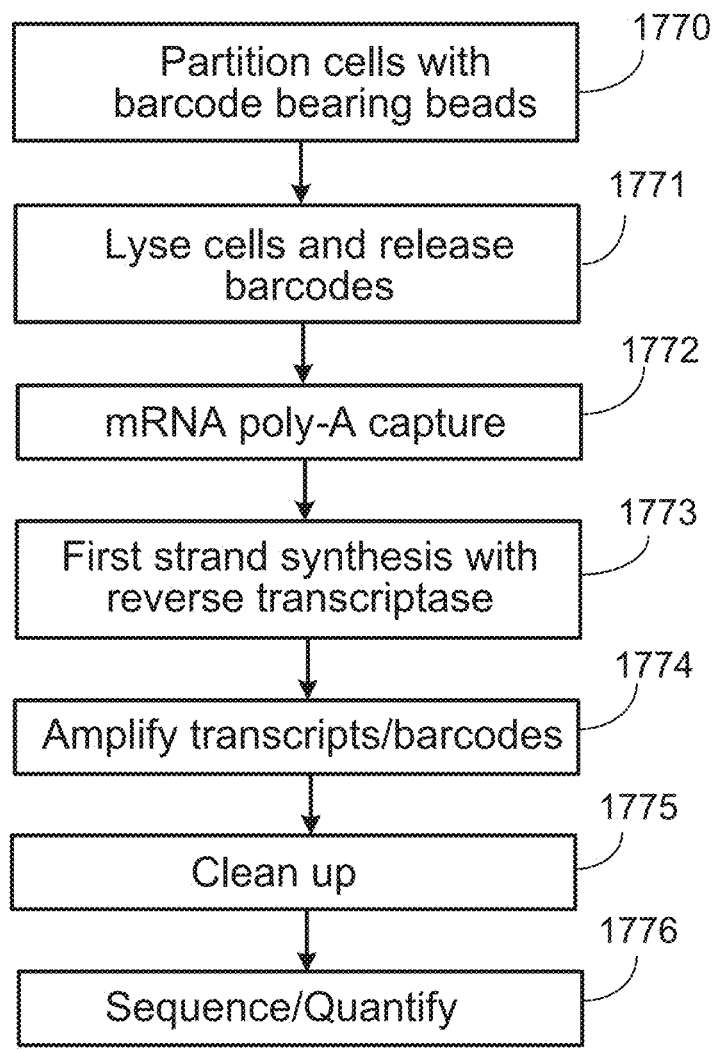
FIG. 17C shows a workflow schematic.

FIG. 17C depicts a workflow wherein cells are partitioned into droplets along with barcode-bearing beads 1770. See FIG. 17A. The droplet forms an isolated reaction chamber wherein the cells can be lysed 1771 and target analytes within the cells can then be captured 1772 and amplified 1773, 1774 according to previously described methods. After sequence library preparation clean-up 1775, the material is sequenced and/or quantified 1776 according to methods described herein.

It should be noted that while the example workflow in FIG. 17C includes steps specifically for the analysis of mRNA, analogous workflows can be implemented for a wide variety of other analytes, including any of the analytes described previously.

By way of example, in the context of analyzing sample RNA as shown in FIG. 17C, the poly(T) segment of one of the released nucleic acid molecules (e.g., from the bead) can hybridize to the poly(A) tail of a mRNA molecule. Reverse transcription can result in a cDNA transcript of the mRNA, which transcript includes each of the sequence segments of the nucleic acid molecule. If the nucleic acid molecule includes an anchoring sequence, it will more likely hybridize to and prime reverse transcription at the sequence end of the poly(A) tail of the mRNA.

Within any given partition, all of the cDNA transcripts of the individual mRNA molecules can include a common barcode sequence segment. However, the transcripts made from the different mRNA molecules within a given partition can vary at the unique molecular identifying sequence segment (e.g., UMI segment). Beneficially, even following any subsequent amplification of the contents of a given partition, the number of different UMIs can be indicative of the quantity of mRNA originating from a given partition. As noted above, the transcripts can be amplified, cleaned up and sequenced to identify the sequence of the cDNA transcript of the mRNA, as well as to sequence the barcode segment and the UMI segment. While a poly(T) primer sequence is described, other targeted or random priming sequences can also be used in priming the reverse transcription reaction. Likewise, although described as releasing the barcoded oligonucleotides into the partition, in some cases, the nucleic acid molecules bound to the bead can be used to hybridize and capture the mRNA on the solid phase of the bead, for example, in order to facilitate the separation of the RNA from other cell contents.

In some embodiments, precursors that include a functional group that is reactive or capable of being activated such that it becomes reactive can be polymerized with other precursors to generate gel beads that include the activated or activatable functional group. The functional group can then be used to attach additional species (e.g., disulfide linkers, primers, other oligonucleotides, etc.) to the gel beads. For example, some precursors featuring a carboxylic acid (COOH) group can co-polymerize with other precursors to form a bead that also includes a COOH functional group. In some cases, acrylic acid (a species comprising free COOH groups), acrylamide, and bis(acryloyl)cystamine can be co-polymerized together to generate a bead with free COOH groups. The COOH groups of the bead can be activated (e.g., via 1-Ethyl-3-(3-dimethylaminopropyl)carbodiimide (EDC) and N-Hydroxysuccinimide (NHS) or 4-(4,6-Dimethoxy-1,3,5-triazin-2-yl)-4-methylmorpholinium chloride (DMTMM)) such that they are reactive (e.g., reactive to amine functional groups where EDC/NHS or DMTMM are used for activation). The activated COOH groups can then react with an appropriate species (e.g., a species comprising an amine functional group where the carboxylic acid groups are activated to be reactive with an amine functional group) comprising a moiety to be linked to the bead.

In some embodiments, a degradable bead can be introduced into a partition, such that the bead degrades within the partition and any associated species (e.g., oligonucleotides) are released within the droplet when the appropriate stimulus is applied. The free species (e.g., oligonucleotides, nucleic acid molecules) can interact with other reagents contained in the partition. For example, a polyacrylamide bead featuring cystamine and linked, via a disulfide bond, to a barcode sequence, can be combined with a reducing agent within a droplet of a water-in-oil emulsion. Within the droplet, the reducing agent can break the various disulfide bonds, resulting in bead degradation and release of the barcode sequence into the aqueous, inner environment of the droplet. In another example, heating of a droplet with a bead-bound barcode sequence in basic solution can also result in bead degradation and release of the attached barcode sequence into the aqueous, inner environment of the droplet.

Any suitable number of species (e.g., primer, barcoded oligonucleotide) can be associated with a bead such that, upon release from the bead, the species (e.g., primer, e.g., barcoded oligonucleotide) are present in the partition at a pre-defined concentration. Such pre-defined concentration can be selected to facilitate certain reactions for generating a sequencing library, e.g., amplification, within the partition. In some cases, the pre-defined concentration of the primer can be limited by the process of producing nucleic acid molecule (e.g., oligonucleotide) bearing beads.

A degradable bead can include one or more species with a labile bond such that, when the bead/species is exposed to the appropriate stimulus, the bond is broken and the bead degrades. The labile bond can be a chemical bond (e.g., covalent bond, ionic bond) or can be another type of physical interaction (e.g., van der Waals interactions, dipole-dipole interactions, etc.) In some embodiments, a crosslinker used to generate a bead can include a labile bond. Upon exposure to the appropriate conditions, the labile bond can be broken and the bead degraded. For example, upon exposure of a polyacrylamide gel bead that includes cysta-mine crosslinkers to a reducing agent, the disulfide bonds of the cystamine can be broken and the bead degraded.

A degradable bead can be useful in more quickly releasing an attached species (e.g., a nucleic acid molecule, a barcode sequence, a primer, etc.) from the bead when the appropriate stimulus is applied to the bead as compared to a bead that does not degrade. For example, for a species bound to an inner surface of a porous bead or in the case of an encapsulated species, the species can have greater mobility and accessibility to other species in solution upon degradation of the bead. In some embodiments, a species can also be attached to a degradable bead via a degradable linker (e.g., disulfide linker). The degradable linker can respond to the same stimuli as the degradable bead or the two degradable species can respond to different stimuli. For example, a barcode sequence can be attached, via a disulfide bond, to a polyacrylamide bead comprising cystamine. Upon exposure of the barcoded-bead to a reducing agent, the bead degrades and the barcode sequence is released upon breakage of both the disulfide linkage between the barcode sequence and the bead and the disulfide linkages of the cystamine in the bead.

As will be appreciated from the above description, while referred to as degradation of a bead, in many embodiments, degradation can refer to the disassociation of a bound or entrained species from a bead, both with and without structurally degrading the physical bead itself. For example, entrained species can be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In some embodiments, osmotic shrinking of a bead can cause a bead to better retain an entrained species due to pore size contraction. Numerous chemical triggers can be used to trigger the degradation of beads within partitions. Examples of these chemical changes can include, but are not limited to pH-mediated changes to the integrity of a component within the bead, degradation of a component of a bead via cleavage of cross-linked bonds, and depolymerization of a component of a bead.

In some embodiments, a bead can be formed from materials that include degradable chemical cross-linkers, such as BAC or cystamine. Degradation of such degradable cross-linkers can be accomplished through a number of mechanisms. In some examples, a bead can be contacted with a chemical degrading agent that can induce oxidation, reduction or other chemical changes. For example, a chemical degrading agent can be a reducing agent, such as dithiothreitol (DTT). Additional examples of reducing agents can include β-mercaptoethanol, (2S)-2-amino-1,4-dimercaptobutane (dithiobutylamine or DTBA), tris(2-carboxyethyl)phosphine (TCEP), or combinations thereof. A reducing agent can degrade the disulfide bonds formed between gel precursors forming the bead, and thus, degrade the bead.

In certain embodiments, a change in pH of a solution, such as an increase in pH, can trigger degradation of a bead. In other embodiments, exposure to an aqueous solution, such as water, can trigger hydrolytic degradation, and thus degradation of the bead. In some cases, any combination of stimuli can trigger degradation of a bead. For example, a change in pH can enable a chemical agent (e.g., DTT) to become an effective reducing agent.

Beads can also be induced to release their contents upon the application of a thermal stimulus. A change in temperature can cause a variety of changes to a bead. For example, heat can cause a solid bead to liquefy. A change in heat can cause melting of a bead such that a portion of the bead degrades. In other cases, heat can increase the internal pressure of the bead components such that the bead ruptures or explodes. Heat can also act upon heat-sensitive polymers used as materials to construct beads.

In addition to beads and analytes, partitions that are formed can include a variety of different reagents and species. For example, when lysis reagents are present within the partitions, the lysis reagents can facilitate the release of analytes within the partition. Examples of lysis agents include bioactive reagents, such as lysis enzymes that are used for lysis of different cell types, e.g., gram positive or negative bacteria, plants, yeast, mammalian, etc., such as lysozymes, achromopeptidase, lysostaphin, labiase, kitalase, lyticase, and a variety of other lysis enzymes available from, e.g., Sigma-Aldrich, Inc. (St. Louis, MO), as well as other commercially available lysis enzymes. Other lysis agents can additionally or alternatively be co-partitioned to cause the release analytes into the partitions. For example, in some cases, surfactant-based lysis solutions can be used to lyse cells, although these can be less desirable for emulsion based systems where the surfactants can interfere with stable emulsions. In some embodiments, lysis solutions can include non-ionic surfactants such as, for example, TritonX-100 and Tween 20. In some embodiments, lysis solutions can include ionic surfactants such as, for example, sarcosyl and sodium dodecyl sulfate (SDS). Electroporation, thermal, acoustic or mechanical cellular disruption can also be used in certain embodiments, e.g., non-emulsion based partitioning such as encapsulation of analytes that can be in addition to or in place of droplet partitioning, where any pore size of the encapsulate is sufficiently small to retain nucleic acid fragments of a given size, following cellular disruption.

Examples of other species that can be co-partitioned with analytes in the partitions include, but are not limited to, DNase and RNase inactivating agents or inhibitors, such as proteinase K, chelating agents, such as EDTA, and other reagents employed in removing or otherwise reducing negative activity or impact of different cell lysate components on subsequent processing of nucleic acids. Additional reagents can also be co-partitioned, including endonucleases to fragment DNA, DNA polymerase enzymes and dNTPs used to amplify nucleic acid fragments and to attach the barcode molecular tags to the amplified fragments.

Additional reagents can also include reverse transcriptase enzymes, including enzymes with terminal transferase activity, primers and oligonucleotides, and switch oligonucleotides (also referred to herein as "switch oligos" or "template switching oligonucleotides") which can be used for template switching. In some embodiments, template switching can be used to increase the length of a cDNA. Template switching can be used to append a predefined nucleic acid sequence to the cDNA. In an example of template switching, cDNA can be generated from reverse transcription of a template, e.g., cellular mRNA, where a reverse transcriptase with terminal transferase activity can add additional nucleotides, e.g., poly(C), to the cDNA in a template independent manner. Switch oligos can include sequences complementary to the additional nucleotides, e.g., poly(G). The additional nucleotides (e.g., poly(C)) on the cDNA can hybridize to the additional nucleotides (e.g., poly(G)) on the switch oligo, whereby the switch oligo can be used by the reverse transcriptase as template to further extend the cDNA. Template switching oligonucleotides can include a hybridization region and a template region. The hybridization region can include any sequence capable of hybridizing to the target. In some cases, the hybridization region includes a series of G bases to complement the overhanging C bases at the 3' end of a cDNA molecule. The series of G bases can include 1 G base, 2 G bases, 3 G bases, 4 G bases, 5 G bases or more than 5 G bases. The template sequence can include any sequence to be incorporated into the cDNA. In some cases, the template region includes at least 1 (e.g., at least 2, 3, 4, 5 or more) tag sequences and/or functional sequences. Switch oligos can include deoxyribonucleic acids; ribonucleic acids; bridged nucleic acids, modified nucleic acids including 2-Aminopurine, 2,6-Diaminopurine (2-Amino-dA), inverted dT, 5-Methyl dC, 2'-deoxyInosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' Fluoro bases (e.g., Fluoro C, Fluoro U, Fluoro A, and Fluoro G), and combinations of the foregoing.

In some embodiments, beads that are partitioned with the analyte can include different types of oligonucleotides bound to the bead, where the different types of oligonucleotides bind to different types of analytes. For example, a bead can include one or more first oligonucleotides (which can be capture probes, for example) that can bind or hybridize to a first type of analyte, such as mRNA for example, and one or more second oligonucleotides (which can be capture probes, for example) that can bind or hybridize to a second type of analyte, such as gDNA for example. Partitions can also include lysis agents that aid in releasing nucleic acids from the co-partitioned cell, and can also include an agent (e.g., a reducing agent) that can degrade the bead and/or break covalent linkages between the oligonucleotides and the bead, releasing the oligonucleotides into the partition. The released barcoded oligonucleotides (which can also be barcoded) can hybridize with mRNA released from the cell and also with gDNA released from the cell.

Barcoded constructs thus formed from hybridization can include a first type of construct that includes a sequence corresponding to an original barcode sequence from the bead and a sequence corresponding to a transcript from the cell, and a second type of construct that includes a sequence corresponding to the original barcode sequence from the bead and a sequence corresponding to genomic DNA from the cell. The barcoded constructs can then be released/removed from the partition and, in some embodiments, further processed to add any additional sequences. The resulting constructs can then be sequenced, the sequencing data processed, and the results used to spatially characterize the mRNA and the gDNA from the cell.

In another example, a partition includes a bead that includes a first type of oligonucleotide (e.g., a first capture probe) with a first barcode sequence, a poly(T) priming sequence that can hybridize with the poly(A) tail of an mRNA transcript, and a UMI barcode sequence that can uniquely identify a given transcript. The bead also includes a second type of oligonucleotide (e.g., a second capture probe) with a second barcode sequence, a targeted priming sequence that is capable of specifically hybridizing with a third barcoded oligonucleotide (e.g., an analyte capture agent) coupled to an antibody that is bound to the surface of the partitioned cell. The third barcoded oligonucleotide includes a UMI barcode sequence that uniquely identifies the antibody (and thus, the particular cell surface feature to which it is bound).

In this example, the first and second barcoded oligonucleotides include the same spatial barcode sequence (e.g., the first and second barcode sequences are the same), which permits downstream association of barcoded nucleic acids with the partition. In some embodiments, however, the first and second barcode sequences are different.

The partition also includes lysis agents that aid in releasing nucleic acids from the cell and can also include an agent (e.g., a reducing agent) that can degrade the bead and/or break a covalent linkage between the barcoded oligonucleotides and the bead, releasing them into the partition. The first type of released barcoded oligonucleotide can hybridize with mRNA released from the cell and the second type of released barcoded oligonucleotide can hybridize with the third type of barcoded oligonucleotide, forming barcoded constructs.

The first type of barcoded construct includes a spatial barcode sequence corresponding to the first barcode sequence from the bead and a sequence corresponding to the UMI barcode sequence from the first type of oligonucleotide, which identifies cell transcripts. The second type of barcoded construct includes a spatial barcode sequence corresponding to the second barcode sequence from the second type of oligonucleotide, and a UMI barcode sequence corresponding to the third type of oligonucleotide (e.g., the analyte capture agent) and used to identify the cell surface feature. The barcoded constructs can then be released/removed from the partition and, in some embodiments, further processed to add any additional sequences. The resulting constructs are then sequenced, sequencing data processed, and the results used to characterize the mRNA and cell surface feature of the cell.

The foregoing discussion involves two specific examples of beads with oligonucleotides for analyzing two different analytes within a partition. More generally, beads that are partitioned can have any of the structures described previously, and can include any of the described combinations of oligonucleotides for analysis of two or more (e.g., three or more, four or more, five or more, six or more, eight or more, ten or more, 12 or more, 15 or more, 20 or more, 25 or more, 30 or more, 40 or more, 50 or more) different types of analytes within a partition. Examples of beads with combinations of different types of oligonucleotides (e.g., capture probes) for concurrently analyzing different combinations of analytes within partitions include, but are not limited to: (a) genomic DNA and cell surface features (e.g., using the analyte capture agents described herein); (b) mRNA and a lineage tracing construct; (c) mRNA and cell methylation status; (d) mRNA and accessible chromatin (e.g., ATAC-seq, DNase-seq, and/or MNase-seq); (e) mRNA and cell surface or intracellular proteins and/or metabolites; (f) a barcoded analyte capture agent (e.g., the MHC multimers described herein) and a V(D)J sequence of an immune cell receptor (e.g., T-cell receptor); and (g) mRNA and a perturbation agent (e.g., a CRISPR crRNA/sgRNA, TALEN, zinc finger nuclease, and/or antisense oligonucleotide as described herein).

Additionally, in some embodiments, the unaggregated cell or disaggregated cells introduced and processed within partitions or droplets as described herein, can be removed from the partition, contacted with a spatial array, and spatially barcoded according to methods described herein. For example, single cells of an unaggregated cell sample can be partitioned into partitions or droplets as described herein. The partitions or droplets can include reagents to permeabilize a cell, barcode targeted cellular analyte(s) with a cellular barcode, and amplify the barcoded analytes. The partitions or droplets can be contacted with any of the spatial arrays described herein. In some embodiments, the partition can be dissolved, such that the contents of the partition are placed in contact with the capture probes of the spatial array. The capture probes of the spatial array can then capture target analytes from the ruptured partitions or the droplets, and processed by the spatial workflows described herein.

(g) Analysis of Captured Analytes

Removal of Sample from Array

In some embodiments, after contacting a biological sample with a substrate that includes capture probes, a removal step can optionally be performed to remove all or a portion of the biological sample from the substrate. In some embodiments, the removal step includes enzymatic and/or chemical degradation of cells of the biological sample. For example, the removal step can include treating the biological sample with an enzyme (e.g., a proteinase, e.g., proteinase K) to remove at least a portion of the biological sample from the substrate. In some embodiments, the removal step can include ablation of the tissue (e.g., laser ablation).

In some embodiments, provided herein are methods for spatially detecting an analyte (e.g., detecting the location of an analyte, e.g., a biological analyte) from a biological sample (e.g., present in a biological sample), the method comprising: (a) optionally staining and/or imaging a biological sample on a substrate; (b) permeabilizing (e.g., providing a solution comprising a permeabilization reagent to) the biological sample on the substrate; (c) contacting the biological sample with an array comprising a plurality of capture probes, wherein a capture probe of the plurality captures the biological analyte; and (d) analyzing the captured biological analyte, thereby spatially detecting the biological analyte; wherein the biological sample is fully or partially removed from the substrate.

In some embodiments, a biological sample is not removed from the substrate. For example, the biological sample is not removed from the substrate prior to releasing a capture probe (e.g., a capture probe bound to an analyte) from the substrate. In some embodiments, such releasing comprises cleavage of the capture probe from the substrate (e.g., via a cleavage domain). In some embodiments, such releasing does not comprise releasing the capture probe from the substrate (e.g., a copy of the capture probe bound to an analyte can be made and the copy can be released from the substrate, e.g., via denaturation). In some embodiments, the biological sample is not removed from the substrate prior to analysis of an analyte bound to a capture probe after it is released from the substrate. In some embodiments, the biological sample remains on the substrate during removal of a capture probe from the substrate and/or analysis of an analyte bound to the capture probe after it is released from the substrate. In some embodiments, analysis of an analyte bound to capture probe from the substrate can be performed without subjecting the biological sample to enzymatic and/or chemical degradation of the cells (e.g., permeabilized cells) or ablation of the tissue (e.g., laser ablation).

In some embodiments, at least a portion of the biological sample is not removed from the substrate. For example, a portion of the biological sample can remain on the substrate prior to releasing a capture probe (e.g., a capture prove bound to an analyte) from the substrate and/or analyzing an analyte bound to a capture probe released from the substrate. In some embodiments, at least a portion of the biological sample is not subjected to enzymatic and/or chemical degradation of the cells (e.g., permeabilized cells) or ablation of the tissue (e.g., laser ablation) prior to analysis of an analyte bound to a capture probe from the substrate.

In some embodiments, provided herein are methods for spatially detecting an analyte (e.g., detecting the location of an analyte, e.g., a biological analyte) from a biological sample (e.g., present in a biological sample) that include: (a) optionally staining and/or imaging a biological sample on a substrate; (b) permeabilizing (e.g., providing a solution comprising a permeabilization reagent to) the biological sample on the substrate; (c) contacting the biological sample with an array comprising a plurality of capture probes, wherein a capture probe of the plurality captures the biological analyte; and (d) analyzing the captured biological analyte, thereby spatially detecting the biological analyte; where the biological sample is not removed from the substrate.

In some embodiments, provided herein are methods for spatially detecting a biological analyte of interest from a biological sample that include: (a) staining and imaging a biological sample on a substrate; (b) providing a solution comprising a permeabilization reagent to the biological sample on the substrate; (c) contacting the biological sample with an array on a substrate, wherein the array comprises one or more capture probe pluralities thereby allowing the one or more pluralities of capture probes to capture the biological analyte of interest; and (d) analyzing the captured biological analyte, thereby spatially detecting the biological analyte of interest; where the biological sample is not removed from the substrate.

In some embodiments, the method further includes selecting a region of interest in the biological sample to subject to spatial transcriptomic analysis. In some embodiments, one or more of the one or more capture probes include a capture domain. In some embodiments, one or more of the one or more capture probe pluralities comprise a unique molecular identifier (UMI). In some embodiments, one or more of the one or more capture probe pluralities comprise a cleavage domain. In some embodiments, the cleavage domain comprises a sequence recognized and cleaved by a uracil-DNA glycosylase, apurinic/apyrimidinic (AP) endonuclease (APE1), U uracil-specific excision reagent (USER), and/or an endonuclease VIII. In some embodiments, one or more capture probes do not comprise a cleavage domain and is not cleaved from the array.

A set of experiments performed determined methods that did not remove the biological sample from the substrate yielded higher quality sequencing data, higher median genes per cell, and higher median UMI counts per cell compared to a similar methods where the biological sample was removed from the substrate (data not shown).

In some embodiments, a capture probe can be extended. For example, extending a capture probe can includes generating cDNA from a captured (hybridized) RNA. This process involves synthesis of a complementary strand of the hybridized nucleic acid, e.g., generating cDNA based on the captured RNA template (the RNA hybridized to the capture domain of the capture probe). Thus, in an initial step of extending a capture probe, e.g., the cDNA generation, the captured (hybridized) nucleic acid, e.g., RNA, acts as a template for the extension, e.g., reverse transcription, step.

In some embodiments, the capture probe is extended using reverse transcription. For example, reverse transcription includes synthesizing cDNA (complementary or copy DNA) from RNA, e.g., (messenger RNA), using a reverse transcriptase. In some embodiments, reverse transcription is performed while the tissue is still in place, generating an analyte library, where the analyte library includes the spatial barcodes from the adjacent capture probes. In some embodiments, the capture probe is extended using one or more DNA polymerases.

In some embodiments, a capture domain of a capture probe includes a primer for producing the complementary strand of a nucleic acid hybridized to the capture probe, e.g., a primer for DNA polymerase and/or reverse transcription. The nucleic acid, e.g., DNA and/or cDNA, molecules generated by the extension reaction incorporate the sequence of the capture probe. The extension of the capture probe, e.g., a DNA polymerase and/or reverse transcription reaction, can be performed using a variety of suitable enzymes and protocols.

In some embodiments, a full-length DNA, e.g. cDNA, molecule is generated. In some embodiments, a "full-length" DNA molecule refers to the whole of the captured nucleic acid molecule. However, if the nucleic acid, e.g. RNA, was partially degraded in the tissue sample, then the captured nucleic acid molecules will not be the same length as the initial RNA in the tissue sample. In some embodiments, the 3' end of the extended probes, e.g., first strand cDNA molecules, is modified. For example, a linker or adaptor can be ligated to the 3' end of the extended probes. This can be achieved using single stranded ligation enzymes such as T4 RNA ligase or Circligase™ (available from Epicentre Biotechnologies, Madison, WI). In some embodiments, template switching oligonucleotides are used to extend cDNA in order to generate a full-length cDNA (or as close to a full-length cDNA as possible). In some embodiments, a second strand synthesis helper probe (a partially double stranded DNA molecule capable of hybridizing to the 3' end of the extended capture probe), can be ligated to the 3' end of the extended probe, e.g., first strand cDNA, molecule using a double stranded ligation enzyme such as T4 DNA ligase. Other enzymes appropriate for the ligation step are known in the art and include, e.g., Tth DNA ligase, Taq DNA ligase, *Thermococcus* sp. (strain 9° N) DNA ligase (9° N™ DNA ligase, New England Biolabs), Ampligase™ (available from Epicentre Biotechnologies, Madison, WI), and SplintR (available from New England Biolabs, Ipswich, MA). In some embodiments, a polynucleotide tail, e.g., a poly(A) tail, is incorporated at the 3' end of the extended probe molecules. In some embodiments, the polynucleotide tail is incorporated using a terminal transferase active enzyme.

In some embodiments, double-stranded extended capture probes are treated to remove any unextended capture probes prior to amplification and/or analysis, e.g. sequence analysis. This can be achieved by a variety of methods, e.g., using an enzyme to degrade the unextended probes, such as an exonuclease enzyme, or purification columns.

In some embodiments, extended capture probes are amplified to yield quantities that are sufficient for analysis, e.g., via DNA sequencing. In some embodiments, the first strand of the extended capture probes (e.g., DNA and/or cDNA molecules) acts as a template for the amplification reaction (e.g., a polymerase chain reaction).

In some embodiments, the amplification reaction incorporates an affinity group onto the extended capture probe (e.g., RNA-cDNA hybrid) using a primer including the affinity group. In some embodiments, the primer includes an affinity group and the extended capture probes includes the affinity group. The affinity group can correspond to any of the affinity groups described previously.

In some embodiments, the extended capture probes including the affinity group can be coupled to a substrate specific for the affinity group. In some embodiments, the substrate can include an antibody or antibody fragment. In some embodiments, the substrate includes avidin or streptavidin and the affinity group includes biotin. In some embodiments, the substrate includes maltose and the affinity group includes maltose-binding protein. In some embodiments, the substrate includes maltose-binding protein and the affinity group includes maltose. In some embodiments, amplifying the extended capture probes can function to release the extended probes from the surface of the substrate, insofar as copies of the extended probes are not immobilized on the substrate.

In some embodiments, the extended capture probe or complement or amplicon thereof is released. The step of releasing the extended capture probe or complement or amplicon thereof from the surface of the substrate can be achieved in a number of ways. In some embodiments, an extended capture probe or a complement thereof is released from the array by nucleic acid cleavage and/or by denaturation (e.g. by heating to denature a double-stranded molecule).

In some embodiments, the extended capture probe or complement or amplicon thereof is released from the surface of the substrate (e.g., array) by physical means. For example, where the extended capture probe is indirectly immobilized on the array substrate, e.g. via hybridization to a surface probe, it can be sufficient to disrupt the interaction between the extended capture probe and the surface probe. Methods for disrupting the interaction between nucleic acid molecules include denaturing double stranded nucleic acid molecules art. A straightforward method for releasing the DNA molecules (i.e., of stripping the array of the extended probes) is to use a solution that interferes with the hydrogen bonds of the double stranded molecules. In some embodiments, the extended capture probe is released by applying heated water such as water or buffer of at least 85° C., e.g., at least 90, 91, 92, 93, 94, 95, 96, 97, 98, or 99° C. In some embodiments, a solution including salts, surfactants, etc. that can further destabilize the interaction between the nucleic acid molecules is added to release the extended capture probe from the substrate.

In some embodiments, where the extended capture probe includes a cleavage domain, the extended capture probe is released from the surface of the substrate by cleavage. For example, the cleavage domain of the extended capture probe can be cleaved by any of the methods described herein. In some embodiments, the extended capture probe is released from the surface of the substrate, e.g., via cleavage of a cleavage domain in the extended capture probe, prior to the step of amplifying the extended capture probe.

Capture probes can optionally include a "cleavage domain," where one or more segments or regions of the capture probe (e.g., spatial barcodes and/or UMIs) can be releasably, cleavably, or reversibly attached to a feature, or some other substrate, so that spatial barcodes and/or UMIs can be released or be releasable through cleavage of a linkage between the capture probe and the feature, or released through degradation of the underlying support, allowing the spatial barcode(s) and/or UMI(s) of the cleaved capture probe to be accessed or be accessible by other reagents, or both.

In some embodiments, the capture probe is linked, via a disulfide bond, to a feature. In some embodiments, the capture probe is linked to a feature via a propylene group (e.g., Spacer C3). A reducing agent can be added to break the various disulfide bonds, resulting in release of the capture probe including the spatial barcode sequence. In another example, heating can also result in degradation and release of the attached capture probe. In some embodiments, the heating is done by laser (e.g., laser ablation) and features at specific locations can be degraded. In addition to thermally cleavable bonds, disulfide bonds, photo-sensitive bonds, and UV sensitive bonds, other non-limiting examples of labile bonds that can be coupled to a capture probe (i.e., spatial barcode) include an ester linkage (e.g., cleavable with an acid, a base, or hydroxylamine), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), or a phosphodiester linkage (e.g., cleavable via a nuclease (e.g., DNAase)).

In some embodiments, the cleavage domain includes a sequence that is recognized by one or more enzymes capable of cleaving a nucleic acid molecule, e.g., capable of breaking the phosphodiester linkage between two or more nucleotides. A bond can be cleavable via other nucleic acid molecule targeting enzymes, such as restriction enzymes (e.g., restriction endonucleases). For example, the cleavage domain can include a restriction endonuclease (restriction enzyme) recognition sequence. Restriction enzymes cut double-stranded or single stranded DNA at specific recognition nucleotide sequences known as restriction sites. In some embodiments, a rare-cutting restriction enzyme, i.e., enzymes with a long recognition site (at least 8 base pairs in length), is used to reduce the possibility of cleaving elsewhere in the capture probe.

In some embodiments, the cleavage domain includes a poly(U) sequence which can be cleaved by a mixture of Uracil DNA glycosylase (UDG) and the DNA glycosylase-lyase Endonuclease VIII, commercially known as the USER™ enzyme. In some embodiments, the cleavage domain can be a single U. In some embodiments, the cleavage domain can be an abasic site that can be cleaved with an abasic site-specific endonuclease (e.g., Endonucleoase IV or Endonuclease VIII). Releasable capture probes can be available for reaction once released. Thus, for example, an activatable capture probe can be activated by releasing the capture probes from a feature.

In some embodiments, the cleavage domain of the capture probe is a nucleotide sequence within the capture probe that is cleaved specifically, e.g., physically by light or heat, chemically or enzymatically. The location of the cleavage domain within the capture probe will depend on whether or not the capture probe is immobilized on the substrate such that it has a free 3' end capable of functioning as an extension primer (e.g. by its 5' or 3' end). For example, if the capture probe is immobilized by its 5' end, the cleavage domain will be located 5' to the spatial barcode and/or UMI, and cleavage of said domain results in the release of part of the capture probe including the spatial barcode and/or UMI and the sequence 3' to the spatial barcode, and optionally part of the cleavage domain, from a feature. Alternatively, if the capture probe is immobilized by its 3' end, the cleavage domain will be located 3' to the capture domain (and spatial barcode) and cleavage of said domain results in the release of part of the capture probe including the spatial barcode and the sequence 3' to the spatial barcode from a feature. In some embodiments, cleavage results in partial removal of the cleavage domain. In some embodiments, cleavage results in complete removal of the cleavage domain, particularly when the capture probes are immobilized via their 3' end as the presence of a part of the cleavage domain can interfere with the hybridization of the capture domain and the target nucleic acid and/or its subsequent extension.

In some embodiments, where the capture probe is immobilized to the substrate indirectly, e.g., via a surface probe defined below, the cleavage domain includes one or more mismatch nucleotides, so that the complementary parts of the surface probe and the capture probe are not 100% complementary (for example, the number of mismatched base pairs can one, two, or three base pairs). Such a mismatch is recognized, e.g., by the MutY and T7 endonuclease I enzymes, which results in cleavage of the nucleic acid molecule at the position of the mismatch.

In some embodiments, where the capture probe is immobilized to the feature indirectly, e.g., via a surface probe, the cleavage domain includes a nickase recognition site or sequence. In this respect, nickase enzymes cleave only one strand in a nucleic acid duplex. Nickases are endonucleases which cleave only a single strand of a DNA duplex. Thus, the cleavage domain can include a nickase recognition site close to the 5' end of the surface probe (and/or the 5' end of the capture probe) such that cleavage of the surface probe or capture probe destabilizes the duplex between the surface probe and capture probe thereby releasing the capture probe) from the feature.

Nickase enzymes can also be used in some embodiments where the capture probe is immobilized to the feature directly. For example, the substrate can be contacted with a nucleic acid molecule that hybridizes to the cleavage domain of the capture probe to provide or reconstitute a nickase recognition site, e.g., a cleavage helper probe. Thus, contact with a nickase enzyme will result in cleavage of the cleavage domain thereby releasing the capture probe from the feature. Such cleavage helper probes can also be used to provide or reconstitute cleavage recognition sites for other cleavage enzymes, e.g., restriction enzymes.

Some nickases introduce single-stranded nicks only at particular sites on a DNA molecule, by binding to and recognizing a particular nucleotide recognition sequence. A number of naturally-occurring nickases have been discovered, of which at present the sequence recognition properties have been determined for at least four. Nickases are described in U.S. Pat. No. 6,867,028, which is herein incorporated by reference in its entirety. In general, any suitable nickase can be used to bind to a complementary nickase recognition site of a cleavage domain. Following use, the nickase enzyme can be removed from the assay or inactivated following release of the capture probes to prevent unwanted cleavage of the capture probes.

In some embodiments, a cleavage domain for separating spatial barcodes from a feature is absent from the capture probe. For example, a substrate having a capture probe lacking a cleavage domain can be used for spatial analysis (see, e.g., corresponding substrates and probes described Macosko et al., (2015) Cell 161, 1202-1214, the entire contents of which are incorporated herein by reference.

In some embodiments, the region of the capture probe corresponding to the cleavage domain can be used for some other function. For example, an additional region for nucleic acid extension or amplification can be included where the cleavage domain would normally be positioned. In such embodiments, the region can supplement the functional domain or even exist as an additional functional domain. In some embodiments, the cleavage domain is present but its use is optional.

After analytes from the sample have hybridized or otherwise been associated with capture probes, analyte capture agents, or other barcoded oligonucleotide sequences according to any of the methods described above in connection with the general spatial cell-based analytical methodology, the barcoded constructs that result from hybridization/association are analyzed via sequencing to identify the analytes.

In some embodiments, where a sample is barcoded directly via hybridization with capture probes or analyte capture agents hybridized, bound, or associated with either the cell surface, or introduced into the cell, as described above, sequencing can be performed on the intact sample. Alternatively, if the barcoded sample has been separated into fragments, cell groups, or individual cells, as described above, sequencing can be performed on individual fragments, cell groups, or cells. For analytes that have been barcoded via partitioning with beads, as described above, individual analytes (e.g., cells, or cellular contents following lysis of cells) can be extracted from the partitions by breaking the partitions, and then analyzed by sequencing to identify the analytes.

A wide variety of different sequencing methods can be used to analyze barcoded analyte constructs. In general, sequenced polynucleotides can be, for example, nucleic acid molecules such as deoxyribonucleic acid (DNA) or ribonucleic acid (RNA), including variants or derivatives thereof (e.g., single stranded DNA or DNA/RNA hybrids, and nucleic acid molecules with a nucleotide analog).

Sequencing of polynucleotides can be performed by various commercial systems. More generally, sequencing can be performed using nucleic acid amplification, polymerase chain reaction (PCR) (e.g., digital PCR and droplet digital PCR (ddPCR), quantitative PCR, real time PCR, multiplex PCR, PCR-based singleplex methods, emulsion PCR), and/or isothermal amplification.

Other examples of methods for sequencing genetic material include, but are not limited to, DNA hybridization methods (e.g., Southern blotting), restriction enzyme digestion methods, Sanger sequencing methods, next-generation sequencing methods (e.g., single-molecule real-time sequencing, nanopore sequencing, and Polony sequencing), ligation methods, and microarray methods. Additional examples of sequencing methods that can be used include targeted sequencing, single molecule real-time sequencing, exon sequencing, electron microscopy-based sequencing, panel sequencing, transistor-mediated sequencing, direct sequencing, random shotgun sequencing, Sanger dideoxy termination sequencing, whole-genome sequencing, sequencing by hybridization, pyrosequencing, capillary electrophoresis, gel electrophoresis, duplex sequencing, cycle sequencing, single-base extension sequencing, solid-phase sequencing, high-throughput sequencing, massively parallel signature sequencing, co-amplification at lower denaturation temperature-PCR (COLD-PCR), sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, 454 sequencing, Solexa Genome Analyzer sequencing, SOLiD™ sequencing, MS-PET sequencing, and any combinations thereof.

Sequence analysis of the nucleic acid molecules (including barcoded nucleic acid molecules or derivatives thereof) can be direct or indirect. Thus, the sequence analysis substrate (which can be viewed as the molecule which is subjected to the sequence analysis step or process) can directly be the barcoded nucleic acid molecule or it can be a molecule which is derived therefrom (e.g., a complement thereof). Thus, for example, in the sequence analysis step of a sequencing reaction, the sequencing template can be the barcoded nucleic acid molecule or it can be a molecule derived therefrom. For example, a first and/or second strand DNA molecule can be directly subjected to sequence analysis (e.g. sequencing), i.e., can directly take part in the sequence analysis reaction or process (e.g. the sequencing reaction or sequencing process, or be the molecule which is sequenced or otherwise identified). Alternatively, the barcoded nucleic acid molecule can be subjected to a step of second strand synthesis or amplification before sequence analysis (e.g. sequencing or identification by another technique). The sequence analysis substrate (e.g., template) can thus be an amplicon or a second strand of a barcoded nucleic acid molecule.

In some embodiments, both strands of a double stranded molecule can be subjected to sequence analysis (e.g., sequenced). In some embodiments, single stranded molecules (e.g. barcoded nucleic acid molecules) can be analyzed (e.g. sequenced). To perform single molecule sequencing, the nucleic acid strand can be modified at the 3' end.

Massively parallel sequencing techniques can be used for sequencing nucleic acids, as described above. In one embodiment, a massively parallel sequencing technique can be based on reversible dye-terminators. As an example, DNA molecules are first attached to primers on, e.g., a glass or silicon substrate, and amplified so that local clonal colonies are formed (bridge amplification). Four types of ddNTPs are added, and non-incorporated nucleotides are washed away. Unlike pyrosequencing, the DNA is only extended one nucleotide at a time due to a blocking group (e.g., 3' blocking group present on the sugar moiety of the ddNTP). A detector acquires images of the fluorescently labelled nucleotides, and then the dye along with the terminal 3' blocking group is chemically removed from the DNA, as a precursor to a subsequent cycle. This process can be repeated until the required sequence data is obtained.

As another example, massively parallel pyrosequencing techniques can also be used for sequencing nucleic acids. In pyrosequencing, the nucleic acid is amplified inside water droplets in an oil solution (emulsion PCR), with each droplet containing a single nucleic acid template attached to a single primer-coated bead that then forms a clonal colony. The sequencing system contains many picolitre-volume wells each containing a single bead and sequencing enzymes. Pyrosequencing uses luciferase to generate light for detection of the individual nucleotides added to the nascent nucleic acid and the combined data are used to generate sequence reads.

As another example application of pyrosequencing, released PPi can be detected by being immediately converted to adenosine triphosphate (ATP) by ATP sulfurylase, and the level of ATP generated can be detected via luciferase-produced photons, such as described in Ronaghi, et al., Anal. Biochem. 242(1), 84-9 (1996); Ronaghi, Genome Res. 11(1), 3-11 (2001); Ronaghi et al. Science 281 (5375), 363 (1998); and U.S. Pat. Nos. 6,210,891, 6,258,568, and 6,274,320, the entire contents of each of which are incorporated herein by reference.

In some embodiments, sequencing is performed by detection of hydrogen ions that are released during the polymerization of DNA. A microwell containing a template DNA strand to be sequenced can be flooded with a single type of nucleotide. If the introduced nucleotide is complementary to the leading template nucleotide, it is incorporated into the growing complementary strand. This causes the release of a hydrogen ion that triggers a hypersensitive ion sensor, which indicates that a reaction has occurred. If homopolymer repeats are present in the template sequence, multiple nucleotides will be incorporated in a single cycle. This leads to a corresponding number of released hydrogen ions and a proportionally higher electronic signal.

In some embodiments, sequencing can be performed in-situ. In-situ sequencing methods are particularly useful, for example, when the biological sample remains intact after analytes on the sample surface (e.g., cell surface analytes) or within the sample (e.g., intracellular analytes) have been barcoded. In-situ sequencing typically involves incorporation of a labeled nucleotide (e.g., fluorescently labeled mononucleotides or dinucleotides) in a sequential, template-dependent manner or hybridization of a labeled primer (e.g., a labeled random hexamer) to a nucleic acid template such that the identities (i.e., nucleotide sequence) of the incorporated nucleotides or labeled primer extension products can be determined, and consequently, the nucleotide sequence of the corresponding template nucleic acid. Aspects of in-situ sequencing are described, for example, in Mitra et al., (2003) Anal. Biochem. 320, 55-65, and Lee et al., (2014) Science, 343(6177), 1360-1363, the entire contents of each of which are incorporated herein by reference.

In addition, examples of methods and systems for performing in-situ sequencing are described in PCT Patent Application Publication Nos. WO2014/163886, WO2018/045181, WO2018/045186, and in U.S. Pat. Nos. 10,138,509 and 10,179,932, the entire contents of each of which are incorporated herein by reference. Example techniques for in-situ sequencing include, but are not limited to, STARmap (described for example in Wang et al., (2018) Science, 361(6499) 5691), MERFISH (described for example in Moffitt, (2016) Methods in Enzymology, 572, 1-49), and FISSEQ (described for example in U.S. Patent Application Publication No. 2019/0032121). The entire contents of each of the foregoing references are incorporated herein by reference.

For analytes that have been barcoded via partitioning, barcoded nucleic acid molecules or derivatives thereof (e.g., barcoded nucleic acid molecules to which one or more functional sequences have been added, or from which one or more features have been removed) can be pooled and processed together for subsequent analysis such as sequencing on high throughput sequencers. Processing with pooling can be implemented using barcode sequences. For example, barcoded nucleic acid molecules of a given partition can have the same barcode, which is different from barcodes of other spatial partitions. Alternatively, barcoded nucleic acid molecules of different partitions can be processed separately for subsequent analysis (e.g., sequencing).

In some embodiments, where capture probes do not contain a spatial barcode, the spatial barcode can be added after the capture probe captures analytes from a biological sample and before analysis of the analytes. When a spatial barcode is added after an analyte is captured, the barcode can be added after amplification of the analyte (e.g., reverse transcription and polymerase amplification of RNA). In some embodiments, analyte analysis uses direct sequencing of one or more captured analytes, such as direct sequencing of hybridized RNA. In some embodiments, direct sequencing is performed after reverse transcription of hybridized RNA. In some embodiments direct sequencing is performed after amplification of reverse transcription of hybridized RNA.

In some embodiments, direct sequencing of captured RNA is performed by sequencing-by-synthesis (SBS). In some embodiments, a sequencing primer is complementary to a sequence in one or more of the domains of a capture probe (e.g., functional domain). In such embodiments, sequencing-by-synthesis can include reverse transcription and/or amplification in order to generate a template sequence (e.g., functional domain) from which a primer sequence can bind.

SBS can involve hybridizing an appropriate primer, sometimes referred to as a sequencing primer, with the nucleic acid template to be sequenced, extending the primer, and detecting the nucleotides used to extend the primer. Preferably, the nucleic acid used to extend the primer is detected before a further nucleotide is added to the growing nucleic acid chain, thus allowing base-by-base in situ nucleic acid sequencing. The detection of incorporated nucleotides is facilitated by including one or more labelled nucleotides in the primer extension reaction. To allow the hybridization of an appropriate sequencing primer to the nucleic acid template to be sequenced, the nucleic acid template should normally be in a single stranded form. If the nucleic acid templates making up the nucleic acid spots are present in a double stranded form these can be processed to provide single stranded nucleic acid templates using methods well known in the art, for example by denaturation, cleavage etc. The sequencing primers which are hybridized to the nucleic acid template and used for primer extension are preferably short oligonucleotides, for example, 15 to 25 nucleotides in length. The sequencing primers can be provided in solution or in an immobilized form. Once the sequencing primer has been annealed to the nucleic acid template to be sequenced by subjecting the nucleic acid template and sequencing primer to appropriate conditions, primer extension is carried out, for example using a nucleic acid polymerase and a supply of nucleotides, at least some of which are provided in a labelled form, and conditions suitable for primer extension if a suitable nucleotide is provided.

Preferably after each primer extension step, a washing step is included in order to remove unincorporated nucleotides which can interfere with subsequent steps. Once the primer extension step has been carried out, the nucleic acid colony is monitored to determine whether a labelled nucleotide has been incorporated into an extended primer. The primer extension step can then be repeated to determine the next and subsequent nucleotides incorporated into an extended primer. If the sequence being determined is unknown, the nucleotides applied to a given colony are usually applied in a chosen order which is then repeated throughout the analysis, for example dATP, dTTP, dCTP, dGTP.

SBS techniques which can be used are described for example, but not limited to, those in U.S. Patent App. Pub. No. 2007/0166705, U.S. Patent App. Pub. No. 2006/0188901, U.S. Pat. No. 7,057,026, U.S. Patent App. Pub. No. 2006/0240439, U.S. Patent App. Pub. No. 2006/0281109, PCT Patent App. Pub. No. WO 05/065814, U.S. Patent App. Pub. No. 2005/0100900, PCT Patent App. Pub. No. WO 06/064199, PCT Patent App. Pub. No. WO07/010,251, U.S. Patent App. Pub. No. 2012/0270305, U.S. Patent App. Pub. No. 2013/0260372, and U.S. Patent App. Pub. No. 2013/0079232, the entire contents of each of which are incorporated herein by reference.

In some embodiments, direct sequencing of captured RNA is performed by sequential fluorescence hybridization (e.g., sequencing by hybridization). In some embodiments, a hybridization reaction where RNA is hybridized to a capture probe is performed in situ. In some embodiments, captured RNA is not amplified prior to hybridization with a sequencing probe. In some embodiments, RNA is amplified prior to hybridization with sequencing probes (e.g., reverse transcription to cDNA and amplification of cDNA). In some embodiments, amplification is performed using single-molecule hybridization chain reaction. In some embodiments, amplification is performed using rolling chain amplification.

Sequential fluorescence hybridization can involve sequential hybridization of probes including degenerate primer sequences and a detectable label. A degenerate primer sequence is a short oligonucleotide sequence which is capable of hybridizing to any nucleic acid fragment independent of the sequence of said nucleic acid fragment. For example, such a method could include the steps of: (a) providing a mixture including four probes, each of which includes either A, C, G, or T at the 5'-terminus, further including degenerate nucleotide sequence of 5 to 11 nucleotides in length, and further including a functional domain (e.g., fluorescent molecule) that is distinct for probes with A, C, G, or T at the 5'-terminus; (b) associating the probes of step (a) to the target polynucleotide sequences, whose sequence needs will be determined by this method; (c) measuring the activities of the four functional domains and recording the relative spatial location of the activities; (d) removing the reagents from steps (a)-(b) from the target polynucleotide sequences; and repeating steps (a)-(d) for n cycles, until the nucleotide sequence of the spatial domain for each bead is determined, with modification that the oligonucleotides used in step (a) are complementary to part of the target polynucleotide sequences and the positions 1 through n flanking the part of the sequences. Because the barcode sequences are different, in some embodiments, these additional flanking sequences are degenerate sequences. The fluorescent signal from each spot on the array for cycles 1 through n can be used to determine the sequence of the target polynucleotide sequences.

In some embodiments, direct sequencing of captured RNA using sequential fluorescence hybridization is performed in vitro. In some embodiments, captured RNA is amplified prior to hybridization with a sequencing probe (e.g., reverse transcription to cDNA and amplification of cDNA). In some embodiments, a capture probe containing captured RNA is exposed to the sequencing probe targeting coding regions of RNA. In some embodiments, one or more sequencing probes are targeted to each coding region. In some embodiments, the sequencing probe is designed to hybridize with sequencing reagents (e.g., a dye-labeled readout oligonucleotides). A sequencing probe can then hybridize with sequencing reagents. In some embodiments, output from the sequencing reaction is imaged. In some embodiments, a specific sequence of cDNA is resolved from an image of a sequencing reaction. In some embodiments, reverse transcription of captured RNA is performed prior to hybridization to the sequencing probe. In some embodiments, the sequencing probe is designed to target complementary sequences of the coding regions of RNA (e.g., targeting cDNA).

In some embodiments, a captured RNA is directly sequenced using a nanopore-based method. In some embodiments, direct sequencing is performed using nanopore direct RNA sequencing in which captured RNA is translocated through a nanopore. A nanopore current can be recorded and converted into a base sequence. In some embodiments, captured RNA remains attached to a substrate during nanopore sequencing. In some embodiments, captured RNA is released from the substrate prior to nanopore sequencing. In some embodiments, where the analyte of interest is a protein, direct sequencing of the protein can be performed using nanopore-based methods. Examples of nanopore-based sequencing methods that can be used are described in Deamer et al., Trends Biotechnol. 18, 14 7-151 (2000); Deamer et al., Acc. Chem. Res. 35:817-825 (2002); Li et al., Nat. Mater. 2:611-615 (2003); Soni et al., Clin. Chem. 53, 1996-2001 (2007); Healy et al., Nanomed. 2, 459-481 (2007); Cockroft et al., J. Am. Chem. Soc. 130, 818-820 (2008); and in U.S. Pat. No. 7,001,792. The entire contents of each of the foregoing references are incorporated herein by reference.

In some embodiments, direct sequencing of captured RNA is performed using single molecule sequencing by ligation. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. Aspects and features involved in sequencing by ligation are described, for example, in Shendure et al. Science (2005), 309: 1728-1732, and in U.S. Pat. Nos. 5,599,675; 5,750,341; 6,969,488; 6,172,218; and 6,306,597, the entire contents of each of which are incorporated herein by reference.

In some embodiments, nucleic acid hybridization can be used for sequencing. These methods utilize labeled nucleic acid decoder probes that are complementary to at least a portion of a barcode sequence. Multiplex decoding can be performed with pools of many different probes with distinguishable labels. Non-limiting examples of nucleic acid hybridization sequencing are described for example in U.S. Pat. No. 8,460,865, and in Gunderson et al., Genome Research 14:870-877 (2004), the entire contents of each of which are incorporated herein by reference.

In some embodiments, commercial high-throughput digital sequencing techniques can be used to analyze barcode sequences, in which DNA templates are prepared for sequencing not one at a time, but in a bulk process, and where many sequences are read out preferably in parallel, or alternatively using an ultra-high throughput serial process that itself may be parallelized. Examples of such techniques include Illumina© sequencing (e.g., flow cell-based sequencing techniques), sequencing by synthesis using modified nucleotides (such as commercialized in TruSeq™ and HiSeq™ technology by Illumina, Inc., San Diego, CA), HeliScope™ by Helicos Biosciences Corporation, Cambridge, MA, and PacBio RS by Pacific Biosciences of California, Inc., Menlo Park, CA), sequencing by ion detection technologies (Ion Torrent, Inc., South San Francisco, CA), and sequencing of DNA nanoballs (Complete Genomics, Inc., Mountain View, CA).

In some embodiments, detection of a proton released upon incorporation of a nucleotide into an extension product can be used in the methods described herein. For example, the sequencing methods and systems described in U.S. Patent Application Publication Nos. 2009/0026082, 2009/0127589, 2010/0137143, and 2010/0282617, can be used to directly sequence barcodes.

In some embodiments, real-time monitoring of DNA polymerase activity can be used during sequencing. For example, nucleotide incorporations can be detected through fluorescence resonance energy transfer (FRET), as described for example in Levene et al., Science (2003), 299, 682-686, Lundquist et al., Opt. Lett. (2008), 33, 1026-1028, and Korlach et al., Proc. Natl. Acad. Sci. USA (2008), 105, 1176-1181. The entire contents of each of the foregoing references are incorporated herein by reference herein.

In some embodiments, the methods described herein can be used to assess analyte levels and/or expression in a cell or a biological sample over time (e.g., before or after treatment with an agent or different stages of differentiation). In some examples, the methods described herein can be performed on multiple similar biological samples or cells obtained from the subject at a different time points (e.g., before or after treatment with an agent, different stages of differentiation, different stages of disease progression, different ages of the subject, or before or after development of resistance to an agent).

(h) Spatially Resolving Analyte Information

In some embodiments, a lookup table (LUT) can be used to associate one property with another property of a feature. These properties include, e.g., locations, barcodes (e.g., nucleic acid barcode molecules), spatial barcodes, optical labels, molecular tags, and other properties.

In some embodiments, a lookup table can associate the plurality of nucleic acid barcode molecules with the features. In some embodiments, the optical label of a feature can permit associating the feature with the biological particle (e.g., cell or nuclei). The association of the feature with the biological particle can further permit associating a nucleic acid sequence of a nucleic acid molecule of the biological particle to one or more physical properties of the biological particle (e.g., a type of a cell or a location of the cell). For example, based on the relationship between the barcode and the optical label, the optical label can be used to determine the location of a feature, thus associating the location of the feature with the barcode sequence of the feature. Subsequent analysis (e.g., sequencing) can associate the barcode sequence and the analyte from the sample. Accordingly, based on the relationship between the location and the barcode sequence, the location of the biological analyte can be determined (e.g., in a specific type of cell, in a cell at a specific location of the biological sample).

In some embodiments, the feature can have a plurality of nucleic acid barcode molecules attached thereto. The plurality of nucleic acid barcode molecules can include barcode sequences. The plurality of nucleic acid molecules attached to a given feature can have the same barcode sequences, or two or more different barcode sequences. Different barcode sequences can be used to provide improved spatial location accuracy.

As discussed above, analytes obtained from a sample, such as RNA, DNA, peptides, lipids, and proteins, can be further processed. In particular, the contents of individual cells from the sample can be provided with unique spatial barcode sequences such that, upon characterization of the analytes, the analytes can be attributed as having been derived from the same cell. More generally, spatial barcodes can be used to attribute analytes to corresponding spatial locations in the sample. For example, hierarchical spatial positioning of multiple pluralities of spatial barcodes can be used to identify and characterize analytes over a particular spatial region of the sample. In some embodiments, the spatial region corresponds to a particular spatial region of interest previously identified, e.g., a particular structure of cytoarchitecture previously identified. In some embodiments, the spatial region corresponds to a small structure or group of cells that cannot be seen with the naked eye. In some embodiments, a unique molecular identifier can be used to identify and characterize analytes at a single cell level.

The analyte can include a nucleic acid molecule, which can be barcoded with a barcode sequence of a nucleic acid barcode molecule. In some embodiments, the barcoded analyte can be sequenced to obtain a nucleic acid sequence. In some embodiments, the nucleic acid sequence can include genetic information associate with the sample. The nucleic acid sequence can include the barcode sequence, or a complement thereof. The barcode sequence, or a complement thereof, of the nucleic acid sequence can be electronically associated with the property (e.g., color and/or intensity) of the analyte using the LUT to identify the associated feature in an array.

In some embodiments, two- or three-dimensional spatial profiling of one or more analytes present in a biological sample can be performed using a proximity capture reaction, which is a reaction that detects two analytes that are spatially close to each other and/or interacting with each other. For example, a proximity capture reaction can be used to detect sequences of DNA that are close in space to each other, e.g., the DNA sequences can be within the same chromosome, but separated by about 700 bp or less. As another example, a proximity capture reaction can be used to detect protein associations, e.g., two proteins that interact with each other. A proximity capture reaction can be performed in situ to detect two analytes that are spatially close to each other and/or interacting with each other inside a cell. Non-limiting examples of proximity capture reactions include DNA nanoscopy, DNA microscopy, and chromosome conformation capture methods. Chromosome conformation capture (3C) and derivative experimental procedures can be used to estimate the spatial proximity between different genomic elements. Non-limiting examples of chromatin capture methods include chromosome conformation capture (3-C), conformation capture-on-chip (4-C), 5-C, ChIA-PET, Hi-C, targeted chromatin capture (T2C). Examples of such methods are described, for example, in Miele et al., Methods Mol Biol. (2009), 464, Simonis et al., Nat. Genet. (2006), 38(11): 1348-54, Raab et al., Embo. J. (2012), 31(2): 330-350, and Eagen et al., Trends Biochem. Sci. (2018) 43(6): 469-478, the entire contents of each of which is incorporated herein by reference.

In some embodiments, the proximity capture reaction includes proximity ligation. In some embodiments, proximity ligation can include using antibodies with attached DNA strands that can participate in ligation, replication, and sequence decoding reactions. For example, a proximity ligation reaction can include oligonucleotides attached to pairs of antibodies that can be joined by ligation if the antibodies have been brought in proximity to each oligonucleotide, e.g., by binding the same target protein (complex), and the DNA ligation products that form are then used to template PCR amplification, as described for example in Söderberg et al., Methods. (2008), 45(3): 227-32, the entire contents of which are incorporated herein by reference. In some embodiments, proximity ligation can include chromosome conformation capture methods. In some embodiments, the proximity capture reaction is performed on analytes within about 400 nm distance (e.g., about 300 nm, about 200 nm, about 150 nm, about 100 nm, about 50 nm, about 25 nm, about 10 nm, or about 5 nm) from each other. In general, proximity capture reactions can be reversible or irreversible.

III. General Spatial Cell-Based Analytical Methodology (a) Barcoding Biological Sample In some embodiments, provided herein are methods and materials for attaching and/or introducing a molecule (e.g., a nucleic acid molecule) having a barcode (e.g., a spatial barcode) to a biological sample (e.g., to a cell in a biological sample) for use in spatial analysis. In some embodiments, a plurality of molecules (e.g., a plurality of nucleic acid molecules) having a plurality of barcodes (e.g., a plurality of spatial barcodes) are introduced to a biological sample (e.g., to a plurality of cells in a biological sample) for use in spatial analysis.

Figure 18:
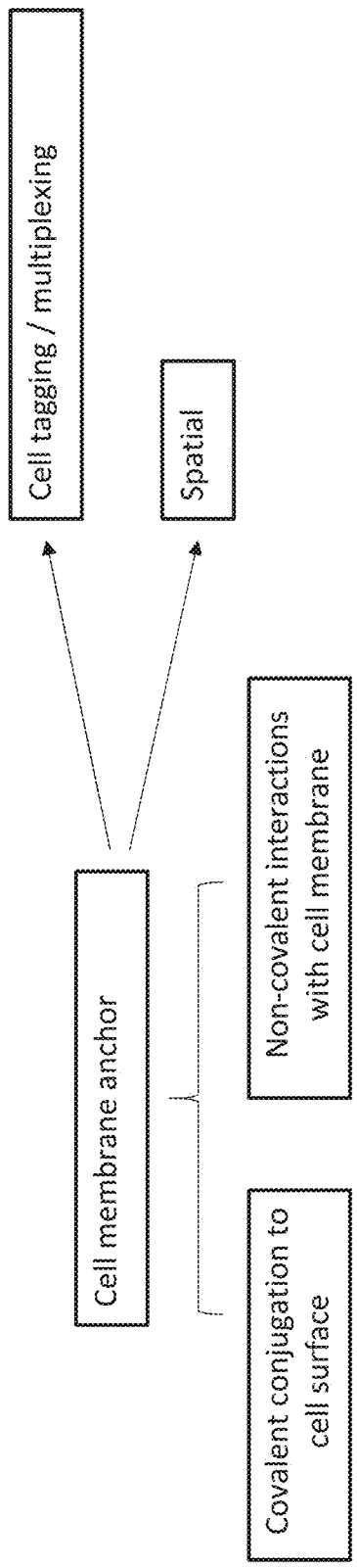
FIG. 18 is a schematic depicting cell tagging using either covalent conjugation of the analyte binding moiety to the cell surface or non-covalent interactions with cell membrane elements.

FIG. 18 is a schematic diagram depicting cell tagging using either covalent conjugation of the analyte binding moiety to the cell surface or non-covalent interactions with cell membrane elements. FIG. 18 lists non-exhaustive examples of a covalent analyte binding moiety/cell surface interactions, including protein targeting, amine conjugation using NHS chemistry, cyanuric chloride, thiol conjugation via maleimide addition, as well as targeting glycoproteins/glycolipids expressed on the cell surface via click chemistry. Non-exhaustive examples of non-covalent interactions with cell membrane elements include lipid modified oligos, biocompatible anchor for cell membrane (oleyl-PEG-NHS), lipid modified positive neutral polymer, and antibody to membrane proteins. The cell tag can be used in combination with an analyte capture agent and cleavable or non-cleavable spatially-barcoded capture probes for spatial and multiplexing applications.

In some embodiments, a plurality of molecules (e.g., a plurality of nucleic acid molecules) having a plurality of barcodes (e.g., a plurality of spatial barcodes) are introduced to a biological sample (e.g., to a plurality of cells in a biological sample) for use in spatial analysis, wherein the plurality of molecules are introduced to the biological sample in an arrayed format. In some embodiments, a plurality of molecules (e.g., a plurality of nucleic acid molecules) having a plurality of barcodes are provided on a substrate (e.g., any of the variety of substrates described herein) in any of the variety of arrayed formats described herein, and the biological sample is contacted with the molecules on the substrate such that the molecules are introduced to the biological sample. In some embodiments, the molecules that are introduced to the biological sample are cleavably attached to the substrate, and are cleaved from the substrate and released to the biological sample when contacted with the biological sample. In some embodiments, the molecules that are introduced to the biological sample are attached to the substrate covalently prior to cleavage. In some embodiments, the molecules that are introduced to the biological sample are non-covalently attached to the substrate (e.g., via hybridization), and are released from the substrate to the biological sample when contacted with the biological sample.

In some embodiments, a plurality of molecules (e.g., a plurality of nucleic acid molecules) having a plurality of barcodes (e.g., a plurality of spatial barcodes) are migrated or transferred from a substrate to cells of a biological sample. In some embodiments, migrating a plurality of molecules from a substrate to cells of a biological sample includes applying a force (e.g., mechanical, centrifugal, or electrophoretic) to the substrate and/or the biological sample to facilitate migration of the plurality of molecules from the substrate to the biological sample.

In some embodiments of any of the spatial analysis methods described herein, physical force is used to facilitate attachment to or introduction of a molecule (e.g., a nucleic acid molecule) having a barcode (e.g., a spatial barcode) into a biological sample (e.g., a cell present in a biological sample). As used herein, "physical force" refers to the use of a physical force to counteract the cell membrane barrier in facilitating intracellular delivery of molecules. Examples of physical force instruments and methods that can be used in accordance with materials and methods described herein include the use of a needle, ballistic DNA, electroporation, sonoporation, photoporation, magnetofection, hydroporation, and combinations thereof.

In some embodiments, biological samples (e.g., cells in a biological sample) can be labelled using cell-tagging agents where the cell-tagging agents facilitate the introduction of the molecules (e.g., nucleic acid molecules) having barcodes (e.g., spatial barcodes) into the biological sample (e.g., into cells in a biological sample). As used herein, the term "cell-tagging agent" refers to a molecule having a moiety that is capable of attaching to the surface of a cell (e.g., thus attaching the barcode to the surface of the cell) and/or penetrating and passing through the cell membrane (e.g., thus introducing the barcode to the interior of the cell). In some embodiments, a cell-tagging agent includes a barcode (e.g., a spatial barcode). The barcode of a barcoded cell-tagging agent can be any of the variety of barcodes described herein. In some embodiments, the barcode of a barcoded cell-tagging agent is a spatial barcode. In some embodiments, a cell-tagging agent comprises a nucleic acid molecule that includes the barcode (e.g., the spatial barcode). In some embodiments, the barcode of a barcoded cell-tagging agent identifies the associated molecule, where each spatial barcode is associated with a particular molecule. In some embodiments, one or more molecules are applied to a sample. In some embodiments, a nucleic acid molecule that includes the barcode is covalently attached to the cell-tagging agent. In some embodiments, a nucleic acid molecule that includes the barcode is non-covalently attached to the cell-tagging agent. A non-limiting example of non-covalent attachment includes hybridizing the nucleic acid molecule that includes the barcode to a nucleic acid molecule on the cell-tagging agent (which nucleic acid molecule on the cell-tagging agent can be bound to the cell-tagging agent covalently or non-covalently). In some embodiments, a nucleic acid molecule that is attached to a cell-tagging agent that includes a barcode (e.g., a spatial barcode) also includes one or more additional domains. Such additional domains include, without limitation, a PCR handle, a sequencing priming site, a domain for hybridizing to another nucleic acid molecule, and combinations thereof.

In some embodiments, a cell-tagging agent attaches to the surface of a cell. When the cell-tagging agent includes a barcode (e.g., a nucleic acid that includes a spatial barcode), the barcode is also attached to the surface of the cell. In some embodiments of any of the spatial analysis methods described herein, a cell-tagging agent attaches covalently to the cell surface to facilitate introduction of the spatial profiling reagents. In some embodiments of any of the spatial analysis methods described herein, a cell-tagging agent attaches non-covalently to the cell surface to facilitate introduction of the spatial profiling reagents.

In some embodiments, once a cell or cells in a biological sample is spatially tagged with a cell-tagging agent(s), spatial analysis of analytes present in the biological sample is performed. In some embodiments, such spatial analysis includes dissociating the spatially-tagged cells of the biological sample (or a subset of the spatially-tagged cells of the biological sample) and analyzing analytes present in those cells on a cell-by-cell basis. Any of a variety of methods for analyzing analytes present in cells on a cell-by-cell basis can be used. Non-limiting examples include any of the variety of methods described herein and methods described in PCT Application Publication No. WO 2019/113533A1, the content of which is incorporated herein by reference in its entirety. For example, the spatially-tagged cells can be encapsulated with beads comprising one or more nucleic acid molecules having a barcode (e.g., a cellular barcode) (e.g., an emulsion). The nucleic acid present on the bead can have a domain that hybridizes to a domain on a nucleic acid present on the tagged cell (e.g., a domain on a nucleic acid that is attached to a cell-tagging agent), thus linking the spatial barcode of the cell to the cellular barcode of the bead. Once the spatial barcode of the cell and the cellular barcode of the bead are linked, analytes present in the cell can be analyzed using capture probes (e.g., capture probes present on the bead). This allows the nucleic acids produced (using these methods) from specific cells to be amplified and sequenced separately (e.g. within separate partitions or droplets).

In some embodiments, once a cell or cells in a biological sample is spatially tagged with a cell-tagging agent(s), spatial analysis of analytes present in the biological sample is performed in which the cells of the biological sample are not dissociated into single cells. In such embodiments, various methods of spatial analysis such as any of those provided herein can be employed. For example, once a cell or cells in a biological sample is spatially tagged with a cell-tagging agent(s), analytes in the cells can be captured and assayed. In some embodiments, cell-tagging agents include both a spatial barcode and a capture domain that can be used to capture analytes present in a cell. For example, cell-tagging agents that include both a spatial barcode and a capture domain can be introduced to cells of the biological sample in a way such that locations of the cell-tagging agents are known (or can be determined after introducing them to the cells). One non-limiting example of introducing cell-tagging agents to a biological sample is to provide the cell-tagging agents in an arrayed format (e.g., arrayed on a substrate such as any of the variety of substrates and arrays provided herein), where the positions of the cell-tagging agents on the array are known at the time of introduction (or can be determined after introduction). The cells can be permeabilized as necessary (e.g., using permeabilization agents and methods described herein), reagents for analyte analysis can be provided to the cells (e.g., a reverse transcriptase, a polymerase, nucleotides, etc., in the case where the analyte is a nucleic acid that binds to the capture probe), and the analytes can be assayed. In some embodiments, the assayed analytes (and/or copies thereof) can be released from the substrate and analyzed. In some embodiments, the assayed analytes (and/or copies thereof) are assayed in situ.

Introducing a Cell-Tagging Agent to the Surface of a Cell

Non-limiting examples of cell-tagging agents and systems that attach to the surface of a cell (e.g., thus introducing the cell-tagging agent and any barcode attached thereto to the exterior of the cell) that can be used in accordance with materials and methods provided herein for spatially profiling an analyte or analytes in a biological sample include: lipid tagged primers/lipophilic-tagged moieties, positive or neutral oligo-conjugated polymers, antibody-tagged primers, streptavidin-conjugated oligonucleotides, dye-tagged oligonucleotides, click-chemistry, receptor-ligand systems, covalent binding systems via amine or thiol functionalities, and combinations thereof.

Lipid Tagged Primers/Lipophilic-Tagged Moieties

In some embodiments of any of the spatial profiling methods described herein, a molecule (e.g., a nucleic acid molecule) having a barcode (e.g., a spatial barcode) is coupled to a lipophilic molecule. In some embodiments, the lipophilic molecule enables the delivery of the molecule to the cell membrane or the nuclear membrane. In some embodiments, a molecule (e.g., a nucleic acid molecule) having a barcode (e.g., a spatial barcode) coupled to a lipophilic molecule can associate with and/or insert into lipid membranes such as cell membranes and nuclear membranes. In some cases, the insertion can be reversible. In some cases, the association between the lipophilic molecule and the cell may be such that the cell retains the lipophilic molecule (e.g., and associated components, such as nucleic acid barcode molecules) during subsequent processing (e.g., partitioning, cell permeabilization, amplification, pooling, etc.). In some embodiments, a molecule (e.g., a nucleic acid molecule) having a barcode (e.g., a spatial barcode) coupled to a lipophilic molecule may enter into the intracellular space and/or a cell nucleus.

Non-limiting examples of lipophilic molecules that can be used in embodiments described herein include sterol lipids such as cholesterol, tocopherol, steryl, palmitate, lignoceric acid, and derivatives thereof. In some embodiments, the lipophilic molecules are neutral lipids that are conjugated to hydrophobic moieties (e.g., cholesterol, squalene, or fatty acids) (See Raouane et al. Bioconjugate Chem., 23(6):1091-1104 (2012) which is herein incorporated by reference in its entirety). In some embodiments, a molecule (e.g., a nucleic acid molecule) having a barcode (e.g., a spatial barcode) may be attached to the lipophilic moiety via a linker, such as a tetra-ethylene glycol (TEG) linker. Other exemplary linkers include, but are not limited to, Amino Linker C6, Amino Linker C12, Spacer C3, Spacer C6, Spacer C12, Spacer 9, and Spacer 18. In some embodiments, a molecule (e.g., a nucleic acid molecule) having a barcode (e.g., a spatial barcode) is indirectly coupled (e.g., via hybridization or ligand-ligand interactions, such as biotin-streptavidin) to a lipophilic molecule. Other lipophilic molecules that may be used in accordance with methods provided herein include amphiphilic molecules wherein the headgroup (e.g., charge, aliphatic content, and/or aromatic content) and/or fatty acid chain length (e.g., C12, C14, C16, or C18) can be varied. For instance, fatty acid side chains (e.g., C12, C14, C16, or C18) can be coupled to glycerol or glycerol derivatives (e.g., 3-t-butyldiphenylsilylglycerol), which can also comprise, e.g., a cationic head group. In some embodiments, a molecule (e.g., a nucleic acid molecule) having a barcode (e.g., a spatial barcode) disclosed herein can then be coupled (either directly or indirectly) to these amphiphilic molecules. In some embodiments, a molecule (e.g., a nucleic acid molecule) having a barcode (e.g., a spatial barcode) coupled to an amphiphilic molecule may associate with and/or insert into a membrane (e.g., a cell, cell bead, or nuclear membrane). In some cases, an amphiphilic or lipophilic moiety may cross a cell membrane and provide a molecule (e.g., a nucleic acid molecule) having a barcode (e.g., a spatial barcode) to an internal region of a cell and/or cell bead.

In some embodiments, wherein the molecule (e.g., with a nucleic acid sequence) has an amino group within the molecule, the molecule (e.g., a nucleic acid molecule) having a barcode (e.g., a spatial barcode) and an amino group can be coupled to an amine-reactive lipophilic molecule. For example, a molecule (e.g., a nucleic acid molecule) having a barcode (e.g., a spatial barcode) and an amino group can be conjugated to DSPE-PEG(2000)-cyanuric chloride (1,2-distearoyl-sn-glycero-3-phosphoethanolamine-N-[cyanur(polyethylene glycol)-2000]).

In some embodiments, a cell tagging agent can attach to a surface of a cell through a combination of lipophilic and covalent attachment. For example, a cell tagging agent can include an oligonucleotide attached to a lipid to target the oligonucleotide to a cell membrane, and an amine group that can be covalently linked to a cell surface protein(s) via any number of chemistries described herein. In these embodiments, the lipid can increase the surface concentration of the oligonucleotide and can promote the covalent reaction.

Positive or Neutral Oligo-Conjugated Polymers

In some embodiments of any of the spatial analysis methods described herein, a molecule (e.g., a nucleic acid molecule) having a barcode (e.g., a spatial barcode) can be coupled to a glycol chitosan derivative. The glycol chitosan derivative (e.g., glycol chitosan-cholesterol) can serve as a hydrophobic anchor (see Wang et al. J. Mater. Chem. B., 30:6165 (2015), which is herein incorporated by reference in its entirety). Non-limiting examples of chitosan derivatives that can be coupled to a molecule (e.g., a nucleic acid molecule) having a barcode (e.g., a spatial barcode) can be found in Cheung et al., Marine Drugs, 13(8): 5156-5186 (2015), which is herein incorporated by reference in its entirety.

Antibody-Tagged Primers

In some embodiments of any of the spatial analysis methods described herein, a molecule (e.g., a nucleic acid molecule) having a barcode (e.g., a spatial barcode) can be coupled to an antibody or antigen binding fragment thereof in a manner that facilitates attachment of the molecule (e.g., a nucleic acid molecule) having a barcode (e.g., a spatial barcode) to the surface of a cell. In some embodiments, facilitating attachment to the cell surface facilitates introduction of the molecule (e.g., a nucleic acid molecule) having a barcode (e.g., a spatial barcode) into the cell. In some embodiments, the molecule (e.g., a nucleic acid molecule) having a barcode (e.g., a spatial barcode) can be coupled to an antibody that is directed to an antigen that is present on the surface of a cell. In some embodiments, the molecule (e.g., a nucleic acid molecule) having a barcode (e.g., a spatial barcode) can be coupled to an antibody that is directed to an antigen that is present on the surface of a plurality of cells (e.g., a plurality of cells in a biological sample). In some embodiments, the molecule (e.g., a nucleic acid molecule) having a barcode (e.g., a spatial barcode) can be coupled to an antibody that is directed to an antigen that is present on the surface of all or substantially all the cells present in a biological sample. Any of the exemplary methods described herein of attaching a molecule (e.g., a nucleic acid molecule) having a barcode (e.g., a spatial barcode) to another molecule (e.g., a cell-tagging agent) can be used.

Streptavidin-Conjugated Oligonucleotides

In some embodiments of any of the spatial analysis methods described herein, a molecule (e.g., a nucleic acid molecule) having a barcode (e.g., a spatial barcode) can attach to the surface of a cell using biotin-streptavidin. In some embodiments, primary amines in the side chain of lysine residues of cell surface polypeptides are labelled with NHS-activated biotin reagents. For example, the N-terminus of a polypeptide can react with NHS-activated biotin reagents to form stable amide bonds. In some embodiments, cell-tagging agents include molecules (e.g., a nucleic acid molecule) having barcodes (e.g., a spatial barcode) conjugated to streptavidin. In some cases, streptavidin can be conjugated to the molecule (e.g., a nucleic acid molecule) having a barcode (e.g., a spatial barcode) using click chemistry (e.g., maleimide modification) as described herein. In some embodiments, a cell containing NHS-activated biotin incorporated into lysine side chains of a cell surface protein forms a non-covalent bond with the streptavidin conjugated to the molecule (e.g., a nucleic acid molecule) having a barcode (e.g., a spatial barcode). In some embodiments, the molecule (e.g., a nucleic acid molecule) having a barcode (e.g., a spatial barcode) conjugated to streptavidin is itself part of a cell-tagging agent.

Dye-Tagged Oligonucleotides

In some embodiments of any of the spatial analysis methods described herein, a molecule (e.g., a nucleic acid molecule) having a barcode (e.g., a spatial barcode) is directly linked to a fluorescent tag. In some embodiments, the physical properties of the fluorescent tags (e.g., hydrophobic properties) can overcome the hydrophilic nature of the molecule (e.g., a nucleic acid molecule) having a barcode (e.g., a spatial barcode). For example, in some embodiments, wherein the molecule is a nucleic acid molecule, a fluorescent tag (e.g., BODIPY, Cy3, Atto 647N, and Rhodamine Red C2) can be coupled to a 5' end of the nucleic acid molecule having a barcode (e.g., a spatial barcode). In some embodiments, wherein the molecule is a nucleic acid molecule, any fluorescent tag having hydrophobic properties can be coupled to the nucleic acid molecule having a barcode (e.g., a spatial barcode) in a manner that overcomes the hydrophilic nature of the nucleic acid molecule. Non-limiting examples of fluorescent tags with hydrophobic properties include BODIPY, Cy3, Atto 647N, and Rhodamine Red C2.

Click-Chemistry

In some embodiments of any of the spatial analysis methods described herein, molecules (e.g., a nucleic acid molecule) having barcodes (e.g., a spatial barcode) are coupled to click-chemistry moieties. As used herein, the term "click chemistry," generally refers to reactions that are modular, wide in scope, give high yields, generate only inoffensive byproducts, such as those that can be removed by nonchromatographic methods, and are stereospecific (but not necessarily enantioselective) (see, e.g., Angew. Chem. Int. Ed., 2001, 40(11):2004-2021, which is incorporated herein by reference in its entirety). In some cases, click chemistry can describe pairs of functional groups that can selectively react with each other in mild, aqueous conditions.

An example of a click chemistry reaction is the Huisgen 1,3-dipolar cycloaddition of an azide and an alkyne, i.e., copper-catalysed reaction of an azide with an alkyne to form the 5-membered heteroatom ring 1,2,3-triazole. The reaction is also known as a Cu(I)-Catalyzed Azide-Alkyne Cycloaddition (CuAAC), a Cu(I) click chemistry or a Cu+ click chemistry. Catalysts for the click chemistry include, but are not limited to, Cu(I) salts, or Cu(I) salts made in situ by reducing Cu(II) reagents to Cu(I) reagents with a reducing reagent (Pharm Res. 2008, 25(10): 2216-2230, which is incorporated herein by reference in its entirety). Known Cu(II) reagents for the click chemistry can include, but are not limited to, the Cu(II)-(TBTA) complex and the Cu(II) (THPTA) complex. TBTA, which is tris-[(1-benzyl-1H-1,2, 3-triazol-4-yl)methyl]amine, also known as tris-(benzyltriazolylmethyl)amine, can be a stabilizing ligand for Cu(I) salts. THPTA, which is tris-(hydroxypropyltriazolylmethyl) amine, is another example of a stabilizing agent for Cu(I). Other conditions can also be used to construct the 1,2,3-triazole ring from an azide and an alkyne using copper-free click chemistry, such as the Strain-promoted Azide-Alkyne Click chemistry reaction (SPAAC) (see, e.g., Chem. Commun., 2011, 47:6257-6259 and Nature, 2015, 519(7544): 486-90, each of which is incorporated herein by reference in its entirety).

Receptor-Ligand Systems

In some embodiments of any of the spatial analysis methods described herein, a molecule (e.g., a nucleic acid molecule) having a barcode (e.g., a spatial barcode) can be coupled to a ligand, wherein the ligand is part of a receptor-ligand interaction on the surface of a cell. For example, a molecule (e.g., a nucleic acid molecule) having a barcode (e.g., a spatial barcode) can be coupled to a ligand that interacts selectively with a cell surface receptor thereby targeting the molecule (e.g., a nucleic acid molecule) having a barcode (e.g., a spatial barcode) to a specific cell. Non-limiting examples of receptor-ligand systems that can be used include integrin receptor-ligand interactions, GPCR receptor-ligand interactions, RTK receptor-ligand interactions, and TLR-ligand interactions (see Juliano, Nucleic Acids Res., 44(14): 6518-6548 (2016), which is incorporated herein by reference in its entirety). Any of the methods described herein for attaching a molecule (e.g., a nucleic acid molecule) having a barcode (e.g., a spatial barcode) to a ligand (e.g., any of the methods described herein relating to attaching a molecule (e.g., a nucleic acid molecule) having a barcode (e.g., a spatial barcode) to an antibody) can be used.

Covalent Binding Systems Via Amine or Thiol Functionalities

In some embodiments of any of the spatial analysis methods described herein, a molecule (e.g., a nucleic acid molecule) having a barcode (e.g., a spatial barcode) can incorporate reactive functional groups at sites within the molecule (e.g., with a nucleic acid sequence). In such cases, the reactive functional groups can facilitate conjugation to ligands and/or surfaces. In some embodiments, a molecule (e.g., a nucleic acid molecule) having a barcode (e.g., a spatial barcode) can include thiol modifiers that are designed to react with a broad array of activated accepting groups (e.g., maleimide and gold microspheres). For example, a molecule (e.g., a nucleic acid molecule) having a barcode (e.g., a spatial barcode) having thiol modifiers can interact with a maleimide-conjugated peptide thereby resulting in labelling of the peptide. In some embodiments, maleimide-conjugated peptides are present on the surface of a cell whereupon interaction with the thiol-modified molecule (e.g., a nucleic acid molecule) having a barcode (e.g., a spatial barcode), the molecule (e.g., a nucleic acid molecule) having a barcode (e.g., a spatial barcode) is coupled to the surface of the cell. Non-limiting examples of thiol modifiers include: 5' thiol modifier C6 S—S, 3' thiol modifier C3 S—S, dithiol, 3'thiol modifier oxa 6-S—S, and dithiol serinol.

In some embodiments of any of the spatial analysis methods described herein, a molecule (e.g., a nucleic acid molecule) having a barcode (e.g., a spatial barcode) can include amine modifiers, e.g., amine modifiers that are designed to attach to another molecule in the presence of an acylating agent. In some embodiments, a molecule (e.g., a nucleic acid molecule) having a barcode (e.g., a spatial barcode) can include amine modifiers that are designed to attach to a broad array of linkage groups (e.g., carbonyl amide, thiourea, sulfonamide, and carboxamide). For example, a molecule (e.g., a nucleic acid molecule) having a barcode (e.g., a spatial barcode) and an amine modifier can interact with a sulfonamide-conjugated peptide thereby resulting in labelling of the peptide. In some embodiments, sulfonamide-conjugated peptides are present on the surface of a cell whereupon interaction with the amine-modified molecule (e.g., a nucleic acid molecule) having a barcode (e.g., a spatial barcode), the molecule (e.g., a nucleic acid molecule) having a barcode (e.g., a spatial barcode) is coupled to the surface of the cell. Non-limiting example of amine modifiers include: DMS(O)MT-Amino-Modifier-C6, Amino-Modifier-C3-TFA, Amino-Modifier-C12, Amino-Modifier-C6-TFA, Amino-dT, Amino-Modifier-5, Amino-Modifier-C2-dT, Amino-Modifier-C6-dT, and 3'-Amino-Modifier-C7.

As another example, a molecule (e.g., a nucleic acid molecule) having a barcode (e.g., a spatial barcode) can incorporate reactive functional groups at sites within the molecule (e.g., with a nucleic acid sequence) such as N-hydroxysuccinimide (NHS). In some embodiments, amines (e.g., amine-containing peptides) are present on the surface of a cell whereupon interaction with the NHS-modified molecule (e.g., a nucleic acid molecule) having a barcode (e.g., a spatial barcode), the molecule (e.g., a nucleic acid molecule) having a barcode (e.g., a spatial barcode) is coupled to the surface of the cell. In some embodiments, a molecule (e.g., a nucleic acid molecule) having a barcode (e.g., a spatial barcode) is reacted with a bifunctional NHS linker to form an NHS-modified molecule (e.g., a nucleic acid molecule) having a barcode (e.g., a spatial barcode).

In some embodiments, a molecule (e.g., a nucleic acid molecule) having a barcode (e.g., a spatial barcode) can be coupled to a biocompatible anchor for cell membrane (BAM). For example, a BAM can include molecules that comprise an oleyl group and PEG. The oleyl group can facilitate anchoring the molecule (e.g., a nucleic acid molecule) having a barcode (e.g., a spatial barcode) to a cell, and the PEG can increase water solubility. In some embodiments, oleyl-PEG-NHS can be coupled to a molecule (e.g., a nucleic acid molecule) having a barcode (e.g., a spatial barcode) using NHS chemistry.

Azide-Based Systems

In some embodiments, wherein the molecule (e.g., with a nucleic acid sequence) incorporates reactive functional groups at sites within the molecule, a molecule (e.g., a nucleic acid molecule) having a barcode (e.g., a spatial barcode) can be coupled to an azide group on a cell surface. In some embodiments, the reactive functional group is an alkynyl group. In some embodiments, click chemistry as described herein can be used to attach the alkynyl-modified molecule (e.g., a nucleic acid molecule) having a barcode (e.g., a spatial barcode) to an azide group on the cell surface. An azide group can be attached to the cell surface through a variety of methods. For example, NHS chemistry can be used to attach an azide group to the cell surface. In some embodiments, N-azidoacetylmannosamine-tetraacylated (Ac4ManNAz), which contains an azide group, can react with sialic acid on the surface of a cell to attach azide to the cell surface. In some embodiments, azide is attached to the cell surface by bio-orthogonal expression of azide.

Lectin-Based Systems

In some embodiments of any of the spatial analysis methods described herein, a molecule (e.g., a nucleic acid molecule) having a barcode (e.g., a spatial barcode) can be coupled to a lectin that facilitates attachment of the molecule (e.g., a nucleic acid molecule) having a barcode (e.g., a spatial barcode) to a cell surface. Lectin can bind to glycans, e.g., glycans on the surface of cells. In some embodiments, the molecule (e.g., a nucleic acid molecule) having a barcode (e.g., a spatial barcode) has an incorporated reactive functional group such as an azide group. In some embodiments, the molecule (e.g., a nucleic acid molecule) having a barcode (e.g., a spatial barcode) and an azide group is reacted with a modified lectin, e.g., a lectin modified using NHS chemistry to introduce an azide reactive group. In some embodiments, a live cell is labelled with a lectin-modified molecule (e.g., a nucleic acid molecule) having a barcode (e.g., a spatial barcode). In some embodiments, a fixed cell is labelled with a lectin-modified molecule (e.g., a nucleic acid molecule) having a barcode (e.g., a spatial barcode). In some embodiments, a permeabilized cell is labelled with a lectin-modified molecule (e.g., a nucleic acid molecule) having a barcode (e.g., a spatial barcode). In some embodiments, organelles in the secretory pathway can be labelled with a lectin-modified molecule (e.g., a nucleic acid molecule) having a barcode (e.g., a spatial barcode).

(b) Introducing a Cell-Tagging Agent to the Interior of a Cell

Non-limiting examples of cell-tagging agents and systems that penetrate and/or pass through the cell membrane (e.g., thus introducing the cell-tagging agent and any barcode attached thereto to the interior of the cell) that can be used in accordance with materials and methods provided herein for spatially profiling an analyte or analytes in a biological sample include: a cell-penetrating agent (e.g., a cell-penetrating peptide), a nanoparticle, a liposome, a polymersome, a peptide-based chemical vector, electroporation, sonoporation, lentiviral vectors, retroviral vectors, and combinations thereof.

Figure 19:
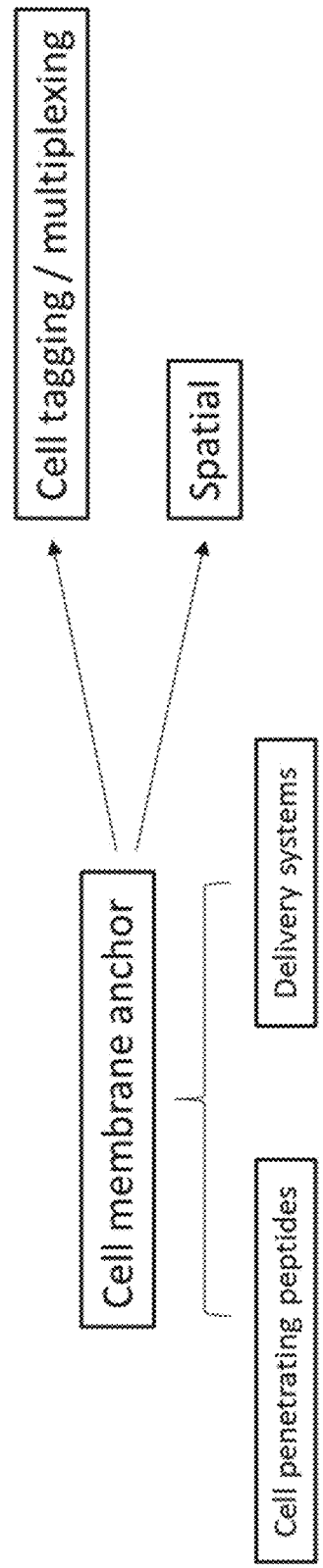
FIG. 19 is a schematic depicting cell tagging using either cell-penetrating peptides or delivery systems.

FIG. 19 is a schematic showing an exemplary cell tagging method. Non-exhaustive examples of oligo delivery vehicles may include a cell penetrating peptide or a nanoparticle. Non-exhaustive examples of the delivery systems can include lipid-based polymeric and metallic nanoparticles or oligos that can be conjugated or encapsulated within the delivery system. The cell tag can be used in combination with a capture agent barcode domain and a cleavable or non-cleavable spatially barcoded capture probes for spatial and multiplexing applications.

Cell-Penetrating Agent

In some embodiments of any of the spatial profiling methods described herein, capture of a biological analyte by a molecule (e.g., a nucleic acid molecule) having a barcode (e.g., a spatial barcode) and a capture domain is facilitated by a cell-penetrating agent. In some embodiments, a molecule (e.g., a nucleic acid molecule) having a barcode (e.g., a spatial barcode) and a capture domain is coupled to a cell-penetrating agent, and the cell-penetrating agent allows the molecule to interact with an analyte inside the cell. A "cell-penetrating agent" as used herein refers to an agent capable of facilitating the introduction of a molecule (e.g., a nucleic acid molecule) having a barcode (e.g., a spatial barcode) and a capture domain into a cell of a biological sample (see, e.g., Lovatt et al. Nat Methods. 2014 February; 11(2):190-6, which is incorporated herein by reference in its entirety). In some embodiments, a cell-penetrating agent is a cell-penetrating peptide. A "cell-penetrating peptide" as used herein refers to a peptide (e.g., a short peptide, e.g., a peptide not usually exceeding 30 residues) that has the capacity to cross cellular membranes.

In some embodiments of any of the spatial profiling methods described herein, a cell-penetrating peptide coupled to a molecule (e.g., a nucleic acid molecule) having a barcode (e.g., a spatial barcode) and a capture domain can cross a cellular membrane using an energy dependent or an energy independent mechanism. For example, a cell-penetrating peptide can cross a cellular membrane through direct translocation through physical perturbation of the plasma membrane, endocytosis, adaptive translocation, pore-formation, electroporation-like permeabilization, and/or entry at microdomain boundaries. Non-limiting examples of a cell-penetrating peptide include: penetratin, tat peptide, pVEC, transportan, MPG, Pep-1, a polyarginine peptide, MAP, R6W3, (D-Arg)9, Cys(Npys)-(D-Arg)9, Anti-BetaGamma (MPS-Phosducin-like protein C terminus), Cys (Npys) antennapedia, Cys(Npys)-(Arg)9, Cys(Npys)-TAT (47-57), HIV-1 Tat (48-60), KALA, mastoparan, penetratin-Arg, pep-1-cysteamine, TAT(47-57)GGG-Cys(Npys), Tat-NR2Bct, transdermal peptide, SynB1, SynB3, PTD-4, PTD-5, FHV Coat-(35-49), BMV Gag-(7-25), HTLV-II Rex-(4-16), R9-tat, SBP, FBP, MPG, MPG(ΔNLS), Pep-2, MTS, plsl, and a polylysine peptide (see, e.g., Bechara et al. FEBS Lett. 2013 Jun. 19; 587(12):1693-702, which is incorporated by reference herein in its entirety).

Nanoparticles

In some embodiments of any of the spatial profiling methods described herein, capture of a biological analyte by a molecule (e.g., a nucleic acid molecule) having a barcode (e.g., a spatial barcode) and a capture domain is facilitated by an inorganic particle (e.g., a nanoparticle). In some embodiments, a molecule (e.g., a nucleic acid molecule)

having a barcode (e.g., a spatial barcode) and a capture domain is coupled to an inorganic particle (e.g., a nanoparticle), and the molecule (e.g., a nucleic acid molecule) having a barcode (e.g., a spatial barcode) and a capture domain uses the nanoparticle to get access to analytes inside the cell. Non-limiting examples of nanoparticles that can be used in embodiments herein to deliver a molecule (e.g., a nucleic acid molecule) having a barcode (e.g., a spatial barcode) and a capture domain into a cell and/or cell bead include inorganic nanoparticles prepared from metals, (e.g., iron, gold, and silver), inorganic salts, and ceramics (e.g., phosphate or carbonate salts of calcium, magnesium, or silicon). The surface of a nanoparticle can be coated to facilitate binding of the molecule (e.g., a nucleic acid molecule) having a barcode (e.g., a spatial barcode) and a capture domain, or the surface can be chemically modified to facilitate attachment of the molecule (e.g., a nucleic acid molecule) having a barcode (e.g., a spatial barcode) and a capture domain. Magnetic nanoparticles (e.g., supermagnetic iron oxide), fullerenes (e.g., soluble carbon molecules), carbon nanotubes (e.g., cylindrical fullerenes), quantum dots and supramolecular systems can also be used.

Liposomes

In some embodiments of any of the spatial analysis methods described herein, capture of a biological analyte by a molecule (e.g., a nucleic acid molecule) having a barcode (e.g., a spatial barcode) and a capture domain is facilitated by a liposome. Various types of lipids, including cationic lipids, can be used in liposome delivery. In some cases, a molecule (e.g., a nucleic acid molecule) having a barcode (e.g., a spatial barcode) and a capture domain is delivered to a cell via a lipid nano-emulsion. A lipid emulsion refers to a dispersion of one immiscible liquid in another stabilized by emulsifying agent. Labeling cells can comprise use of a solid lipid nanoparticle.

Polymersomes

In some embodiments of any of the spatial analysis methods described herein, capture of a biological analyte by a molecule (e.g., a nucleic acid molecule) having a barcode (e.g., a spatial barcode) and a capture domain is facilitated by a polymersome. In some embodiments, a molecule (e.g., a nucleic acid molecule) having a barcode (e.g., a spatial barcode) and a capture domain is contained in the polymersome, and the molecule (e.g., a nucleic acid molecule) having a barcode (e.g., a spatial barcode) and a capture domain uses the polymersome to get access to analytes inside the cell. A "polymersome" as referred to herein is an artificial vesicle. For example, a polymersome can be a vesicle similar to a liposome, but the membrane comprises amphiphilic synthetic block copolymers (see, e.g., Rideau et al. Chem. Soc. Rev., 2018, 47, 8572-8610, which is incorporated by reference herein in its entirety). In some embodiments, polymersomes comprise di-(AB) or tri-block copolymers (e.g., ABA or ABC), where A and C are a hydrophilic block and B is a hydrophobic block. In some embodiments, a polymersome comprises poly(butadiene)-b-poly(ethylene oxide), poly(ethyl ethylene)-b-poly(ethylene oxide), polystyrene-b-poly(ethylene oxide), poly(2-vinylpyridine)-b-poly(ethylene oxide), polydimethylsiloxane-b-poly(ethylene oxide), polydimethylsiloxane-g-poly(ethylene oxide), polycaprolactone-b-poly(ethylene oxide), polyisobutylene-b-poly(ethylene oxide), polystyrene-b-polyacrylic acid, polydimethylsiloxane-b-poly-2-methyl-2-oxazoline, or a combination thereof (wherein b=block and g=grafted).

Peptide-Based Chemical Vectors

In some embodiments of any of the spatial analysis methods described herein, capture of a biological analyte by a molecule (e.g., a nucleic acid molecule) having a barcode (e.g., a spatial barcode) and a capture domain is facilitated by a peptide-based chemical vector, e.g., a cationic peptide-based chemical vector. Cationic peptides can be rich in basic residues like lysine and/or arginine. In some embodiments of any of the spatial analysis methods described herein, capture of a biological analyte by a molecule (e.g., a nucleic acid molecule) having a barcode (e.g., a spatial barcode) and a capture domain is facilitated by a polymer-based chemical vector. Cationic polymers, when mixed with a molecule (e.g., a nucleic acid molecule) having a barcode (e.g., a spatial barcode) and a capture domain, can form nanosized complexes called polyplexes. Polymer based vectors can comprise natural proteins, peptides and/or polysaccharides. Polymer based vectors can comprise synthetic polymers. In some embodiments, a polymer-based vector comprises polyethylenimine (PEI). PEI can condense DNA into positively-charged particles, which bind to anionic cell surface residues and are brought into the cell via endocytosis. In some embodiments, a polymer-based chemical vector comprises poly(L)-lysine (PLL), poly (DL-lactic acid) (PLA), poly (DL-lactide-co-glycoside) (PLGA), polyornithine, polyarginine, histones, protamines, or a combination thereof. Polymer-based vectors can comprise a mixture of polymers, for example, PEG and PLL. Other non-limiting examples of polymers include dendrimers, chitosans, synthetic amino derivatives of dextran, and cationic acrylic polymers.

Electroporation

In some embodiments of any of the spatial analysis methods described herein, capture of a biological analyte by a molecule (e.g., a nucleic acid molecule) having a barcode (e.g., a spatial barcode) and a capture domain is facilitated by electroporation. With electroporation, a biological analyte by a molecule (e.g., a nucleic acid molecule) having a barcode (e.g., a spatial barcode) and a capture domain can enter a cell through one or more pores in the cellular membrane formed by applied electricity. The pore of the membrane can be reversible based on the applied field strength and pulse duration.

Sonoporation

In some embodiments of any of the spatial analysis methods described herein, capture of a biological analyte by a molecule (e.g., a nucleic acid molecule) having a barcode (e.g., a spatial barcode) and a capture domain is facilitated by sonoporation. Cell membranes can be temporarily permeabilized using sound waves, allowing cellular uptake of a biological analyte by a molecule (e.g., a nucleic acid molecule) having a barcode (e.g., a spatial barcode) and a capture domain.

Lentiviral Vectors and Retroviral Vectors

In some embodiments of any of the spatial analysis methods described herein, capture of a biological analyte by a molecule (e.g., a nucleic acid molecule) having a barcode (e.g., a spatial barcode) and a capture domain is facilitated by vectors. For example, a vector as described herein can be an expression vector where the expression vector includes a promoter sequence operably linked to the sequence encoding the molecule (e.g., a nucleic acid molecule) having a barcode (e.g., a spatial barcode) and a capture domain. Non-limiting examples of vectors include plasmids, transposons, cosmids, and viral vectors (e.g., any adenoviral vectors (e.g., pSV or pCMV vectors), adeno-associated virus (AAV) vectors, lentivirus vectors, and retroviral vectors), and any Gateway® vectors. A vector can, for example, include sufficient cis-acting elements for expression where other elements for expression can be supplied by the host mammalian cell or in an in vitro expression system. Skilled practitioners will be capable of selecting suitable vectors and mammalian cells for introducing any of spatial profiling reagents described herein.

Other Methods and Cell-Tagging Agents for Intracellular Introduction of a Molecule In some embodiments of any of the spatial analysis methods described herein, capture of a biological analyte by a molecule (e.g., a nucleic acid molecule) having a barcode (e.g., a spatial barcode) and a capture domain is facilitated by the use of a needle, for example for injection (e.g., microinjection), particle bombardment, photoporation, magnetofection, and/or hydroporation. For example, with particle bombardment, a molecule (e.g., a nucleic acid molecule) having a barcode (e.g., a spatial barcode) and a capture domain can be coated with heavy metal particles and delivered to a cell at a high speed. In photoporation, a transient pore in a cell membrane can be generated using a laser pulse, allowing cellular uptake of a molecule (e.g., a nucleic acid molecule) having a barcode (e.g., a spatial barcode) and a capture domain. In magnetofection, a molecule (e.g., a nucleic acid molecule) having a barcode (e.g., a spatial barcode) and a capture domain can be coupled to a magnetic particle (e.g., magnetic nanoparticle, nanowires, etc.) and localized to a target cell via an applied magnetic field. In hydroporation, a molecule (e.g., a nucleic acid molecule) having a barcode (e.g., a spatial barcode) and a capture domain can be delivered to a cell and/or cell bead via hydrodynamic pressure.

(c) Methods for Separating Sample into Single Cells or Cell Groups

Some embodiments of any of the methods described herein can include separating a biological sample into single cells, cell groups, types of cells, or a region or regions of interest. For example, a biological sample can be separated into single cells, cell groups, types of cells, or a region or regions of interest before being contacted with one or more capture probes. In other examples, a biological sample is first contacted with one or more capture probes, and then separated into single cells, cell groups, types of cells, or a region or regions of interest.

In some embodiments, a biological sample can be separated into chucks using pixelation. Pixelation can include the steps of providing a biological sample, and punching out one or more portions of the biological sample. The punched out portions of the biological sample can then be used to perform any of the methods described herein. In some embodiments, the punched-out portions of the biological sample can be in a random pattern or a designed pattern. In some embodiments, the punched-out portions of the biological sample can be focused on a region of interest or a subcellular structure in the biological sample.

Figure 20A:
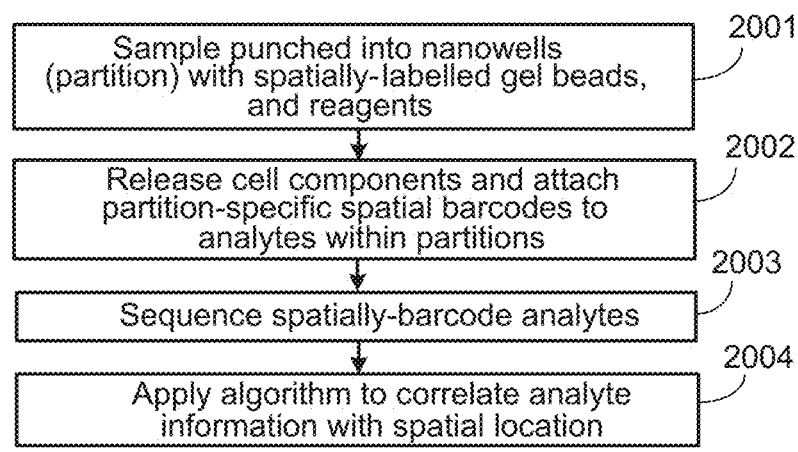
FIG. 20A is a workflow schematic illustrating exemplary, non-limiting, non-exhaustive steps for "pixelating" a sample, wherein the sample is cut, stamped, microdissected, or transferred by hollow-needle or microneedle, moving a small portion of the sample into an individual partition or well.

FIG. 20A is a workflow schematic illustrating exemplary, non-limiting, non-exhaustive steps for "pixelating" a sample, wherein the sample is cut, stamped, microdissected, or transferred by hollow-needle or microneedle, moving a small portion of the sample into an individual partition or well.

Figure 20B:
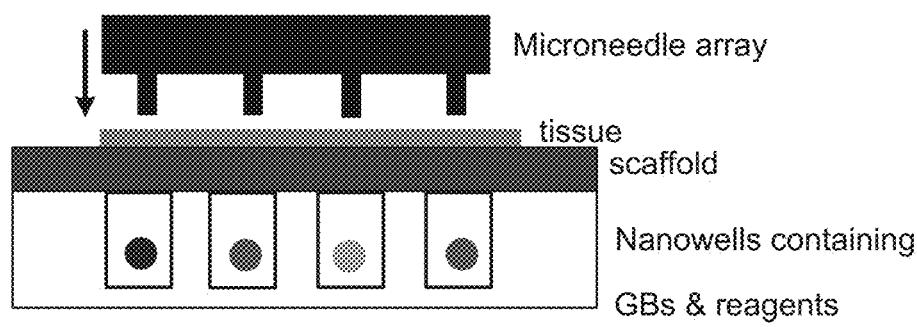
FIG. 20B is a schematic depicting multi-needle pixilation, wherein an array of needles punched through a sample on a scaffold and into nanowells containing gel beads and reagents below. Once the needle is in the nanowell, the cell(s) are ejected.

FIG. 20B is a schematic depicting multi-needle pixelation, wherein an array of needles punched through a sample on a scaffold and into nanowells containing gel beads and reagents below. Once the needle is in the nanowell, the cell(s) are ejected.

In some embodiments, a biological sample is divided into chucks before performance of any of the spatial analysis methods described herein. In some embodiments, the methods can include spatial barcoding of FFPE "chunks" via barcodes applied in spatially well-defined pattern (like in DNA microarray printing). The DNA barcode is either long so that it will not diffuse out in subsequent steps or is covalently applied to the FFPE sample. To enable barcodes to get embedded into an FFPE slide, the wax can be heated, barcodes can be added to the slide before cooling, and then the chunks can be cut. The cutting can be done in various ways such as using laser microdissection, or via mechanical or acoustic means. Other alternates are to embed some fluorophores/Qdots, etc. to preserve spatial information into the sample. The barcoding at this step enables massively parallel random encapsulation of chunks while retaining local spatial information (e.g., tumor vs normal cells).

In some embodiments, a biological sample can be divided or portioned using laser capture microdissection (e.g., highly-multiplexed laser capture microdissection).

(d) Release and Amplification of Analytes

In some embodiments, lysis reagents can be added to the sample to facilitate the release of analyte(s) from a sample. Examples of lysis agents include, but are not limited to, bioactive reagents such as lysis enzymes that are used for lysis of different cell types, e.g., gram positive or negative bacteria, plants, yeast, mammalian, such as lysozymes, achromopeptidase, lysostaphin, labiase, kitalase, lyticase, and a variety of other commercially available lysis enzymes. Other lysis agents can additionally or alternatively be co-partitioned with the biological sample to cause the release of the sample's contents into the partitions. In some embodiments, surfactant-based lysis solutions can be used to lyse cells, although these can be less desirable for emulsion-based systems where the surfactants can interfere with stable emulsions. Lysis solutions can include ionic surfactants such as, for example, sarcosyl and sodium dodecyl sulfate (SDS). Electroporation, thermal, acoustic or mechanical cellular disruption can also be used in certain embodiments, e.g., non-emulsion based partitioning such as encapsulation of biological materials that can be in addition to or in place of droplet partitioning, where any pore size of the encapsulate is sufficiently small to retain nucleic acid fragments of a given size, following cellular disruption.

In addition to the permeabilization agents, other reagents can also be added to interact with the biological sample, including, for example, DNase and RNase inactivating agents or inhibitors, such as proteinase K, chelating agents, such as EDTA, and other reagents to allow for subsequent processing of analytes from the sample.

Further reagents that can be added to a sample, include, for example, endonucleases to fragment DNA, DNA polymerase enzymes, and dNTPs used to amplify nucleic acids. Other enzymes that can also be added to the sample include, but are not limited to, polymerase, transposase, ligase, proteinase K, and DNAse, etc. Additional reagents can also include reverse transcriptase enzymes, including enzymes with terminal transferase activity, primers, and switch oligonucleotides. In some embodiments, template switching can be used to increase the length of a cDNA, e.g., by appending a predefined nucleic acid sequence to the cDNA.

If a tissue sample is not permeabilized sufficiently, the amount of analyte captured on the substrate can be too low to enable adequate analysis. Conversely, if the tissue sample is too permeable, the analyte can diffuse away from its origin in the tissue sample, such that the relative spatial relationship of the analytes within the tissue sample is lost. Hence, a balance between permeabilizing the tissue sample enough to obtain good signal intensity while still maintaining the spatial resolution of the analyte distribution in the tissue sample is desired.

In some embodiments, where the biological sample includes live cells, permeabilization conditions can be modified so that the live cells experience only brief permeabilization (e.g., through short repetitive bursts of electric field application), thereby allowing one or more analytes to migrate from the live cells to the substrate while retaining cellular viability. In some embodiments, after contacting a biological sample with a substrate that include capture probes, a removal step is performed to remove all or a portion of the biological sample from the substrate. In some embodiments, the removal step includes enzymatic or chemical degradation of the permeabilized cells of the biological sample. For example, the removal step can include treating the biological samples with an enzyme (e.g., proteinase K) to remove at least a portion of the biological sample from the first substrates. In some embodiments, the removal step can include ablation of the tissue (e.g., laser ablation).

In some embodiments, where RNA is captured from cells in a sample, one or more RNA species of interest can be selectively enriched. For example, one or more species of RNA of interest can be selected by addition of one or more oligonucleotides. One or more species of RNA can be selectively down-selected (e.g., removed) using any of a variety of methods. For example, probes can be administered to a sample that selectively hybridize to ribosomal RNA (rRNA), thereby reducing the pool and concentration of rRNA in the sample. Subsequent application of the capture probes to the sample can result in improved RNA capture due to the reduction in non-specific RNA present in the sample. In some embodiments, the additional oligonucleotide is a sequence used for priming a reaction by a polymerase. For example, one or more primer sequences with sequence complementarity to one or more RNAs of interest, can be used to amplify the one or more RNAs of interest, thereby selectively enriching these RNAs. In some embodiments, an oligonucleotide with sequence complementarity to the complementary strand of captured RNA (e.g., cDNA) can bind to the cDNA. In one non-limiting example, biotinylated oligonucleotides with sequence complementary to one or more cDNA of interest binds to the cDNA and can be selected using biotinylation-strepavidin affinity in any number of methods known to the field (e.g., streptavidin beads).

Nucleic acid analytes can be amplified using a polymerase chain reaction (e.g., digital PCR, quantitative PCR, or real time PCR), or isothermal amplification, or any of the nucleic acid amplification or extension reactions described herein.

(e) Partitioning

As discussed above, in some embodiments, the sample can optionally be separated into single cells, cell groups, or other fragments/pieces that are smaller than the original, unfragmented sample. Each of these smaller portions of the sample can be analyzed to obtain spatially-resolved analyte information from the sample. Non-limiting partitioning methods are described herein.

For samples that have been separated into smaller fragments—and particularly, for samples that have been disaggregated, dissociated, or otherwise separated into individual cells—one method for analyzing the fragments involves partitioning the fragments into individual partitions (e.g., fluid droplets), and then analyzing the contents of the partitions. In general, each partition maintains separation of its own contents from the contents of other partitions. For example, the partition can be a droplet in an emulsion.

In addition to analytes, a partition can include additional components, and in particular, one or more beads. A partition can include a single gel bead, a single cell bead, or both a single cell bead and single gel bead.

A partition can also include one or more reagents. Unique identifiers, such as barcodes, can be injected into the droplets previous to, subsequent to, or concurrently with droplet generation, such as via a microcapsule (e.g., bead). Microfluidic channel networks (e.g., on a chip) can be utilized to generate partitions. Alternative mechanisms can also be employed in the partitioning of individual biological particles, including porous membranes through which aqueous mixtures of cells are extruded into non-aqueous fluids.

The partitions can be flowable within fluid streams. The partitions can include, for example, micro-vesicles that have an outer barrier surrounding an inner fluid center or core. In some cases, the partitions can include a porous matrix that is capable of entraining and/or retaining materials within its matrix. The partitions can be droplets of a first phase within a second phase, wherein the first and second phases are immiscible. For example, the partitions can be droplets of aqueous fluid within a non-aqueous continuous phase (e.g., oil phase). In another example, the partitions can be droplets of a non-aqueous fluid within an aqueous phase. In some examples, the partitions can be provided in a water-in-oil emulsion or oil-in-water emulsion. A variety of different vessels are described in, for example, U.S. Patent Application Publication No. 2014/0155295, the entire contents of which are incorporated herein by reference. Emulsion systems for creating stable droplets in non-aqueous or oil continuous phases are described, for example, in U.S. Patent Application Publication No. 2010/0105112, the entire contents of which are incorporated herein by reference.

For droplets in an emulsion, allocating individual particles to discrete partitions can be accomplished, for example, by introducing a flowing stream of particles in an aqueous fluid into a flowing stream of a non-aqueous fluid, such that droplets are generated at the junction of the two streams. Fluid properties (e.g., fluid flow rates, fluid viscosities, etc.), particle properties (e.g., volume fraction, particle size, particle concentration, etc.), microfluidic architectures (e.g., channel geometry, etc.), and other parameters can be adjusted to control the occupancy of the resulting partitions (e.g., number of analytes per partition, number of beads per partition, etc.) For example, partition occupancy can be controlled by providing the aqueous stream at a certain concentration and/or flow rate of analytes.

To generate single analyte partitions, the relative flow rates of the immiscible fluids can be selected such that, on average, the partitions can contain less than one analyte per partition to ensure that those partitions that are occupied are primarily singly occupied. In some cases, partitions among a plurality of partitions can contain at most one analyte. In some embodiments, the various parameters (e.g., fluid properties, particle properties, microfluidic architectures, etc.) can be selected or adjusted such that a majority of partitions are occupied, for example, allowing for only a small percentage of unoccupied partitions. The flows and channel architectures can be controlled as to ensure a given number of singly occupied partitions, less than a certain level of unoccupied partitions and/or less than a certain level of multiply occupied partitions.

The channel segments described herein can be coupled to any of a variety of different fluid sources or receiving components, including reservoirs, tubing, manifolds, or fluidic components of other systems. As will be appreciated, the microfluidic channel structure can have a variety of geometries. For example, a microfluidic channel structure can have one or more than one channel junction. As another example, a microfluidic channel structure can have 2, 3, 4, or 5 channel segments each carrying particles that meet at a channel junction. Fluid can be directed to flow along one or more channels or reservoirs via one or more fluid flow units. A fluid flow unit can include compressors (e.g., providing positive pressure), pumps (e.g., providing negative pressure), actuators, and the like to control flow of the fluid. Fluid can also or otherwise be controlled via applied pressure differentials, centrifugal force, electrokinetic pumping, vacuum, capillary, and/or gravity flow.

A partition can include one or more unique identifiers, such as barcodes. Barcodes can be previously, subsequently, or concurrently delivered to the partitions that hold the compartmentalized or partitioned biological particle. For example, barcodes can be injected into droplets previous to, subsequent to, or concurrently with droplet generation. The delivery of the barcodes to a particular partition allows for the later attribution of the characteristics of the individual biological particle to the particular partition. Barcodes can be delivered, for example on a nucleic acid molecule (e.g., an oligonucleotide), to a partition via any suitable mechanism. Barcoded nucleic acid molecules can be delivered to a partition via a microcapsule. A microcapsule, in some instances, can include a bead.

In some embodiments, barcoded nucleic acid molecules can be initially associated with the microcapsule and then released from the microcapsule. Release of the barcoded nucleic acid molecules can be passive (e.g., by diffusion out of the microcapsule). In addition or alternatively, release from the microcapsule can be upon application of a stimulus which allows the barcoded nucleic acid nucleic acid molecules to dissociate or to be released from the microcapsule. Such stimulus can disrupt the microcapsule, an interaction that couples the barcoded nucleic acid molecules to or within the microcapsule, or both. Such stimulus can include, for example, a thermal stimulus, photo-stimulus, chemical stimulus (e.g., change in pH or use of a reducing agent(s)), a mechanical stimulus, a radiation stimulus; a biological stimulus (e.g., enzyme), or any combination thereof.

In some embodiments, one more barcodes (e.g., spatial barcodes, UMIs, or a combination thereof) can be introduced into a partition as part of the analyte. As described previously, barcodes can be bound to the analyte directly, or can form part of a capture probe or analyte capture agent that is hybridized to, conjugated to, or otherwise associated with an analyte, such that when the analyte is introduced into the partition, the barcode(s) are introduced as well.

Figure 21:
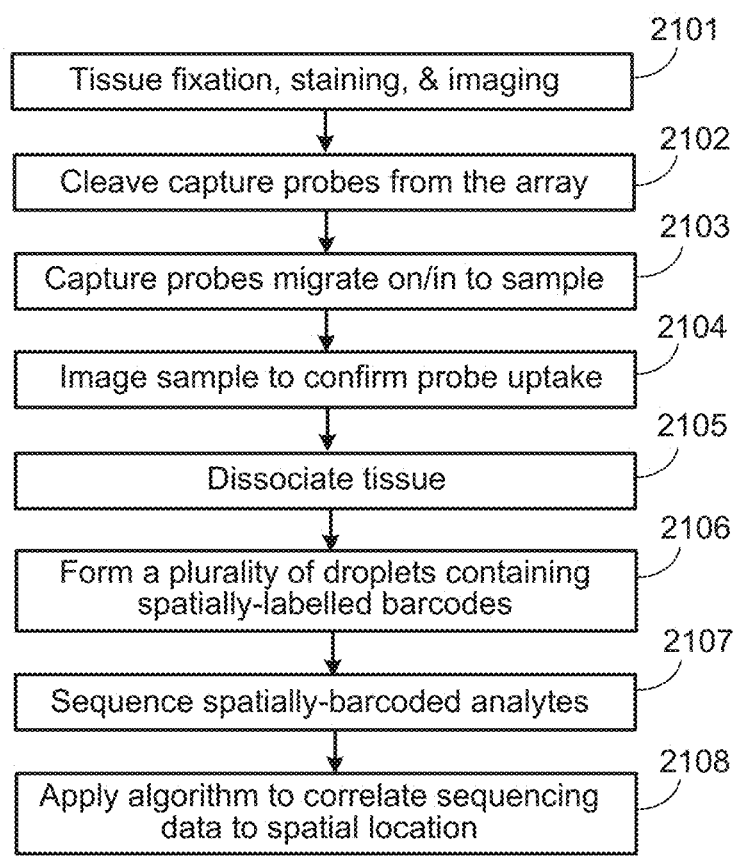
FIG. 21 shows a workflow schematic illustrating exemplary, non-limiting, non-exhaustive steps for dissociating a spatially-barcoded sample for analysis via droplet or flow cell analysis methods.
Figure 24A:
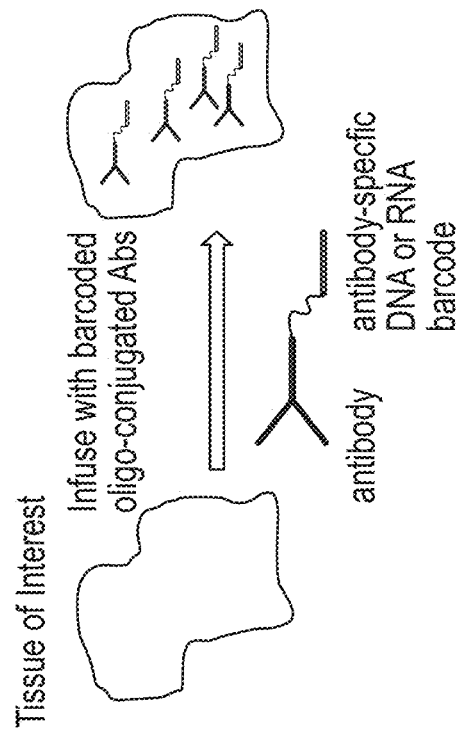
FIGS. 24A-C is a schematic diagram showing an example of multiplex detection of analytes in a biological sample.
Figure 24B:
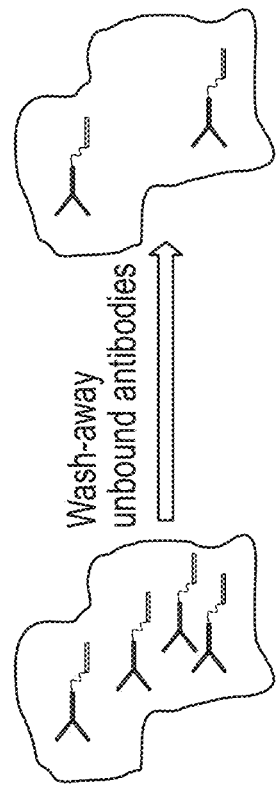
Figure 24C:
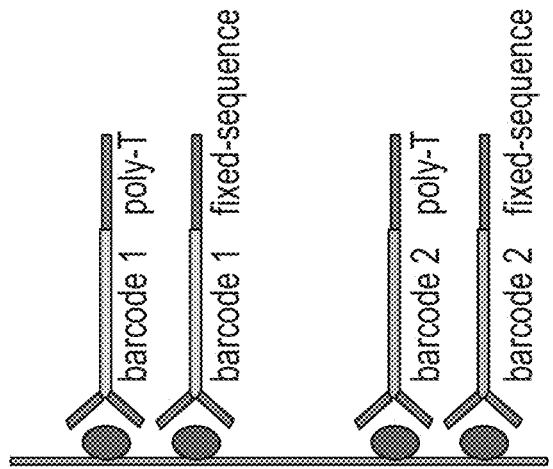
Figure 25:
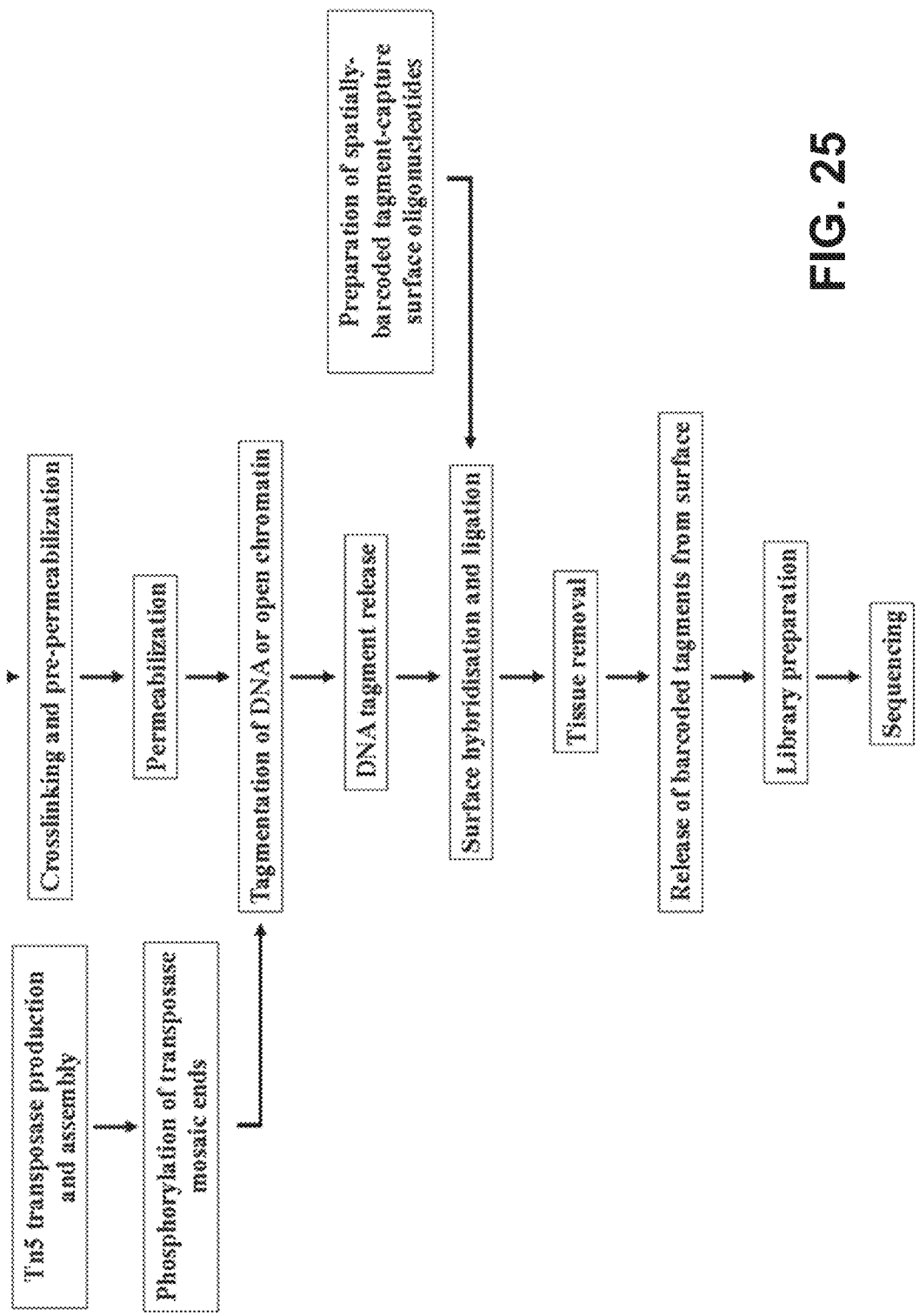
FIG. 25 is a schematic diagram showing a representative workflow of the invention.
Figure 26:
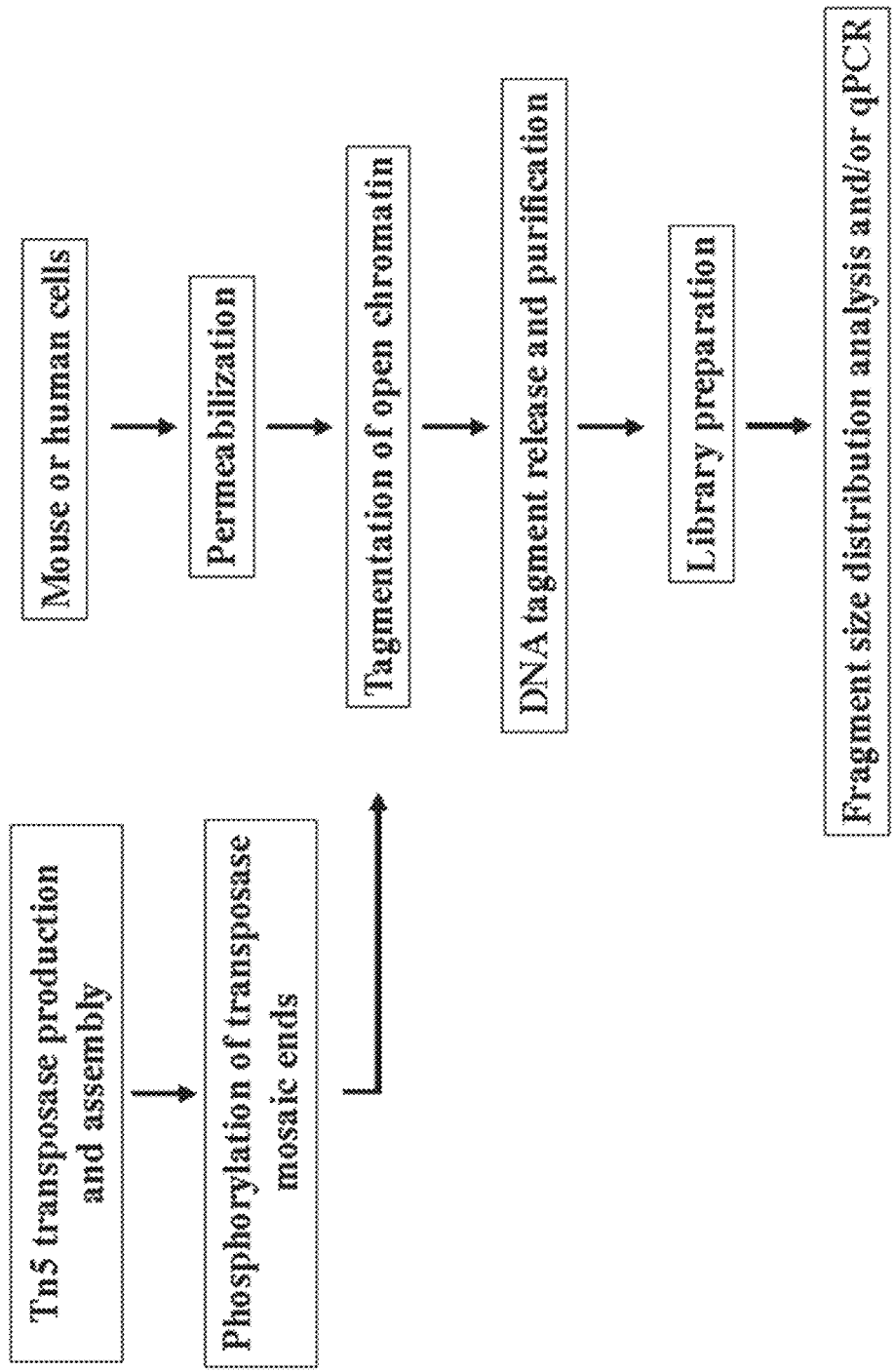
FIG. 26 is a schematic diagram showing a representative workflow of the procedure used to investigate Tn5 transposase/transposome efficiency.

FIG. 21 depicts an exemplary workflow, where a sample is contacted with a spatially-barcoded capture probe array and the sample is fixed, stained, and imaged 2101, as described elsewhere herein. The capture probes can be cleaved from the array 2102 using any method as described herein. The capture probes can diffuse toward the cells by either passive or active migration as described elsewhere herein. The capture probes may then be introduced to the sample 2103 as described elsewhere herein, wherein the capture probe is able to gain entry into the cell in the absence of cell permeabilization, using one of the cell penetrating peptides or lipid delivery systems described herein. The sample can then be optionally imaged in order to confirm probe uptake, via a reporter molecule incorporated within the capture probe 2104. The sample can then be separated from the array and undergo dissociation 2105, wherein the sample is separated into single cells or small groups of cells. Once the sample is dissociated, the single cells can be introduced to an oil-in water droplet 2106, wherein a single cell is combined with reagents within the droplet and processed so that the spatial barcode that penetrated the cell labels the contents of that cell within the droplet. Other cells undergo separately partitioned reactions concurrently. The contents of the droplet is then sequenced 2107 in order to associate a particular cell or cells with a particular spatial location within the sample 2108.

As described above, FIG. 16 shows an example of a microfluidic channel structure for partitioning individual analytes (e.g., cells) into discrete partitions. FIGS. 17A and 17C also show other examples of microfluidic channel structures that can be used for delivering beads to droplets.

A variety of different beads can be incorporated into partitions as described above. In some embodiments, for example, non-barcoded beads can be incorporated into the partitions. For example, where the biological particle (e.g., a cell) that is incorporated into the partitions carries one or more barcodes (e.g., spatial barcode(s), UMI(s), and combinations thereof), the bead can be a non-barcoded bead.

In some embodiments, a barcode carrying bead can be incorporated into partitions. For example, a nucleic acid molecule, such as an oligonucleotide, can be coupled to a bead by a releasable linkage, such as, for example, a disulfide linker. The same bead can be coupled (e.g., via releasable linkage) to one or more other nucleic acid molecules. The nucleic acid molecule can be or include a barcode. As noted elsewhere herein, the structure of the barcode can include a number of sequence elements.

The nucleic acid molecule can include a functional domain that can be used in subsequent processing. For example, the functional domain can include one or more of a sequencer specific flow cell attachment sequence (e.g., a P5 sequence for Illumina® sequencing systems) and a sequencing primer sequence (e.g., a R1 primer for Illumina® sequencing systems). The nucleic acid molecule can include a barcode sequence for use in barcoding the sample (e.g., DNA, RNA, protein, etc.). In some cases, the barcode sequence can be bead-specific such that the barcode sequence is common to all nucleic acid molecules coupled to the same bead. Alternatively or in addition, the barcode sequence can be partition-specific such that the barcode sequence is common to all nucleic acid molecules coupled to one or more beads that are partitioned into the same partition. The nucleic acid molecule can include a specific priming sequence, such as an mRNA specific priming sequence (e.g., poly (T) sequence), a targeted priming sequence, and/or a random priming sequence. The nucleic acid molecule can include an anchoring sequence to ensure that the specific priming sequence hybridizes at the sequence end (e.g., of the mRNA). For example, the anchoring sequence can include a random short sequence of nucleotides, such as a 1-mer, 2-mer, 3-mer or longer sequence, which can ensure that a poly(T) segment is more likely to hybridize at the sequence end of the poly(A) tail of the mRNA.

The nucleic acid molecule can include a unique molecular identifying sequence (e.g., unique molecular identifier (UMI)). In some embodiments, the unique molecular identifying sequence can include from about 5 to about 8 nucleotides. Alternatively, the unique molecular identifying sequence can include less than about 5 or more than about 8 nucleotides. The unique molecular identifying sequence can be a unique sequence that varies across individual nucleic acid molecules coupled to a single bead.

In some embodiments, the unique molecular identifying sequence can be a random sequence (e.g., such as a random N-mer sequence). For example, the UMI can provide a unique identifier of the starting mRNA molecule that was captured, in order to allow quantitation of the number of original expressed RNA.

In general, an individual bead can be coupled to any number of individual nucleic acid molecules, for example, from one to tens to hundreds of thousands or even millions of individual nucleic acid molecules. The respective barcodes for the individual nucleic acid molecules can include both common sequence segments or relatively common sequence segments and variable or unique sequence segments between different individual nucleic acid molecules coupled to the same bead.

Within any given partition, all of the cDNA transcripts of the individual mRNA molecules can include a common barcode sequence segment. However, the transcripts made from the different mRNA molecules within a given partition can vary at the unique molecular identifying sequence segment (e.g., UMI segment). Beneficially, even following any subsequent amplification of the contents of a given partition, the number of different UMIs can be indicative of the quantity of mRNA originating from a given partition. As noted above, the transcripts can be amplified, cleaned up and sequenced to identify the sequence of the cDNA transcript of the mRNA, as well as to sequence the barcode segment and the UMI segment. While a poly(T) primer sequence is described, other targeted or random priming sequences can also be used in priming the reverse transcription reaction. Likewise, although described as releasing the barcoded oligonucleotides into the partition, in some cases, the nucleic acid molecules bound to the bead can be used to hybridize and capture the mRNA on the solid phase of the bead, for example, in order to facilitate the separation of the RNA from other cell contents.

In some embodiments, precursors that include a functional group that is reactive or capable of being activated such that it becomes reactive can be polymerized with other precursors to generate gel beads that include the activated or activatable functional group. The functional group can then be used to attach additional species (e.g., disulfide linkers, primers, other oligonucleotides, etc.) to the gel beads. For example, some precursors featuring a carboxylic acid (COOH) group can co-polymerize with other precursors to form a bead that also includes a COOH functional group. In some cases, acrylic acid (a species comprising free COOH groups), acrylamide, and bis(acryloyl)cystamine can be co-polymerized together to generate a bead with free COOH groups. The COOH groups of the bead can be activated (e.g., via 1-Ethyl-3-(3-dimethylaminopropyl)carbodiimide (EDC) and N-Hydroxysuccinimide (NHS) or 4-(4,6-Dimethoxy-1,3,5-triazin-2-yl)-4-methylmorpholinium chloride (DMTMM)) such that they are reactive (e.g., reactive to amine functional groups where EDC/NHS or DMTMM are used for activation). The activated COOH groups can then react with an appropriate species (e.g., a species comprising an amine functional group where the carboxylic acid groups are activated to be reactive with an amine functional group) comprising a moiety to be linked to the bead.

In some embodiments, a degradable bead can be introduced into a partition, such that the bead degrades within the partition and any associated species (e.g., oligonucleotides) are released within the droplet when the appropriate stimulus is applied. The free species (e.g., oligonucleotides, nucleic acid molecules) can interact with other reagents contained in the partition. For example, a polyacrylamide bead featuring cystamine and linked, via a disulfide bond, to a barcode sequence, can be combined with a reducing agent within a droplet of a water-in-oil emulsion. Within the droplet, the reducing agent can break the various disulfide bonds, resulting in bead degradation and release of the barcode sequence into the aqueous, inner environment of the droplet. In another example, heating of a droplet with a bead-bound barcode sequence in basic solution can also result in bead degradation and release of the attached barcode sequence into the aqueous, inner environment of the droplet.

Any suitable number of species (e.g., primer, barcoded oligonucleotide) can be associated with a bead such that, upon release from the bead, the species (e.g., primer, e.g., barcoded oligonucleotide) are present in the partition at a pre-defined concentration. Such pre-defined concentration can be selected to facilitate certain reactions for generating a sequencing library, e.g., amplification, within the partition. In some cases, the pre-defined concentration of the primer can be limited by the process of producing nucleic acid molecule (e.g., oligonucleotide) bearing beads.

A degradable bead can include one or more species with a labile bond such that, when the bead/species is exposed to the appropriate stimulus, the bond is broken and the bead degrades. The labile bond can be a chemical bond (e.g., covalent bond, ionic bond) or can be another type of physical interaction (e.g., van der Waals interactions, dipole-dipole interactions, etc.). In some embodiments, a cross-linker used to generate a bead can include a labile bond. Upon exposure to the appropriate conditions, the labile bond can be broken and the bead degraded. For example, upon exposure of a polyacrylamide gel bead that includes cystamine crosslinkers to a reducing agent, the disulfide bonds of the cystamine can be broken and the bead degraded.

A degradable bead can be useful in more quickly releasing an attached species (e.g., a nucleic acid molecule, a barcode sequence, a primer, etc.) from the bead when the appropriate stimulus is applied to the bead as compared to a bead that does not degrade. For example, for a species bound to an inner surface of a porous bead or in the case of an encapsulated species, the species can have greater mobility and accessibility to other species in solution upon degradation of the bead. In some embodiments, a species can also be attached to a degradable bead via a degradable linker (e.g., disulfide linker). The degradable linker can respond to the same stimuli as the degradable bead or the two degradable species can respond to different stimuli. For example, a barcode sequence can be attached, via a disulfide bond, to a polyacrylamide bead comprising cystamine. Upon exposure of the barcoded-bead to a reducing agent, the bead degrades and the barcode sequence is released upon breakage of both the disulfide linkage between the barcode sequence and the bead and the disulfide linkages of the cystamine in the bead.

As will be appreciated from the above description, while referred to as degradation of a bead, in many embodiments, degradation can refer to the disassociation of a bound or entrained species from a bead, both with and without structurally degrading the physical bead itself. For example, entrained species can be released from beads through osmotic pressure differences due to, for example, changing chemical environments. By way of example, alteration of bead pore sizes due to osmotic pressure differences can generally occur without structural degradation of the bead itself. In some cases, an increase in pore size due to osmotic swelling of a bead can permit the release of entrained species within the bead. In some embodiments, osmotic shrinking of a bead can cause a bead to better retain an entrained species due to pore size contraction. Numerous chemical triggers can be used to trigger the degradation of beads within partitions. Examples of these chemical changes can include, but are not limited to pH-mediated changes to the integrity of a component within the bead, degradation of a component of a bead via cleavage of cross-linked bonds, and depolymerization of a component of a bead.

In some embodiments, a bead can be formed from materials that include degradable chemical cross-linkers, such as BAC or cystamine. Degradation of such degradable cross-linkers can be accomplished through a number of mechanisms. In some examples, a bead can be contacted with a chemical degrading agent that can induce oxidation, reduction or other chemical changes. For example, a chemical degrading agent can be a reducing agent, such as dithiothreitol (DTT). Additional examples of reducing agents can include β-mercaptoethanol, (2S)-2-amino-1,4-dimercaptobutane (dithiobutylamine or DTBA), tris(2-carboxyethyl) phosphine (TCEP), or combinations thereof. A reducing agent can degrade the disulfide bonds formed between gel precursors forming the bead, and thus, degrade the bead.

In certain embodiments, a change in pH of a solution, such as an increase in pH, can trigger degradation of a bead. In other embodiments, exposure to an aqueous solution, such as water, can trigger hydrolytic degradation, and thus degradation of the bead. In some cases, any combination of stimuli can trigger degradation of a bead. For example, a change in pH can enable a chemical agent (e.g., DTT) to become an effective reducing agent.

Beads can also be induced to release their contents upon the application of a thermal stimulus. A change in temperature can cause a variety of changes to a bead. For example, heat can cause a solid bead to liquefy. A change in heat can cause melting of a bead such that a portion of the bead degrades. In other cases, heat can increase the internal pressure of the bead components such that the bead ruptures or explodes. Heat can also act upon heat-sensitive polymers used as materials to construct beads.

In addition to beads and analytes, partitions that are formed can include a variety of different reagents and species. For example, when lysis reagents are present within the partitions, the lysis reagents can facilitate the release of analytes within the partition. Examples of lysis agents include bioactive reagents, such as lysis enzymes that are used for lysis of different cell types, e.g., gram positive or negative bacteria, plants, yeast, mammalian, etc., such as lysozymes, achromopeptidase, lysostaphin, labiase, kitalase, lyticase, and a variety of other lysis enzymes available from, e.g., Sigma-Aldrich, Inc. (St. Louis, MO), as well as other commercially available lysis enzymes. Other lysis agents can additionally or alternatively be co-partitioned to cause the release analytes into the partitions. For example, in some cases, surfactant-based lysis solutions can be used to lyse cells, although these can be less desirable for emulsion based systems where the surfactants can interfere with stable emulsions. In some embodiments, lysis solutions can include non-ionic surfactants such as, for example, TritonX-100 and Tween 20. In some embodiments, lysis solutions can include ionic surfactants such as, for example, sarcosyl and sodium dodecyl sulfate (SDS). Electroporation, thermal, acoustic or mechanical cellular disruption can also be used in certain embodiments, e.g., non-emulsion based partitioning such as encapsulation of analytes that can be in addition to or in place of droplet partitioning, where any pore size of the encapsulate is sufficiently small to retain nucleic acid fragments of a given size, following cellular disruption.

Examples of other species that can be co-partitioned with analytes in the partitions include, but are not limited to, DNase and RNase inactivating agents or inhibitors, such as proteinase K, chelating agents, such as EDTA, and other reagents employed in removing or otherwise reducing negative activity or impact of different cell lysate components on subsequent processing of nucleic acids. Additional reagents can also be co-partitioned, including endonucleases to fragment DNA, DNA polymerase enzymes and dNTPs used to amplify nucleic acid fragments and to attach the barcode molecular tags to the amplified fragments. Additional reagents can also include reverse transcriptase enzymes, including enzymes with terminal transferase activity, primers and oligonucleotides, and switch oligonucleotides (also referred to herein as "switch oligos" or "template switching oligonucleotides") which can be used for template switching. In some embodiments, template switching can be used to increase the length of a cDNA. Template switching can be used to append a predefined nucleic acid sequence to the cDNA. In an example of template switching, cDNA can be generated from reverse transcription of a template, e.g., cellular mRNA, where a reverse transcriptase with terminal transferase activity can add additional nucleotides, e.g., poly(C), to the cDNA in a template independent manner. Switch oligos can include sequences complementary to the additional nucleotides, e.g., poly(G). The additional nucleotides (e.g., poly(C)) on the cDNA can hybridize to the additional nucleotides (e.g., poly(G)) on the switch oligo, whereby the switch oligo can be used by the reverse transcriptase as template to further extend the cDNA. Template switching oligonucleotides can include a hybridization region and a template region. The hybridization region can include any sequence capable of hybridizing to the target. In some cases, the hybridization region includes a series of G bases to complement the overhanging C bases at the 3' end of a cDNA molecule. The series of G bases can include 1 G base, 2 G bases, 3 G bases, 4 G bases, 5 G bases or more than 5 G bases. The template sequence can include any sequence to be incorporated into the cDNA. In some cases, the template region includes at least 1 (e.g., at least 2, 3, 4, 5 or more) tag sequences and/or functional sequences. Switch oligos can include deoxyribonucleic acids; ribonucleic acids; modified nucleic acids including 2-Aminopurine, 2,6-Diaminopurine (2-Amino-dA), inverted dT, 5-Methyl dC, 2'-deoxyInosine, Super T (5-hydroxybutynl-2'-deoxyuridine), Super G (8-aza-7-deazaguanosine), locked nucleic acids (LNAs), unlocked nucleic acids (UNAs, e.g., UNA-A, UNA-U, UNA-C, UNA-G), Iso-dG, Iso-dC, 2' Fluoro bases (e.g., Fluoro C, Fluoro U, Fluoro A, and Fluoro G), and combinations of the foregoing.

In some embodiments, beads that are partitioned with the analyte can include different types of oligonucleotides bound to the bead, where the different types of oligonucleotides bind to different types of analytes. For example, a bead can include one or more first oligonucleotides (which can be capture probes, for example) that can bind or hybridize to a first type of analyte, such as mRNA for example, and one or more second oligonucleotides (which can be capture probes, for example) that can bind or hybridize to a second type of analyte, such as gDNA for example. Partitions can also include lysis agents that aid in releasing nucleic acids from the co-partitioned cell, and can also include an agent (e.g., a reducing agent) that can degrade the bead and/or break covalent linkages between the oligonucleotides and the bead, releasing the oligonucleotides into the partition. The released barcoded oligonucleotides (which can also be barcoded) can hybridize with mRNA released from the cell and also with gDNA released from the cell.

Barcoded constructs thus formed from hybridization can include a first type of construct that includes a sequence corresponding to an original barcode sequence from the bead and a sequence corresponding to a transcript from the cell, and a second type of construct that includes a sequence corresponding to the original barcode sequence from the bead and a sequence corresponding to genomic DNA from the cell. The barcoded constructs can then be released/removed from the partition and, in some embodiments, further processed to add any additional sequences. The resulting constructs can then be sequenced, the sequencing data processed, and the results used to spatially characterize the mRNA and the gDNA from the cell.

In another example, a partition includes a bead that includes a first type of oligonucleotide (e.g., a first capture probe) with a first barcode sequence, a poly(T) priming sequence that can hybridize with the poly(A) tail of an mRNA transcript, and a UMI barcode sequence that can uniquely identify a given transcript. The bead also includes a second type of oligonucleotide (e.g., a second capture probe) with a second barcode sequence, a targeted priming sequence that is capable of specifically hybridizing with a third barcoded oligonucleotide (e.g., an analyte capture agent) coupled to an antibody that is bound to the surface of the partitioned cell. The third barcoded oligonucleotide includes a UMI barcode sequence that uniquely identifies the antibody (and thus, the particular cell surface feature to which it is bound).

In this example, the first and second barcoded oligonucleotides include the same spatial barcode sequence (e.g., the first and second barcode sequences are the same), which permits downstream association of barcoded nucleic acids with the partition. In some embodiments, however, the first and second barcode sequences are different.

The partition also includes lysis agents that aid in releasing nucleic acids from the cell and can also include an agent (e.g., a reducing agent) that can degrade the bead and/or break a covalent linkage between the barcoded oligonucleotides and the bead, releasing them into the partition. The first type of released barcoded oligonucleotide can hybridize with mRNA released from the cell and the second type of released barcoded oligonucleotide can hybridize with the third type of barcoded oligonucleotide, forming barcoded constructs.

The first type of barcoded construct includes a spatial barcode sequence corresponding to the first barcode sequence from the bead and a sequence corresponding to the UMI barcode sequence from the first type of oligonucleotide, which identifies cell transcripts. The second type of barcoded construct includes a spatial barcode sequence corresponding to the second barcode sequence from the second type of oligonucleotide, and a UMI barcode sequence corresponding to the third type of oligonucleotide (e.g., the analyte capture agent) and used to identify the cell surface feature. The barcoded constructs can then be released/removed from the partition and, in some embodiments, further processed to add any additional sequences. The resulting constructs are then sequenced, sequencing data processed, and the results used to characterize the mRNA and cell surface feature of the cell.

The foregoing discussion involves two specific examples of beads with oligonucleotides for analyzing two different analytes within a partition. More generally, beads that are partitioned can have any of the structures described previously, and can include any of the described combinations of oligonucleotides for analysis of two or more (e.g., three or more, four or more, five or more, six or more, eight or more, ten or more, 12 or more, 15 or more, 20 or more, 25 or more, 30 or more, 40 or more, 50 or more) different types of analytes within a partition. Examples of beads with combinations of different types of oligonucleotides (e.g., capture probes) for concurrently analyzing different combinations of analytes within partitions include, but are not limited to: (a) genomic DNA and cell surface features (e.g., using the analyte capture agents described herein); (b) mRNA and a lineage tracing construct; (c) mRNA and cell methylation status; (d) mRNA and accessible chromatin (e.g., ATAC-seq, DNase-seq, and/or MNase-seq); (e) mRNA and cell surface or intracellular proteins and/or metabolites; (f) a barcoded analyte capture agent (e.g., the MHC multimers described herein) and a V(D)J sequence of an immune cell receptor (e.g., T-cell receptor); and (g) mRNA and a perturbation agent (e.g., a CRISPR crRNA/sgRNA, TALEN, zinc finger nuclease, and/or antisense oligonucleotide as described herein).

(f) Sequencing Analysis

After analytes from the sample have hybridized or otherwise been associated with capture probes, analyte capture agents, or other barcoded oligonucleotide sequences according to any of the methods described above in connection with the general spatial cell-based analytical methodology, the barcoded constructs that result from hybridization/association are analyzed via sequencing to identify the analytes.

In some embodiments, where a sample is barcoded directly via hybridization with capture probes or analyte capture agents hybridized, bound, or associated with either the cell surface, or introduced into the cell, as described above, sequencing can be performed on the intact sample. Alternatively, if the barcoded sample has been separated into fragments, cell groups, or individual cells, as described above, sequencing can be performed on individual fragments, cell groups, or cells. For analytes that have been barcoded via partitioning with beads, as described above, individual analytes (e.g., cells, or cellular contents following lysis of cells) can be extracted from the partitions by breaking the partitions, and then analyzed by sequencing to identify the analytes.

A wide variety of different sequencing methods can be used to analyze barcoded analyte constructs. In general, sequenced polynucleotides can be, for example, nucleic acid molecules such as deoxyribonucleic acid (DNA) or ribonucleic acid (RNA), including variants or derivatives thereof (e.g., single stranded DNA or DNA/RNA hybrids, and nucleic acid molecules with a nucleotide analog).

Sequencing of polynucleotides can be performed by various commercial systems. More generally, sequencing can be performed using nucleic acid amplification, polymerase chain reaction (PCR) (e.g., digital PCR and droplet digital PCR (ddPCR), quantitative PCR, real time PCR, multiplex PCR, PCR-based singleplex methods, emulsion PCR), and/or isothermal amplification.

Other examples of methods for sequencing genetic material include, but are not limited to, DNA hybridization methods (e.g., Southern blotting), restriction enzyme digestion methods, Sanger sequencing methods, next-generation sequencing methods (e.g., single-molecule real-time sequencing, nanopore sequencing, and Polony sequencing), ligation methods, and microarray methods. Additional examples of sequencing methods that can be used include targeted sequencing, single molecule real-time sequencing, exon sequencing, electron microscopy-based sequencing, panel sequencing, transistor-mediated sequencing, direct sequencing, random shotgun sequencing, Sanger dideoxy termination sequencing, whole-genome sequencing, sequencing by hybridization, pyrosequencing, capillary electrophoresis, gel electrophoresis, duplex sequencing, cycle sequencing, single-base extension sequencing, solid-phase sequencing, high-throughput sequencing, massively parallel signature sequencing, co-amplification at lower denaturation temperature-PCR (COLD-PCR), sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, 454 sequencing, Solexa Genome Analyzer sequencing, SOLiD™ sequencing, MS-PET sequencing, and any combinations thereof.

Sequence analysis of the nucleic acid molecules (including barcoded nucleic acid molecules or derivatives thereof) can be direct or indirect. Thus, the sequence analysis substrate (which can be viewed as the molecule which is subjected to the sequence analysis step or process) can directly be the barcoded nucleic acid molecule or it can be a molecule which is derived therefrom (e.g., a complement thereof). Thus, for example, in the sequence analysis step of a sequencing reaction, the sequencing template can be the barcoded nucleic acid molecule or it can be a molecule derived therefrom. For example, a first and/or second strand DNA molecule can be directly subjected to sequence analysis (e.g. sequencing), i.e., can directly take part in the sequence analysis reaction or process (e.g. the sequencing reaction or sequencing process, or be the molecule which is sequenced or otherwise identified). Alternatively, the barcoded nucleic acid molecule can be subjected to a step of second strand synthesis or amplification before sequence analysis (e.g. sequencing or identification by another technique). The sequence analysis substrate (e.g., template) can thus be an amplicon or a second strand of a barcoded nucleic acid molecule.

In some embodiments, both strands of a double stranded molecule can be subjected to sequence analysis (e.g., sequenced). In some embodiments, single stranded molecules (e.g. barcoded nucleic acid molecules) can be analyzed (e.g. sequenced). To perform single molecule sequencing, the nucleic acid strand can be modified at the 3' end.

Massively parallel sequencing techniques can be used for sequencing nucleic acids, as described above. In one embodiment, a massively parallel sequencing technique can be based on reversible dye-terminators. As an example, DNA molecules are first attached to primers on, e.g., a glass or silicon substrate, and amplified so that local clonal colonies are formed (bridge amplification). Four types of ddNTPs are added, and non-incorporated nucleotides are washed away. Unlike pyrosequencing, the DNA is only extended one nucleotide at a time due to a blocking group (e.g., 3' blocking group present on the sugar moiety of the ddNTP). A detector acquires images of the fluorescently labelled nucleotides, and then the dye along with the terminal 3' blocking group is chemically removed from the DNA, as a precursor to a subsequent cycle. This process can be repeated until the required sequence data is obtained.

As another example, massively parallel pyrosequencing techniques can also be used for sequencing nucleic acids. In pyrosequencing, the nucleic acid is amplified inside water droplets in an oil solution (emulsion PCR), with each droplet containing a single nucleic acid template attached to a single primer-coated bead that then forms a clonal colony. The sequencing system contains many picolitre-volume wells each containing a single bead and sequencing enzymes. Pyrosequencing uses luciferase to generate light for detection of the individual nucleotides added to the nascent nucleic acid and the combined data are used to generate sequence reads.

As another example application of pyrosequencing, released PPi can be detected by being immediately converted to adenosine triphosphate (ATP) by ATP sulfurylase, and the level of ATP generated can be detected via luciferase-produced photons, such as described in Ronaghi, et al., Anal. Biochem. 242(1), 84-9 (1996); Ronaghi, Genome Res. 11(1), 3-11 (2001); Ronaghi et al. Science 281 (5375), 363 (1998); and U.S. Pat. Nos. 6,210,891, 6,258,568, and 6,274,320, the entire contents of each of which are incorporated herein by reference.

In some embodiments, sequencing is performed by detection of hydrogen ions that are released during the polymerization of DNA. A microwell containing a template DNA strand to be sequenced can be flooded with a single type of nucleotide. If the introduced nucleotide is complementary to the leading template nucleotide, it is incorporated into the growing complementary strand. This causes the release of a hydrogen ion that triggers a hypersensitive ion sensor, which indicates that a reaction has occurred. If homopolymer repeats are present in the template sequence, multiple nucleotides will be incorporated in a single cycle. This leads to a corresponding number of released hydrogen ions and a proportionally higher electronic signal.

In some embodiments, sequencing can be performed in-situ. In-situ sequencing methods are particularly useful, for example, when the biological sample remains intact after analytes on the sample surface (e.g., cell surface analytes) or within the sample (e.g., intracellular analytes) have been barcoded. In-situ sequencing typically involves incorporation of a labeled nucleotide (e.g., fluorescently labeled mononucleotides or dinucleotides) in a sequential, template-dependent manner or hybridization of a labeled primer (e.g., a labeled random hexamer) to a nucleic acid template such that the identities (i.e., nucleotide sequence) of the incorporated nucleotides or labeled primer extension products can be determined, and consequently, the nucleotide sequence of the corresponding template nucleic acid. Aspects of in-situ sequencing are described, for example, in Mitra et al., (2003) Anal. Biochem., 320, 55-65, and Lee et al., (2014) Science, 343(6177), 1360-1363, the entire contents of each of which are incorporated herein by reference.

In addition, examples of methods and systems for performing in-situ sequencing are described in PCT Patent Application Publication Nos. WO2014/163886, WO2018/045181, WO2018/045186, and in U.S. Pat. Nos. 10,138,509 and 10,179,932, the entire contents of each of which are incorporated herein by reference. Example techniques for in-situ sequencing include, but are not limited to, STARmap (described for example in Wang et al., (2018) Science, 361(6499) 5691), MERFISH (described for example in Moffitt, (2016) Methods in Enzymology, 572, 1-49), and FISSEQ (described for example in U.S. Patent Application Publication No. 2019/0032121). The entire contents of each of the foregoing references are incorporated herein by reference.

For analytes that have been barcoded via partitioning, barcoded nucleic acid molecules or derivatives thereof (e.g., barcoded nucleic acid molecules to which one or more functional sequences have been added, or from which one or more features have been removed) can be pooled and processed together for subsequent analysis such as sequencing on high throughput sequencers. Processing with pooling can be implemented using barcode sequences. For example, barcoded nucleic acid molecules of a given partition can have the same barcode, which is different from barcodes of other spatial partitions. Alternatively, barcoded nucleic acid molecules of different partitions can be processed separately for subsequent analysis (e.g., sequencing).

In some embodiments, where capture probes do not contain a spatial barcode, the spatial barcode can be added after the capture probe captures analytes from a biological sample and before analysis of the analytes. When a spatial barcode is added after an analyte is captured, the barcode can be added after amplification of the analyte (e.g., reverse transcription and polymerase amplification of RNA). In some embodiments, analyte analysis uses direct sequencing of one or more captured analytes, such as direct sequencing of hybridized RNA. In some embodiments, direct sequencing is performed after reverse transcription of hybridized RNA. In some embodiments direct sequencing is performed after amplification of reverse transcription of hybridized RNA.

In some embodiments, direct sequencing of captured RNA is performed by sequencing-by-synthesis (SBS). In some embodiments, a sequencing primer is complementary to a sequence in one or more of the domains of a capture probe (e.g., functional domain). In such embodiments, sequencing-by-synthesis can include reverse transcription and/or amplification in order to generate a template sequence (e.g., functional domain) from which a primer sequence can bind.

SBS can involve hybridizing an appropriate primer, sometimes referred to as a sequencing primer, with the nucleic acid template to be sequenced, extending the primer, and detecting the nucleotides used to extend the primer. Preferably, the nucleic acid used to extend the primer is detected before a further nucleotide is added to the growing nucleic acid chain, thus allowing base-by-base in situ nucleic acid sequencing. The detection of incorporated nucleotides is facilitated by including one or more labelled nucleotides in the primer extension reaction. To allow the hybridization of an appropriate sequencing primer to the nucleic acid template to be sequenced, the nucleic acid template should normally be in a single stranded form. If the nucleic acid templates making up the nucleic acid spots are present in a double stranded form these can be processed to provide single stranded nucleic acid templates using methods well known in the art, for example by denaturation, cleavage etc. The sequencing primers which are hybridized to the nucleic acid template and used for primer extension are preferably short oligonucleotides, for example, 15 to 25 nucleotides in length. The sequencing primers can be greater than 25 nucleotides in length as well. For example, sequencing primers can be about 20 to about 60 nucleotides in length, or more than 60 nucleotides in length. The sequencing primers can be provided in solution or in an immobilized form. Once the sequencing primer has been annealed to the nucleic acid template to be sequenced by subjecting the nucleic acid template and sequencing primer to appropriate conditions, primer extension is carried out, for example using a nucleic acid polymerase and a supply of nucleotides, at least some of which are provided in a labelled form, and conditions suitable for primer extension if a suitable nucleotide is provided.

Preferably after each primer extension step, a washing step is included in order to remove unincorporated nucleotides which can interfere with subsequent steps. Once the primer extension step has been carried out, the nucleic acid colony is monitored to determine whether a labelled nucleotide has been incorporated into an extended primer. The primer extension step can then be repeated to determine the next and subsequent nucleotides incorporated into an extended primer. If the sequence being determined is unknown, the nucleotides applied to a given colony are usually applied in a chosen order which is then repeated throughout the analysis, for example dATP, dTTP, dCTP, dGTP.

SBS techniques which can be used are described for example, but not limited to, those in U.S. Patent App. Pub. No. 2007/0166705, U.S. Patent App. Pub. No. 2006/0188901, U.S. Pat. No. 7,057,026, U.S. Patent App. Pub. No. 2006/0240439, U.S. Patent App. Pub. No. 2006/0281109, PCT Patent App. Pub. No. WO 05/065814, U.S. Patent App. Pub. No. 2005/0100900, PCT Patent App. Pub. No. WO 06/064199, PCT Patent App. Pub. No. WO07/010, 251, U.S. Patent App. Pub. No. 2012/0270305, U.S. Patent App. Pub. No. 2013/0260372, and U.S. Patent App. Pub. No. 2013/0079232, the entire contents of each of which are incorporated herein by reference.

In some embodiments, direct sequencing of captured RNA is performed by sequential fluorescence hybridization (e.g., sequencing by hybridization). In some embodiments, a hybridization reaction where RNA is hybridized to a capture probe is performed in situ. In some embodiments, captured RNA is not amplified prior to hybridization with a sequencing probe. In some embodiments, RNA is amplified prior to hybridization with sequencing probes (e.g., reverse transcription to cDNA and amplification of cDNA). In some embodiments, amplification is performed using single-molecule hybridization chain reaction. In some embodiments, amplification is performed using rolling chain amplification.

Sequential fluorescence hybridization can involve sequential hybridization of probes including degenerate primer sequences and a detectable label. A degenerate primer sequence is a short oligonucleotide sequence which is capable of hybridizing to any nucleic acid fragment independent of the sequence of said nucleic acid fragment. For example, such a method could include the steps of: (a) providing a mixture including four probes, each of which includes either A, C, G, or T at the 5'-terminus, further including degenerate nucleotide sequence of 5 to 11 nucleotides in length, and further including a functional domain (e.g., fluorescent molecule) that is distinct for probes with A, C, G, or T at the 5'-terminus; (b) associating the probes of step (a) to the target polynucleotide sequences, whose sequence needs will be determined by this method; (c) measuring the activities of the four functional domains and recording the relative spatial location of the activities; (d) removing the reagents from steps (a)-(b) from the target polynucleotide sequences; and repeating steps (a)-(d) for n cycles, until the nucleotide sequence of the spatial domain for each bead is determined, with modification that the oligonucleotides used in step (a) are complementary to part of the target polynucleotide sequences and the positions 1 through n flanking the part of the sequences. Because the barcode sequences are different, in some embodiments, these additional flanking sequences are degenerate sequences. The fluorescent signal from each spot on the array for cycles 1 through n can be used to determine the sequence of the target polynucleotide sequences.

In some embodiments, direct sequencing of captured RNA using sequential fluorescence hybridization is performed in vitro. In some embodiments, captured RNA is amplified prior to hybridization with a sequencing probe (e.g., reverse transcription to cDNA and amplification of cDNA). In some embodiments, a capture probe containing captured RNA is exposed to the sequencing probe targeting coding regions of RNA. In some embodiments, one or more sequencing probes are targeted to each coding region. In some embodiments, the sequencing probe is designed to hybridize with sequencing reagents (e.g., a dye-labeled readout oligonucleotides). A sequencing probe can then hybridize with sequencing reagents. In some embodiments, output from the sequencing reaction is imaged. In some embodiments, a specific sequence of cDNA is resolved from an image of a sequencing reaction. In some embodiments, reverse transcription of captured RNA is performed prior to hybridization to the sequencing probe. In some embodiments, the sequencing probe is designed to target complementary sequences of the coding regions of RNA (e.g., targeting cDNA).

In some embodiments, a captured RNA is directly sequenced using a nanopore-based method. In some embodiments, direct sequencing is performed using nanopore direct RNA sequencing in which captured RNA is translocated through a nanopore. A nanopore current can be recorded and converted into a base sequence. In some embodiments, captured RNA remains attached to a substrate during nanopore sequencing. In some embodiments, captured RNA is released from the substrate prior to nanopore sequencing. In some embodiments, where the analyte of interest is a protein, direct sequencing of the protein can be performed using nanopore-based methods. Examples of nanopore-based sequencing methods that can be used are described in Deamer et al., Trends Biotechnol. 18, 14 7-151 (2000); Deamer et al., Acc. Chem. Res. 35:817-825 (2002); Li et al., Nat. Mater. 2:611-615 (2003); Soni et al., Clin. Chem. 53, 1996-2001 (2007); Healy et al., Nanomed. 2, 459-481 (2007); Cockroft et al., J. Am. Chem. Soc. 130, 818-820 (2008); and in U.S. Pat. No. 7,001,792. The entire contents of each of the foregoing references are incorporated herein by reference.

In some embodiments, direct sequencing of captured RNA is performed using single molecule sequencing by ligation. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. Aspects and features involved in sequencing by ligation are described, for example, in Shendure et al. Science (2005), 309: 1728-1732, and in U.S. Pat. Nos. 5,599,675; 5,750,341; 6,969,488; 6,172,218; and 6,306,597, the entire contents of each of which are incorporated herein by reference.

In some embodiments, nucleic acid hybridization can be used for sequencing. These methods utilize labeled nucleic acid decoder probes that are complementary to at least a portion of a barcode sequence. Multiplex decoding can be performed with pools of many different probes with distinguishable labels. Non-limiting examples of nucleic acid hybridization sequencing are described for example in U.S. Pat. No. 8,460,865, and in Gunderson et al., Genome Research 14:870-877 (2004), the entire contents of each of which are incorporated herein by reference.

In some embodiments, commercial high-throughput digital sequencing techniques can be used to analyze barcode sequences, in which DNA templates are prepared for sequencing not one at a time, but in a bulk process, and where many sequences are read out preferably in parallel, or alternatively using an ultra-high throughput serial process that itself may be parallelized. Examples of such techniques include Illumina© sequencing (e.g., flow cell-based sequencing techniques), sequencing by synthesis using modified nucleotides (such as commercialized in TruSeq™ and HiSeq™ technology by Illumina, Inc., San Diego, CA), HeliScope™ by Helicos Biosciences Corporation, Cambridge, MA, and PacBio RS by Pacific Biosciences of California, Inc., Menlo Park, CA), sequencing by ion detection technologies (Ion Torrent, Inc., South San Francisco, CA), and sequencing of DNA nanoballs (Complete Genomics, Inc., Mountain View, CA).

In some embodiments, detection of a proton released upon incorporation of a nucleotide into an extension product can be used in the methods described herein. For example, the sequencing methods and systems described in U.S. Patent Application Publication Nos. 2009/0026082, 2009/0127589, 2010/0137143, and 2010/0282617, can be used to directly sequence barcodes. The entire contents of each of the foregoing references are incorporated herein by reference.

In some embodiments, real-time monitoring of DNA polymerase activity can be used during sequencing. For example, nucleotide incorporations can be detected through fluorescence resonance energy transfer (FRET), as described for example in Levene et al., Science (2003), 299, 682-686, Lundquist et al., Opt. Lett. (2008), 33, 1026-1028, and Korlach et al., Proc. Natl. Acad. Sci. USA (2008), 105, 1176-1181. The entire contents of each of the foregoing references are herein incorporated by reference.

IV. Multiplexing (a) Multiplexing Generally

In various embodiments of spatial analysis as described herein, features can include different types of capture probes for analyzing both intrinsic and extrinsic information for individual cells. For example, a feature can include one or more of the following: 1) a capture probe featuring a capture domain that binds to one or more endogenous nucleic acids in the cell; 2) a capture probe featuring a capture domain that binds to one or more exogenous nucleic acids in the cell (e.g., nucleic acids from a microorganism (e.g., a virus, a bacterium)) that infects the cell, nucleic acids introduced into the cell (e.g., such as plasmids or nucleic acid derived therefrom), nucleic acids for gene editing (e.g., CRISPR-related RNA such as crRNA, guide RNA); 3) a capture probe featuring a capture domain that binds to a analyte capture agent (e.g., an antibody coupled to a oligonucleotide that includes a capture agent barcode domain having an analyte capture sequence that binds the capture domain), and 4) a capture moiety featuring a domain that binds to a protein (e.g., an exogenous protein expressed in the cell, a protein from a microorganism (e.g., a virus, a bacterium)) that infects the cell, or a binding partner for a protein of the cell (e.g., an antigen for an immune cell receptor).

In some embodiments of any of the spatial analysis methods as described herein, spatial profiling includes concurrent analysis of two different types of analytes. A feature can be a gel bead, which is coupled (e.g., reversibly coupled) to one or more capture probes. The capture probes can include a spatial barcode sequence and a poly (T) priming sequence that can hybridize with the poly (A) tail of an mRNA transcript. The capture probe can also include a UMI sequence that can uniquely identify a given transcript. The capture probe can also include a spatial barcode sequence and a random N-mer priming sequence that is capable of randomly hybridizing with gDNA. In this configuration, capture probes can include the same spatial barcode sequence, which permits association of downstream sequencing reads with the feature.

In some embodiments of any of the spatial analysis methods as described herein, a feature can be a gel bead, which is coupled (e.g., reversibly coupled) to capture probes. The Capture probe can include a spatial barcode sequence and a poly(T) priming sequence 614 that can hybridize with the poly(A) tail of an mRNA transcript. The capture probe can also include a UMI sequence that can uniquely identify a given transcript. The capture probe can include a spatial barcode sequence and a capture domain that is capable of specifically hybridizing with an analyte capture agent. The analyte capture agent can includes an oligonucleotide that includes an analyte capture sequence that interacts with the capture domain coupled to the feature. The oligonucleotide of the analyte capture agent can be coupled to an antibody that is bound to the surface of a cell. The oligonucleotide includes a barcode sequence (e.g., an analyte binding moiety barcode) that uniquely identifies the antibody (and thus, the particular cell surface feature to which it is bound). In this configuration, the capture probes include the same spatial barcode sequence, which permit downstream association of barcoded nucleic acids with the location on the spatial array. In some embodiments of any of the spatial profiling methods described herein, the analyte capture agents can be can be produced by any suitable route, including via example coupling schemes described elsewhere herein.

In some embodiments of any of the spatial analysis methods described herein, other combinations of two or more biological analytes that can be concurrently measured include, without limitation: (a) genomic DNA and cell surface features (e.g., via analyte capture agents that bind to a cell surface feature), (b) mRNA and a lineage tracing construct, (c) mRNA and cell methylation status, (d) mRNA and accessible chromatin (e.g., ATAC-seq, DNase-seq, and/or MNase-seq), (e) mRNA and cell surface or intracellular proteins and/or metabolites, (f) mRNA and chromatin (spatial organization of chromatin in a cell), (g) an analyte capture agent (e.g., any of the MHC multimers described herein) and a V(D)J sequence of an immune cell receptor (e.g., T-cell receptor), (h) mRNA and a perturbation agent (e.g., a CRISPR crRNA/sgRNA, TALEN, zinc finger nuclease, and/or antisense oligonucleotide as described herein), (i) genomic DNA and a perturbation agent, (j) an analyte capture agent and a perturbation reagents, (k) accessible chromatin and a perturbation reagent, (l) chromatin (e.g., spatial organization of chromatin in a cell) and a perturbation reagent, and (m) cell surface or intracellular proteins and/or metabolites and a perturbation reagent, or any combination thereof.

In some embodiments of any of the spatial analysis methods described herein, the first analyte can include a nucleic acid molecule with a nucleic acid sequence (e.g., mRNA, complementary DNA derived from reverse transcription of mRNA) encoding at least a portion of a V(D)J sequence of an immune cell receptor (e.g., a TCR or BCR). In some embodiments, the nucleic acid molecule with a nucleic acid sequence encoding at least a portion of a V(D)J sequence of an immune cell receptor is cDNA first generated from reverse transcription of the corresponding mRNA, using a poly(T) containing primer. The cDNA that is generated can then be barcoded using a primer, featuring a spatial barcode sequence (and optionally, a UMI sequence) that hybridizes with at least a portion of the cDNA that is generated. In some embodiments, a template switching oligonucleotide in conjunction a terminal transferase or a reverse transcriptase having terminal transferase activity can be employed to generate a priming region on the cDNA to which a barcoded primer can hybridize during cDNA generation. Terminal transferase activity can, for example, add a poly(C) tail to a 3' end of the cDNA such that the template switching oligonucleotide can bind via a poly(G) priming sequence and the 3' end of the cDNA can be further extended. The original mRNA template and template switching oligonucleotide can then be denatured from the cDNA and the barcoded primer comprising a sequence complementary to at least a portion of the generated priming region on the cDNA can then hybridize with the cDNA and a barcoded construct comprising the barcode sequence (and any optional UMI sequence) and a complement of the cDNA generated. Additional methods and compositions suitable for barcoding cDNA generated from mRNA transcripts including those encoding V(D)J regions of an immune cell receptor and/or barcoding methods and composition including a template switch oligonucleotide are described, for example, in PCT Patent Application Publication No. WO 2018/075693, and in U.S. Patent Application Publication No. 2018/0105808, the entire contents of each of which are incorporated herein by reference.

In some embodiments, V(D)J analysis can be performed using methods similar to those described herein. For example, V(D)J analysis can be completed with the use of one or more analyte capture agents that bind to particular surface features of immune cells and are associated with barcode sequences (e.g., analyte binding moiety barcodes). The one or more analyte capture agents can include an MHC or MHC multimer. A barcoded oligonucleotide coupled to a bead that can be used for V(D)J analysis. The oligonucleotide is coupled to a bead by a releasable linkage, such as a disulfide linker. The oligonucleotide can include functional sequences that are useful for subsequent processing, such as functional sequence, which can include a sequencer specific flow cell attachment sequence, e.g., a P5 sequence, as well as functional sequence, which can include sequencing primer sequences, e.g., a R1 primer binding site. In some embodiments, the sequence can include a P7 sequence and a R2 primer binding site. A barcode sequence can be included within the structure for use in barcoding the template polynucleotide. The functional sequences can be selected for compatibility with a variety of different sequencing systems, e.g., 454 Sequencing, Ion Torrent Proton or PGM, Illumina X10, etc., and the requirements thereof. In some embodiments, the barcode sequence, functional sequences (e.g., flow cell attachment sequence) and additional sequences (e.g., sequencing primer sequences) can be common to all of the oligonucleotides attached to a given bead. The barcoded oligonucleotide can also include a sequence to facilitate template switching (e.g., a poly(G) sequence). In some embodiments, the additional sequence provides a unique molecular identifier (UMI) sequence segment, as described elsewhere herein.

In an exemplary method of cellular polynucleotide analysis using a barcode oligonucleotide, a cell is co-partitioned along with a bead bearing a barcoded oligonucleotide and additional reagents such as a reverse transcriptase, primers, oligonucleotides (e.g., template switching oligonucleotides), dNTPs, and a reducing agent into a partition (e.g., a droplet in an emulsion). Within the partition, the cell can be lysed to yield a plurality of template polynucleotides (e.g., DNA such as genomic DNA, RNA such as mRNA, etc.).

A reaction mixture featuring a template polynucleotide from a cell and (i) the primer having a sequence towards a 3' end that hybridizes to the template polynucleotide (e.g., poly(T)) and (ii) a template switching oligonucleotide that includes a first oligonucleotide towards a 5' end can be subjected to an amplification reaction to yield a first amplification product. In some embodiments, the template polynucleotide is an mRNA with a poly(A) tail and the primer that hybridizes to the template polynucleotide includes a poly(T) sequence towards a 3' end, which is complementary to the poly(A) segment. The first oligonucleotide can include at least one of an adaptor sequence, a barcode sequence, a unique molecular identifier (UMI) sequence, a primer binding site, and a sequencing primer binding site or any combination thereof. In some cases, a first oligonucleotide is a sequence that can be common to all partitions of a plurality of partitions. For example, the first oligonucleotide can include a flow cell attachment sequence, an amplification primer binding site, or a sequencing primer binding site and the first amplification reaction facilitates the attachment the oligonucleotide to the template polynucleotide from the cell. In some embodiments, the first oligonucleotide includes a primer binding site. In some embodiments, the first oligonucleotide includes a sequencing primer binding site.

The sequence towards a 3' end (e.g., poly(T)) of the primer hybridizes to the template polynucleotide. In a first amplification reaction, extension reaction reagents, e.g., reverse transcriptase, nucleoside triphosphates, co-factors (e.g., $Mg^{2+}$ or $Mn^{2+}$), that are also co-partitioned, can extend the primer sequence using the cell's nucleic acid as a template, to produce a transcript, e.g., cDNA, having a fragment complementary to the strand of the cell's nucleic acid to which the primer annealed. In some embodiments, the reverse transcriptase has terminal transferase activity and the reverse transcriptase adds additional nucleotides, e.g., poly(C), to the cDNA in a template independent manner.

The template switching oligonucleotide, for example a template switching oligonucleotide which includes a poly (G) sequence, can hybridize to the cDNA and facilitate template switching in the first amplification reaction. The transcript, therefore, can include the sequence of the primer, a sequence complementary to the template polynucleotide from the cell, and a sequence complementary to the template switching oligonucleotide.

In some embodiments of any of the spatial analysis methods described herein, subsequent to the first amplification reaction, the first amplification product or transcript can be subjected to a second amplification reaction to generate a second amplification product. In some embodiments, additional sequences (e.g., functional sequences such as flow cell attachment sequence, sequencing primer binding sequences, barcode sequences, etc.) are attached. The first and second amplification reactions can be performed in the same volume, such as for example in a droplet. In some embodiments, the first amplification product is subjected to a second amplification reaction in the presence of a barcoded oligonucleotide to generate a second amplification product having a barcode sequence. The barcode sequence can be unique to a partition, that is, each partition can have a unique barcode sequence. The barcoded oligonucleotide can include a sequence of at least a segment of the template switching oligonucleotide and at least a second oligonucleotide. The segment of the template switching oligonucleotide on the barcoded oligonucleotide can facilitate hybridization of the barcoded oligonucleotide to the transcript, e.g., cDNA, to facilitate the generation of a second amplification product. In addition to a barcode sequence, the barcoded oligonucleotide can include a second oligonucleotide such as at least one of an adaptor sequence, a unique molecular identifier (UMI) sequence, a primer binding site, and a sequencing primer binding site, or any combination thereof.

In some embodiments of any of the spatial analysis methods described herein, the second amplification reaction uses the first amplification product as a template and the barcoded oligonucleotide as a primer. In some embodiments, the segment of the template switching oligonucleotide on the barcoded oligonucleotide can hybridize to the portion of the cDNA or complementary fragment having a sequence complementary to the template switching oligonucleotide or that which was copied from the template switching oligonucleotide. In the second amplification reaction, extension reaction reagents, e.g., polymerase, nucleoside triphosphates, co-factors (e.g., $Mg^{2+}$ or $Mn^{2+}$), that are also co-partitioned, can extend the primer sequence using the first amplification product as template. The second amplification product can include a second oligonucleotide, a sequence of a segment of the template polynucleotide (e.g., mRNA), and a sequence complementary to the primer.

In some embodiments of any of the spatial analysis methods described herein, the second amplification product uses the barcoded oligonucleotide as a template and at least a portion of the first amplification product as a primer. The segment of the first amplification product (e.g., cDNA) having a sequence complementary to the template switching oligonucleotide can hybridize to the segment of the barcoded oligonucleotide comprising a sequence of at least a segment of the template switching oligonucleotide. In the second amplification reaction, extension reaction reagents, e.g., polymerase, nucleoside triphosphates, co-factors (e.g., $Mg^{2+}$ or $Mn^{2+}$), that are also co-partitioned, can extend the primer sequence (e.g., first amplification product) using the barcoded oligonucleotide as template. The second amplification product can include the sequence of the primer, a sequence which is complementary to the sequence of the template polynucleotide (e.g., mRNA), and a sequence complementary to the second oligonucleotide.

In some embodiments of any of the spatial analysis methods described herein, three or more classes of biological analytes can be concurrently measured. For example, a feature can include capture probes that can participate in an assay of at least three different types of analytes via three different capture domains. A bead can be coupled to a barcoded oligonucleotide that includes a capture domain that includes a poly(T) priming sequence for mRNA analysis; a barcoded oligonucleotide that includes a capture domain that includes a random N-mer priming sequence for gDNA analysis; and a barcoded oligonucleotide that includes a capture domain that can specifically bind a an analyte capture agent (e.g., an antibody with a spatial barcode), via its analyte capture sequence.

In some embodiments of any of the spatial analysis methods described herein, other combinations of three or more biological analytes that can be concurrently measured include, without limitation: (a) mRNA, a lineage tracing construct, and cell surface and/or intracellular proteins and/or metabolites; (b) mRNA, accessible chromatin (e.g., ATAC-seq, DNase-seq, and/or MNase-seq), and cell surface and/or intracellular proteins and/or metabolites; (c) mRNA, genomic DNA, and a perturbation reagent (e.g., a CRISPR crRNA/sgRNA, TALEN, zinc finger nuclease, and/or antisense oligonucleotide as described herein); (d) mRNA, accessible chromatin, and a perturbation reagent; (e) mRNA, an analyte capture agent (e.g., any of the MHC multimers described herein), and a perturbation reagent; (f) mRNA, cell surface and/or intracellular proteins and/or metabolites, and a perturbation agent; (g) mRNA, a V(D)J sequence of an immune cell receptor (e.g., T-cell receptor), and a perturbation reagent; (h) mRNA, an analyte capture agent, and a V(D)J sequence of an immune cell receptor; (i) cell surface and/or intracellular proteins and/or metabolites, a an analyte capture agent (e.g., the MHC multimers described herein), and a V(D)J sequence of an immune cell receptor; (j) methylation status, mRNA, and cell surface and/or intracellular proteins and/or metabolites; (k) mRNA, chromatin (e.g., spatial organization of chromatin in a cell), and a perturbation reagent; (l) a V(D)J sequence of an immune cell receptor, chromatin (e.g., spatial organization of chromatin in a cell); and a perturbation reagent; and (m) mRNA, a V(D)J sequence of an immune cell receptor, and chromatin (e.g., spatial organization of chromatin in a cell), or any combination thereof.

In some embodiments of any of the spatial analysis methods described herein, four or more classes biological analytes can be concurrently measured. A feature can be a bead that is coupled to barcoded primers that can each participate in an assay of a different type of analyte. The feature is coupled (e.g., reversibly coupled) to a capture probe that includes a capture domain that includes a poly(T) priming sequence for mRNA analysis and is also coupled (e.g., reversibly coupled) to capture probe that includes a capture domain that includes a random N-mer priming sequence for gDNA analysis. Moreover, the feature is also coupled (e.g., reversibly coupled) to a capture probe that binds an analyte capture sequence of an analyte capture agent via its capture domain. The feature can also be coupled (e.g., reversibly coupled) to a capture probe that can specifically bind a nucleic acid molecule that can function as a perturbation agent (e.g., a CRISPR crRNA/sgRNA, TALEN, zinc finger nuclease, and/or antisense oligonucleotide as described herein), via its capture domain.

In some embodiments of any of the spatial analysis methods described herein, each of the various spatially barcoded capture probes present at a given feature or on a given bead include the same spatial barcode sequence. In some embodiments, each barcoded capture probe can be released from the feature in a manner suitable for analysis of its respective analyte. For example, barcoded constructs A, B, C and D can be generated as described elsewhere herein and analyzed. Barcoded construct A can include a sequence corresponding to the barcode sequence from the bead (e.g., a spatial barcode) and a DNA sequence corresponding to a target mRNA. Barcoded construct B can include a sequence corresponding to the barcode sequence from the bead (e.g., a spatial barcode) and a sequence corresponding to genomic DNA. Barcoded construct C can include a sequence corresponding to the barcode sequence from the bead (e.g., a spatial barcode) and a sequence corresponding to barcode sequence associated with an analyte capture agent (e.g., an analyte binding moiety barcode). Barcoded construct D can include a sequence corresponding to the barcode sequence from the bead (e.g., a spatial barcode) and a sequence corresponding to a CRISPR nucleic acid (which, in some embodiments, also includes a barcode sequence). Each construct can be analyzed (e.g., via any of a variety of sequencing methods) and the results can be associated with the given cell from which the various analytes originated. Barcoded (or even non-barcoded) constructs can be tailored for analyses of any given analyte associated with a nucleic acid and capable of binding with such a construct.

In some embodiments of any of the spatial analysis methods described herein, other combinations of four or more biological analytes that can be concurrently measured include, without limitation: (a) mRNA, a lineage tracing construct, cell surface and/or intracellular proteins and/or metabolites, and gDNA; (b) mRNA, accessible chromatin (e.g., ATAC-seq, DNase-seq, and/or MNase-seq), cell surface and/or intracellular proteins and/or metabolites, and a perturbation agent (e.g., a CRISPR crRNA/sgRNA, TALEN, zinc finger nuclease, and/or antisense oligonucleotide as described herein); (c) mRNA, cell surface and/or intracellular proteins and/or metabolites, an analyte capture agent (e.g., the MHC multimers described herein), and a V(D)J sequence of an immune cell receptor (e.g., T-cell receptor); (d) mRNA, genomic DNA, a perturbation reagent, and accessible chromatin; (e) mRNA, cell surface and/or intracellular proteins and/or metabolites, an analyte capture agent (e.g., the MHC multimers described herein), and a perturbation reagent; (f) mRNA, cell surface and/or intracellular proteins and/or metabolites, a perturbation reagent, and a V(D)J sequence of an immune cell receptor (e.g., T-cell receptor); (g) mRNA, a perturbation reagent, an analyte capture agent (e.g., the MHC multimers described herein), and a V(D)J sequence of an immune cell receptor (e.g., T-cell receptor); (h) mRNA, chromatin (e.g., spatial organization of chromatin in a cell), and a perturbation reagent; (i) a V(D)J sequence of an immune cell receptor, chromatin (e.g., spatial organization of chromatin in a cell); and a perturbation reagent; (j) mRNA, a V(D)J sequence of an immune cell receptor, chromatin (e.g., spatial organization of chromatin in a cell), and genomic DNA; (k) mRNA, a V(D)J sequence of an immune cell receptor, chromatin (e.g., spatial organization of chromatin in a cell), and a perturbation reagent, or any combination thereof.

(b) Construction of Spatial Arrays for Multi-Analyte Analysis

This disclosure also provides methods and materials for constructing a spatial array capable of multi-analyte analysis. In some embodiments, a spatial array includes a plurality of features on a substrate where one or more members of the plurality of features include a plurality of oligonucleotides having a first type functional sequence and oligonucleotides having a second, different type of functional sequence. In some embodiments, a feature can include oligonucleotides with two types of functional sequences. A feature can be coupled to oligonucleotides comprising a TruSeq functional sequence and also to oligonucleotides comprising a Nextera functional sequence. In some embodiments, one or more members of the plurality of features comprises both types of functional sequences. In some embodiments, one or more members of the plurality features includes a first type of functional sequence. In some embodiments, one or more members of the plurality of features includes a second type of functional sequence. In some embodiments, an additional oligonucleotide can be added to the functional sequence to generate a full oligonucleotide where the full oligonucleotide includes a spatial barcode sequence, an optional UMI sequence, a priming sequence, and a capture domain. Attachment of these sequences can be via ligation (including via splint ligation as is described in U.S. Patent Application Publication No. 20140378345, the entire contents of which are incorporated herein by reference), or any other suitable route. As discussed herein, oligonucleotides can be hybridized with splint sequences that can be helpful in constructing complete full oligonucleotides (e.g., oligonucleotides that are capable of spatial analysis).

In some embodiments, the oligonucleotides that hybridize to the functional sequences (e.g., TruSeq and Nextera) located on the features include capture domains capable of capturing different types of analytes (e.g., mRNA, genomic DNA, cell surface proteins, or accessible chromatin). In some examples, oligonucleotides that can bind to the TruSeq functional sequences can include capture domains that include poly(T) capture sequences. In addition to the poly (T) capture sequences, the oligonucleotides that can bind the TruSeq functional groups can also include a capture domain that includes a random N-mer sequence for capturing genomic DNA (e.g., or any other sequence or domain as described herein capable of capturing any of the biological analytes described herein). In such cases, the spatial arrays can be constructed by applying ratios of TruSeq-poly(T) and TruSeq-N-mer oligonucleotides to the features comprising the functional TruSeq sequences. This can produce spatial arrays where a portion of the oligonucleotides can capture mRNA and a different portion of oligonucleotides can capture genomic DNA. In some embodiments, one or more members of a plurality of features include both TruSeq and Nextera functional sequences. In such cases, a feature including both types of functional sequences is capable of binding oligonucleotides specific to each functional sequence. For example, an oligonucleotide capable of binding to a TruSeq functional sequence could be used to deliver an oligonucleotide including a poly(T) capture domain and an oligonucleotide capable of binding to a Nextera functional sequence could be used to deliver an oligonucleotide including an N-mer capture domain for capturing genomic DNA. It will be appreciated by a person of ordinary skill in the art that any combination of capture domains (e.g., capture domains having any of the variety of capture sequences described herein capable of binding to any of the different types of analytes as described herein) could be combined with oligonucleotides capable of binding to TruSeq and Nextera functional sequences to construct a spatial array.

In some embodiments, an oligonucleotide that includes a capture domain (e.g., an oligonucleotide capable of coupling to an analyte) or an analyte capture agent can include an oligonucleotide sequence that is capable of binding or ligating to an assay primer. The adapter can allow the capture probe or the analyte capture agent to be attached to any suitable assay primers and used in any suitable assays. The assay primer can include a priming region and a sequence that is capable of binding or ligating to the adapter. In some embodiments, the adapter can be a non-specific primer (e.g., a 5' overhang) and the assay primer can include a 3' overhang that can be ligated to the 5' overhang. The priming region on the assay primer can be any primer described herein, e.g., a poly (T) primer, a random N-mer primer, a target-specific primer, or an analyte capture agent capture sequence.

In some examples, an oligonucleotide can includes an adapter, e.g., a 5' overhang with 10 nucleotides. The adapter can be ligated to assay primers, each of which includes a 3' overhang with 10 nucleotides that complementary to the 5' overhang of the adapter. The capture probe can be used in any assay by attaching to the assay primer designed for that assay.

Adapters and assay primers can be used to allow the capture probe or the analyte capture agent to be attached to any suitable assay primers and used in any suitable assays. A capture probe that includes a spatial barcode can be attached to a bead that includes a poly(dT) sequence. A capture probe including a spatial barcode and a poly(T) sequence can be used to assay multiple biological analytes as generally described herein (e.g., the biological analyte includes a poly(A) sequence or is coupled to or otherwise is associated with an analyte capture agent comprising a poly (A) sequence as the analyte capture sequence).

A splint oligonucleotide with a poly(A) sequence can be used to facilitate coupling to a capture probe that includes a spatial barcode and a second sequence that facilitates coupling with an assay primer. Assay primers include a sequence complementary to the splint oligo second sequence and an assay-specific sequence that determines assay primer functionality (e.g., a poly(T) primer, a random N-mer primer, a target-specific primer, or an analyte capture agent capture sequence as described herein).

In some embodiments of any of the spatial profiling methods described herein, a feature can include a capture probe that includes a spatial barcode comprising a switch oligonucleotide, e.g., with a 3' end 3rG. For example, a feature (e.g., a gel bead) with a spatial barcode functionalized with a 3rG sequence can be used that enables template switching (e.g., reverse transcriptase template switching), but is not specific for any particular assay. In some embodiments, the assay primers added to the reaction can determine which type of analytes are analyzed. For example, the assay primers can include binding domains capable of binding to target biological analytes (e.g., poly (T) for mRNA, N-mer for genomic DNA, etc.). A capture probe (e.g., an oligonucleotide capable of spatial profiling) can be generated by using a reverse transcriptase enzyme/polymerase to extend, which is followed by template switching onto the barcoded adapter oligonucleotide to incorporate the barcode and other functional sequences. In some embodiments, the assay primers include capture domains capable of binding to a poly(T) sequence for mRNA analysis, random primers for genomic DNA analysis, or a capture sequence that can bind a nucleic acid molecule coupled to an analyte binding moiety (e.g., a an analyte capture sequence of an analyte capture agent) or a nucleic acid molecule that can function in as a perturbation reagent (e.g., a CRISPR crRNA/sgRNA, TALEN, zinc finger nuclease, and/or antisense oligonucleotide as described herein).

V. Systems for Sample Analysis

The methods described above for analyzing biological samples can be implemented using a variety of hardware components. In this section, examples of such components are described. However, it should be understood that in general, the various steps and techniques discussed herein can be performed using a variety of different devices and system components, not all of which are expressly set forth.

Figure 46A:
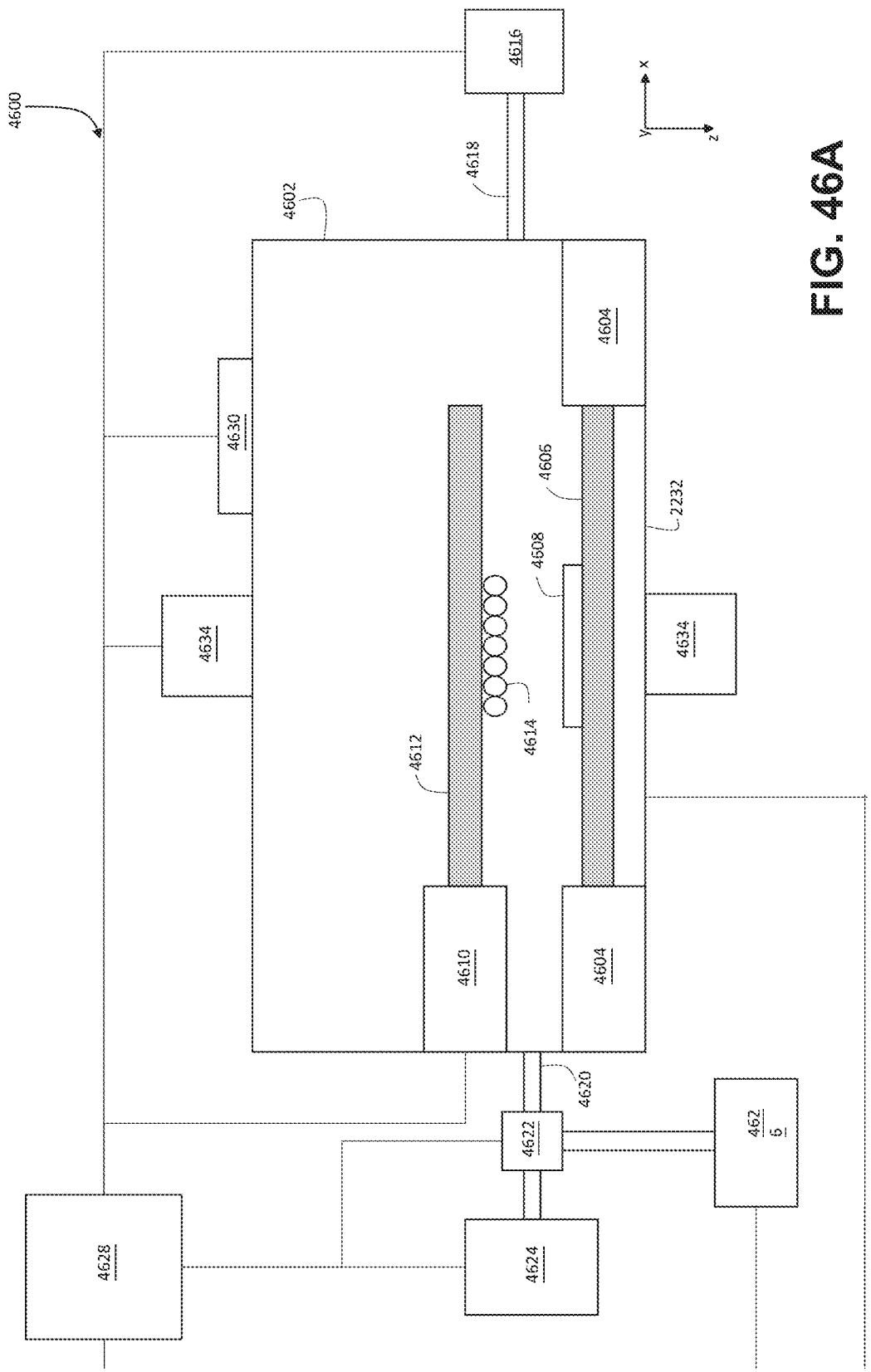
FIG. 46A is a schematic diagram showing an example sample handling apparatus that can be used to implement various steps and methods described herein.

FIG. 46A is a schematic diagram showing an example sample handling apparatus 4600. Sample handling apparatus 4600 includes a sample chamber 4602 that, when closed or sealed, is fluid-tight. Within chamber 4602, a first holder 4604 holds a first substrate 4606 on which a sample 4608 is positioned. Sample chamber 4602 also includes a second holder 4610 that holds a second substrate 4612 with an array of features 4614, as described above.

A fluid reservoir 4616 is connected to the interior volume of sample chamber 4602 via a fluid inlet 4618. Fluid outlet 4620 is also connected to the interior volume of sample chamber 4602, and to valve 4622. In turn, valve 4622 is connected to waste reservoir 4624 and, optionally, to analysis apparatus 4626. A control unit 4628 is electrically connected to second holder 4610, to valve 4622, to waste reservoir 4624, and to fluid reservoir 4616.

During operation of apparatus 4600, any of the reagents, solutions, and other biochemical components described above can be delivered into sample chamber 4602 from fluid reservoir 4616 via fluid inlet 4618. Control unit 4628, connected to fluid reservoir 4616, can control the delivery of reagents, solutions, and components, and adjust the volumes and flow rates according to programmed analytical protocols for various sample types and analysis procedures. In some embodiments, fluid reservoir 4616 includes a pump, which can be controlled by control unit 4628, to facilitate delivery of substances into sample chamber 4602.

In certain embodiments, fluid reservoir 4616 includes a plurality of chambers, each of which is connected to fluid inlet 4618 via a manifold (not shown). Control unit 4628 can selectively deliver substances from any one or more of the multiple chambers into sample chamber 4602 by adjusting the manifold to ensure that the selected chambers are fluidically connected to fluid inlet 4618.

In general, control unit 4628 can be configured to introduce substances from fluid reservoir 4616 into sample chamber 4602 before, after, or both before and after, sample 4608 on first substrate 4606 has interacted with the array of features 4614 on first substrate 4612. Many examples of such substances have been described previously. Examples of such substances include, but are not limited to, permeabilizing agents, buffers, fixatives, staining solutions, washing solutions, and solutions of various biological reagents (e.g., enzymes, peptides, oligonucleotides, primers).

To initiate interaction between sample 4608 and feature array 4614, the sample and array are brought into spatial proximity. To facilitate this step, second holder 4610—under the control of control unit 4628—can translate second substrate 4612 in any of the x-, y-, and z-coordinate directions. In particular, control unit 4628 can direct second holder 4610 to translate second substrate 4612 in the z-direction so that sample 4608 contacts, or nearly contacts, feature array 4614.

In some embodiments, apparatus 4600 can optionally include an alignment sub-system 4630, which can be electrically connected to control unit 4628. Alignment sub-system 4630 functions to ensure that sample 4608 and feature array 4614 are aligned in the x-y plane prior to translating second substrate 4612 in the z-direction so that sample 4608 contacts, or nearly contacts, feature array 4614.

Alignment sub-system 4630 can be implemented in a variety of ways. In some embodiments, for example, alignment sub-system 4630 includes an imaging unit that obtains one or more images showing fiducial markings on first substrate 4606 and/or second substrate 4612. Control unit 4618 analyzes the image(s) to determine appropriate translations of second substrate 4612 in the x- and/or y-coordinate directions to ensure that sample 4608 and feature array 4614 are aligned prior to translation in the z-coordinate direction.

In certain embodiments, control unit 4628 can optionally regulate the removal of substances from sample chamber 4602. For example, control unit 4628 can selectively adjust valve 4622 so that substances introduced into sample chamber 4602 from fluid reservoir 4616 are directed into waste reservoir 4624. In some embodiments, waste reservoir 4624 can include a reduced-pressure source (not shown) electrically connected to control unit 4628. Control unit 4628 can adjust the fluid pressure in fluid outlet 4620 to control the rate at which fluids are removed from sample chamber 4602 into waste reservoir 4624.

In some embodiments, analytes from sample 4608 or from feature array 4614 can be selectively delivered to analysis apparatus 4626 via suitable adjustment of valve 4622 by control unit 4628. As described above, in some embodiments, analysis apparatus 4626 includes a reduced-pressure source (not shown) electrically connected to control unit 4628, so that control unit 4628 can adjust the rate at which analytes are delivered to analysis apparatus 4626. As such, fluid outlet 4620 effectively functions as an analyte collector, while analysis of the analytes is performed by analysis apparatus 4626. It should be noted that not all of the workflows and methods described herein are implemented via analysis apparatus 4626. For example, in some embodiments, analytes that are captured by feature array 4614 remain bound to the array (i.e., are not cleaved from the array), and feature array 4614 is directly analyzed to identify specifically-bound sample components.

In addition to the components described above, apparatus 4600 can optionally include other features as well. In some embodiments, for example, sample chamber 4602 includes a heating sub-system 4632 electrically connected to control unit 4628. Control unit 4628 can activate heating sub-system 4632 to heat sample 4608 and/or feature array 4614, which can help to facilitate certain steps of the methods described herein.

In certain embodiments, sample chamber 4602 includes an electrode 4634 electrically connected to control unit 4628. Control unit 4628 can optionally activate electrode 4634, thereby establishing an electric field between the first and second substrates. Such fields can be used, for example, to facilitate migration of analytes from sample 4608 toward feature array 4614.

In some of the methods described herein, one or more images of a sample and/or a feature array are acquired. Imaging apparatus that is used to obtain such images can generally be implemented in a variety of ways. FIG. 46B shows one example of an imaging apparatus 4650. Imaging apparatus 4650 includes a light source 4652, light conditioning optics 4654, light delivery optics 4656, light collection optics 4660, light adjusting optics 4662, and a detection sub-system 4664. Each of the foregoing components can optionally be connected to control unit 4628, or alternatively, to another control unit. For purposes of explanation below, it will be assumed that control unit 4628 is connected to the components of imaging apparatus 4650.

During operation of imaging apparatus 4650, light source 4652 generates light. In general, the light generated by source 4652 can include light in any one or more of the ultraviolet, visible, and/or infrared regions of the electromagnetic spectrum. A variety of different light source elements can be used to generate the light, including (but not limited to) light emitting diodes, laser diodes, laser sources, fluorescent sources, incandescent sources, and glow-discharge sources.

The light generated by light source 4652 is received by light conditioning optics 4654. In general, light conditioning optics 4654 modify the light generated by light source 4652 for specific imaging applications. For example, in some embodiments, light conditioning optics 4654 modify the spectral properties of the light, e.g., by filtering out certain wavelengths of the light. For this purpose, light conditioning optics 4654 can include a variety of spectral optical elements, such as optical filters, gratings, prisms, and chromatic beam splitters.

In certain embodiments, light conditioning optics 4654 modify the spatial properties of the light generated by light source 4652. Examples of components that can be used for this purpose include (but are not limited to) apertures, phase masks, apodizing elements, and diffusers.

After modification by light conditioning optics 4654, the light is received by light delivery optics 4656 and directed onto sample 4608 or feature array 4614, either of which is positioned on a mount 4658. Light conditioning optics 4654 generally function to collect and direct light onto the surface of the sample or array. A variety of different optical elements can be used for this purpose, and examples of such elements include, but are not limited to, lenses, mirrors, beam splitters, and various other elements having non-zero optical power.

Light emerging from sample 4608 or feature array 4614 is collected by light collection optics 4660. In general, light collection optics 4660 can include elements similar to any of those described above in connection with light delivery optics 4656. The collected light can then optionally be modified by light adjusting optics 4662, which can generally include any of the elements described above in connection with light conditioning optics 4654.

The light is then detected by detection sub-system 4664. Generally, detection sub-system 4664 functions to generate one or more images of sample 4608 or feature array 4614 by detecting light from the sample or feature array. A variety of different imaging elements can be used in detection sub-system 4664, including CCD detectors and other image capture devices.

Each of the foregoing components can optionally be connected to control unit 4628 as shown in FIG. 46B, so that control unit 4628 can adjust various properties of the imaging apparatus. For example, control unit 4628 can adjust the position of sample 4608 or feature array 4614 relative to the position of the incident light, and also with respect to the focal plane of the incident light (if the incident light is focused). Control unit 4628 can also selectively filter both the incident light and the light emerging from the sample.

Imaging apparatus 4650 can typically obtain images in a variety of different imaging modalities. In some embodiments, for example, the images are transmitted light images, as shown in FIG. 46B. In certain embodiments, apparatus 4650 is configured to obtain reflection images. In some embodiments, apparatus 4650 can be configured to obtain birefringence images, fluorescence images, phosphorescence images, multiphoton absorption images, and more generally, any known image type.

In general, control unit 4628 can perform any of the method steps described herein that do not expressly require user intervention by transmitting suitable control signals to the components of sample handling apparatus 4600 and/or imaging apparatus 4650. To perform such steps, control unit 4628 generally includes software instructions that, when executed, cause control unit 4628 to undertake specific steps. In some embodiments, control unit 4628 includes an electronic processor and software instructions that are readable by the electronic processor, and cause the processor to carry out the steps describe herein. In certain embodiments, control unit 4628 includes one or more application-specific integrated circuits having circuit configurations that effectively function as software instructions.

Control unit 4628 can be implemented in a variety of ways. FIG. 46C is a schematic diagram showing one example of control unit 4628, including an electronic processor 4680, a memory unit 4682, a storage device 4684, and an input/output interface 4686. Processor 4680 is capable of processing instructions stored in memory unit 4682 or in storage device 4684, and to display information on input/output interface 4686.

Memory unit 4682 stores information. In some embodiments, memory unit 4682 is a computer-readable medium. Memory unit 4682 can include volatile memory and/or non-volatile memory. Storage device 4684 is capable of providing mass storage, and in some embodiments, is a computer-readable medium. In certain embodiments, storage device 4684 may be a floppy disk device, a hard disk device, an optical disk device, a tape device, a solid state device, or another type of writeable medium.

The input/output interface 4686 implements input/output operations. In some embodiments, the input/output interface 4686 includes a keyboard and/or pointing device. In some embodiments, the input/output interface 4686 includes a display unit for displaying graphical user interfaces and/or display information.

Instructions that are executed and cause control unit 4628 to perform any of the steps or procedures described herein can be implemented in digital electronic circuitry, or in computer hardware, firmware, or in combinations of these. The instructions can be implemented in a computer program product tangibly embodied in an information carrier, e.g., in a machine-readable storage device, for execution by a programmable processor (e.g., processor 4680). The computer program can be written in any form of programming language, including compiled or interpreted languages, and it can be deployed in any form, including as a stand-alone program or as a module, component, subroutine, or other unit suitable for use in a computing environment. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

Processor 4680 can include any one or more of a variety of suitable processors. Suitable processors for the execution of a program of instructions include, by way of example, both general and special purpose microprocessors, and the sole processor or one of multiple processors of any kind of computer or computing device.

VI. Systems, Methods, and Compositions for Method for Transposase-Mediated Spatial Tagging and Analyzing Genomic DNA in a Biological Sample The human body includes a large collection of diverse cell types, each providing a specialized and context-specific function. Understanding a cell's chromatin structure can reveal information about the cell's function. Open chromatin, or accessible chromatin, is often indicative of transcriptionally active sequences, e.g., genes, in a particular cell. Further understanding the transcriptionally active regions within chromatin will enable identification of which genes contribute to a cell's function and/or phenotype.

Methods have been developed to study epigenomes, e.g., chromatin accessibility assays (ATAC-seq) or identifying proteins associated with chromatin e.g., (ChIP-seq). These assays help identify regulators (e.g., cis regulators and/or trans regulators) that contribute to dynamic cellular phenotypes. While ATAC-Seq and ChIP-Seq have been invaluable in defining epigenetic variability within a cell population, conventional applications of these methods are limited in their ability to spatially resolve the three dimensional structures and associated genes that promote cellular variation.

Thus, the present disclosure relates generally to the spatial tagging and analysis of nucleic acids. In some embodiments, provided herein are methods that utilize a transposase enzyme to facilitate the capture of fragmented DNA and enable the simultaneous capture of DNA and RNA from a biological sample, thus revealing epigenomic insights regarding the structural features contributing to cellular regulation.

In some embodiments, provided herein are methods for spatial analysis of nucleic acids (e.g., genomic DNA, mRNA) in a biological sample. In some embodiments, a substrate is provided, wherein the substrate comprises a plurality of capture probes. In some embodiments, the capture probes may be attached directly to the substrate. In some embodiments, the capture probes may be attached indirectly to the substrate. For example, the capture probes can be attached to features on the substrate. In some embodiments, the capture probes comprise a spatial barcode and a capture domain. In some embodiments, the capture probe can be partially double stranded. In some embodiments, the capture probe can bind a complementary oligonucleotide. In some embodiments, the complementary oligonucleotide (e.g., splint oligonucleotide) can have a single stranded capture domain. In some embodiments, the single stranded capture domain can bind fragmented (e.g., tagmented) DNA. In some embodiments, the complementary oligonucleotide with the single stranded capture domain can be a splint oligonucleotide. In some embodiments, a biological sample is treated under conditions sufficient to make nucleic acids in cells of the biological sample (e.g., genomic DNA) accessible to a transposon insertion. In some embodiments, a transposon sequence and a transposase enzyme are provided to the biological sample such that the transposon sequence can be inserted into the genomic DNA of cells present in the biological sample. In some embodiments, the transposase enzyme can excise (e.g., cut out, remove) the inserted transposon sequence from the nucleic acid (e.g., genomic DNA), thereby fragmenting the genomic DNA.

In some embodiments, the biological sample comprising nucleic acids (e.g., genomic DNA, mRNA) is contacted to the substrate such that a capture probe can interact with the fragmented (e.g., tagmented) genomic DNA. In some embodiments, the biological sample comprising nucleic acids (e.g., genomic DNA, mRNA) is contacted with the substrate such that the capture probe can interact with both the fragmented genomic DNA and the mRNA present in the biological sample.

In some embodiments, the location of the capture probe on the substrate can be correlated to a location in the biological sample, thereby spatially analyzing the fragmented (e.g., tagmented) genomic DNA. In some embodiments, the location of the capture probe on the substrate can be correlated to a location in the biological sample, thereby spatially analyzing the fragmented genomic DNA and mRNA.

Spatial ATAC-Seq

In some embodiments, of any of the spatial analysis methods described herein, ATAC-seq is used to generate genome-wide chromatin accessibility maps. These genome-wide accessibility maps can be integrated with additional genome-wide profiling data (e.g., RNA-seq, ChIP-seq, Methyl-Seq) to produce gene regulatory interaction maps that facilitate understanding of transcriptional regulation. For example, interrogation of genome-wide accessibility maps can reveal the underlying transcription factors and the transcription factor motifs responsible for chromatin accessibility at a given genomic location. Correlating changes in chromatin accessibility with changes in gene expression (RNA-seq), changes in TF binding (e.g., ChIP-seq) and/or changes in DNA methylation levels (e.g., Methyl-seq) can identify the transcription regulation driving these changes. In disease states, there is often an imbalance in this transcriptional regulation. Thus, analyzing both chromatin accessibility and, for example, gene expression using spatial analysis methods enables identification of causes underlying the imbalances in transcriptional regulation.

In some embodiments, where spatial profiling includes concurrent analysis of different types of analytes from a single cell or a subpopulation of cells within a biological sample (e.g., a tissue section), an additional layer of spatial information can be integrated into the genome regulatory interaction maps. In some embodiments, the spatial profiling can be done on whole genomes. In some embodiments, the spatial profiling can be done on an immobilized biological sample (e.g., fixed biological sample).

In some embodiments, the genome-wide chromatin accessibility maps generated by spatial ATAC-seq can be used for cell type identification. For example, traditional cell type classification relies on mRNA expression levels but chromatin accessibility can be more adept at capturing cell identity. Furthermore, in some embodiments, correlations between transcriptionally active regions (e.g., open chromatin) with expression profiles (e.g., expression profiles of mRNA) can be determined in a spatial manner.

Permeabilizing the Biological Sample

The present disclosure generally describes methods of fragmenting (e.g., tagmenting) genomic DNA to generate DNA fragments in a biological sample. Generally, a biological sample needs to be permeabilized under conditions sufficient to access genomic DNA. However, permeabilization conditions typically used in DNA tagmentation reactions in cellular preparations (e.g., IGEPAL, Digitonin, NP-40, Tween or Triton-X-100) are insufficient to enable successful fragmentation (e.g., tagmentation) in biological samples immobilized on a substrate, e.g., a support, an array. As described further in the Examples below, a chemical or enzymatic "pre-permeabilization" of biological samples immobilized on a substrate can be employed to make DNA in the biological sample accessible to a transposase enzyme (e.g. a transposome). In some embodiments, permeabilizing the biological sample can be a two-step process (e.g., pre-permeabilization treatment, followed by a permeabilization treatment). In some embodiments, permeabilizing the biological sample can be a one-step process (e.g., a single permeabilization treatment sufficient to permeabilize the cellular and nuclear membranes in the biological sample). In some embodiments, the "pre-permeabilization" conditions can be adapted to yield uniform DNA fragmentation to enable capture of DNA tagments regardless of chromatin accessibility or to yield fragments with a pronounced nucleosomal pattern.

In some embodiments, pre-permeabilization can include an enzymatic or chemical condition. In some embodiments, pre-permeabilization can be performed with an enzyme (e.g., a protease). In some embodiments, in a non-limiting way, the protease can include trypsin, pepsin, dispase, papain, accuses, or collagenase. In some embodiments, pre-permeabilization can include an enzymatic treatment with pepsin. In some embodiments, pre-permeabilization can include pepsin in 0.5M acetic acid. In some embodiments, pre-permeabilization can include pepsin in Exonuclease-1 buffer. In some embodiments, the pH of the buffer can be acidic. In some embodiments, pre-permeabilization can include enzymatic treatment with collagenase. In some embodiments, pre-permeabilization can include collagenase in HBSS buffer. In some embodiments, the HBSS buffer can include bovine serum albumin (BSA). In some embodiments, pre-permeabilization can include Proteinase K in PKD buffer. In some embodiments, the ratio of Proteinase K to PKD Buffer can be between about 1:1 to about 1:20. In some embodiments, the ratio of Proteinase K to PKD Buffer can be between about 1:5 to about 1:15. In some embodiments, the ratio of Proteinase K to PKD Buffer can be about 1:8. In some embodiments, enzymatic treatment with Proteinase K can be at about 37° C. In some embodiments, pre-permeabilization can include an enzymatic treatment with trypsin. In some embodiments, enzymatic treatment with trypsin can be at about 20° C., about 30° C., or about 40° C. In some embodiments, enzymatic treatment with trypsin can be at about 37° C. In some embodiments, pre-permeabilization can last for about 1 to minute to about 20 minutes. In some embodiments, pre-permeabilization can last for about 2, about 3, about 4, about 5, about 6, about 7, about 8, about 9, about 10, about 11, about 12, about 13, about 14, about 15, about 16, about 17, about 18, or about 19 minutes. In some embodiments, pre-permeabilization can last for about 10 minutes to about one hour. For example, in some embodiments, pre-permeabilization can last for about 20, about 30, about 40, or about 50 minutes.

In some embodiments, permeabilizing the biological sample comprises an enzymatic treatment. In some embodiments, the enzymatic treatment can be a pepsin enzyme, or a pepsin-like enzyme treatment. In some embodiments, the enzymatic treatment can be protease treatment. In some embodiments, enzymatic treatment can be performed in the presence of reagents. In some embodiments, the enzymatic treatment (e.g., pre-permeabilization) can include contacting the biological specimen with an acidic solution including a protease enzyme. In some embodiments, the reagent can be HCl. In some embodiments, the reagent can be acetic acid. In some embodiments, the concentration of HCl can be about 100 mM. In some embodiments, the about 100 mM HCl can have a pH of around, or about 1.0. In some embodiments, the additional reagent can be 0.5M acetic acid, having a pH of around, or about 2.5. It is noted that enzymatic treatment of the biological sample can have different effects on tagmentation. For example, enzymatic treatment with pepsin and 100 mM HCl can result in tagmentation of chromatin regardless of chromatin accessibility. In some embodiments, enzymatic treatment with pepsin and 0.5M acetic acid can result in tagmentation of chromatin that can retain a nucleosomal pattern indicative of tagmentation.

In some embodiments, the enzymatic treatment can comprise contacting the biological sample with a reaction mixture (e.g., solution) comprising an aspartyl protease (e.g., pepsin) in an acidic buffer, e.g., a buffer with a pH of about 4.0 or less, such as about 3.0 or less, e.g., about 0.5 to about 3.0, or about 1.0 to about 2.5. In some embodiments, the aspartyl protease is a pepsin enzyme, pepsin-like enzyme, or a functional equivalent thereof. Thus, any enzyme or combination of enzymes in the enzyme commission number 3.4.23.1.

In some embodiments, the enzymatic treatment with pepsin enzyme, or pepsin like enzyme, can be selected from the following (UniProtKB/Swiss-Prot accession numbers): P03954/PEPA1_MACFU; P28712/PEPA1_RABIT; P27677/PEPA2_MACFU; P27821/PEPA2_RABIT; P0DJD8/PEPA3_HUMAN; P27822/PEPA3_RABIT; P0DJD7/PEPA4_HUMAN; P27678/PEPA4_MACFU; P28713/PEPA4_RABIT; P0DJD9/PEPA5_HUMAN; Q9D106/PEPA5_MOUSE; P27823/PEPAF_RABIT; P00792/PEPA_BOVIN; Q9N2D4/PEPA_CALJA; Q9GMY6/PEPA_CANLF; P00793/PEPA_CHICK; P11489/PEPA_MACMU; P00791/PEPA_PIG; Q9GMY7/PEPA_RHIFE; Q9GMY8/PEPA_SORUN; P81497/PEPA_SUNMU; P13636/PEPA_URSTH and functional variants and derivatives thereof, or a combination thereof. In some embodiments, the pepsin enzyme is selected from (UniProtKB/Swiss-Prot accession numbers): P00791/PEPA_PIG; P00792/PEPA_BOVIN and functional variants and derivatives thereof or a combination thereof.

In some embodiments, the pepsin enzyme or functional variant or derivative thereof, comprises an amino acid sequence with at least 80% sequence identity to a sequence as set forth in SEQ ID NOs: 3 or 4. Preferably the polypeptide includes a sequence having at least about 90, 91, 92, 93, 94, 95, 96, 97, 98 or 99% sequence identity to the sequence to which it is compared (e.g., SEQ ID NOs. 3 or 4).

In some embodiments, the enzymatic treatment (e.g., pre-permeabilization) can be a Proteinase K or Proteinase K-like treatment. In some embodiments, enzymatic treatment with Proteinase K can result in tagmentation of accessible chromatin in the biological sample. In some embodiments, enzymatic treatment (e.g., pre-permeabilization and permeabilization) with Proteinase K can result in tagmentation of inaccessible chromatin, (e.g., nucleosomal DNA). In some embodiments, the enzymatic treatment comprises contacting the biological sample with a serine protease (e.g., Proteinase K) with reagents and under conditions suitable for proteolytic activity. For example, the serine protease is functional under a wide range of pH conditions (e.g., from about 6.5 to about 9.5), denaturing conditions (e.g., presence of SDS, urea), metal chelating agents (e.g., EDTA), and temperatures (e.g., about 450 to about 65°). In some embodiments, it can be useful to stop enzymatic activity of the serine protease (e.g., Proteinase K) with an inhibitor. For example, following enzymatic treatment, Proteinase K can be inhibited by a small molecule (e.g., Sigma Cat. No. 539470).

In some embodiments, the serine protease is a proteinase K enzyme, proteinase K-like enzyme, or a functional equivalent thereof. For example, any enzyme or combination of enzymes in the enzyme commission number 3.4.21.64 can be used. In some embodiments, the Proteinase K is P06873/PRTK_PARAQ, (UniProtKB/Swiss-Prot accession number), or a functional variant or derivative thereof (as described herein), or a combination thereof.

In some embodiments, the proteinase K enzyme, or functional variant or derivative thereof, comprises an amino acid sequence with at least 80% sequence identity to a sequence as set forth in SEQ ID NO. 7. In some embodiments, the polypeptide sequence is an amino acid sequence having about at least 90, 91, 92, 93, 94, 95, 96, 97, 98 or 99% sequence identity to the sequence to which it is compared (e.g. SEQ ID NO. 7)

In some embodiments, the enzymatic treatment (e.g., pre-permeabilization) can be performed using collagenase. In some embodiments, enzymatic treatment with collagenase can provide access to the genomic DNA for the transposase while preserving nuclear integrity. In some embodiments, pre-permeabilization (e.g., enzymatic treatment) with collagenase yields nucleosomal patterns generally associated with tagmentation. Collagenases can be isolated from *Clostridium histolyticum*. In some embodiments, enzymatic treatment with a zinc endopeptidase (e.g., collagenase) with reagents and under conditions suitable for proteolytic activity comprises a buffered solution with a pH of about 7.0 to about 8.0 (e.g., about 7.4). Collagenases are zinc endopeptidases and can be inhibited by either EDTA or EGTA, or both. Therefore, in some embodiments, the biological sample can be contacted with a zinc endopeptidase (e.g., collagenase) in the absence of a chelator of divalent cations, (e.g., EDTA, EGTA). In some embodiments, it can be useful to stop the zinc endopeptidase (e.g., collagenase) and the permeabilization step can be stopped (e.g., inhibited) by contacting the biological sample with a chelator of divalent cations (e.g., EDTA, EGTA).

In some embodiments, the zinc endopeptidase is a collagenase enzyme, collagenase-like enzyme, or a functional equivalent thereof. In such embodiments, any enzyme or combination of enzymes in the enzyme commission number 3.4.23.3 can be used in accordance with materials and methods described herein. In some embodiments, the collagenase is one or more collagenases from the following group, (UniProtKB/Swiss-Prot accession numbers): P43153/COLA_CLOPE; P43154/COLA_VIBAL; Q9KRJ0/COLA_VIBCH; Q56696/COLA_VIBPA; Q8D4Y9/COLA_VIBVU; Q9X721/COLG_HATHI; Q46085/COLH_HATHI; Q899Y1/COLT_CLOTE URSTH and functional variants and derivatives thereof (described herein), or a combination thereof.

In some embodiments, the collagenase enzyme, or functional variant or derivative thereof, comprises an amino acid sequence with at least 80% sequence identity to a sequence as set forth in SEQ ID NOs. 5 or 6. In some embodiments, said polypeptide sequence is a sequence having at least about 90, 91, 92, 93, 94, 95, 96, 97, 98 or 99% sequence identity to the sequence to which it is compared (e.g., SEQ ID NOs. 5 or 6).

Methods of permeabilizing biological samples are well known in the art. It will be known to a person skilled in the art that different sources of biological samples can be treated with different reagents (e.g., proteases, RNAses, detergents, buffers) and under different conditions (e.g., pressure, temperature, concentration, pH, time). In some embodiments, permeabilizing the biological sample can comprise reagents and conditions to sufficiently disrupt the cell membrane of the biological sample to capture nucleic acid (e.g., mRNA). In some embodiments, permeabilizing the biological sample can comprise reagents and conditions to sufficiently disrupt the nuclear membrane of the biological sample to capture nucleic acid (e.g., genomic DNA). In some embodiments, commercially available proteases isolated from their native (e.g., animal, microbial source) can be used. In some embodiments, proteases produced recombinantly (e.g., bacterial expression system) can be used. In some embodiments, pre-permeabilizing and permeabilizing a biological sample can be a one-step process (e.g., enzymatic treatment). In some embodiments, pre-permeabilizing and permeabilizing a biological sample can be a two-step process (e.g., enzymatic treatment, followed by chemical or detergent treatment).

In some embodiments, the chemical permeabilization conditions comprise contacting the biological specimen with an alkaline solution, e.g. a buffered solution with a pH of about 8.0 to about 11.0, such as about 8.5 to about 10.5 or about 9.0 to about 10.0, e.g. about 9.5. In some embodiments, the buffer is a glycine-KOH buffer. Other buffers are known in the art.

In some embodiments, a biological sample can be treated with a detergent following an enzymatic treatment (e.g., permeabilization following a pre-permeabilization step). Detergents are known in the art. Any suitable detergent can be used, including, in a non-limiting way NP-40 or equivalent, Digitonin, Tween-20, IGEPAL-40 or equivalent, Saponin, SDS, Pitsop2, or combinations thereof. In some embodiments, a biological sample can be treated with other chemicals known to permeabilize cellular membranes. As further exemplified in the examples below, detergents described herein can be used at a concentration of between about 0.01% to about 0.1%. In some embodiments, detergents described herein can be used at a concentration of about 0.2%, about 0.3%, about 0.4%, about 0.5%, about 0.6%, about 0.7%, about 0.8%, or about 0.9%. In some embodiments, detergents described herein can be used at a concentration of about 1.1% to about 10% or more. In some embodiments, detergents described herein can be used at a concentration of about 2%, about 3%, about 4%, about 5%, about 6%, about 7%, about 8%, or about 9%.

Additional methods for sample permeabilization are described, for example, in Jamur et al., Method Mol. Biol. 588:63-66, 2010, the entire contents of which are incorporated herein by reference. Any suitable method for biological sample permeabilization can generally be used in connection with the biological samples described herein.

Different sources of biological samples can be treated with different reagents (e.g., proteases, RNAses, detergents, buffers) and under different suitable conditions (e.g., pressure, temperature, concentration, pH, time) to achieve sufficient pre-permeabilization and permeabilization to capture nucleic acids (e.g., genomic DNA, mRNA). For example, enzymatic treatment (e.g., pepsin, collagenase, Proteinase K) can be used at a concentration of about 0.05 mg/ml to about 1 mg/ml, e.g., about 0.1 mg/ml to about 0.5 mg/ml. In some embodiments, enzymatic treatment can be used at a concentration of about 1.1 mg/ml to about 1.9 mg/mL. In some embodiments, the biological sample can be incubated with the protease enzymes and/or chemical reagents (e.g., alkaline buffer) for about 1-10 minutes, e.g., about 2, about 3, about 4, about 5, about 6, about 7, about 8, or about 9 minutes. In some embodiments, the biological sample can be incubated with the protease enzymes and/or chemical reagents (e.g., alkaline buffer) for at least about 5 minutes, e.g. at least about 10, about 12, about 15, about 18, or about 20 minutes. For instance, the collagenase enzymes (or functional equivalents thereof) can be incubated with the biological sample for about 10 to about 30 minutes, e.g., about 20 minutes.

In some embodiments, the biological sample can be incubated with the protease enzymes and/or chemical reagents (e.g., alkaline buffer) for up to about 1 hour, e.g., for up to about 10, about 20, about 30, about 40, or about 50 minutes. In some embodiments, the biological sample can be incubated with the protease enzymes and/or chemical reagents (e.g., alkaline buffer) for up to about 4 hours, e.g., for up to about 2 or about 3 hours. The incubation period can depend on the concentration of the enzyme and the conditions of use, e.g., buffer, temperature etc. In some embodiments, the protease enzymes can be incubated with the biological specimen for more or less time than the periods set out above.

In some embodiments, pre-permeabilization and permeabilization conditions can be impacted by various temperatures. For example, representative temperature conditions for the pre-permeabilization and permeabilization step include incubation at about 10 to about 70° C., depending on the enzyme. For example, pepsin and collagenase may be used at about 10 to about 44°, about 11 to about 43°, about 12 to about 42°, about 13 to about 410, about 14 to about 40°, about 15 to about 39°, about 16 to about 38°, about 17 to about 37° C., e.g., about 10°, about 12°, about 15°, about 18°, about 20°, about 22°, about 25°, about 28°, about 30°, about 33°, about 35°, or about 37° C., e.g., about 30 to about 40° C., e.g., about 37° C. Proteinase K may be used at about 40 to about 70° C., e.g. about 50 to about 70° C., about 60 to about 70° C. e.g., about 65° C.

In some embodiments, the pre-permeabilization and permeabilization step can be stopped (e.g., the protease activity may be stopped) by any suitable means. For instance, the reaction mixture (e.g., solution) comprising the protease enzymes and/or chemical reagents can be removed from the substrate (e.g., a support) and separated from the biological sample. Alternatively or additionally, the protease enzyme(s) can be inhibited (e.g., by the addition of an inhibitor, such as EDTA for collagenase) or denatured (e.g., by the addition of a denaturing agent or increasing the temperature).

In some embodiments, the reaction mixture (e.g., solution) including the proteases described herein can contain other reagents, (e.g., buffer, salt, etc.) sufficient to ensure that the proteases are functional. For instance, the reaction mixture can further include an albumin protein, (e.g., BSA). In some embodiments, the reaction mixture (e.g., solution) including the collagenase enzyme (or functional variant or derivative thereof) includes an albumin protein, (e.g., BSA).

Tagmentation

Transposase enzymes and transposons can be utilized in methods of spatial genomic analysis. Generally, transposition is the process by which a specific genetic sequence (e.g., a transposon sequence) is relocated from one place in a genome to another. Many transposition methods and transposable elements are known in the art (e.g., DNA transposons, retrotransposons, autonomous transposons, non-autonomous transposons). One non-limiting example of a transposition event is conservative transposition. Conservative transposition is a non-replicative mode of transposition in which the transposon is completely removed from the genome and reintegrated into a new locus, such that the transposon sequence is conserved, (e.g., a conservative transposition event can be thought of as a "cut and paste" event) (See, e.g., Griffiths A. J., et. al., Mechanism of transposition in prokaryotes. An Introduction to Genetic Analysis (7th Ed.). New York: W. H. Freeman (2000)).

In one example, cut and paste transposition can occur when a transposase enzyme binds a sequence flanking the ends of the transposome (e.g., a recognition sequence, e.g., a mosaic end sequence). A transposome (e.g., a transposition complex) forms and the endogenous DNA can be manipulated into a pre-excision complex such that two transposases enzymes can interact. In some embodiments, when the transposases interact double stranded breaks are introduced into the DNA resulting in the excision of the transposon sequence. The transposase enzymes can locate and bind a target site in the DNA, create a double stranded break, and insert the transposon sequence (See, e.g., Skipper, K. A., et. al., DNA transposon-based gene vehicles-scenes from an evolutionary drive, *J Biomed Sci.,* 20: 92 (2013) doi: 10.1186/1423-0127-20-92). Alternative cut and paste transposases include Tn552 (College, et al, J. BacterioL, 183: 2384-8, 2001; Kirby C et al, Mol. Microbiol, 43: 173-86, 2002), Tyl (Devine & Boeke, Nucleic Acids Res., 22: 3765-72, 1994 and International Publication WO 95/23875), Transposon Tn7 (Craig, N L, Science. 271: 1512, 1996; Craig, N L, Review in: Curr Top Microbiol Immunol, 204:27-48, 1996), Tn/O and IS10 (Kleckner N, et al, Curr Top Microbiol Immunol, 204:49-82, 1996), Mariner transposase (Lampe D J, et al, EMBO J., 15: 5470-9, 1996), Tel (Plasterk R H, Curr. Topics Microbiol. Immunol, 204: 125-43, 1996), P Element (Gloor, G B, Methods Mol. Biol, 260: 97-114, 2004), Tn3 (Ichikawa & Ohtsubo, J Biol. Chem. 265: 18829-32, 1990), bacterial insertion sequences (Ohtsubo & Sekine, Curr. Top. Microbiol. Immunol. 204: 1-26, 1996), retroviruses (Brown, et al, Proc Natl Acad Sci USA, 86:2525-9, 1989), and retrotransposon of yeast (Boeke & Corces, Annu Rev Microbiol. 43:403-34, 1989). More examples include IS5, TnlO, Tn903, IS911, and engineered versions of transposase family enzymes (Zhang et al, (2009) PLoS Genet. 5:e1000689. Epub 2009 Oct. 16; Wilson C. et al (2007) J. Microbiol. Methods 71:332-5).

In some methods of spatial genomic analysis, DNA is fragmented in such a manner that a sequence complementary to a capture domain of a capture probe (e.g., capture domain of a splint oligonucleotide) is attached to the fragmented DNA (e.g., the fragmented DNA is "tagged"), such that the attached sequence (e.g. an adapter, e.g., Nextera adapter) can hybridize to the capture probe. In some embodiments, the capture probe is present on a substrate. In some embodiments, the capture probe (e.g., a surface probe and a splint oligonucleotide) is present on a feature. Transposome-mediated fragmentation ("tagmentation") is a process of transposase-mediated fragmentation and tagging of DNA. A transposome is a complex of a transposase enzyme and DNA which comprises a transposon end sequence (also known as "transposase recognition sequence" or "mosaic end" (MEs)). A transposome dimer is able to simultaneously fragment DNA based on its transposon recognition sequences and ligate DNA from the transposome to the fragmented DNA (e.g., tagmented DNA). This system has been adapted using hyperactive transposase enzymes and modified DNA molecules (adaptors) comprising MEs to fragment DNA and tag both strands of DNA duplex fragments with functional DNA molecules (e.g., primer binding sites). For instance, the Tn5 transposase may be produced as purified protein monomers. Tn5 transposase is also commercially available (e.g., manufacturer Illumina, Illumina.com, Catalog No. 15027865, TD Tagment DNA Buffer Catalog No. 15027866). These can be subsequently loaded with the oligonucleotides of interest, e.g., ssDNA oligonucleotides containing MEs for Tn5 recognition and additional functional sequences (e.g., Nextera adapters, e.g., primer binding sites) are annealed to form a dsDNA mosaic end oligonucleotide (MEDS) that is recognized by Tn5 during dimer assembly (e.g., transposome dimerization). In some embodiments, a hyperactive Tn5 transposase can be loaded with adapters (e.g., oligonucleotides of interest) which can simultaneously fragment and tag a genome with the adapter sequences.

As used herein, the term "tagmentation" refers to a step in the Assay for Transposase Accessible Chromatin using sequencing (ATAC-seq). (See, e.g., Buenrostro, J. D., Giresi, P. G., Zaba, L. C, Chang, H. Y., Greenleaf, W. J., Transposition of native chromatin for fast and sensitive epi genomic profiling of open chromatin, DNA-binding proteins and nucleosome position, *Nature Methods,* 10 (12): 1213-1218 (2013)). ATAC-seq identifies regions of open chromatin using a hyperactive prokaryotic Tn5-transposase, which preferentially inserts into accessible chromatin and tags the sites with adaptors (Buenrostro, J. D., et. al., Transposition of native chromatin for fast and sensitive epigenomic profiling of open chromatin, DNA-binding proteins and nucleosome position. *Nat Methods,* 10: 1213-1218 (2013)).

In some embodiments, the step of fragmenting the genomic DNA in cells of the biological sample comprises contacting the biological sample containing the genomic DNA with the transposase enzyme (e.g., a transposome, e.g., a reaction mixture (e.g., solution)) including a transposase), under any suitable conditions. In some embodiments, such suitable conditions result in the fragmentation (e.g., tagmentation) of the genomic DNA of cells present in the biological sample. Typical conditions will depend on the transposase enzyme used and can be determined using routine methods known in the art. Therefore, suitable conditions can be conditions (e.g., buffer, salt, concentration, pH, temperature, time conditions) under which the transposase enzyme is functional, e.g., in which the transposase enzyme displays transposase activity, particularly tagmentation activity, in the biological sample.

The term "functional", as used herein in reference to transposase enzymes, is meant to include embodiments in which the transposase enzyme can show some reduced activity relative to the activity of the transposase enzyme in conditions that are optimum for the enzyme, e.g., in the buffer, salt and temperature conditions recommended by the manufacturer. Thus, the transposase can be considered to be "functional" if it has at least about 50%, e.g., at least about 60, about 70, about 80, about 85, about 90, about 95, about 96, about 97, about 98, about 99, or about 100%, activity relative to the activity of the transposase in conditions that are optimum for the transposase enzyme.

In one non-limiting example, the reaction mixture comprises a transposase enzyme in a buffered solution (e.g., Tris-acetate) having a pH of about 6.5 to about 8.5, e.g., about 7.0 to about 8.0 such as about 7.5. Additionally or alternatively, the reaction mixture can be used at any suitable temperature, such as about 100 to about 55° C., e.g., about 100 to about 54°, about 110 to about 53°, about 120 to about 52°, about 130 to about 51°, about 140 to about 50°, about 150 to about 49°, about 160 to about 48°, about 170 to about 47° C., e.g., about 10°, about 12°, about 15°, about 18°, about 20°, about 22°, about 25°, about 28°, about 30°, about 33°, about 35°, about or 37° C., preferably about 300 to about 40° C., e.g., about 37° C. In some embodiments, the transposase enzyme can be contacted with the biological sample for about 10 minutes to about one hour. In some embodiments, the transposase enzyme can be contacted with the biological sample for about 20, about 30, about 40, or about 50 minutes. In some embodiments, the transposase enzyme can be contacted with the biological sample for about 1 hour to about 4 hours.

In some embodiments, the transposase enzyme is a Tn5 transposase, or a functional derivate or variant thereof. (See, e.g., Reznikoff et al, WO 2001/009363, U.S. Pat. Nos. 5,925,545, 5,965,443, 7,083,980, and 7,608,434, and Goryshin and Reznikoff, J. Biol. Chem. 273:7367, (1998), which are herein incorporated by reference). For example, the Tn5 transposase can be a fusion protein (e.g., a Tn5 fusion protein). Tn5 is a member of the RNase superfamily of proteins. The Tn5 transposon is a composite transposon in which two near-identical insertion sequences (IS50L and IS50R) flank three antibiotic resistance genes. Each IS50 contains two inverted 19-bp end sequences (ESs), an outside end (OE) and an inside end (IE). Wild-type Tn5 transposase enzyme is generally inactive (e.g., low transposition event activity). However, amino acid substitutions can result in hyperactive variants or derivatives. In one non-limiting example, amino acid substitution, L372P, substitutes a leucine amino acid for a proline amino acid which results in an alpha helix break, thus inducing a conformational change to the C-terminal domain. The alpha helix break separates the C-terminal domain and N-terminal domain sufficiently to promote higher transposition event activity (See, Reznikoff, W. S., Tn5 as a model for understanding DNA transposition, *Mol Microbiol*, 47(5): 1199-1206 (2003)). Other amino acid substitutions resulting in hyperactive Tn5 are known in the art. For example, the improved avidity of the modified transposase enzyme (e.g., modified Tn5 transposase enzyme) for the repeat sequences for OE termini (class (1) mutation) can be achieved by providing a lysine residue at amino acid 54, which is glutamic acid in wild-type Tn5 transposase enzyme (See U.S. Pat. No. 5,925,545). The mutation strongly alters the preference of the modified transposase enzyme (e.g., modified Tn5 transposase enzyme) for OE termini, as opposed to IE termini. The higher binding of this mutation, known as EK54, to OE termini results in a transposition rate that is about 10-fold higher than is seen with wild-type transposase enzyme (e.g., wild type Tn5 transposase enzyme). A similar change at position 54 to valine (e.g., EV54) also results in somewhat increased binding/transposition for OE termini, as does a threonine to proline change at position 47 (e.g., TP47; about 10-fold higher) (See U.S. Pat. No. 5,925,545).

Other examples of modified transposase enzymes (e.g., modified Tn5 transposase enzymes) are known. For example, a modified Tn5 transposase enzyme that differs from wild-type Tn5 transposase enzyme in that it binds to the repeat sequences of the donor DNA with greater avidity than wild-type Tn5 transposase enzyme and also is less likely than the wild-type transposase enzyme to assume an inactive multimeric form (U.S. Pat. No. 5,925,545, which is incorporated by reference in its entirety). Furthermore, techniques generally describing introducing any transposable element (e.g., Tn5) from a donor DNA (e.g., adapter sequence, e.g., Nextera adapters (e.g., top and bottom adapter) into a target are known in the art. (See, e.g., U.S. Pat. No. 5,925,545). Further study has identified classes of mutations resulting in a modified transposase enzyme (e.g., modified Tn5 transposase enzyme) (See, U.S. Pat. No. 5,965,443, which is incorporated by reference in its entirety). For example, a modified transposase enzyme (e.g., modified Tn5 transposase enzyme) with a "class 1 mutation" binds to repeat sequences of donor DNA with greater avidity than wild-type Tn5 transposase enzyme. Additionally, a modified transposase enzyme (e.g., modified Tn5 transposase enzyme) with a "class 2 mutation" is less likely than the wild-type Tn5 transposase enzyme to assume an inactive multimeric form. It has been shown that a modified transposase enzyme that contains both a class 1 and a class 2 mutation can induce at least about 100-fold (+10%) more transposition than the wild-type transposase enzyme, when tested in combination with an in vivo conjugation assay as described by Weinreich, M. D., "Evidence that the cis Preference of the Tn5 Transposase is Caused by Nonproductive Multimerization," Genes and Development 8:2363-2374 (1994), incorporated herein by reference (See e.g., U.S. Pat. No. 5,965,443). Further, under sufficient conditions, transposition using the modified transposase enzyme (e.g., modified Tn5 transposase enzyme) may be higher. A modified transposase enzyme containing only a class 1 mutation can bind to the repeat sequences with sufficiently greater avidity than the wild-type Tn5 transposase enzyme such that a Tn5 transposase enzyme induces about 5- to about 50-fold more transposition than the wild-type transposase enzyme, when measured in vivo. A modified transposase enzyme containing only a class 2 mutation (e.g., a mutation that reduces the Tn5 transposase enzyme from assuming an inactive form) is sufficiently less likely than the wild-type Tn5 transposase enzyme to assume the multimeric form that such a Tn5 transposase enzyme also induces about 5- to about 50-fold more transposition than the wild-type transposase enzyme, when measured in vivo (See U.S. Pat. No. 5,965,443)

Other methods of using a modified transposase enzyme (e.g., modified Tn5 transposase enzyme are further generally described in U.S. Pat. No. 5,965,443. For example, a modified transposase enzyme could provide selective markers to target DNA, to provide portable regions of homology to a target DNA, to facilitate insertion of specialized DNA sequences into target DNA, to provide primer binding sites or tags for DNA sequencing, or to facilitate production of genetic fusions for gene expression. Studies and protein domain mapping, as well as, to bring together other desired combinations of DNA sequences (combinatorial genetics) (U.S. Pat. No. 5,965,443).

Still other methods of inserting a transposable element (e.g., transposon) at random or semi-random locations in chromosomal or extra-chromosomal nucleic acid are known. For example, methods including a step of combining in a biological sample nucleic acid (e.g., genomic DNA) with a synaptic complex that comprises a Tn5 transposase enzyme complexed with a sequence comprising a pair of nucleotide sequences adapted for operably interacting with Tn5 transposase enzyme and a transposable element (e.g., transposon) under conditions that mediate transposition events into the genomic DNA. In this method, a synaptic complex can be formed in vitro under conditions that disfavor or prevent synaptic complexes from undergoing a transposition event. The frequency of transposition (e.g., transposition events) can be increased by using either a hyperactive transposase enzyme (e.g., a mutant transposase enzyme) or a transposable element (e.g., transposon) that contains sequences well adapted for efficient transposition events in the presence of a hyperactive transposase enzyme (e.g., hyperactive Tn5 transposase enzyme), or both (U.S. Pat. No. 6,159,736, which is incorporated herein by reference).

Methods, compositions, and kits for treating nucleic acid, and in particular, methods and compositions for fragmenting and tagging DNA using transposon compositions are described in detail in U.S. Patent Application Publication No. US 2010/0120098, U.S. Patent Application Publication No. US2011/0287435, and Satpathy, A. T., et. al., Massively parallel single-cell chromatin landscapes of human immune cell development and intratumoral T-cell exhaustion, *Nat Biotechnol.*, 37, 925-936 (2019), the contents of which are herein incorporated by reference in their entireties.

Any transposase enzyme with tagmentation activity, e.g., any transposase enzyme capable of fragmenting DNA and ligating oligonucleotides (e.g., adapters, e.g. Nextera index adapters) to the ends of the fragmented (e.g., tagmented) DNA, can be used. In some embodiments, the transposase is any transpose capable of conservative transposition. In some embodiments, the transposase is a cut and paste transposase. Other kinds of transposase are known in the art and are within the scope of this disclosure. For example, suitable transposase enzymes include, without limitation, Mos-1, HyperMu™, Ts-Tn5, Ts-Tn5059, Hermes, Tn7, or any functional variant or derivative of the previously listed transposase enzymes.

In some embodiments, a hyperactive variant of the Tn5 transposase enzyme is capable of mediating the fragmentation of double-stranded DNA and ligation of synthetic oligonucleotides (e.g., Nextera adapters) at both 5' ends of the DNA in a reaction that takes a short period of time (e.g., about 5 minutes). However, as wild-type end sequences have a relatively low activity, they are sometimes replaced in vitro by hyperactive mosaic end (ME) sequences. A complex of the Tn5 transposase with 19-bp ME facilitates transposition, provided that the intervening DNA is long enough to bring two of these sequences close together to form an active Tn5 transposase enzyme homodimer.

In some embodiments, the Tn5 transposase enzyme, or functional variant or derivative thereof, comprises an amino acid sequence having at least 80% sequence identity to SEQ. ID NO. 1. In some embodiments, the Tn5 transposase enzyme, or functional variant or derivative thereof, comprises an amino acid sequence having a sequence identity of at least about 90, 91, 92, 93, 94, 95, 96, 97, 98, or 99% amino acid sequence identity to SEQ ID NO. 1.

In some embodiments, the transposase enzyme is a Mu transposase enzyme, or a functional variant or derivative thereof. In some embodiments, the Mu transposase enzyme, or functional variant or derivative thereof, comprises an amino acid sequence having at least 80% sequence identity to SEQ. ID NO. 2. In some embodiments, the Mu transposase enzyme, or functional variant or derivative thereof, comprises an amino acid sequence having a sequence identity of at least about 90, 91, 92, 93, 94, 95, 96, 97, 98, or 99% amino acid sequence identity to SEQ ID NO. 2.

The adaptors (e.g., Nextera adaptors) in the complex with the transposase enzyme (e.g., that form part of the transposome, e.g., MEDS described herein) can include partially double stranded oligonucleotides. In some embodiments, there is a first adapter and a second adapter. In some embodiments, the first adapter can be complexed with a first monomer. In some embodiments, the second adapter can be complexed with a second monomer. In some embodiments, the first monomer complexed with the first adapter and the second monomer complexed with the second monomer can be assembled to form a dimer. In some embodiments, the double stranded portion of the adaptors contains Mosaic End (ME) sequences. In some embodiments, the single stranded portion of the adaptors (e.g., Nextera index adapters) (5' overhang) contains the functional domain or sequence to be incorporated in the fragmented (e.g., tagmented) DNA. In some embodiments, the adapters can be Nextera adapters (e.g., index adapter) (for example, reagents including, Nextera DNA Library Prep Kit for ATAC-seq (no longer available), TDE-1 Tagment DNA Enzyme (Catalog No. 15027865), TD Tagment DNA Buffer (Catalog No. 15027866), available from manufacturer, Illumina, Illumina.com). In some embodiments, the sequence incorporated into the fragmented (e.g., tagmented) DNA is a sequence complementary to a capture domain of a capture probe. In some embodiments, the sequence complementary to the capture domain of the capture probe is a first adapter. In such embodiments, the functional domain is on the strand of the adaptor that will be ligated to the capture probe. In other words, the functional domain can be located upstream (e.g., 5' to) the ME sequence, e.g., in the 5' overhang of the adapter.

The adaptors (e.g., Nextera index adapters, e.g., first and second adapters) ligated to the fragmented (e.g., tagmented) DNA can be any suitable sequence. For example, the sequence can be a viral sequence. In some embodiments, the sequence can be a CRISPR sequence. In some embodiments, the adaptor (e.g., oligonucleotides) ligated to the fragmented DNA (e.g., tagmented DNA) can be a CRISPR guide sequence. In some embodiments, the CRISPR guide sequence can target a sequence of interest (e.g., genomic locus of interest e.g., gene specific).

In some embodiments, the ME sequence is a Tn5 transposase recognition sequence having at least 80% sequence identity to SEQ ID NO. 8. In some embodiments, the Tn5 transposase recognition sequence comprises a sequence having a sequence identity of at least about 90, 91, 92, 93, 94, 95, 96, 97, 98, or 99% sequence identity to SEQ ID NO. 8, so long as the Tn5 transposase enzyme, or variant or derivative, thereof can recognize the Tn5 transposase sequence to induce a transposition event.

In some embodiments, the mosaic end (e.g., ME) sequence is a Mu transposase recognition sequence having at least 80% identity to any one of SEQ ID NOs. 9-14. In some embodiments, the Mu transposase recognition sequence comprises a sequence having a sequence identity of at least about 90, 91, 92, 93, 94, 95, 96, 97, 98, or 99% sequence identity to any one of the sequence to which it is compared (e.g., any one of SEQ ID NOs. 9-14), so long as the Mu5 transposase enzyme, or variant or derivative thereof, can recognize the Mu5 transposase sequence to induce a transposition event.

In some embodiments, a composition comprising a transposase enzyme (e.g., any transposase enzyme described herein) complexed with adapters (e.g., first and second adapters complexed with first and second monomers, respectively) comprising transposon end sequences (e.g., mosaic end sequences) is used in a method for spatially tagging nucleic acids in a biological sample. In some embodiments, a composition comprising a transposase enzyme further comprises a domain that binds to a capture probe as described herein (e.g., Nextera adapter, e.g., first adapter) and a second adapter is used in a method for spatially tagging nucleic acids of a biological sample, such as any of the methods described herein.

In some embodiments, the transposase enzyme can be in the form of a transposome comprising adaptors (MEDS) in which the 5' overhang can be phosphorylated. In some embodiments, the adaptors (e.g., Nextera adaptors, e.g., first and second adapters) may be phosphorylated prior to their assembly with the transposase enzyme to form the transposome. In some embodiments, phosphorylation of adaptors can occur when complexed with a transposase enzyme (e.g., phosphorylation in situ in the transposome).

As exemplified in the Examples provided herein, transposomes can include adaptors (e.g., MEDS, e.g., adaptors including 5' overhangs, e.g., Nextera adaptors). In some embodiments, the 5' overhang of the adaptor is not phosphorylated prior to its assembly in the transposome. In such embodiments, the 5' overhang can have accessible 5' hydroxyl groups outside of the mosaic-end transposase sequence. In some embodiments, phosphorylation of the 5' overhang of the assembled transposome complexes can be achieved by exposing these 5' ends of transposome complexes to a polynucleotide kinase (e.g., T4-polynucleotide kinase (T4-PNK)) in the presence of ATP.

In some embodiments, fragmenting (e.g., tagmenting) genomic DNA of the biological sample with a transposome (e.g., any of the transposomes described herein) can comprise a further step of phosphorylating the 5' ends of the adaptors (e.g., the 5' overhangs of the Nextera adaptors, e.g., MEDS) in the transposome complex.

In some embodiments, methods provided herein comprise a step of providing a transposome that has been treated to phosphorylate the 5' ends of the adaptors (e.g., the 5' overhangs of the Nextera adaptors (e.g., first and second adapters), e.g., MEDS) in the transposome complex, thus fragmenting the biological sample with a transposome that has been treated to phosphorylate the 5' ends of the adaptors in the transposome complex.

Any suitable enzyme and/or conditions can be used to phosphorylate the 5' ends of the adaptors (e.g., the 5' overhangs of the adaptors, e.g., MEDS) in the transposome complex, e.g., T4-PNK or T7-PNK. In some embodiments, the phosphorylation reaction can be carried out by contacting the transposome with a polynucleotide kinase (e.g., T4-PNK or T7-PNK) in a buffered solution (e.g., Tris-HCl, pH about 7.0 to about 8.0, e.g., about 7.6) at about 20 to about 40° C., e.g., about 25 to about 37° C., for about 1 to about 60 minutes, e.g., about 5 to about 50, about 10 to about 40, about 20 to about 30 minutes. In some embodiments, gap filling and ligating breaks can be performed on the fragmented (e.g., tagmented) DNA.

In some embodiments, spatially tagging the genomic DNA can be performed by insertion of the transposon sequence into the genomic DNA with adapters described herein. In some embodiments, the transposon sequence is not excised from the genomic DNA. An amplification step can be performed with primers to the adapters (e.g., inserted adapters into the genomic DNA). The amplified products can contain accessible genomic DNA which can be spatially tagged by methods described herein.

In some embodiments, spatially tagging the genomic DNA can be performed by transposome complexes immobilized on the surface of the substrate. In some embodiments, spatially tagging the genomic DNA can be performed by transposome complexes immobilized on a feature (e.g., a bead). In some embodiments, the transposome complexes are assembled prior to adding the biological sample to the substrate or features. In some embodiments, the transposome complexes are assembled after adding the biological sample to the substrate or features on a substrate. For example, a spatially barcoded substrate (e.g., array) can include a plurality of capture probes that include a Mosaic End sequence (e.g., a transposase recognition sequence). The Mosaic End sequence can be at the 3' end of the capture probe (e.g., the capture probe is immobilized by its 5' end and the Mosaic End sequence is at the 3' most end of the capture probe). The Mosaic End sequence can be a Mosaic End sequence for any of the transposase enzymes described herein. The Mosaic End sequence (e.g., a transposase recognition sequence) can be hybridized to a reverse complement sequence (e.g., oligonucleotide). For example, the reverse complement sequence (e.g., reverse complement to the Mosaic End sequence) can hybridize to the Mosaic End sequence thereby generating a portion of double stranded DNA on the capture probe. The reverse complement to the Mosaic End sequence (e.g., oligonucleotide) can be provided to the spatially barcoded array prior to the biological sample being provided to the substrate. In some embodiments, the reverse complement to the Mosaic End sequence can be provided after the biological sample has been provided to the substrate. Transposase enzymes can be provided to the substrate and assemble at the double stranded portion of the capture probe (e.g., reverse complement oligonucleotide and the Mosaic End sequence hybridized to each other) thereby generating a transposome complex. For example, a transposome homodimer can be formed at the double stranded portion of the capture probe. A biological sample can be provided to the substrate such that the position of the capture probe on the substrate can be correlated with a position (e.g., location) in the biological sample. The transposome complexes can fragment (e.g., tagment) and spatially tag the genomic DNA.

In some embodiments, spatially tagging genomic DNA can be performed by hybridizing a single stranded capture probe to the fragmented (e.g., tagmented) DNA. In some embodiments the single stranded capture probe can be a degenerate sequence. In some embodiments, the single stranded capture can be a random sequence. The single stranded capture probe can have a functional domain, a spatial barcode, a unique molecular identifier, a cleavage domain, or combinations thereof. The single stranded capture probe (e.g., random sequence, degenerate sequence) can non-specifically hybridize tagmented genomic DNA, thereby spatially capturing the fragmented (e.g., tagmented) DNA. Methods for extension reactions are known in the art and any suitable extension reaction method described herein can be performed.

Splint Oligonucleotides

As used herein, the term "splint oligonucleotide" refers to an oligonucleotide that, when hybridized to other polynucleotides, acts as a "splint" (e.g., splint helper probe) to position the polynucleotides next to one another so that they can be ligated together. In some embodiments, the splint oligonucleotide is DNA or RNA. The splint oligonucleotide can include a nucleotide sequence that is partially complementary to nucleotide sequences from two or more different oligonucleotides. In some embodiments, the splint oligonucleotide assists in ligating a "donor" oligonucleotide and an "acceptor" oligonucleotide. In some embodiments, an RNA ligase, a DNA ligase, or other ligase can be used to ligate two nucleotide sequences together.

In some embodiments, the splint oligonucleotide can be between about 10 and about 50 nucleotides in length, e.g., between about 10 and about 45, about 10 and about 40, about 10 and about 35, about 10 and about 30, about 10 and about 25, or about 10 and about 20 nucleotides in length. In some embodiments, the splint oligonucleotide can be between about 15 and about 50, about 15 and about 45, about 15 and about 40, about 15 and about 35, about 15 and about 30, about 15 and about 30, or about 15 and about 25 nucleotides in length. In some embodiments, the fragmented DNA can include a sequence that is added (e.g., ligated) during fragmentation of the DNA. For example, during a transposition event (e.g., a Tn5 transposition event) an additional sequence can be attached (e.g., covalently attached, e.g., via a ligation event) to the fragmented DNA (e.g., fragmented genomic DNA, e.g., tagmented genomic DNA). In some embodiments, the splint oligonucleotide can have a sequence that is complementary (e.g., a capture domain) to the fragmented DNA (e.g., fragmented genomic DNA, e.g., fragmented genomic DNA that includes a sequence that is added during fragmentation of the DNA, e.g. a first adapter attached during fragmentation of the DNA) and a sequence that is complementary to the surface probe (e.g., a portion of a capture probe). In some embodiments, the splint oligonucleotide can be viewed as part of the capture probe. For example, the capture probe can be partially double stranded where a portion of the capture probe can function as a splint oligonucleotide that binds a portion of the capture probe (e.g., dsDNA portion) and can have a single strand portion that can bind (e.g., capture domain) the fragmented DNA (e.g., fragmented genomic DNA e.g., tagmented, e.g., an adapter attached during fragmentation of the DNA, e.g., a Nextera adapter). The first adapter sequence (e.g., the sequence attached to the fragmented DNA complementary to the capture domain, e.g., Nextera adapter) can be any suitable sequence. In some embodiments, the adapter sequence can be between about 15 and 25 nucleotides long. In some embodiments, the adapter sequence can be about 16, about 17, about 18, about 19, about 20, about 21, about 22, about 23, or about 24 nucleotides long. In some embodiments, the first adapter sequence (e.g., Nextera adapter) (e.g., the first adapter) includes the sequence, GTCTCGTGGGCTCGG (SEQ ID NO: 16). In some embodiments, the additional sequence attached to the fragmented (e.g., tagmented) DNA includes a sequence having at least 80% sequence identity to SEQ ID NO. 16. In some embodiments, the additional sequence attached (e.g., Nextera adapter) to the fragmented DNA includes a sequence having at least about 90, 91, 92, 93, 94, 95, 96, 97, 98, or 99% sequence identity to SEQ ID NO. 16. In some embodiments, a second adapter sequence (e.g., Nextera adapter) can be attached to the fragmented DNA (e.g., tagmented DNA) that includes a sequence, TCGTCGGCAGCGTC (SEQ ID NO. 20). In some embodiments, the second adapter sequence attached (e.g., Nextera adapter) to the fragmented DNA (e.g., tagmented DNA) includes a sequence having at least 80% sequence identity to SEQ ID NO. 20. In some embodiments, the second adapter sequence (e.g., Nextera adapter) attached to the fragmented (e.g., tagmented) DNA includes a sequence having at least about 90, 91, 92, 93, 94, 95, 96, 97, 98, or 99% sequence identity to SEQ ID NO. 20. In some embodiments, a splint oligonucleotide can include a sequence that is complementary (e.g., capture domain) to the first adapter attached to the fragmented DNA (e.g., tagmented DNA). In some embodiments, the capture domain (e.g., complementary to the first adapter (e.g., Nextera adapter)) of the splint oligonucleotide (e.g., splint oligonucleotide of the capture probe) can include the sequence CCGAGCCCACGAGAC (See FIG. 40; SEQ ID NO. 17). In some embodiments, the capture domain includes a sequence having at least 80% identity to SEQ ID NO. 17. In some embodiments, the capture domain (e.g., sequence that is complementary to the first adapter e.g., Nextera adapter) includes a sequence having at least about 90, 91, 92, 93, 94, 95, 96, 97, 98, or 99% sequence identity to SEQ ID NO. 17. In some embodiments, the splint oligonucleotide includes a sequence that is not perfectly complementary to the first adapter (e.g., Nextera adapter) attached to the fragmented DNA (e.g., tagmented DNA), but is still capable of hybridizing the first adapter sequence (e.g., sequence complementary to the capture domain) ligated on to the fragmented DNA (e.g., Nextera adapter).

Any of a variety of capture probes having hybridization domains that hybridize to a splint oligonucleotide can be used in accordance with materials and methods described herein. As described herein, a hybridization domain is a domain on a surface probe capable of hybridizing the splint oligonucleotide to form a partially double stranded capture probe. For example, a single stranded surface probe can have a sequence complementary (e.g., hybridization domain) to a portion of the splint oligonucleotide, such that a partially double stranded capture probe is formed with a single stranded capture domain (e.g., capture domain on the splint oligonucleotide). In some embodiments, the surface probe (e.g., of the capture probe) can include a hybridization domain that includes the sequence TGCACGCGGTGTA-CAGACGT (SEQ ID NO. 18). In some embodiments, the surface probe (e.g., of the capture probe) can include a hybridization domain including a sequence having at least 80% identity to SEQ ID NO. 18. In some embodiments, the capture domain includes a sequence having at least about 90, 91, 92, 93, 94, 95, 96, 97, 98, or 99% sequence identity to SEQ ID NO. 18. In some embodiments, a splint oligonucleotide includes a sequence that is complementary (e.g., at least partially complementary) to the hybridization domain of the surface probe. In some embodiments, the sequence of the splint oligonucleotide (e.g., of the capture probe) that is complementary to the hybridization domain of the surface probe (SEQ ID NO. 18) includes the sequence ACGTCTGTACACCGCGTGCA (SEQ ID NO. 19). In some embodiments, the sequence of the splint oligonucleotide that is complementary to the capture domain of the capture includes a sequence having at least 80% sequence identity to SEQ ID NO. 19. In some embodiments, the sequence of the splint oligonucleotide that is complementary (e.g., at least partially complementary) to the hybridization domain of the surface probe includes a sequence having at least about 90, 91, 92, 93, 94, 95, 96, 97, 98, or 99% sequence identity to SEQ ID NO. 19. In some embodiments, the splint oligonucleotide includes a sequence that is not perfectly complementary to the hybridization domain of the surface probe, but is still capable of hybridizing the hybridization domain of the surface probe. In some embodiments, the splint oligonucleotide can hybridize to both the first adapter (e.g., additional sequence attached to the fragmented DNA e.g., tagmented DNA) via its capture domain and the hybridization domain of the surface probe via its sequence complementary to the hybridization domain. In such embodiments, where the splint oligonucleotide can hybridize to both the first adapter (e.g., Nextera adapter, additional sequence attached to the fragmented DNA e.g., tagmented DNA), and the hybridization domain of the surface probe, the splint oligonucleotide can be viewed as part of the capture probe. In some embodiments, a primer can have a sequence capable of hybridizing the surface probe (e.g., surface probe of the capture probe) sequence. For example, the primer can have a sequence that includes the sequence ACACGACGCTCTTCCGATCT (SEQ ID NO. 21). In some embodiments, the sequence that is capable of hybridizing a portion of the surface probe of the capture probe (e.g., A-short forward, See FIG. 40) includes a sequence having at least 80% sequence identity to SEQ ID NO. 21. In some embodiments, the sequence that is complementary (e.g., at least partially complementary) to a portion of the capture probe (e.g., A-short forward) includes a sequence having at least about 90, 91, 92, 93, 94, 95, 96, 97, 98, or 99% sequence identity to SEQ ID NO. 21.

In some embodiments, the splint oligonucleotide can have a capture domain that is homopolymeric. For example, the capture domain can be a poly(T) capture domain.

In some embodiments, a splint oligonucleotide can facilitate ligation of the fragmented DNA (e.g. tagmented DNA) and the surface probe. Any variety of suitable ligases known in the art or described herein can be used. In some embodiments, the ligase is T4 DNA ligase. In some embodiments, the ligation reaction can last for about 1 to about 5 hours. In some embodiments, the ligation reaction can last for about 2, about 3, or about 4 hours. In some embodiments, after ligation, strand displacement polymerization can be performed. In some embodiments, a DNA polymerase can be used to perform the strand displacement polymerization. In some embodiments, the DNA polymerase is DNA polymerase I.

Multiplex Analysis

The present disclosure describes methods for permeabilizing biological samples under conditions sufficient to allow fragmentation (e.g., tagmentation) of genomic DNA. The fragmented (e.g., tagmented) DNA can be captured via a capture probe (e.g., surface probe and a splint oligonucleotide), however, at times it can be useful to simultaneously capture fragmented (e.g., tagmented DNA) and other nuclei acids (e.g., mRNA). For example, expression profiles of transcripts can be correlated (or not) with open chromatin. Put another way, the presence of transcripts can correlate with open chromatin (e.g., accessible chromatin) corresponding to the genes (e.g., genomic DNA) from which the transcripts were transcribed.

The present disclosure describes methods regarding the simultaneous capture of fragmented DNA (e.g., tagmented DNA) and mRNA on spatially barcoded arrays. For example, a spatially barcoded array can have a plurality of capture probes immobilized on a substrate surface. Alternatively, a spatially barcoded array can have a plurality of capture probes immobilized on a feature. In some embodiments, the feature with a plurality of capture probes can be on a substrate. The capture probes can have unique spatial barcodes corresponding to a position (e.g., location) on the substrate. In some embodiments, the capture probes can further have a unique molecular identifier, functional domain, and a cleavage domain, or combinations thereof. In some embodiments, the capture probe can have a capture domain. In some embodiments, the capture probe can be a homopolymeric sequence. For example, in a non-limiting way, the homopolymeric sequence can be a poly(T) sequence. In some embodiments, nucleic acid (e.g., mRNA) can be captured by the capture domain by binding (e.g., hybridizing) of poly(A) tails of mRNA transcripts. In some embodiments, fragmented DNA (e.g., tagmented DNA) can be captured by the capture domain of the capture probe by binding (e.g., hybridizing) a poly(A) tailed fragmented DNA (e.g., tagmented DNA). For example, after fragmenting the genomic DNA, gap filing (e.g., no strand displacement) polymerases and ligases can repair gaps and ligate breaks in the fragmented (e.g., tagmented DNA). In some embodiments, a sequence complementary to the capture domain can be introduced to the fragmented DNA. For example, a poly(A) tail can be added to the fragmented (e.g., tagmented) DNA, such that the capture domain (e.g., poly(T) sequence) of the capture probe can bind (e.g., hybridize) to the poly(A) tailed fragmented (e.g., tagmented DNA) (See, e.g., WO 2012/140224, which is incorporated herein by reference). In some embodiments, a poly(A) tail could be added to the fragmented DNA (e.g., tagmented) by a terminal transferase enzyme. In some embodiments, the terminal transferase enzyme could be terminal deoxynucleotidyl transferase (TDT), or a mutant variant thereof. TDT is an independent polymerase (e.g., it does not require a template molecule) that can catalyze the addition of deoxynucleotides to the 3' hydroxyl terminus of DNA molecules. Other template independent polymerases are known in the art. For example, Polymerase II, or a mutant variant thereof, may be used as a terminal transferase enzyme (See, e.g., Kent, T., Polymerase II is a robust terminal transferase that oscillates between three different mechanisms during end-joining, eLIFE, 5: e13740 doi: 10.7554/eLife.13740, (2016)). Other methods of introducing a poly(A) tail are known in the art. In some embodiments, a poly(A) tail can be introduced to the fragmented DNA (e.g., tagmented DNA) by a non-proof reading polymerase. In some embodiments, a poly(A) tail can be introduced to the fragmented DNA by a polynucleotide kinase.

In some embodiments, the TDT enzyme will generate fragments (e.g., tagments) with a 3' poly(A) tail, thereby mimicking the poly(A) tail of an mRNA. In some embodiments, the capture domain (e.g., poly(T) sequence) of the capture probe would interact with the poly(A) tail of the mRNA and the generated (e.g., synthesized) poly(A) tail added to the fragmented (e.g., tagmented) DNA, thereby simultaneously capturing the fragmented DNA (e.g., tagmented DNA) and the mRNA transcript. The generated (e.g., synthesized) poly(A) tail on the fragmented DNA (e.g., tagmented DNA) could be between about 10 nucleotides to about 30 nucleotides long. The generated (e.g., synthesized) poly(A) tail on the fragmented DNA (e.g., tagmented DNA) could be about 11, about 12, about 13, about 14, about 15, about 16, about 17, about 18, about 19, about 20, about 21, about 22, about 23, about 24, about 25, about 26, about 27, about 28, or about 29 nucleotides long.

Additionally and alternatively, instead of a sequential (e.g. two-step) reaction (e.g., gap filling and ligating, followed by a terminal transferase) the fragmented (e.g., tagmented) DNA can be contacted with a polymerase. For example, the polymerase may be a DNA polymerase that may perform an extension reaction on the fragmented (e.g., tagmented DNA. Any variety of DNA polymerases known in the art or described herein can be used. The extended products can be captured and processed (e.g., amplified and sequenced) by any method described herein.

Post-hybridization steps are identical as described in Ståahl P. L., et al., Visualization and analysis of gene expression in tissue sections by spatial transcriptomics *Science*, vol. 353, 6294, pp. 78-82 (2016), which in incorporated herein by reference).

qPCR and Analysis

Also provided herein are methods and materials for quantifying capture efficiency. In some embodiments, quantification of capture efficiency includes quantification of captured fragments (e.g., genomic DNA fragments, e.g., tagmented DNA fragments) from any of the spatial analysis methods described herein. In some embodiments, quantification includes PCR, qPCR, electrophoresis, capillary electrophoresis, fluorescence spectroscopy and/or UV spectrophotometry. In some embodiments, qPCR includes intercalating fluorescent dyes (e.g., SYBR green) and/or fluorescent labeled-probes (e.g., without limitation, Taqman probes or PrimeTime probes). In some embodiments, a NGS library quantification kit is used for quantification. For example, quantification can be performed using a KAPA library quantification kit (KAPA Biosystems), qPCR NGS Library Quantification Kit (Agilent), GeneRead Library Quant System (Qiagen), and/or PerfeCTa NGS Quantification Kit (Quantabio). In some embodiments that use qPCR for quantification, qPCR can include, without limitation, digital PCR, droplet digital (ddPCR), and ddPCR-Tail. In some embodiments that use electrophoresis for quantification, electrophoresis can include, without limitation, automated electrophoresis (e.g., TapeStation System, Agilent, and/or Bioanalzyer, Agilent) and capillary electrophoresis (e.g., Fragment Analyzer, Applied Biosystems). In some embodiments that use spectroscopy for quantification, the spectroscopy can include, without limitation, fluorescence spectroscopy (e.g., Qubit, Thermo Fisher). In some embodiments, NGS can be used to quantify capture efficiency.

In some embodiments, quantitative PCR (qPCR) is performed on the captured tagments. In some embodiments, the fragmented (e.g., tagmented) DNA is amplified, by any method described herein, before capture. For example, after capture of the fragmented DNA (e.g., tagmented DNA), ligation and strand displacement hybridization qPCR can be performed. In some embodiments, a DNA polymerase can be used to perform the strand displacement polymerization. Any suitable strand displacement polymerase known in the art can be used. In some embodiments, the DNA polymerase is DNA polymerase I. As exemplified in the Examples, DNA polymerase I can be incubated for strand displacement of the fragmented DNA (e.g., tagmented DNA) with reagents (e.g., BSA, dNTPs, buffer). In some embodiments, DNA polymerase I can be incubated with reagents on the substrate (e.g., on a feature e.g., a well) for about 30 minutes to about 2 hours. In some embodiments, DNA polymerase I can be incubated with reagents on the substrate for about 40 minutes, about 50 minutes, about 60 minutes, about 70 minutes, about 80 minutes, about 90 minutes, about 100 minutes, or about 110 minutes. In some embodiments, DNA polymerase I can be incubated with reagents on the substrate (e.g., on a feature e.g., a well) at about 35° C. to about 40° C. In some embodiments, DNA polymerase I can be incubated with reagents on the substrate at about 36° C., about 37° C., about 38° C., or about ° C., or about 39° C. In some embodiments, DNA polymerase I can be incubated with reagents on the substrate for about 1 hour at about 37° C.

After strand displacement hybridization is complete a qPCR reaction can be performed. As exemplified in the Examples below, the capture probes ligated to the fragmented DNA (e.g., tagmented DNA), can be released from the surface of the substrate (e.g., feature). In some embodiments, a solution (e.g., release mix) can be incubated with the substrate to release the capture probes from the surface of the substrate. The release mix can contain reagents (e.g., BSA, enzymes, buffer). Methods of releasing capture probes from the substrate (e.g., a feature) are described herein. In some embodiments, an enzyme can cleave the capture probe. In some embodiments, the enzyme can be USER (uracil-specific excision reagent) enzyme. In some embodiments, the USER enzyme can be incubated with reagents on the substrate (e.g., a feature e.g., a well) for about 30 minutes to about 2 hours. In some embodiments, the USER enzyme can be incubated with reagents on the substrate for about 40 minutes, about 50 minutes, about 60 minutes, about 70 minutes, about 80 minutes, about 90 minutes, about 100 minutes, or about 110 minutes. In some embodiments, the USER enzyme with reagents on the substrate (e.g., a feature e.g., a well) at about 35° C. to about 40° C. In some embodiments, the USER enzyme can be incubated with reagents on the substrate at about 36° C., about 37° C., about 38° C., or about 39° C. In some embodiments, the USER enzyme can be incubated with reagents on the substrate for about 1 hour at about 37° C.

After incubation with the USER enzyme, the samples (e.g., released capture probes ligated to fragmented DNA (e.g., tagmented DNA) in release mix, or a portion thereof) can be collected. In some embodiments, the sample volume can be reduced. Methods of reducing sample volume are known in the art and any suitable method can be used. In some embodiments, sample volume reduction can be performed with a Speed Vacuum (e.g., a SpeedVac). In some embodiments, the sample volume reduction can be about 50, about 55, about 60, about 65, about 70, about 75, about 80, about 85, or about 90% sample volume reduction. In some embodiments, the sample volume reduction can be about between 80% and 90% sample volume reduction. In some embodiments, the sample volume reduction can be about 81, about 82, about 83, about 84, about 85, about 86, about 87, about 88, or about 89% sample volume reduction. In some embodiments, the sample volume reduction can be about 85% (e.g., about 10 µL after sample volume reduction).

In some embodiments, a qPCR reaction can be performed with the reduced sample volume. As described herein, any suitable method of qPCR can be performed. As exemplified in the Examples, a 1×KAPA HiFI HotStart Ready, 1x EVA green, and primers can be used. Amplification can be performed according to known methods in the art. For example, amplification can be performed accordingly: 72° C. for 10 minutes, 98° C. for 3 minutes, followed by cycling at 98° C. for 20 seconds, 60° C. for 30 seconds and 72° C. for 30 seconds.

Figure 40:
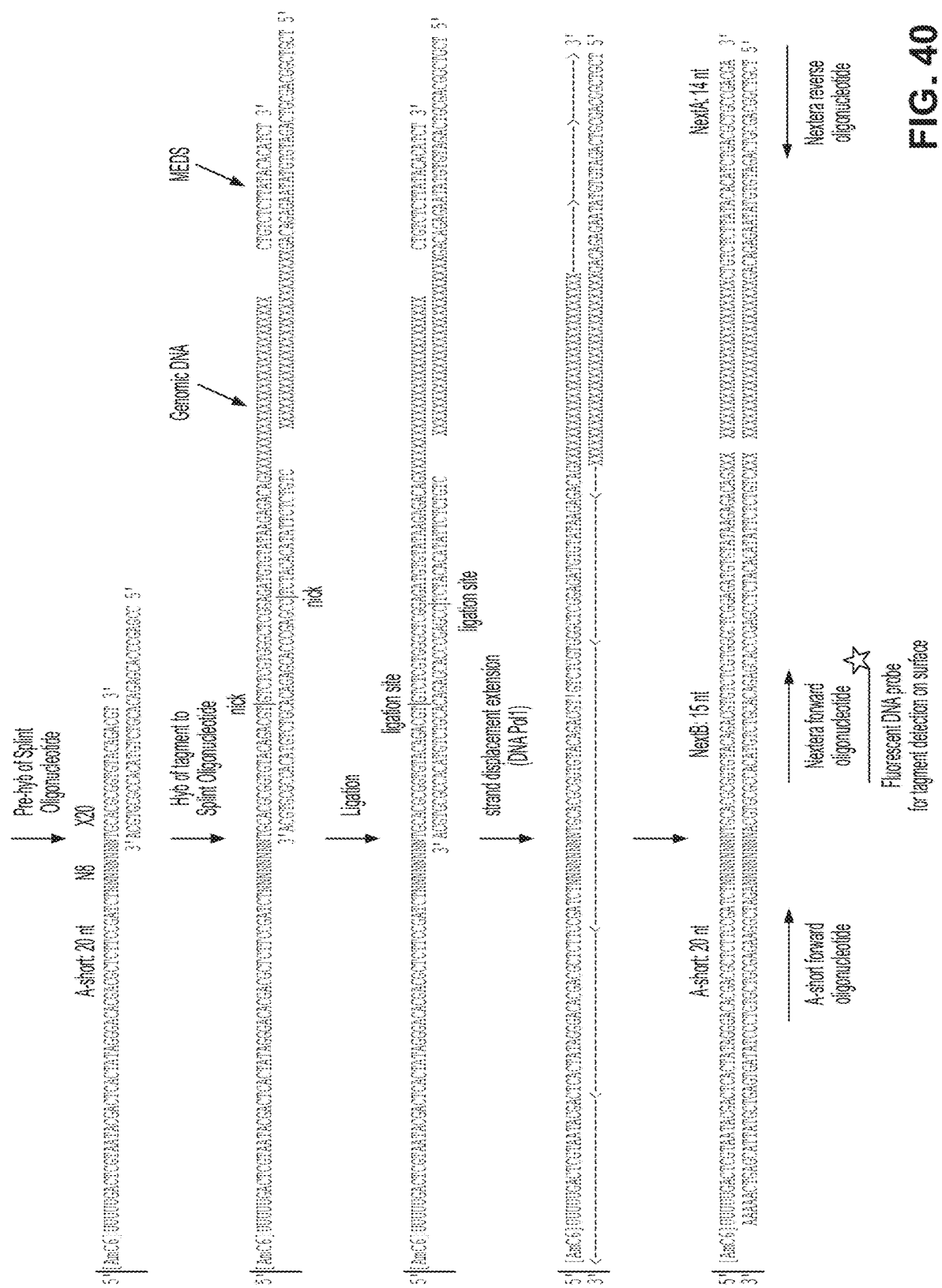
FIG. 40 shows a schematic representation of an exemplary oligonucleotide capture strategy and the respective sequences. Readout is performed by qPCR with oligonucleotides specific to tagments successfully ligated to the surface (e.g., A-short and Nextera reverse) or to all tagments (e.g., Nextera forward and Nextera reverse).

In some embodiments, one or more primer pairs can be used during the qPCR reaction. As described in the Examples herein, a primer pair can cover the ligated portion (e.g., ligation site where the capture probe and adapter sequence (e.g., attached sequence to the fragmented DNA e.g., tagmented DNA)). For example, a primer pair, (A-short forward and Nextera reverse (FIG. 40); SEQ ID NOs. 21 and 20, respectively) covers the ligated portion and the capture probe. An amplification product will only be detected if ligation, and not just hybridization has occurred. In some embodiments, a different primer pair (e.g., Nextera forward and Nextera reverse (FIG. 40); SEQ ID NOs. 16 and 20, respectively) can cover the fragmented DNA (e.g. tagmented DNA) only. In some embodiments, the primer pair that covers the fragmented DNA (e.g., tagmented DNA) only can be a control for ligation. In some embodiments, qPCR can be performed with any of labeled nucleotides described herein.

In some embodiments, the samples can be purified. In some embodiments, the samples can be purified according to Lundin et al., Increased Throughput by Parallelization of Library Preparation for Massive Sequencing, *PLOS ONE*, 5(4), doi.org/10.1371/journal.pone.0010029 (2010), which is herein incorporated by reference.

In some embodiments, the average length of the captured fragmented DNA (e.g., tagmented DNA) can be determined. In some embodiments, a bioanalyzer (e.g., a 2100 Bioanalyzer (Agilent)) can be used. Any suitable bioanalyzer known in the art can be used. In some embodiments, qPCR and bioanalyzer analysis can be done on whole genomes (e.g., purified fragmented DNA e.g., tagmented DNA). In some embodiments, the qPCR and bioanalyzer analysis can be done on an immobilized biological sample (e.g., a fixed biological sample). For example, the methods described herein (e.g., pre-permeabilization, permeabilization) can be performed to capture fragmented DNA (e.g., tagmented DNA) and to optimize qPCR and bioanalyzer analysis for different biological samples.

In some embodiments, after ligation, a surface based denaturation step can be performed. Put another way, after ligation of the fragmented DNA (e.g., tagmented DNA) to the capture probe, followed by strand displacement hybridization described herein (e.g., DNA Polymerase I), a surface based denaturation step can be performed in a parallel workstream. In some embodiments, a basic solution can perform the surface based denaturation. For example, the basic solution can denature the captured double stranded fragmented DNA (e.g., tagmented DNA), thus generating captured single stranded capture probes ligated to fragmented DNA (e.g., tagmented DNA). In some embodiments, the basic solution can be about 1M NaOH. Other basic solutions can be used in the methods described herein. In some embodiments, the basic solution can be applied for about 1 minute to about 1 hour. In some embodiments, the basic solution can be applied for about 10, about 20, about 30, about 40, or about 50 minutes. In some embodiments, the basic solution can be applied for about 1 to about 20 minutes. In some embodiments, the basic solution about be applied for about 2, about 3, about 4, about 5, about 6, about 7, about 8, about 9, about 10, about 11, about 12, about 13, about 14 about 15, about 16, about 17, about 18, or about 19 minutes. In some embodiments, the basic solution can be applied at a temperature of between about 30° C. to about 40° C. In some embodiments, the basic solution can be applied at about 31° C., about 32° C., about 33° C., about 34° C., about 35° C., about 36° C., about 37° C., about 38° C., or about 39° C. In some embodiments, the basic solution can be applied for about 10 minutes at about 37° C.

In some embodiments, the denaturation step can expose the fragmented DNA (e.g., tagmented DNA) to hybridization by a probe. In some embodiments, the probe can be an oligonucleotide probe. In some embodiments, the oligonucleotide probe can have a detectable label (e.g., any of the variety of detectable labels described herein). In some embodiments, the detectable label can be Cy5. In some embodiments, the oligonucleotide probe can be Cy5 labeled. In some embodiments, the Cy5 labeled oligonucleotide probe can hybridize to a complementary sequence in the fragmented DNA (e.g., tagmented DNA). In some embodiments, the Cy5 labeled oligonucleotide can hybridize to the sequence attached (e.g., Nextera adapter, e.g., first adapter or second adapter) to the fragmented DNA (e.g., tagmented DNA). In some embodiments, the Cy5 label can be detected. For example, detecting the Cy5 label in the oligonucleotide probe can reveal the spatial location of the DNA tagments.

In some embodiments, the biological sample can be stained (e.g., hematoxylin and eosin stain). Methods of staining a biological sample are known in the art and described herein. In some embodiments, the biological sample can be imaged.

EMBODIMENTS

Accordingly, in one embodiment the present invention provides a method for spatially tagging nucleic acids of a biological specimen comprising:
  (a) providing a solid substrate on which multiple species of capture probes are immobilized such that each species occupies a distinct position on the solid substrate, wherein said capture probes are for an extension or ligation reaction and wherein each species of said capture probes comprise a nucleic acid molecule comprising:
    (i) a positional domain that corresponds to the position of the capture probe on the solid substrate, and
    (iii) a capture domain;
  (b) contacting said solid substrate with a biological specimen;
  (c) permeabilizing the biological specimen under conditions sufficient to make DNA in the biological specimen accessible to a transposase enzyme;
  (d) fragmenting the DNA in said biological specimen with a transposase enzyme;
  (e) hybridizing the fragmented DNA present in the biological specimen from (d) to the capture domains of the capture probes; and
  (f) extending the capture probes:
    (i) using the DNA hybridized to said capture probes as extension or ligation templates to produce extended probes that comprise the sequences of the positional domains and sequences complementary to the DNA that hybridizes to the capture domains of the capture probes; or
    (ii) using the capture probes as ligation templates to produce extended probes that comprise the sequence of the positional domains or a complement thereof and sequences of the DNA that hybridize to the capture domains of the capture probes, thereby spatially tagging the DNA of the biological specimen.

As discussed in more detail below, the method of the invention may comprise an additional step of analysing the extended probes. In this respect, it is evident that the combination of spatial tagging of the nucleic acids from a biological specimen and subsequent analysis of said tagged nucleic acids facilitates the localised detection of a nucleic acid in a biological specimen, e.g. tissue sample. Thus, in one embodiment, the method of the invention may be used for determining and/or analysing all of the genome or the genome and transcriptome of a biological specimen. However, the method is not limited to this and encompasses determining and/or analysing all or part of the genome or all of part of the genome and transcriptome. Thus, the method may involve determining and/or analysing a part or subset of the genome or genome and transcriptome, e.g. a genome corresponding to a subset of genes, e.g. a set of particular genes, for example related to a particular disease or condition, tissue type etc.

In other embodiments, the invention provides a method for spatially tagging nucleic acids of a biological specimen comprising:
  (a) providing a solid substrate comprising a plurality of capture probes attached to the solid substrate, wherein a capture probe of the plurality of capture probes comprises a capture domain and a position domain, wherein the position domain corresponds to a distinct position on the solid substrate;

(b) contacting said solid substrate with a biological specimen;

(c) permeabilizing the biological specimen under conditions sufficient to make DNA in the biological specimen accessible to a transposase enzyme;

(d) fragmenting the DNA in said biological specimen with the transposase enzyme;

(e) contacting the fragmented DNA present in the biological specimen from (d) to the capture domains of the capture probes; and (f) extending the capture probes, thereby spatially tagging the DNA of the biological specimen.

In some embodiments, step (e) of contacting the fragmented DNA comprises (i) using the DNA contacted with said capture probes as extension or ligation templates to produce extended probes that comprise the sequences of the positional domains and sequences complementary to the DNA that hybridizes to the capture domains of the capture probes, (ii) using the capture probes as ligation templates to produce extended probes that comprise the sequence of the positional domains or a complement thereof and sequences of the DNA that hybridizes to the capture domains of the capture probes.

Viewed from another aspect, the method steps set out above can be seen as providing a method of obtaining a spatially defined genome or genome and transcriptome, and in particular the spatially defined global genome or genome and transcriptome of a biological specimen, e.g. tissue sample.

Alternatively viewed, the method of the invention may be seen as a method for localised or spatial detection of nucleic acid, whether DNA or both DNA and RNA, in a biological specimen, e.g. tissue sample, or for localised or spatial determination and/or analysis of nucleic acid (DNA or both DNA and RNA) in a tissue sample. In particular, the method may be used for the localised or spatial detection or determination and/or analysis of genomic variation or genomic variation and gene expression in a tissue sample. The localised/spatial detection/determination/analysis means that the DNA or both DNA and RNA may be localised to its native position or location within a cell or tissue in the tissue sample. Thus for example, the DNA or both DNA and RNA may be localised to a cell or group of cells, or type of cells in the sample, or to particular regions of areas within a tissue sample. The native location or position of the DNA or DNA and RNA (or in other words, the location or position of the DNA or DNA and RNA in the tissue sample), e.g. a genomic locus or genomic locus and expressed gene, may be determined.

Thus, in some embodiments, the invention provides a method for localised detection of nucleic acid in a biological specimen comprising:

(a) providing a solid substrate on which multiple species of capture probes are immobilized such that each species occupies a distinct position on the solid substrate, wherein said capture probes are for an extension or ligation reaction and wherein each species of said capture probes comprise a nucleic acid molecule comprising:

(i) a positional domain that corresponds to the position of the capture probe on the solid substrate, and (ii) a capture domain;

(b) contacting said solid substrate with a biological specimen;

(c) permeabilizing the biological specimen under conditions sufficient to make DNA in the biological specimen accessible to a transposase enzyme;

(d) fragmenting the DNA in said biological specimen with the transposase enzyme;

(e) hybridizing the fragmented DNA present in the biological specimen from (d) to the capture domains of the capture probes; and (f) extending the capture probes:

(i) using the DNA hybridized to said capture probes as extension or ligation templates to produce extended probes that comprise the sequences of the positional domains and sequences complementary to the DNA that hybridizes to the capture domains of the capture probes; or (ii) using the capture probes as ligation templates to produce extended probes that comprise sequences of the positional domains or complements thereof and sequences of the DNA that hybridizes to the capture domains of the capture probes, thereby spatially tagging the DNA of the biological specimen; and (g) analysing the extended probes of (f), i.e. analysing the spatially tagged nucleic acids of the biological specimen.

The method may further comprise a step of releasing the extended probes of (f) from the surface of the solid substrate, i.e. extended probes that comprise the sequences of the positional domains and sequences complementary to the nucleic acids that hybridize to the capture domains of the capture probes or extended probes that comprise sequences of positional domains or complements thereof and sequences of the DNA that hybridizes to the capture domains of the capture probes. As discussed in more detail below, the extended probes may be released from the surface of the substrate by any suitable means. In some embodiments, the extended probes may be released prior to the analysis step (step (g)), but this is not essential. For instance, the extended probes may be released from the surface of the substrate as part of the analysis step.

Any method of nucleic acid analysis may be used in the analysis step (step (g)). Typically this may involve sequencing, i.e. analysing the sequence of the extended probes, but it is not necessary to perform an actual sequence determination. For example sequence-specific methods of analysis may be used. For example a sequence-specific amplification reaction may be performed, for example using primers which are specific for the positional domain and/or for a specific target sequence, e.g. a particular target DNA to be detected (i.e. corresponding to a particular cDNA/RNA and/or gene, intergenic or intragenic region etc.). An exemplary analysis method is a sequence-specific PCR reaction.

The sequence analysis information obtained in step (g) may be used to obtain spatial information as to the DNA and/or RNA in the biological specimen, e.g. tissue sample. In other words the sequence analysis information may provide information as to the location of the DNA and/or RNA in the biological specimen, e.g. tissue sample. This spatial information may be derived from the nature of the sequence analysis information determined, for example it may reveal the presence of a particular DNA and/or RNA which may itself be spatially informative in the context of the biological specimen, e.g. tissue sample, used, and/or the spatial information (e.g. spatial localisation) may be derived from the position of the biological specimen, e.g. tissue sample, on the solid substrate, e.g. array, coupled with the sequencing information. Thus, the method may involve simply correlating the sequence analysis information to a position in the biological specimen, e.g. tissue sample, e.g. by virtue of the positional tag and its correlation to a position in the biological specimen, e.g. tissue sample. However, in some embodiments, spatial information may conveniently be obtained by correlating the sequence analysis data to an image of the biological specimen, e.g. tissue sample. Accordingly, in a preferred embodiment the method also includes a step of:
  (h) correlating said sequence analysis information with an image of said biological specimen, wherein the biological specimen is imaged after step (b). In some embodiments, the biological specimen is imaged before step (c) or (d).

It will be seen therefore that the array of the present invention may be used to capture DNA (e.g. genomic DNA) or both DNA and RNA (e.g. mRNA) of a biological specimen, e.g. tissue sample, that is contacted with said solid substrate, e.g. array. The methods of the invention may thus be considered as methods of quantifying the spatial variation of one or more genes in a tissue sample (e.g. copy number variation). Expressed another way, the methods of the present invention may be used to detect the spatial variation of one or more genes in a biological specimen, e.g. tissue sample. In yet another way, the methods of the present invention may be used to determine simultaneously the variation of one or more genes at one or more positions within a biological specimen, e.g. tissue sample. Still further, the methods may be seen as methods for partial or global genome or genome and transcriptome analysis of a biological specimen, e.g. tissue sample, with two-dimensional spatial resolution.

It will be evident that when the method of the invention is used to analyse DNA or both DNA and RNA in a tissue section of a biological specimen to yield a two-dimensional genome or genome and transcriptome, data from analyses of other tissue sections from the same biological specimen (tissue sample), particularly adjacent tissue sections, may be compiled to provide a three-dimensional genome or genome and transcriptome of the biological specimen.

Thus, at its broadest, the present invention may be viewed as the use of tagmentation in an immobilized biological specimen (e.g. a tissue section on a solid substrate) to facilitate the spatial tagging of DNA in the biological specimen, preferably using a method as defined herein.

In another aspect, the invention provides a kit for use in the methods described herein. The kit may comprise any two or more of:
  (i) a solid substrate (e.g. array) on which multiple species of capture probes are immobilized as defined above;
  (ii) means for permeabilizing a biological specimen to make it accessible to a transposase enzyme, particularly enzymatic or chemical means as defined herein;
  (iii) means for tagmenting DNA in a biological specimen, particularly a transposome as defined herein;
  (iv) means for extending the capture probes, such as a reverse transcriptase, DNA polymerase, DNA ligase or a mixture thereof as defined above; and
  (v) means for releasing the extended probes from the solid substrate, particularly a cleavage enzyme or mixture thereof as defined above.

In some embodiments, the kit may additionally or alternatively comprise components for use with means defined above, e.g. buffers and substrates (e.g. dNTPs) suitable for the enzymes defined above. In some embodiments, the kit may comprise means for generating second strand DNA molecules (e.g. helper probes, primers, adaptors etc) and/or for amplifying the extended probes (e.g. DNA polymerases, primers, substrates, buffers etc.).

In some embodiments, the kit may comprise components for producing the solid substrate. For instance, the solid substrate may be provided with surface probes and the kit may comprise reagents for producing the capture probes of the invention, e.g. capture domain oligonucleotides. In some embodiments, the kit comprises a solid substrate and means for generating capture probes using bridge amplification as described above. In some embodiments, the kit may comprise means for generating a bead array for use in the methods of the invention as described above, e.g. a solid substrate on which beads may be immobilized and beads on which capture probes of the invention are immobilized. In some embodiments, the kit may comprise means for decoding an array, e.g. decoder probes as described above.

In some embodiments, the kit may comprise means for fixing and/or staining the biological specimen.

In some embodiments, the kit may comprise means for purifying extended probes and/or their amplicons that have been released from the surface of the substrate.

"Tagmentation" refers to a process of transposase-mediated fragmentation and tagging of DNA. Tagmentation typically involves the modification of DNA by a transposome complex and results in the formation of "tagments", or tagged DNA fragments.

A "transposome" or "transposome complex" is a complex of a transposase enzyme and DNA which comprises a transposon end sequence (also known as "transposase recognition sequence" or "mosaic end" (ME)).

The DNA that forms a complex with a transposase enzyme (i.e. the DNA of a transposome) contains a partially double stranded (e.g. DNA) oligonucleotide, wherein each strand contains an ME specific for the transposase, which forms the double stranded part of the oligonucleotide. The single-stranded portion of the oligonucleotide is at the 5' end of the oligonucleotide (i.e. forms a 5' overhang) and may comprise a functional sequence (e.g. a capture probe binding site). Thus, the partially double stranded oligonucleotide in the transposome may be viewed as an adaptor that can be ligated to the fragmented DNA. Thus, alternatively viewed the transposome comprises a transposase enzyme complexed with an adaptor comprising transposon end sequences (or mosaic ends) and tagmentation results in the simultaneous fragmentation of DNA and ligation of the adapters to the 5' ends of both strands of DNA duplex fragments.

Thus, alternatively viewed step (d) may be viewed as tagmenting the DNA of the biological specimen comprising contacting the biological specimen with a transposome, i.e. under conditions sufficient to result in tagmentation of the DNA.

It will be evident that tagmentation can be used to provide fragmented DNA with a binding domain capable of binding (hybridizing) to the capture domain of the capture probes of the invention. Moreover, the binding domain may be provided directly or indirectly.

Thus, in some embodiments, step (d) may be viewed as fragmenting the DNA of the biological specimen and providing the DNA fragments with a binding domain capable of binding (hybridizing) to the capture domain of the capture probes of the invention.

For example, in some embodiments, the adaptors of the transposome comprise a functional domain or sequence that may be configured to couple to all or a portion of a capture domain. The functional domain or sequence which may be a binding domain capable of binding (hybridizing) to the capture domain of the capture probes of the invention (e.g. a homopolymeric sequence, e.g. poly-A sequence, as defined below). In other words, the single-stranded portion of the adaptor (5' overhang) comprises a binding domain capable of binding to the capture domain of the capture probes of the invention. Accordingly, tagmentation results fragmentation of DNA of the biological specimen and ligation of the binding domain capable of binding to the capture domain of the capture probes of the invention to the DNA of the biological specimen, i.e. providing the DNA of the biological specimen with a binding domain directly.

In one embodiment, the functional domain or sequence is configured to couple to or attach to a portion of the capture domain through click chemistry. As used herein, the term "click chemistry," generally refers to reactions that are modular, wide in scope, give high yields, generate only inoffensive byproducts, such as those that can be removed by nonchromatographic methods, and are stereospecific (but not necessarily enantioselective). See, e.g., Angew. Chem. Int. Ed., 2001, 40(11):2004-2021, which is entirely incorporated herein by reference for all purposes. In some cases, click chemistry can describe pairs of functional groups that can selectively react with each other in mild, aqueous conditions.

An example of click chemistry reaction can be the Huisgen 1,3-dipolar cycloaddition of an azide and an alkyne, i.e., Copper-catalysed reaction of an azide with an alkyne to form a 5-membered heteroatom ring called 1,2,3-triazole. The reaction can also be known as a Cu(I)-Catalyzed Azide-Alkyne Cycloaddition (CuAAC), a Cu(I) click chemistry or a Cu+ click chemistry. Catalyst for the click chemistry can be Cu(I) salts, or Cu(I) salts made in situ by reducing Cu(II) reagent to Cu(I) reagent with a reducing reagent (Pharm Res. 2008, 25(10): 2216-2230). Known Cu(II) reagents for the click chemistry can include, but are not limited to, Cu(II)-(TBTA) complex and Cu(II) (THPTA) complex. TBTA, which is tris-[(1-benzyl-1H-1,2,3-triazol-4-yl)methyl] amine, also known as tris-(benzyltriazolylmethyl)amine, can be a stabilizing ligand for Cu(I) salts. THPTA, which is tris-(hydroxypropyltriazolylmethyl)amine, can be another example of stabilizing agent for Cu(I). Other conditions can also be accomplished to construct the 1,2,3-triazole ring from an azide and an alkyne using copper-free click chemistry, such as by the Strain-promoted Azide-Alkyne Click chemistry reaction (SPAAC, see, e.g., Chem. Commun., 2011, 47:6257-6259 and Nature, 2015, 519(7544):486-90), each of which is entirely incorporated herein by reference for all purposes.

Thus, in some embodiments, step (d) may be viewed as contacting the biological specimen with a transposase complexed with an adaptor comprising transposon end (e.g. mosaic end) sequences (i.e. a transposome) and a nucleotide sequence that is complementary to the capture domain of the capture probes and wherein the transposase ligates the adaptor to the fragmented DNA, i.e. the 5' ends of the fragmented DNA.

In other embodiments, step (d) may be viewed as contacting the biological specimen with a transposase complexed with an adaptor comprising transposon end (e.g. mosaic end) sequences (i.e. a transposome) and a click chemistry moiety(ies) that is compatible with another click chemistry moiety(ies) on the capture domain of the capture probes and wherein the transposase ligates the adaptor to the fragmented DNA, i.e., the 5' ends of the fragmented DNA.

In some embodiments, the adaptor of the transposome comprises (i) a domain capable of (i.e. suitable for) facilitating the introduction of a binding domain capable of binding (hybridizing) to the capture domain of the capture probes of the invention or (ii) a domain capable of (i.e. suitable for) facilitating the introduction of a click chemistry moiety(ies) configured to interact with another click chemistry moiety(ies) on the capture domain of the capture probes of the invention.

Thus, in some embodiments, step (d) may be viewed as fragmenting the DNA of the biological specimen and providing the DNA fragments with a domain capable of (i.e. suitable for) facilitating the introduction of a binding domain capable of binding (hybridizing) to the capture domain of the capture probes of the invention.

In a representative embodiment, the adaptor of the transposome may comprise a domain with a nucleotide sequence that templates the ligation of a universal adaptor to the tagmented DNA. The universal adaptor comprises a binding domain capable of binding (hybridizing) to the capture domain of the capture probes of the invention. Thus, in some embodiments, tagmentation provides the DNA of the biological specimen with a binding domain indirectly.

In another representative embodiment, the adaptor of the transposome may comprise a domain with a nucleotide sequence that is a substrate in a ligation reaction that introduces a universal adaptor to the tagmented DNA, e.g. a domain to which a universal adaptor may bind. For instance, the universal adaptor may be a partially double-stranded oligonucleotide having a first strand comprising a single-stranded portion containing domain that binds to the adaptor sequence ligated to the fragmented (i.e. tagmented) DNA and a second strand comprising a domain that binds to the first strand and a domain capable of binding (hybridizing) to the capture domain of the capture probes of the invention. Ligation of the universal adaptor to the fragmented (i.e. tagmented) DNA provides the tagmented DNA with a domain that binds to the capture domain of the capture probes of the invention. Thus, in some embodiments, tagmentation provides the DNA of the biological specimen with a binding domain indirectly.

As tagmentation results in DNA that comprises gaps between the 3' ends of the DNA of the biological specimen and the 5' ends at the double stranded portion of the adaptors (i.e. the 5' ends of the adaptors containing the MEs are not ligated to the 3' ends of the fragmented DNA of the biological specimen), providing the tagmented DNA with a binding domain capable of binding (hybridizing) to the capture domain of the capture probes of the invention may require a step of "gap filling" the tagmented DNA.

Gap filling may be achieved using a suitable polymerase enzyme, i.e. a DNA polymerase (e.g. selected from the list below). In this respect, the 3' ends of the tagmented DNA are extended using the complementary strands of the tagmented DNA as templates. Once the gaps have been filled, the 3' ends of the tagmented DNA are joined to the 5' ends of the adaptors by a ligation step, using a suitable ligase enzyme (e.g. selected from the list below).

It will be understood in this regard that the 5' end of adaptors containing the ME is phosphorylated to enable ligation to take place. The transposome may comprise an adaptor in which one or both 5' ends are phosphorylated. In embodiments where the transposome comprises an adaptor in which the 5' end of adaptor containing the ME is not phosphorylated, the gap filling process may comprise a further step of phosphorylating the 5' end of the adaptor, e.g. using a kinase enzyme, such as T4 polynucleotide kinase.

In some embodiments, the 3' ends of the tagmented DNA may be extended using a DNA polymerase with strand displacement activity using the complementary strands of the tagmented DNA as templates. This results in the displacement of the strands of the adaptors that are not ligated to the fragmented DNA and the generation of fully double stranded DNA molecules. These molecules may be provided with a domain capable of binding to the capture domain of the capture probes by any suitable means, e.g. ligation of adaptors, "tailing" with a terminal transferase enzyme etc.

Thus, in some embodiments, the method comprises a step of extending the 3' ends of the fragmented (i.e. tagmented) DNA using a polymerase with strand displacement activity to produce fully double stranded DNA molecules.

In some embodiments, the fully double stranded DNA molecules may be provided with a binding domain capable of binding to the capture domain of the capture probes. In some embodiments, a binding domain may be provided by ligation of adaptors to the double stranded DNA molecules or via the use of a terminal transferase active enzyme to incorporate a polynucleotide tail, e.g. homopolymeric sequence (e.g. a poly-A tail), at the 3' ends of the double stranded DNA molecules.

Thus, in preferred embodiments, step (d) results, directly or indirectly, in a biological specimen containing fragmented DNA (i.e. tagmented DNA) comprising a domain that binds to the capture domain of the capture probes of the invention. It will be evident from the disclosures in WO 2012/140224 (herein incorporated by reference) that the fragmented DNA may be spatially tagged using various means, according to step (f). Representative embodiments of step (f) are described in more detail below.

A "transposase" is an enzyme that binds to the end of a transposon and catalyzes its movement to another part of the genome by a cut and paste mechanism or a replicative transposition mechanism.

Transposase Tn5 is a member of the RNase superfamily of proteins. The Tn5 transposon is a composite transposon in which two near-identical insertion sequences (IS50L and IS50R) flank three antibiotic resistance genes. Each IS50 contains two inverted 19-bp end sequences (ESs), an outside end (OE) and an inside end (IE).

A hyperactive variant of the Tn5 transposase is capable of mediating the fragmentation of double-stranded DNA and ligation of synthetic oligonucleotides (adaptors) at both 5' ends of the DNA in a reaction that takes about 5 minutes. However, as wild-type end sequences have a relatively low activity, they are preferably replaced in vitro by hyperactive mosaic end (ME) sequences. A complex of the Tn5 transposase with 19-bp ME is thus all that is necessary for transposition to occur, provided that the intervening DNA is long enough to bring two of these sequences close together to form an active Tn5 transposase homodimer.

Methods, compositions, and kits for treating nucleic acid, and in particular, methods and compositions for fragmenting and tagging DNA using transposon compositions are described in detail in US2010/0120098 and US2011/0287435, which are hereby incorporated by reference in their entireties.

Thus, any transposase enzyme with tagmentation activity, i.e. capable of fragmenting DNA and ligating oligonucleotides to the ends of the fragmented DNA, may be used in the methods of the present invention. In some embodiments, the transposase is a Tn5 or Mu transposase or a functional variant or derivative thereof.

Thus, in some embodiments, the transposase, e.g. Tn5 or Mu or functional variant or derivative thereof, comprises an amino acid sequence with at least 80% sequence identity to a sequence as set forth in SEQ ID NOs: 1 or 2. In some embodiments, the functional variant or derivative is a hyperactive variant or derivative, i.e. a variant or derivative with increased transposase activity relative to the naturally-occurring protein.

Preferably said polypeptide sequence is at least 90, 91, 92, 93, 94, 95, 96, 97, 98 or 99% identical to the sequence to which it is compared.

Sequence identity of polypeptide molecules may be determined by, e.g. using the SWISS-PROT protein sequence databank using FASTA pep-cmp with a variable pamfactor, and gap creation penalty set at 12.0 and gap extension penalty set at 4.0, and a window of 2 amino acids. Preferably said comparison is made over the full length of the sequence, but may be made over a smaller window of comparison, e.g. less than 600, 500, 400, 300, 200, 100 or 50 contiguous amino acids.

Preferably such sequence identity related polypeptides are functionally equivalent to the one of the polypeptides set forth in SEQ ID NOs: 1 or 2. As such, the polypeptides with a sequence as set forth in SEQ ID NOs: 1 or 2 may be modified without affecting the sequence of the polypeptide.

Modifications that do not affect the sequence of the polypeptide include, e.g. chemical modification, including by deglycosylation or glycosylation. Such polypeptides may be prepared by post-synthesis/isolation modification of the polypeptide without affecting functionality, e.g. certain glycosylation, methylation etc. of particular residues.

As referred to herein, to achieve "functional equivalence" the polypeptide may show some increased or reduced efficacy in transposase (e.g. tagmentation) activity relative to the parent molecule (i.e. the molecule from which it was derived, e.g. by amino acid substitution), but preferably is as efficient or is more efficient. Thus, functional equivalence relates to a polypeptide which has transposase activity capable of fragmenting DNA and ligating oligonucleotides to the DNA fragments. This may be tested by comparison of the transposase activity of the derivative polypeptide relative to the polypeptide from which it is derived in a quantitative manner. The derivative is preferably at least 30, 50, 70 or 90% as effective as the parent polypeptide in the methods of the invention. As noted above, in some preferred embodiments, the polypeptide is hyperactive relative to the parent polypeptide exemplified above, i.e. is at least about 110, 120, 130, 140, 150, 200, 250 or 300% as effective as the parent polypeptide in the methods of the invention.

Functionally-equivalent proteins which are related to or derived from the naturally-occurring protein, may be obtained by modifying the native amino acid sequence by single or multiple amino acid substitution, addition and/or deletion (providing they satisfy the above-mentioned sequence identity requirements), but without destroying the molecule's function. Preferably the native sequence has less than 20 substitutions, additions or deletions, e.g. less than 10, 5, 4, 3, 2, or 1 such modifications. Such proteins are encoded by "functionally-equivalent nucleic acid molecules" which are generated by appropriate substitution, addition and/or deletion of one or more bases. As noted above, the inventors have determined that typical detergent-based permeabilization conditions are not sufficient to enable a transposase (e.g. a transposome) to access its substrate, i.e. DNA (e.g. genomic DNA), when the biological specimen (e.g. tissue section) is immobilized on a solid substrate, e.g. array. Accordingly, the step of "permeabilizing the biological specimen under conditions sufficient to make DNA in the biological specimen accessible to a transposase enzyme" refers to the use of any conditions that enable a transposase to access its substrate, i.e. DNA (e.g. genomic DNA), when the biological specimen (e.g. tissue section) is immobilized on a solid substrate, e.g. array.

It will be evident that biological specimens, e.g. tissue samples, from different sources may require different treatments to make them accessible to the transposase (i.e. to enable the transposase to access and act on its substrate). If the tissue sample is not permeabilized sufficiently the transposase will not interact with the DNA of the biological specimen and the amount of tagmentation may be too low to enable further analysis. Conversely, if the biological specimen, e.g. tissue sample, is too permeable, tagmented DNA (and other nucleic acids, e.g. RNA) may diffuse away from its origin in the biological specimen, e.g. tissue sample, i.e. the tagments (and other nucleic acids, e.g. RNA) captured by the capture probes may not correlate accurately with their original spatial distribution in the biological specimen, e.g. tissue sample. Hence, there must be a balance between permeabilizing the biological specimen, e.g. tissue sample, enough to obtain enable efficient interaction between the transposase and DNA whilst maintaining the spatial resolution of the nucleic acid distribution in the biological specimen, e.g. tissue sample.

Thus, the permeabilization conditions in step (c) may be adapted to the characteristics of the biological specimen. For instance, the enzyme(s) and/or chemicals (e.g. buffer(s)) used in step (c) may be selected according to the tissue type.

Moreover, the inventors have determined that the permeabilization conditions in step (c) may be adapted to enable uniform DNA fragmentation to enable capture of DNA tagments regardless of chromatin accessibility or to yield fragments with a pronounced nucleosomal pattern. Thus, the permeabilization conditions in step (c) may be selected according to the level of fragmentation required or the DNA molecules of interest, i.e. the DNA molecules to be spatially tagged according to the methods of the invention.

Representative permeabilization conditions are described below. It will be evident that these representative conditions may be modified or adapted to suit the biological specimen, transposase and DNA fragmentation, and such modifications are within the purview of the skilled person.

The permeabilization conditions in step (c) may comprise subjecting the biological specimen to chemical and/or enzymatic permeabilization conditions.

In some embodiments, the chemical permeabilization conditions comprise contacting the biological specimen with an alkaline solution, e.g. a buffered solution with a pH of about 8.0-11.0, such as about 8.5-10.5 or about 9.0-10.0, e.g. about 9.5. In some embodiments, the buffer is a glycine-KOH buffer.

As shown in the Examples, the inventors have found that permeabilization may be performed using pepsin. Notably, the level of DNA fragmentation upon treatment with a transposase can be controlled by changing the pepsin permeabilization conditions. For instance, permeabilization using pepsin in the presence of 100 mM HCl (i.e. having a pH of about 1.0) induces uniform DNA fragmentation and may be used to capture DNA tagments regardless of chromatin accessibility. Alternatively, permeabilization using pepsin in the presence of 0.5M acetic acid (i.e. having a pH of about 2.5) provides partial recovery of the nucleosomal pattern typically associated with accessible chromatin.

Thus, in some embodiments, the permeabilization conditions in step (c) may comprise contacting the biological specimen with an acidic solution comprising a protease enzyme.

In some embodiments, the permeabilization conditions in step (c) may comprise contacting the biological specimen with a reaction mixture (e.g. solution) comprising an aspartyl protease (e.g. pepsin) in an acidic buffer, e.g. a buffer with a pH of about 4.0 or less, such as about 3.0 or less, e.g. about 0.5-3.0 or about 1.0-2.5.

In a preferred embodiment, the aspartyl protease is a pepsin enzyme, pepsin-like enzyme or a functional equivalent thereof. Thus, any enzyme or combination of enzymes in the enzyme commission number 3.4.23.1 may be used in the present invention.

Thus, in some embodiments, the pepsin enzyme is selected from the following group, which refers to the UniProtKB/Swiss-Prot accession numbers: P03954/PEPA1_MACFU; P28712/PEPA1_RABIT; P27677/PEPA2_MACFU; P27821/PEPA2_RABIT; PODJD8/PEPA3_HUMAN; P27822/PEPA3_RABIT; PODJD7/PEPA4_HUMAN; P27678/PEPA4_MACFU; P28713/PEPA4_RABIT; PODJD9/PEPA5_HUMAN; Q9D106/PEPA5_MOUSE; P27823/PEPAF_RABIT; P00792/PEPA_BOVIN; Q9N2D4/PEPA_CALJA; Q9GMY6/PEPA_CANLF; P00793/PEPA_CHICK; P11489/PEPA_MACMU; P00791/PEPA_PIG; Q9GMY7/PEPA_RHIFE; Q9GMY8/PEPA_SORUN; P81497/PEPA_SUNMU; P13636/PEPA_URSTH and functional variants and derivatives thereof or a combination thereof.

In some embodiments, the pepsin enzyme is selected from following group, which refers to the UniProtKB/Swiss-Prot accession numbers: P00791/PEPA_PIG; P00792/PEPA_BOVIN and functional variants and derivatives thereof or a combination thereof.

By a "functional variant or derivative" is meant that a mutant or modified protease (i.e. containing one or more amino acid substitutions, deletions or additions relative to the protease from which is was derived), which may show some reduced protease activity relative to the activity of the protease from which it is derived in conditions that are optimum for the enzyme, e.g. in the buffer, salt and temperature conditions recommended by the manufacturer. Thus, a variant or derivative protease may be considered to be functional if it has at least 50%, e.g. at least 60, 70, 80, 85, 90, 95, 96, 97, 98, 99 or 100%, activity relative to the activity of the protease from which it was derived in conditions that are optimum for the enzyme.

Thus, in some embodiments, the pepsin enzyme or functional variant or derivative thereof, comprises an amino acid sequence with at least 80% sequence identity to a sequence as set forth in SEQ ID NOs: 3 or 4.

Preferably said polypeptide sequence is at least 90, 91, 92, 93, 94, 95, 96, 97, 98 or 99% identical to the sequence to which it is compared.

The inventors have alternatively found that permeabilization may be performed using collagenase, which provides efficient genome accessibility to the transposase while preserving nuclear integrity. Notably, permeabilization with collagenase yields pronounced nucleosomal pattern that is typically associated with chromatin tagmentation. Collagenases are zinc endopeptidases and are typically inhibited by both EDTA and EGTA. Collagenases may be isolated from *Clostridium histolyticum*.

Thus, in some preferred embodiments, step (c) comprises contacting the biological specimen with a zinc endopeptidase (e.g. collagenase) under conditions suitable for proteolytic (e.g. collagenase) activity, e.g. in a buffered solution with a pH of about 7.0-8.0, e.g. about 7.4.

Thus, in some embodiments, the biological specimen is contacted with a zinc endopeptidase (e.g. collagenase) in the absence of a chelator of divalent cations, such as EDTA or EGTA. In some embodiments, it may be useful to stop the zinc endopeptidase (e.g. collagenase) permeabilization step by contacting the biological specimen with a chelator of divalent cations, such as EDTA or EGTA.

In a preferred embodiment, the zinc endopeptidase is a collagenase enzyme, collagenase-like enzyme or a functional equivalent thereof. Thus, any enzyme or combination of enzymes in the enzyme commission number 3.4.23.3 may be used in the present invention.

Thus, in some embodiments, the collagenase is selected from the following group, which refers to the UniProtKB/Swiss-Prot accession numbers: P43153/COLA_CLOPE; P43154/COLA_VIBAL; Q9KRJ0/COLA_VIBCH; Q56696/COLA_VIBPA; Q8D4Y9/COLA_VIBVU; Q9X721/COLG_HATHI; Q46085/COLH_HATHI; Q899Y1/COLT_CLOTE URSTH and functional variants and derivatives thereof (defined above) or a combination thereof.

In some embodiments, the pepsin enzyme is selected from following group, which refers to the UniProtKB/Swiss-Prot accession numbers: Q9X721/COLG_HATHI; Q46085/COLH_HATHI and functional variants and derivatives thereof or a combination thereof.

Thus, in some embodiments, the collagenase enzyme or functional variant or derivative thereof, comprises an amino acid sequence with at least 80% sequence identity to a sequence as set forth in SEQ ID NOs: 5 or 6.

Preferably said polypeptide sequence is at least 90, 91, 92, 93, 94, 95, 96, 97, 98 or 99% identical to the sequence to which it is compared.

The inventors have also found that permeabilization may be performed using proteinase K, which allows recovery of unprotected DNA tagments, i.e. permeabilization with proteinase K may be used to capture DNA tagments regardless of chromatin accessibility.

Thus, in some preferred embodiments, step (c) comprises contacting the biological specimen with a serine protease (e.g. proteinase K) under conditions suitable for proteolytic (e.g. proteinase K) activity. Advantageously, the serine protease (e.g. proteinase K) is active over a wide pH range (e.g. from about 6.5 and 9.5), under denaturing conditions (e.g., in the presence of SDS or urea), in the presence of metal chelating agents (e.g., EDTA) and at comparatively high temperatures (e.g. about 45° C. to about 65° C.).

In a preferred embodiment, the serine protease is a proteinase K enzyme, proteinase K-like enzyme or a functional equivalent thereof. Thus, any enzyme or combination of enzymes in the enzyme commission number 3.4.21.64 may be used in the present invention.

Thus, in some embodiments, the proteinase K is P06873/PRTK_PARAQ, which refers to the UniProtKB/Swiss-Prot accession numbers, or a functional variant or derivative thereof (defined above) or a combination thereof.

Thus, in some embodiments, the proteinase K enzyme or functional variant or derivative thereof, comprises an amino acid sequence with at least 80% sequence identity to a sequence as set forth in SEQ ID NO: 7.

Preferably said polypeptide sequence is at least 90, 91, 92, 93, 94, 95, 96, 97, 98 or 99% identical to the sequence to which it is compared.

Commercially available proteases are commonly isolated from their native, e.g. animal or microbial source. However, the proteases may be produced recombinantly, e.g. from a microbial, e.g. bacterial, expression system. The source of the protease for use in the present invention is not particularly important and both natural and recombinant proteases are contemplated for use in the methods described herein.

The step of permeabilizing the biological specimen using the chemical and/or enzymatic reagents defined above may be performed under any suitable conditions, e.g. concentration, time, temperature etc. which may be adapted based on the origin of the biological specimen (e.g. the organism and/or organ from which the biological specimen was obtained) and the chemical and/or enzymatic reagents.

In some embodiments, the protease enzymes may be used at a concentration of about 0.05 mg/ml to about 1 mg/ml, e.g. about 0.1 mg/ml to about 0.5 mg/ml.

In some embodiments, the biological specimen may be incubated with the protease enzymes and/or chemical reagents (e.g. alkaline buffer) for about 1-5 minutes, e.g. about 1, 2, 3, 4, 5 minutes. For instance, the pepsin and proteinase K enzymes (or functional equivalents etc.) may be incubated with the biological specimen for about 2-4 minutes, e.g. about 3 minutes. It will be evident that the incubation period may depend on the concentration of the enzyme and the conditions of use, e.g. buffer, temperature etc. Thus, in some embodiments, the protease enzymes may be incubated with the biological specimen for more or less time than the periods set out above. Such modifications are within the purview of the skilled person.

Thus, in some embodiments, the biological specimen may be incubated with the protease enzymes and/or chemical reagents (e.g. alkaline buffer) for at least about 5 minutes, e.g. at least about 10, 12, 15, 18 or 20 minutes. For instance, the collagenase enzymes (or functional equivalents etc.) may be incubated with the biological specimen for about 10-30 minutes, e.g. about 20 minutes.

The permeabilization step may be stopped (e.g. the protease activity may be stopped) by any suitable means. For instance, the reaction mixture (e.g. solution) comprising the protease enzymes and/or chemical reagents may be removed from the solid substrate (e.g. array), i.e. separated from the biological specimen. Alternatively or additionally, the protease enzyme(s) may be inhibited (e.g. by the addition of an inhibitor, such as EDTA for collagenase) or denatured (e.g. by the addition of a denaturing agent or increasing the temperature).

Representative temperature conditions for the permeabilization step include incubation at about 10-70° C. depending on the enzyme. For instance, pepsin and collagenase may be used at about 10-44, 11-43, 12-42, 13-41, 14-40, 15-39, 16-38, 17-37° C., e.g. about 10, 12, 15, 18, 20, 22, 25, 28, 30, 33, 35 or 37° C., preferably about 30-40° C., e.g. about 37° C. Proteinase K may be used at about 40-70° C., e.g. about 50-70, 60-70 e.g. about 65° C.

In some embodiments, the reaction mixture (e.g. solution) comprising the proteases defined above may contain other components, e.g. buffer, salt, etc. sufficient to ensure that the proteases are functional. For instance, in some embodiments, the reaction mixture further comprises an albumin protein, such as BSA. In some preferred embodiments, the reaction mixture (e.g. solution) comprising the collagenase enzyme (or functional variant or derivative thereof) comprises an albumin protein, such as BSA.

The step of fragmenting the DNA in the biological specimen comprises contacting the biological specimen containing DNA with the transposase, e.g. transposome, i.e. a reaction mixture (e.g. solution) comprising a transposase, e.g. transposome, as defined herein under any suitable conditions, i.e. conditions that result in the fragmentation (e.g. tagmentation) of said biological specimen. Typical conditions will depend on the transposase used and may be determined using routine methods known in the art. Thus, alternatively viewed, suitable conditions may be conditions (e.g. buffer, salt, temperature conditions) under which the transposase is functional, e.g. displays transposase activity, particularly tagmentation activity in the biological specimen.

By "functional" is meant that the transposase may show some reduced activity relative to the activity of the transposase in conditions that are optimum for the enzyme, e.g. in the buffer, salt and temperature conditions recommended by the manufacturer. Thus, the transposase may be considered to be functional if it has at least 50%, e.g. at least 60, 70, 80, 85, 90, 95, 96, 97, 98, 99 or 100%, activity relative to the activity of the transposase in conditions that are optimum for the enzyme.

In some embodiments, the reaction mixture (solution) comprising the transposase may contain other components, e.g. buffer, salt, etc. sufficient to ensure that the transposase is functional. For instance, in some embodiments, the reaction mixture further comprises spermidine.

In a representative example, the reaction mixture comprises a transposase enzyme in a buffered solution (e.g. Tris-acetate) having a pH of about 6.5-8.5, e.g. about 7.0-8.0 such as about 7.5. Additionally or alternatively, the reaction mixture may be used at any suitable temperature, such as about 10-45° C., e.g. about 10-44, 11-43, 12-42, 13-41, 14-40, 15-39, 16-38, 17-37° C., e.g. about 10, 12, 15, 18, 20, 22, 25, 28, 30, 33, 35 or 37° C., preferably about 30-40° C., e.g. about 37° C.

The "adaptors" or "oligonucleotides" in the complex with the transposase (i.e. that form part of the transposome, MEDS as described above) comprise partially double stranded oligonucleotides. The double stranded portion of the adaptors contains Mosaic End (ME) sequences. The single stranded portion of the adaptors (5' overhang) contains the functional domain or sequence to be incorporated in the fragmented (i.e. tagmented) DNA. Thus, the functional domain is on the strand of the adaptor that will be ligated to the fragmented DNA. In other words, the functional domain is located upstream (i.e. 5' to) the ME sequence, i.e. in the 5' overhang of the adaptor.

As noted above, in some embodiments, the functional domain may be a domain that binds to the capture domain of the capture probes of the invention.

In some embodiments, the functional domain may be a domain that facilitates the introduction of a binding domain that binds to the capture domain of the capture probes of the invention, i.e. a domain that hybridises to a universal adaptor or templates the ligation of a universal adaptor to the tagmented DNA.

In some embodiments, the ME sequence is a Tn5 transposase recognition sequence (e.g. as set forth in SEQ ID NO: 8). In some embodiments, the ME sequence is a Mu transposase recognition sequence (e.g. as set forth in any one of SEQ ID NOs: 9-14).

Thus, in a further aspect, the invention may be seen as providing a composition comprising a transposase enzyme (e.g. as defined herein) complexed with an adaptor comprising transposon end sequences (or mosaic ends as defined herein) and a domain that binds to a capture probe as defined herein (e.g. a homopolymeric sequence) for use in a method for spatially tagging nucleic acids of a biological specimen, such as the methods defined herein.

A transposome may be produced by loading a transposase enzyme (e.g. a purified enzyme) with the adaptors described above. It will be evident from the representative embodiments described herein that the single stranded portion of the adaptor of the transposome may require a phosphorylated 5' end, e.g. to enable ligation of tagmented DNA to the capture probes.

Thus, in some embodiments, the transposase used in step (d) (or in the composition defined above) is in the form of a transposome comprising an adaptor (MEDS) in which the 5' overhang is phosphorylated.

Whilst the adaptors may be phosphorylated prior to their assembly with the transposase to form the transposome, in-solution assembly of the transposome is inefficient. In this respect, the inventors have determined that phosphorylation of adaptors when complexed with a transposase (i.e. phosphorylation in situ in the transposome) results in improved tagmentation, e.g. relative to a transposome produced by in-solution assembly with adaptors (MEDS) with phosphorylated 5' overhangs.

As described in the Examples, transposomes comprise the adaptors (MEDS) described above (i.e. comprising 5' overhangs). If the 5' overhang of the adaptor is not phosphorylated prior to its assembly in the transposome, it will have accessible 5' hydroxyl groups outside of the mosaic-end transposase binding site. Thus, phosphorylation of the 5' overhang of the assembled transposome complexes may be achieved by exposing these 5' ends of transposome complexes to a polynucleotide kinase (e.g. T4-polynucleotide kinase (T4-PNK)) in the presence of ATP.

Thus, in some embodiments, step (d) comprises fragmenting DNA of the biological specimen with a transposome as defined herein and may comprise a further step of phosphorylating the 5' ends of the adaptors (particularly the 5' overhangs of the adaptors, i.e. MEDS) in the transposome complex.

Alternatively viewed, in some embodiments, the method comprises a step of providing a transposome that has been treated to phosphorylate the 5' ends of the adaptors (particularly the 5' overhangs of the adaptors, i.e. MEDS) in the transposome complex, i.e. step (d) comprises fragmenting the biological specimen with a transposome that has been treated to phosphorylate the 5' ends of the adaptors (particularly the 5' overhangs of the adaptors, i.e. MEDS) in the transposome complex.

Any suitable enzyme and conditions may be used to phosphorylate the 5' ends of the adaptors (particularly the 5' overhangs of the adaptors, i.e. MEDS) in the transposome complex, e.g. T4-PNK or T7-PNK. In a representative embodiment, the phosphorylation reaction may be carried out by contacting the transposome with a polynucleotide kinase (e.g. T4-PNK or T7-PNK) in a buffered solution (e.g. Tris-HCl, pH about 7.0-8.0, e.g. about 7.6) at about 20-40° C., e.g. about 25-37° C., for about 1-60 minutes, e.g. about 5-50, 10-40, 20-30 minutes.

In some embodiments, the step (d) comprises the formation of a plurality of transposase-DNA fragment complexes, wherein a transposase-DNA fragment complex of the plurality of transposase-DNA fragment complexes comprises a DNA fragment. In an additional embodiment, prior to step (e) the plurality of transposase-DNA fragment complexes is treated to dissociate a transposase from a transposase-DNA fragment complex of the plurality of transposase-DNA fragment complexes. In one other embodiment, a DNA fragment is released from the dissociated transposase. In one embodiment, the dissociation of the transposase from a DNA fragment is achieved by contacting the transposase-DNA fragment complex with a stimulus. In other embodiments, the stimulus may be a chemical stimulus (e.g., EDTA) or a temperature stimulus.

In one embodiment, the fragmented DNA of (d) is subjected to one or more nucleic acid reactions. In one other embodiment, prior to (e) the fragment the fragmented DNA of (c) is subjected to one or more nucleic acid reactions. In other embodiments, the one or more nucleic acid reactions comprise a nucleic acid amplification and/or a nucleic acid modification. In another embodiment, the nucleic acid amplification is by an RNA polymerase or a DNA polymerase.

Step (f)(i) in the method above may involve extending the capture probes using the nucleic acid molecules hybridised to the capture probes (i.e. "captured" by the capture probes) as extension templates to produce extended probes thereby spatially tagging the nucleic acids (e.g. tagments) of the biological specimen.

In the context of DNA, step (f)(i) may be viewed as generating DNA (particularly tagged DNA) from the captured DNA, e.g. relating to the synthesis of a complementary strand of DNA. This may involve a step of DNA polymerisation, extending the capture probe, which functions as the primer, using the captured DNA (e.g. tagments) as a template to produce a complementary strand of the DNA hybridized to the capture probe.

As described above, step (d) of the method involves providing the fragmented DNA with a domain that binds to the capture domain in the capture probe, directly or indirectly. Thus, in embodiments of step (f)(i) where the capture probes are extended using the DNA hybridized to the capture probes as extension templates, the domain that binds to the capture domain in the capture probes is provided at the 3' end of the fragmented (i.e. tagmented) DNA (see e.g. FIG. 13). As tagmentation results in the ligation of adaptor sequences to the 5' ends of the fragmented DNA, in this embodiment a domain that binds to the capture domain in the capture probes must be provided indirectly.

In some embodiments, the domain that binds to the capture domain in the capture probes forms a single stranded domain at the 3' end of the tagmented DNA, i.e. a 3' overhang, such as a homopolymeric sequence (e.g. poly-A sequence). Thus, the 3' overhang binds to the capture domain of the capture probes (step (e)) and the bound DNA strand templates the extension of the capture probe via a polymerization reaction. If the DNA hybridized to the capture probes is partially double stranded, the extension reaction may use a DNA polymerase with strand displacement activity as described below.

In some embodiments, it may be advantageous or necessary to make the tagmented DNA single-stranded, e.g. where the domain that binds to the capture domain in the capture probes does not form a 3' overhang. For instance, the domain that binds to the capture domain in the capture probes may be formed by extending the 3' end of the tagmented DNA to generate a sequence that is complementary to the functional domain in the adaptor ligated to the tagmented DNA. In a representative embodiment, the functional domain of the adaptor ligated to the DNA may comprise a homopolymeric sequence (e.g. a poly-T sequence) and extending the 3' end of the tagmented DNA results in the production of a complementary homopolymeric sequence (e.g. a poly-A sequence) that binds to the capture domain of the capture probes. Thus, in some embodiments, step (e) may comprise a step of making the tagmented DNA single-stranded, e.g. denaturing the DNA. Suitable methods for generating single-stranded DNA are known in the art, e.g. heat.

Other embodiments of step (f)(i) in the method above may involve extending the capture probes using the nucleic acid molecules (e.g. tagments) hybridised to the capture probes (i.e. "captured" by the capture probes) as ligation templates to produce extended probes thereby spatially tagging the nucleic acids of the biological specimen.

Thus, in the context of DNA, step (f)(i) may be viewed as generating DNA (particularly tagged DNA) from the captured DNA relating to the ligation of the DNA. This may involve a step of DNA ligation, extending the capture probe, which is ligated to the complementary strand of the DNA hybridized to the capture probe using the captured DNA as a ligation template.

It will be evident that the way in which the tagmented DNA is ligated to the capture probe will depend on the orientation of the capture probe on the array, e.g. whether it is immobilized via its 3' end or 5' end, and whether the capture probe is immobilized on the solid substrate (e.g. array) directly or indirectly (e.g. via a hybridization to an oligonucleotide that is directly immobilized on the array, e.g. a surface probe).

Whilst it is contemplated that the capture probes of the invention may be immobilized via their 3' ends, such that they have a free 5' end that can be ligated to the tagmented DNA, it is preferred that the capture probes are immobilized via their 5' ends, i.e. such that they have a free 3' end that can participate in a ligation or extension reaction.

Thus, in a representative embodiment of step (f)(i), the tagmented DNA is provided with a domain that binds to the capture domain in the capture probes at the 3' end of the fragmented (i.e. tagmented) DNA as described above, i.e. a 3' overhang, such as a homopolymeric sequence (e.g. poly-A sequence). Thus, the 3' overhang binds to the capture domain of the capture probes (step (e)) and the bound DNA strand templates the ligation of the capture probe to the strand that is complementary to the bound DNA strand. As described above, it is preferred that the adaptor of the transposome (i.e. the functional domain of the adaptor) contains a phosphorylated 5' end to enable ligation of tagmented DNA to the capture probes. However, in some embodiments, the adaptors may not contain phosphorylated 5' ends and thus the tagmented DNA may be phosphorylated after step (d).

Step (f)(ii) may be viewed as generating DNA (particularly tagged DNA) from the captured DNA involving a step of DNA ligation, extending the capture probe, which is ligated to the strand of the DNA hybridized to the capture probe using the capture probe as a ligation template.

It will be evident that the way in which the tagmented DNA is ligated to the capture probe will depend on the orientation of the capture probe on the array, e.g. whether it is immobilized via its 3' end or 5' end, and whether the capture probe is immobilized on the directly or indirectly (e.g. via a hybridization to an oligonucleotide that is directly immobilized on the array, e.g. a surface probe).

In some embodiments, the capture probes may be immobilized indirectly on the array via hybridization to so-called surface probes. Thus, in some embodiments, the capture probes may be viewed as partially double-stranded probes, wherein at least the capture domain of the capture probe is single stranded.

Thus, in a representative embodiment, the capture probes are partially double-stranded probes containing a first strand comprising a capture domain and positional domain (a "capture domain oligonucleotide") and a second strand (a "surface probe") comprising a sequence that is complementary to the positional domain, wherein the positional domain and sequence that is complementary to the positional domain form the double stranded portion of the capture probe. The second strand may further comprise an amplification domain and/or cleavage domain as described below. Thus, the second strand of the partially double-stranded probe is a so-called surface probe.

In some embodiments, the surface probe (i.e. second strand of the capture probe) is immobilized on the array via its 5' end and tagmented DNA is provided with a domain that binds to the capture domain of the capture probe directly, i.e. the adaptor of the transposome comprises an ME sequence and a nucleotide sequence (functional domain) that is complementary to the capture domain of the capture probes (i.e. the first strand of the partially double stranded capture probe). Accordingly, step (f)(ii) comprises a step extending the second strands (surface probes) of the partially double-stranded capture probes using the capture domain oligonucleotide as a ligation template to ligate the nucleic acids that hybridize to the capture domains of the capture probes to the second strands (surface probes) of the partially double-stranded capture probes thereby extending the capture probes (the second strands (surface probes) of the partially double-stranded capture probes) to produce extended probes (i.e. probes that comprise the nucleic acids that hybridize to the capture domains of the capture probes and sequences complementary to the positional domains of the capture probes), thereby spatially tagging the nucleic acids of the biological specimen.

It will be evident that the first strand of the partially double stranded capture probes (the capture domain oligonucleotide) does not need to be hybridized to the second strand (surface probe) during all of the steps of the method described herein. It is only necessary for the first strand to be present in steps (e) and (f) of the method, i.e. to enable the tagmented DNA to hybridise to the capture probes and to template the ligation reaction. Thus, in some embodiments, the method may comprise a further step of hybridizing a capture domain oligonucleotide to surface probes immobilized on the array. In some embodiments, this step occurs as part of step (e).

Whilst it is preferred that the first strand of the partially double stranded capture probes contains the capture domain and the positional domain, such that the first and second strands of the partially double stranded capture probes are hybridised via the positional domain, it will be evident that this is not essential to spatially tag nucleic acids in the embodiment described above. In this respect, it may be advantageous for the capture domain and positional domain to be provided on different strands of the partially double-stranded capture probes. For instance, the surface probes may comprise the positional domain and a domain that is complementary to a domain in the capture domain oligonucleotide. When the surface probes are immobilized via their 5' ends, the domain that binds to the capture domain oligonucleotide is downstream (i.e. 3' of) the domain of the positional domain. Thus, in some embodiments, the capture domain and positional domain are provided on separate strands of a partially double stranded capture probe. This embodiment is particularly advantageous when the first strand of the partially double stranded capture probe (i.e. comprising the capture domain, the "capture domain oligonucleotide") is provided during step (e) as described above. For instance, the domain that forms the double stranded portion of the first and second strands of the capture probes may be common to all of the surface probes and capture domain oligonucleotides, such that the same capture domain oligonucleotide hybridizes to all of the surface probes to produce the partially double stranded capture probes of the invention.

It will be understood that equivalent embodiments may be performed in which the "surface probes" are immobilized via their 3' end. In these embodiments, it may be necessary that the 5' end of the second strand of the capture probe (surface probe) is phosphorylated to enable ligation to take place.

The method of the invention enables the capture of DNA and RNA from the same biological specimen, e.g. simultaneous capture.

Thus, step (f)(i) in the method above will be seen as relating to using DNA or both DNA and RNA hybridized to the capture probes as extension templates to produce extended probes. In some embodiments, step (f)(i) may involve using only tagmented DNA as extension templates to produce extended capture probes, i.e. step (f)(i) involves a DNA polymerase reaction to produce DNA. In some embodiments, step (f)(i) may involve using both RNA and DNA as the extension templates to produce extended capture probes, i.e. step (f)(i) involves a reverse transcription reaction to produce cDNA and a DNA polymerase reaction to produce DNA.

In some embodiments, it may be desirable to perform separate extension reactions for each type of nucleic acid to be detected. For instance, it is well-known in the art that RNA is less stable than DNA. Thus, in some embodiments, step (f)(i) may comprise a first extension reaction, which is a reverse transcription reaction (to produce first strand of cDNA) followed by a second extension reaction which is a DNA polymerase reaction (to produce a DNA strand that is complementary to the DNA strand hybridized to the probe). In some embodiments, the first extension reaction is a DNA polymerase reaction and the second extension reaction is a reverse transcription reaction.

In some embodiments, it may be desired to capture RNA via an extension reaction and DNA via a ligation reaction. For instance, in some embodiments, step (f) may comprise an extension reaction, which is a reverse transcription reaction (to produce first strand of cDNA) followed by a ligation reaction. Thus, in some embodiments, the method comprises spatially tagging DNA (e.g. gDNA) by ligating the DNA fragments to the surface probes and spatially tagging RNA by producing extended probes comprising cDNA as described below.

As described above the method may involve a step of providing the DNA fragments with a binding domain capable of hybridizing to the capture domain of the capture probe. In some embodiments, the binding domain is the same domain used to hybridize RNA in the biological specimen to the capture probes, e.g. a poly-A domain. In some embodiments, the capture domain may be a random sequence, e.g. a random hexamer sequence.

In some embodiments, it may be advantageous to perform the extension reactions simultaneously. For instance, the extension reactions may be performed simultaneously by combining the means for achieving RNA templated extension of said capture probes (e.g. a reverse transcriptase) with the means for achieving DNA templated extension or ligation of the capture probes (e.g. a DNA polymerase or DNA ligase).

It is established in the art that some reverse transcriptase enzymes (e.g. Avian Myeloblastosis Virus (AMV) Reverse Transcriptase and Moloney Murine Leukemia Virus (M-MuLV, MMLV) Reverse Transcriptase) can synthesize a complementary DNA strand using both RNA (cDNA synthesis) and single-stranded DNA (ssDNA) as a template. Thus, in some embodiments, the extension reaction may utilize an enzyme (reverse transcriptase) that is capable of using both RNA and ssDNA as the template for an extension reaction, e.g. an AMV or MMLV reverse transcriptase. Simultaneous extension reactions does not necessarily mean that all capture probes will be extended at the same time, but rather that the means for extending the capture probes are applied to the solid substrate, e.g. array, simultaneously, i.e. at substantially the same time.

The phrase "at the same time" means substantially the same time, i.e. one component may be contacted with the solid substrate before the other component, e.g. within seconds, (e.g. within 15, 30, 45, 60, 90, 120 or 180 seconds) or minutes (e.g. within 1, 2, 3, 4, 5, 6, 7, 8, 9, 10, 12 or 15 minutes), but such that the reactions are allowed to proceed together. If one component is contacted with the solid substrate before the other component it is preferred that the means for achieving RNA templated extension of said capture probes (e.g. reverse transcriptase) is contacted first and the means for achieving DNA templated extension of said capture probes (e.g. DNA polymerase or DNA ligase) is contacted within seconds or minutes as defined above. However, in some embodiments, it may be desirable to contact the means for achieving DNA templated extension of said capture probes first and contact the means for achieving RNA templated extension of said capture probes within seconds or minutes as defined above.

In view of the fact that step (f) may comprise sequential extension reactions, it will be evident that the sequential extension reactions may be achieved by contacting the solid substrate with the means for achieving RNA templated extension of said capture probes and means for achieving DNA templated extension or ligation of said capture probes separately.

Thus, in some embodiments, step (f) may be seen to comprise contacting said solid substrate, e.g. array, with means for achieving RNA templated extension of said capture probes and subsequently contacting said solid substrate, e.g. array, with means for achieving DNA templated extension or ligation of said capture probes.

The term "subsequently" means that the means for achieving DNA templated extension or ligation of said capture probes is contacted with the solid substrate after the means for achieving RNA templated extension of said capture probes is contacted with the solid substrate or vice versa. There is no particular limit on the amount of time that may be allowed to lapse between the first and second reactions. However, if the first reaction comprises a DNA templated extension or ligation of said capture probes it is preferred that the second reaction is performed (i.e. means for the RNA templated extension of said capture probes is contacted with the solid substrate) before the RNA molecules have substantially degraded. Thus, in some embodiments, "subsequently" means performing the second reaction minutes or hours after the first extension reaction is completed. For instance, the second reaction may be performed at least 1, 2, 3, 4, 5, 6, 7, 8, 9, 10, 15, 20, 25, 30, 40, 50 or 60 minutes after the first reaction is completed, e.g. within 120, 90 or 60 minutes, i.e. between 1-120, 5-90, 10-60 minutes after the first reaction is completed. In some embodiments, the second reaction may be performed at least 1, 2, 3, 4, 5, 6, 7, 8, 9, 10, 12, 18, 24, 36 or 48 hours after the first reaction is completed, e.g. within 72, 48 or 24 hours, i.e. between 1-72, 6-48, 12-24 hours after the first reaction is completed.

In some embodiments, the means for achieving RNA templated extension of said capture probes (e.g. reverse transcriptase) and means for achieving DNA templated extension or ligation of said capture probes (e.g. DNA polymerase or DNA ligase) are combined in a single reaction mixture, which is contacted with the solid substrate (e.g. array), e.g. the reverse transcriptase and DNA polymerase activities are provided by separate enzymes. Thus, in some embodiments, step (f) comprises contacting said solid substrate (e.g. array) with a reaction mixture comprising:
 (i) a DNA polymerase enzyme capable of extending said capture probes using DNA hybridised to the capture probes as extension templates or a DNA ligase enzyme capable of extending said capture probes using DNA hybridised to the capture probes or the capture probes as ligation templates; and
 (ii) a reverse transcriptase enzyme capable of extending said capture probes using RNA hybridised to the capture probes as extension templates.

Accordingly, the invention can be seen to provide the use of a reaction mixture comprising:
 (i) a DNA polymerase enzyme capable of extending said capture probes using DNA hybridised to the capture probes as extension templates or a DNA ligase enzyme capable of extending said capture probes using DNA hybridised to the capture probes or the capture probes as ligation templates; and
 (ii) a reverse transcriptase enzyme capable of extending said capture probes using RNA hybridised to the capture probes as extension templates,
 in a method for spatially tagging nucleic acids of a biological specimen, such as the methods defined herein.

In embodiments where step (f) comprises the use of a reaction mixture comprising a DNA polymerase enzyme or DNA ligase enzyme and a reverse transcriptase enzyme the enzymes must be functional in the same conditions, e.g. functional in the same buffer, salt, temperature conditions.

By "functional" is meant that the enzymes may show some reduced polymerase or ligase activity (target templated extension or ligation) relative to the activity in conditions that are optimum for the enzymes, e.g. in the buffer, salt and temperature conditions recommended by the manufacturer. Thus, the enzymes may be considered to be functional if they have at least 50%, e.g. at least 60, 70, 80, 85, 90, 95, 96, 97, 98, 99 or 100%, activity relative to the activity of the polymerases in conditions that are optimum for the enzyme.

As noted above, In some embodiments, the means for achieving RNA templated extension of said capture probes (e.g. reverse transcriptase) and means for achieving DNA templated extension of said capture probes (e.g. DNA polymerase) are provided by a single enzyme that is capable of using both RNA and ssDNA as the template for an extension reaction, e.g. an AMV or MMLV reverse transcriptase.

The method of the invention may be used to capture (i.e. spatially tag) DNA (e.g. genomic DNA) or both DNA and RNA.

In embodiments in which DNA is captured, the DNA may be any DNA molecule which may occur in a cell. Thus it may be genomic, i.e. nuclear, DNA, mitochondrial DNA or plastid DNA, e.g. chloroplast DNA. In a preferred embodiment, the DNA is genomic DNA.

In embodiments in which RNA is captured, the RNA may be any RNA molecule which may occur in a cell. Thus it may be mRNA, tRNA, rRNA, viral RNA, small nuclear RNA (snRNA), small nucleolar RNA (snoRNA), microRNA (miRNA), small interfering RNA (siRNA), piwi-interacting RNA (piRNA), ribozymal RNA, antisense RNA or non-coding RNA. Preferably however it is mRNA.

In the context of RNA, step (f) may be viewed as generating cDNA (particularly tagged cDNA) from the captured RNA, i.e. relating to the synthesis of the cDNA. This will involve a step of reverse transcription (RT) of the captured RNA, extending the capture probe, which functions as the RT primer, using the captured RNA as template. Such a step generates so-called first strand cDNA, i.e. an extended probe.

In the context of DNA, step (f) may be viewed as generating DNA (particularly tagged DNA) from the captured DNA, i.e. relating to the synthesis of a complementary strand of DNA or ligation of one of the DNA strands to the capture probes. This may involve a step of DNA polymerization, extending the capture probe, which may function as a primer for the extension, using the captured DNA as template to produce a complementary strand of the DNA hybridized to the capture probe. Alternatively, this may involve a step of DNA ligation, extending the capture probe, which may function as a substrate and optionally the template in a ligation reaction.

As will be described in more detail below, generating a complement of the extended probe (e.g. second strand cDNA synthesis) may take place in a separate step, prior to the step of analyzing the extended probes (e.g. the sequence of the extended probes) or may take place as part of the analysis step. Thus, for instance, generating a complement of the extended probe (e.g. second strand synthesis) may occur in the first step of amplification of an extended probe. In some embodiments, generating a complement of the extended probe (e.g. second strand synthesis) may occur contemporaneously with the extension of the capture probe (e.g. first strand synthesis) or may be performed immediately following the extension of the capture probe (e.g. first strand synthesis reaction). For instance, second strand synthesis may occur contemporaneously with the first strand synthesis reaction when a template switching reaction is used for second strand synthesis. Template switching reactions are described in detail below.

Thus, in some embodiments, (i.e. when the method is used to capture RNA), the extension reaction comprises the use of a reverse transcriptase enzyme. The desired reverse transcriptase activity may be provided by one or more distinct reverse transcriptase enzymes, wherein suitable examples are: M-MLV, MuLV, AMV, HIV, ArrayScript™, MultiScribe™ ThermoScript™, and SuperScript® I, II, and III enzymes. As used herein, the term "reverse transcriptase" includes not only naturally occurring enzymes but also all such modified derivatives, including also derivatives of naturally occurring reverse transcriptase enzymes.

Particularly preferred reverse transcriptase enzymes for use in the methods of the present application include M-MLV, MuLV, AMV and HIV reverse transcriptase enzymes and derivatives, e.g. sequence-modified derivatives, or mutants thereof.

Sequence-modified derivatives or mutants of M-MLV, MuLV, AMV and HIV reverse transcriptase enzymes include mutants that retain at least some of the functional, e.g. reverse transcriptase, activity of the wild-type sequence. Mutations may affect the activity profile of the enzymes, e.g. enhance or reduce the rate of polymerisation, under different reaction conditions, e.g. temperature, template concentration, primer concentration etc. Mutations or sequence-modifications may also affect the RNase activity and/or thermostability of the enzyme. The reverse transcriptase enzyme may be provided as part of a composition which comprises other components, e.g. stabilizing components, that enhance or improve the activity of the reverse transcriptase enzyme, such as RNase inhibitor(s), inhibitors of DNA-dependent DNA synthesis, e.g. actinomycin D. Many sequence-modified derivative or mutants of reverse transcriptase enzymes, e.g. M-MLV, and compositions comprising unmodified and modified enzymes are known in the art and are commercially available, e.g. ArrayScript™, MultiScribe™ ThermoScript™, and SuperScript® I, II, III and IV enzymes, and all such enzymes are considered to be useful in the methods of the invention.

In some embodiments, (i.e. when the method is used to capture DNA), the extension reaction comprises the use of a DNA polymerase enzyme. The desired DNA polymerase activity may be provided by one or more distinct DNA polymerase enzymes. In some embodiments, the DNA polymerase enzyme is from a bacterium, i.e. the DNA polymerase enzyme is a bacterial DNA polymerase enzyme. For instance, the DNA polymerase may be from a bacterium of the genus *Escherichia, Bacillus, Thermophilus* or *Pyrococcus*.

Suitable examples of DNA polymerases that may find utility in the methods of the invention include: *E. coli* DNA polymerase I, Bsu DNA polymerase, Bst DNA polymerase, Taq DNA polymerase, Klenow fragment, Pwo DNA polymerase, Pfu DNA polymerase, T4 DNA polymerase and T7 DNA polymerase enzymes. As used herein, the term "DNA polymerase" includes not only naturally occurring enzymes but also all such modified derivatives, including also derivatives of naturally occurring DNA polymerase enzymes. For instance, in some embodiments, the DNA polymerase may have been modified to remove 5'-3' exonuclease activity.

Particularly preferred DNA polymerase enzymes for use in the methods of the present application include *E. coli* DNA polymerase I, Bsu DNA polymerase and Klenow fragment enzymes and derivatives, e.g. sequence-modified derivatives, or mutants thereof.

Sequence-modified derivatives or mutants of DNA polymerase enzymes include mutants that retain at least some of the functional, e.g. reverse transcriptase, activity of the wild-type sequence. Mutations may affect the activity profile of the enzymes, e.g. enhance or reduce the rate of polymerisation, under different reaction conditions, e.g. temperature, template concentration, primer concentration etc. Mutations or sequence-modifications may also affect the exonuclease activity and/or thermostability of the enzyme.

In some embodiments, (i.e. when the method is used to capture DNA), the extension reaction comprises the use of a DNA ligase enzyme. The desired DNA ligase activity may be provided by one or more distinct DNA ligase. In some embodiments, the DNA ligase enzyme is from a bacterium, i.e. the DNA ligase enzyme is a bacterial DNA ligase enzyme. For instance, the DNA ligase may be T4 DNA ligase. Other enzymes appropriate for the ligation step are known in the art and include, e.g. Tth DNA ligase, Taq DNA ligase, *Thermococcus* sp. (strain 9oN) DNA ligase (9oN™ DNA ligase, New England Biolabs), and Ampligase™ (Epicentre Biotechnologies). Derivatives, e.g. sequence-modified derivatives, or mutants thereof (defined above) may also find utility in the methods of the invention.

As mentioned above, WO 2018/091676 (herein incorporated by reference), discloses a method which combines step of releasing the probes from surface of the solid substrate, e.g. array, with the step of extending the probes using the captured nucleic acids as templates for extension. Thus, it is contemplated that step (f) of the method of the present invention may be combined with a step of releasing the extended probes from the solid substrate.

In embodiments in which the extension and release steps are combined the capture probes are not restricted to a particular orientation on the array. In this respect, the combination of the release and extension steps eliminates the requirement for a particular orientation of the capture probes on the solid substrate. However, in some embodiments, it is preferred that the capture probes are immobilized on the solid substrate such that they have a free 3' end capable of functioning as an extension primer.

Thus, in preferred embodiments, the capture probes are immobilized on the array (preferably directly) via their 5' end and comprise a nucleic acid molecule with 5' to 3':
(i) a positional domain that corresponds to the position of the capture probe on the array, and
(ii) a capture domain.

Furthermore, as the capture probes may be oriented on the solid substrate such that the capture domain is not free or available to interact with (i.e. bind or hybridise to) the nucleic acid molecules in the biological specimen (i.e. the capture probes may be immobilized via their 3' ends), step (d) may occur simultaneously with step (e), i.e. step (e) may be performed under conditions that allow (i.e. are suitable for or facilitate) the nucleic acids of the biological specimen to hybridise to the capture domain in said capture probes. However, in preferred embodiments (e.g. where the capture probes are immobilized on the solid substrate such that they have a free 3' end capable of functioning as an extension primer, e.g. via their 5' ends) step (e) (and optionally steps (b), (c) and/or (d)) may be performed under conditions that allow the nucleic acids of the biological specimen to hybridise to the capture domain in said capture probes.

Thus, in embodiments where step (f) of the method of the present invention is combined with a step of releasing the capture (e.g. extended) probes from the solid substrate and where the capture probes are immobilized on the solid substrate such that they have a free 3' end capable of functioning as an extension primer (e.g. by their 5' end), some capture probes may be released from the solid substrate prior to their extension, i.e. some capture probes are released and subsequently extended. Moreover, some capture probes may be extended at the same time as they are released from the solid substrate, i.e. some capture probes are extended and released from the solid substrate simultaneously.

The step of releasing the capture probes (e.g. extended probes) from the surface of the solid substrate may be achieved in a number of ways. The primary aim of the release step is to yield molecules into which the positional domain of the capture probe (or its complement) is incorporated (or included), such that the DNA, e.g. cDNA molecules or their amplicons are "tagged" according to their feature (or position) on the array. The release step thus untethers or removes DNA, e.g. cDNA molecules (extended probes) or amplicons thereof from the solid substrate (array). The DNA, e.g. cDNA molecules (extended probes) or amplicons include the positional domain or its complement (by virtue of it being part of the extended probe, e.g. the first strand DNA by extension of the capture probe, and optionally copied in the complementary stand of the extended probe (i.e. second strand DNA) if complementary/second strand synthesis takes place on the array, or copied into amplicons if amplification takes place on the array). Hence, in order to yield sequence analysis data that can be correlated with the various regions in the tissue sample it is essential that the extended probes (e.g. released extended probes or their complements) comprise the positional domain of the capture probe (or its complement).

EXAMPLES

Example 1

While investigating the utility of transposase-mediated fragmentation in methods of capture and spatial tagging of DNA from a biological sample using methods described in WO 2012/140224, it was determined that permeabilization conditions that are typically used in tagmentation reactions in cellular suspensions (e.g., as described (Corces, et. al, 2016, supra) are not suitable for biological samples (e.g., tissue sections) immobilized on a substrate, such as an array.

Figure 27:
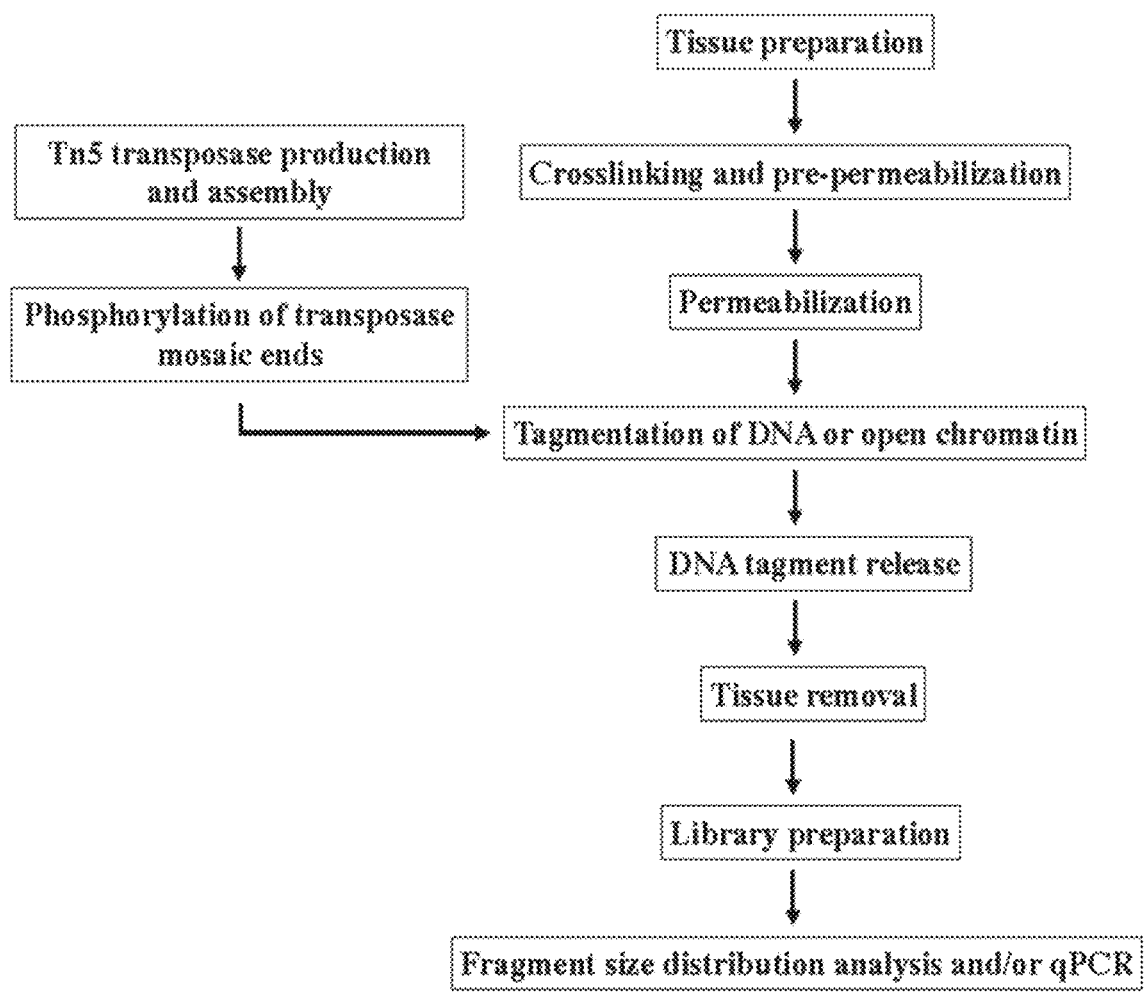
FIG. 27 is a schematic diagram showing a representative workflow of the procedure used to investigate tagmentation conditions in immobilized tissue sections.
Figure 28:
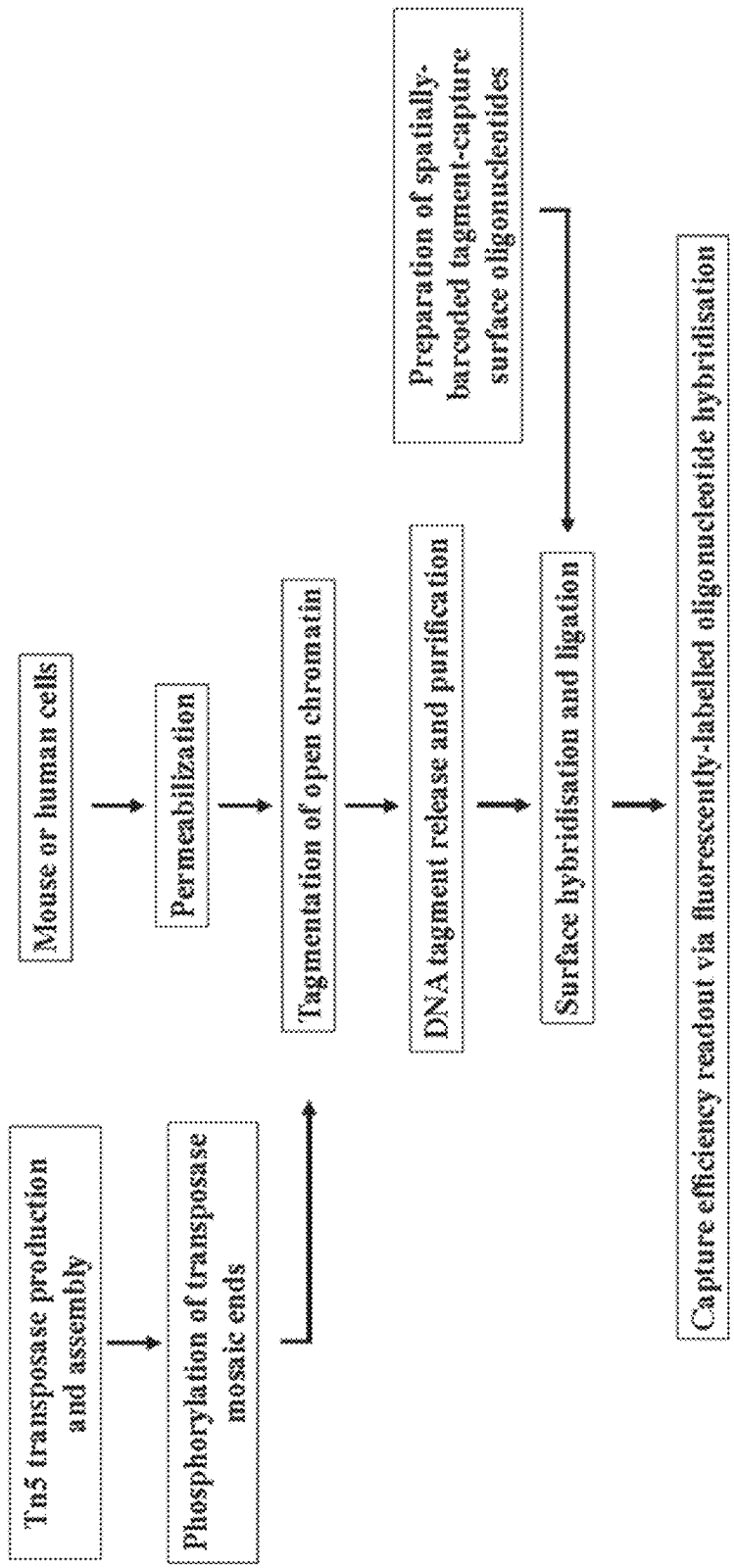
FIG. 28 is a schematic diagram showing a representative workflow of the procedure used to investigate hybridization and ligation conditions of phosphorylated DNA tagments.
Figure 29:
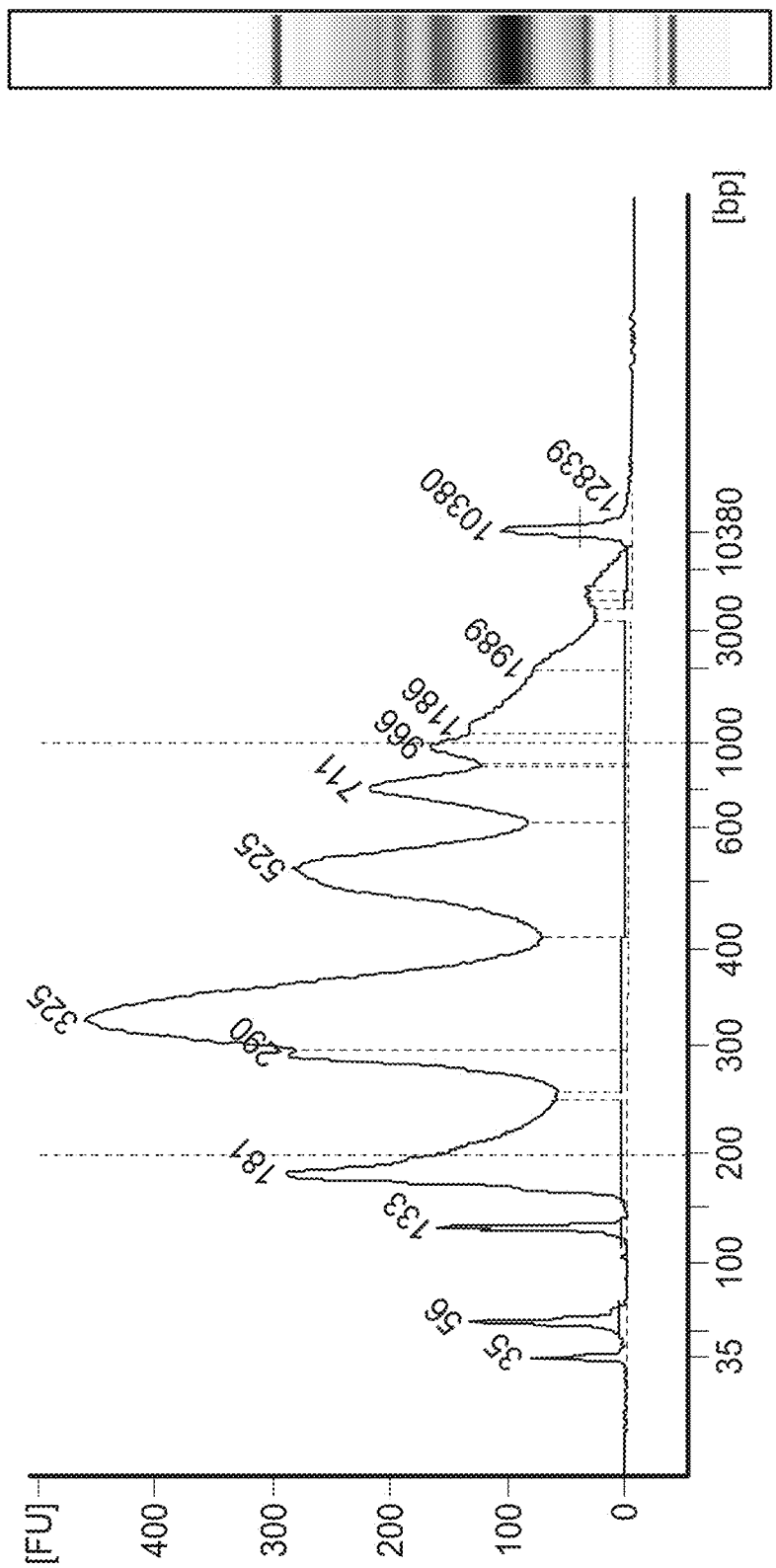
FIG. 29 shows DNA fragment analysis of a reference tagmentation reaction performed in a cellular suspension as described (Corces, M. R., et. al., Lineage-specific and single-cell chromatin accessibility charts human hematopoiesis and leukemia evolution, *Nat Genetic*. vol. 48(10): pp. 1193-1203 (2016)). Fragment distribution analysis is used to determine the success of open chromatin tagmentation, wherein a successful tagmentation reaction of accessible chromatin reveals a periodicity (approx. 170-180 bp; nucleosome-wrapped DNA and PCR handles) in the size of PCR-amplified nucleosome-protected DNA fragments.

Using the workflow set out in FIG. 27, the effects of detergents in the pre-permeabilization step were compared. In brief, tissue sections from frozen tissue samples were crosslinked in 1% or 4% formaldehyde solution for 10 minutes at 25° C. and formaldehyde was quenched by adding 0.125M Glycine and incubation for 5 minutes at 25° C. The tissue sections were rinsed in DPBS to remove crosslinking reagents. The tissue sections were subsequently dehydrated with isopropanol and air-dried. These tissue sections are suitable for histological analysis. The tissue sections were then re-hydrated in D-PBS prior to pre-permeabilization.

Pre-permeabilization involved incubating the re-hydrated tissue sections in: detergents, 0.1% Triton-X-100, IGEPAL 0.1% or Tween 0.1%, Digitonin 0.01% and NP-40 0.1% for 10 minutes at 25° C.

The Tn5 transposome was assembled as described in Picelli et al. 2014 (supra) and tagmentation was performed using conditions similar to those in Corces, M. R., et. al., An improved ATAC-seq protocol reduces background and enables interrogation of frozen tissues, *Nat Methods, vol.* 14(10): 959-962 (2017). In particular, the pre-permeabilization solution was removed from the tissue sections and 50 µl of tagmentation mix was added to the tissue sections (tagmentation mix):

| | |
|---|---|
| 2x TD buffer | 25 µl |
| Digitonin 1% | 0.5 µl |
| Tween-20 10% | 0.5 µl |
| DPBS | 16.5 µl |
| H₂O | 6.25 µl |
| Tn5 (MEDS-40 µM) | 1.25 µL. |

| 2X TD buffer: | | |
|---|---|---|
| Stock | Volume for 100 ml | Final conc. |
| Tris HCl pH7.6 | 2 ml | 20 mM |
| 1M MgCl₂ | 1 ml | 10 mM |
| Dimethyl Formamide (DMF) | 20 ml | 20% |
| Sterile H₂O | Up to 100 ml | NA |

The TD buffer was adjusted to pH 7.6 with acetic acid prior to the addition of DMF.

The tissue sections were incubated in the tagmentation mix for 30 minutes at 37° C. while shaking at 300 rpm (an adhesive lid was provided to prevent loss of the tagmentation mix). Nucleic acid samples obtained from the tissue samples were analysed for fragment size distribution, e.g. with an Agilent Bioanalyzer (Agilent).

Figure 30E:
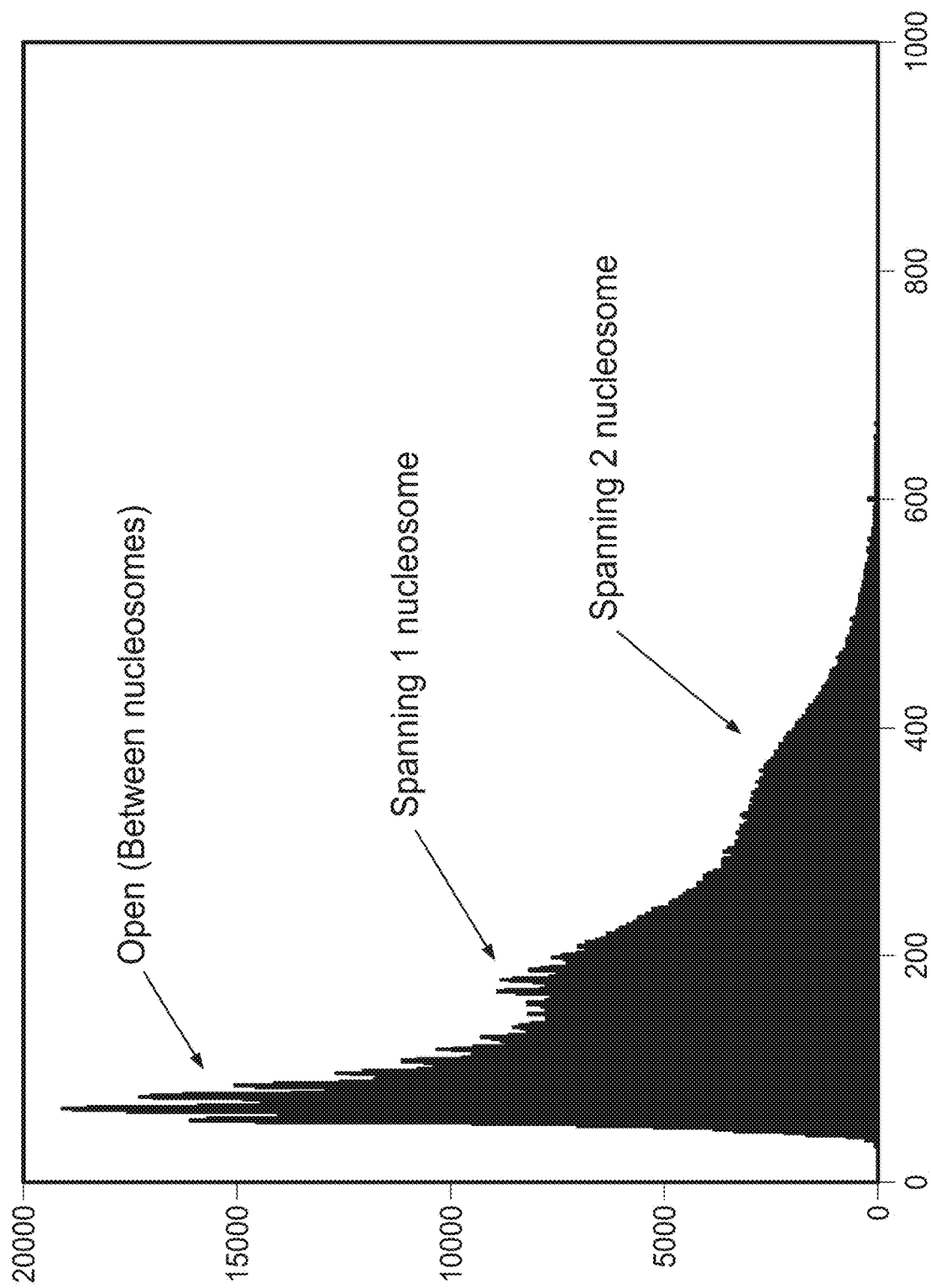

FIG. 30 shows that none of the tested detergents yield the nucleosomal pattern typically associated with tagmentation. While not wishing to be bound by theory, it is hypothesized that none of the detergents used are sufficient for efficient nuclear accessibility for the Tn5 transposase in immobilized tissue sections given the large fragment size distribution.

In order to make the nuclear envelope accessible to enzymes in subsequent reactions, tissue sections were then subjected to various chemical or enzymatic pre-permeabilization conditions.

Figure 31A:
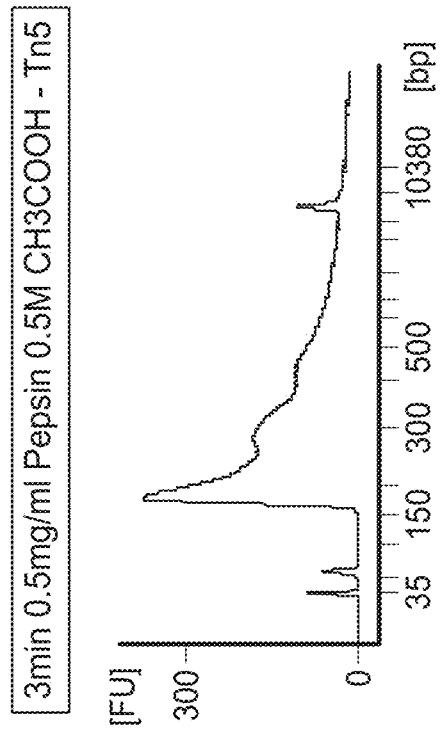
FIGS. 31A-D shows a DNA fragment analysis of tagmentation reactions performed according to the workflow in FIG. 27 comparing different protease treatments (3 minutes) on an immobilized tissue section.
Figure 31B:
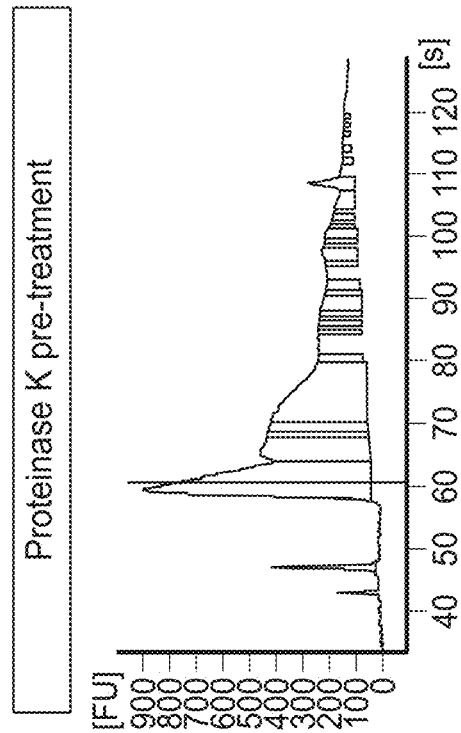
Figure 31C:
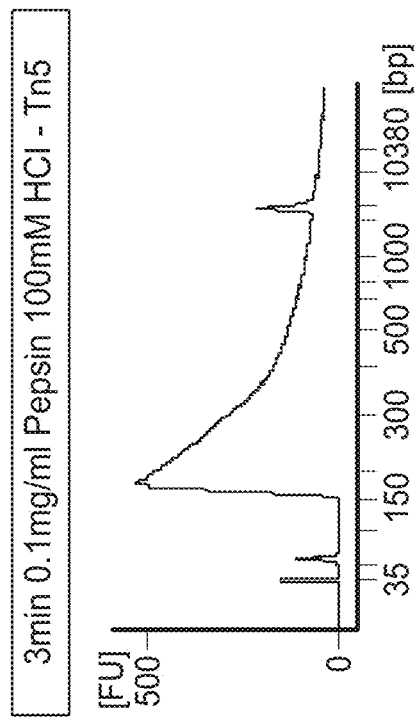

FIG. 32 shows that successful pre-permeabilization may be obtained using pepsin in 0.5M acetic acid or Exonuclease-1 buffer. It was found that the acidity of the buffers required for pepsin digestion can induce genomic fragmentation (FIGS. 31A-C).

Figure 31D:
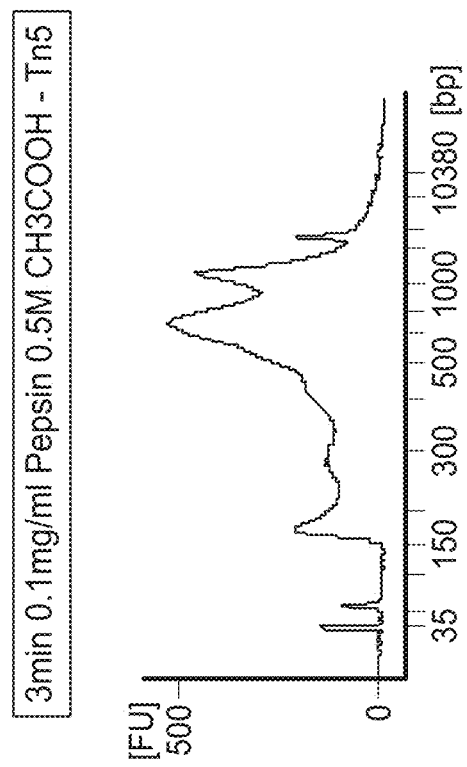

The most efficient genomic accessibility achieved, while preserving nuclear integrity, was obtained using collagenase in the presence of BSA. The time of digestion at 37° C. can be adjusted according to the nature of the tissue. For example, mouse brain tissues can be pre-permeabilized for 20 minutes in collagenase solution for optimal accessibility (FIG. 32C). Longer permeabilization incubation times in collagenase, Pepsin, or Proteinase-K (FIG. 31D) can be used to capture genomic DNA fragments regardless of their chromatin accessibility.

Example 2

Transposome Assembly

Tn5 transposase may be produced as previously described (Picelli et al., 2014 supra). In brief, Tn5 transposase protein monomers are produced and purified and subsequently loaded with the oligonucleotides of interest. The ssDNA oligonucleotides contain mosaic ends for Tn5 recognition and are annealed to form a dsDNA mosaic end oligonucleotide (MEDS) that is recognized by Tn5 during dimer assembly. The oligonucleotides may contain desired 5' overhangs for functionalization of tagmented DNA. The oligonucleotide can also contain an additional single stranded domains.

Effects of 5' Phosphorylation on Tagmentation

As described above, the functional domain of the MEDS can employ a phosphorylated 5' end to allow ligation of tagmented DNA to the capture probes. This can be achieved by assembling Tn5 with 5' phosphorylated MEDS oligonucleotides in solution.

Figures 33A, 33B, 33C:
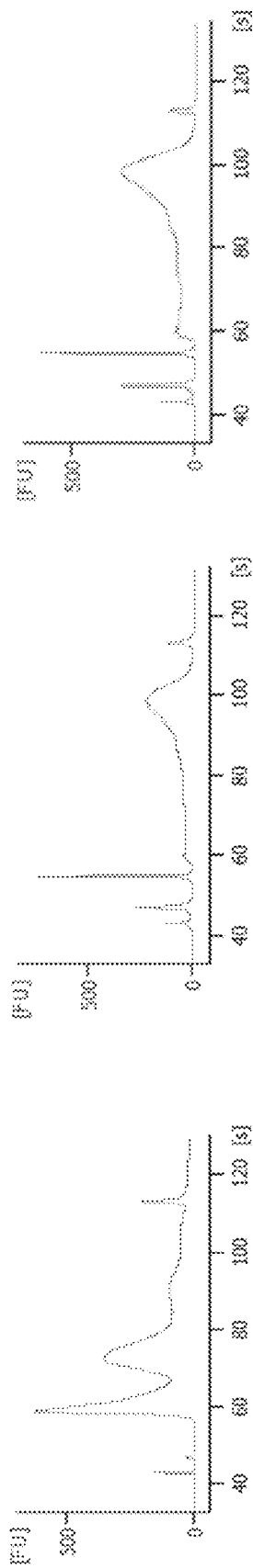
FIGS. 33A-C shows a DNA fragment analysis of tagmentation reactions performed according to the workflow in FIG. 27 comparing different Tn5 assembly methods on an immobilized tissue section.

It was found that tagmentation using in-solution assembly of 5' phosphorylated MEDS onto Tn5 protein is inefficient (FIG. 33C). As unphosphorylated MEDS oligonucleotides with 5' overhangs have accessible 5' hydroxyl groups outside of the mosaic-end Tn5 binding site, the assembled complexes were phosphorylated by exposing these 5' ends of the MEDS-Tn5 complexes to T4-polynucleotide kinase (T4-PNK) in the presence of ATP. Specifically, 2.5 µl of the Tn5 assembled complex was added to a reaction mixture containing:

| T4 PNK Reaction Buffer (10x) | 1 µl |
|---|---|
| ATP (10 mM) | 1 µl |
| T4 PNK (10 U/µl) | 0.5 µl |
| Nuclease free H₂O | 5 µl |

The reaction was carried out at 37° C. for 30 minutes and the phosphorylated Tn5 complex was termed "Phospho-Tn5".

Tagmentation was performed as described in Example 1, wherein in the reaction mixture containing the "Phospho-Tn5" (PNK-MEDS-Tn5) contained:

| 2x TD buffer | 25 µl |
|---|---|
| Digitonin 1% | 0.5 µl |
| Tween-20 10% | 0.5 µl |
| DPBS | 16.5 µl |
| H₂O | 2.5 µl |
| "Phospho-Tn5" | 5 µl |

Figure 34:
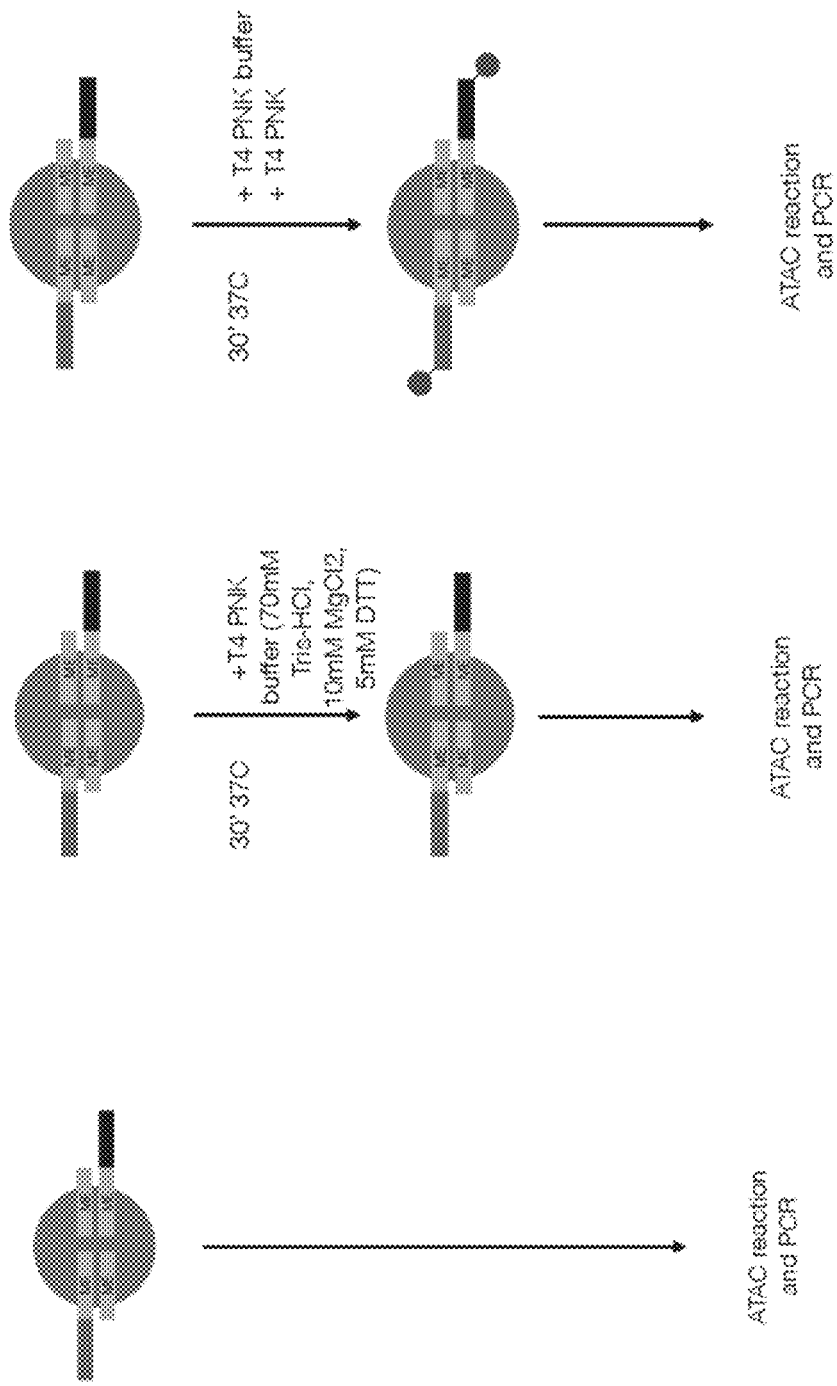
FIG. 34 is a schematic diagram showing a representation of the tests to assess the effect of post-assembly T4-PNK phosphorylation and reaction conditions on MEDS Tn5 complexes.
Figure 36A:
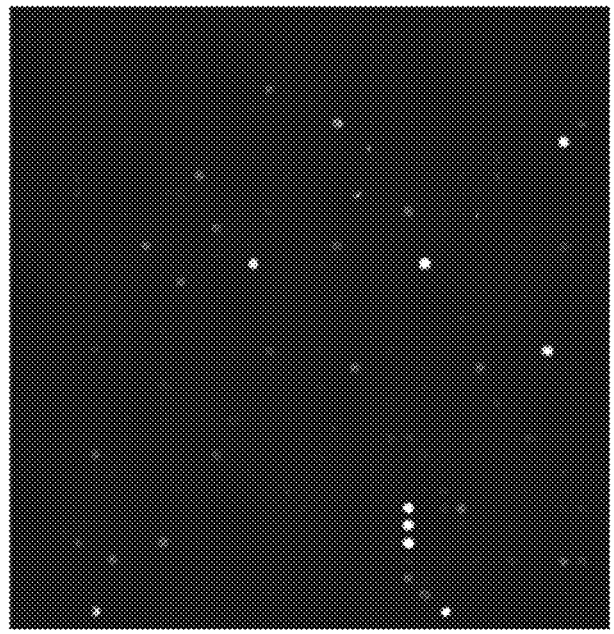
FIGS. 36A-B shows photographs of arrays generated according to the workflow in FIG. 28, depicting the ligation efficiency of DNA tagments onto capture probe oligonucleotides (FIG. 36A) without and (FIG. 36B) with post-assembly phosphorylation.
Figure 36B:
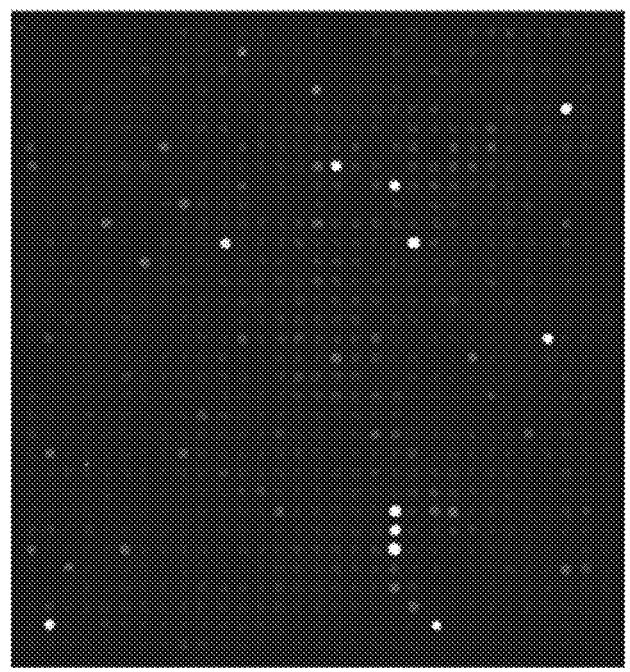

It was found that the phosphorylated MEDS-Tn5 complexes (PNK-MEDS-Tn5) retain most of the transposition activity unlike MEDS-Tn5 assemblies generated in-solution in the presence of excess MEDS (FIGS. 34 and 35).

Example 3

Capturing of the tagments onto the substrate, spatially barcoded array, can be performed using two main capture strategies, hybridization and ligation. The strategy may depend on the purpose of the experiment, e.g., whether the tagments are to be captured alone or simultaneously with mRNA-transcripts. Representative embodiments for each capture strategy are described below.

Simultaneous Capture of Tagments and mRNAs Using Hybridization

Figure 37:
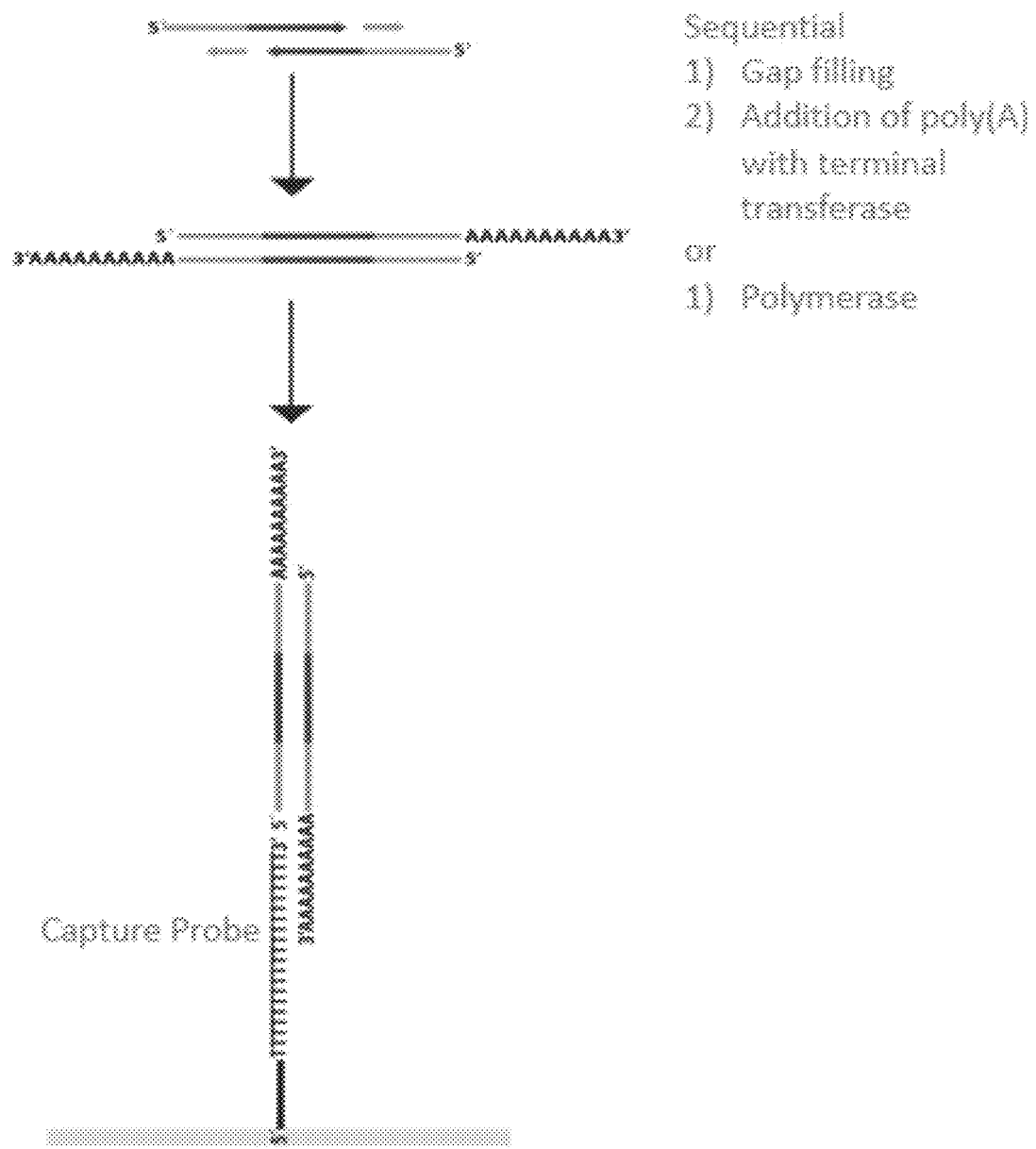
FIG. 37 is a schematic depicting a representative embodiment of the invention in which tagments are gap-filled with a polymerase with slippery activity (e.g., stuttering), creating poly-A-sticky end (3' overhang) at the 3'-ends (mimicking an mRNA poly(A)-tail) with a terminal transferase and subsequent hybridization to the capture domain of a capture probe (this embodiment would allow simultaneous hybridization of mRNA-transcripts). Alternatively, a polymerase can be used to extend the tagment prior to capture.

Simultaneous capture of tagments and mRNA on standard spatially barcoded arrays is performed using hybridization of poly(A) tails of mRNA transcripts and poly(A) tailed tagmented DNA to the polyT sequences on the capture probes (See e.g., WO 2012/140224). This is possible by adding a poly(A) tail to the tagments, e.g. by gap-filling and ligating breaks in the tagmented DNA and subsequently adding a poly(A) tail with a terminal transferase enzyme, such as terminal transferase deoxynucleotidyl transferase. This will create tagments with 3'-poly(A) sticky ends, mimicking the poly(A) tail of mRNA, thus allowing for simultaneous capture of the tagmented DNA and the mRNA transcripts (FIG. 37). Optimally, the length of the obtained sticky-end of poly-A should be 18 bases or longer. Alternatively, instead of a sequential reaction (e.g., gap filling followed by a terminal transferase), a single reaction with a polymerase (e.g., DNA polymerase) may be performed. The post-hybridization steps are identical as described in Ståhl P. L., et al. Visualization and analysis of gene expression in tissue sections by spatial transcriptomics *Science*, vol. 353, 6294, pp. 78-82 (2016)).

Capturing Tagments Using Ligation

Figure 38:
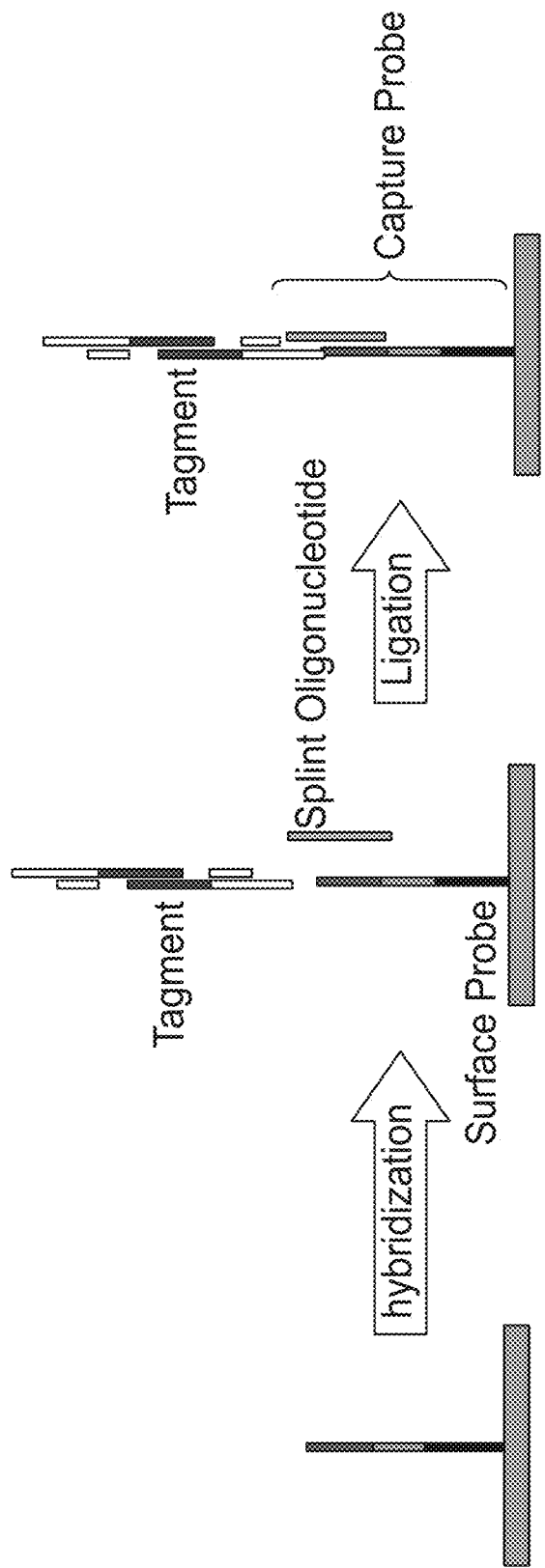
FIG. 38 is a schematic diagram of a representative embodiment of the invention in which tagments are ligated to partially double stranded capture probes using the capture domain strand of the capture probe (e.g., a capture domain oligonucleotide) as a ligation template.

Following tagmentation with Tn5, a further permeabilization step is performed to allow the intra-nuclear tagments to diffuse out of the tissue section and ligate to the surface probes onto the array. The ligation uses a partially double stranded capture probe, comprising a capture domain oligonucleotide (e.g., a splint oligonucleotide) and a surface probe. The capture domain oligonucleotide may be viewed as a "splint oligonucleotide" that hybridizes to the adapter sequence (SEQ ID NO. 18) ligated to the tagmented DNA by the hyperactive Tn5 transposase and a complementary sequence on a surface probe (FIG. 38). The ligation incubation mix contains 1×T4 DNA ligase buffer, 0.02 µM splint oligonucleotide, 0.01 µM BSA, nuclease-free water and T4 DNA ligase at a volume half of the T4 DNA ligase buffer. This mix is added to each of the array-wells and incubated at room temperature overnight.

Example 4

Figure 39:
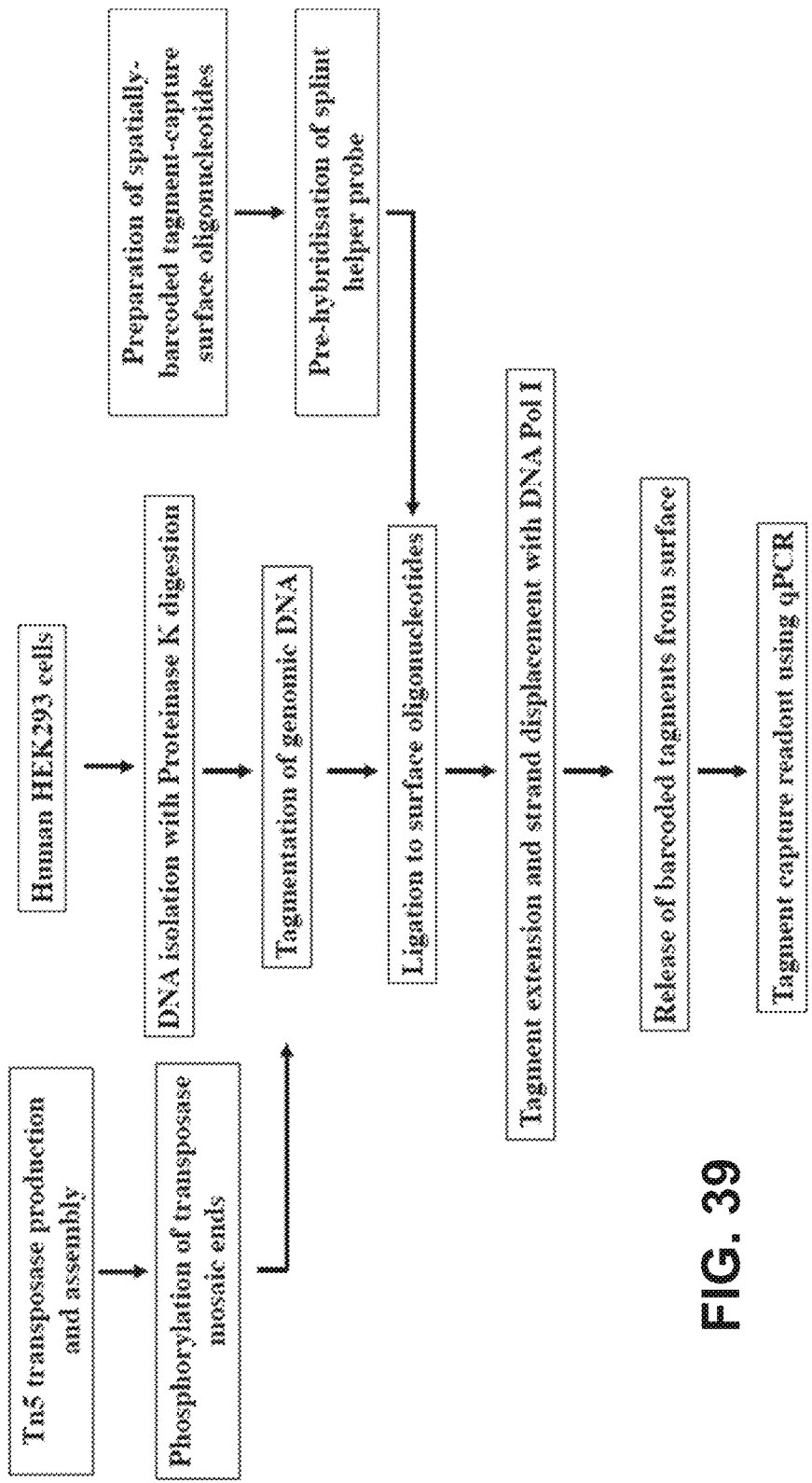
FIG. 39 is a schematic diagram showing a representative workflow of the procedure used to investigate ligation of phosphorylated DNA tagments from a whole human genome and downstream qPCR analysis.

Ligation of purified DNA tagments from a whole human genome to a capture probe on the substrate surface (e.g., a partially double stranded capture probe comprising a surface probe and a splint oligonucleotide with a capture domain) was performed, followed by qPCR and bioanalyzer analysis (FIG. 39).

Immobilization of the surface probe portion of the capture probe (IDT) to enable ligation was performed on the surface of Codelink Activated microscope glass slides (#DN01-0025, Surmodics), according to the manufacturer's instructions. The oligonucleotide (e.g., surface probe) immobilized on the surface is shown below (SEQ ID NO. 15):

[AmC6]UUUUUGACTCGTAATACGACTCACTATAGGGACACGACGCTCTT

CCGATCTNNNNNNNNNTGCACGCGGTGTACAGACGT

Hybridization of splint oligonucleotides (2 μM diluted in PBS) to surface probes was performed for 30 min at 44° C. (FIG. 40) thus generating the capture probe.

Ligation and Strand Displacement Hybridization

Ligation was performed for 2 hours at 37° C. (0.005 weiss U/μl T4 DNA ligase, 0.2 mg/ml BSA, 1×T4 DNA Ligase Buffer, 8.75 ng/μl tagments) by adding 70 μl to each well (FIG. 41A). After ligation, strand displacement polymerization was performed (0.27 U/μl DNA polymerase I (#18010-017, Invitrogen), 0.27 μg/μl BSA, 0.6 mM dNTPs, 1x DNA pol 1 Reaction Buffer) by incubation at 37° C. for 1 hour.

Release of Capture Probes and Downstream Analysis

For each well, 70 μl release mix (0.20 μg/μl BSA, 0.1 U/μl USER Enzyme (#M5505, NEB) was added and incubated at 37° C. for 1 hour and 65 μl from each well were collected. Volume reduction using a SpeedVac down to ~10 μl was performed. A qPCR reaction was then performed containing a total reaction volume of 10 μl (1×KAPA HiFi HotStart ReadyMix (#KK2601, KAPA Biosystems), 1x EVA green (#31000, Biotium), and primers (25 RM)). Amplification was performed with the following protocol: 72° C. for 10 minutes, 98° C. for 3 minutes, followed by cycling at 98° C. for 20 seconds, 60° C. for 30 seconds and 72° C. for 30 seconds. Two primer pairs were used for qPCR, one pair that included A-short forward and Nextera reverse (covers ligated part+capture probe; SEQ ID NOs. 21 and 20, respectively) and the other pair that included Nextera forward and Nextera reverse (covers the tagment-part only). The second pair (Nextera forward and Nextera reverse; SEQ ID NOs. 16 and 20, respectively) served as a control for the ligation since only hybridization of the tagment to the splint oligonucleotide is required, and not ligation (FIG. 40).

Figure 41B:
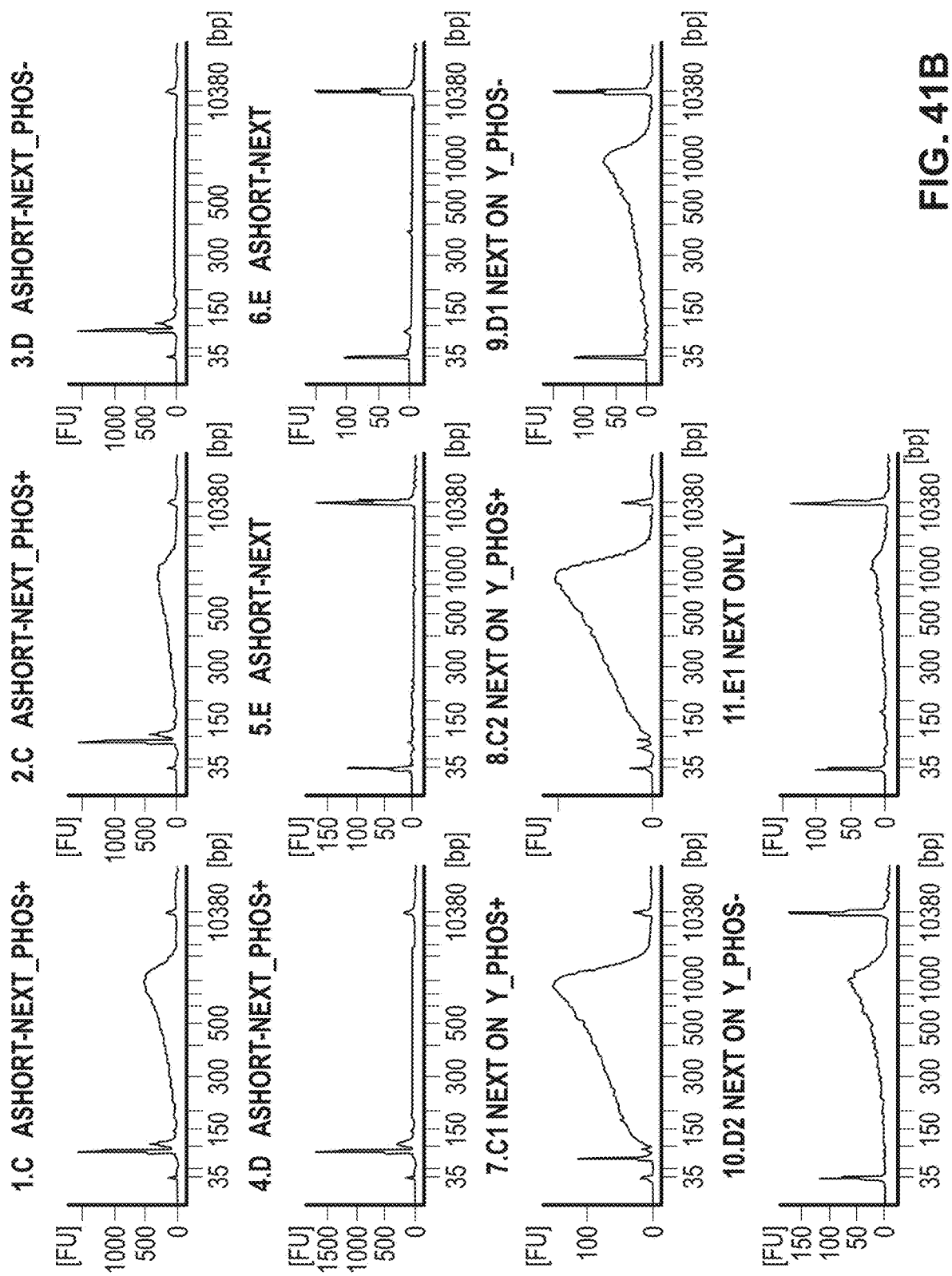
FIG. 41B shows a DNA fragment analysis of tagmentation reactions performed according to the workflow shown in FIG. 39. The PCR primer pair "Ashort-Next" covers both the surface probe and the tagment. This primer pair only results in a PCR product when hybridization and ligation have occurred. Samples 1 and 2 represent tagments with phosphate groups added to facilitate ligation. Samples 3 and 4 had tagments lacking phosphate groups and served as negative controls and samples 5 and 6 had MQ water instead of tagments. Further, a pair of Nextera primers ("NEXT ONLY", samples 7-11) show the PCR products when both ligation and hybridization have occurred, thus resulting in a signal from the D and E wells.
Figure 41C:
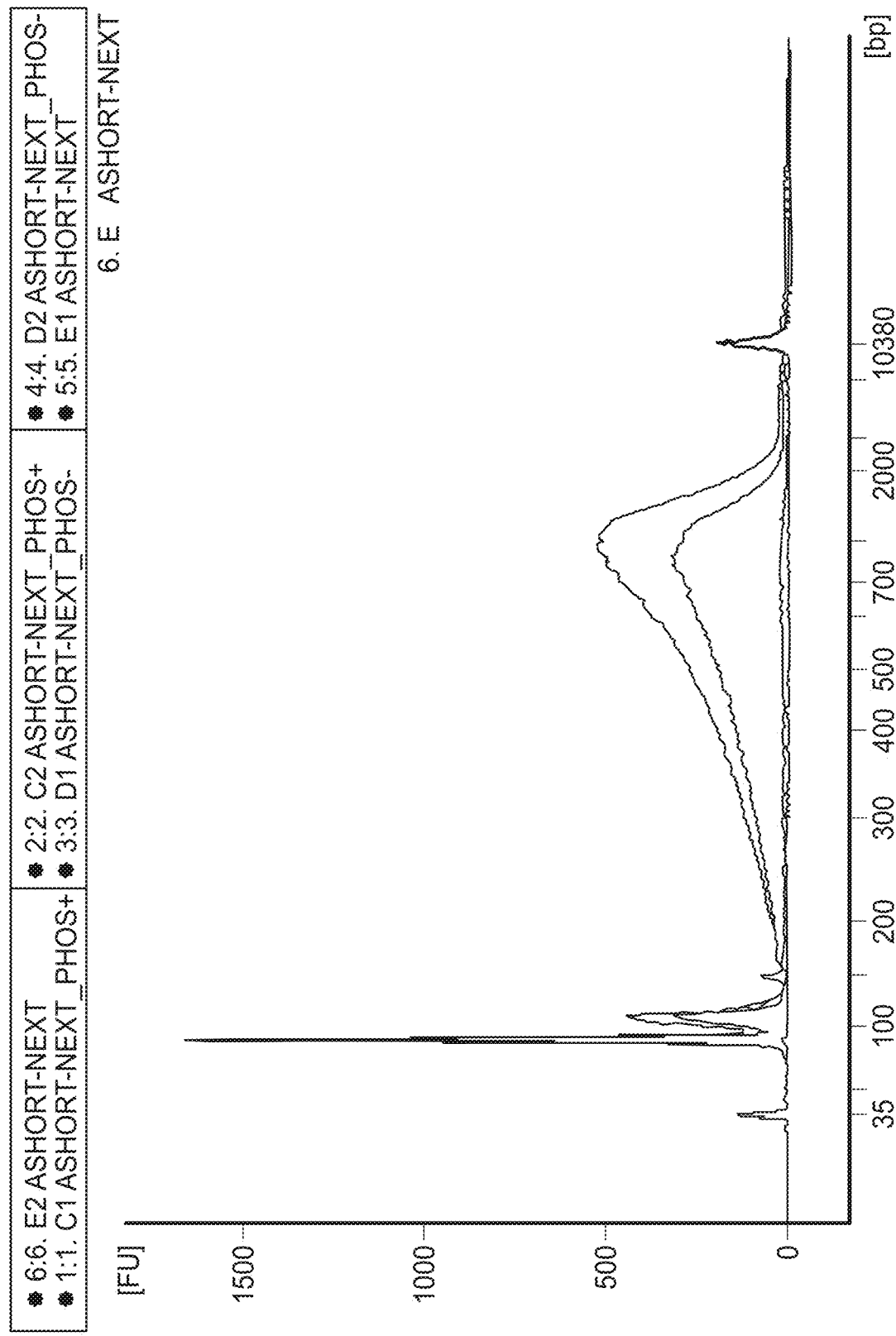
FIG. 41C shows a graph showing an alignment of PCR products. The graph shows ligation (ligated qPCR products) with "Ashort-Next" primers, whereas minimal ligation occurred in all four negative controls.

The samples were purified as described elsewhere (Lundin et al., Increased Throughput by Parallelization of Library Preparation for Massive Sequencing, *PLOS ONE*, 5(4), doi.org/10.1371/journal.pone.0010029 (2010) which is herein incorporated by reference) and then diluted in 20 μl elution buffer (#19086, Qiagen). Average fragment length was determined using the DNA HS Kit (Agilent) with a 2100 Bioanalyzer according to the manufacturer's protocol (FIGS. 41B-C). These results show successful capture of fragments from the DNA not restricted to open chromatin and that the negative controls (at two levels) were true negatives.

Example 5

Figure 42:
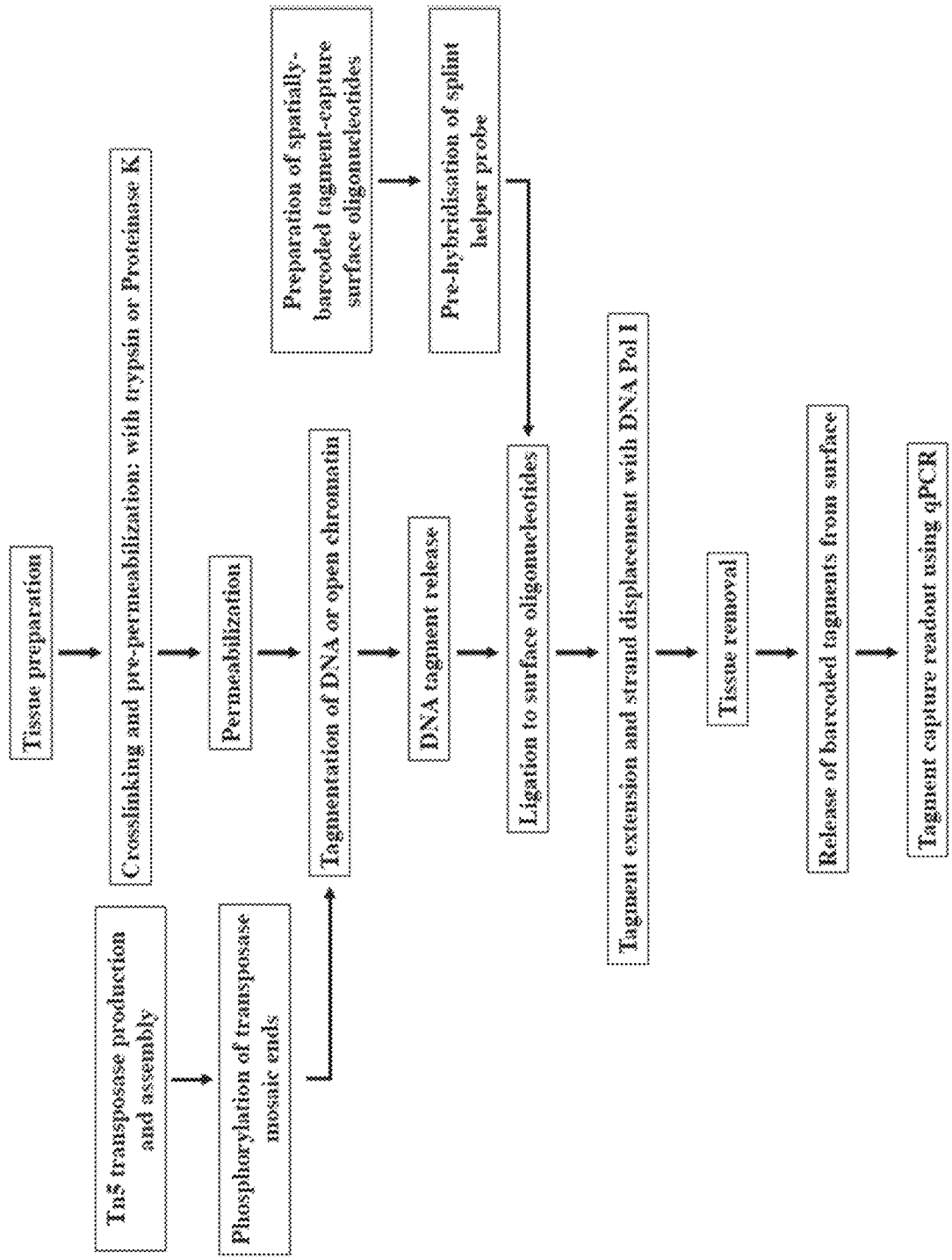
FIG. 42 shows a schematic diagram showing a representative workflow of the procedure used to investigate permeabilization and tagmentation conditions of DNA tagments in immobilized tissue sections. Results from partial protein digestion with trypsin or Proteinase-K during pre-permeabilization are shown.

Ligation of purified DNA tagments from an immobilized tissue sections to capture probes on a substrate surface was performed, followed by qPCR and bioanalyzer analysis according to the workflow shown in FIG. 42. Capture probe (e.g., the surface probe of the capture probe) immobilization and hybridization of the splint oligonucleotide were performed as described in Example 4. Tissue handling and additional permeabilization optimization conditions are described in this Example.

Fixation, Permeabilization and DNA Tagmentation

Tissue sections (10 μm) were placed onto the arrays and incubated at 37° C. for 1 minute followed by crosslinking in 4% formaldehyde solution for 10 minutes at 25° C. The tissue sections were then rinsed in PBS to remove crosslinking reagents. Pre-permeabilization was performed using collagenase in HBSS buffer (0.2 U/μl collagenase, 0.2 mg/μl BSA) at 37° C. for 20 min.

Figure 43B:
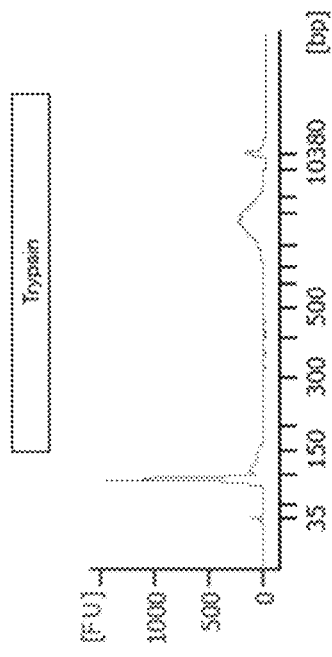
FIGS. 43A-C shows graphs showing the effect of collagenase treatment followed by either Proteinase-K (FIG. 43A) or trypsin (FIG. 43B) pre-permeabilization on tagmentation efficiency according to the workflow shown in FIG. 42. The experiment was performed in duplicate. Proteinase-K pre-permeabilization treatment resulted in uniformly high signal of amplified tagments compared to trypsin pre-permeabilization treatment or (FIG. 43C) the negative control (phosphate negative tagments).
Figure 43A:
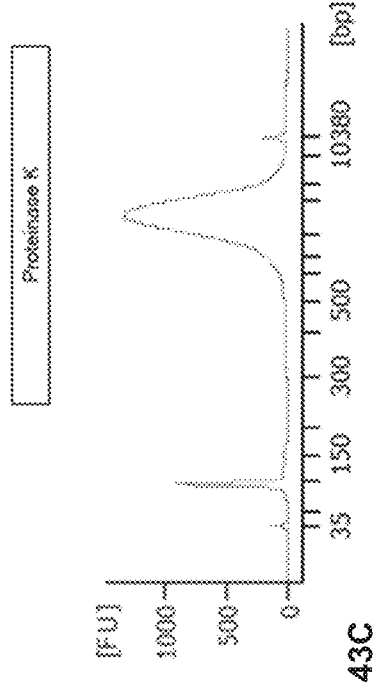
Figure 43C:
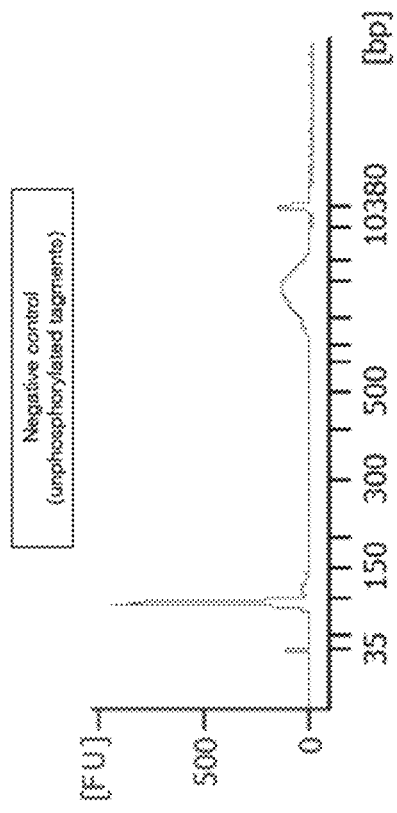
Figure 44:
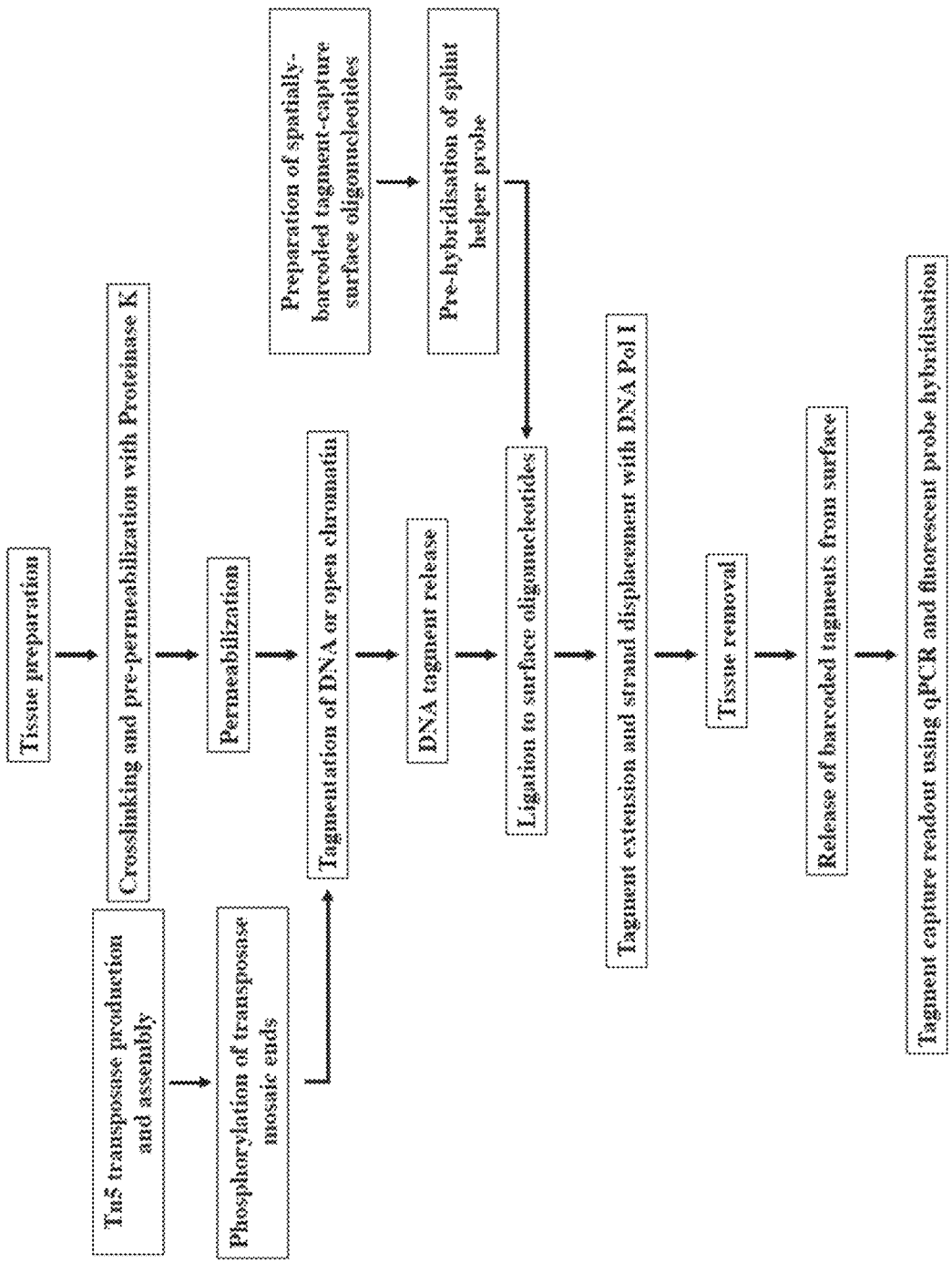
FIG. 44 shows a schematic diagram showing a representative workflow of the procedure used to investigate the capture of DNA tagments from immobilized tissue sections.

Pre-permeabilization using either Proteinase K (#19131, Qiagen) and PKD Buffer (#1034963, Qiagen), at a ratio of 1:8 at 37° C. for 10 minutes or 15% trypsin at 37° C. for 10 minutes was performed. The procedure was performed according to the workflow shown in FIG. 42 including qPCR and bioanalyzer analysis and the results are shown in FIG. 43, These results show that tagmentation, ligation, and downstream analysis (e.g., qPCR and bioanalyzer analysis) can be performed on immobilized (e.g., fixed) biological samples (e.g., tissue section).

Example 6

Ligation of purified DNA tagments (via adapters) from immobilized tissue sections to surface probes on a substrate surface was performed followed by qPCR and hybridization of Cy5-labeled oligonucleotides. The workflow follows Example 5, but with the following changes:

Pre-permeabilization and permeabilization were performed using only Proteinase K (#19131, Qiagen) and PKD Buffer (#1034963, Qiagen), at a ratio of 1:8 at 37° C. for 10 minutes and tagmentation time was extended to 45 minutes instead of 30 minutes.

Additionally, a parallel downstream analysis after tissue removal included surface-based denaturation (1M NaOH) of ligated tagments at room temperature for 10 minutes followed by hybridization of Cy5-labeled oligonucleotides. FIG. 45 shows qPCR data from two experiments (FIG. 45A-B) with a negative control (unphosphorylated tagments) (FIG. 45C). FIG. 45D shows an image of the spatial capture pattern of the DNA tagments with Cy5-labeled oligonucleotides. The bioanalyzer results gave a reduced signal in tissue section 2 (FIG. 45B), and a more sporadic peak pattern. FIG. 45D shows that the Cy5-image (right) resembles the hematoxylin-eosin image (left).

Tn5 Transposase
SEQ ID NO: 1
MITSALHRAADWAKSVFSSAALGDPRRTARLVNVAAQLAKYSGKSITISS

EGSEAMQEGAYRFIRNPNVSAEAIRKAGAMQTVKLAQEFPELLAIEDTTS

LSYRHQVAEELGKLGSIQDKSRGWWVHSVLLLEATTFRTVGLLHQEWWMR

PDDPADADEKESGKWLAAAATSRLRMGSMMSNVIAVCDREADIHAYLQDK

LAHNERFVVRSKHPRKDVESGLYLYDHLKNQPELGGYQISIPQKGVVDKR

GKRKNRPARKASLSLRSGRITLKQGNITLNAVLAEEINPPKGETPLKWLL

-continued

LTSEPVESLAQALRVIDIYTHRWRIEEFHKAWKTGAGAERQRMEEPDNLE
RMVSILSFVAVRLLQLRESFTLPQALRAQGLLKEAEHVESQSAETVLTPD
ECQLLGYLDKGKRKREKAGSLQWAYMAIARLGGFMDSKRTGIASWGALW
EGWEALQSKLDGFLAAKDLMAQGIKI

Bacteriophage Mu Transposase

SEQ ID NO: 2
MKEWYTAKELLGLAGLPKQATNITRKAQREGWEFRQVAGTKGVSFEFNIK
SFPVALRAEILLQQGRIETSQGYFEIARPTLEAHDYDREALWSKWDNASD
SQRRLAEKWLPAVQAADEMLNQGISTKTAFATVAGHYQVSASTLRDKYYQ
VQKFAKPDWAAALVDGRGASRRNVHKSEFDEDAWQFLIADYLRPEKPAFR
KCYERLELAAREHGWSIPSRATAFRRIQQLDEAMVVACREGEHALMHLIP
AQQRTVEHLDAMQWINGDGYLHNVFVRWFNGDVIRPKTWFWQDVKTRKIL
GWRCDVSENIDSIRLSFMDVVTRYGIPEDFHITIDNTRGAANKWLTGGAP
NRYRFKVKEDDPKGLFLLMGAKMHWTSVVAGKGWGQAKPVERAFGVGGLE
EYVDKHPALAGAYTGPNPQAKPDNYGDRAVDAELFLKTLAEGVAMFNART
GRETEMCGGKLSFDDVFEREYARTIVRKPTEEQKRMLLLPAEAVNVSRKG
EFALKVGGSLKGAKNVYYNMALMNAGVKKVVVRFDPQQLHSTVYCYTLDG
RFICEAECLAPVAFNDAAAGREYRRRQKQLKSATKAAIKAQKQMDALEVA
ELLPQIAEPEAPESRIVGIFRPSGNTERVKNQERDDEYETERDEYLNHSL
DILEQNRRKKAI

Pepsin

SEQ ID NO: 3
IGDEPLENYLDTEYFGTIGIGTPAQDFTVIFDTGSSNLWVPSVYCSSLAC
SDHNQFNPDDSSTFEATSQELSITYGTGSMTGILGYDTVQVGGISDTNQI
FGLSETEPGSFLYYAPFDGILGLAYPSISASGATPVFDNLWDQGLVSQDL
FSVYLSSNDDSGSVVLLGGIDSSYYTGSLNWVPVSVEGYWQITLDSITMD
GETIACSGGCQAIVDTGTSLLTGPTSAIANIQSDIGASENSDGEMVISCS
SIDSLPDIVFTINGVQYPLSPSAYILQDDDSCTSGFEGMDVPTSSGELWI
LGDVFIRQYYTVEDRANNKVGLAPVA

Pepsin

SEQ ID NO: 4
AATLVSEQPLQNYLDTEYFGTIGIGTPAQDFTVIFDTGSSNLWVPSIYCS
SEACTNHNRFNPQDSSTYEATSETLSITYGTGSMTGILGYDTVQVGGISD
TNQIFGLSETEPGSFLYYAPFDGILGLAYPSISSSGATPVFDNIWDQGLV
SQDLFSVYLSSNEESGSVVIFGDIDSSYYSGSLNWVPVSVEGYWQITVDS
ITMNGESIACSDGCQAIVDTGTSLLAGPTTAISNIQSYIGASEDSSGEVV
ISCSSIDSLPDIVFTINGVQYPVPPSAYILQSNGICSSGFEGMDISTSSG
DLWILGDVFIRQYFTVFDRGNNQIGLAPVA

Collagenase

SEQ ID NO: 5
IANTNSEKYDFEYLNGLSYTELTNLIKNIKWNQINGLFNYSTGSQKFFGD
KNRVQAIINALQESGRTYTANDMKGIETFTEVLRAGFYLGYYNDGLSYLN
DRNFQDKCIPAMIAIQKNPNFKLGTAVQDEVITSLGKLIGNASANAEVVN
NCVPVLKQFRENLNQYAPDYVKGTAVNELIKGIEFDFSGAAYEKDVKTMP
WYGKIDPFINELKALGLYGNITSATEWASDVGIYYLSKFGLYSTNRNDIV

-continued

QSLEKAVDMYKYGKIAFVAMERITWDYDGIGSNGKKVDHDKFLDDAEKHY
LPKTYTFDNGTFIIRAGDKVSEEKIKRLYWASREVKSQFHRVVGNDKALE
VGNADDVLTMKIFNSPEEYKFNTNINGVSTDNGGLYIEPRGTFYTYERTP
QQSIFSLEELFRHEYTHYLQARYLVDGLWGQGPFYEKNRLTWFDEGTAEF
FAGSTRTSGVLPRKSILGYLAKDKVDHRYSLKKTLNSGYDDSDWMFYNYG
FAVAHYLYEKDMPTFIKMNKAILNTDVKSYDEIIKKLSDDANKNTEYQNH
IQELADKYQGAGIPLVSDDYLKDHGYKKASEVYSEISKAASLTNTSVTAE
KSQYFNTFTLRGTYTGETSKGEFKDWDEMSKKLDGTLESLAKNSWSGYKT
LTAYFTNYRVTSDNKVQYDVVFHGVLTDNADISNNKAPIAKVTGPSTGAV
GRNIEFSGKDSKDEDGKIVSYDWDFGDGATSRGKNSVHAYKKAGTYNVTL
KVTDDKGATATESFTIEIKNEDTTTPITKEMEPNDDIKEANGPIVEGVTV
KGDLNGSDDADTFYFDVKEDGDVTIELPYSGSSNFTWLVYKEGDDQNHIA
SGIDKNNSKVGTFKSTKGRHYVFIYKHDSASNISYSLNIKGLGNEKLKEK
ENNDSSDKATVIPNFNTTMQGSLLGDDSRDYYSFEVKEEGEVNIELDKKD
EFGVTWTLHPESNINDRITYGQVDGNKVSNKVKLRPGKYYLLVYKYSGSG
NYELRVNK

Collagenase

SEQ ID NO: 6
VQNESKRYTVSYLKTLNYYDLVDLLVKTEIENLPDLFQYSSDAKEFYGNK
TRMSFIMDEIGRRAPQYTEIDHKGIPTLVEVVRAGFYLGFHNKELNEINK
RSFKERVIPSILAIQKNPNFKLGTEVQDKIVSATGLLAGNETAPPEVVNN
FTPILQDCIKNIDRYALDDLKSKALFNVLAAPTYDITEYLRATKEKPENT
PWYGKIDGFINELKKLALYGKINDNNSWIIDNGIYHIAPLGKLHSNNKIG
IETLTEVMKVYPYLSMQHLQSADQIKRHYDSKDAEGNKIPLDKFKKEGKE
KYCPKTYTFDDGKVIIKAGARVEEEKVKRLYWASKEVNSQFFRVYGIDKP
LEEGNPDDILTMVIYNSPEEYKLNSVLYGYDTNNGGMYIEPEGTFFTYER
EAQESTYTLEELFRHEYTHYLQGRYAVPGQWGRTKLYDNDRLTWYEEGGA
ELFAGSTRTSGILPRKSIVSNIHNTTRNNRYKLSDTVHSKYGASFEFYNY
ACMFMDYMYNKDMGILNKLNDLAKNNDVDGYDNYIRDLSSNYALNDKYQD
HMQERIDNYENLTVPFVADDYLVRHAYKNPNEIYSEISEVAKLKDAKSEV
KKSQYFSTFTLRGSYTGGASKGKLEDQKAMNKFIDDSLKKLDTYSWSGYK
TLTAYFTNYKVDSSNRVTYDVVFHGYLPNEGDSKNSLPYGKINGTYKGTE
KEKIKFSSEGSFDPDGKIVSYEWDFGDGNKSNEENPEHSYDKVGTYTVKL
KVTDDKGESSVSTTTAEIKDLSENKLPVIYMHVPKSGALNQKVVFYGKGT
YDPDGSIAGYQWDFGDGSDFSSEQNPSHVYTKKGEYTVTLRVMDSSGQMS
EKTMKIKITDPVYPIGTEKEPNNSKETASGPIVPGIPVSGTIENTSDQDY
FYFDVITPGEVKIDINKLGYGGATWVVYDENNNAVSYATDDGQNLSGKFK
ADKPGRYYIHLYMFNGSYMPYRINIEGSVGR

Proteinase K

SEQ ID NO: 7
AAQTNAPWGLARISSTSPGTSTYYYDESAGQGSCVYVIDTGIEASHPEFE
GRAQMVKTYYYSSRDGNGHGTHCAGTVGSRTYGVAKKTQLFGVKVLDDNG

-continued

SGQYSTIIAGMDFVASDKNNRNCPKGVVASLSLGGGYSSSVNSAAARLQS

SGVMVAVAAGNNNADARNYSPASEPSVCTVGASDRYDRRSSFSNYGSVLD

IFGPGTSILSTWIGGSTRSISGTSMATPHVAGLAAYLMTLGKTTAASACR

YIADTANKGDLSNIPFGTVNLLAYNNYQA

Tn5 Mosaic end sequence
SEQ ID NO: 8
CTGTCTCTTA TACACATCT

Mu Transposase Recognition Sequence
SEQ ID NO: 9
TGAAGCGGCG CACGAAAAAC GCGAAAG

Mu Transposase Recognition Sequence
SEQ ID NO: 10
GCGTTTCACG ATAAATGCGA AAA

Mu Transposase Recognition Sequence
SEQ ID NO: 11
CTGTTTCATT TGAAGCGCGA AAG

Mu Transposase Recognition Sequence
SEQ ID NO: 12
TGTATTGATT CACTTGAAGT ACGAAAA

Mu Transposase Recognition Sequence
SEQ ID NO: 13
CCTTAATCAA TGAAACGCGA AAG

-continued

Mu Transposase Recognition Sequence
SEQ ID NO: 14
TTGTTTCATT GAAAATACGA AAA

Surface probe of the capture probe
SEQ ID NO: 15
UUUUUGACTC GTAATACGAC TCACTATAGG GACACGACGC
TCTTCCGATC TNNNNNNNNT GCACGCGGTG TACAGACGT First adapter
SEQ ID NO: 16
GTCTCGTGGG CTCGG Capture domain
SEQ ID NO: 17
CCGAGCCCAC GAGAC Hybridization domain
SEQ ID NO: 18
TGCACGCGGT GTACAGACGT Splint oligonucleotide complementary to hybridization domain
SEQ ID NO: 19
ACGTCTGTAC ACCGCGTGCA Second adapter
SEQ ID NO: 20
TCGTCGGCAG CGTC A-short forward
SEQ ID NO: 21
ACACGACGCT CTTCCGATCT

---

What is claimed is:

1. A method for determining a spatial location of accessible chromatin in a tissue section, the method comprising:
   (a) providing a substrate with the tissue section;
   (b) permeabilizing the tissue section;
   (c) contacting the permeabilized tissue section with a transposome to insert transposon end sequences into accessible chromatin, thereby generating fragmented accessible chromatin;
   (d) incorporating into the fragmented accessible chromatin: (i) a first barcode sequence and (ii) a second barcode sequence, thereby generating a plurality of barcoded accessible chromatin fragments, and wherein the first barcode sequence and the second barcode sequence are sub-barcode sequences that function as a single barcode sequence and indicate the spatial location where the first barcode sequence and the second barcode sequence were delivered in the tissue section, respectively;
   (e) amplifying the plurality of barcoded accessible chromatin fragments, thereby generating amplicons comprising the barcoded accessible chromatin fragments or complements thereof;
   (f) determining (i) the first barcode sequence of one or more of the amplicons, or complements thereof (ii) the second barcode sequence of one or more of the amplicons, or complements thereof, and (iii) the sequence of the accessible chromatin of one or more of the amplicons, or complements thereof; and
   (g) using the sequences of (i), (ii), and (iii) to determine the spatial location of accessible chromatin in the tissue section.

2. The method of claim 1, wherein the substrate is an array that comprises one or more features.

3. The method of claim 2, wherein the one or more features is a bead, a well, a spot, or a hydrogel.

4. The method of claim 1, wherein permeabilizing the tissue section in (b) comprises enzymatic permeabilization or chemical permeabilization.

5. The method of claim 4, wherein enzymatic permeabilization comprises a proteinase K enzyme, a proteinase K-like enzyme, or a functional equivalent thereof comprising a sequence that is at least 80% identical to SEQ ID NO: 7.

6. The method of claim 4, wherein chemical permeabilization comprises an alkaline buffered solution.

7. The method of claim 1, wherein the transposome comprises a Tn5 transposase enzyme, a Mu transposase enzyme, a Tn7 transposase enzyme, or functional derivatives thereof.

8. The method of claim 7, wherein the Tn5 transposase enzyme comprises a sequence that is at least 80% identical to SEQ ID NO: 1 and wherein transposon end sequences comprise a sequence that is at least 80% identical to SEQ ID NO: 8.

9. The method of claim 1, wherein transposon end sequences further comprise a first adapter sequence and a second adapter sequence.

10. The method of claim 9, wherein the first adapter sequence and the second adapter sequence are used for one or more of ligation, hybridization, and tagmentation.

11. The method of claim 9, wherein the first adapter sequence and the second adapter sequence are functional sequences used as spacer sequences, primer binding site sequences, or unique molecular identifier sequences.

12. The method of claim 1, wherein the method further comprises performing gap repair of single-stranded breaks in the fragmented accessible chromatin.

13. The method of claim 1, wherein the method further comprises staining and imaging the tissue section before (b).

14. The method of claim 13, wherein the staining comprises staining the tissue section with hematoxylin or eosin.

15. The method of claim 1, wherein the amplifying in (e) comprises amplifying the barcoded accessible chromatin fragments and adding sequencing primer sequences to 5' and 3' ends of the amplicons.

16. The method of claim 1, wherein the amplifying comprises polymerase chain reaction.

17. The method of claim 1, wherein the determining in (f) comprises next generation sequencing or fluorescence detection.

18. The method of claim 1, wherein the determining in (f) comprises next generation sequencing.

19. The method of claim 1, wherein the method further comprises using one or more microfluidic channels to deliver one or more reagents to the tissue section.

20. The method of claim 1, wherein determining the spatial location of accessible chromatin in the tissue section is performed in/at a region of interest in the tissue section.

21. The method of claim 20, wherein the region of interest in the tissue section is a specific area or sub-area of the tissue section.

22. The method of claim 21, further comprises imaging the region of interest of the tissue section.

* * * * *